US010851115B2

(12) United States Patent
Kim et al.

(10) Patent No.: US 10,851,115 B2
(45) Date of Patent: Dec. 1, 2020

(54) HETEROCYCLIC COMPOUNDS AS RSV INHIBITORS

(71) Applicant: Enanta Pharmaceuticals, Inc., Watertown, MA (US)

(72) Inventors: In Jong Kim, Lexington, MA (US); Joseph Panarese, Malden, MA (US); Thomas P. Blaisdell, Brighton, MA (US); Jianming Yu, Plainsboro, NJ (US); Brian C. Shook, Holliston, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 16/023,363

(22) Filed: Jun. 29, 2018

(65) Prior Publication Data

US 2019/0002478 A1 Jan. 3, 2019

Related U.S. Application Data

(60) Provisional application No. 62/527,390, filed on Jun. 30, 2017.

(51) Int. Cl.
*C07D 519/00* (2006.01)
*A61P 31/16* (2006.01)

(52) U.S. Cl.
CPC ............ *C07D 519/00* (2013.01); *A61P 31/16* (2018.01)

(58) Field of Classification Search
CPC ............................... C07D 519/00; A61P 31/16
See application file for complete search history.

(56) References Cited

U.S. PATENT DOCUMENTS

| | | | |
|---|---|---|---|
| 4,010,153 | A | 3/1977 | Kajfez et al. |
| 4,511,510 | A | 4/1985 | Mauri |
| 5,571,809 | A | 11/1996 | Hargrave et al. |
| 5,637,697 | A | 6/1997 | Finch et al. |
| 5,646,140 | A | 7/1997 | Sugg et al. |
| 5,681,833 | A | 10/1997 | Castro et al. |
| 7,582,624 | B2 | 9/2009 | Carter et al. |
| 8,999,969 | B2 | 4/2015 | Mackman et al. |
| 9,732,098 | B2 | 8/2017 | Hunt et al. |
| 9,957,281 | B2 | 5/2018 | Shook et al. |
| 10,358,441 | B2 | 7/2019 | Kim et al. |
| 10,398,706 | B2 | 9/2019 | Shook et al. |
| 2006/0040923 | A1 | 2/2006 | Carter et al. |
| 2006/0083741 | A1 | 4/2006 | Hoffman et al. |
| 2007/0142403 | A1 | 6/2007 | Powell et al. |
| 2007/0185094 | A1 | 8/2007 | Lattmann et al. |
| 2007/0185096 | A1 | 8/2007 | Powell et al. |
| 2007/0293482 | A1 | 12/2007 | Dowdell et al. |
| 2008/0139536 | A1 | 6/2008 | Dowdell et al. |
| 2009/0274655 | A1 | 11/2009 | Grimes et al. |
| 2010/0015063 | A1 | 1/2010 | Carter et al. |
| 2012/0196846 | A1 | 8/2012 | Mackman et al. |
| 2014/0038947 | A1 | 2/2014 | Glick et al. |

(Continued)

FOREIGN PATENT DOCUMENTS

| | | | |
|---|---|---|---|
| EP | 0703222 | A1 | 3/1996 |
| WO | 9308175 | A1 | 4/1993 |

(Continued)

OTHER PUBLICATIONS

Xiong, Blood & MEd Chem Lett, vol. 23, 6789-3793, 2013. (Year: 2013).*
Pubchem—CID: 10595203, p. 3, Fig, Oct. 25, 2006, 1-9.
Albright, et al., (Document No. 129:54301) retrieved from STN; entered in STN on Jun. 17, 1998.
Albright, et al., (Document No. 130:153583) retrieved from STN; entered in STN on Feb. 16, 1999.
Andrzej, et al., (Document No. 144:274313) retrieved from STN; entered in STN on Mar. 3, 2006.
Carter, M. C. et al., "1,4-Benzodiazepines as Inhibitors of Respiratory Syncytial Virus", Journal of Medicinal Chemistry, vol. 49, Mar. 9, 2006, 2311-2319.

(Continued)

*Primary Examiner* — D Margaret M Seaman
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

(I)

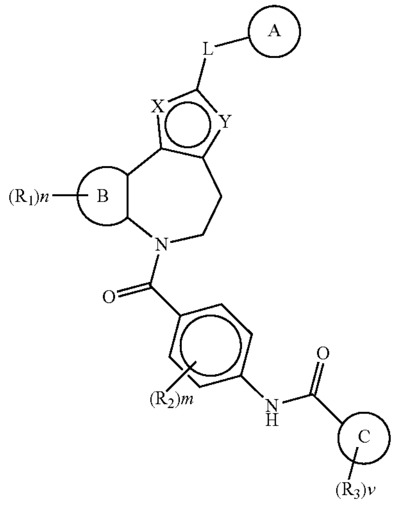

(I)

which inhibit Respiratory Syncytial Virus (RSV). The present invention further relates to pharmaceutical compositions comprising the aforementioned compounds for administration to a subject suffering from RSV infection. The invention also relates to methods of treating an RSV infection in a subject by administering a pharmaceutical composition comprising the compounds of the present invention.

23 Claims, No Drawings

(56) References Cited

U.S. PATENT DOCUMENTS

| | | | |
|---|---|---|---|
| 2014/0100365 A1 | 4/2014 | Gavai et al. | |
| 2015/0065504 A1 | 3/2015 | Wang et al. | |
| 2015/0299210 A1 | 10/2015 | Bailey et al. | |
| 2017/0022221 A1 | 1/2017 | Blaisdell et al. | |
| 2017/0226127 A1 | 8/2017 | Estrada et al. | |
| 2017/0226129 A1 | 8/2017 | Yu et al. | |
| 2017/0305935 A1 | 10/2017 | Hunt et al. | |
| 2017/0355717 A1 | 12/2017 | Hunt et al. | |
| 2018/0193352 A1 | 7/2018 | Shook et al. | |
| 2018/0237425 A1 | 8/2018 | Kim et al. | |
| 2018/0258102 A1 | 9/2018 | Shook et al. | |
| 2018/0354912 A1 | 12/2018 | Or et al. | |
| 2019/0002478 A1 | 1/2019 | Kim et al. | |
| 2019/0002479 A1 | 1/2019 | Kim et al. | |
| 2019/0092791 A1* | 3/2019 | Hunt | A61P 31/14 |
| 2019/0152968 A1 | 5/2019 | Blaisdell et al. | |
| 2019/0177283 A1 | 6/2019 | Hague | |
| 2019/0192535 A1 | 6/2019 | Shook et al. | |
| 2019/0315766 A1 | 10/2019 | Yu et al. | |

FOREIGN PATENT DOCUMENTS

| | | |
|---|---|---|
| WO | 9426718 A1 | 11/1994 |
| WO | 2004026843 A1 | 4/2004 |
| WO | 2004106310 A1 | 12/2004 |
| WO | 2005089769 A1 | 9/2005 |
| WO | 2005090319 A1 | 9/2005 |
| WO | 2006081389 A1 | 8/2006 |
| WO | 2011005842 A1 | 1/2011 |
| WO | 2011151651 A1 | 12/2011 |
| WO | 2014047369 A1 | 3/2014 |
| WO | 2014125444 A1 | 8/2014 |
| WO | 2014184350 A1 | 11/2014 |
| WO | 2016022464 A1 | 2/2016 |
| WO | 2016055791 A1 | 4/2016 |
| WO | 2016055792 A1 | 4/2016 |
| WO | 2016097761 A1 | 6/2016 |
| WO | 2016166546 A1 | 10/2016 |
| WO | 2017015449 A1 | 1/2017 |
| WO | 2017123884 A1 | 7/2017 |
| WO | 2017175000 A1 | 10/2017 |

OTHER PUBLICATIONS

Fordyce, et al., "Discovery of novel benzothienoazepine derivatives as potent inhibitors of respiratory syncytial virus", Bioorganic & Medicinal Chemistry Letters, 27, 2017, 2201-2206.

Heeney, et al. (Document No. 153:359062) retrieved from STN; entered in STN on Sep. 2, 2010.

Henderson, E. A. et al., "1,4-Benzodiazepines as Inhibitors of Respiratory Syncytial Virus. The Identification of a Clinical Candidate", Journal of Medicinal Chemistry, vol. 50, Mar. 7, 2007, 1685-1692.

Lee, et al., (Document No. 140:69941) retrieved from STN; entered in STN on Jul. 8, 2003.

Mayo Clinic Staff, Respiratory syncytial virus (RSV) [online], retrieved from internet on Jun. 25, 2017.; URL http://www.mayoclinic.org/diseases-condiitons/respiratory-syncytial-virus/basics/prevention.

Peesapati, et al., (Document No. 120:244848) retrieved from STN; entered in STN on May 14, 1994.

Wang, et al., (Document No. 160:385666) retrieved from STN; entered in STN on Feb. 27, 2014.

Xiong, et al., (Document No. 160:101182) retrieved from STN; entered in STN on Nov. 12, 2013.

Xiong, H., "Discovery of a Potent Respiratory Syncytial Virus RNA Polymerase Inhibitor", Bioorganic & Medicinal Chemistry Letters, 23, 2013, 6789-6793.

Zheng, et al., (Document No. 161 :399872) retrieved from STN; entered in STN on Jul. 23, 2014.

Aquino, Christopher J. et al., "Discovery of 1,5-Benzodiazepines with Peripheral Cholecystokinin (CCK-A) Receptor Agonist Activity. 1. Optimization of the Agonist "Trigger"", J. Med. Chem. 1996, 39, 1996, 562-569.

Chapman, Joanna et al., "RSV604, a Novel Inhibitor of Respiratory Syncytial Virus Replication", Antimicrobial Agents and Chemotherapy, vol. 51, No. 9, 2007, 3346-3353.

Setoi, Hiroyuki et al., "Preparation of heterocyclylbenzamide derivatives as vasopressin antagonists", Document No. 131:116236, retrieved from STN; entered in STN on Aug. 6, 1999, Aug. 6, 1999.

Armstrong, et al., "An Efficient Asymmetric Synthesis of (R)-3-Amino-2,3,4,5-tetrahydro-1H-[1]benzazepine-2-one", Tetrahedron Letters, 35(20), 1994, 3239-3242.

Karmakar, et al., "Crystallization-Induced Dynamic Resolution toward the Synthesis of (S)-7-Amino-5H,7H-dibenzo[b,d]-azepin-6-one: An Important Scaffold for γ-Secretase Inhibitors", Organic Process Research & Development, 20, 2016, 1717-1720.

Offel, M. et al., "Synthesis of Substituted 3-Anilino-5-phenyl-1,3-dihydro-2H-l, 4-benzodiazepine-2-ones and their Evaluation as Cholecystokinin-Ligands", Archiv Der Pharmazie, vol. 339, No. 4, Apr. 1, 2006, 163-173.

Olszewska, Wieslawa et al., "Emerging drugs for respiratory syncytial virus infection", Expert Opin. Emerg. Drugs (2009), 14(2), 207-217.

Perron, Michel et al., "GS-5806 Inhibits a Broad Range of Respiratory Syncytial Virus Clinical Isolates by Blocking the Virus-Cell Fusion Process", Antimicrobial Agents and Chemotherapy, 2016, 60(3), 1264-1273.

Reider, et al., "Metalated Allylaminosilane: A New, Practical Reagent for Stereoselective a-Hydroxyallylation of Aldehydes to Erythro-1,2-diol Skeletons", J. Org. Chem, 52, 1987, 957.

Sudo, Kenji et al., "YM-53403, a unique anti-respiratory syncytial virus agent with a novel mechanism of action", Antiviral Research, 2005, vol. 65, 2005, 125-131.

* cited by examiner

HETEROCYCLIC COMPOUNDS AS RSV INHIBITORS

RELATED APPLICATIONS

This application claims the benefit of U.S. Provisional Application No. 62/527,390, filed on Jun. 30, 2017. The entire teachings of the above application are incorporated herein by reference.

TECHNICAL FIELD

The present invention relates generally to compounds and pharmaceutical compositions useful as Respiratory Syncytial Virus (RSV) inhibitors.

BACKGROUND OF THE INVENTION

Human respiratory syncytial virus (HRSV) is a negative-sense, single stranded, RNA paramyxovirus (K M. Empey, et al., *Rev. Anti-Infective Agents,* 2010, 50(1 May), 1258-1267). RSV is the leading cause of acute lower respiratory tract infections (ALRI) and affects patients of all ages. The symptoms in adults are usually not severe and are typically analogous to a mild cold. However, in infants and toddlers the virus can cause lower respiratory tract infections including bronchiolitis or pneumonia with many of them requiring hospitalization. Nearly all children have been infected by age 3. There are known high-risk groups that infection with RSV is more likely to progress into the ALRI. Premature infants and/or infants suffering from lung or cardiac disease are at the highest risk to develop ALRI. Additional high-risk groups include the elderly, adults with chronic heart and/or lung disease, stem cell transplant patients and the immunosuppressed.

Currently, there is no vaccine available to prevent HRSV infection. Palivizumab is a monoclonal antibody that is used prophylactically to prevent HRSV infection in high risk infants, e.g. premature infants, and infants with cardiac and/or lung disease. The high cost of palivizumab treatment limits its use for general purposes. Ribavirin has also been used to treat HRSV infections but its effectiveness is limited. There is a major medical need for new and effective HRSV treatments that can be used generally by all population types and ages.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, WO 2016/055792, WO 2016/097761, and J. Med. Chem. 2015, 58, 1630-1643. Examples of other N-protein inhibitors for treatment of HRSV have been disclosed in the following publications: WO 2004/026843, *J. Med. Chem.* 2006, 49, 2311-2319, and *J. Med. Chem.* 2007, 50, 1685-1692. Examples of L-protein inhibitors for HRSV have been disclosed in the following publications: WO 2011/005842, WO 2005/042530, *Antiviral Res.* 2005, 65, 125-131, and *Bioorg. Med. Chem. Lett.* 2013, 23, 6789-6793, *Bioorg. Med. Chem. Lett.* 2017, 27, 2201-2206. Examples of nucleosides/polymerase inhibitors have been disclosed in the following publications: WO 2013/242525 and *J. Med. Chem.* 2015, 58, 1862-1878.

There is a need for the development of effective treatments for HRSV. The present invention has identified these novel compounds and their inhibitory activity against HRSV. The invention includes methods to prepare the compounds as well as methods of using these compounds to treat disease.

SUMMARY OF THE INVENTION

The present invention provides compounds represented by Formula (I), and pharmaceutically acceptable salts, esters and prodrugs thereof that can be used to treat or prevent viral (particularly HRSV) infection:

(I)

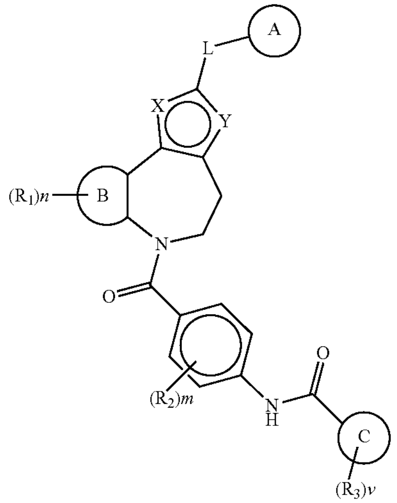

wherein:

Ⓐ is selected from the group consisting of:

1) optionally substituted aryl;
2) optionally substituted heteroaryl;
3) optionally substituted —$C_3$-$C_{12}$ cycloalkyl;
4) optionally substituted —$C_3$-$C_{12}$ cycloalkenyl;
5) optionally substituted 3- to 12-membered heterocycloalkyl;
6) optionally substituted arylalkyl;
7) optionally substituted heteroarylalkyl;
8) optionally substituted-$C_3$-$C_{12}$ cycloalkyl-$C_1$-$C_6$ alkyl;
9) optionally substituted-$C_3$-$C_{12}$ cycloalkenyl-$C_1$-$C_6$ alkyl; and
10) optionally substituted 3- to 12-membered heterocycloalkyl-$C_1$-$C_6$ alkyl;

Ⓑ is heteroaryl, which, when possible, is optionally substituted with one or more substituents which are not $R_1$. Preferably Ⓑ is pyridinyl or thiophenyl, which is optionally substituted with one or more substituents which are not $R_1$.

Ⓒ is aryl or heteroaryl, which, when possible, is optionally substituted with one or more substituents which are not $R_3$;

L is absent, —CONH—, or —NHCO—;

One of X and Y is selected from O, S, and $NR_4$, and the other is N or $CR_5$;

Each $R_1$ and $R_2$ is independently selected from the group consisting of halogen, cyano, nitro, hydroxyl, protected hydroxyl, amino, protected amino, optionally substituted —$C_1$-$C_8$ alkyl, and optionally substituted —$C_1$-$C_8$ alkoxy;

Each $R_3$ is selected from the group consisting of:

1) halogen;
2) optionally substituted —$C_1$-$C_8$ alkoxy;
3) optionally substituted —$C_1$-$C_8$ alkyl;
4) optionally substituted —$C_2$-$C_8$ alkenyl;
5) optionally substituted —$C_2$-$C_8$ alkynyl;

6) optionally substituted $-C_3$-$C_{12}$ cycloalkyl;
7) optionally substituted $-C_3$-$C_{12}$ cycloalkenyl;
8) optionally substituted 3- to 12-membered heterocycloalkyl;
9) optionally substituted aryl;
10) optionally substituted heteroaryl;
11) optionally substituted arylalkyl;
12) optionally substituted aryloxy;
13) $-C(O)R_{12}$;
14) $-C(O)NR_{13}R_{14}$;
15) $-C(O)NR_{11}S(O)_2R_{12}$;
16) $-S(O)_2NR_{13}R_{14}$;
17) $-NR_{13}R_{14}$;
18) $-NR_{11}S(O)_2R_{12}$;
19) $-NR_{11}C(O)R_{12}$;
20) $-NR_{11}C(O)NR_{13}R_{14}$; and
21) $-NR_{11}C(O)NHS(O)_2R_{12}$;

n is 0, 1, 2, 3 or 4;
m is 0, 1, 2, 3 or 4;
v is 0, 1, 2, or 3;
$R_4$ is hydrogen or optionally substituted $-C_1$-$C_8$ alkyl;
$R_5$ is hydrogen, halogen, optionally substituted $-C_1$-$C_8$ alkyl, or optionally substituted $-C_1$-$C_8$ alkoxy;
$R_{12}$ at each occurrence is independently selected from the group consisting of:

1) Hydrogen;
2) Halogen;
3) Hydroxyl;
4) optionally substituted $-C_1$-$C_8$ alkoxy;
5) optionally substituted $-C_1$-$C_8$ alkyl;
6) optionally substituted $-C_2$-$C_8$ alkenyl;
7) optionally substituted $-C_2$-$C_8$ alkynyl;
8) optionally substituted $-C_3$-$C_8$ cycloalkyl;
9) optionally substituted $-C_3$-$C_8$ cycloalkenyl;
10) optionally substituted 3- to 8-membered heterocycloalkyl;
11) optionally substituted aryl;
12) optionally substituted arylalkyl;
13) optionally substituted heteroaryl; and
14) optionally substituted heteroarylalkyl;

$R_{11}$, $R_{13}$ and $R_{14}$ are each independently selected from hydrogen, optionally substituted $-C_1$-$C_8$-alkyl, optionally substituted $-C_2$-$C_8$-alkenyl, optionally substituted $-C_2$-$C_8$-alkynyl; optionally substituted $-C_3$-$C_8$-cycloalkyl, optionally substituted 3- to 8-membered heterocyclic, optionally substituted aryl, optionally substituted arylalkyl, optionally substituted heteroaryl, and optionally substituted heteroarylalkyl; alternatively, $R_{13}$ and $R_{14}$ are taken together with the nitrogen atom to which they are attached to form a heterocyclic ring.

Each preferred group stated above can be taken in combination with one, any or all other preferred groups.

DETAILED DESCRIPTION OF THE INVENTION

In one embodiment, the present invention provides a compound represented by Formula (I) as described above, or a pharmaceutically acceptable salt, ester or prodrug thereof.

In certain embodiments, the present invention relates to compounds of Formula (I), and pharmaceutically acceptable salts, esters and prodrugs thereof, wherein Ⓐ is optionally substituted aryl; preferably Ⓐ is optionally substituted phenyl. The optional substituents are preferably independently selected from, but not limited to, halogen, —CN, —OH, $-NH_2$, $-NO_2$, $-CH_3$, $-CF_3$, $-OCH_3$, $-OCF_3$, $-SO_2CH_3$, $-CH_2N(CH_3)_2$, and $-C(O)CH_3$. In preferred embodiments, there are 0 to 2 substituents and, more preferably, 0 or 1 substituent.

In certain embodiments, the present invention relates to compounds of Formula (I), and pharmaceutically acceptable salts, esters and prodrugs thereof, wherein Ⓐ is optionally substituted heteroaryl, preferably optionally substituted fused bicyclic heteroaryl. When present the substituents are independently selected from, halogen, —CN, —OH, $-NH_2$, $-NO_2$, $-CH_3$, $-CF_3$, $-OCH_3$, $-OCF_3$, $-SO_2CH_3$, $-CH_2N(CH_3)_2$, and $-C(O)CH_3$. In preferred embodiments, there are 0 to 2 substituents and, more preferably, 0 or 1 substituent.

In one embodiment, the present invention relates to compounds of Formula (I), and pharmaceutically acceptable salts, esters and prodrugs thereof, wherein Ⓐ is one of the following by removal of a hydrogen atom:

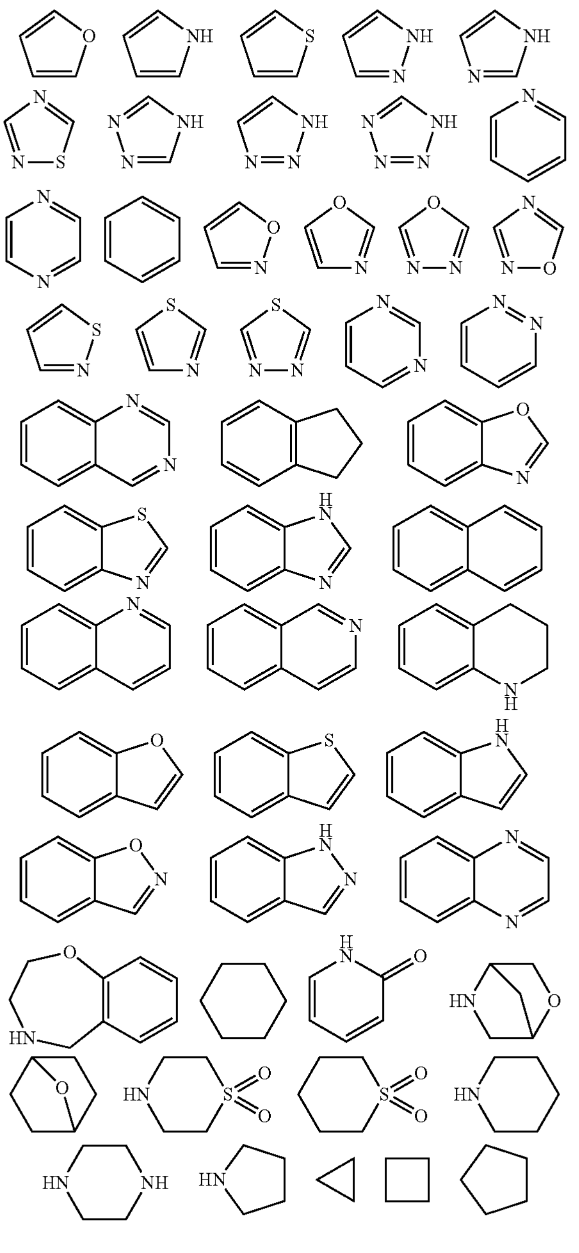

-continued

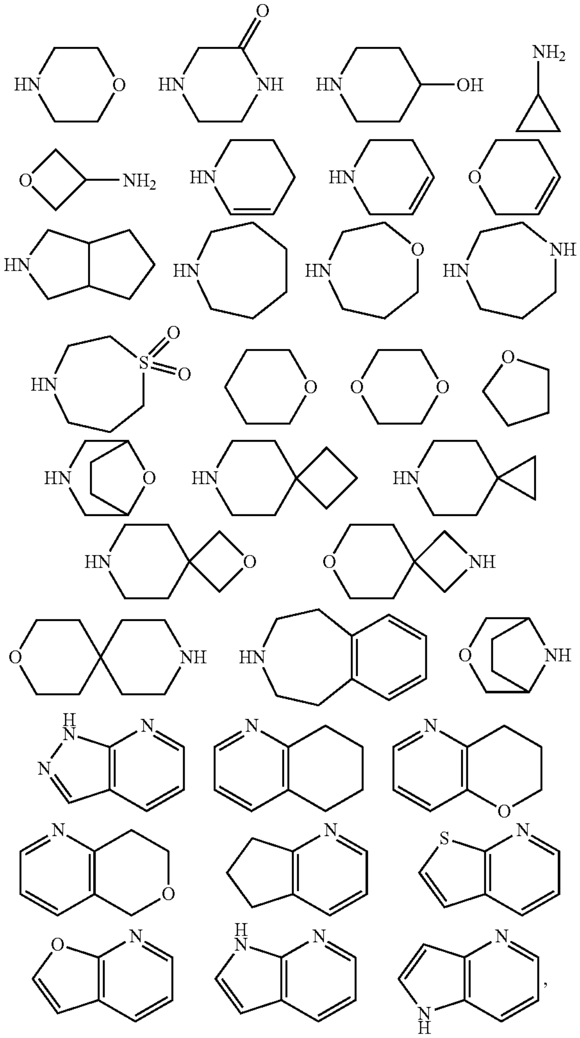
, wherein each of the above is optionally substituted. When Ⓐ is a 5/6 fused bicyclic heteroaryl group, it is preferably attached to L via an available atom in the 5-membered ring. Preferably, when present, the substituents are independently selected from, but not limited to, —CN, —F, —Cl, —$CH_3$, —$CF_3$, —$OCH_3$, and —$OCF_3$.

In one embodiment, the present invention relates to compounds of Formula (I), and pharmaceutically acceptable salts, esters and prodrugs thereof, wherein Ⓐ is —$CH_2$—ⓐ, or —$C_2H_4$—ⓐ, wherein ⓐ is one of the following by removal of a hydrogen atom:

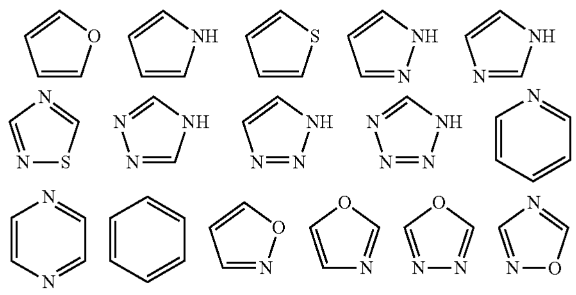

-continued

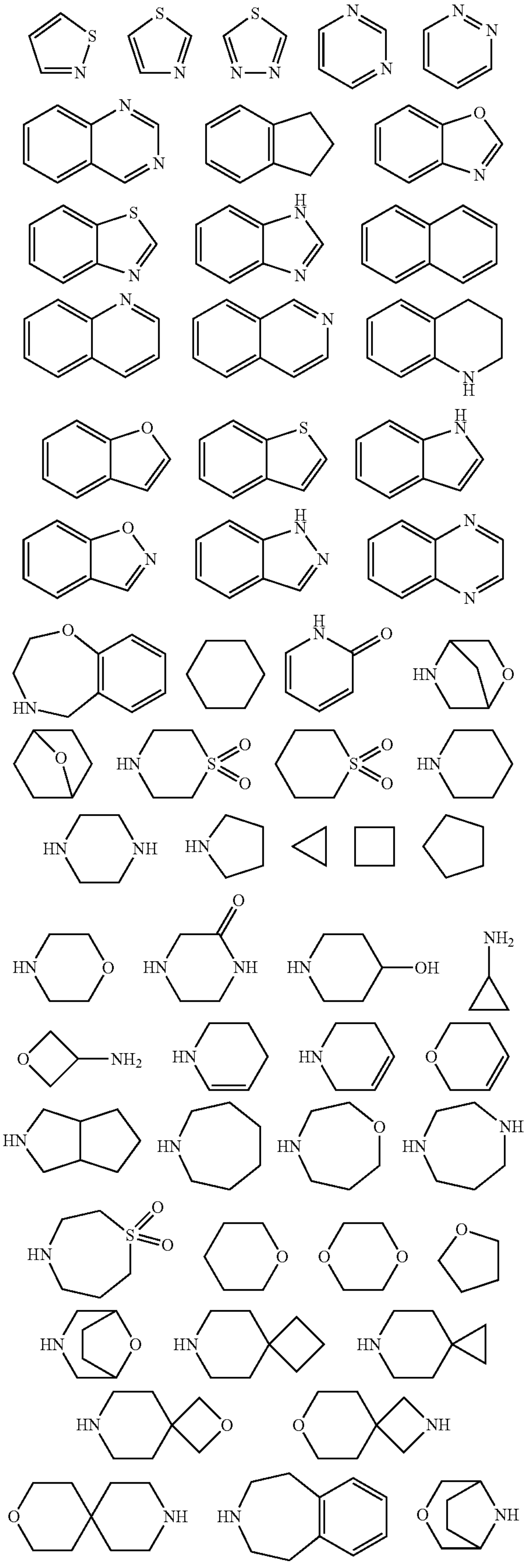

-continued

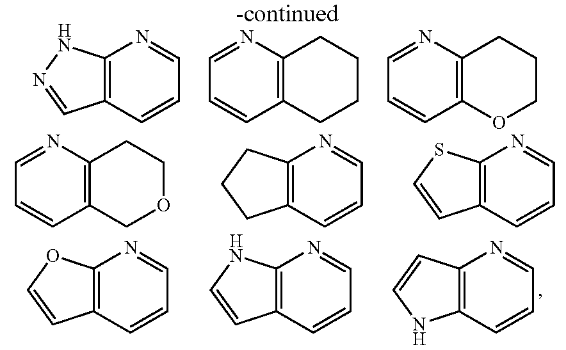

wherein each of the above is optionally substituted. Preferably, when present, the substituents are independently selected from, but not limited to, —CN, —F, —Cl, $—CH_3$, $—CF_3$, $—OCH_3$, and $—OCF_3$.

In one embodiment, the present invention relates to compounds of Formula (I), and pharmaceutically acceptable salts, esters and prodrugs thereof, wherein Ⓐ is one of the following:

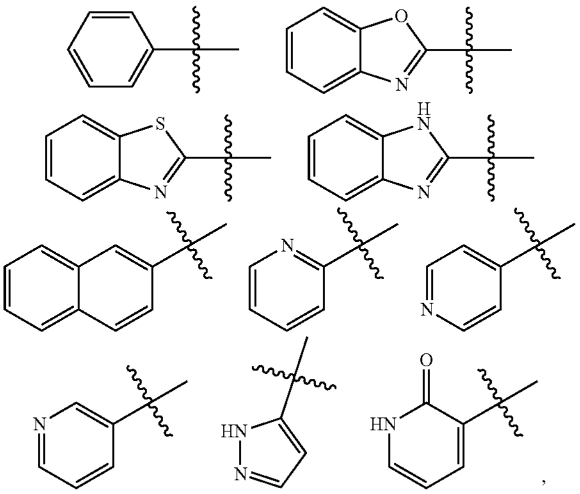

wherein each of the above is optionally substituted. Preferably, when present, the substituents are independently selected from, but not limited to, —CN, —F, —Cl, $—CH_3$, $—CF_3$, $—OCH_3$, and $—OCF_3$.

In one embodiment, the present invention relates to compounds of Formula (I), and pharmaceutically acceptable salts, esters and prodrugs thereof, wherein Ⓑ is derived from one of the following by removal of the hydrogen atoms from two adjacent carbon atoms:

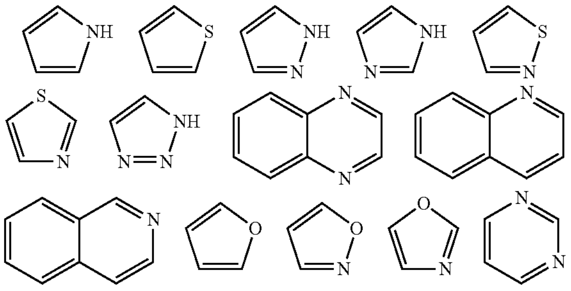

-continued

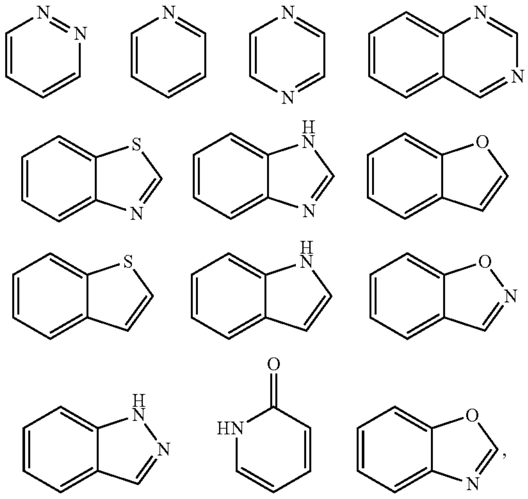

wherein each of the above is optionally substituted when possible.

In one embodiment, the present invention relates to compounds of Formula (I), and pharmaceutically acceptable salts, esters and prodrugs thereof, wherein Ⓑ is one of the following:

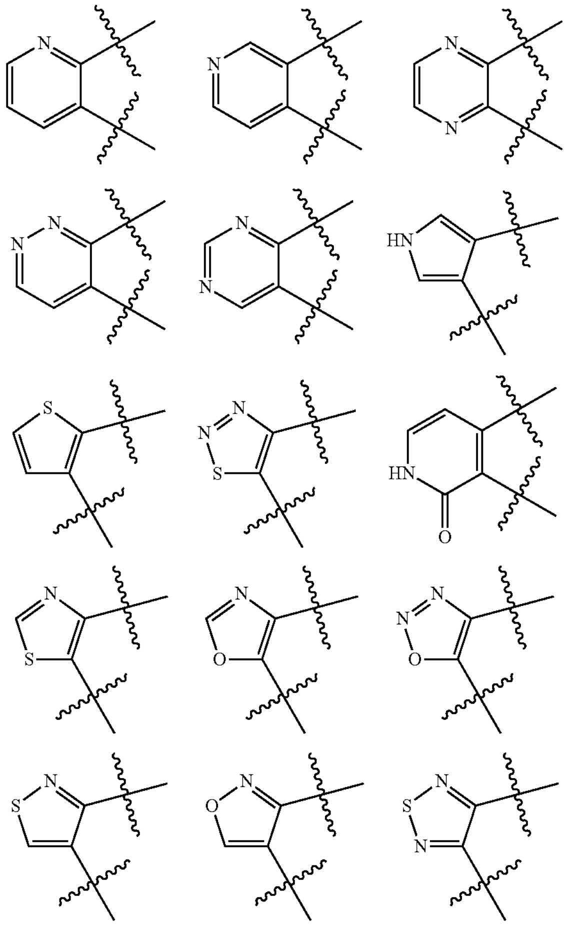

-continued

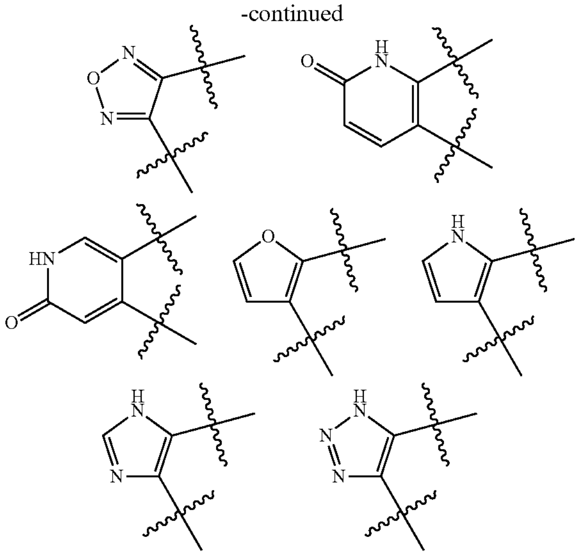

-continued

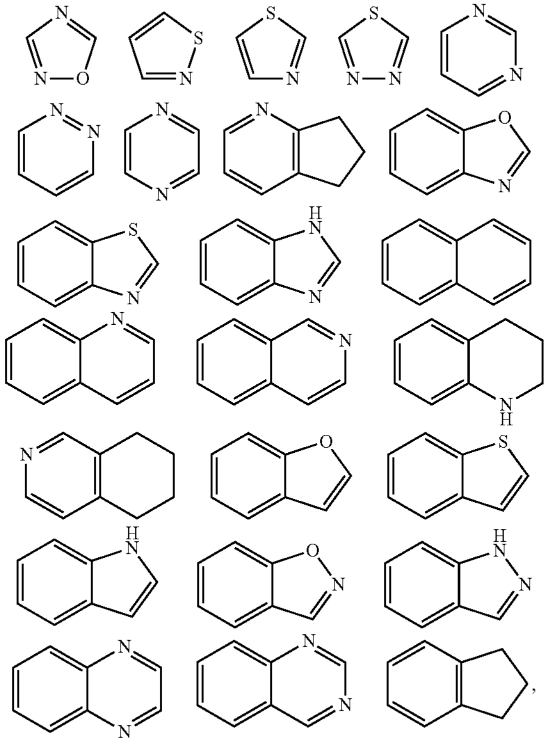

wherein each of the above is optionally substituted when possible. Preferably, when present, the substituents are independently selected from, but not limited to, halo, —CN, —$SO_2$Me, —$CH_2N(CH_3)_2$, —$C_1$-$C_8$-alkoxy, —$C_1$-$C_8$-alkyl, and —$C(O)CH_3$. It is to be understood that depending on the heteroaryl group, there can be 0, 1, 2 or 3 substituents, more preferably the substituents are independently selected from —F, —Cl, —$CH_3$, —$CF_3$, —$OCH_3$, and —$OCF_3$.

In certain embodiments, the present invention relates to compounds of Formula (I), and pharmaceutically acceptable salts, esters and prodrugs thereof, wherein © is heteroaryl, preferably © is pyridinyl or fused bicyclic heteroaryl, each of which is optionally substituted with one or more substituents in addition to any $R_3$ groups; preferably these substituents are independently selected from, but not limited to, —CN, —OH, —$NH_2$, —$NO_2$—$SO_2CH_3$, and —$CH_2N(CH_3)_2$.

In certain embodiments, the present invention relates to compounds of Formula (I), and pharmaceutically acceptable salts, esters and prodrugs thereof, wherein © is optionally substituted bicyclic aryl or bicyclic heteroaryl.

In one embodiment, the present invention relates to compounds of Formula (I), and pharmaceutically acceptable salts, esters and prodrugs thereof, wherein © is derived from one of the following by removal of a hydrogen atom:

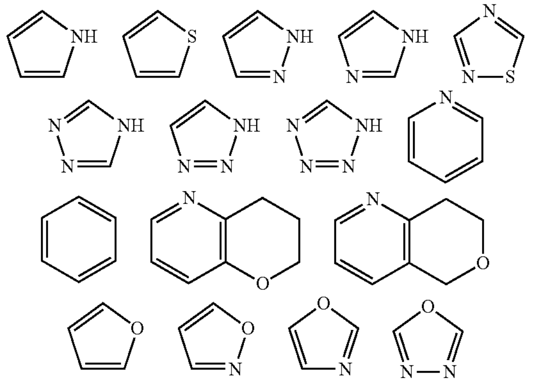

wherein each of the above is, in addition to any $R_3$ groups present, optionally further substituted with one or more substituents which are not $R_3$.

In one embodiment, the present invention relates to compounds of Formula (I), and pharmaceutically acceptable salts, esters and prodrugs thereof, wherein © is one of the following:

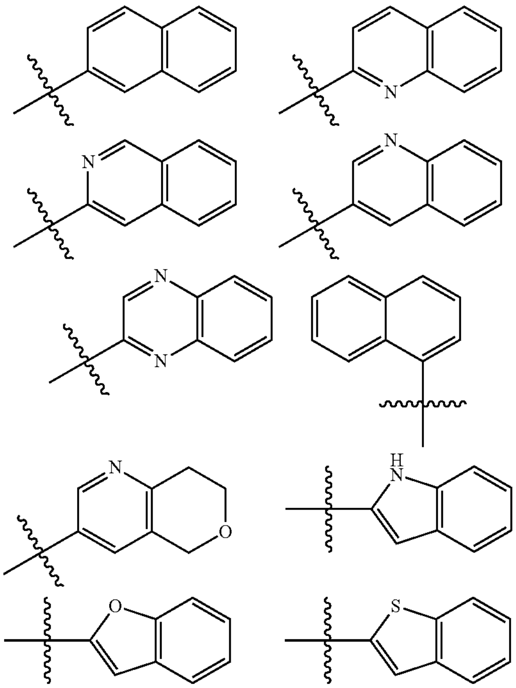

-continued
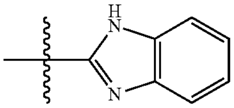
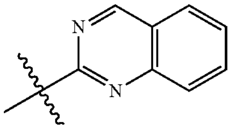
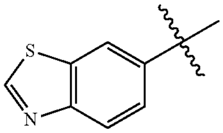
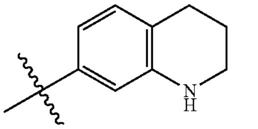
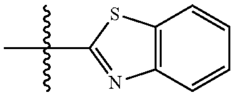
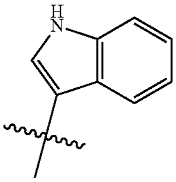
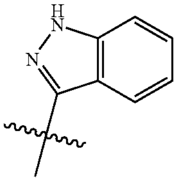
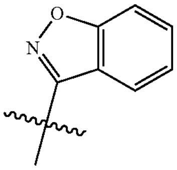
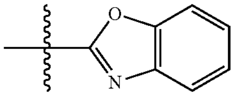
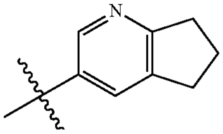
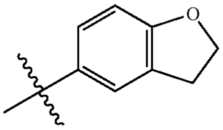
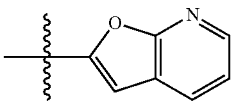
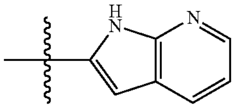
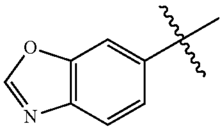
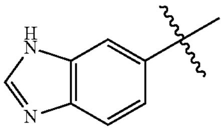
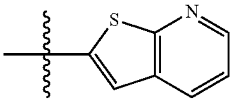
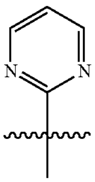
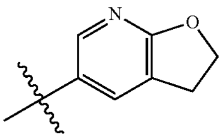
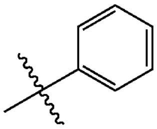
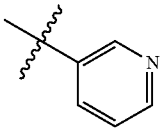
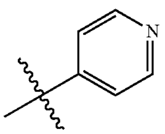
-continued
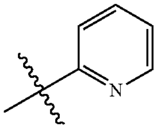
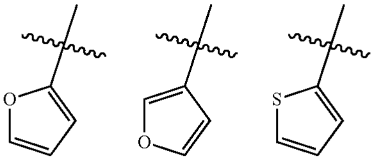
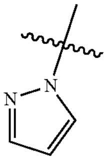
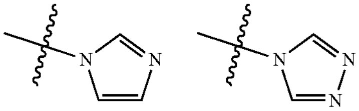
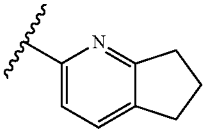
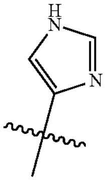
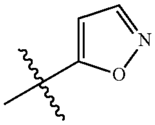
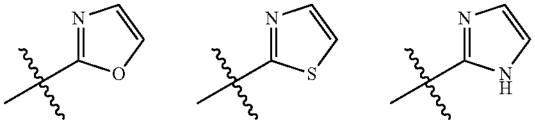
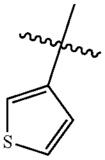
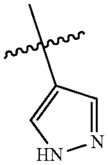
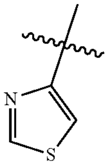
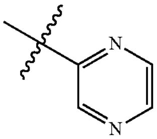
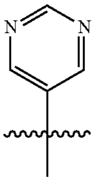
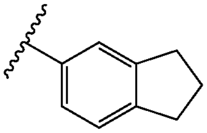
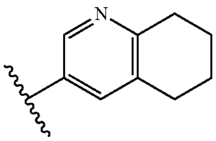
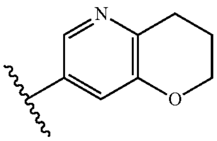
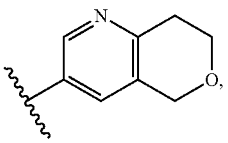
wherein each of the above is, in addition to any $R_3$ groups present, optionally further substituted with one or more substituents which are not $R_3$.

In certain embodiments,

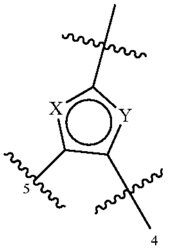

is selected from the groups below, where "4" and "5" indicate respectively the point of attachment to the 4- and 5-positions of the benzoazepine ring system:

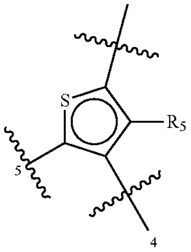
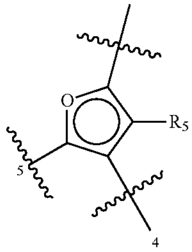

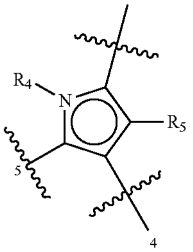
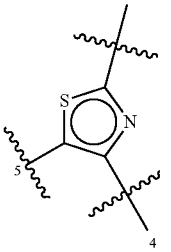
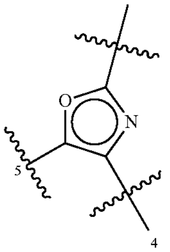

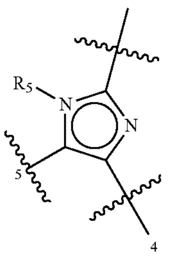
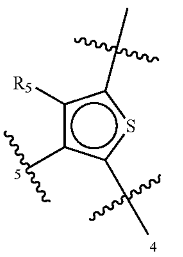
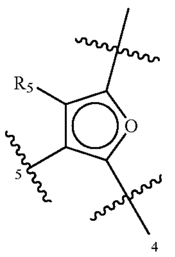

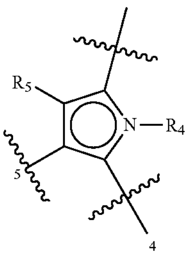
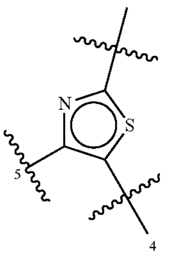
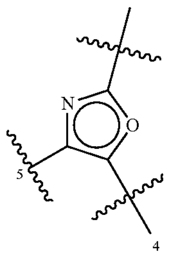

-continued

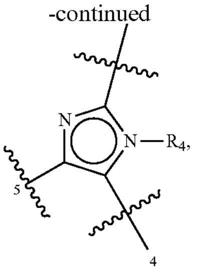

wherein $R_4$ and $R_5$ are previously defined, preferably, $R_4$ is hydrogen; $R_5$ is hydrogen or halogen.

In certain embodiments, the present invention relates to compounds of Formula (I), and pharmaceutically acceptable salts, esters and prodrugs thereof, wherein n is 0, 1, 2 or 3, and when n is 1, 2, or 3, each $R_1$ independently is halogen or optionally substituted —$C_1$-$C_8$ alkyl; Preferably each $R_1$ is independently Cl, F, —$CH_3$, or —$CF_3$; and n is 0, 1, or 2.

In certain embodiments, the present invention relates to compounds of Formula (I), and pharmaceutically acceptable salts, esters and prodrugs thereof, wherein m is 0, 1, or 2, and when m is 1, or 2, each $R_2$ is independently halogen or optionally substituted —$C_1$-$C_8$ alkyl; and m is 0, 1, or 2. Preferably m is 0 or 1, and $R_2$ is F, Cl, —$CH_3$, or —$CF_3$.

In certain embodiments, the present invention relates to compounds of Formula (I), and pharmaceutically acceptable salts, esters and prodrugs thereof, wherein each $R_1$ is Cl, F, —$CH_3$, or —$CF_3$; n is 1 or 2; and m is 0.

In certain embodiments, the present invention relates to compounds of Formula (I), and pharmaceutically acceptable salts, esters and prodrugs thereof, wherein one $R_3$ is optionally substituted aryl or optionally substituted heteroaryl.

In certain embodiments, the present invention relates to compounds of Formula (I), and pharmaceutically acceptable salts, esters and prodrugs thereof, wherein one $R_3$ is optionally substituted 3- to 12-membered heterocycloalkyl, preferably $R_3$ is optionally substituted 3- to 12-membered spiro bicyclic heterocycloalkyl.

In certain embodiments, the present invention relates to compounds of Formula (I), and pharmaceutically acceptable salts, esters and prodrugs thereof, wherein one $R_3$ is —$NR_{13}R_{14}$, wherein $R_{13}$ and $R_{14}$ are previously defined.

In certain embodiments, the present invention relates to compounds of Formula (I), and pharmaceutically acceptable salts, esters and prodrugs thereof, wherein one $R_3$ is —$NR_{13}R_{14}$, wherein $R_{13}$ and $R_{14}$ are taken together with the nitrogen atom to which they are attached to form an an optionally substituted 3- to 10- or 3- to 12-membered heterocyclic, preferably the said heterocyclic is spiro heterocyclic.

In one embodiment, the present invention relates to compounds of Formula (I), or a pharmaceutically acceptable salt thereof, v is not 0 and one $R_3$ is derived from one of the groups below by removal of one hydrogen atom, wherein each of these groups is optionally substituted:

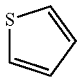
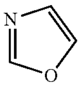
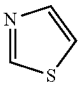
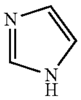
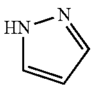

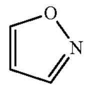
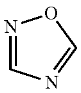
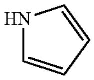
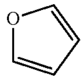
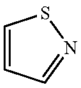

-continued
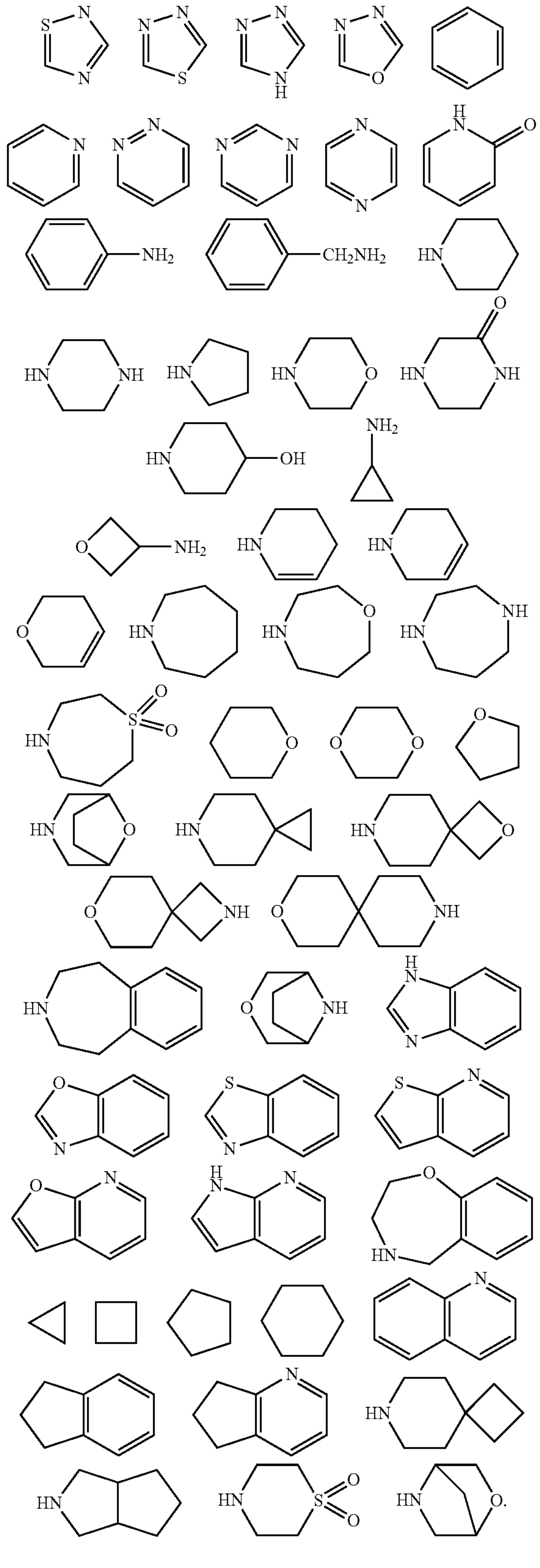
In one embodiment, the present invention relates to compounds of Formula (I), or a pharmaceutically acceptable salt thereof, wherein v is not 0 and one $R_3$ is selected from the groups shown below, each of which can be optionally substituted:
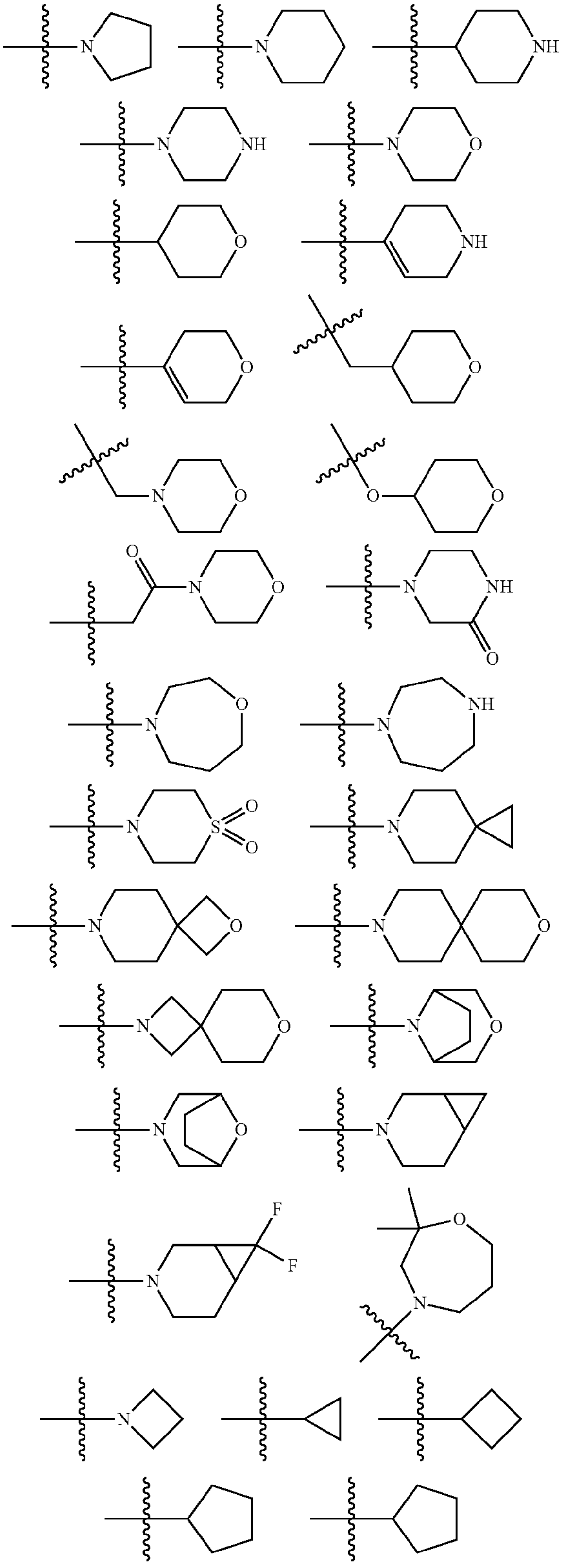

-continued
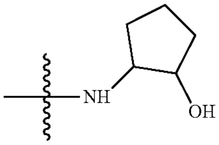
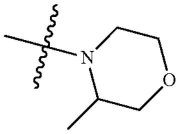
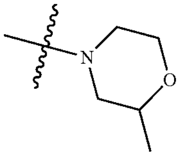
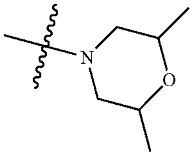
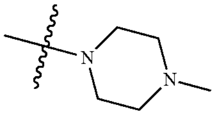
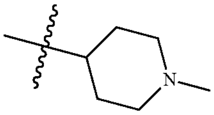
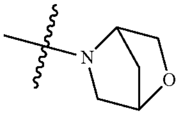
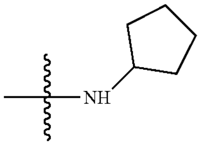
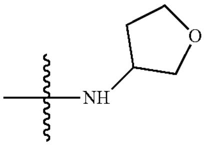
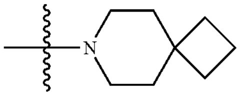
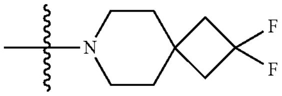
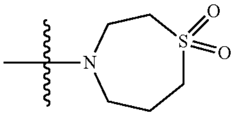
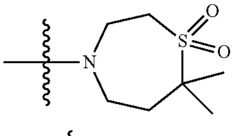
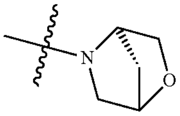
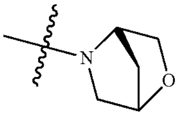
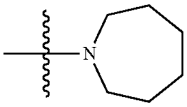
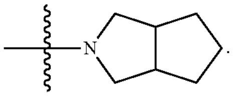
In one embodiment, the present invention relates to compounds of Formula (I), or a pharmaceutically acceptable salt thereof, wherein v is not 0 and one $R_3$ is selected from the groups shown below, each of which can be optionally substituted:
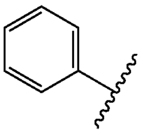
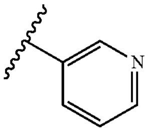
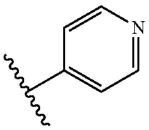
-continued
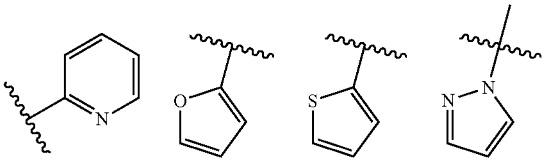
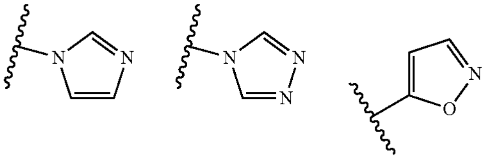
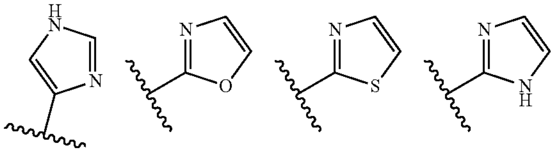
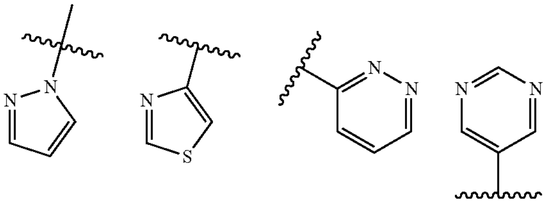
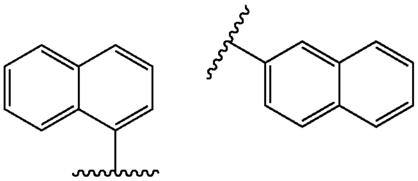
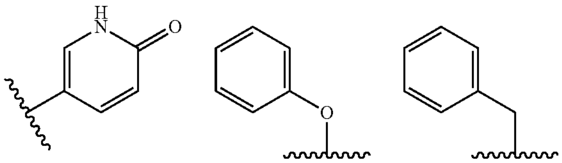
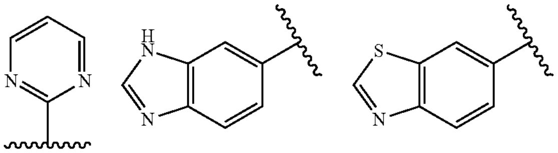
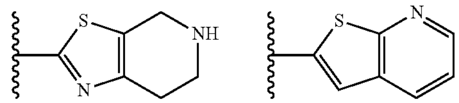
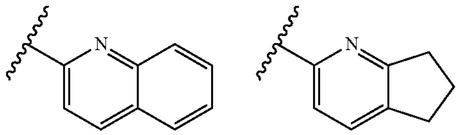
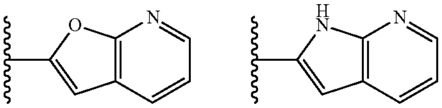

-continued

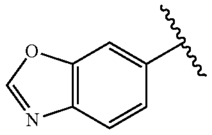

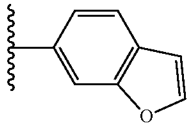

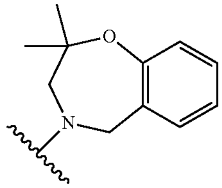

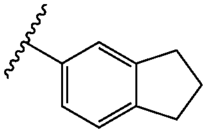

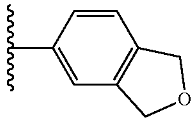

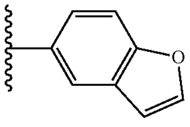

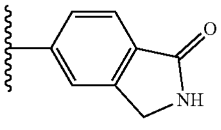

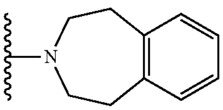

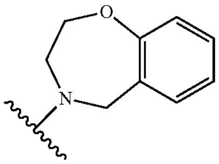

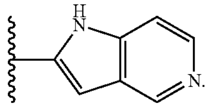

In certain embodiments, v is 0 to 3, 0 to 2, 1 or 0. More preferably, v is 1 or 2.

In another embodiment the invention provides a compound represented by Formula (IIa), or (IIb), or (IIc), or a pharmaceutically acceptable salt, ester or prodrug thereof:

(IIa)

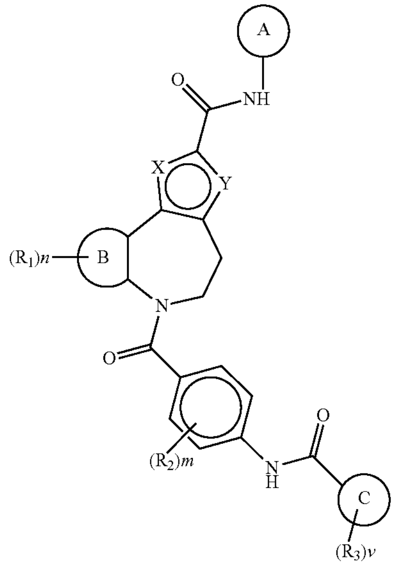

-continued (IIb)

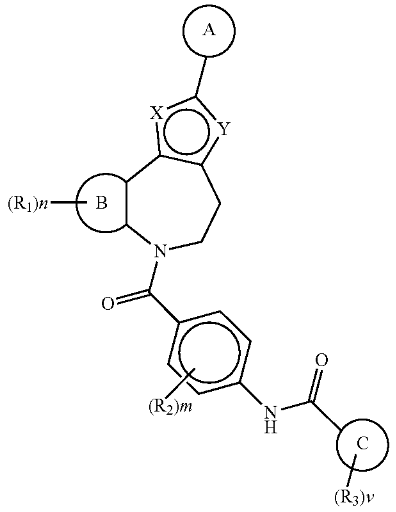

(IIc)

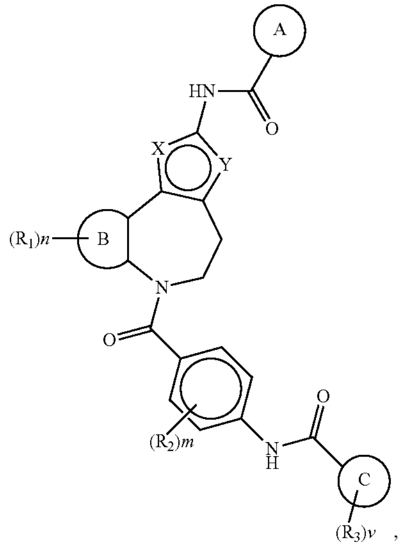

, wherein Ⓐ, Ⓑ, Ⓒ, X, Y, $R_1$, $R_2$, $R_3$, n, m, and v are as previously defined.

In another embodiment invention provides a compound represented by Formula (IIa), or (IIb), or (IIc), or a pharmaceutically acceptable salt, esters and prodrugs thereof, wherein each $R_1$ is independently halogen or optionally substituted —$C_1$-$C_8$ alkyl, and n is 1, 2 or 3. Preferably, each $R_1$ is F or —$CH_3$, and n is 1 or 2.

In another embodiment invention provides a compound represented by Formula (IIa), or (IIb), or (IIc), or a pharmaceutically acceptable salt, ester or prodrug thereof, wherein n is 0 and m is 0.

In another embodiment the invention provides a compound represented by one of Formulae (IIa-1)~(IIa-4), (IIb-1)~(IIb-4), (IIc-1)~(IIc-4), or a pharmaceutically acceptable salt, ester or prodrug thereof:

(IIa-1)
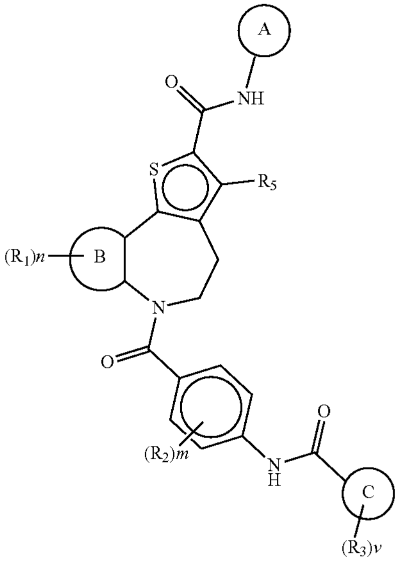
(IIa-2)
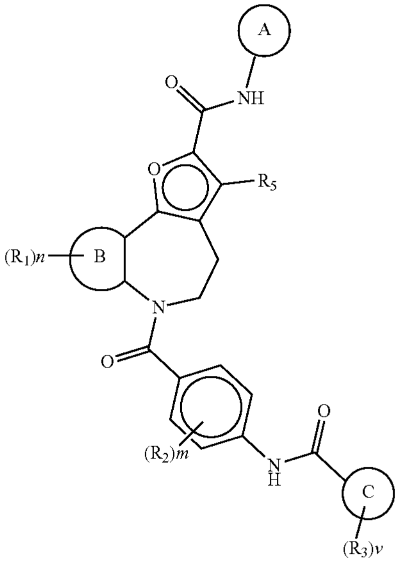
-continued
(IIa-3)
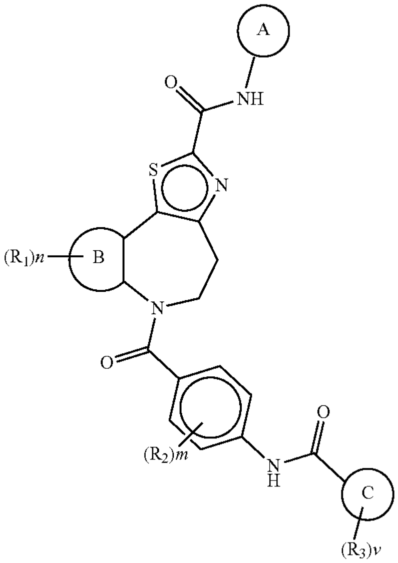
(IIa-4)
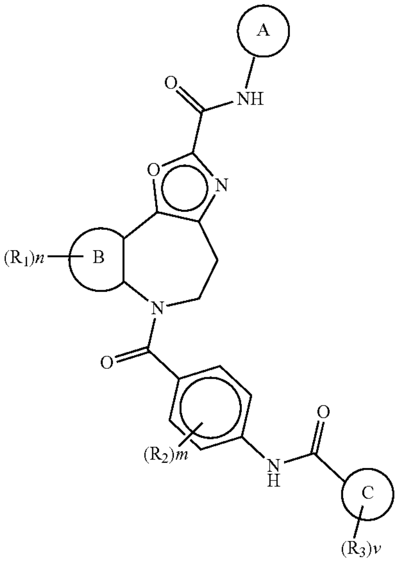
(IIb-1)
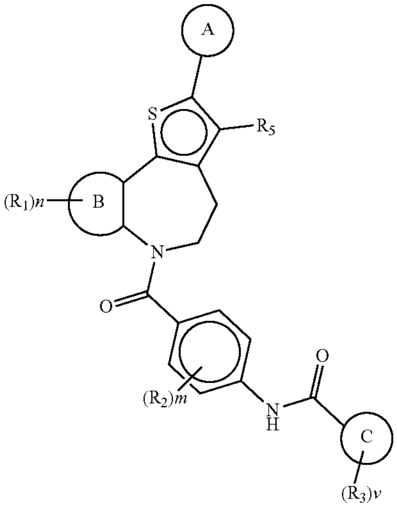

-continued
(IIb-2)
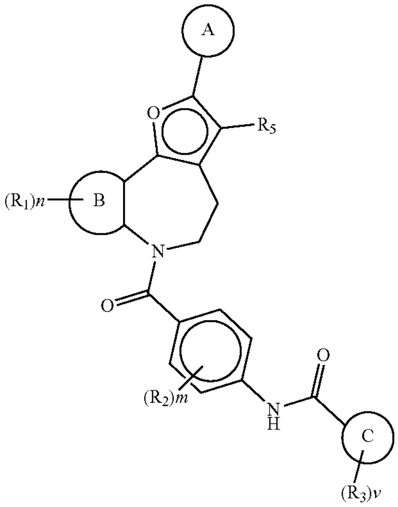
(IIb-3)
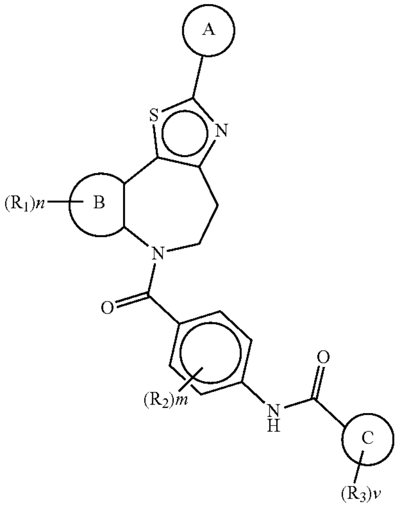
(IIb-4)
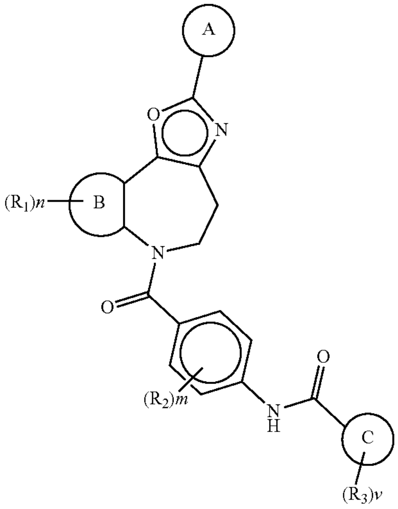
-continued
(IIc-1)
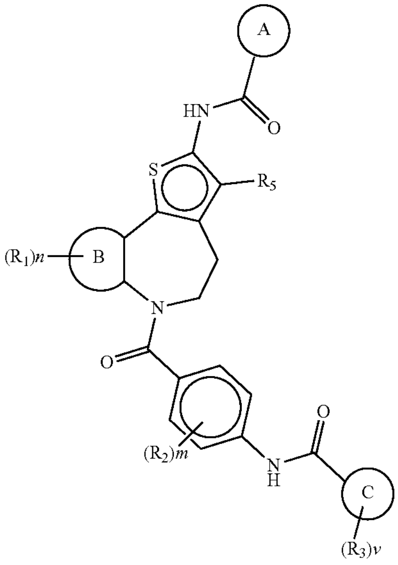
(IIc-2)
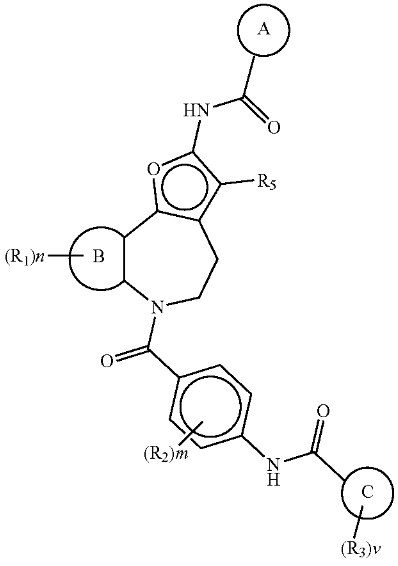

-continued
(IIc-3)
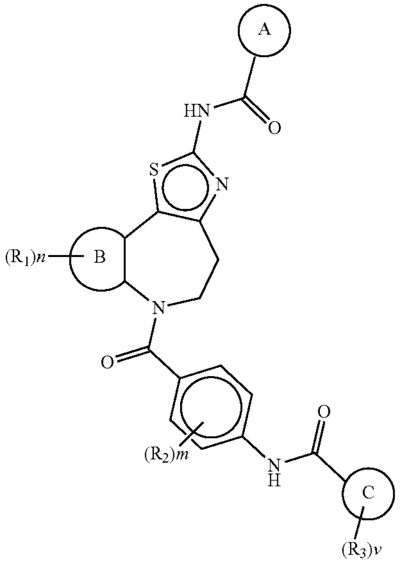
(IIc-4)
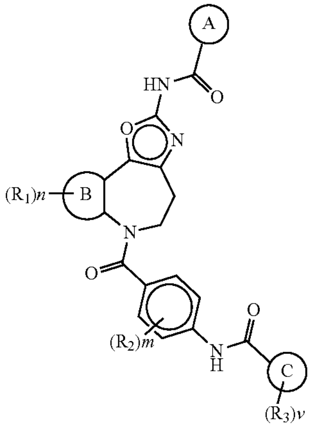
wherein Ⓐ, Ⓑ, Ⓒ, $R_1$, $R_2$, $R_3$, $R_5$, n, m, and v are as previously defined. Preferably $R_5$ is hydrogen, or —F.
In another embodiment the invention provides a compound represented by one of Formulae (IIIa)~(IIId), or a pharmaceutically acceptable salt, ester or prodrug thereof,
(IIIa)
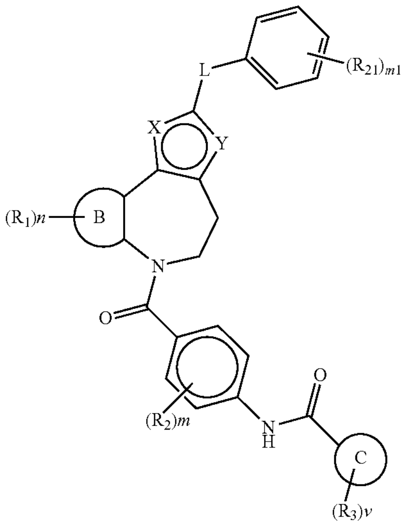
(IIIb)
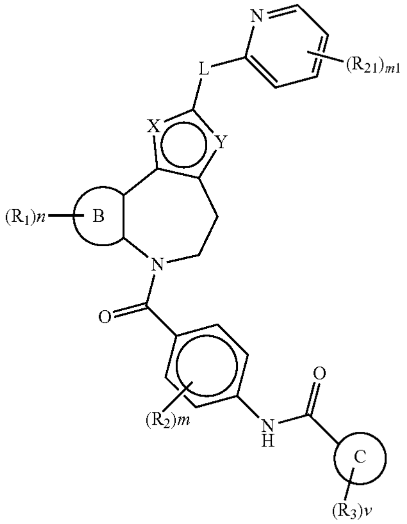
(IIIc)
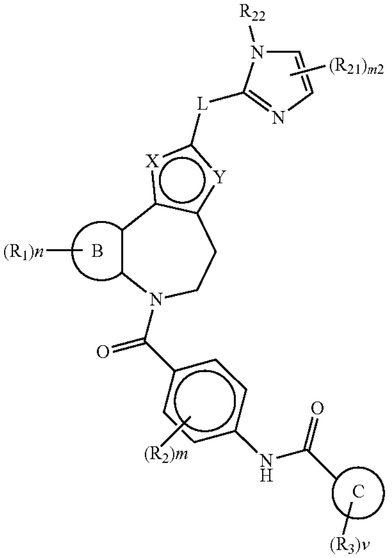

-continued (IIId)

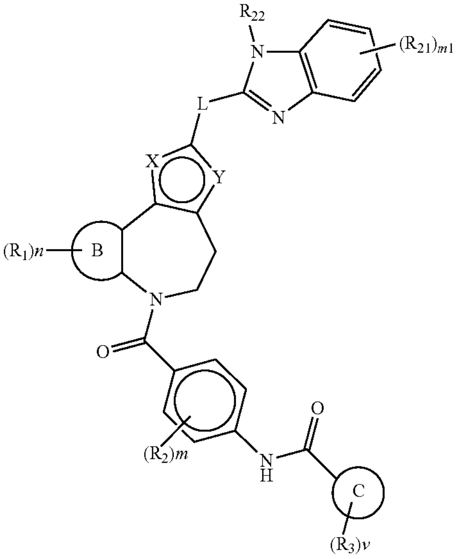

wherein Ⓑ, Ⓒ, X, Y, L, $R_1$, $R_2$, $R_3$, n, m, and v are as previously defined; m1 is 0, 1, 2, 3 or 4; m2 is 0, 1 or 2; each $R_{22}$ is independently selected from hydrogen and —$CH_3$; and each $R_{21}$ independently selected from halogen, —$NH_2$, optionally substituted —$C_1$-$C_3$ alkyl, and optionally substituted —$C_1$-$C_3$ alkoxy. Preferably each $R_{21}$ is independently selected from —F, —Cl, —$NH_2$, and optionally substituted —$CH_3$.

In another embodiment of the invention is a compound represented by one of Formulae (IIIa) (IIId), or a pharmaceutically acceptable salt, ester or prodrug thereof, wherein $R_1$ is halogen, or optionally substituted —$C_1$-$C_8$ alkyl; n is 1, 2 or 3; preferably $R_1$ is —F, or —$CH_3$, and n is 1, or 2.

In another embodiment the invention provides a compound represented by one of Formulae (IIIa-1)~(IIId-1), or (IIIa-2)~(IIId-2), or a pharmaceutically acceptable salt, ester or prodrug thereof:

(IIIa-1)

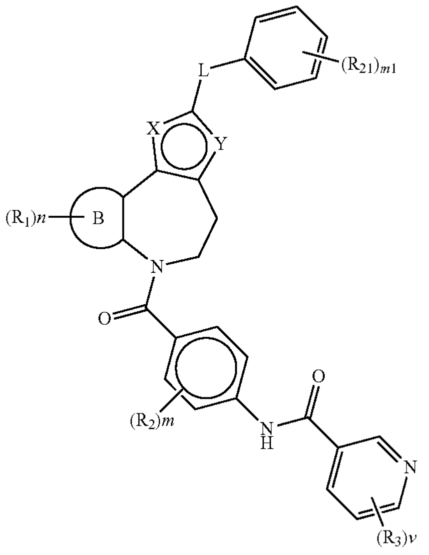

-continued (IIIb-1)

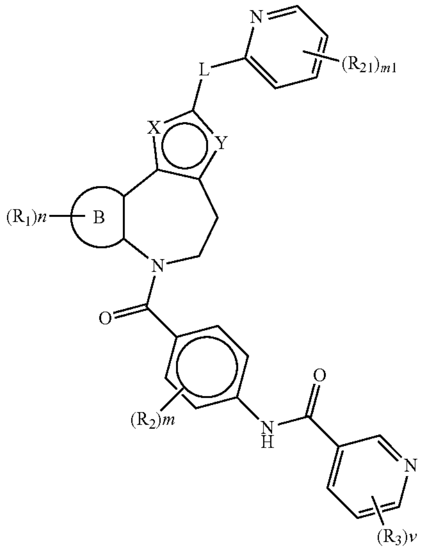

(IIIc-1)

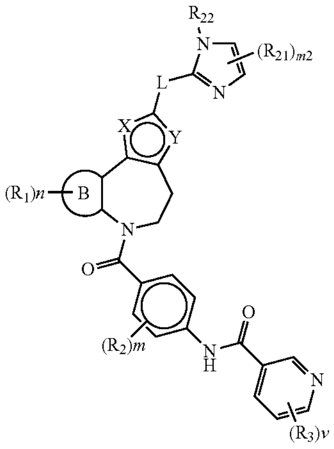

(IIId-1)

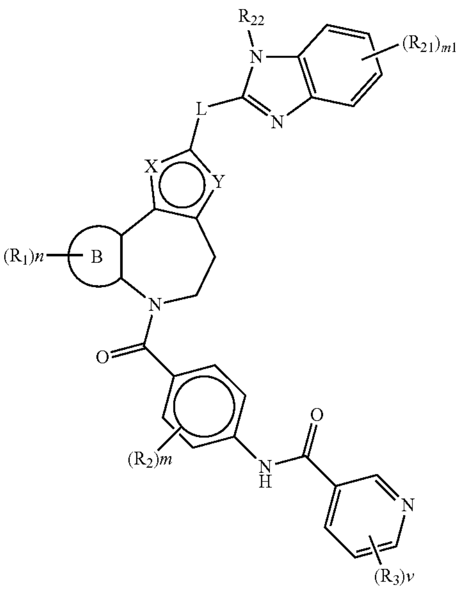

-continued (IIIa-2)

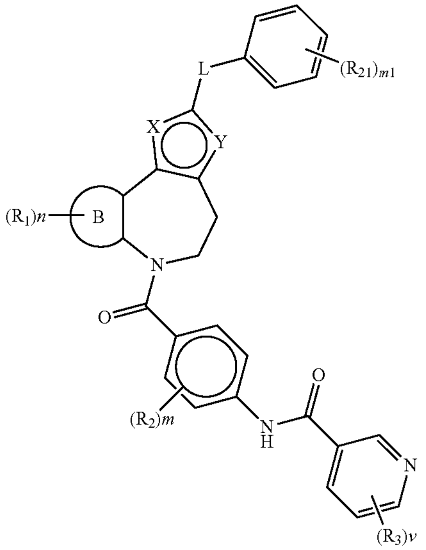

(IIIb-2)

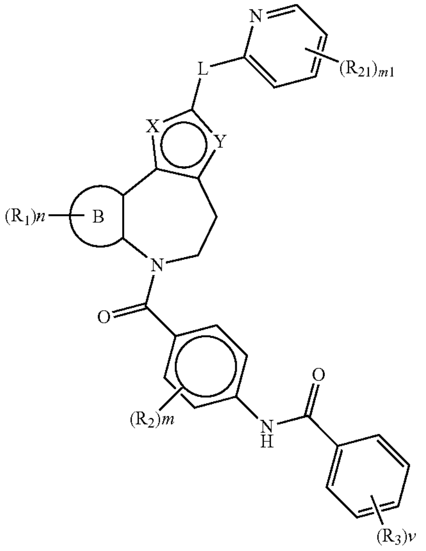

(IIIc-2)

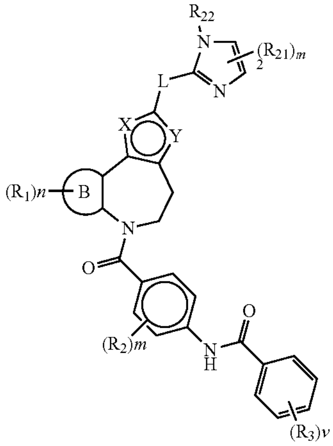

-continued (IIId-2)

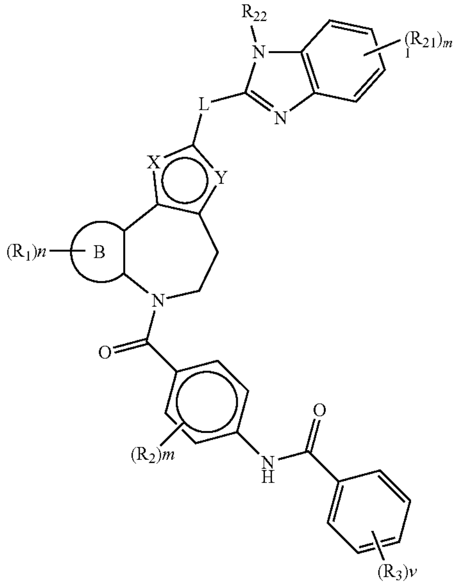

wherein Ⓑ, X, Y, L, $R_1$, $R_2$, $R_3$, $R_{21}$, $R_{22}$, m1, m2, n, m, and v are as previously defined. Preferably each $R_{21}$ is independently selected from —F, —Cl, —$NH_2$, and optionally substituted —$CH_3$; more preferably each $R_1$ is halogen or optionally substituted —$C_1$-$C_8$ alkyl; n is 1, 2 or 3; and each $R_{21}$ is independently selected from —F, —Cl, —$NH_2$, and optionally substituted —$CH_3$.

In another embodiment the invention provides a compound represented by one of Formulae (IIIa-3)~(IIId-3), or (IIIa-4)~(IIId-4), or a pharmaceutically acceptable salt, ester or prodrug thereof:

(IIIa-3)

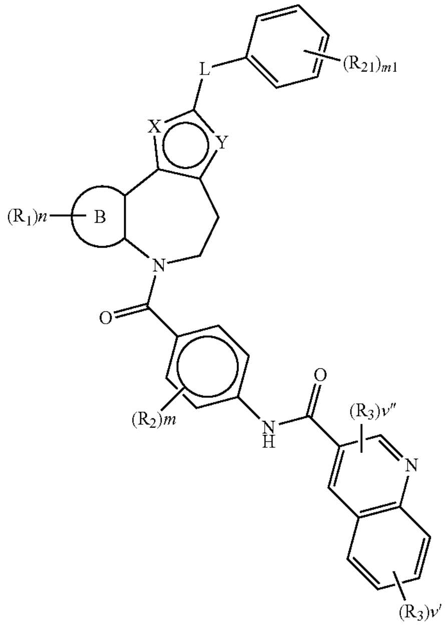

-continued
(IIIb-3)
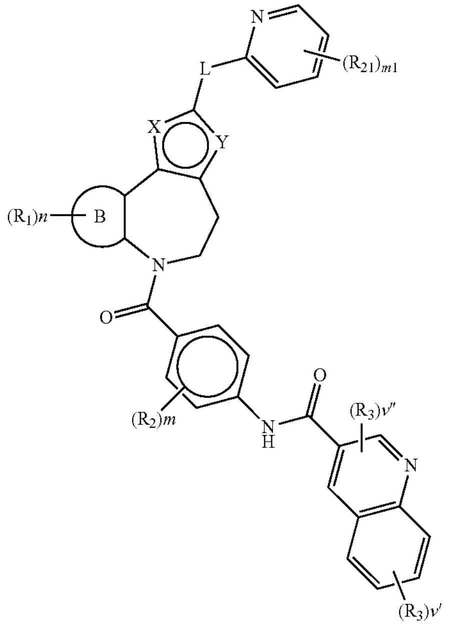
(IIIc-3)
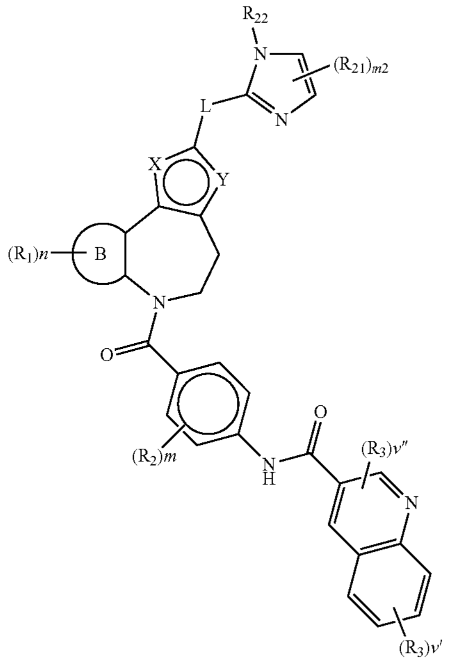
-continued
(IIId-3)
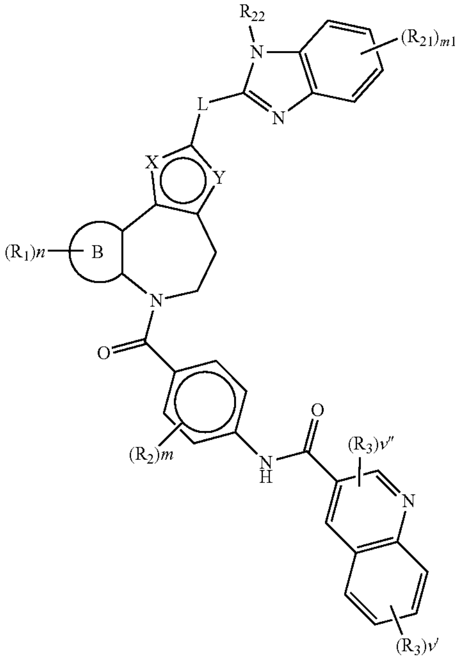
(IIIa-4)
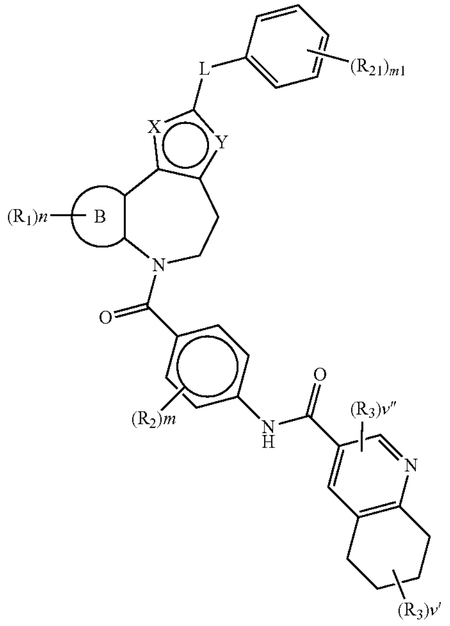

-continued (IIIb-4)

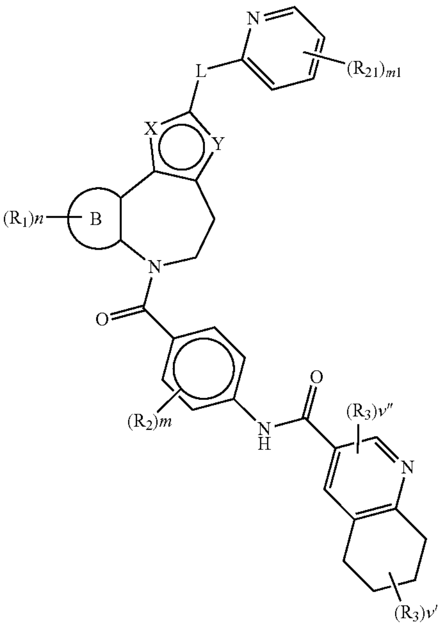

(IIIc-4)

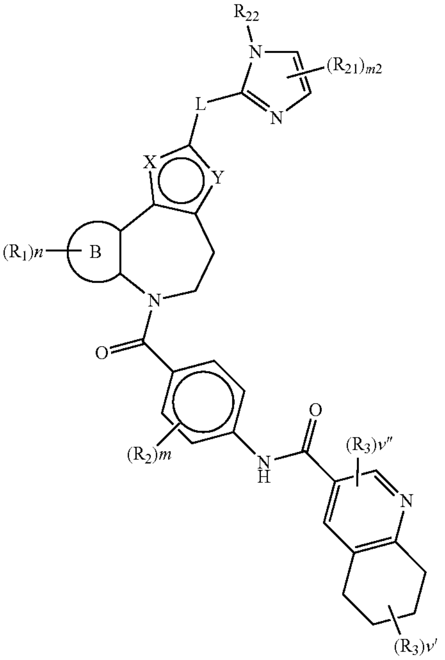

-continued (IIId-4)

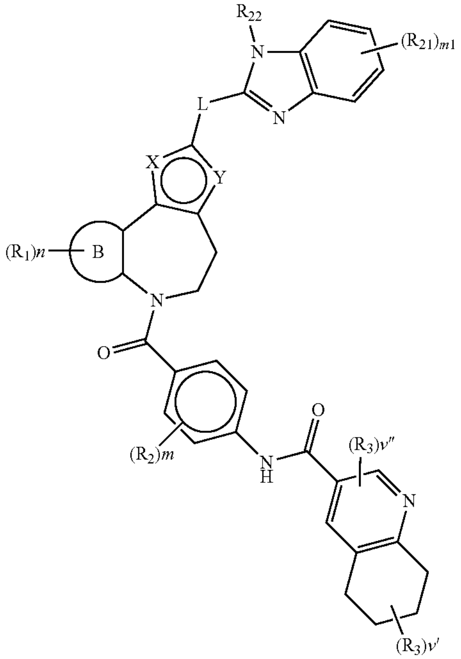

wherein Ⓑ, X, Y, L, $R_1$, $R_2$, $R_3$, $R_{21}$, $R_{22}$, m1, m2, n, and m, are as previously defined; v' is 0, 1, 2, or 3; and v" is 0, 1, or 2; provided that the sum of v' and v" is 3 or less. Preferably each $R_{21}$ is independently selected from —F, —Cl, —$NH_2$, and optionally substituted-$CH_3$; more preferably each $R_1$ is halogen or optionally substituted —$C_1$-$C_8$ alkyl; n is 1, 2 or 3; and each $R_{21}$ is independently selected from —F, —Cl, —$NH_2$, and optionally substituted —$CH_3$.

In another embodiment the invention provides a compound represented by one of Formulae (IVa-1)~(IVd-1), (IVa-2)~(IVd-2), (IVa-3)~(IVd-3), (IVa-4)~(IVd-4), and a pharmaceutically acceptable salt, ester or prodrug thereof:

(IVa-1)

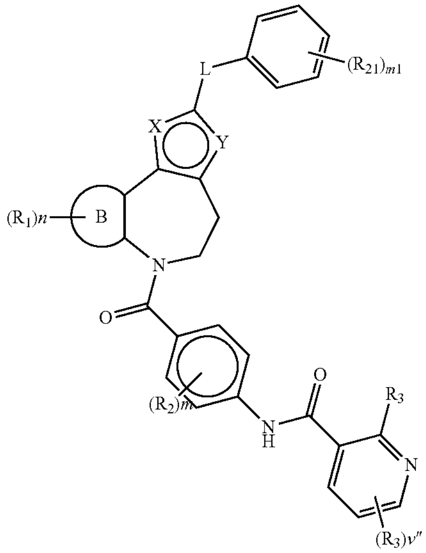

-continued
(IVb-1)
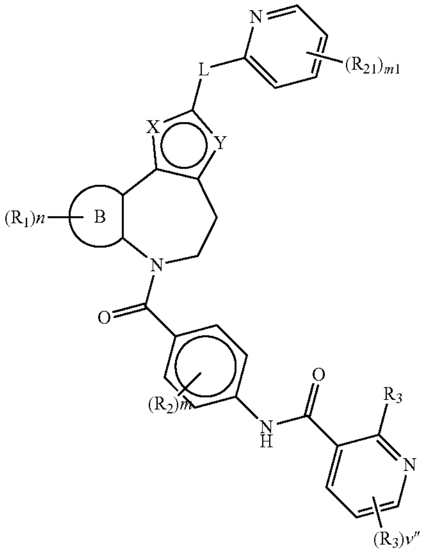
(IVc-1)
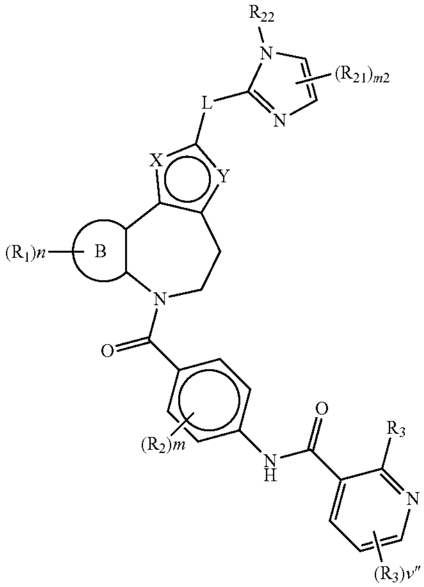
-continued
(IVd-1)
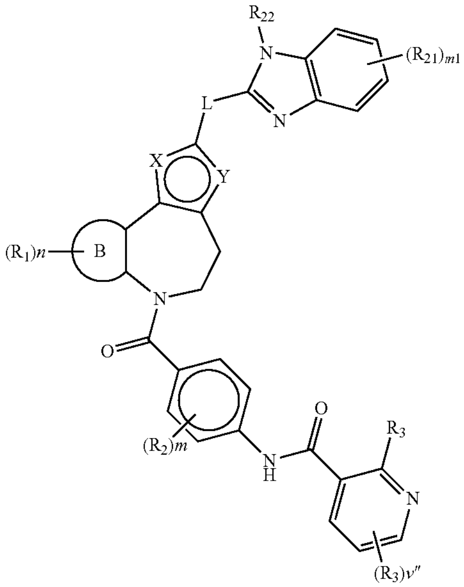
(IVa-2)
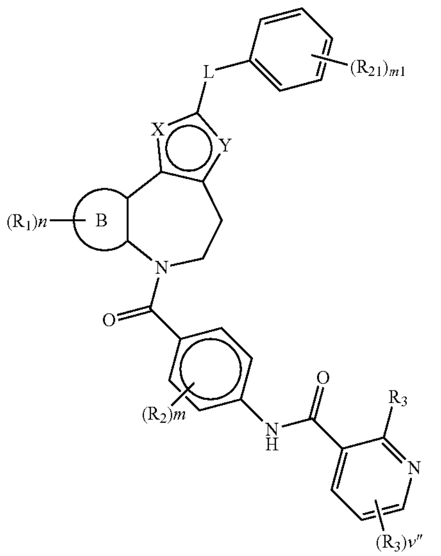

-continued
(IVb-2)
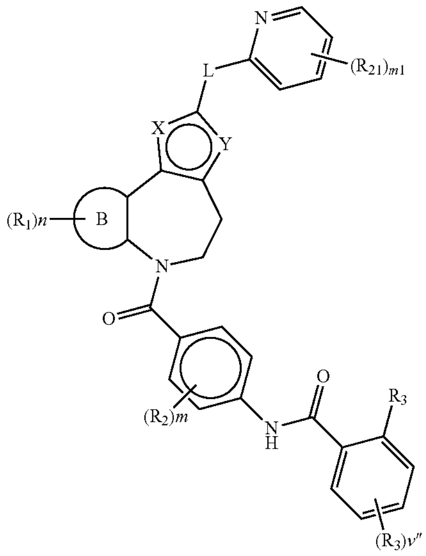
(IVd-2)
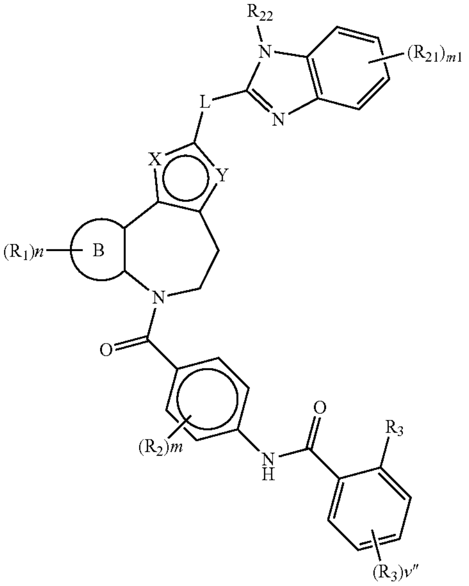
(IVc-2)
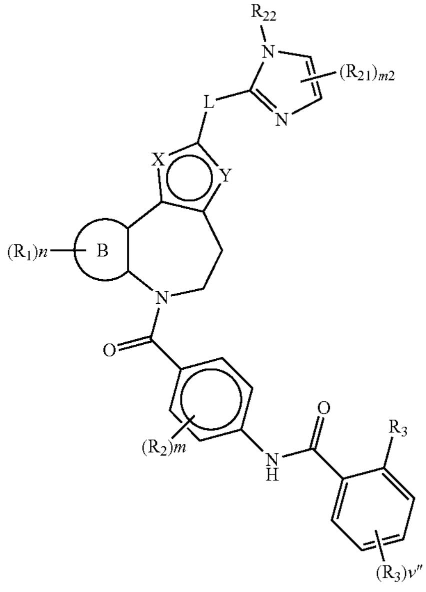
(IVa-3)
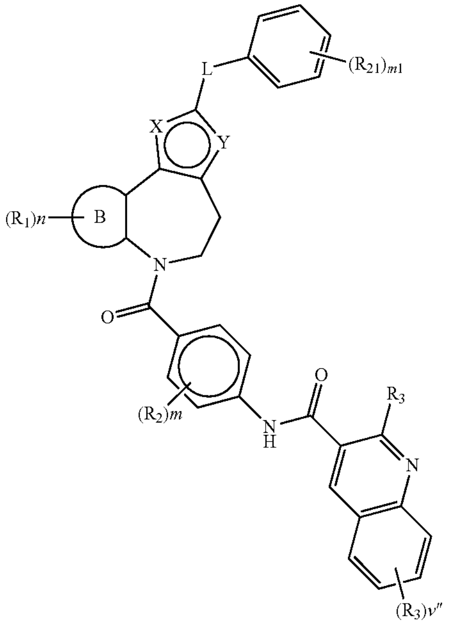

-continued
(IVb-3)
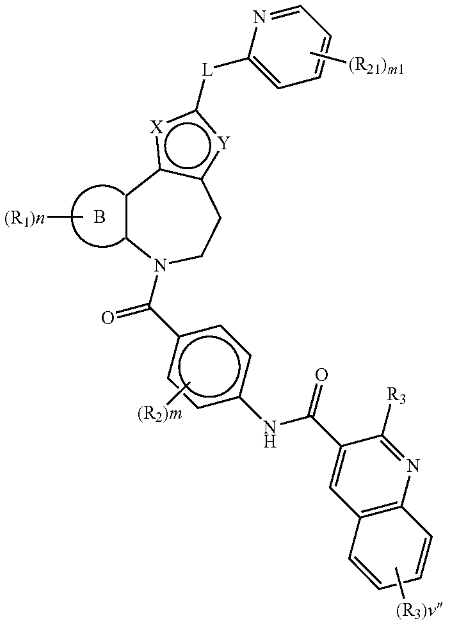
(IVd-3)
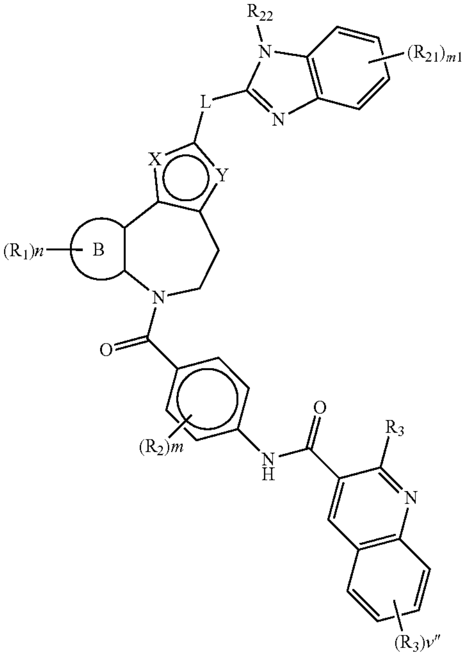
(IVc-3)
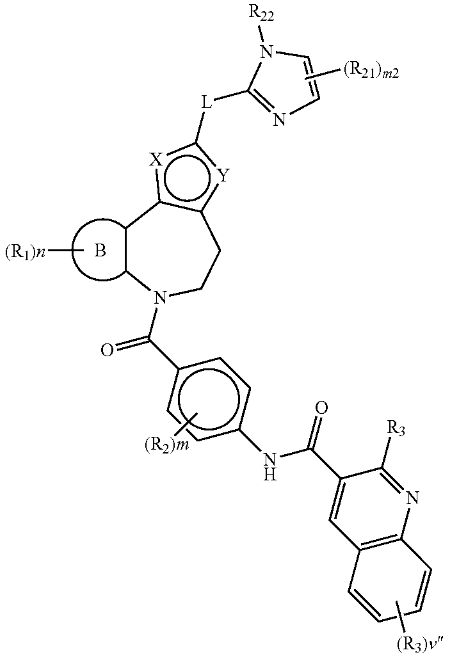
(IVa-4)
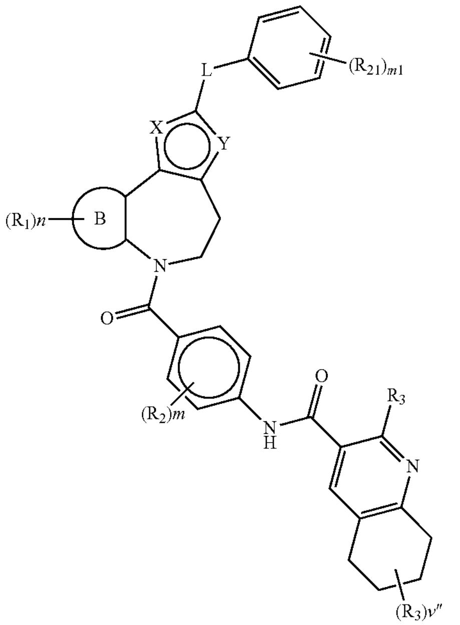

-continued (IVb-4)

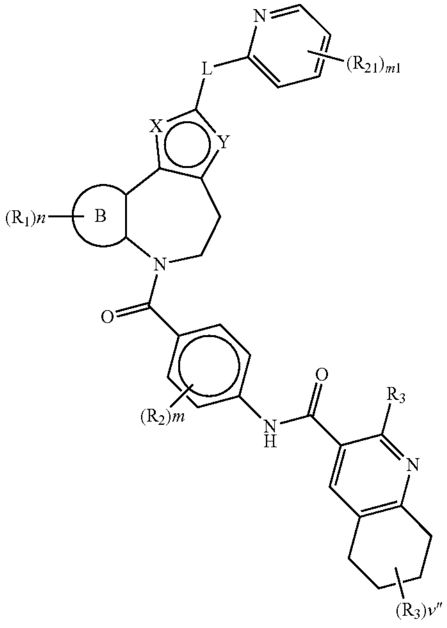

(IVc-4)

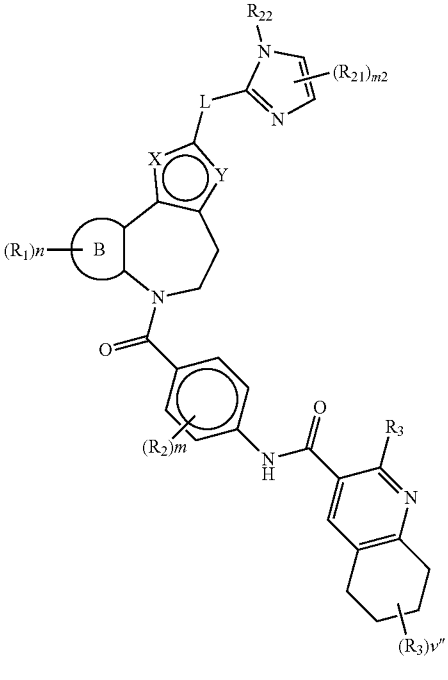

-continued (IVd-4)

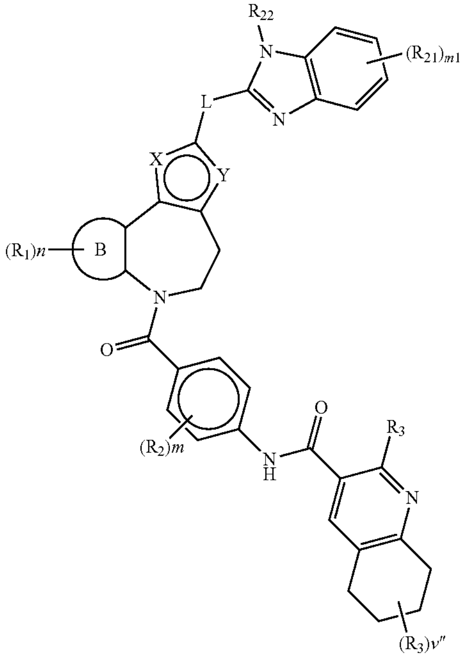

wherein Ⓑ, X, Y, L, $R_1$, $R_2$, $R_3$, $R_{21}$, $R_{22}$, m1, m2, n, m and v" are as previously defined.

Preferably each $R_{21}$ is independently selected from —F, —Cl, —$NH_2$, and optionally substituted —$CH_3$, more preferably each $R_1$ is halogen or optionally substituted —$C_1$-$C_8$ alkyl; n is 1, 2 or 3; and each $R_{21}$ is independently selected from —F, —Cl, —$NH_2$, and optionally substituted —$CH_3$.

In another embodiment of the invention is a compound represented by one of Formulae (IVa-1)~(IVd-1), (IVa-2)~(IVd-2), (IVa-3)~(IVd-3), and (IVa-4)~(IVd-4), or a pharmaceutically acceptable salt, ester or prodrug thereof, wherein the $R_3$ which is fixed is selected from the groups shown below, each of which can be optionally substituted:

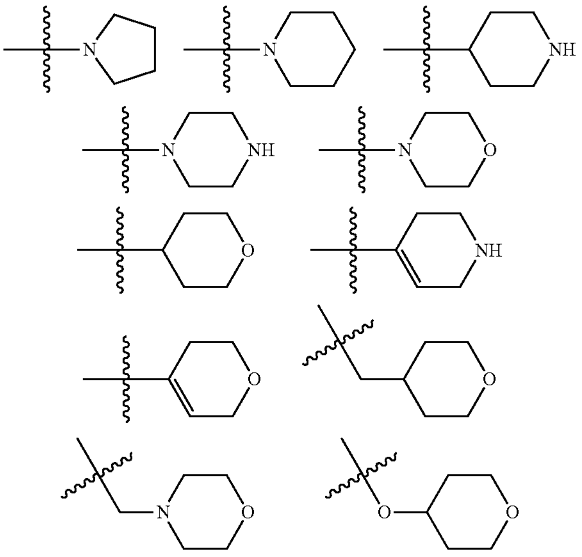

-continued
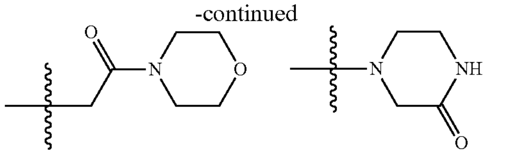
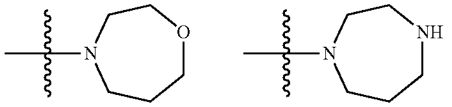
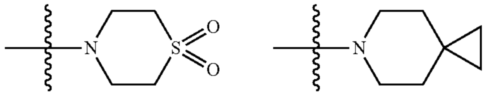
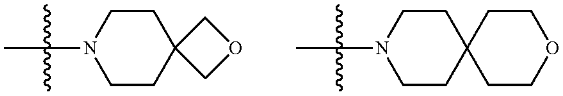
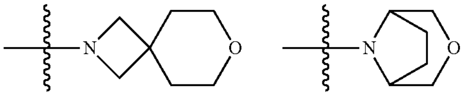
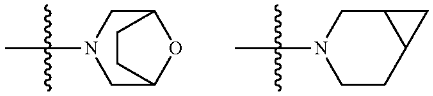
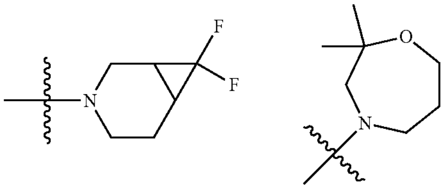
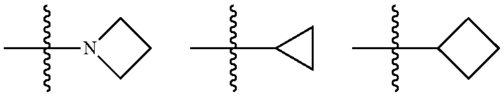
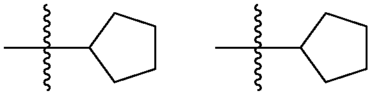
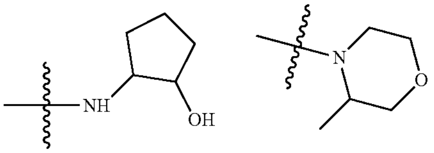
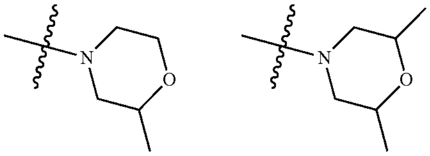
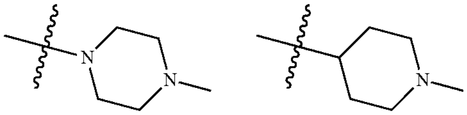
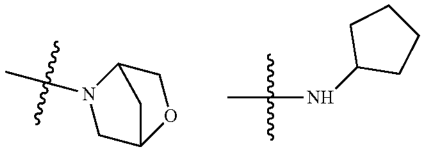
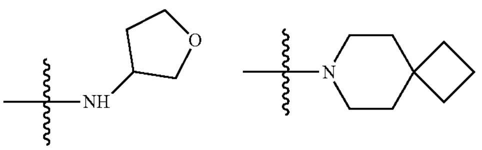
-continued
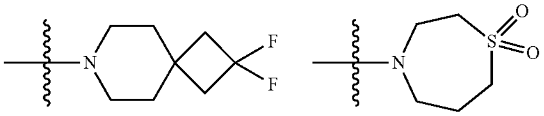
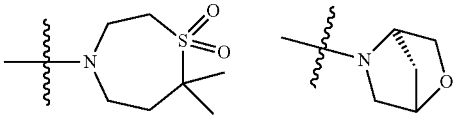
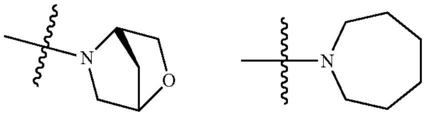
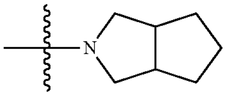
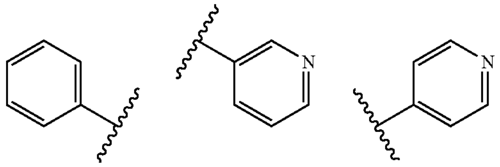
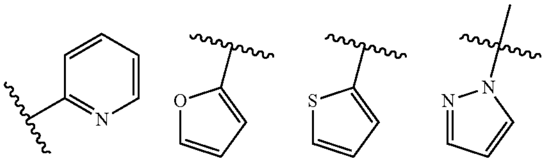
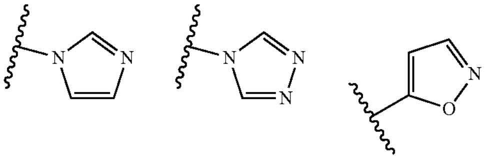
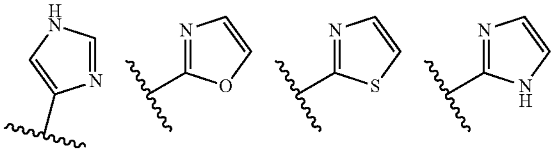
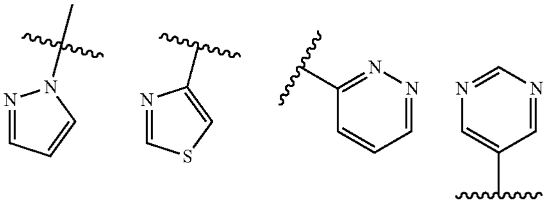
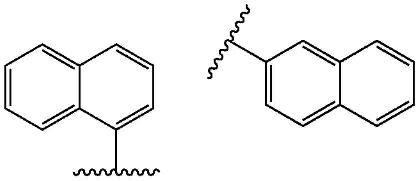
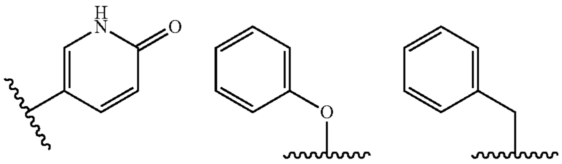

-continued
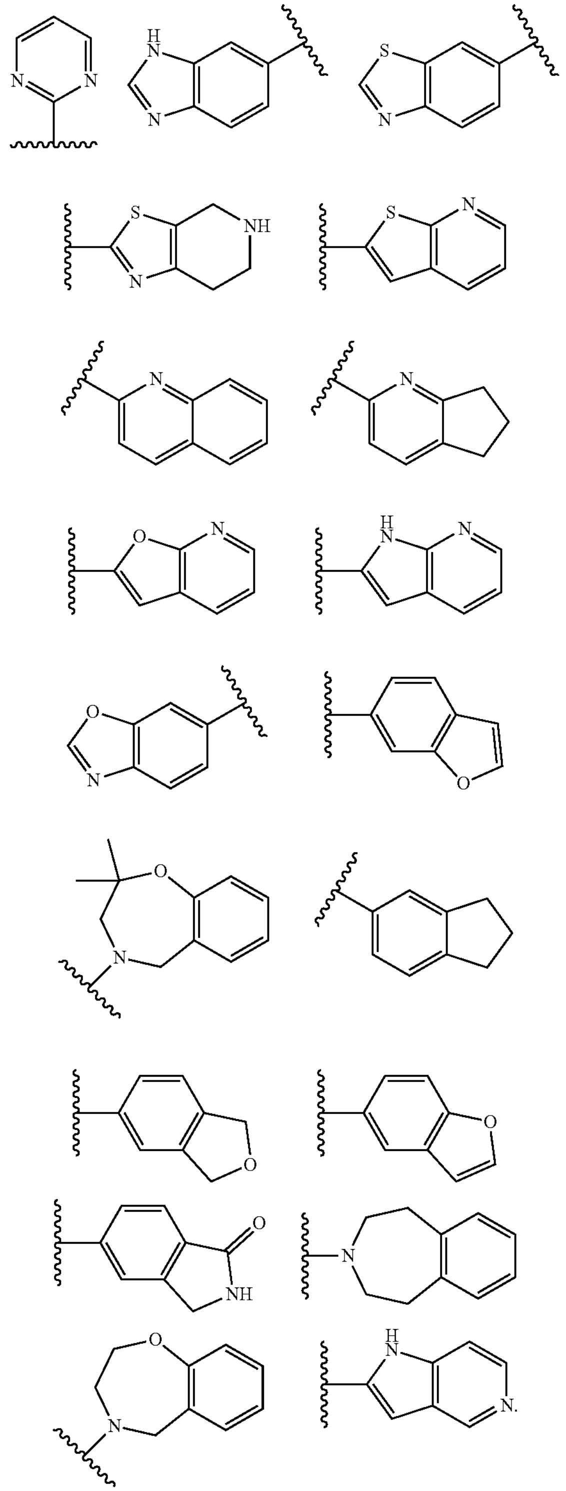
In certain embodiments of the compounds of Formulae (IVa-1)~(IVd-1), (IVa-2)~(IVd-2), (IVa-3)~(IVd-3), (IVa-4)~(IVd-4), v" is 0 or 1. When v" is 1, the $R_3$ group which is not fixed is preferably methyl.
In another embodiment of the invention is a compound represented by one of Formulae (V-1)~(V-7), or a pharmaceutically acceptable salt, ester or prodrug thereof,
(V-1)
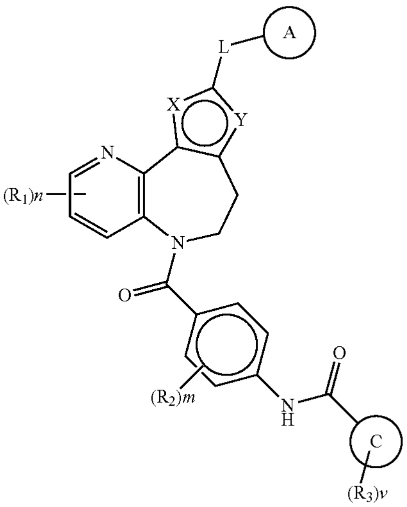
(V-2)
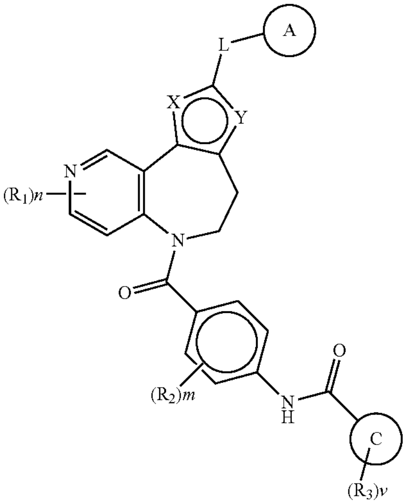
(V-3)
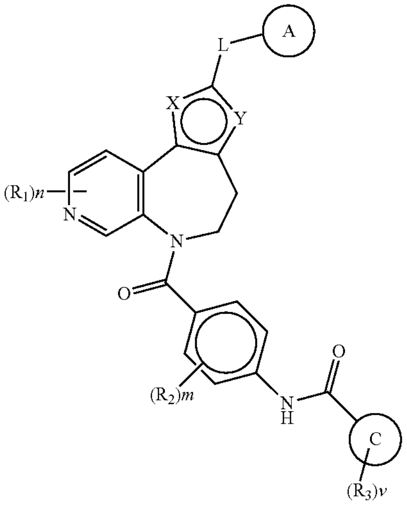

-continued
(V-4)
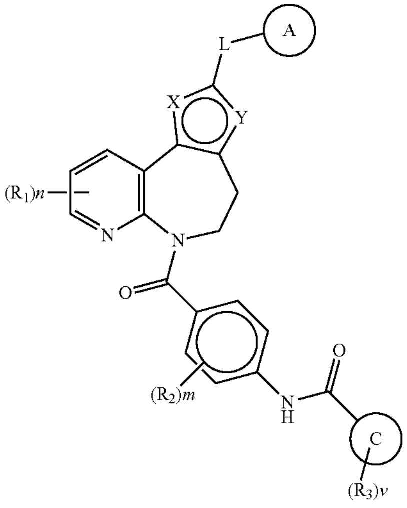
(V-5)
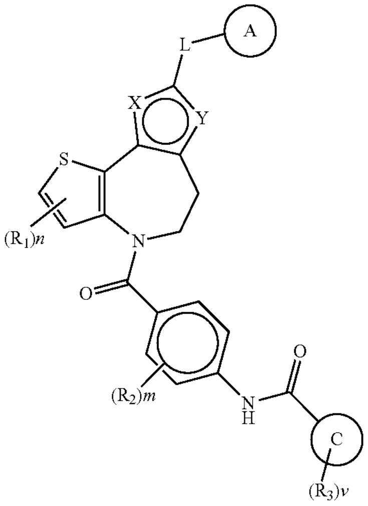
(V-6)
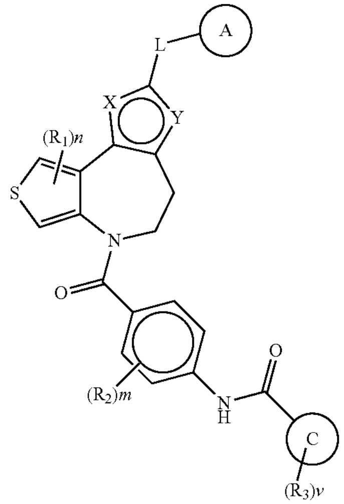
-continued
(V-7)
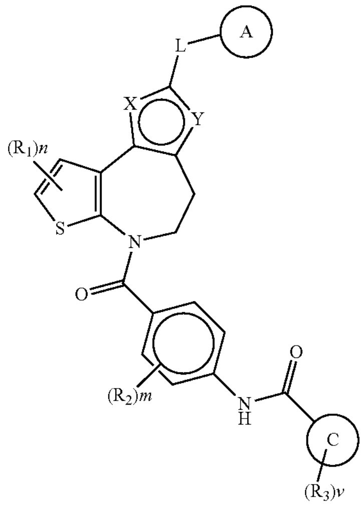
wherein Ⓐ, Ⓒ, X, Y, L, $R_1$, $R_2$, $R_3$, n, m, and v are as previously defined. Preferably $R_1$ is halogen, or optionally substituted —$C_1$-$C_8$ alkyl; n is 1, 2 or 3; more preferably $R_1$ is —F, or —$CH_3$, and n is 1, or 2.
In another embodiment of the invention is a compound represented by one of Formulae (VI-1)~(VI-7), or a pharmaceutically acceptable salt, ester or prodrug thereof:
(VI-1)
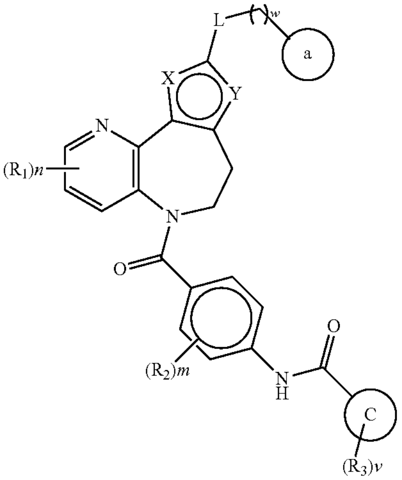

-continued
(VI-2)
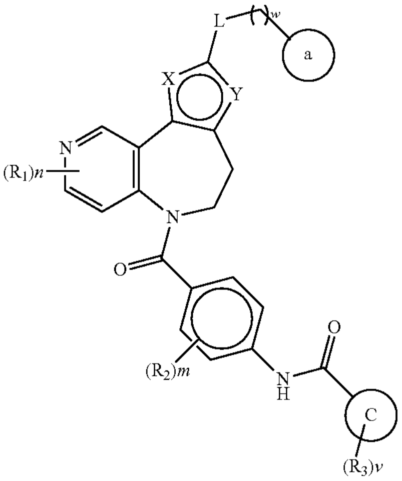
(VI-3)
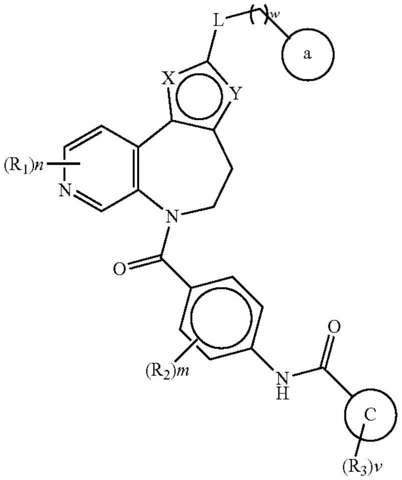
(VI-4)
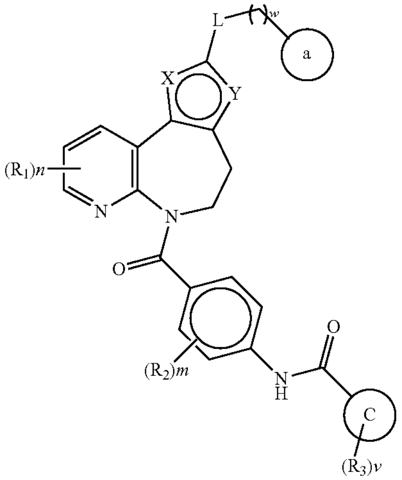
-continued
(VI-5)
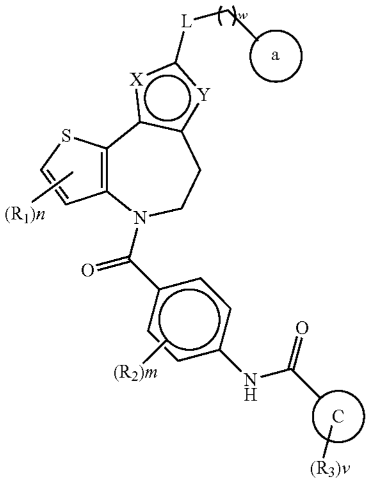
(VI-6)
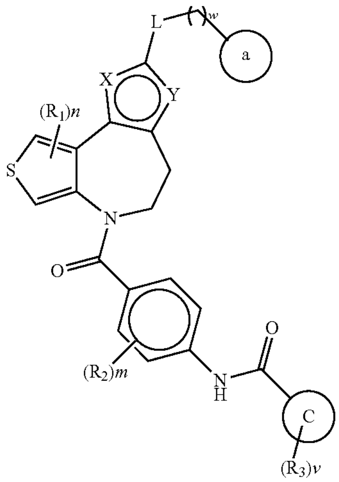
(VI-7)
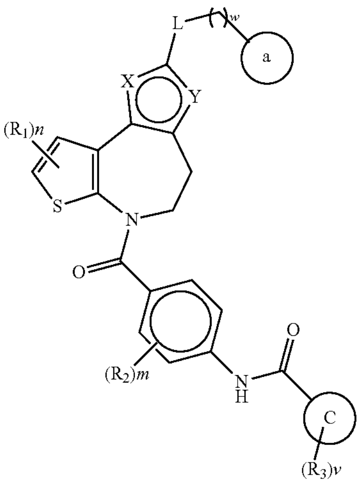
wherein Ⓒ, X, Y, L, $R_1$, $R_2$, $R_3$, n, m, and v are as previously defined; w is 1, 2 or 3; ⓐ is one of the following by removal of a hydrogen atom:

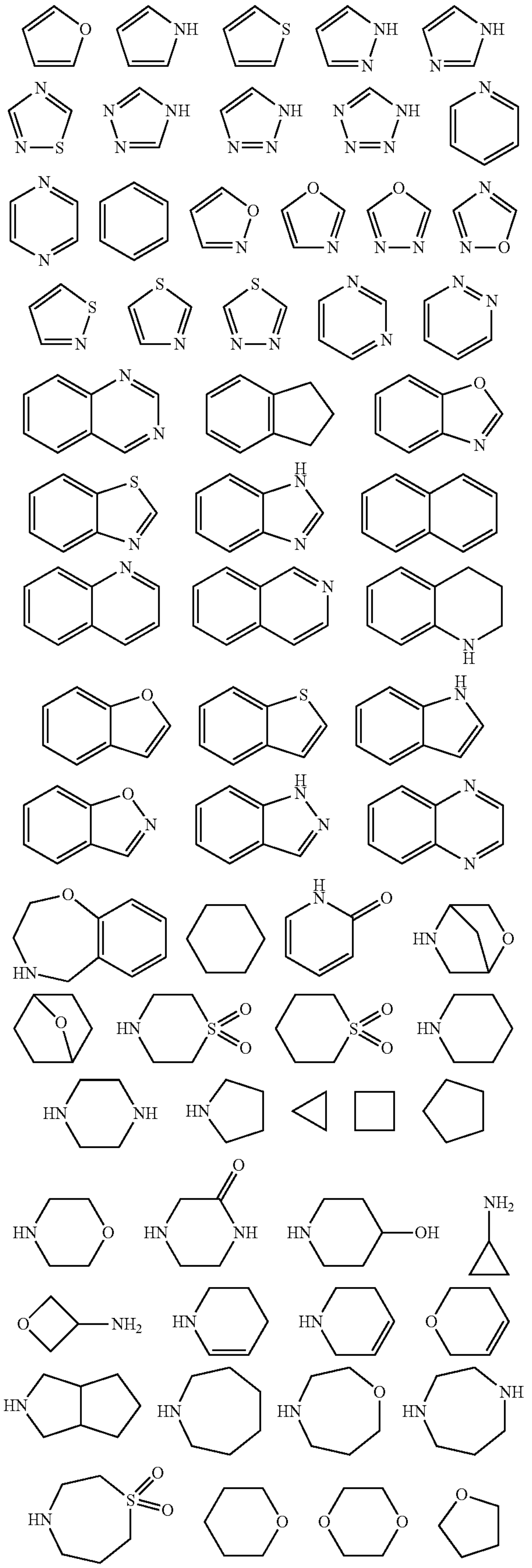

-continued

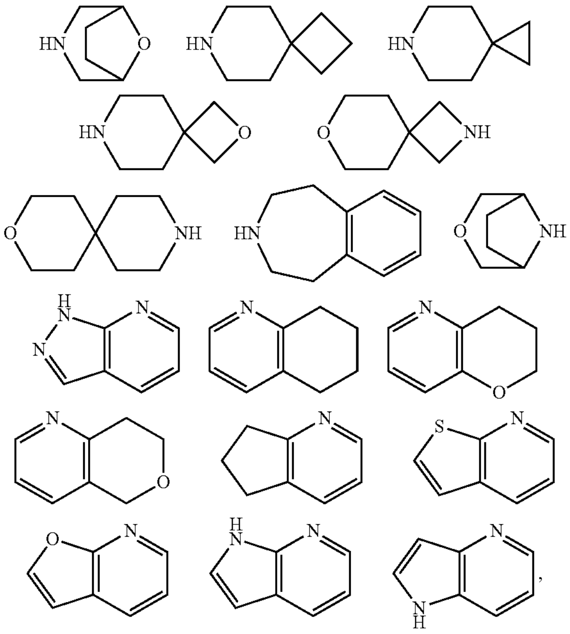

wherein each of the above is optionally substituted. Preferably, when present, the substituents are independently selected from, but not limited to, —CN, —F, —Cl, $—CH_3$, $—CF_3$, $—OCH_3$, and $—OCF_3$.

In another embodiment of the invention is a compound represented by one of Formulae (VI-1)~(VI-7), or a pharmaceutically acceptable salt, ester or prodrug thereof, wherein ⓐ, Ⓒ, X, Y, L, $R_2$, $R_3$, m, and v are as previously defined; $R_1$ is halogen, or optionally substituted $—C_1$-$C_8$ alkyl; n is 1, 2 or 3; w is 1 or 2; preferably $R_1$ is —F, or $—CH_3$; n is 1, or 2; and w is 1.

In another embodiment the invention provides a compound represented by one of Formulae (VII-1)~(VII-4), or d a pharmaceutically acceptable salt, ester or prodrug thereof:

(VII-1)

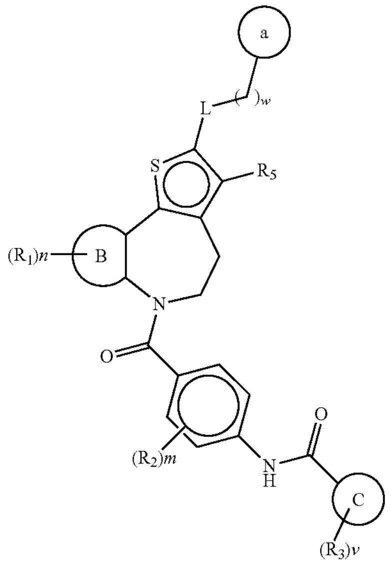

-continued
(VII-2)
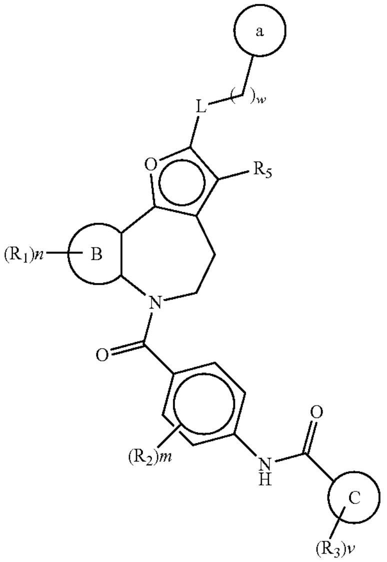
(VII-3)
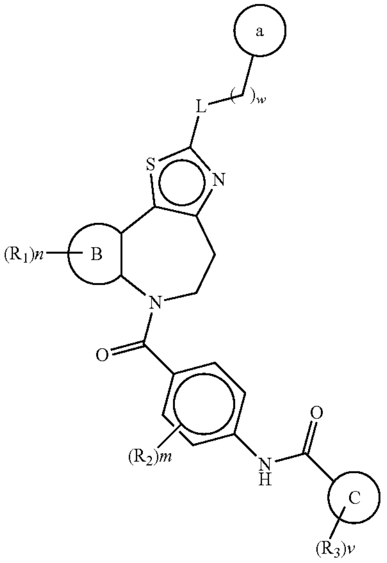
-continued
(VII-4)
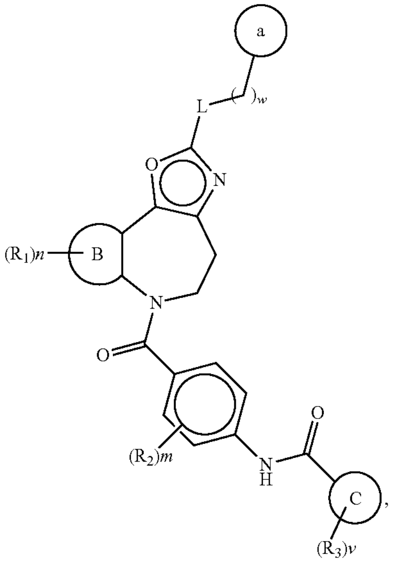
wherein ⓐ, Ⓑ, ©, L, $R_1$, $R_2$, $R_3$, $R_5$, n, m, v and w are as previously defined.
In another embodiment the invention provides a compound represented by one of Formulae (VIII-1)~(VIII-4), or d a pharmaceutically acceptable salt, ester or prodrug thereof:
(VIII-1)
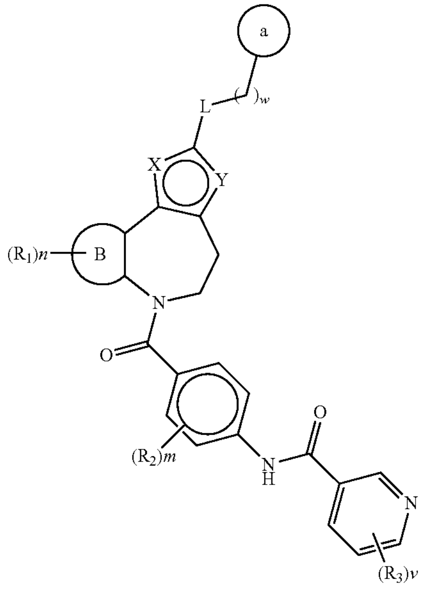

-continued
(VIII-2)
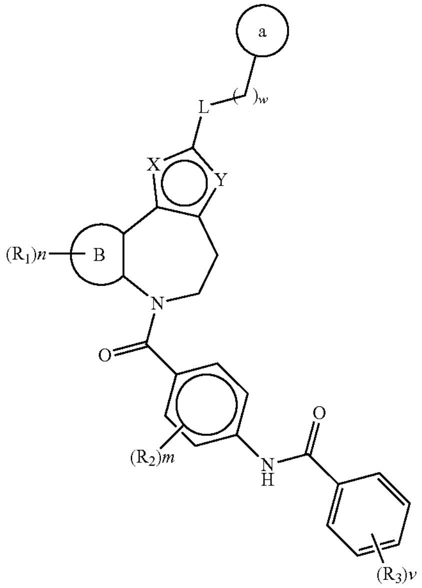
(VIII-3)
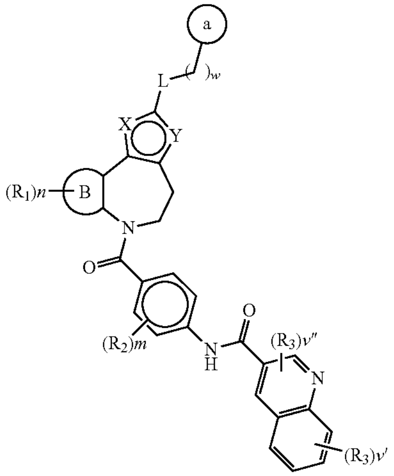
-continued
(VIII-4)
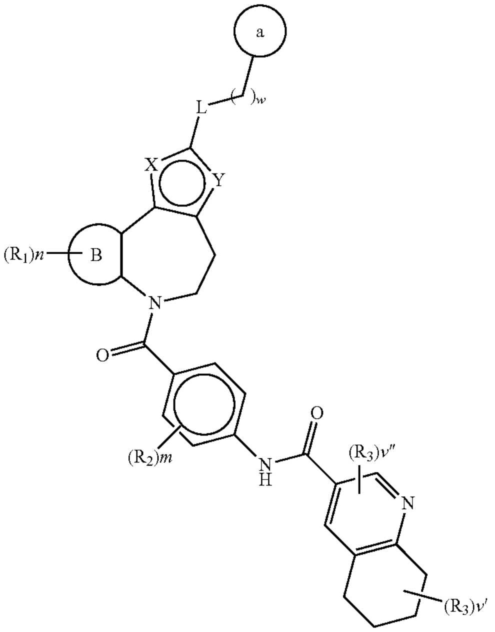
wherein ⓐ, Ⓑ, L, X, Y, $R_1$, $R_2$, $R_3$, n, m, v, v', v", and w are as previously defined.
In certain embodiments of the compounds of the invention,
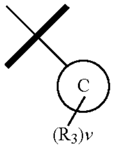
is represented by:
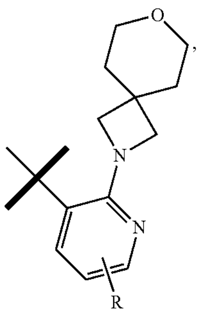
where R is hydrogen or methyl. For example,
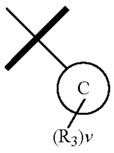
can be selected from the groups below.

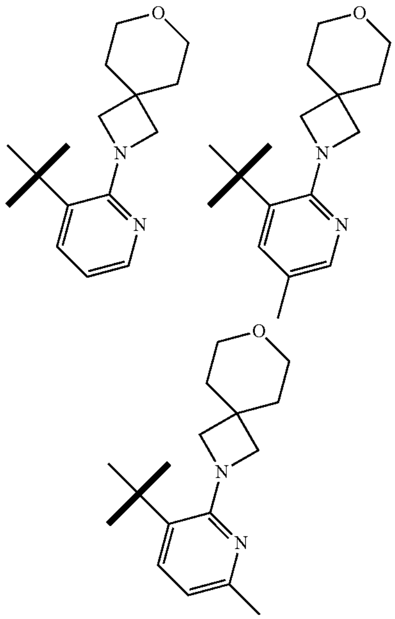

It will be appreciated that the description of the present invention herein should be construed in congruity with the laws and principles of chemical bonding. In some instances it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection in a subject in need thereof. The method comprises administering to the subject a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebuliser containing a medicament which comprises (a) a benzodiazepine derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body. The present invention also relates to a pharmaceutical composition comprising a novel compound as defined above and a pharmaceutically acceptable diluant or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral centre include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono-, bi-, or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono-, bi-, or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl," "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The tem "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHS_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthio-methyl. It is understood that the aryls, heteroaryls, alkyls, cycloalkyls and the like can be further substituted.

In certain embodiments, a substituted alkyl, alkenyl or alkoxy group is substituted with one or more halogen atoms, preferably fluorine atoms. Such substituted alkyl groups include fluoromethyl, difluoromethyl and trifluoromethyl. Such substituted alkoxy groups include fluoromethoxy, difluoromethoxy and trifluoromethoxy.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P.G.M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part*-2, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T.H. Greene and P.G.M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N.Y., 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N.Y., 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T.W. Greene and P.G.M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

In certain embodiments, the invention provides pharmaceutically acceptable prodrugs of the compounds disclosed herein. The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews,* 8:1-38(1992); Bundgaard, J. of *Pharmaceutical Sciences,* 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound. For example, a compound of formula I wherein $R_1$ is an amino acid residue can also be esterified, for example at a hydroxyl group of the sugar residue, to form a compound with two groups that can be removed in vivo to yield the active compound.

The term "treating", as used herein, means relieving, lessening, reducing, eliminating, modulating, or ameliorating, i.e. causing regression of the disease state or condition. Treating can also include inhibiting, i.e. arresting the development, of a existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N.Y., 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the Techniques of Chemistry Series, John Wiley & Sons, N.Y., 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T.W. Greene and P.G.M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

PHARMACEUTICAL COMPOSITIONS

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc;

excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:

MeCN for acetonitrile;
BME for 2-mercaptoethanol;
Boc for t-butoxycarbonyl;
Bz for benzoyl;
Bn for benzyl;
Brine for sodium chloride solution in water;
t-BuOH for tert-butanol;
BTC for bis(trichloromethyl)carbonate; triphosgene;
BzCl for benzoyl chloride;
Cbz for carbobenzyloxy;
CDI for carbonyldiimidazole;
DABCYL for 6-(N-4'-carboxy-4-(dimethylamino)azobenzene)-aminohexyl-;
1-O-(2-cyanoethyl)-(N,N-diisopropyl)-phosphoramidite;
DBU for 1,8-Diazabicycloundec-7-ene;
DCC for N, N'-dicyclohexylcarbodiimide;
DCM for dichloromethane;
DIAD for diisopropyl azodicarboxylate;
DIPEA for diisopropylethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DPPA for diphenylphosphoryl azide;
DSC for N,N'-disuccinimidyl carbonate;
DUPHOS for

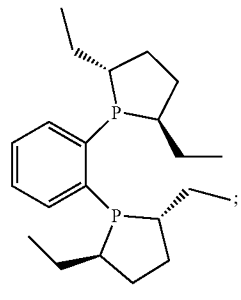 [SMILES: CC[C@@H]1CC[C@@H](CC)P1c1ccccc1P1[C@H](CC)CC[C@H]1CC]

;

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
EtOH for ethyl alcohol;

HATU for O (7-Azabenzotriazole-1-yl)-N,N,N',N'-tetramethyluronium hexafluorophosphate;

HCl for hydrochloric acid;

Hoveyda's Cat. for Dichloro(o-isopropoxyphenylmethylene) (tricyclohexylphosphine)ruthenium(II);

In for indium;

KHMDS is potassium bis(trimethylsilyl) amide;

Ms for mesyl;

NMM for N-4-methylmorpholine;

NMI for N-methylimidazole;

NMO for N-4-methylmorpholine-N-Oxide;

PyBrOP for Bromo-tri-pyrolidino-phosphonium hexafluorophosphate;

Ph for phenyl;

RCM for ring-closing metathesis;

RT for reverse transcription;

RT-PCR for reverse transcription-polymerase chain reaction;

TBME for tert-butyl methyl ether;

TCDI for 1,1'-thiocarbonyldiimidazole;

TEA for triethylamine;

$Tf_2O$ for trifluoromethanesulfonic anhydride;

TFA for trifluoroacetic acid;

THF for tetrahydrofuran;

TLC for thin layer chromatography;

$(TMS)_2NH$ for hexamethyldisilazane;

TMSOTf for trimethylsilyl trifluoromethanesulfonate;

TBS for t-Butyldimethylsilyl;

TMS for trimethylsilyl;

TPAP tetrapropylammonium perruthenate;

TPP or $PPh_3$ for triphenylphosphine;

TrCl for trityl chloride;

DMTrCl for 4,4'-dimethoxytrityl chloride;

tBOC or Boc for tert-butyloxy carbonyl;

Xantphos for 4,5-Bis-diphenylphosphanyl-9,9-dimethyl-9H-xanthene; and

Zhan 1 B for

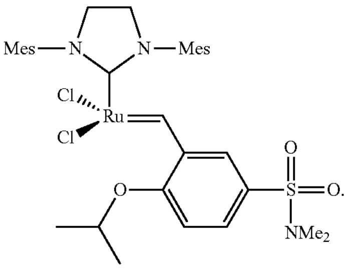

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1

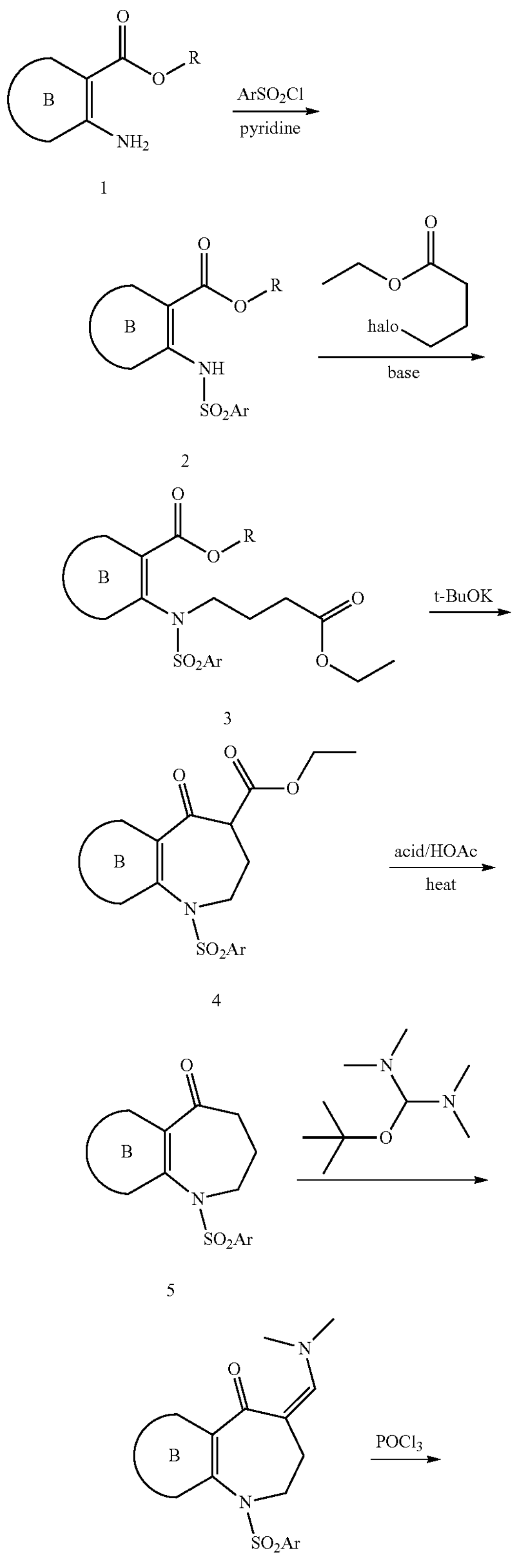

1

2

3

4

5

6

-continued

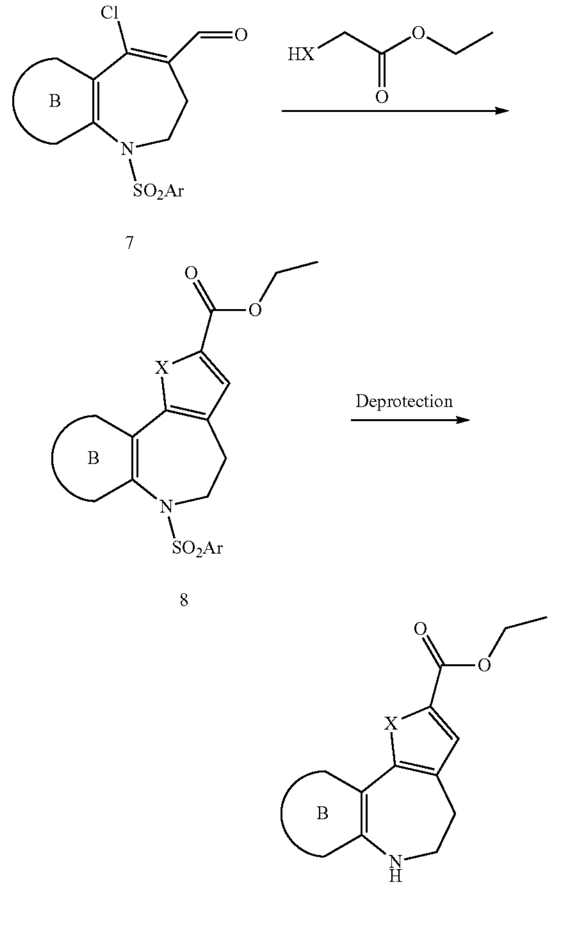

7

8

9

X = S, O
Ar = $C_6H_5$, p-$CH_3C_6H_5$, m-$NO_2C_6H_5$

Scheme 1 illustrates methods for preparing compound of formula 9. Substituted or unsubstituted heteroarylamine 1 is reacted with arylsulfonyl protecting group such as but not limited to, tosyl (Ts)- or nosyl (2-nitrobenzenesulfonyl) chloride to provide compound 2, which is converted to nitrogen protected compound 3 when reacted with 4-halobutyric acid ethyl ester in the presence of base such as but not limited to $K_2CO_3$. Compound 3 is subjected to Dieckmann cyclization in the presence of strong base such as but not limited to, t-BuOK, to afford compound 4, which was converted to compound 5 when heated in acidic condition such as but not limited to HCl in acetic acid. Reaction of compound 5 with [(tert-butoxy)(dimethylamino)-methyl]dimethylamine is followed by activation with $POCl_3$ to give compound 7, which is cyclized with ethyl 2-mercaptoacetate, ethyl 2-hydroxyacetate or the like to provide compound 8. After removing nitrogen protecting group of compound 8 with strong acids (for tosyl) such as but not limited to, $H_2SO_4$ and TFA or sodium benzenethiolate (for nosyl), to afford compound 9.

As shown in scheme 2, compound 9 is, alternatively, prepared from substituted or unsubstituted heteroarylhalide 10. Compound 10 is reacted with 4-aminobutyric ester in the presense of base such as, but not limited to, $K_2CO_3$, to provide compound 11. Nitrogen on compound 12 is protected with protecting group such as but not limited to, Boc or Cbz to afford compound 12, which is converted to compound 9 in the same way as shown in scheme 1.

Scheme 2

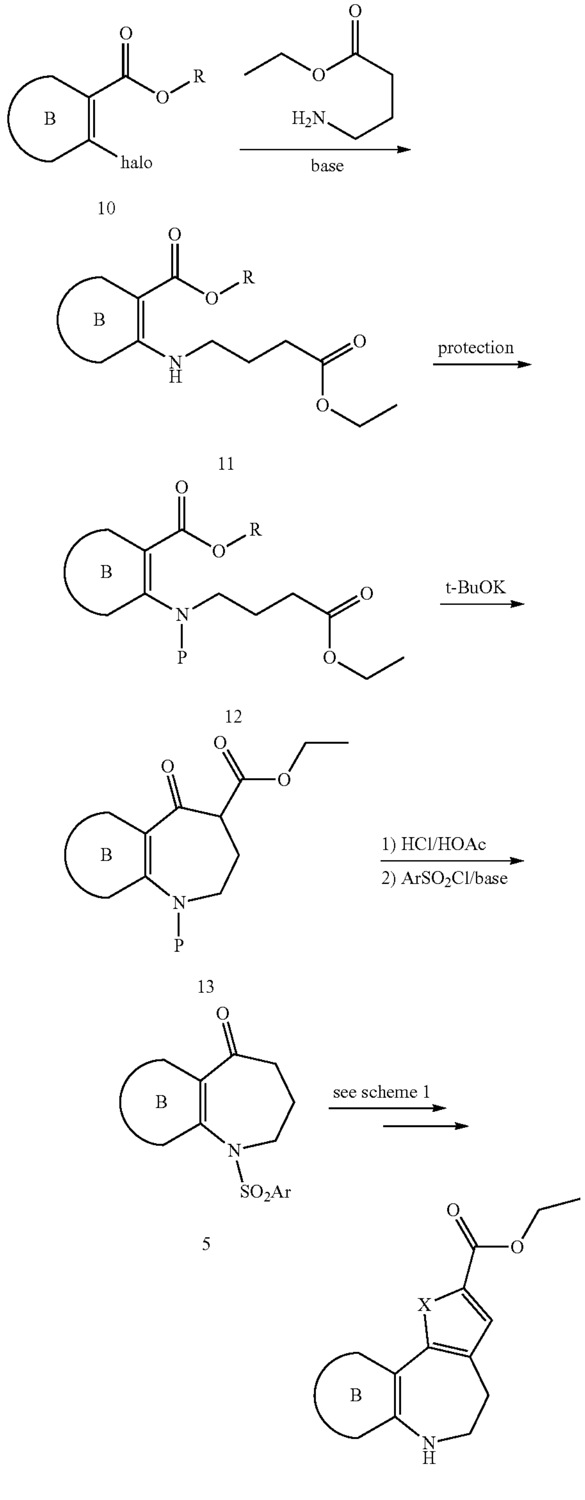

10

11

12

13

5

9

X = S, O
R = Me, Et
P = protection group
Ar = $C_6H_5$, p-$CH_3C_6H_5$, m-$NO_2C_6H_5$ Scheme 3 illustrates methods, wherein ($R_1$), ($R_2$), ($R_3$), n, m, and v are previously defined, to prepare compounds of formula 23. Substituted or unsubstituted heteroarylamine 14 is reacted with arylsulfonyl protection group such as but not limited to, tosyl (Ts)- or nosyl (2-nitrobenzenesulfonyl) chloride to provide compound 15, which is converted to compound 16 via Mitsunobu reaction using dialkyl azodicarboxylate, such as, but not limited to, DIAD, and $PPh_3$ in the presence of 3-thiopheneethanol or 3-furanethanol. Alternatively, compound 16 can be obtained from compound 15 and 3-(2-haloethyl)thiophene or 3-(2-haloethyl)furan in the presence of base such as, but not limited to $K_2CO_3$. Compound 16 is cyclized via intramolecular Heck reaction using organometal catalyst such as but not limited to, Pd (II) to afford compound 17. Compound 17 is converted to ester in two steps: bromination followed by Pd-catalyzed carbonylation in the presence of alcohol to afford compound 18. Alternatively, compound 18 is prepared by photocatalytic carbonylation. This procedure is well demonstrated in the literature, Yang, Q.; Marchini, M.; Xiao, W.; Ceroni, P.; Bandini, M. *Chemistry-Eur. J.* 2015, 21, 18052-18056.

Scheme 3

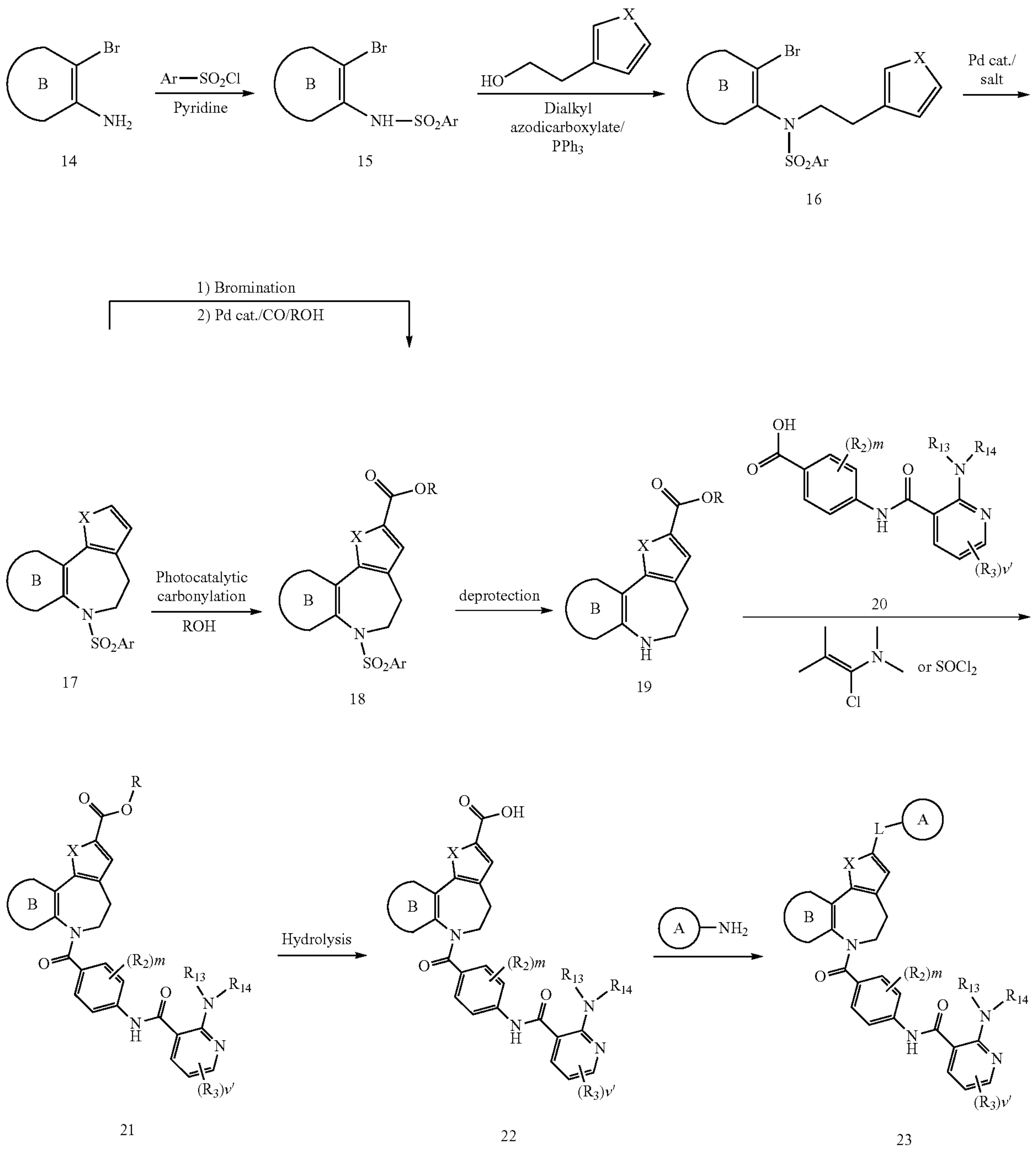

R = Me, Et

Ar = $C_6H_5$, p-$CH_3C_6H_5$, m-$NO_2C_6H_5$

After deprotection of arylsulfonyl protection group on nitrogen with strong acids (for tosyl) such as but not limited to, $H_2SO_4$ and TFA or sodium benzenethiolate (for nosyl), the resulting compound 19 is coupled with acyl chloride 20, wherein m, v', R', R'', ($R_2$) and ($R_3$) are defined as previously described, to provide compound 21, which is subsequently converted to acid compound 22. Compound 23 is prepared from the reaction of compound 16 with various substituted aryl or heteroaryl amines, wherein L and ring A are defined as previously described.

Scheme 4

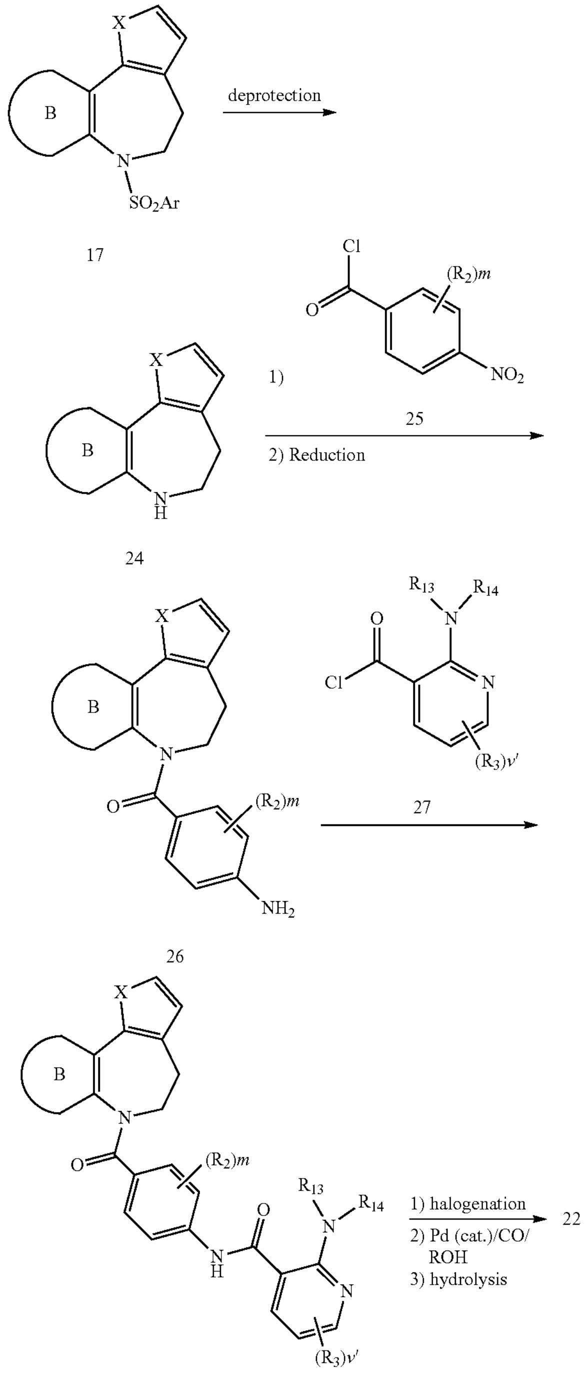

17

25

24

27

26

22

28

Scheme 4 illustrates alternative methods, wherein X, m, ($R_2$), v', ($R_3$) and B ring are defined as previously described, to prepare compounds of formula 22. Compound 17 is deprotected as the same way described in scheme 3 to give compound 24. Substituted 4-nitrobenzoyl chloride 25 is reacted with compound 24 to provide compound 26, which is coupled with functionalized acyl chloride 27, to afford compounds of formula 28. Compound 28 is converted to compound 22 in three steps: bromination followed by Pd-catalyzed carbonylation in the presence of alcohol and hydrolysis to afford compound 22.

Scheme 5 illustrates methods, wherein ($R_1$), ($R_2$), ($R_3$), n, m, and v are previously defined, to prepare for compounds of formula 31. Carboxylic acid 22 is converted to amine 30 via Curtius rearrangement. The key intermediate of Curtius rearrangement, acyl azide can be prepared using various conditions such as but not limited to, diphenylphosphoryl azide (DPPA), from the reaction of acid chlorides or anhydrides with sodilum azide or trimethylsilyl azide. Acyl azide is reacted with nucleophilic alcohol such as but not limited to, tert-butanol and benzyl alcohol to afford to compound 29. After deprotection of amine protection group on nitrogen with acids (tert-butoxycarbonyl) or palladium-carbon (benzyloxycarbonyl) such as but not limited to, HCl and TFA or 10% Pd—C, the resulting compound 30 is coupled with arylacyl chloride to provide compounds of formula 31.

Scheme 5

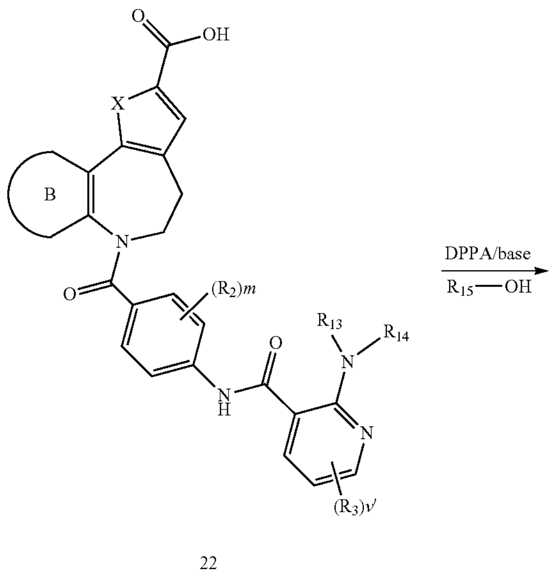

22

-continued

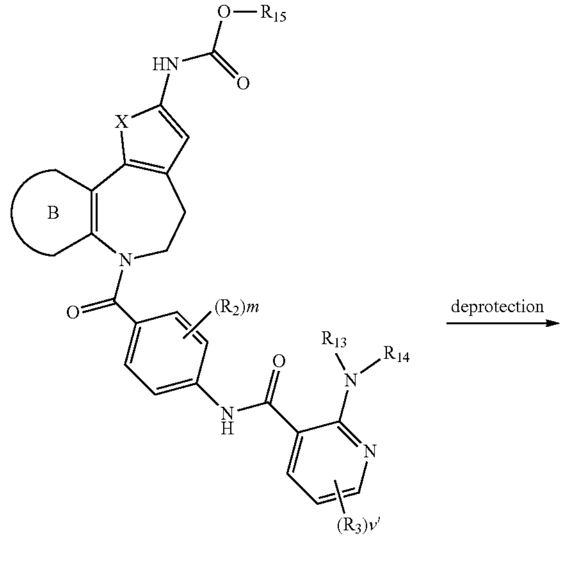

29

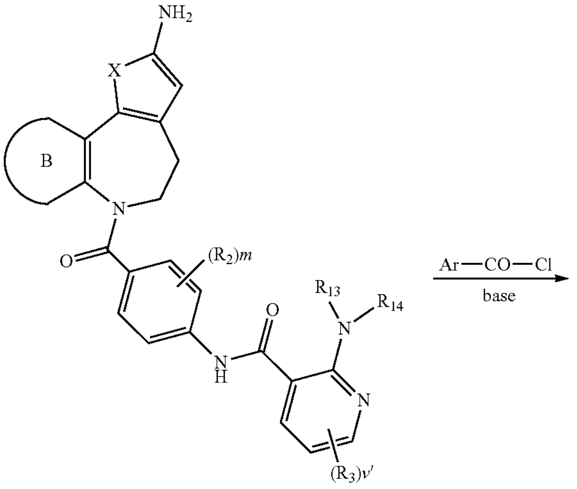

30

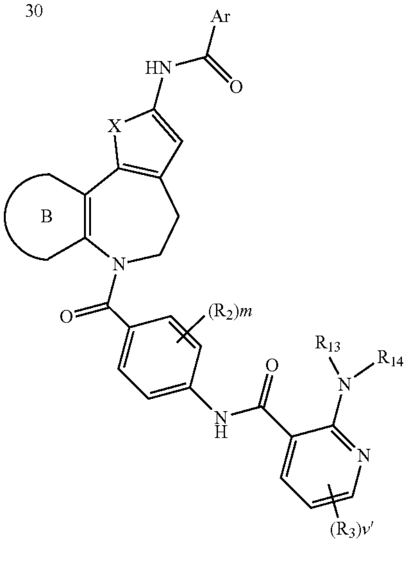

31

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Scheme 6

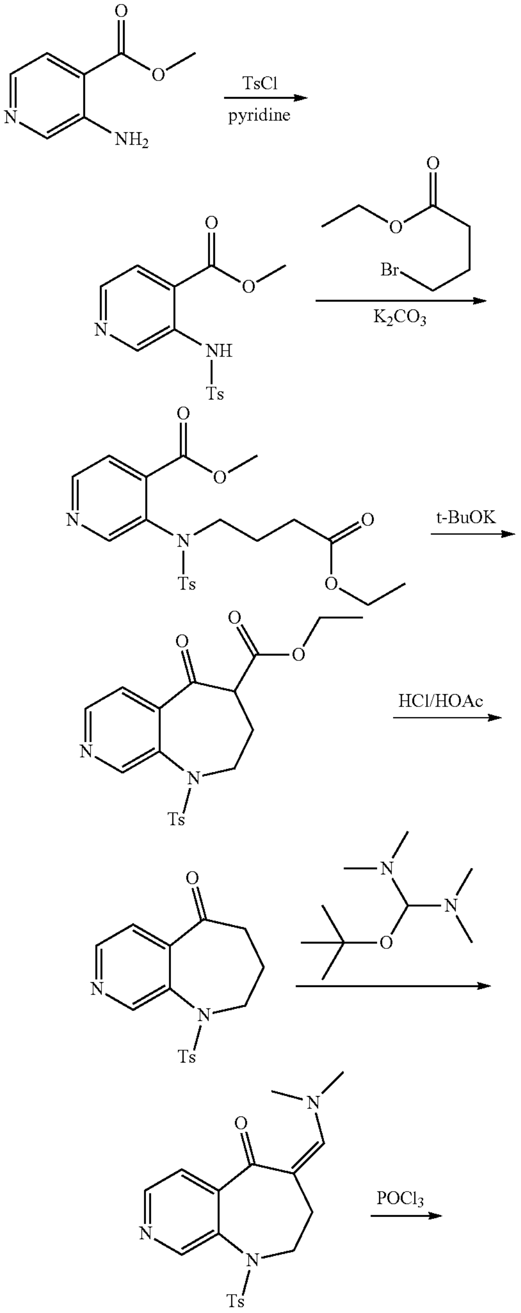

-continued

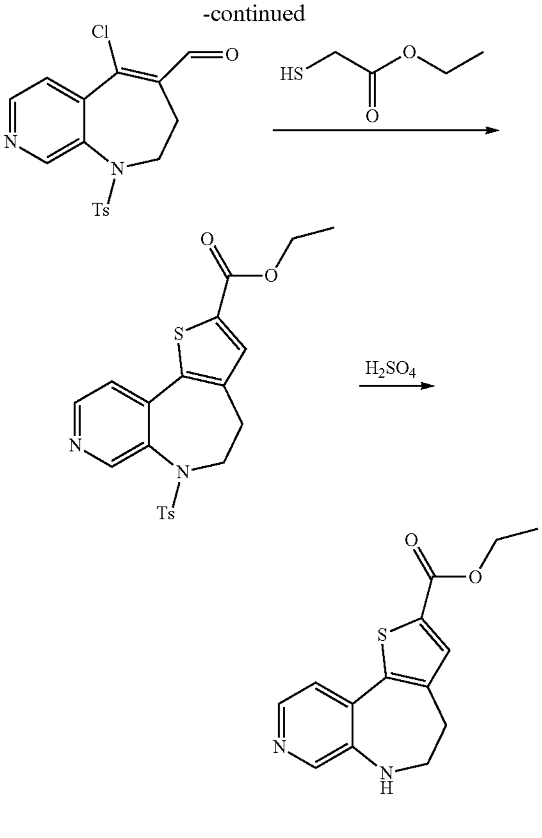

Intermediate 1

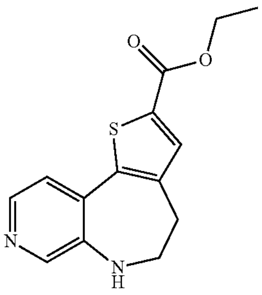

Intermediate 1 step a:

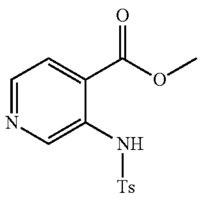 [SMILES: COC(=O)c1ccncc1NS(=O)(=O)c1ccc(C)cc1]

To a mixture of methyl 3-aminopyridine-4-carboxylate (60 g, 394.35 mmol) and pyridine (300 mL) was added TsCl (90 g, 472.07 mmol) under $N_2$. The resulting solution was stirred at 60° C. for overnight. The reaction mixture was cooled. The resulting solution was poured into 1000 mL of ice water. The solids were collected by filtration and washed with HCl (1 N). The solid was dried in an oven under reduced pressure to provide the desired compound (75 g) as a yellow solid. ESI-MS m/z: 307.1 $[M+H]^-$.

Intermediate 1 step b:

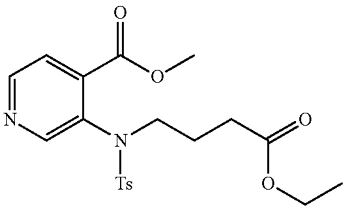 [SMILES: CCOC(=O)CCCN(c1cnccc1C(=O)OC)S(=O)(=O)c1ccc(C)cc1]

To a mixture of methyl 3-[(4-methylbenzene)sulfonamido]-pyridine-4-carboxylate (75 g, 244.83 mmol) and $K_2CO_3$ (33.8 g, 244.56 mmol) in DMF (375 mL). was added ethyl 4-bromobutanoate (57 g, 292.23 mmol). The resulting solution was stirred at 80° C. for overnight. After being cooled. The reaction mixture was diluted with water (1000 mL) and extracted with EtOAc (4×600 mL). The combined organic layer was washed with brine (3×1000 mL), dried over anhydrous sodium sulfate and concentrated under vacuum. The residue was purified by silica gel column with EtOAc/petroleum ether (1:1) to afford the desired compound (50 g) as a yellow solid. ESI-MS m/z: 421.1 $[M+H]^+$.

Intermediate 1 step c:

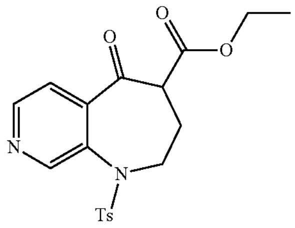 [SMILES: CCOC(=O)C1CCN(S(=O)(=O)c2ccc(C)cc2)c2cnccc2C1=O]

To a solution of t-BuOK (46.7 g, 416.18 mmol, 3.50 equiv) in toluene (500 mL) was dropwise added a solution of the compound from step b (50 g, 118.91 mmol) in toluene (500 mL) at rt for 1.5 hr. The resulting solution was stirred for additional 1.5 hr, diluted with water (1000 mL) and extracted with EtOAc (4×800 mL). The combined organic layer was washed with brine (3×1000 mL), dried over anhydrous sodium sulfate, filtered and concentrated under vacuumto afford the desired compound (40 g) as a yellow solid. ESI-MS m/z: 389.1 $[M+H]^+$.

Intermediate 1 step d:

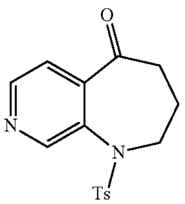 [SMILES: Cc1ccc(S(=O)(=O)N2CCCC(=O)c3ccncc32)cc1]

A mixture of the compound from step c (40 g, 102.98 mmol), 6N—HCl (120 mL) and acetic acid (300 mL) was heated at 110° C. stirred for 1 overnight. After being cooled. The reaction mixture was diluted with water (1000 mL) and extracted with DCM (3×800 mL). The combined organic layer was washed with brine (3×1000 mL), dried over anhydrous sodium sulfate, filtered and concentrated under vacuum. The residue was purified by silica gel column with EtOAc/petroleum ether (1:4) to afford the desired compound (20 g) as a yellow solid. ESI-MS m/z: 317.2 $[M+H]^+$.

Intermediate 1 step e:

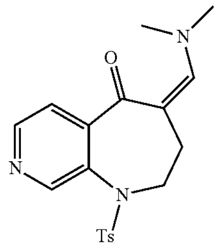 [SMILES: Cc1ccc(S(=O)(=O)N2CC/C(=C/N(C)C)C(=O)c3ccncc32)cc1]

To a mixture of the compound from step d (20 g, 63.22 mmol) in DCM (200 mL) was added [(tert-butoxy)(dimethylamino)methyl]dimethylamine (44 g, 252.46 mmol) and heated at 60° C. for overnight. The resulting mixture was concentrated under vacuum to give the desired compound 25 g (crude) as a yellow solid. ESI-MS m/z: 372.2 $[M+H]^+$.

Intermediate 1 step f:

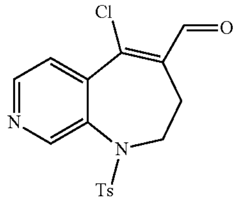 [SMILES: Cc1ccc(S(=O)(=O)N2CCC(C=O)=C(Cl)c3ccncc32)cc1]

To a mixture of the compound from step e (25 g, 67.30 mmol) in DMF (250 mL) was dropwise added $POCl_3$ (31 g, 202.18 mmol) at 0° C. The resulting solution was stirred for additional 0.5 hr at 0° C. After being cooled to rt, the reaction mixture was diluted with water (1000 mL) and extracted with EtOAc (3×600 mL). The combined organic layer was washed with brine (3×1000 mL), dried over anhydrous sodium sulfate, filtered and concentrated under vacuum. The residue was purified by silica gel column with EtOAc/petroleum ether (3:1) to afford the desired compound (13.5 g) as a yellow solid. ESI-MS m/z: 363.2 $[M+H]^+$.

Intermediate 1 step g:

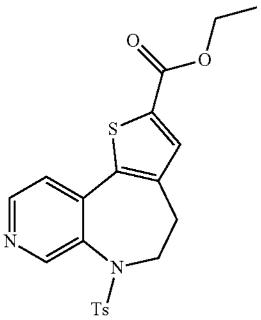 [SMILES: CCOC(=O)c1cc2c(s1)-c1ccncc1N(S(=O)(=O)c1ccc(C)cc1)CC2]

To a mixture of ethyl 2-sulfanylacetate (8.9 g, 74.06 mmol) in DMF (135 mL) was portionwise added NaH (3 g, 0.75 mmol) at 0° C. and stirred 30 min. To this was dropwise added a solution of the compound from step f (13.5 g, 37.21 mmol) DMF (40 mL) and stirred at 25° C. for 1 hr. Then, The reaction was then quenched by addition of water (100 mL). The resulting solid were collected and dried in an oven under reduced pressure to give the desired compound (9 g) as a yellow solid. ESI-MS m/z: 429.2 $[M+H]^+$.

Intermediate 1 step h:

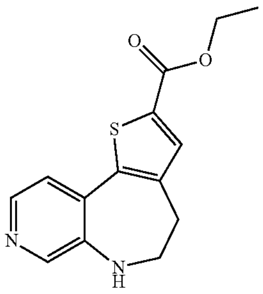 [SMILES: CCOC(=O)c1cc2c(s1)-c1ccncc1NCC2]

Sulfuric acid (90 mL) was slowly added to the compound from step g (9 g, 21.00 mmol) and stirred at rt for 2 hr. Then, the reaction mixture was added to water/ice (300 mL). The pH value of the solution was adjusted to ~8 with addition of $Na_2CO_3$. The solids were collected by filtration, dried in an oven under reduced pressure to provide the desired compound (2.3 g) as a yellow solid. ESI-MS m/z: 275.2 $[M+H]^+$.

$^1$H-NMR (300 MHz, DMSO-$d_6$) δ 1.30 (m, 3H), 3.00-3.10 (m, 2H), 4.29 (m, 2H), 6.86 (d, J=4.5 Hz, 1H), 7.39 (d, J=5.3 Hz, 1H), 7.62 (s, 1H), 7.76 (d, J=5.3 Hz, 1H), 8.13 (s, 1H).

Example 1

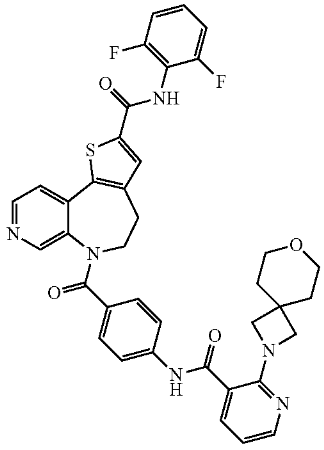

Scheme 7
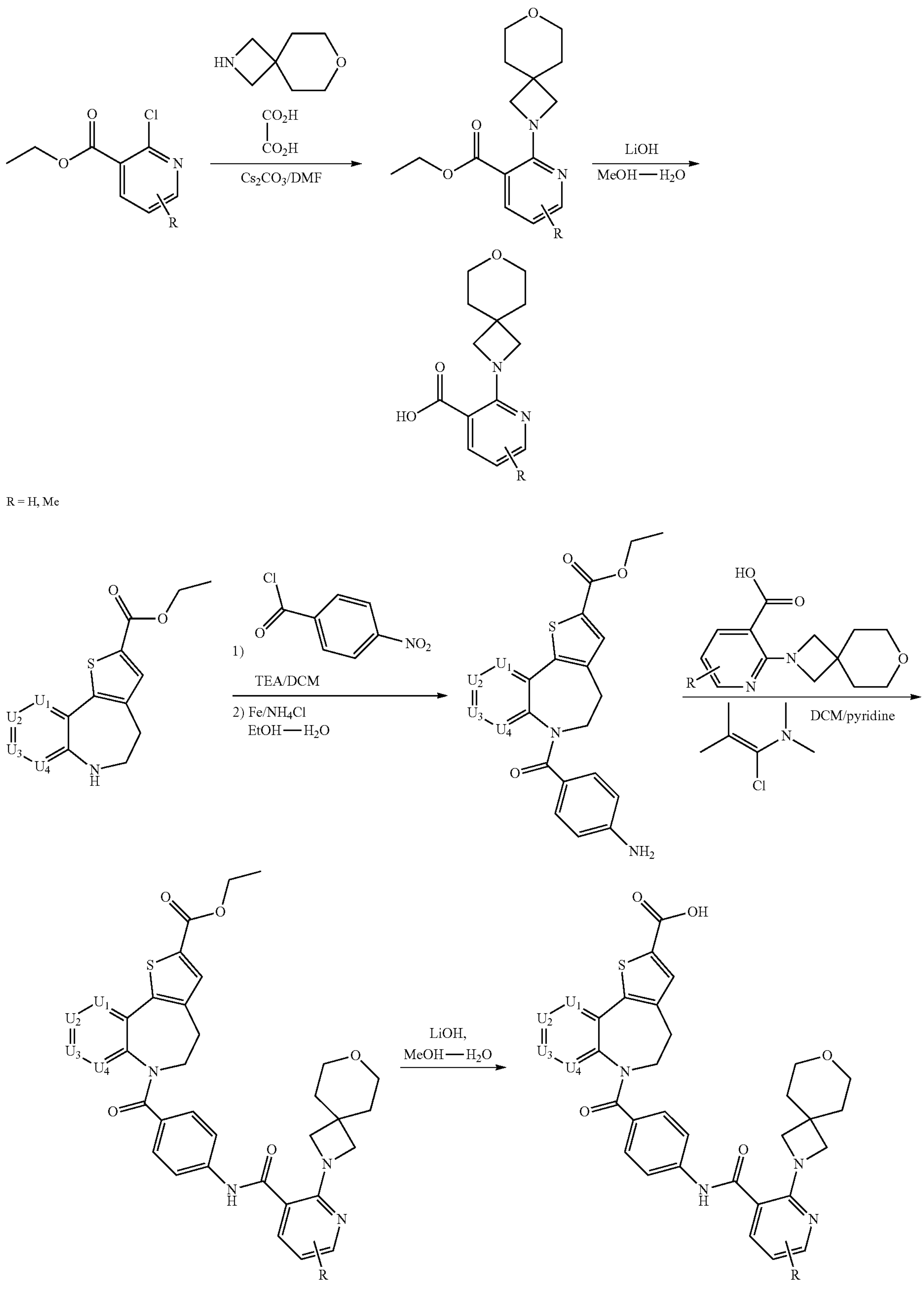

-continued

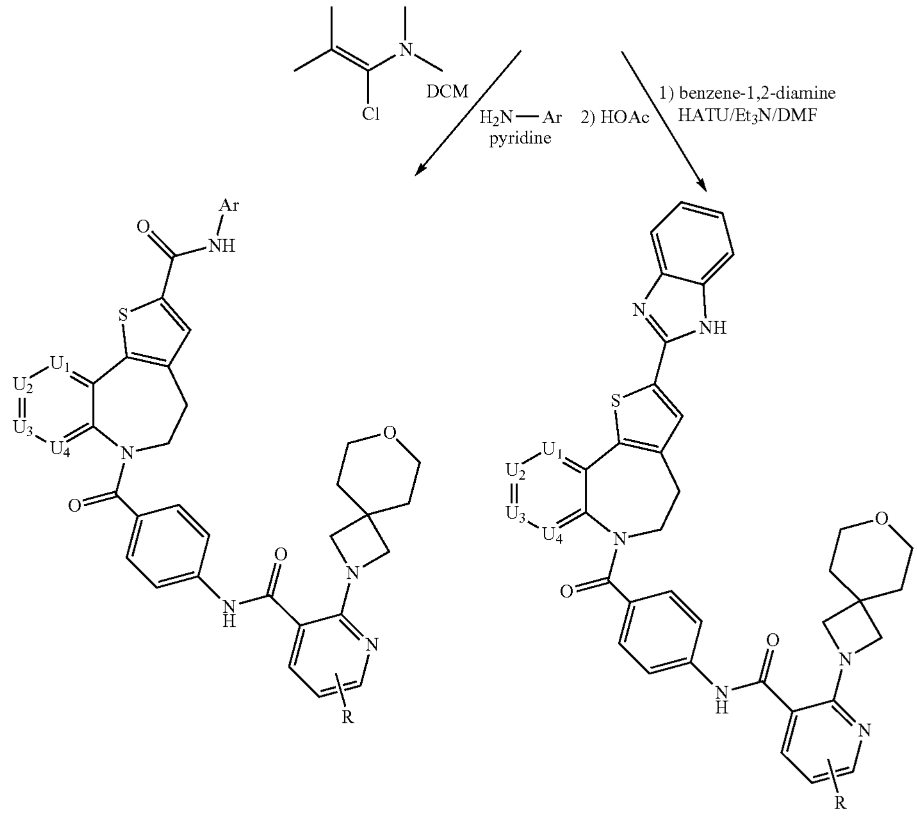

One of $U_1$, $U_2$, $U_3$, and $U_4$ is N, and the others are CH.

R = H, Me

Example 1 Step a

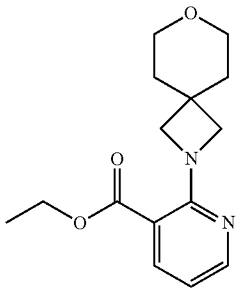 [SMILES: CCOC(=O)c1cccnc1N1CC2(CCOCC2)C1]

A mixture of ethyl 2-chloronicotinate (1.7 g, 9 mmol), 7-oxa-2-azaspiro[3.5]nonane oxalate (2 g, 9 mmol) and $Cs_2CO_3$ (5.9 g, 18 mmol) in DMF (10 mL) was stirred at 100° C. for 1 hr. The reaction mixture was diluted with water (50 mL) and extracted with EtOAc (3×50 mL). The combined organic layer was washed with brine (3×30 mL), dried over anhydrous sodium sulfate, filtered and concentrated under vacuum. The residue was purified by column chromatography with MeCN/$H_2O$ to afford the desired compound (2.2 g) as a yellow solid. ESI-MS m/z: 277.10 $[M+H]^+$.

Example 1 Step b

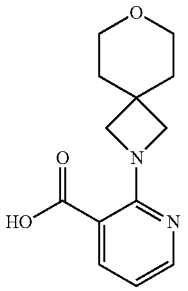 [SMILES: O=C(O)c1cccnc1N1CC2(CCOCC2)C1]

A mixture of the compound from step a (2.2 g, 8 mmol) and LiOH (1.91 g, 80 mmol) in MeOH (30 mL) and water (20 mL) was stirred at 50° C. for 1 hr. The mixture was concentrated and adjusted to pH=2 with 1M HCl, evaporated, purified by column chromatogrphy (MeCN/$H_2O$) to give the desired compound as a white solid (1.7 g).

ESI-MS m/z: 249.15 $[M+H]^+$.

Example 1 Step c

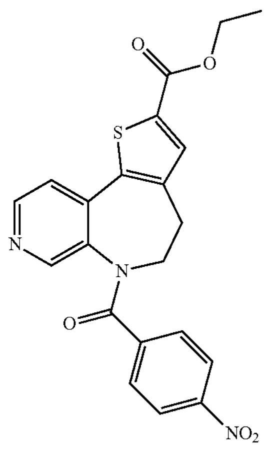

A solution of the compound from intermediate 1 step h (400 mg, 1.45 mmol) and TEA (1 mL) in DCM (10 mL) was added 4-nitrobenzoyl chloride (540 mg, 2.9 mmol) and stirred for 1 hour. The solution was concentrated and purified by column chromatography ($MeCN/H_2O$) to give the desired compound as yellow solid (440 mg). ESI-MS m/z: 424.10 $[M+H]^+$.

Example 1 Step d

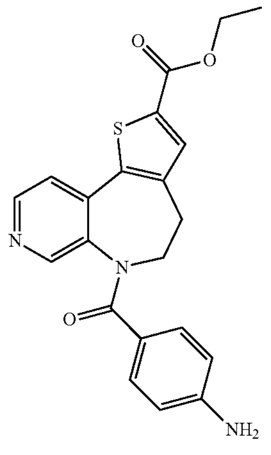 [SMILES: CCOC(=O)c1cc2c(s1)-c1ccncc1N(C(=O)c1ccc([N+](=O)[O-])cc1)CC2]

A mixture of the compound from step c (440 mg, 1.04 mmol), $NH_4Cl$ (276 mg, 5.2 mmol), Fe (291 mg, 5.2 mmol) in EtOH (5 mL) and water (5 mL) was stirred at 80° C. for 1 hr. The reaction mixture was concentrated and purified by silica gel column chromatography DCM-MeOH) to give the desired compound as orange solid (400 mg).

ESI-MS m/z: 394.05 $[M+H]^+$.

Example 1 Step e

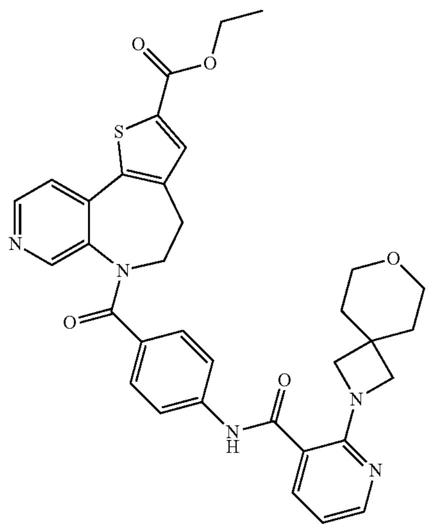 [SMILES: CCOC(=O)c1cc2c(s1)-c1ccncc1N(C(=O)c1ccc(NC(=O)c3cccnc3N3CC4(CCOCC4)C3)cc1)CC2]

1-chloro-N,N,2-trimethylprop-1-en-1-amine (395 mg, 3.06 mmol) was added to the solution of the compound from step b (252 mg, 1.02 mmol) in DCM (5 mL) and stirred for 1 hr before being concentrated. The compound from step d (400 mg, 1.02 mmol) and pyridine (1 mL) in DCM (5 mL) was dropwised added to the above reaction mixture and stirred for 1 hr. The reaction mixture was evaporated and purified by column chromatography ($MeCN/H_2O$) to give the desired compound as a yellow solid (500 mg). ESI-MS m/z: 624.35 $[M+H]^+$.

Example 1 Step f

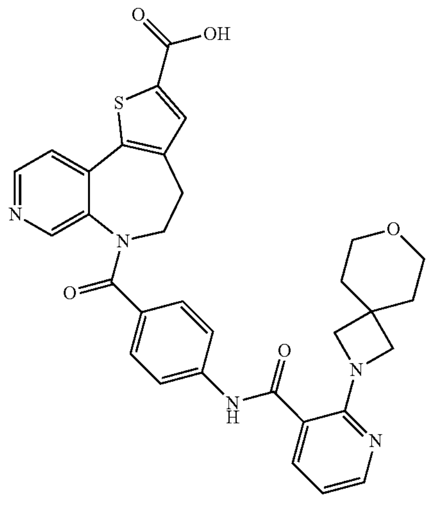 [SMILES: O=C(O)c1cc2c(s1)-c1ccncc1N(C(=O)c1ccc(NC(=O)c3cccnc3N3CC4(CCOCC4)C3)cc1)CC2]

A mixture of the compound from step e (500 mg, 0.8 mmol) and LiOH (193 mg, 8 mmol) in MeOH (20 mL) and water (10 mL) was stirred at rt for 1 hr. The reaction mixture was concentrated and adjusted to pH=2 with 1M HCl, evaporated, purified by silica gel column chromatography (DCM-MeOH) to give the desired compound as a yellow solid (400 mg). ESI-MS m/z: 596.20 $[M+H]^+$.

Example 1 Step g

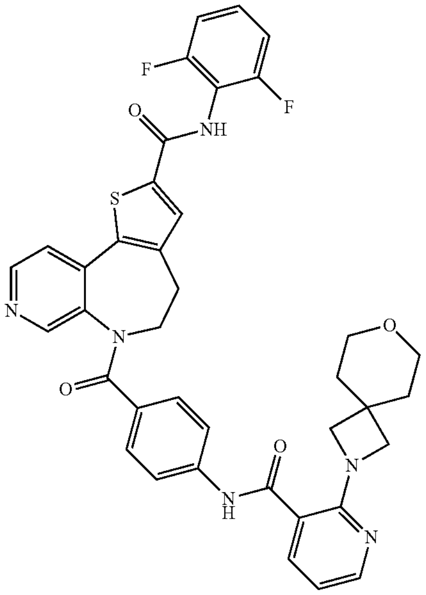 [SMILES: O=C(Nc1c(F)cccc1F)c1cc2c(s1)-c1ccncc1N(C(=O)c1ccc(NC(=O)c3cccnc3N3CC4(CCOCC4)C3)cc1)CC2]

1-chloro-N,N,2-trimethylprop-1-en-1-amine (85 mg, 0.66 mmol) was added to the solution of the compound from step f (130 mg, 0.22 mmol) in DCM (5 mL) and stirred overnight before being concentrated. Then, 2,6-difluoroaniline (28 mg, 0.22 mmol) and pyridine (0.1 mL) in DCM (5 mL) was dropwised added to the above reaction mixture and stirred for 1 hr. The reaction mixture was evaporated and purified by prep-HPLC (MeCN/$H_2O$) to give the desired compound as a yellow solid (17.8 mg). ESI-MS m/z: 707.50 $[M+H]^+$. $^1H$ NMR (400 MHz, DMSO-$d_6$) δ 1.62 (m, 4H), 3.23 (m, 4H), 3.45 (m, 4H), 3.64 (s, 3H), 4.98 (s, 1H), 6.69 (m, 1H), 7.02 (d, J=8.1 Hz, 2H), 7.23 (m, 2H), 7.43 (m, 1H), 7.55 (d, J=8.2 Hz, 2H), 7.62 (m, 1H), 7.78 (d, J=5.3 Hz, 1H), 8.01 (s, 2H), 8.17 (m, 1H), 8.34 (d, J=5.2 Hz, 1H), 10.43 (s, 2H).

Example 2

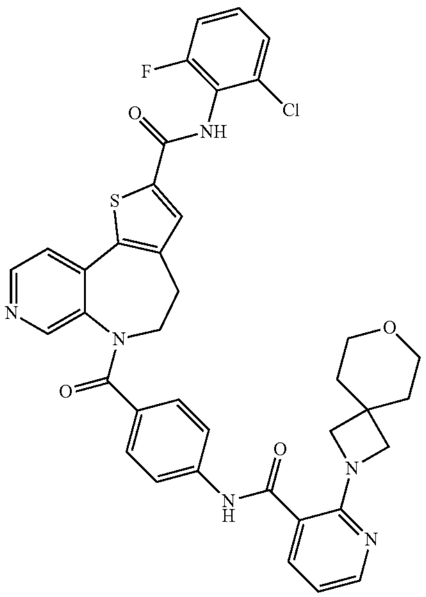 [SMILES: O=C(Nc1c(F)cccc1Cl)c1cc2c(s1)-c1ccncc1N(C(=O)c1ccc(NC(=O)c3cccnc3N3CC4(CCOCC4)C3)cc1)CC2]

Example 2 was prepared using a procedure similar to that used to prepare example 1 step g where 2-fluoro-6-chloroaniline was used in place of 2,6-difluoroaniline in example 1. ESI-MS m/z: 723.10 $[M+H]^+$. $^1H$ NMR (400 MHz, DMSO-$d_6$) δ 1.62 (m, 4H), 3.22 (s, 4H), 3.45 (m, 4H), 3.63 (s, 3H), 4.98 (s, 1H), 6.69 (m, 1H), 7.02 (d, J=8.0 Hz, 2H), 7.33-7.49 (m, 3H), 7.50-7.66 (m, 3H), 7.79 (d, J=5.3 Hz, 1H), 8.02 (s, 2H), 8.17 (m, 1H), 8.34 (d, J=5.3 Hz, 1H), 10.44 (s, 2H).

Example 3

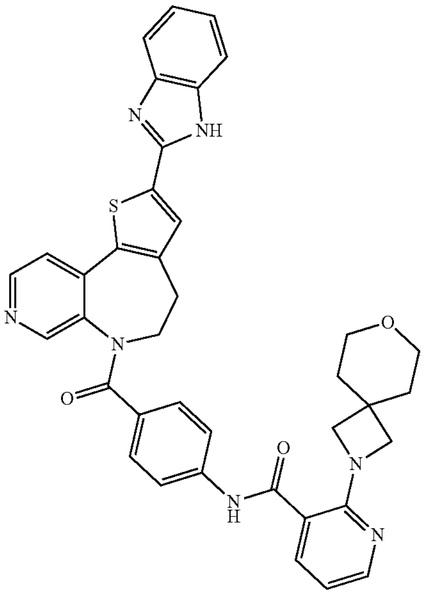 [SMILES: O=C(Nc1ccc(C(=O)N2CCc3cc(-c4nc5ccccc5[nH]4)sc3-c3ccncc32)cc1)c1cccnc1N1CC2(CCOCC2)C1]

Example 3 Step a

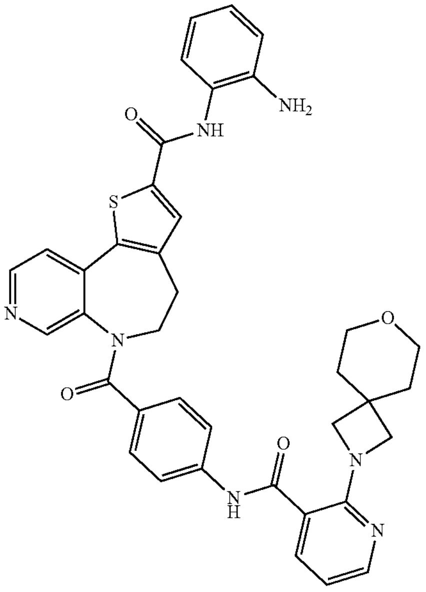 [SMILES: Nc1ccccc1NC(=O)c1cc2c(s1)-c1ccncc1N(C(=O)c1ccc(NC(=O)c3cccnc3N3CC4(CCOCC4)C3)cc1)CC2]

To a solution of the compound from example 1 step f (200 mg, 0.336 mmol), benzene-1,2-diamine (73 mg, 0.672 mmol) and DIPEA (0.5 mL) in DMF (3 mL) was added HATU (255 mg, 0.672 mmol) and stirred at rt for 1 hour. The reaction mixture was diluted with water (10 mL) and extracted with EtOAc (3×10 mL). The combined organic layer was washed with brine (3×10 mL), dried over anhydrous sodium sulfate, filtered and concentrated under vacuum. The residue was purified by column chromatography ($MeCN/H_2O$) to afford the desired compound (200 mg) as a yellow solid. ESI-MS m/z: 686.20 $[M+H]^+$.

Example 3 Step b

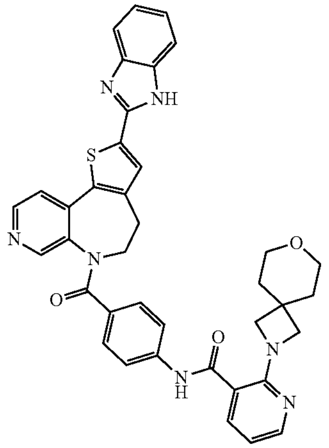 [SMILES: O=C(Nc1ccc(C(=O)N2CCc3cc(-c4nc5ccccc5[nH]4)sc3-c3ccncc32)cc1)c1cccnc1N1CC2(CCOCC2)C1]

A solution of the compound from step a (200 mg, 0.292 mmol) in HOAc (10 mL) was stirred at 90° C. for 1 hr. The solution was evaporated, adjusted to pH=8 with $NaHCO_3$, extracted with EA (×3), dried, concentrated and purified by Prep-HPLC ($MeCN/H_2O$) to give the titled compound as yellow solid (13.1 mg). ESI-MS m/z: 668.15 $[M+H]^+$. $^1H$ NMR (400 MHz, DMSO-$d_6$) δ 1.61 (m, 4H), 3.22 (s, 4H), 3.45 (m, 4H), 3.63 (s, 3H), 5.00 (s, 1H), 6.68 (m, 1H), 7.04 (s, 2H), 7.23 (m, 2H), 7.55 (d, J=7.9 Hz, 2H), 7.58-7.71 (m, 2H), 7.77 (d, J=5.3 Hz, 1H), 7.84 (s, 1H), 8.01 (d, J=10.2 Hz, 1H), 8.16 (m, 1H), 8.35 (m, 2H), 10.43 (s, 1H), 13.19 (s, 1H).

Scheme 8

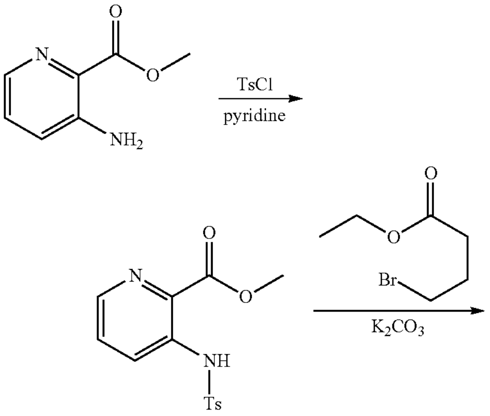

-continued

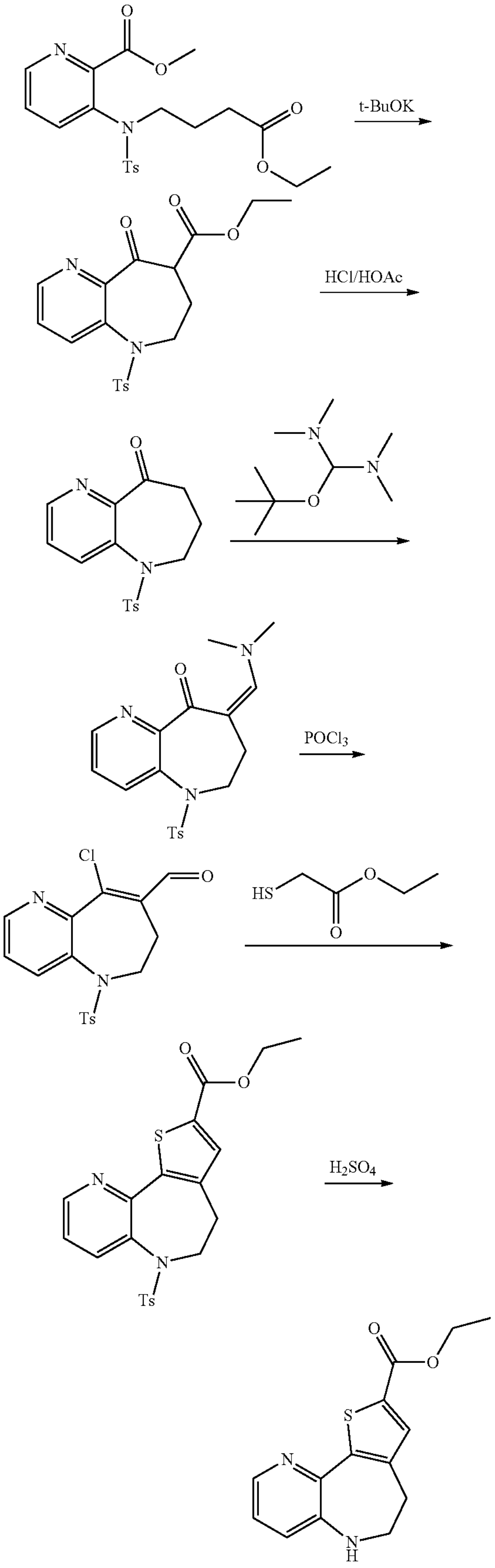

Intermediate 2

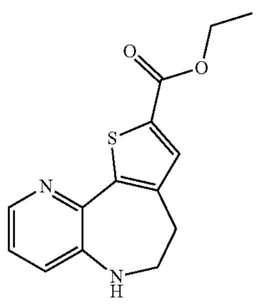 [SMILES: CCOC(=O)c1cc2c(s1)-c1ncccc1NCC2]

Intermediate 2 step a:

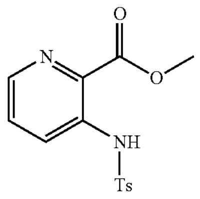 [SMILES: COC(=O)c1ncccc1NS(=O)(=O)c1ccc(C)cc1]

The title compound was prepared using a procedure similar to that used to prepare the compound in intermediate 1 step a. ESI-MS m/z: 307.0 $[M+H]^+$.

Intermediate 2 step b:

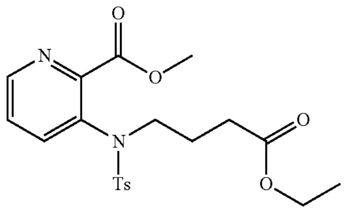 [SMILES: CCOC(=O)CCCN(c1cccnc1C(=O)OC)S(=O)(=O)c1ccc(C)cc1]

The title compound was prepared using a procedure similar to that used to prepare the compound in intermediate 1 step b. ESI-MS m/z: 421.1 $[M+H]^+$.

Intermediate 2 step c:

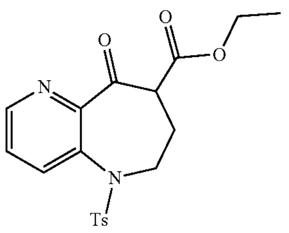 [SMILES: CCOC(=O)C1CCN(S(=O)(=O)c2ccc(C)cc2)c2cccnc2C1=O]

The title compound was prepared using a procedure similar to that used to prepare the compound in intermediate 1 step c.

Intermediate 2 step d:

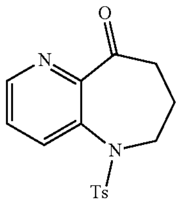 [SMILES: Cc1ccc(S(=O)(=O)N2CCCC(=O)c3ncccc32)cc1]

The title compound was prepared using a procedure similar to that used to prepare the compound in intermediate 1 step d. ESI-MS m/z: 317.0 $[M+H]^+$.

Intermediate 2 step e:

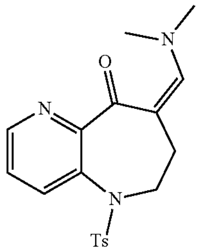 [SMILES: Cc1ccc(S(=O)(=O)N2CC/C(=C/N(C)C)C(=O)c3ncccc32)cc1]

The title compound was prepared using a procedure similar to that used to prepare the compound in intermediate 1 step e.

Intermediate 2 step f:

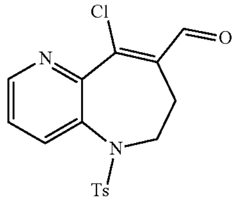 [SMILES: Cc1ccc(S(=O)(=O)N2CCC(C=O)=C(Cl)c3ncccc32)cc1]

The title compound was prepared using a procedure similar to that used to prepare the compound in intermediate 1 step f. ESI-MS m/z: 363.0 $[M+H]^+$.

Intermediate 2 step g:

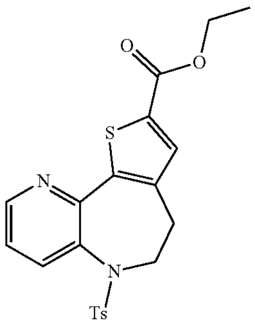 [SMILES: CCOC(=O)c1cc2c(s1)-c1ncccc1N(S(=O)(=O)c1ccc(C)cc1)CC2]

The title compound was prepared using a procedure similar to that used to prepare the compound in intermediate 1 step g. ESI-MS m/z: 429.0 $[M+H]^+$.

Intermediate 2 step h:

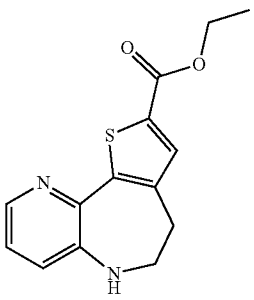 [SMILES: CCOC(=O)c1cc2c(s1)-c1ncccc1NCC2]

The title compound was prepared using a procedure similar to that used to prepare the compound in intermediate 1 step h. ESI-MS m/z: 275.1 [M+H]$^+$.

$^1$H NMR (300 MHz, DMSO-$d_6$, ppm): δ 1.24-1.32 (m, 3H), 3.01-3.04 (m, 2H), 3.28-3.32 (m, 2H), 4.23-4.30 (m, 2H), 6.65 (s, 1H), 7.05-7.09 (m, 1H), 7.16-7.19 (m, 1H), 7.57 (s, 1H), 7.89-7.91 (m, 1H).

Example 4

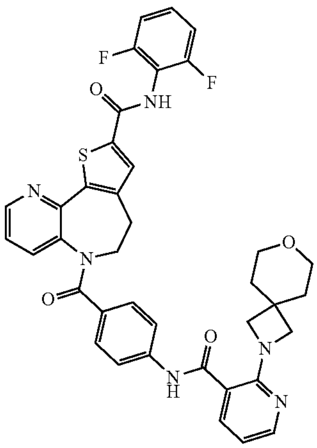 [SMILES: O=C(Nc1c(F)cccc1F)c1cc2c(s1)-c1ncccc1N(C(=O)c1ccc(NC(=O)c3cccnc3N3CC4(CCOCC4)C3)cc1)CC2]

Example 4 Step a

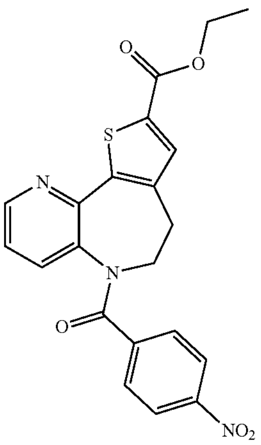 [SMILES: CCOC(=O)c1cc2c(s1)-c1ncccc1N(C(=O)c1ccc([N+](=O)[O-])cc1)CC2]

The title compound was prepared using a procedure similar to that used to prepare the compound in example 1 step c. ESI-MS m/z: 424.20 [M+H]$^+$.

Example 4 Step b

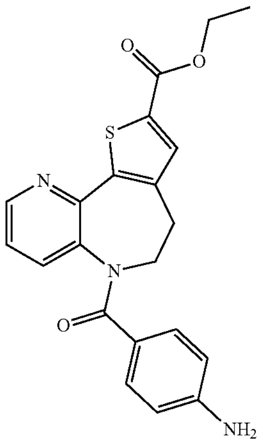

The title compound was prepared using a procedure similar to that used to prepare the compound in example 1 step d. ESI-MS m/z: 394.25 [M+H]$^+$.

Example 4 Step c

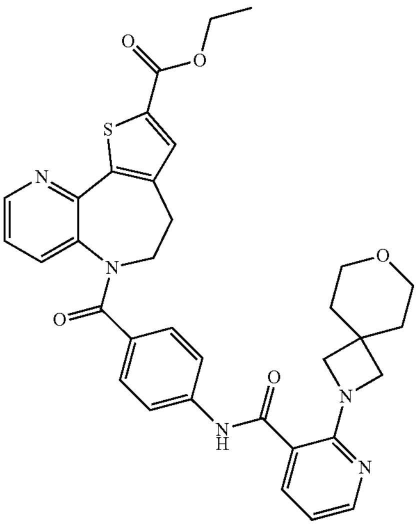 [SMILES: CCOC(=O)c1cc2c(s1)-c1ncccc1N(C(=O)c1ccc(NC(=O)c3cccnc3N3CC4(CCOCC4)C3)cc1)CC2]

The title compound was prepared using a procedure similar to that used to prepare the compound in example 1 step e. ESI-MS m/z: 624.25 [M+H]$^+$.

Example 4 Step f
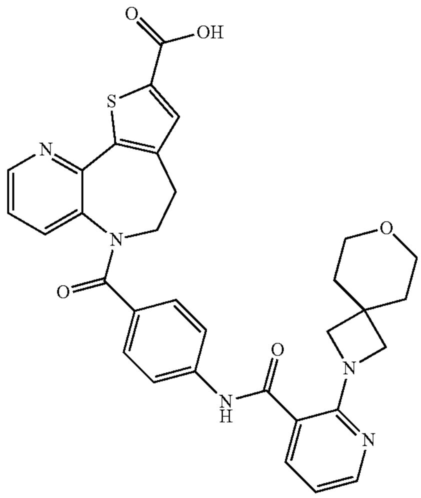 [SMILES: O=C(O)c1cc2c(s1)-c1ncccc1N(C(=O)c1ccc(NC(=O)c3cccnc3N3CC4(CCOCC4)C3)cc1)CC2]
The title compound was prepared using a procedure similar to that used to prepare the compound in example 1 step f
Examples 4-6 shown in table 1 were prepared using the procedure similar to those of example 1 step g or example 3 from the corresponding intermediates.
TABLE 1
| Example | Structure | ESI-MS m/z: [M + H]$^+$ |
| --- | --- | --- |
| 4 | 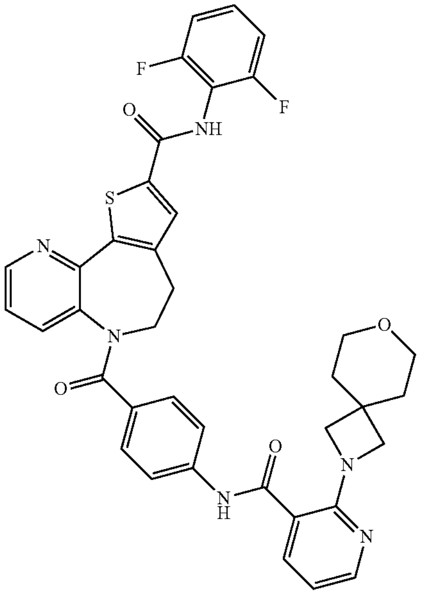 [SMILES: O=C(Nc1c(F)cccc1F)c1cc2c(s1)-c1ncccc1N(C(=O)c1ccc(NC(=O)c3cccnc3N3CC4(CCOCC4)C3)cc1)CC2] | 707.25 |
| 5 | 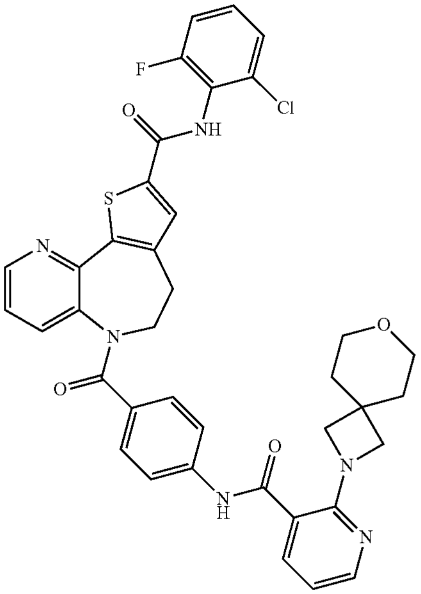 [SMILES: O=C(Nc1c(F)cccc1Cl)c1cc2c(s1)-c1ncccc1N(C(=O)c1ccc(NC(=O)c3cccnc3N3CC4(CCOCC4)C3)cc1)CC2] | 723.50 |
| 6 | 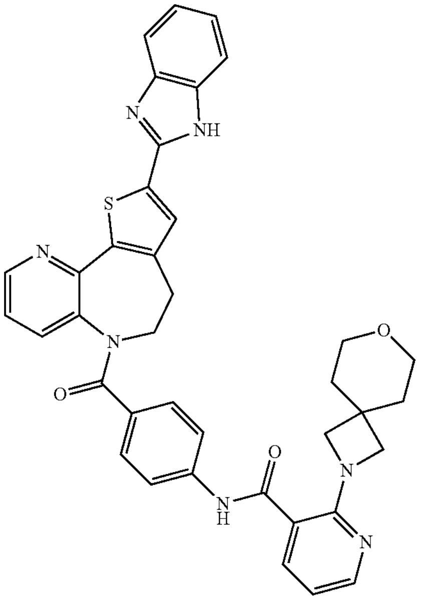 [SMILES: O=C(Nc1ccc(C(=O)N2CCc3cc(-c4nc5ccccc5[nH]4)sc3-c3ncccc32)cc1)c1cccnc1N1CC2(CCOCC2)C1] | 667.85 |

Scheme 9

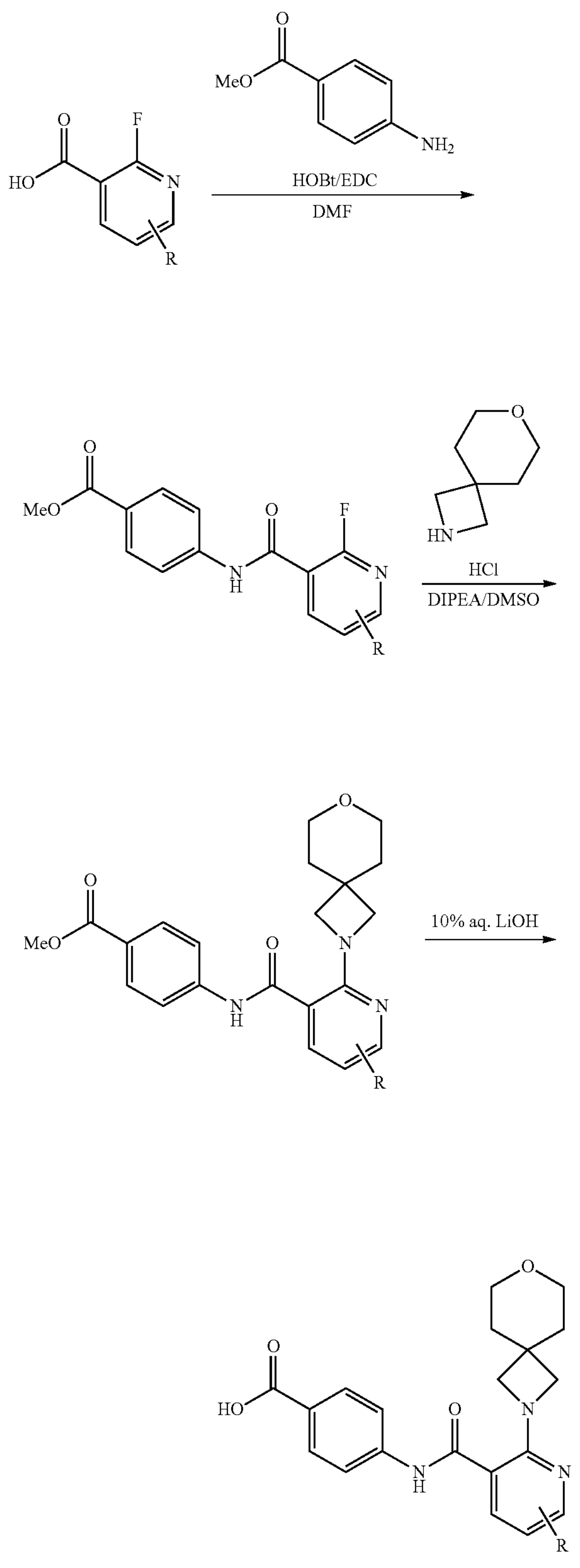

R = H, Me

Example 7

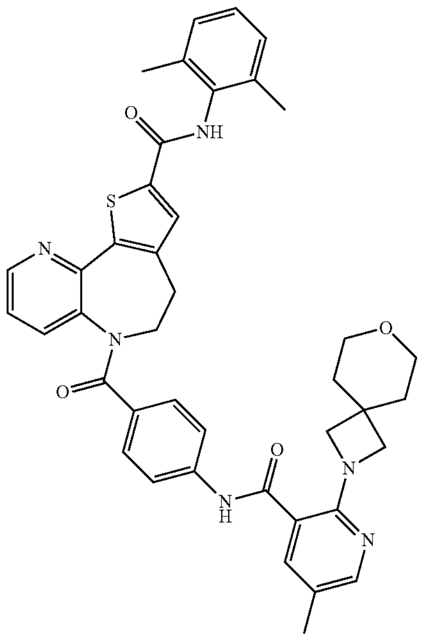 [SMILES: Cc1cnc(N2CC3(CCOCC3)C2)c(C(=O)Nc2ccc(C(=O)N3CCc4cc(C(=O)Nc5c(C)cccc5C)sc4-c4ncccc43)cc2)c1]

Example 7 Step a

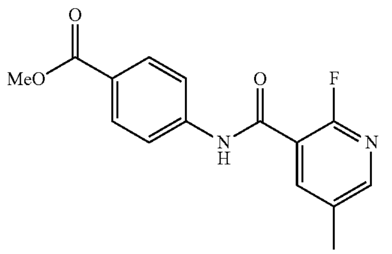 [SMILES: COC(=O)c1ccc(NC(=O)c2cc(C)cnc2F)cc1]

To a cooled to 0° C. mixture of 4-amino-benzoic acid methyl ester (0.930 g, 61.7 mmol) and 2-fluoro-5-methyl-nicotinic acid (10.0 g, 64.5 mmol) was added a solution of HOBt (10.0 g, 74.0 mmol) in dry DMF (100 mL). EDC (11.0 g, 70.9 mmol) was added and the reaction mass was stirred overnight at room temperature. The resulting mixture was poured into cold water (600 mL). The precipitated solid was collected by filtration, washed with water, and dried in vacuum to obtain methyl 4-(2-fluoro-5-methylnicotinamido)benzoate (14.2 g, 80%).

Example 7 Step b

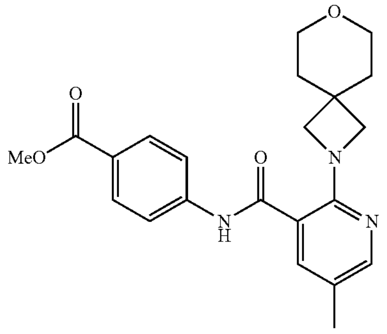 [SMILES: COC(=O)c1ccc(NC(=O)c2cc(C)cnc2N2CC3(CCOCC3)C2)cc1]

A mixture of methyl 4-(2-fluoro-5-methylnicotinamido)benzoate (9.30 g, 32.3 mmol), 7-oxa-2-aza-spiro[3.5]nonane hydrochloride (5.60 g, 34.0 mmol), and DIPEA (7.20 g, 55.7 mmol) in DMSO (50 mL) was stirred at 90° C. for 24 h, cooled to room temperature, and diluted with water. The precipitated solid was collected by filtration, washed with water, 2-propanol, and hexane, and dried to obtain methyl 4-(5-methyl-2-(7-oxa-2-azaspiro[3.5]nonan-2-yl)nicotinamido)benzoate (12.0 g, 94%).

Example 7 Step c

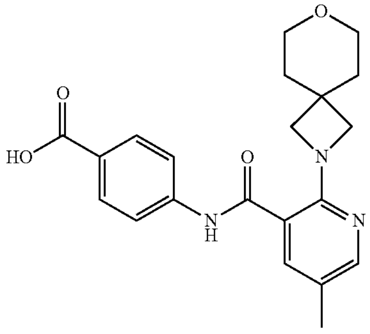 [SMILES: Cc1cnc(N2CC3(CCOCC3)C2)c(C(=O)Nc2ccc(C(=O)O)cc2)c1]

To a solution of methyl 4-(5-methyl-2-(7-oxa-2-azaspiro[3.5]nonan-2-yl)nicotinamido)benzoate (12.0 g, 30.3 mmol) in THF (100 mL), 10% aqueous LiOH (20 mL) was added and the reaction mass was stirred until TLC revealed completion of the reaction (approx. 48 h). The volatiles were evaporated and water (100 mL) was added to the residue. The mixture was acidified to pH 3 with 10% hydrochloric acid and filtered. The obtained solid was washed with water and dried in vacuum to obtain 4-(5-methyl-2-(7-oxa-2-azaspiro[3.5]nonan-2-yl)nicotinamido)benzoic acid (9.60 g, 83%).

Example 7 Step d

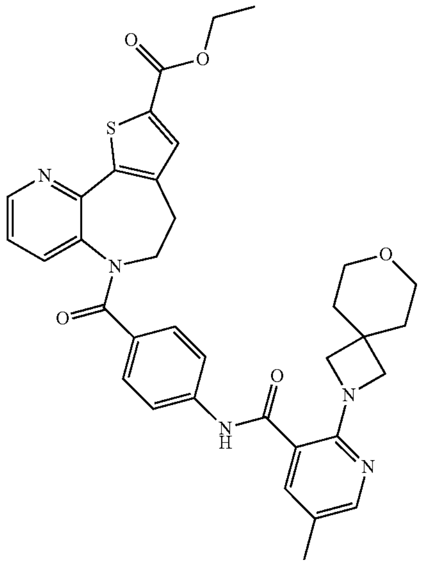 [SMILES: CCOC(=O)c1cc2c(s1)-c1ncccc1N(C(=O)c1ccc(NC(=O)c3cc(C)cnc3N3CC4(CCOCC4)C3)cc1)CC2]

The title compound was prepared from the compounds (example 3 step h and example 7 step c) using a procedure similar to that of intermediate 1 step e.

Example 7 Step e

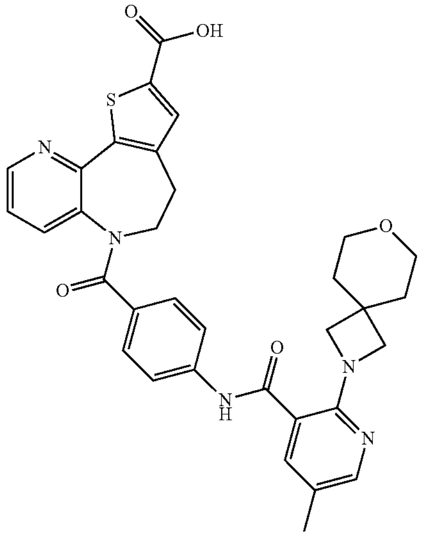 [SMILES: Cc1cnc(N2CC3(CCOCC3)C2)c(C(=O)Nc2ccc(C(=O)N3CCc4cc(C(=O)O)sc4-c4ncccc43)cc2)c1]

The title compound was prepared using a procedure similar to that of example 1 step f.

Examples 7-49 shown in table 2 were prepared using the procedure similar to that of example 1 step g and example 3 from the corresponding intermediates.

TABLE 2
| Example | Structure | ESI-MS m/z: [M + H]+ |
|---|---|---|
| 7 | 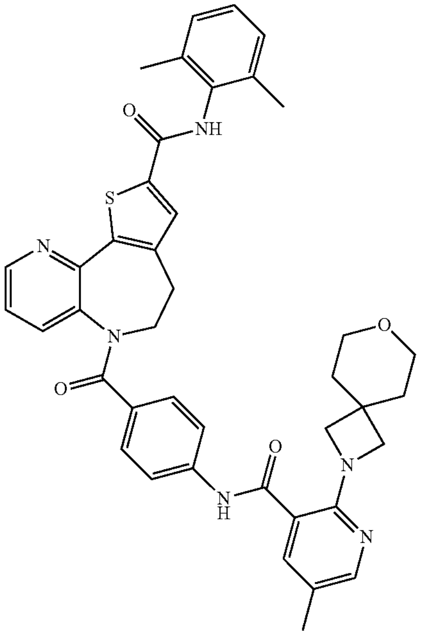 [SMILES: Cc1cnc(N2CC3(CCOCC3)C2)c(C(=O)Nc2ccc(C(=O)N3CCc4cc(C(=O)Nc5c(C)cccc5C)sc4-c4ncccc43)cc2)c1] | 713.0 |
| 8 | 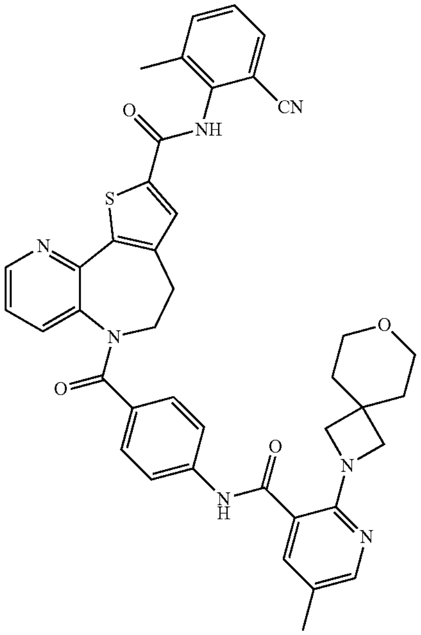 [SMILES: Cc1cnc(N2CC3(CCOCC3)C2)c(C(=O)Nc2ccc(C(=O)N3CCc4cc(C(=O)Nc5c(C)cccc5C#N)sc4-c4ncccc43)cc2)c1] | 724.1 |
TABLE 2-continued
| Example | Structure | ESI-MS m/z: [M + H]+ |
|---|---|---|
| 9 | 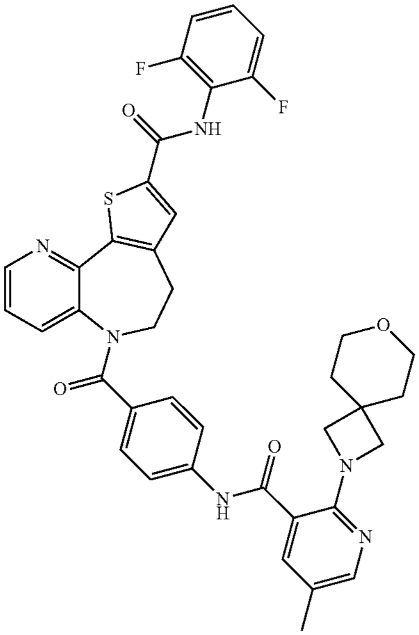 [SMILES: Cc1cnc(N2CC3(CCOCC3)C2)c(C(=O)Nc2ccc(C(=O)N3CCc4cc(C(=O)Nc5c(F)cccc5F)sc4-c4ncccc43)cc2)c1] | 721.1 |
| 10 | 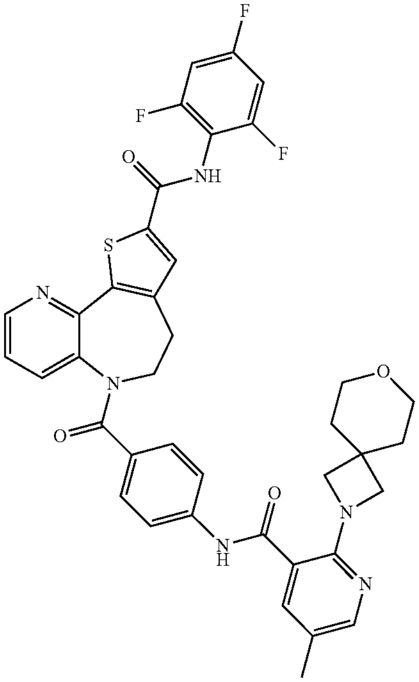 [SMILES: Cc1cnc(N2CC3(CCOCC3)C2)c(C(=O)Nc2ccc(C(=O)N3CCc4cc(C(=O)Nc5c(F)cc(F)cc5F)sc4-c4ncccc43)cc2)c1] | 739.1 |

TABLE 2-continued
| Example | Structure | ESI-MS m/z: [M + H]+ |
|---|---|---|
| 11 | 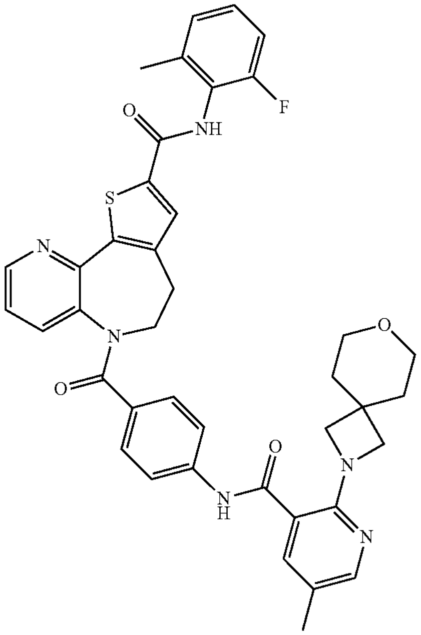 [SMILES: Cc1cnc(N2CC3(CCOCC3)C2)c(C(=O)Nc2ccc(C(=O)N3CCc4cc(C(=O)Nc5c(C)cccc5F)sc4-c4ncccc43)cc2)c1] | 717.1 |
| 12 | 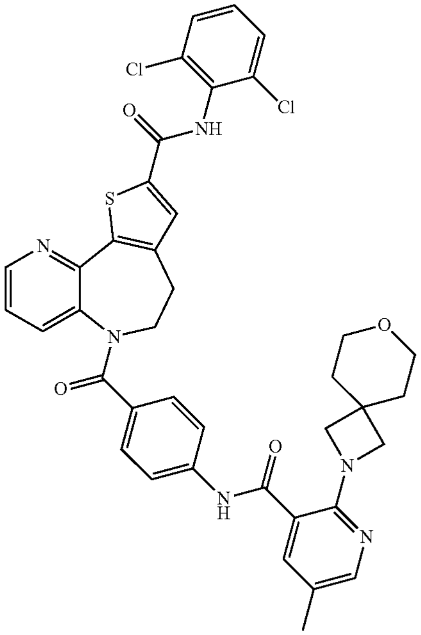 [SMILES: Cc1cnc(N2CC3(CCOCC3)C2)c(C(=O)Nc2ccc(C(=O)N3CCc4cc(C(=O)Nc5c(Cl)cccc5Cl)sc4-c4ncccc43)cc2)c1] | 754.1 |
| 13 | 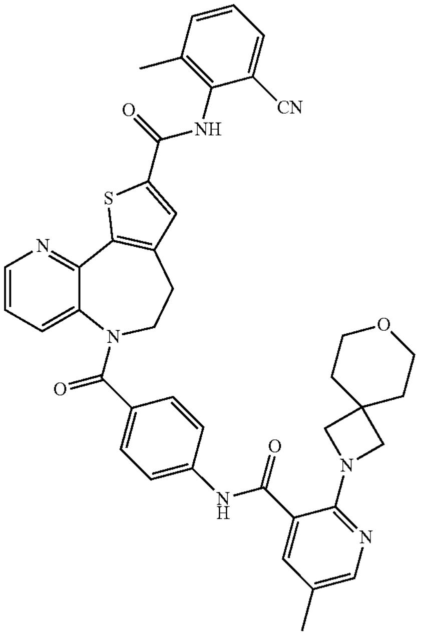 [SMILES: Cc1cnc(N2CC3(CCOCC3)C2)c(C(=O)Nc2ccc(C(=O)N3CCc4cc(C(=O)Nc5c(C)cccc5C#N)sc4-c4ncccc43)cc2)c1] | 724.1 |
| 14 | 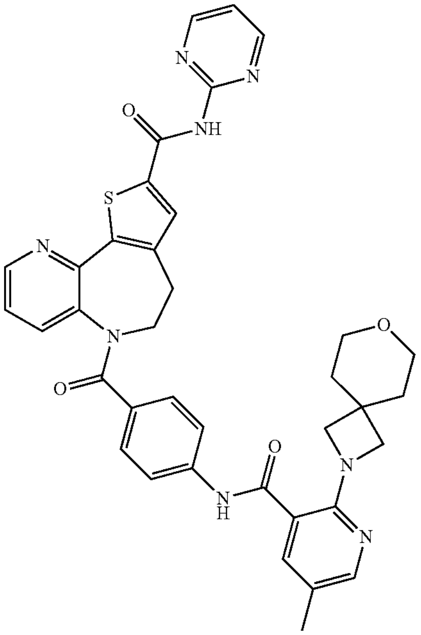 [SMILES: Cc1cnc(N2CC3(CCOCC3)C2)c(C(=O)Nc2ccc(C(=O)N3CCc4cc(C(=O)Nc5ncccn5)sc4-c4ncccc43)cc2)c1] | 687.0 |

TABLE 2-continued
| Example | Structure | ESI-MS m/z: [M + H]+ |
|---|---|---|
| 15 | 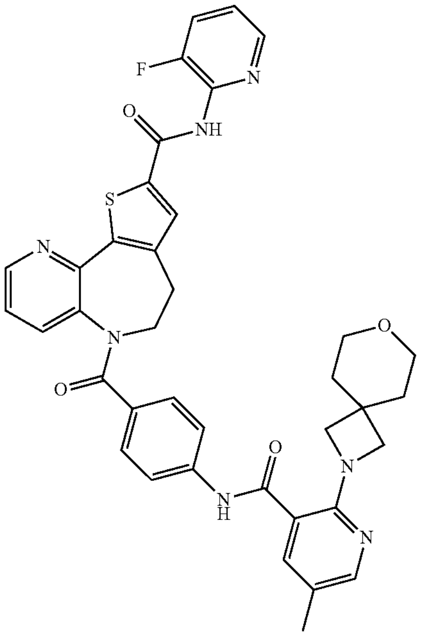 [SMILES: Cc1cnc(N2CC3(CCOCC3)C2)c(C(=O)Nc2ccc(C(=O)N3CCc4cc(C(=O)Nc5ncccc5F)sc4-c4ncccc43)cc2)c1] | 704.0 |
| 16 | 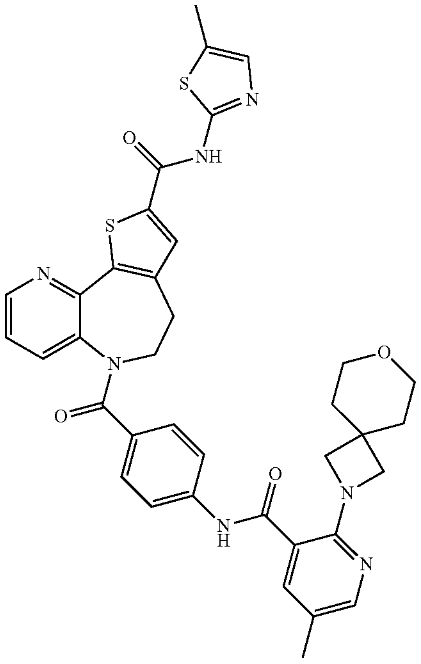 [SMILES: Cc1cnc(N2CC3(CCOCC3)C2)c(C(=O)Nc2ccc(C(=O)N3CCc4cc(C(=O)Nc5ncc(C)s5)sc4-c4ncccc43)cc2)c1] | 706.0 |
TABLE 2-continued
| Example | Structure | ESI-MS m/z: [M + H]+ |
|---|---|---|
| 17 | 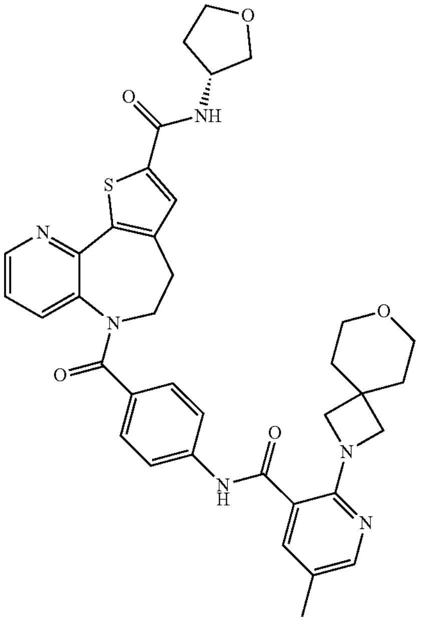 [SMILES: Cc1cnc(N2CC3(CCOCC3)C2)c(C(=O)Nc2ccc(C(=O)N3CCc4cc(C(=O)N[C@@H]5CCOC5)sc4-c4ncccc43)cc2)c1] | 679.0 |
| 18 | 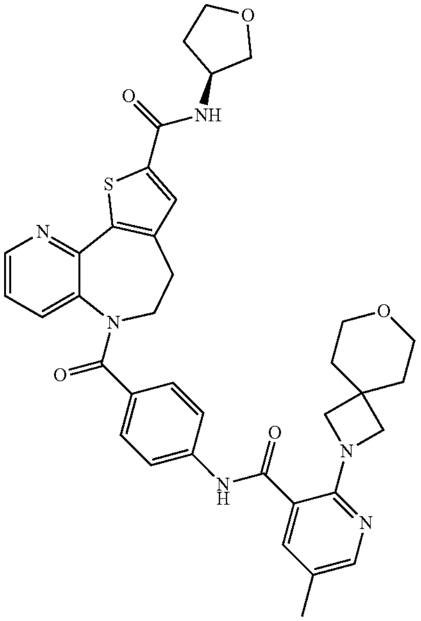 [SMILES: Cc1cnc(N2CC3(CCOCC3)C2)c(C(=O)Nc2ccc(C(=O)N3CCc4cc(C(=O)N[C@H]5CCOC5)sc4-c4ncccc43)cc2)c1] | 679.0 |

TABLE 2-continued
| Example | Structure | ESI-MS m/z: [M + H]+ |
|---|---|---|
| 19 | 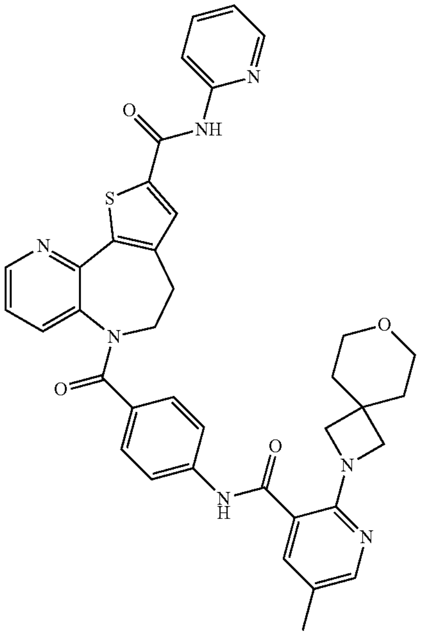 [SMILES: Cc1cnc(N2CC3(CCOCC3)C2)c(C(=O)Nc2ccc(C(=O)N3CCc4cc(C(=O)Nc5ccccn5)sc4-c4ncccc43)cc2)c1] | 686.0 |
| 20 | 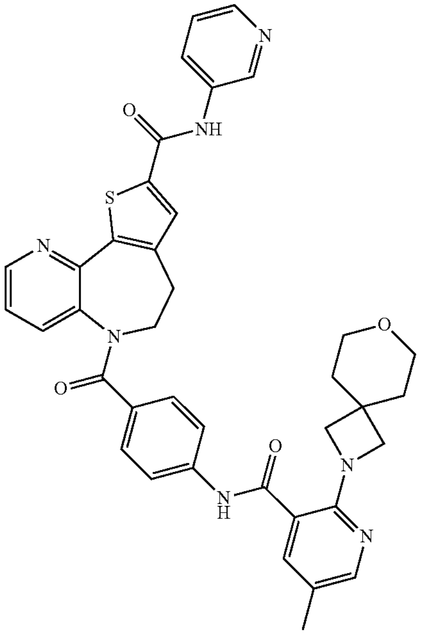 [SMILES: Cc1cnc(N2CC3(CCOCC3)C2)c(C(=O)Nc2ccc(C(=O)N3CCc4cc(C(=O)Nc5cccnc5)sc4-c4ncccc43)cc2)c1] | 686.0 |
TABLE 2-continued
| Example | Structure | ESI-MS m/z: [M + H]+ |
|---|---|---|
| 21 | 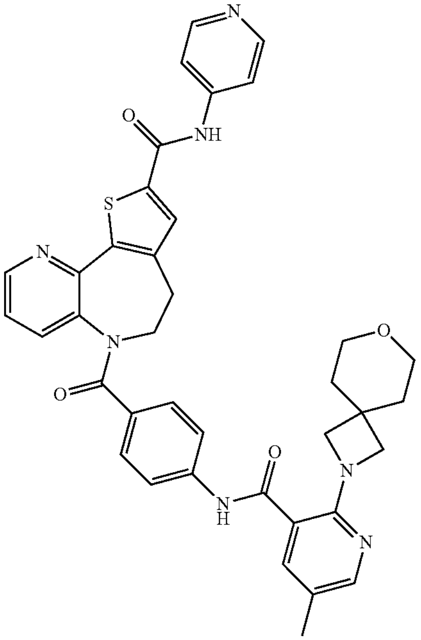 [SMILES: Cc1cnc(N2CC3(CCOCC3)C2)c(C(=O)Nc2ccc(C(=O)N3CCc4cc(C(=O)Nc5ccncc5)sc4-c4ncccc43)cc2)c1] | 686.0 |
| 22 | 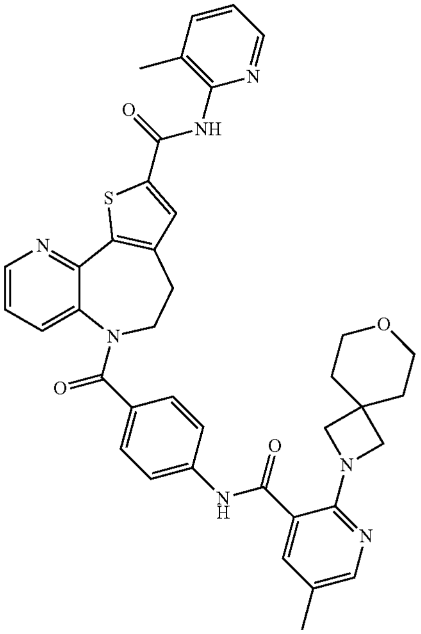 [SMILES: Cc1cnc(N2CC3(CCOCC3)C2)c(C(=O)Nc2ccc(C(=O)N3CCc4cc(C(=O)Nc5ncccc5C)sc4-c4ncccc43)cc2)c1] | 700.0 |

TABLE 2-continued
| Example | Structure | ESI-MS m/z: [M + H]+ |
|---|---|---|
| 23 | 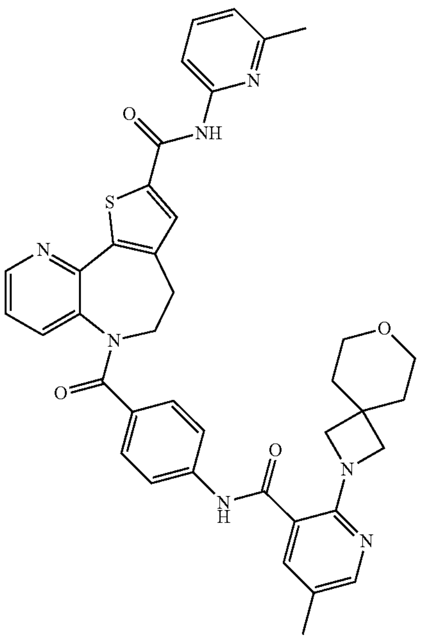 [SMILES: Cc1cnc(N2CC3(CCOCC3)C2)c(C(=O)Nc2ccc(C(=O)N3CCc4cc(C(=O)Nc5cccc(C)n5)sc4-c4ncccc43)cc2)c1] | 700.0 |
| 24 | 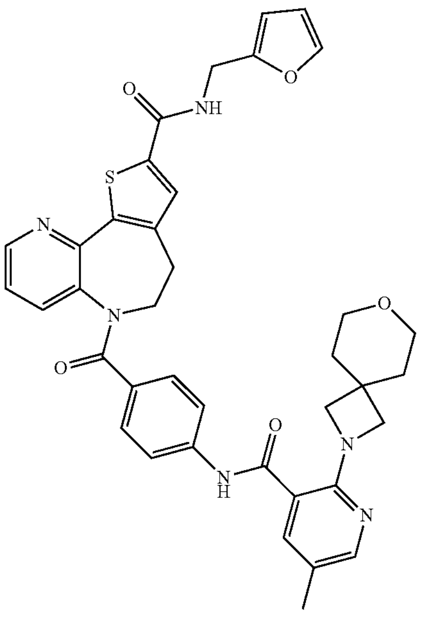 [SMILES: Cc1cnc(N2CC3(CCOCC3)C2)c(C(=O)Nc2ccc(C(=O)N3CCc4cc(C(=O)NCc5ccco5)sc4-c4ncccc43)cc2)c1] | 689.0 |
| 25 | 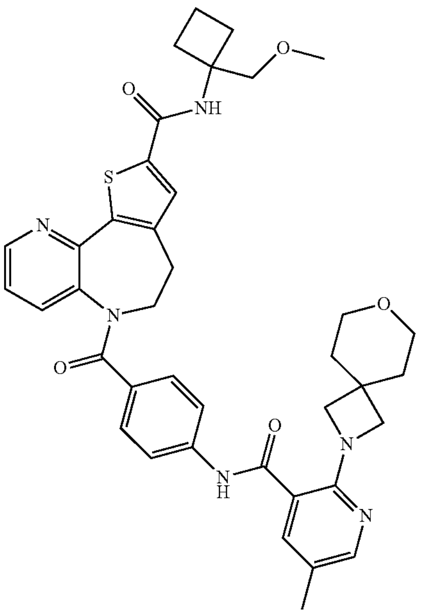 [SMILES: COCC1(NC(=O)c2cc3c(s2)-c2ncccc2N(C(=O)c2ccc(NC(=O)c4cc(C)cnc4N4CC5(CCOCC5)C4)cc2)CC3)CCC1] | 707.0 |
| 26 | 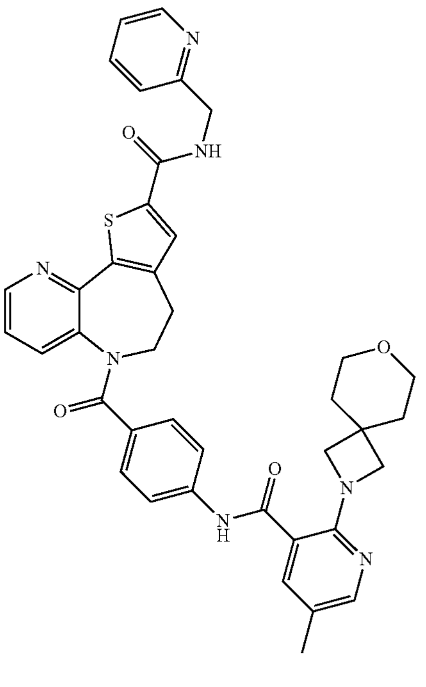 [SMILES: Cc1cnc(N2CC3(CCOCC3)C2)c(C(=O)Nc2ccc(C(=O)N3CCc4cc(C(=O)NCc5ccccn5)sc4-c4ncccc43)cc2)c1] | 700.0 |

TABLE 2-continued
| Example | Structure | ESI-MS m/z: [M + H]+ |
|---|---|---|
| 27 | 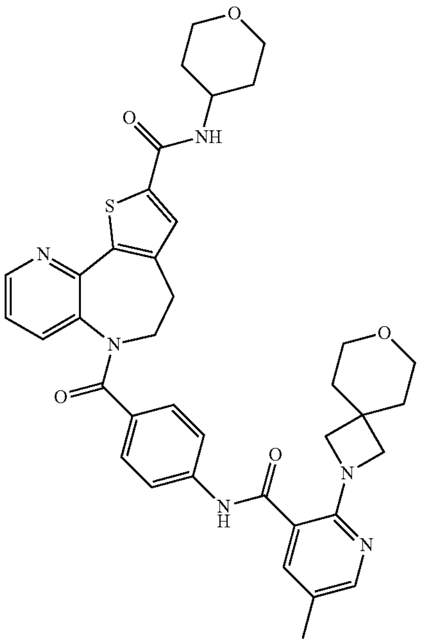 [SMILES: Cc1cnc(N2CC3(CCOCC3)C2)c(C(=O)Nc2ccc(C(=O)N3CCc4cc(C(=O)NC5CCOCC5)sc4-c4ncccc43)cc2)c1] | 693.0 |
| 28 | 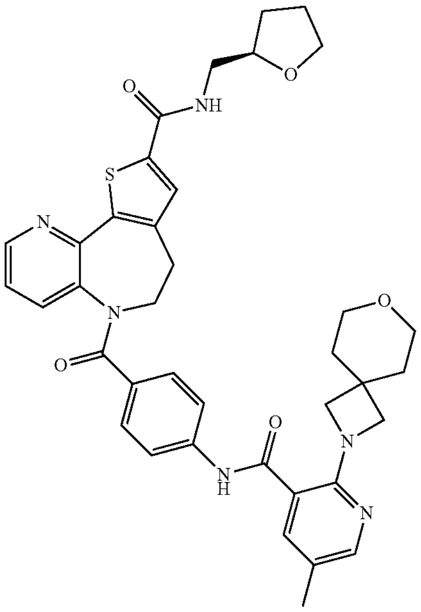 [SMILES: Cc1cnc(N2CC3(CCOCC3)C2)c(C(=O)Nc2ccc(C(=O)N3CCc4cc(C(=O)NC[C@H]5CCCO5)sc4-c4ncccc43)cc2)c1] | 693.0 |
TABLE 2-continued
| Example | Structure | ESI-MS m/z: [M + H]+ |
|---|---|---|
| 29 | 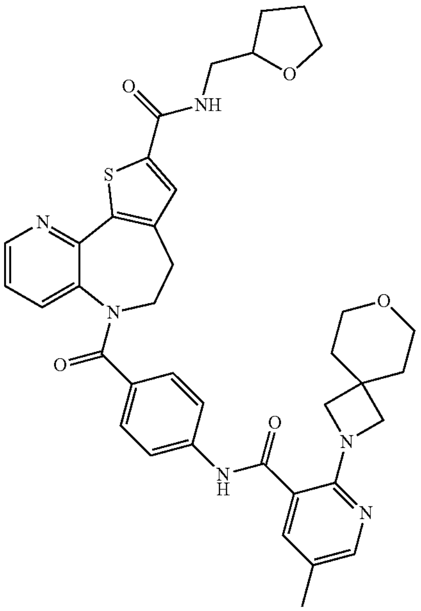 [SMILES: Cc1cnc(N2CC3(CCOCC3)C2)c(C(=O)Nc2ccc(C(=O)N3CCc4cc(C(=O)NCC5CCCO5)sc4-c4ncccc43)cc2)c1] | 693.0 |
| 30 | 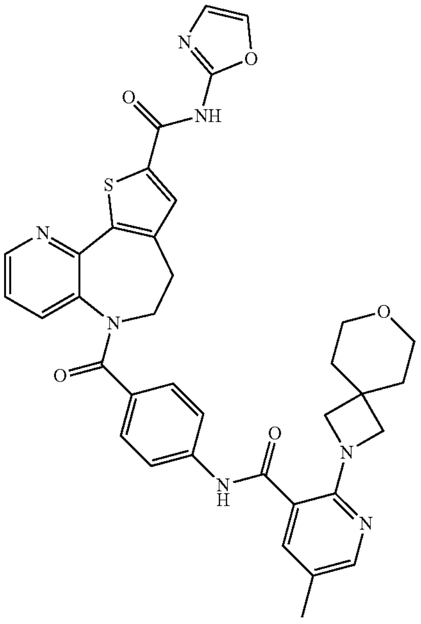 [SMILES: Cc1cnc(N2CC3(CCOCC3)C2)c(C(=O)Nc2ccc(C(=O)N3CCc4cc(C(=O)Nc5ncco5)sc4-c4ncccc43)cc2)c1] | 676.0 |

TABLE 2-continued
| Example | Structure | ESI-MS m/z: [M + H]+ |
|---|---|---|
| 31 | 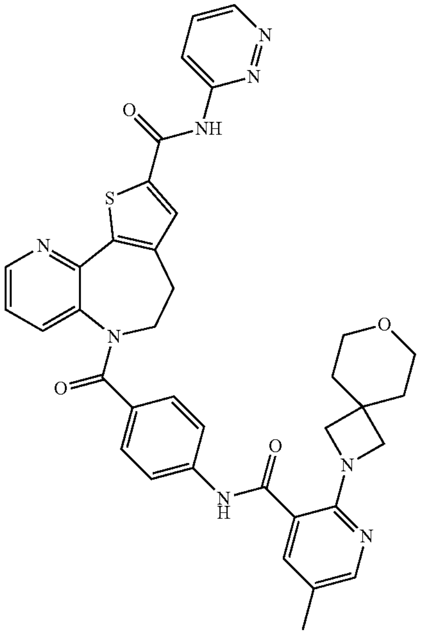 [SMILES: Cc1cnc(N2CC3(CCOCC3)C2)c(C(=O)Nc2ccc(C(=O)N3CCc4cc(C(=O)Nc5cccnn5)sc4-c4ncccc43)cc2)c1] | 687.0 |
| 32 | 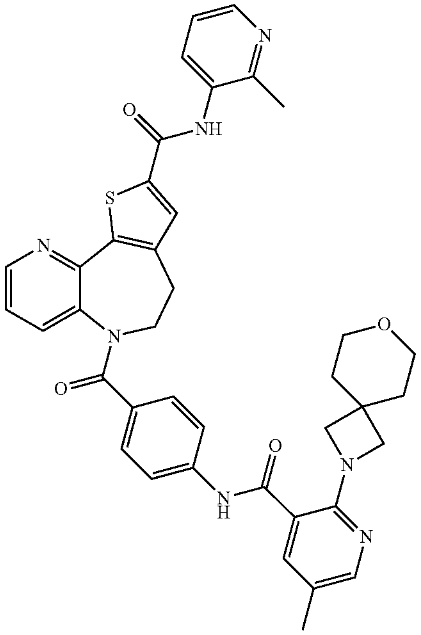 [SMILES: Cc1cnc(N2CC3(CCOCC3)C2)c(C(=O)Nc2ccc(C(=O)N3CCc4cc(C(=O)Nc5cccnc5C)sc4-c4ncccc43)cc2)c1] | 700.0 |
TABLE 2-continued
| Example | Structure | ESI-MS m/z: [M + H]+ |
|---|---|---|
| 33 | 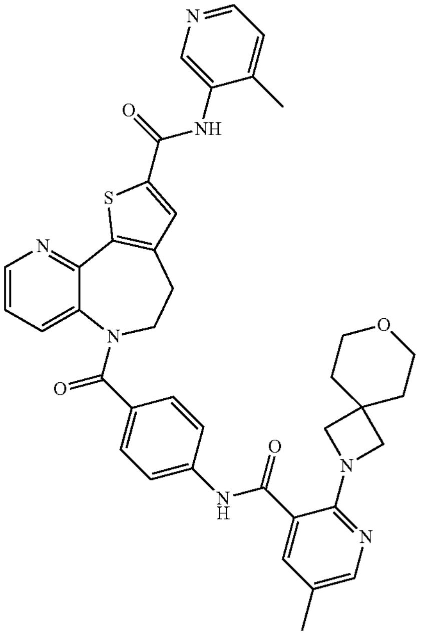 [SMILES: Cc1cnc(N2CC3(CCOCC3)C2)c(C(=O)Nc2ccc(C(=O)N3CCc4cc(C(=O)Nc5cnccc5C)sc4-c4ncccc43)cc2)c1] | 700.0 |
| 34 | 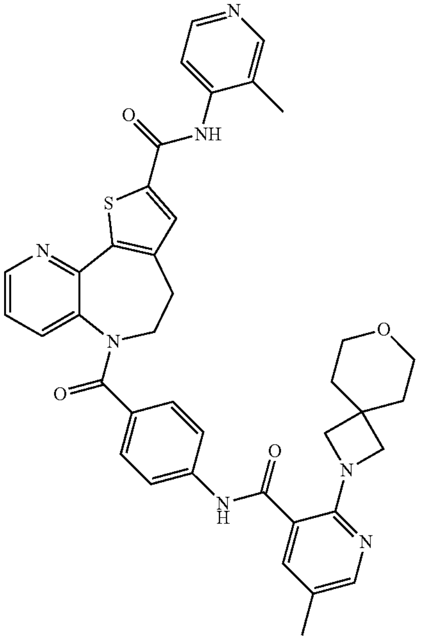 [SMILES: Cc1cnc(N2CC3(CCOCC3)C2)c(C(=O)Nc2ccc(C(=O)N3CCc4cc(C(=O)Nc5ccncc5C)sc4-c4ncccc43)cc2)c1] | 700.0 |

TABLE 2-continued
| Example | Structure | ESI-MS m/z: [M + H]+ |
|---|---|---|
| 35 | 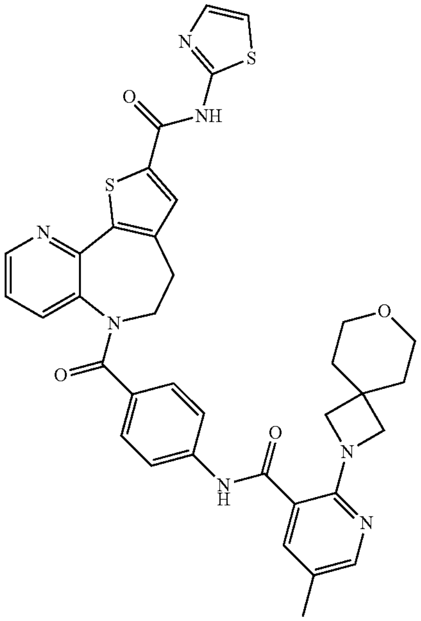 | 692.0 |
| 36 | 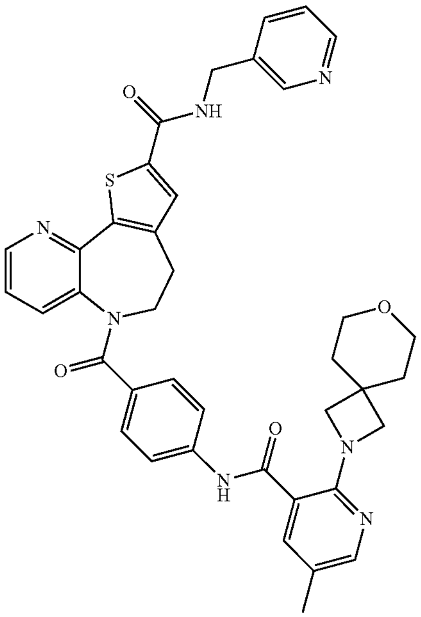 [SMILES: Cc1cnc(N2CC3(CCOCC3)C2)c(C(=O)Nc2ccc(C(=O)N3CCc4cc(C(=O)NCc5cccnc5)sc4-c4ncccc43)cc2)c1] | 700.0 |
TABLE 2-continued
| Example | Structure | ESI-MS m/z: [M + H]+ |
|---|---|---|
| 37 | 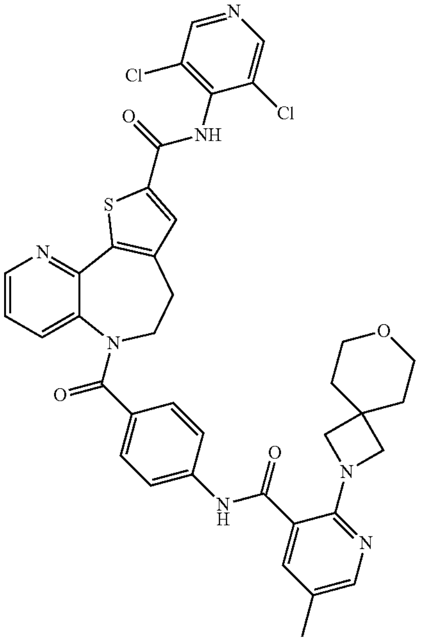 [SMILES: Cc1cnc(N2CC3(CCOCC3)C2)c(C(=O)Nc2ccc(C(=O)N3CCc4cc(C(=O)Nc5c(Cl)cncc5Cl)sc4-c4ncccc43)cc2)c1] | 755.0 |
| 38 | 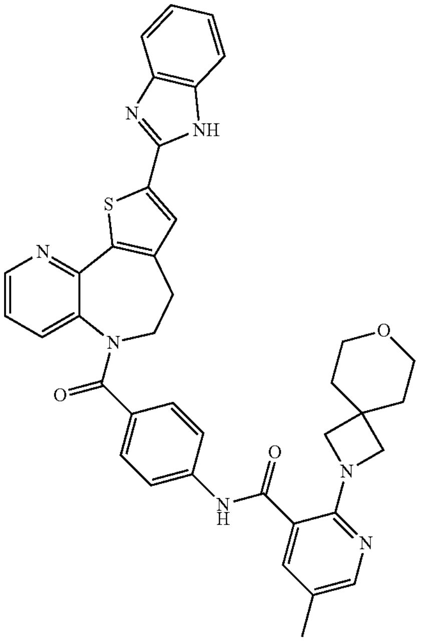 [SMILES: Cc1cnc(N2CC3(CCOCC3)C2)c(C(=O)Nc2ccc(C(=O)N3CCc4cc(-c5nc6ccccc6[nH]5)sc4-c4ncccc43)cc2)c1] | 682.26 |

TABLE 2-continued
| Example | Structure | ESI-MS m/z: [M + H]+ |
|---|---|---|
| 39 | 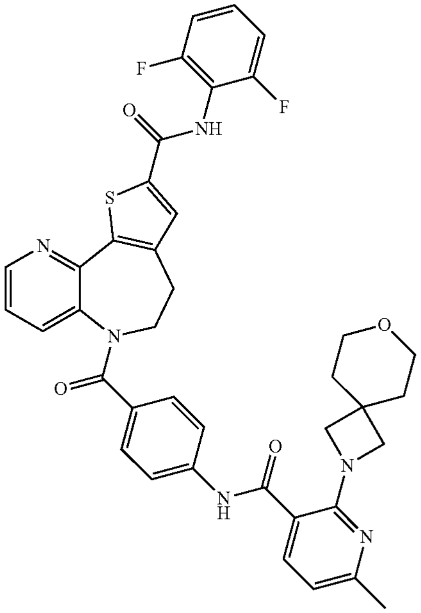 [SMILES: Cc1ccc(C(=O)Nc2ccc(C(=O)N3CCc4cc(C(=O)Nc5c(F)cccc5F)sc4-c4ncccc43)cc2)c(N2CC3(CCOCC3)C2)n1] | 721.22 |
| 40 | 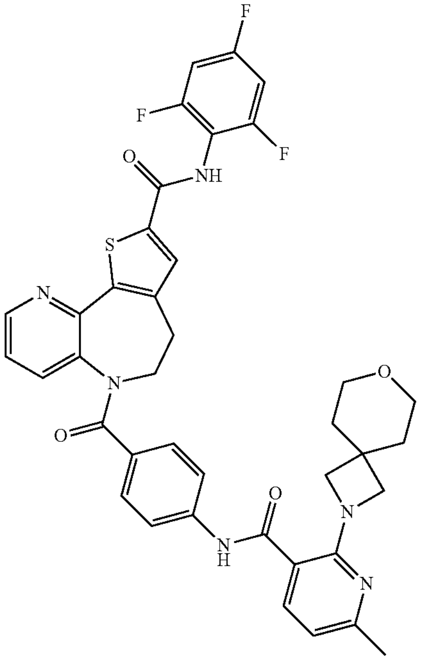 [SMILES: Cc1ccc(C(=O)Nc2ccc(C(=O)N3CCc4cc(C(=O)Nc5c(F)cc(F)cc5F)sc4-c4ncccc43)cc2)c(N2CC3(CCOCC3)C2)n1] | 739.35 |
TABLE 2-continued
| Example | Structure | ESI-MS m/z: [M + H]+ |
|---|---|---|
| 41 | 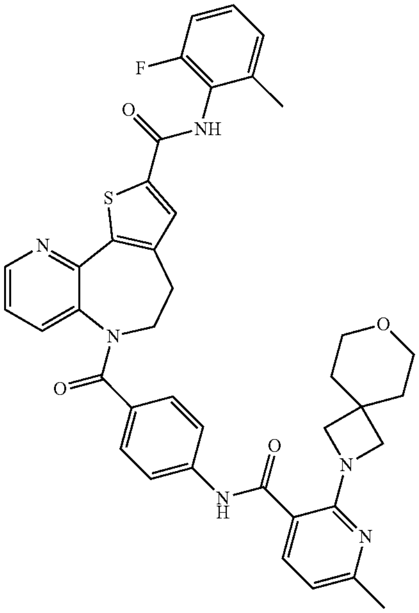 [SMILES: Cc1ccc(C(=O)Nc2ccc(C(=O)N3CCc4cc(C(=O)Nc5c(C)cccc5F)sc4-c4ncccc43)cc2)c(N2CC3(CCOCC3)C2)n1] | 717.3 |
| 42 | 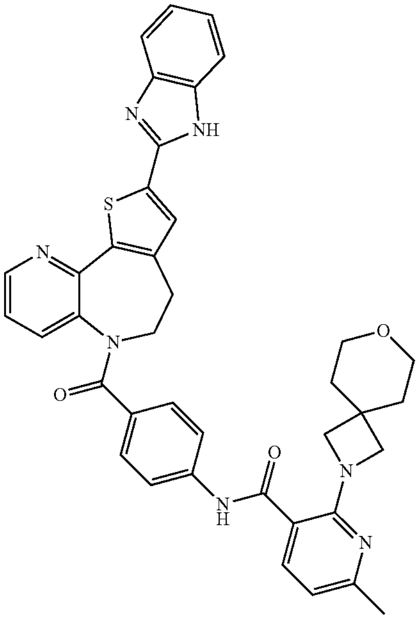 [SMILES: Cc1ccc(C(=O)Nc2ccc(C(=O)N3CCc4cc(-c5nc6ccccc6[nH]5)sc4-c4ncccc43)cc2)c(N2CC3(CCOCC3)C2)n1] | 682.4 |

TABLE 2-continued
| Example | Structure | ESI-MS m/z: [M + H]+ |
|---|---|---|
| 43 | 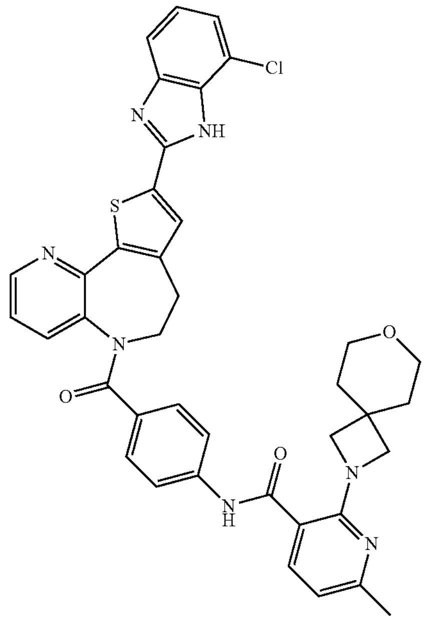 [SMILES: Cc1ccc(C(=O)Nc2ccc(C(=O)N3CCc4cc(-c5nc6cccc(Cl)c6[nH]5)sc4-c4ncccc43)cc2)c(N2CC3(CCOCC3)C2)n1] | 716. 2 |
| 44 | 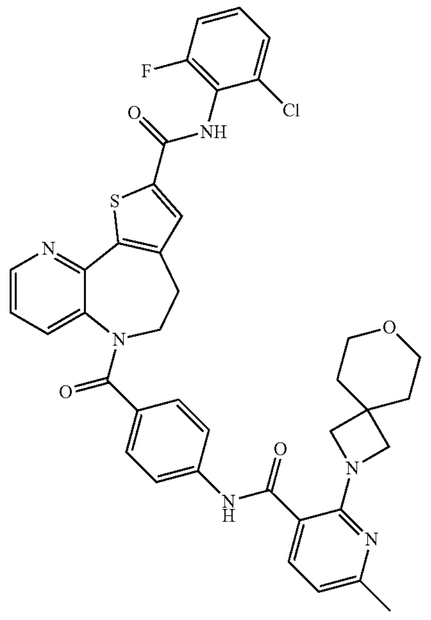 | 737.1 |
TABLE 2-continued
| Example | Structure | ESI-MS m/z: [M + H]+ |
|---|---|---|
| 45 | 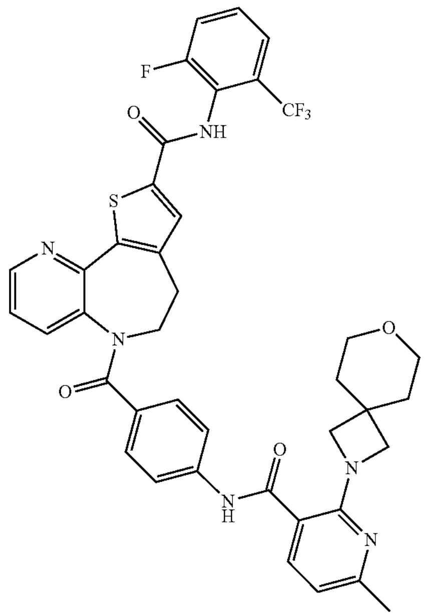 [SMILES: Cc1ccc(C(=O)Nc2ccc(C(=O)N3CCc4cc(C(=O)Nc5c(F)cccc5Cl)sc4-c4ncccc43)cc2)c(N2CC3(CCOCC3)C2)n1] | 771.25 |
| 46 | 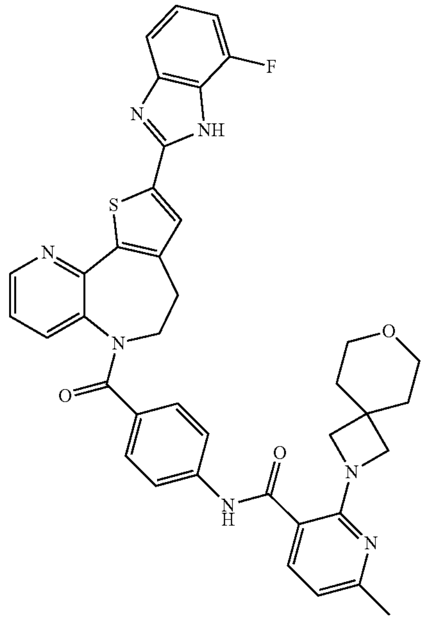 [SMILES: Cc1ccc(C(=O)Nc2ccc(C(=O)N3CCc4cc(-c5nc6cccc(F)c6[nH]5)sc4-c4ncccc43)cc2)c(N2CC3(CCOCC3)C2)n1] | 700.2 |

TABLE 2-continued
| Example | Structure | ESI-MS m/z: [M + H]+ |
|---|---|---|
| 47 | 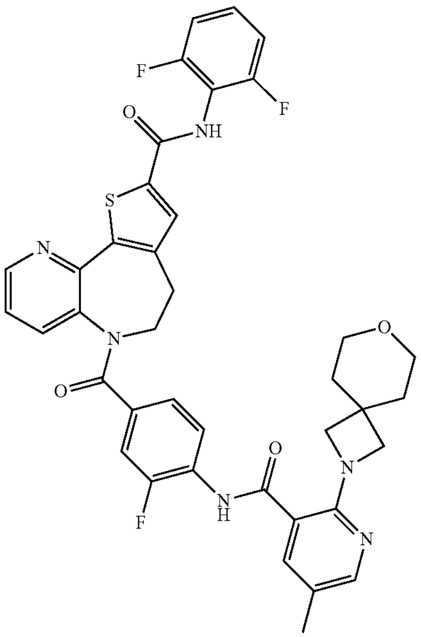 [SMILES: Cc1cnc(N2CC3(CCOCC3)C2)c(C(=O)Nc2ccc(C(=O)N3CCc4cc(C(=O)Nc5c(F)cccc5F)sc4-c4ncccc43)cc2F)c1] | 739.21 |
| 48 | 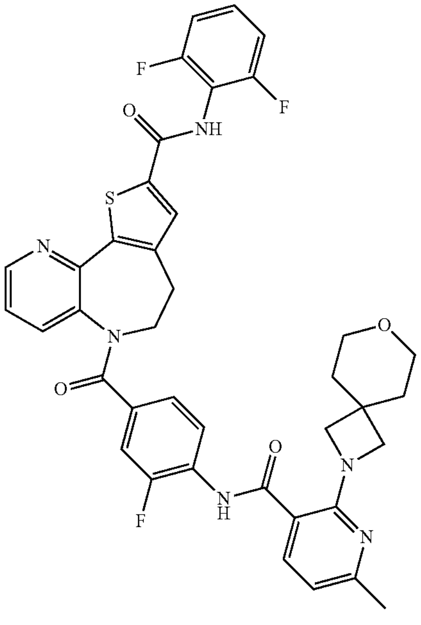 [SMILES: Cc1ccc(C(=O)Nc2ccc(C(=O)N3CCc4cc(C(=O)Nc5c(F)cccc5F)sc4-c4ncccc43)cc2F)c(N2CC3(CCOCC3)C2)n1] | 735.23 |
| 49 | 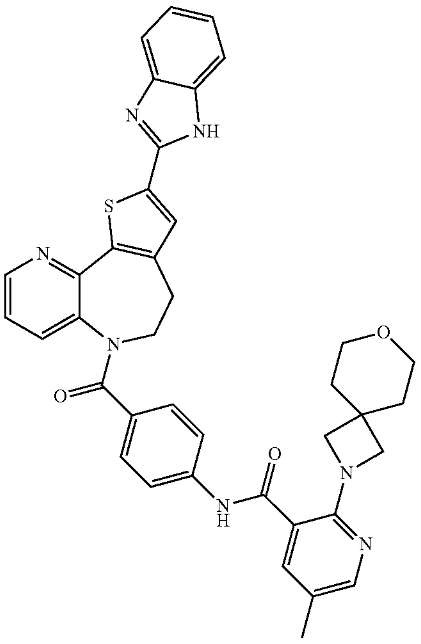 [SMILES: Cc1cnc(N2CC3(CCOCC3)C2)c(C(=O)Nc2ccc(C(=O)N3CCc4cc(-c5nc6ccccc6[nH]5)sc4-c4ncccc43)cc2)c1] | 682.26 |
Scheme 10
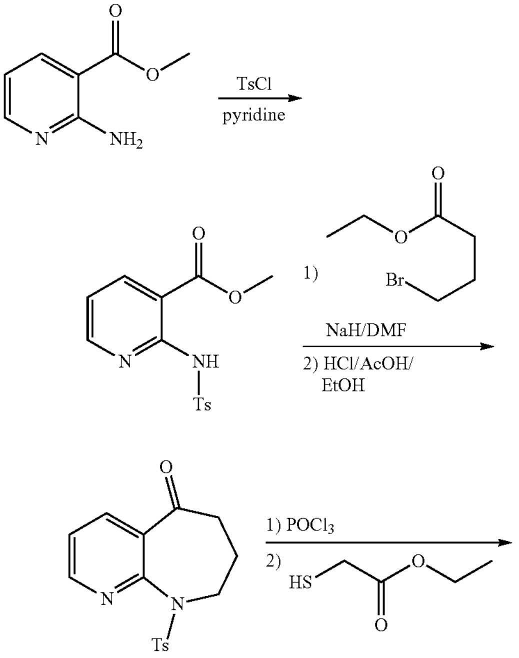

-continued

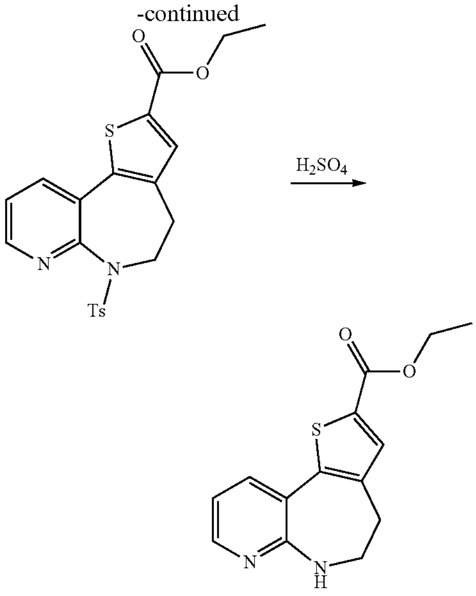

Example 50

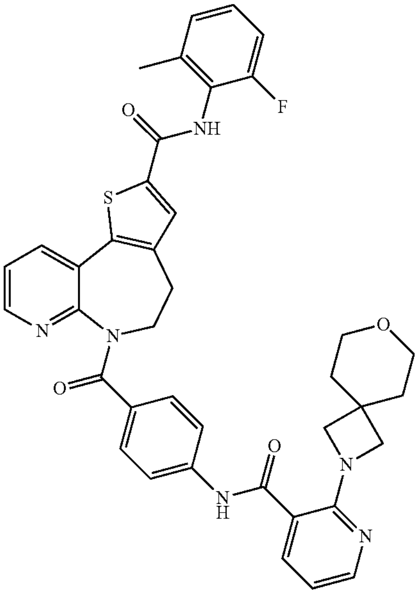 [SMILES: Cc1cccc(F)c1NC(=O)c1cc2c(s1)-c1cccnc1N(C(=O)c1ccc(NC(=O)c3cccnc3N3CC4(CCOCC4)C3)cc1)CC2]

Example 50 Step a

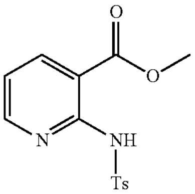 [SMILES: COC(=O)c1cccnc1NS(=O)(=O)c1ccc(C)cc1]

A mixture of methyl 2-aminonicotinate (1.0 g, 6.57 mmol) and Ts-Cl (1.2 g, 7.89 mmol) was stirred in pyridine (0.2 M) for 24 at rt. The mixture was poured into 5 volumes of cold water. The precipitated solid was collected by filtration, washed with water, and dried in vacuum to obtain methyl 2-((4-methylphenyl)sulfonamido)nicotinate (1.7 g, 84%).

Example 50 Step b

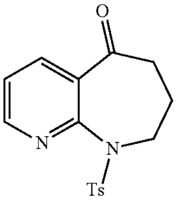 [SMILES: Cc1ccc(S(=O)(=O)N2CCCC(=O)c3cccnc32)cc1]

A stirred solution of the compound from step a (1.0 g, 3.26 mmol) in anhydrous DMF (0.2M) at 0° C. was treated slowly with NaH (60% in mineral oil, 157 mg, 3.92 mmol), then stirred 1.5 h at 0° C. The reaction mixture was treated dropwise with ethyl-4-bromobutanoate (700 mg, 3.59 mmol). After 30 min, the reaction mixture was heated at 90° C. for 10 h, then cooled to 0° C. To the reaction mixture was added NaH (60% in mineral oil, 157 mg, 3.92 mmol), followed by a solution of anhydrous toluene (2.2 mL) and MeOH (56 uL). After 10 h at room temperature, the reaction mixture was concentrated to yield a residue that was quenched with an aqueous $KHSO_4$ solution (1 M) and then extracted with C $HCl_3$. The organic layer was washed with brine, dried over $Na_2SO_4$, and concentrated in vacuo. In succession, the crude residue was dissolved in EtOH/AcOH/HCl conc/$H_2O$ (2/6/1/1 v/v, 0.4 M) solution, placed in a microwave reactor, and heated under microwave irradiation at 160° C. for 10 min. The reaction mixture was brought to pH=4 using an aqueous NaOH solution, and extracted twice with C $HCl_3$. Combined organic layers were washed with brine, dried over $Na_2SO_4$, and concentrated to yield a residue that was purified on silica gel with 0-100% ethyl acetate:hexanes to provide the desired compound (450 mg, 44%).

Example 50 Step c

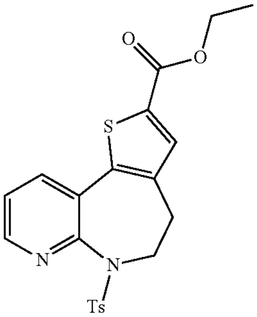 [SMILES: CCOC(=O)c1cc2c(s1)-c1cccnc1N(S(=O)(=O)c1ccc(C)cc1)CC2]

To an oven-dried vial, $POCl_3$ (654 mg, 4.27 mmol) was added dropwise to DMF (0.2 M) at 0° C. under $N_2$. Next, a solution of the compound from step b (450 mg, 1.422 mmol) in DMF (0.2 M) was added to the vial at 0° C. The mixture was then sealed, warmed to room temperature and heated to 80° C. for 3 h. Next, 5 volumes of ice-cooled NaOAc (sat. aq) was added and the intermediate aldehyde was extracted with ethyl acetate (3×). The combined organic layers were washed with brine, dried over anhydrous $Na_2SO_4$, and concentrated. To an oven-dried vial, sodium ethoxide (97 mg, 1.422 mmol) was added to a solution of ethyl 2-mercaptoacetate (187 mg, 1.56 equiv) in ethanol (0.2 M) cooled to 0° C. under $N_2$. The mixture was stirred for 30 minutes and then intermediate aldehyde was added. The resulted mixture was stirred at 0° C. for 30 minutes and then refluxed for 2.5 h. The mixture was then cooled to room temperature and 2N HCl aqueous was added to adjust the pH to 7. The mixture was extracted with ethyl acetate (3×) and the combined organic phase was washed with water and brine. The crude product was dried over anhydrous $Na_2SO_4$, concentrated, then purified on silica gel with 0-100% ethyl acetate: hexanes to provide ethyl 6-tosyl-5,6-dihydro-4H-pyrido[2,3-b]thieno[2,3-d]azepine-2-carboxylate (262 mg, 43%).

Example 50

Step d

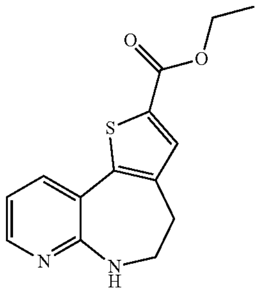 [SMILES: CCOC(=O)c1cc2c(s1)-c1cccnc1NCC2]

A mixture of the compound from step b (780 mg, 1.82 mmol) and conc. $H_2SO_4$ (3 mL) was stirred at 50° C. for 30 min. After cooling to rt, the reaction mixture was poured into 10 volumes of water. The pH was adjusted to 3 by addition of solid NaOH. The product was extracted with ethyl acetate (3×), concentrated, and purified on silica gel with 0-100% ethyl acetate:hexanes to provide the desired compound (375 mg, 75%).

Example 50

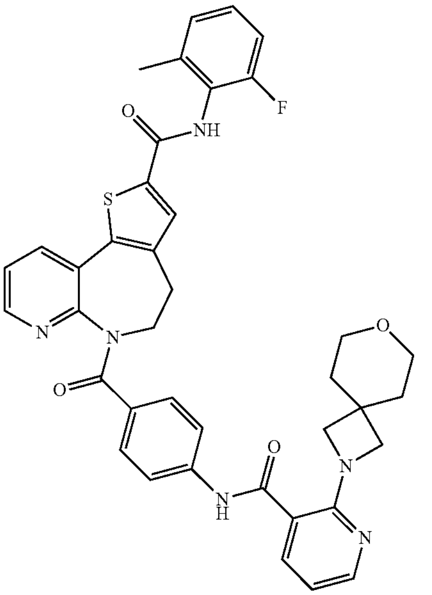 [SMILES: Cc1cccc(F)c1NC(=O)c1cc2c(s1)-c1cccnc1N(C(=O)c1ccc(NC(=O)c3cccnc3N3CC4(CCOCC4)C3)cc1)CC2]

Example 50 was prepared from the compound in step d using the procedure similar to that of example 7.

Scheme 11

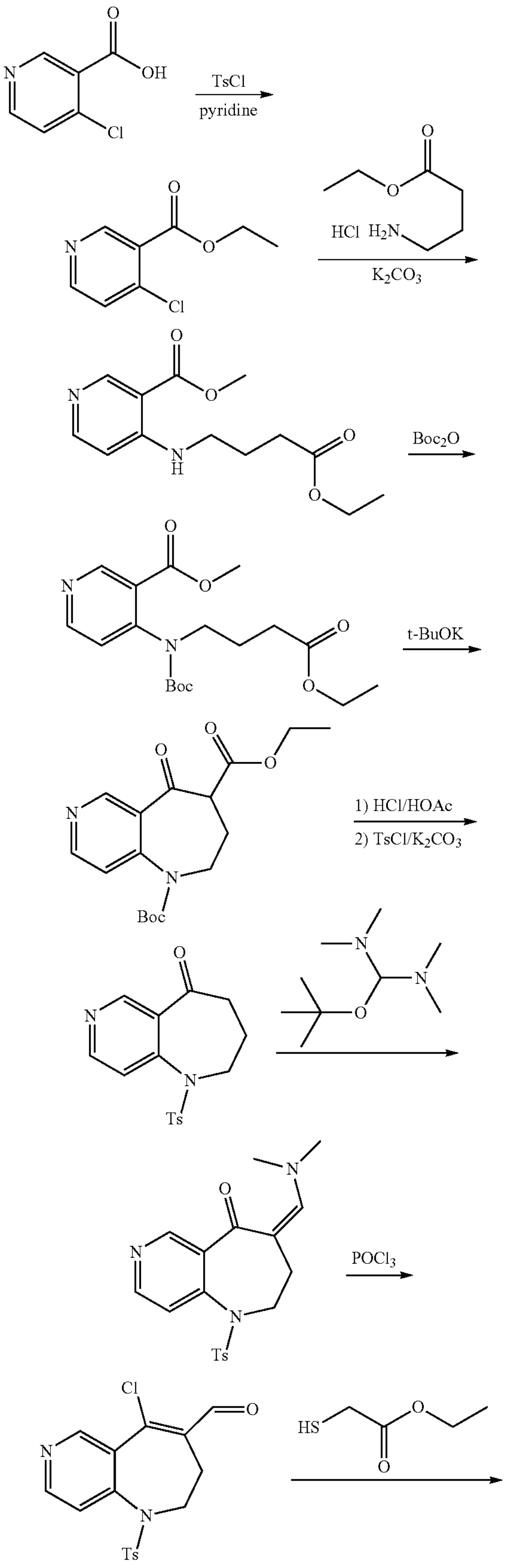

-continued

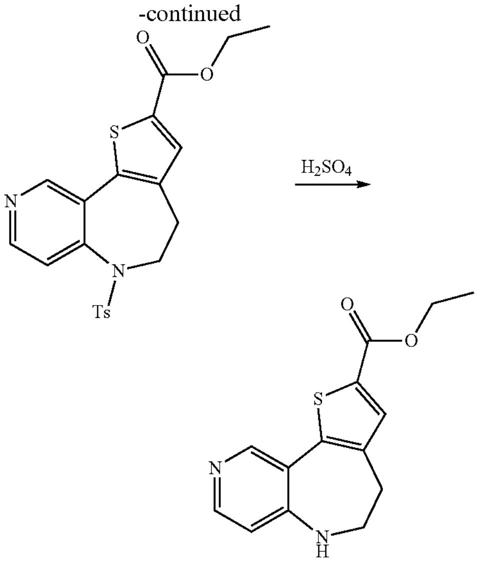

Intermediate 3

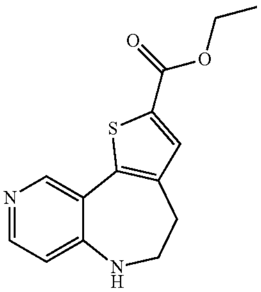 [SMILES: CCOC(=O)c1cc2c(s1)-c1cnccc1NCC2]

Intermediate 3 step a:

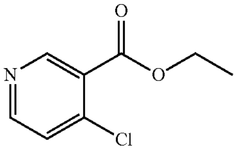

To a mixture of 4-chloropyridine-3-carboxylic acid (40 g, 253.88 mmol) in DCM (400 mL) was dropwise added thionyl chloride (90 g). This was followed by the addition of N,N-dimethylformamide (0.5 mL). The resulting solution was stirred at 90° C. for 3 hrs. Then, the resulting mixture was concentrated under vacuum. To this was added ethanol (400 mL) and triethylamine (51 g) and stirred at rt for overnight. The reaction was then quenched by the addition of water/ice (600 mL). The resulting solution was extracted with DCM (2×500 mL). The combined organic layer was washed with brine (2×500 mL), dried over anhydrous sodium sulfate, filtered and concentrated under vacuum to provide the desired compound (40 g) as a dark red oil.

Intermediate 3 Step b:

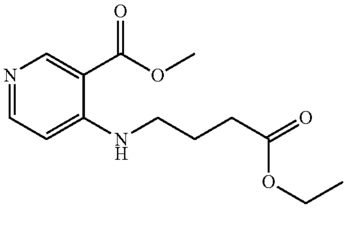 [SMILES: CCOC(=O)CCCNc1ccncc1C(=O)OC]

A mixture of the compound from step a (40 g, 215.51 mmol), $K_2CO_3$ (89 g, 643.95 mmol) and ethyl 4-aminobutanoate hydrochloride (43 g, 256.51 mmol) in DME (500 mL) was stirred at 90° C. for overnight. The resulting mixture was concentrated under vacuum after filtration. The resulting solution was diluted with EtOAc (500 mL), washed with water (2×500 mL) and brine (500 mL), dried over anhydrous sodium sulfate, filtered and concentrated under vacuum. The residue was purified by silica gel column with EtOAc/petroleum ether (1:15-1:2) to afford the desired compound (35 g).

Intermediate 3 Step c:

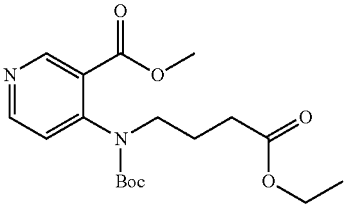 [SMILES: CCOC(=O)CCCN(C(=O)OC(C)(C)C)c1ccncc1C(=O)OC]

A mixture of the compound from step b (35 g, 124.86 mmol) and $Boc_2O$ (500 g, 2.29 mol, 18.35 equiv). The resulting solution was stirred at 90° C. for 16 hrs. After being concentrated, the residue was was purified by silica gel column with EtOAc/petroleum ether (1:50-1:20-1:3) to afford the desired compound (40 g) as a solid. ESI-MS m/z: 381.2 $[M+H]^+$.

Intermediate 3 Step d:

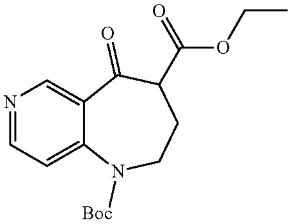 [SMILES: CCOC(=O)C1CCN(C(=O)OC(C)(C)C)c2ccncc2C1=O]

To a mixture of t-BuOK (41 g, 365.39 mmol) in toluene (400 mL) was dropwise added the compound from step c (40 g, 105.14 mmol) in toluene (400 mL) at rt for 1 hr. The resulting solution was stirred at rt for additional 4 hrs. The reaction was then quenched by pouring into ice-water (1000 mL) and extracted with EtOAc (2×600 mL). The combined organic layer was washed with brine dried over anhydrous sodium sulfate, filtered and concentrated under vacuum. The residue was purified by silica gel column with EtOAc/petroleum ether (1:15-1:3) to afford the desired compound (25.5 g) as a solid.

Intermediate 3 Step e:

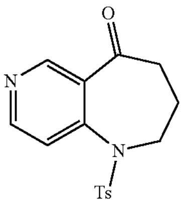 [SMILES: Cc1ccc(S(=O)(=O)N2CCCC(=O)c3cnccc32)cc1]

To a mixture of the compound from step d (25.5 g, 76.26 mmol) in acetic acid (180 mL), was added 6N-hydrogen chloride (80 mL) and heated at 90° C. for overnight. The resulting mixture was concentrated under vacuum to provide HCl salt (14 g) as a gray solid, which was used for next step directly. To a mixture of the above HCl salt (23.5 g, 118.30 mmol) and $K_2CO_3$ (66 g, 477.53 mmol) in MeCN (470 mL), was added TsCl (67.7 g, 355.10 mmol) and heated to reflux for overnight. After being cooled to rt, the reaction mixture was then quenched by the addition of water (600 mL). The resulting solution was extracted with EtOAc (3×500 mL). The combined organic layer was washed with brine (2×800 mL), dried over anhydrous sodium sulfate, filtered and concentrated under vacuum. The residue was purified by silica gel column with EtOAc/petroleum ether (1:6)/MeOH-DCM (1:100-1:60) to afford the desired compound (20 g) as a solid. ESI-MS m/z: 317.1 $[M+H]^+$.

Intermediate 3 Step f:

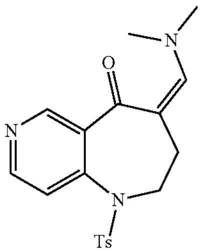 [SMILES: Cc1ccc(S(=O)(=O)N2CC/C(=C/N(C)C)C(=O)c3cnccc32)cc1]

The title compound was prepared using a procedure similar to that used to prepare the compound in intermediate 1 step e.

Intermediate 3 step g:

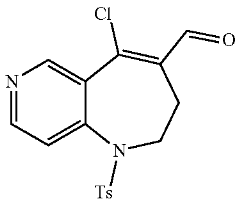 [SMILES: Cc1ccc(S(=O)(=O)N2CCC(C=O)=C(Cl)c3cnccc32)cc1]

The title compound was prepared using a procedure similar to that used to prepare the compound in intermediate 1 step f. ESI-MS m/z: 363.0 $[M+H]^+$.

Intermediate 3 Step h:

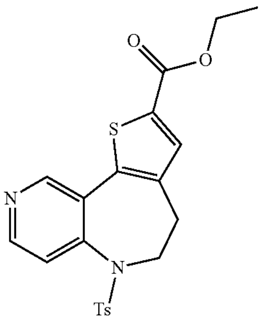 [SMILES: CCOC(=O)c1cc2c(s1)-c1cnccc1N(S(=O)(=O)c1ccc(C)cc1)CC2]

The title compound was prepared using a procedure similar to that used to prepare the compound in intermediate 1 step g. ESI-MS m/z: 429.0 $[M+H]^+$.

Intermediate 3 Step i:

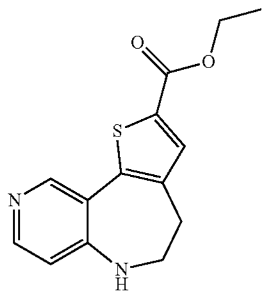 [SMILES: CCOC(=O)c1cc2c(s1)-c1cnccc1NCC2]

The title compound was prepared using a procedure similar to that used to prepare the compound in intermediate 1 step h. ESI-MS m/z: 275.1 $[M+H]^+$.

$^1$H NMR (300 MHz, DMSO-$d_6$) δ 1.27-1.32 (t, 3H), 2.99-3.02 (t, 2H), 3.37-3.38 (m, 2H), 4.25-4.32 (m, 2H), 6.62-6.65 (d, J=5.7 MHz, 1H), 7.39-7.44 (d, J=14.7 MHz, 1H), 7.58 (s, 1H), 7.88-7.90 (d, J=5.7 MHz, 1H), 8.50 (s, 1H).

Examples 51-53 shown in table 3 were prepared using the procedure similar to those of example 1 step c-g or example 3 from the corresponding intermediates.

TABLE 3

| Example | Structure | ESI-MS m/z: $[M + H]^+$ |
|---|---|---|
| 51 | 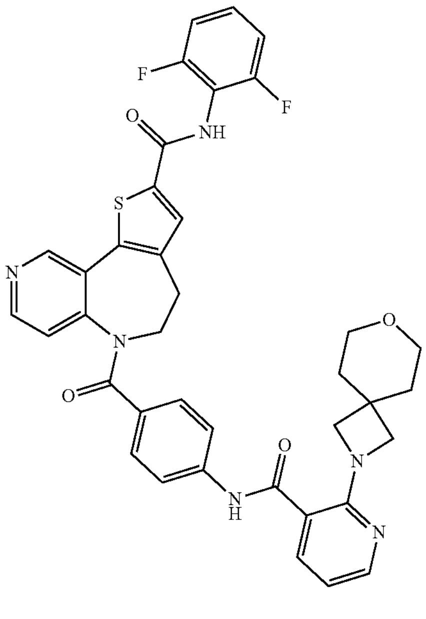 [SMILES: O=C(Nc1c(F)cccc1F)c1cc2c(s1)-c1cnccc1N(C(=O)c1ccc(NC(=O)c3cccnc3N3CC4(CCOCC4)C3)cc1)CC2] | 706.75 |

TABLE 3-continued
| Example | Structure | ESI-MS m/z: [M + H]+ |
| --- | --- | --- |
| 52 | 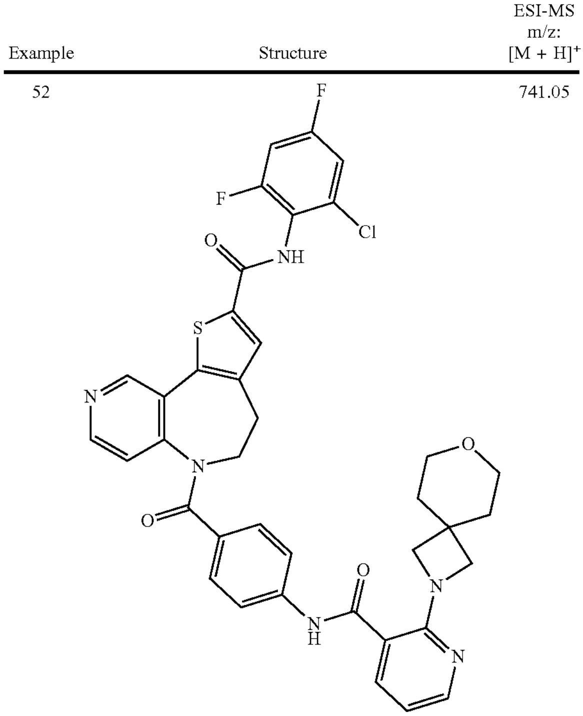 | 741.05 |
TABLE 3-continued
| Example | Structure | ESI-MS m/z: [M + H]+ |
| --- | --- | --- |
| 53 | 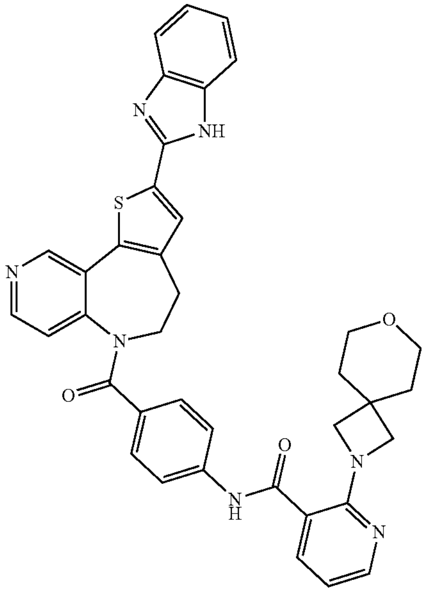 [SMILES: O=C(Nc1ccc(C(=O)N2CCc3cc(-c4nc5ccccc5[nH]4)sc3-c3cnccc32)cc1)c1cccnc1N1CC2(CCOCC2)C1] | 667.85 |
Scheme 12
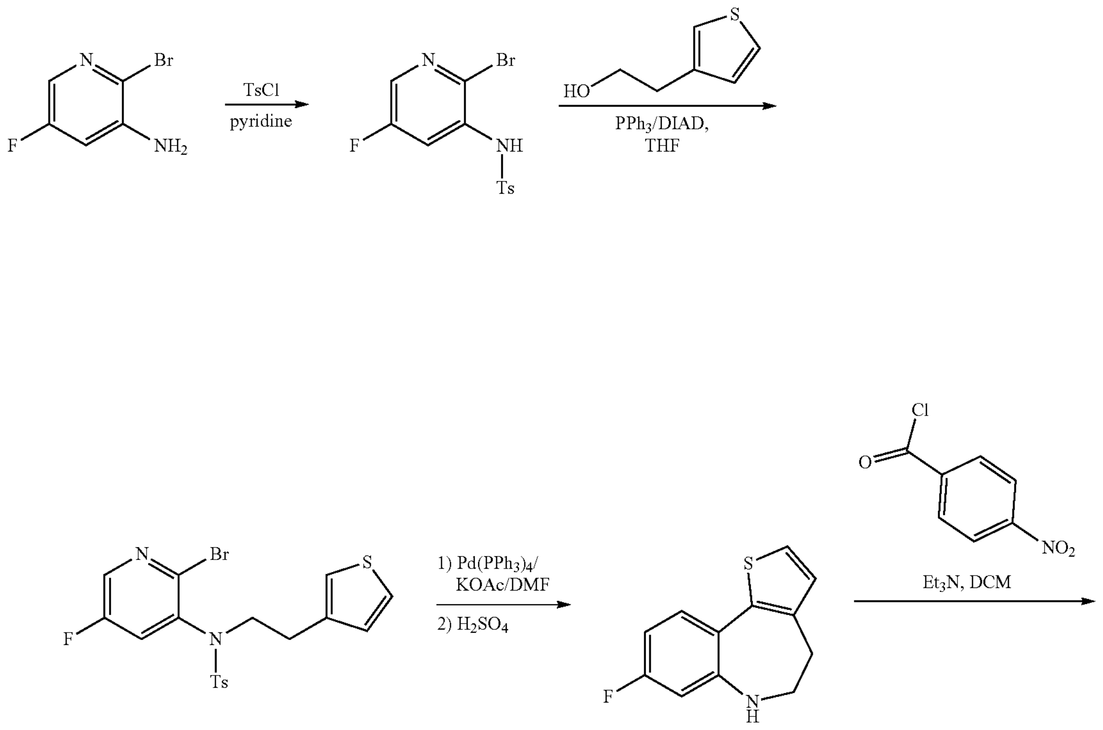

-continued
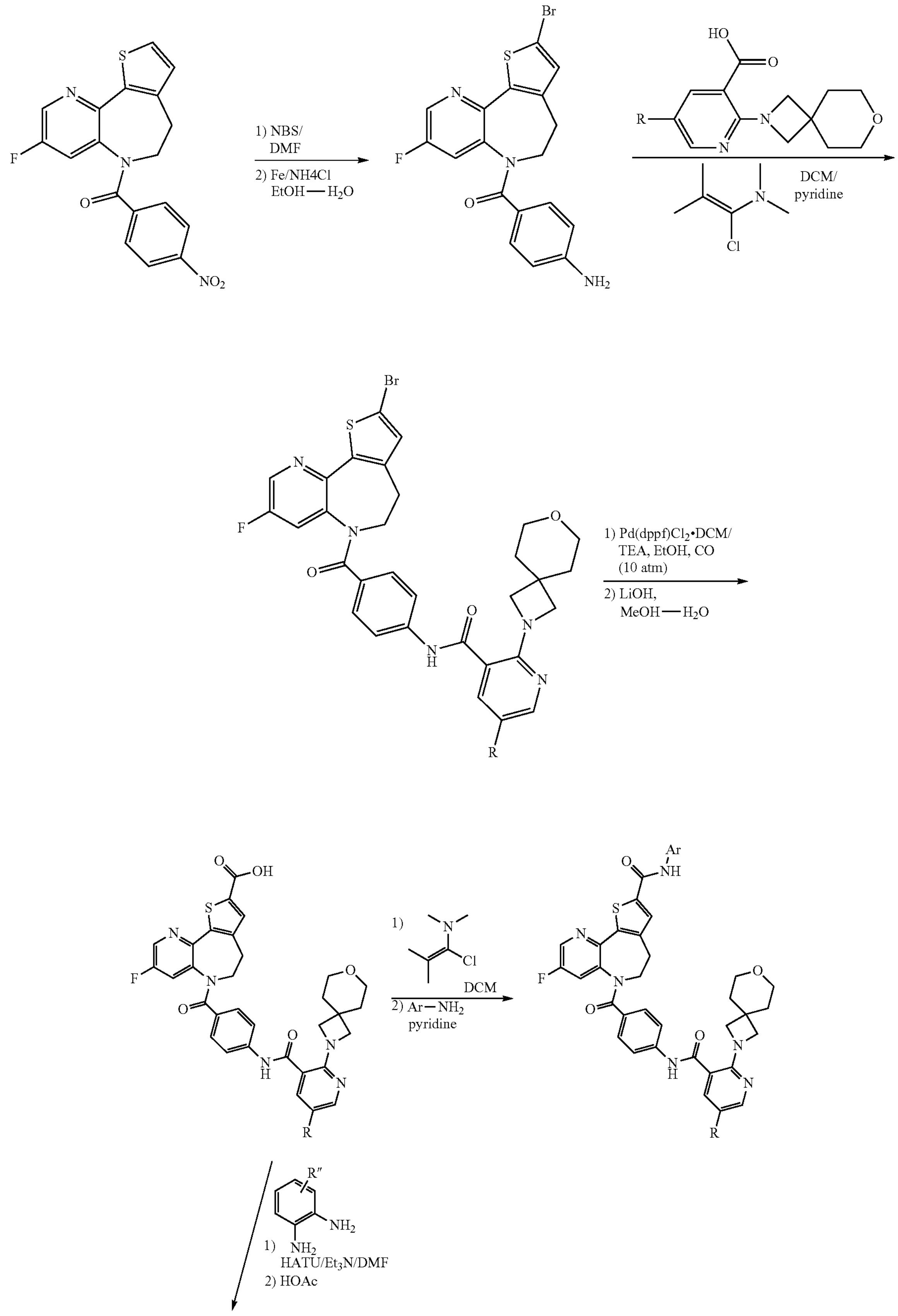

-continued

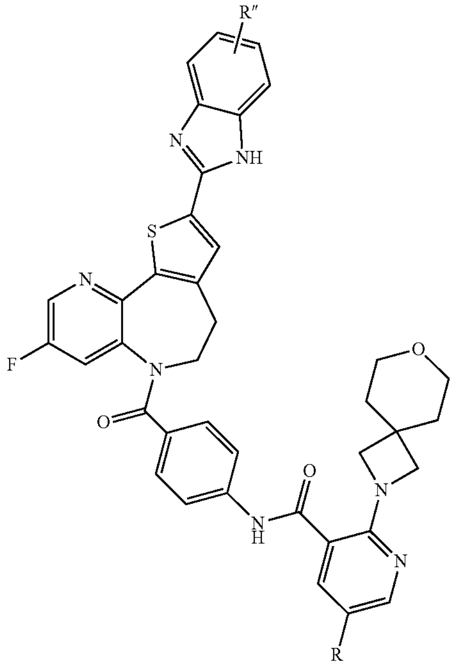

R = H, Me

Example 54

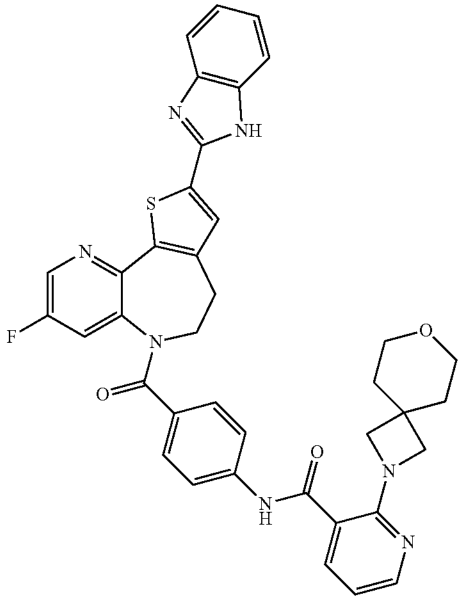 [SMILES: O=C(Nc1ccc(C(=O)N2CCc3cc(-c4nc5ccccc5[nH]4)sc3-c3ncc(F)cc32)cc1)c1cccnc1N1CC2(CCOCC2)C1]

Example 54 Step a

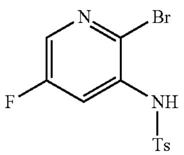 [SMILES: Cc1ccc(S(=O)(=O)Nc2cc(F)cnc2Br)cc1]

To a mixture of 2-bromo-5-fluoroaniline (7 g, 36.84 mmol) in pyridine was portionwise added TsCl (7.7 g, 40.53 mmol) at 0° C. and stirred at rt for overnight. Then, ice-cold water (1.5 L) was added to the reaction mixture, extracted with EtOAc, washed with brine, dried over anhydrous sodium sulfate, filtered and concentrated under vacuum. The residue was purified by column chromatography to afford the desired compound (5 g) as a yellow solid. ESI-MS m/z: 344.90 $[M+H]^+$.

Example 54 Step b

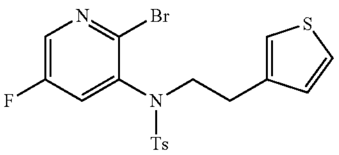 [SMILES: Cc1ccc(S(=O)(=O)N(CCc2ccsc2)c2cc(F)cnc2Br)cc1]

A mixture of the compound from step a (5 g, 14.5 mmol), 2-(thiophen-3-yl)ethan-1-ol (2.8 g, 21.8 mmol), $PPh_3$ (7.6 g, 29.0 mmol) in THF (100 mL) was cooled with ice-$H_2O$ bath under $N_2$ atmosphere. Then, DIAD (5.9 g, 29.0 mmol) was dropwise added to the reaction mixture and stirred at ice-$H_2O$ bath for 10 min, allowed to warm to rt and stirred for additional 1 hr. After being concetrated under vacuum, the residue was purified by silica gel column chromatography (PE:EtOAc=10:1 to PE:EtOAc=5:1) to give the desired compound (2.3 g) as a yellow solid. ESI-MS m/z: 455.00 $[M+H]^+$.

Example 54 Step c

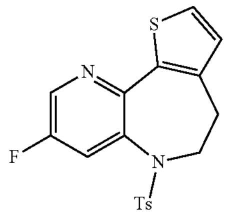 [SMILES: Cc1ccc(S(=O)(=O)N2CCc3ccsc3-c3ncc(F)cc32)cc1]

A mixture of the compound from step b (12.3 g, 27 mmol), $Pd(OAc)_2$ (605 mg, 2.7 mmol) and KOAc (5.30 g, 54 mmol) in DMF (60 mL) was stirred at 120° C. for 2 hrs under $N_2$ atmosphere. After being cooled to rt, the mixture was filtered through a silica gel pad, washed with EtOAc (5×100 mL) and $H_2O$ (6×50 mL). The combined aqueous layers were extracted with EA (3×50 mL). The combined organic layer was washed with brine, dried over anhydrous sodium sulfate, filtered and concentrated under vacuum. The residue was purified by silica gel column to afford the desired compound (6 g) as a yellow solid. ESI-MS m/z: 375.05 $[M+H]^+$.

Example 54 Step d

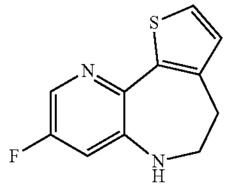 [SMILES: Fc1cnc2c(c1)NCCc1ccsc1-2]

A mixture of the compound from step c (5.0 g, 13.35 mmol) in 90% $H_2SO_4$ aq. (20 mL) was stirred at rt for 1 hr before 500 mL of ice-cold water addition. Then, the reaction mixture was basified with con. NaOH aq., extracted with EA (3×300 mL). The combined organic layer was washed with brine, dried over anhydrous sodium sulfate, filtered and concentrated under vacuum. The residue was purified by silica gel column to afford the desired compound (2.2 g). ESI-MS m/z: 221.05 $[M+H]^+$.

Example 54 Step e

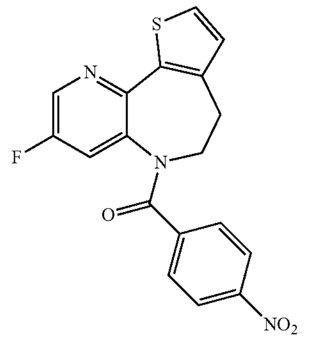 [SMILES: O=C(c1ccc([N+](=O)[O-])cc1)N1CCc2ccsc2-c2ncc(F)cc21]

4-nitrobenzoyl chloride (1.60 g, 8.6 mmol) was added to a mixture of the compound from step d (0.95 g, 4.3 mmol) and $Et_3N$ (3.0 mL, 21.5 mmol) in DCM (50 mL) at the temperature <30° C. for several times and stirred at rt for 2 days. After concentration under vacuum, the residue was diluted with EtOAc (100 mL) and separated. The organic layer was washed with low concentration NaOH aq. (50 mL*2) and 50 mL $H_2O$ subsequently. The combined aqueous layers were extracted with EtOAc (30 mL). The combined organic layer was washed with brine, dried over anhydrous sodium sulfate, filtered and concentrated under vacuum. The residue was purified by silica gel column (PE:DCM:EtOAc=5:1:1) to afford the desired compound (1.37 g). ESI-MS m/z: 370.05 $[M+H]^+$.

Example 54 Step f

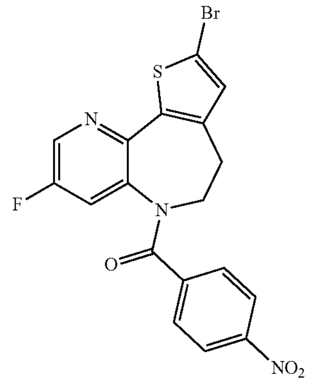

To a mixture of the compound from step e (1.37 g, 3.7 mmol) in DMF (35 mL) was added N-bromosuccimide (0.76 g, 4.27 mmol) at rt for one time and stirred for 15 hrs. The reaction mixture was diluted with EtOAc (150 mL), washed by $H_2O$ (4×35 mL). The combined aqueous layers were extracted with EtOAc (35 mL). The combined organic layer was washed with brine, dried over anhydrous sodium sulfate, filtered and concentrated under vacuum. The residue was passed through a silica gel pad (EtOAc) to afford the desired compound, which was used for next reaction directly. ESI-MS m/z: 447.95 $[M+H]^+$.

Example 54 Step g

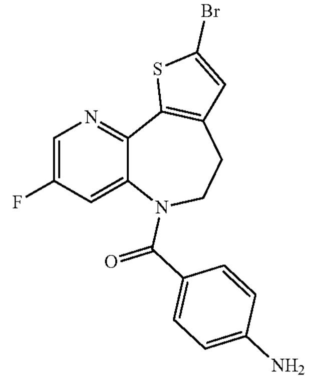

A mixture of the crude compound from step f and Fe (0.62 g, 11.1 mmol) in 95% EtOH (60 mL) and sat. $NH_4Cl$ aq. (15 mL) was stirred at 80° C. for 3 hrs. The mixture was concentrated under vacuum till about 20 mL remained, filtrated through celite, washed with $H_2O$ (40 mL) and EA (3×60 mL). The combined organic layer was washed with brine, dried over anhydrous sodium sulfate, filtered and concentrated under vacuum. The residue was purified by silica gel column (EtOAc) to afford the desired compound (1.7 g). ESI-MS m/z: 417.95 $[M+H]^+$.

Example 54 Step h

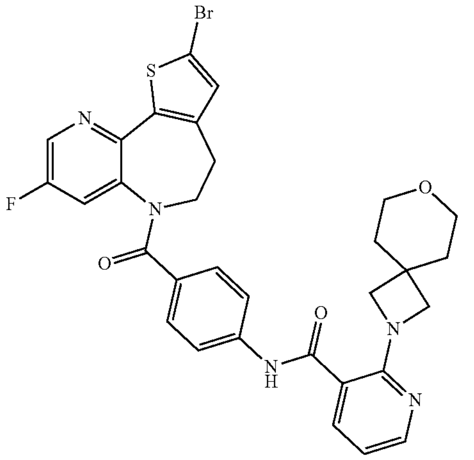 [SMILES: O=C(Nc1ccc(C(=O)N2CCc3cc(Br)sc3-c3ncc(F)cc32)cc1)c1cccnc1N1CC2(CCOCC2)C1]

A solution of 2-(7-oxa-2-azaspiro[3.5]nonan-2-yl)nicotinic acid (1.10 g, 4.44 mmol) in DCM (20 mL) was added 1-chloro-N,N,2-trimethylprop-1-en-1-amine (1.48 g, 11.1 mmol) and stirred at r.t. for 60 mins before being concentrated under vacuum. Then, the residue was dissolved in 20 mL DCM, a solution of the compound from step g (1.7 g, 3.7 mmol) and pyridine (0.9 mL, 11.1 mmol) in 60 mL DCM at were dropwise added to the above solution. The reaction was stirred at rt for 22.5 hrs and quenched by low concentration of aq. NaOH (100 mL) sol'n and separated. The organic layer was washed with additional low concentration of aq. NaOH (100 mL) sol'n and $H_2O$ (50 mL) subsequently. The combined aqueous layers were extracted with DCM (2×30 mL). The combined DCM layer was washed with brine, concentrated under vacuum. The residue was purified by column chromatography to provide the desired product (1.1 g). ESI-MS m/z: 648.05 $[M+H]^+$.

Example 54 Step i

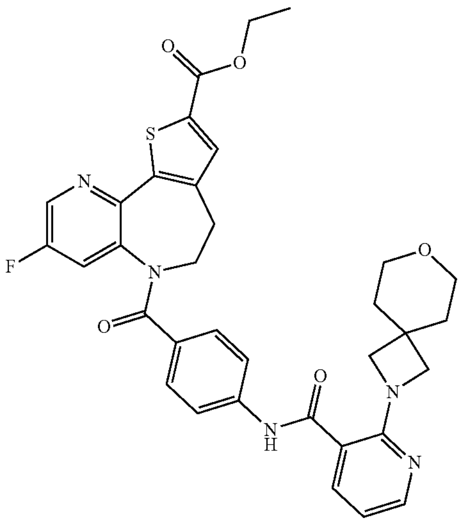 [SMILES: CCOC(=O)c1cc2c(s1)-c1ncc(F)cc1N(C(=O)c1ccc(NC(=O)c3cccnc3N3CC4(CCOCC4)C3)cc1)CC2]

A mixture of compound from step h (1.10 g, 1.54 mmol), $Pd(dppf)Cl_2$.DCM (252 mg, 0.31 mmol) and $Et_3N$ (1.1 mL, 7.7 mmol) in EtOH (15 mL) was stirred at 80° C. for 4 hrs under 10 atm CO atomsphere. After being cooled to rt, the reaction mixture was filtered through celite, washed with EtOH and DCM subsequently. The filtrate was concentrated under vacuum. The residue was purified by silica gel chromatography (EA) to afford the desired compound (1.03 g). ESI-MS m/z: 642.15 $[M+H]^+$.

Example 54 Step j

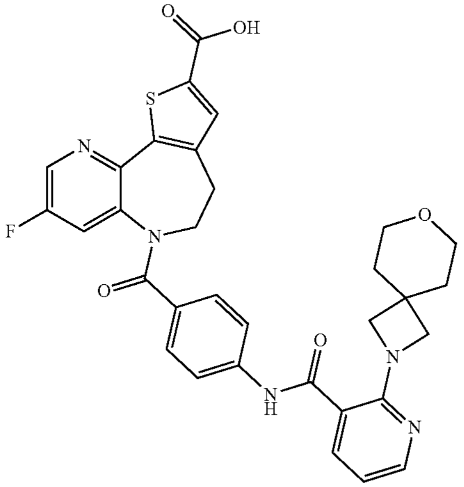 [SMILES: O=C(O)c1cc2c(s1)-c1ncc(F)cc1N(C(=O)c1ccc(NC(=O)c3cccnc3N3CC4(CCOCC4)C3)cc1)CC2]

A mixture of the compound from step i (1.03 g, 1.60 mmol) in MeOH (15 mL) and $H_2O$ (10 mL) was added LiOH (384 mg, 16.05 mmol) and stirred at rt for 15 hrs. After being concentrated under vacuum, $H_2O$ (50 mL) was added to the residue and adjusted pH to 4-5 with c-HCl and extracted with EA (6×100 mL). The combined organic layers were dried over anhydrous sodium sulfate, filtered and concentrated under vacuum. The residue was purified by column chromatography (MeCN/$H_2O$) to give the desired compound (530 mg). ESI-MS m/z: 614.20 $[M+H]^+$.

Example 54 Step k

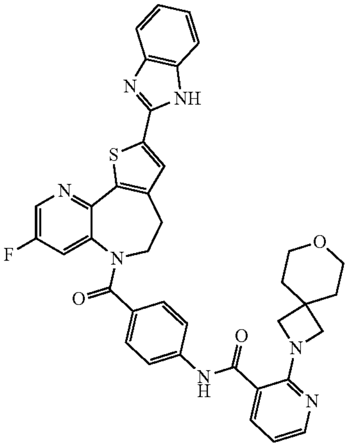 [SMILES: O=C(Nc1ccc(C(=O)N2CCc3cc(-c4nc5ccccc5[nH]4)sc3-c3ncc(F)cc32)cc1)c1cccnc1N1CC2(CCOCC2)C1]

Example 54 was prepared using the procedure similar to that of example 4 from the corresponding intermediates. ESI-MS m/z: 684.15 $[M+H]^+$. $^1H$ NMR (300 MHz, DMSO-$d_6$) δ 1.63 (s, 4H), 3.18-3.30 (m, 3H), 3.41-3.51 (m, 4H), 3.65 (s, 4H), 4.98 (ws, 1H), 6.71 (dd, J=7.5, 4.8 Hz, 1H), 7.11 (d, J=8.3 Hz, 2H), 7.16-7.30 (m, 2H), 7.33-7.45 (m, 1H), 7.49-7.70 (m, 4H), 7.79 (s, 1H), 8.18 (dd, J=4.8, 1.8 Hz, 1H), 8.50 (d, J=2.6 Hz, 1H), 10.47 (s, 1H), 13.15 (s, 1H).

Examples 55-64 shown in table 4 were prepared using the procedure similar to those of example 1 step g or example 3 from the corresponding intermediates.

TABLE 4

TABLE 4-continued

| Example | Structure | ESI-MS m/z: $[M + H]^+$ |
|---|---|---|
| 55 | 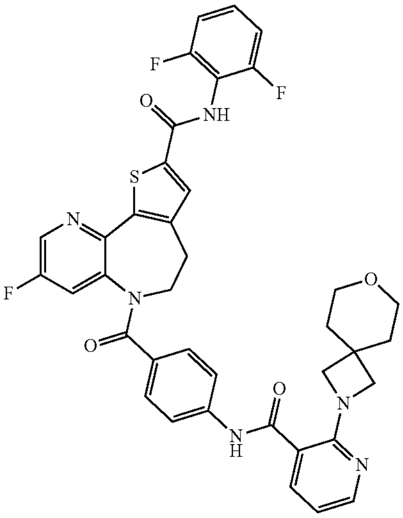 [SMILES: O=C(Nc1c(F)cccc1F)c1cc2c(s1)-c1ncc(F)cc1N(C(=O)c1ccc(NC(=O)c3cccnc3N3CC4(CCOCC4)C3)cc1)CC2] | 725.10 |
| 56 | 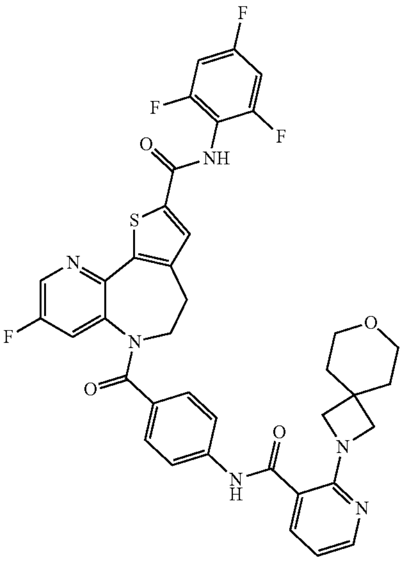 [SMILES: O=C(Nc1c(F)cc(F)cc1F)c1cc2c(s1)-c1ncc(F)cc1N(C(=O)c1ccc(NC(=O)c3cccnc3N3CC4(CCOCC4)C3)cc1)CC2] | 743.42 |
| 57 | 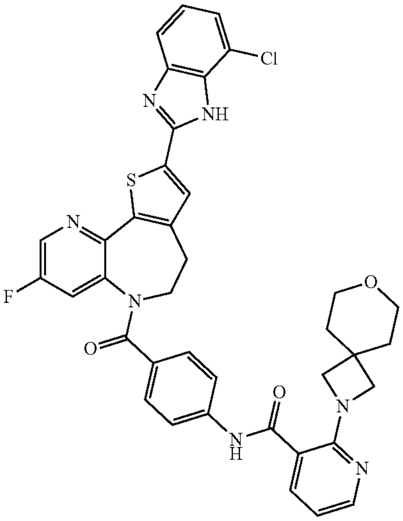 | 720.00 |

TABLE 4-continued
| Example | Structure | ESI-MS m/z: [M + H]$^+$ |
|---|---|---|
| 58 | 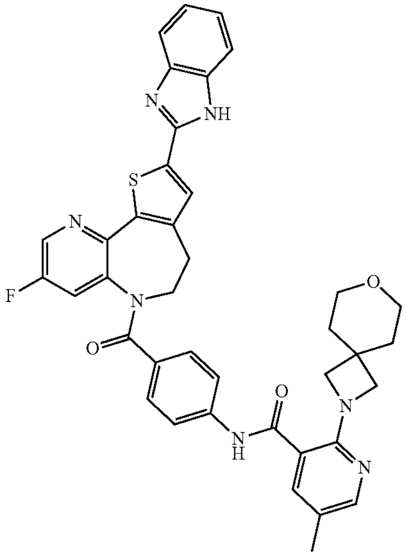 | 700.01 |
| 59 | 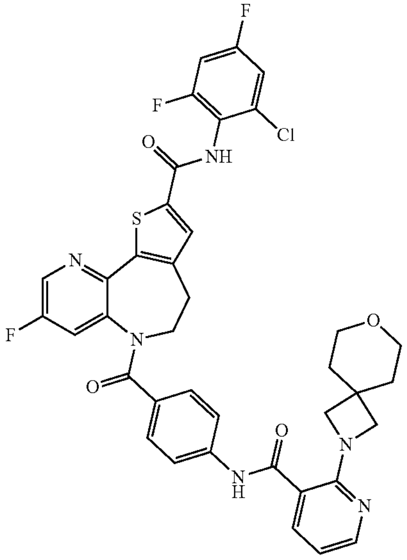 [SMILES: O=C(Nc1c(F)cc(F)cc1Cl)c1cc2c(s1)-c1ncc(F)cc1N(C(=O)c1ccc(NC(=O)c3cccnc3N3CC4(CCOCC4)C3)cc1)CC2] | 759.00 |
| 60 | 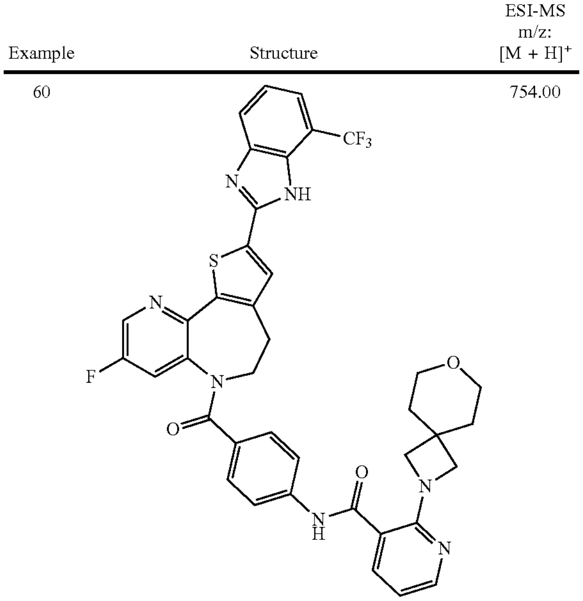 | 754.00 |
| 61 | 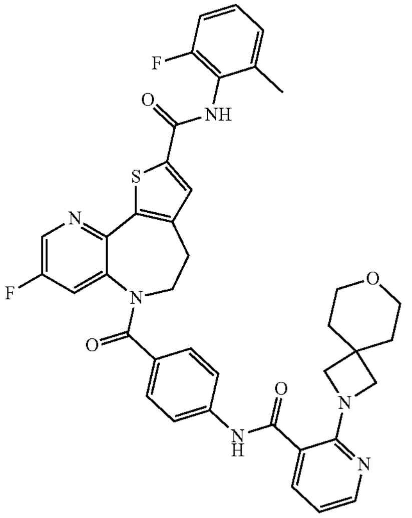 [SMILES: Cc1cccc(F)c1NC(=O)c1cc2c(s1)-c1ncc(F)cc1N(C(=O)c1ccc(NC(=O)c3cccnc3N3CC4(CCOCC4)C3)cc1)CC2] | 721.05 |
| 62 | 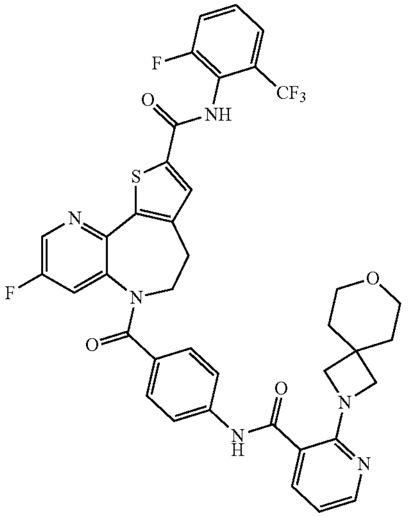 [SMILES: O=C(Nc1c(F)cccc1C(F)(F)F)c1cc2c(s1)-c1ncc(F)cc1N(C(=O)c1ccc(NC(=O)c3cccnc3N3CC4(CCOCC4)C3)cc1)CC2] | 775.00 |

TABLE 4-continued
| Example | Structure | ESI-MS m/z: $[M + H]^+$ |
|---|---|---|
| 63 | 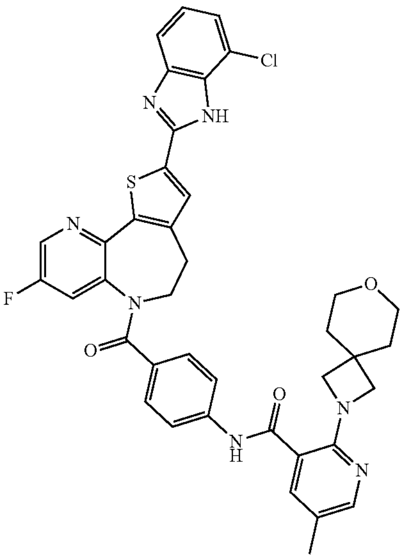 | 734.00 |
| 64 | 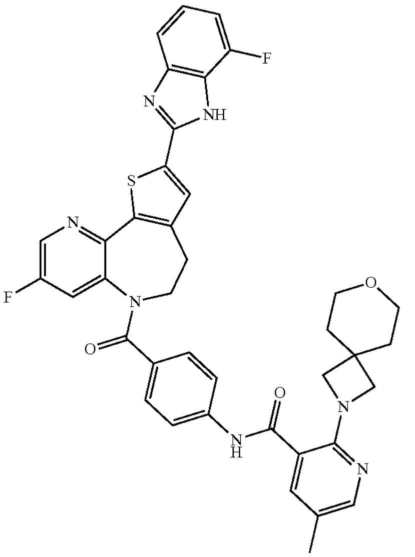 | 718.10 |
Scheme 13
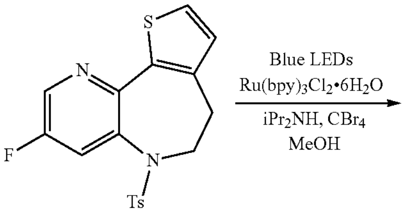
-continued
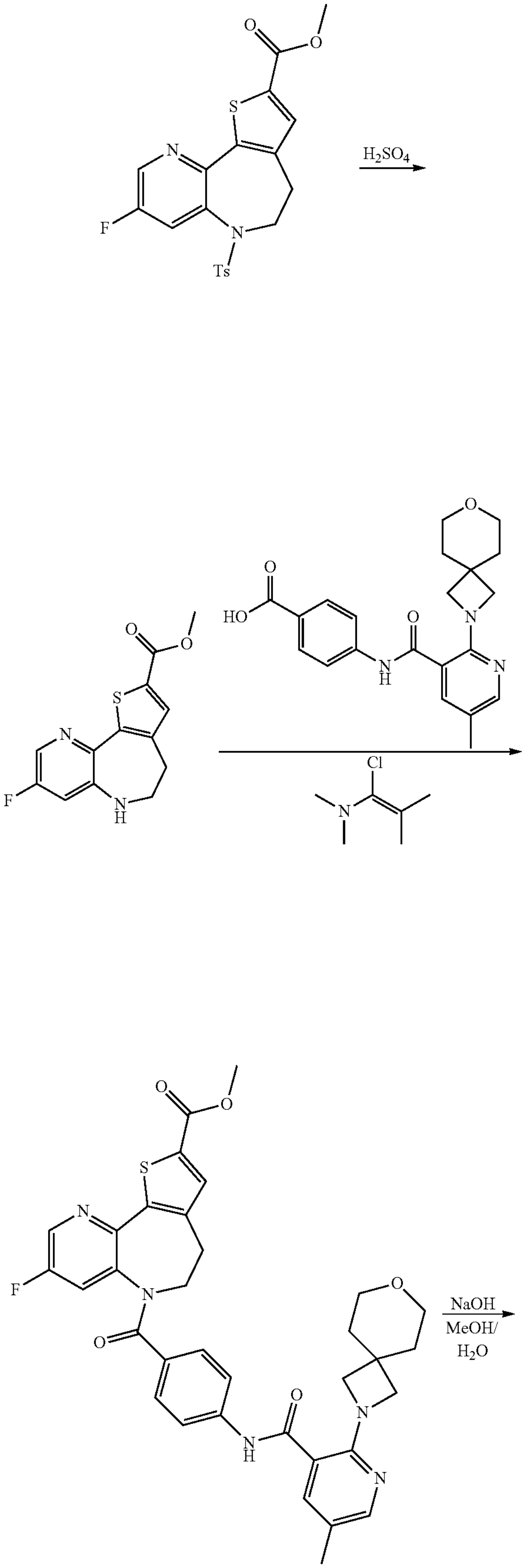

-continued

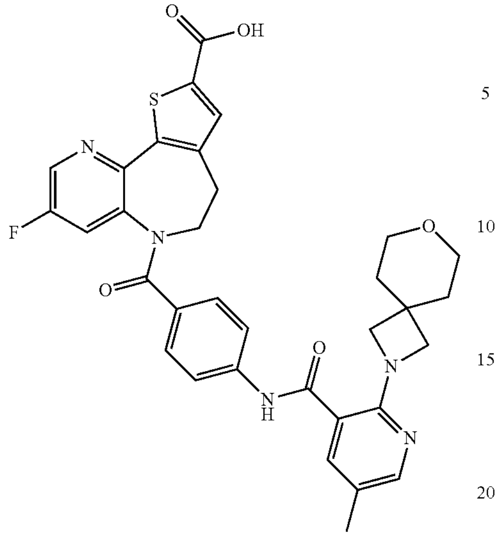

Example 65

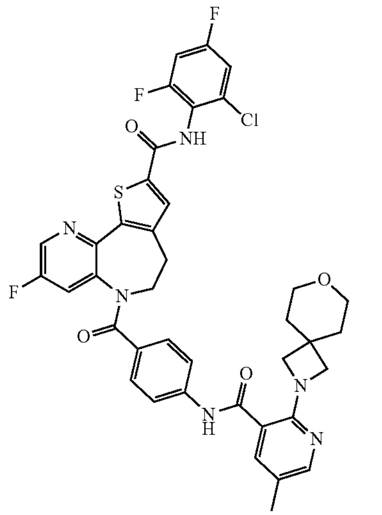 [SMILES: Cc1cnc(N2CC3(CCOCC3)C2)c(C(=O)Nc2ccc(C(=O)N3CCc4cc(C(=O)Nc5c(F)cc(F)cc5Cl)sc4-c4ncc(F)cc43)cc2)c1]

Example 65 Step a

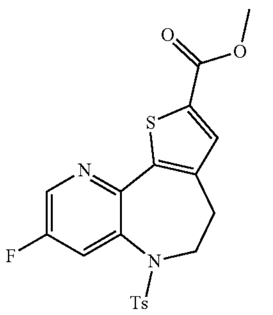 [SMILES: COC(=O)c1cc2c(s1)-c1ncc(F)cc1N(S(=O)(=O)c1ccc(C)cc1)CC2]

A mixture of 3-fluoro-5-tosyl-6,7-dihydro-5H-pyrido[3,2-b]thieno[2,3-d]azepine (2.4 g, 6.41 mmol), Ru(bpy)$_3Cl_2$.6$H_2O$ (96 mg, 0.128 mmol), $CBr_4$ (3.19 g, 9.61 mmol), and diisopropylamine (1.297 g, 12.82 mmol) was stirred in degassed MeOH (0.2 M). The reaction mixture was irradiated with 3 W blue LEDs for 48 hours. The methanol was removed under reduced pressure and the product was purified on silica gel with 0-100% ethyl acetate:hexanes to provide methyl 3-fluoro-5-tosyl-6,7-dihydro-5H-pyrido[3,2-b]thieno[2,3-d]azepine-9-carboxylate (1.4 g, 51%).

Example 65 Step b

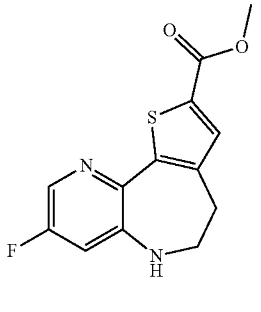 [SMILES: COC(=O)c1cc2c(s1)-c1ncc(F)cc1NCC2]

A mixture of the compound from step a (1.5 g, 0.255 mmol) in conc. $H_2SO_4$ (5 mL) was stirred at 50° C. for 30 min. The reaction mixture was diluted with 10 volumes of water. The pH was adjusted to 3 by addition of powdered NaOH. The product was extracted with ethyl acetate (3×), concentrated, and the residue was purified on silica gel with 0-100% ethyl acetate:hexanes to provide the desired compound (319 mg, 33%).

Example 65 Step c

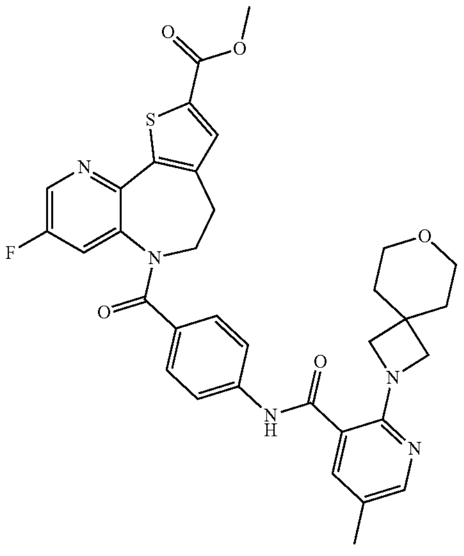 [SMILES: COC(=O)c1cc2c(s1)-c1ncc(F)cc1N(C(=O)c1ccc(NC(=O)c3cc(C)cnc3N3CC4(CCOCC4)C3)cc1)CC2]

4-(5-methyl-2-(7-oxa-2-azaspiro[3.5]nonan-2-yl)nicotinamido)benzoic acid (685 mg, 1.797 mmol) was stirred in DCM (0.5 M). 1-chloro-N,N,2-trimethylprop-1-en-1-amine (0.713 mL, 5.39 mmol) was added at rt and stirred for one hour. The DCM was removed under a stream of nitrogen gas and the crude residue was further dried on high vaccum. The crude mixture was dissolved in pyridine (0.2 M). The compound from step b (500 mg, 1.797 mmol) was added and the reaction mixture was stirred at 80° C. for 18 h. The pyridine was removed under a stream of nitrogen gas, and the crude residue was partitioned between water and ethyl acetate. The product was extracted with ethyl acetate (3×), and concentrated. The residue was purified on silica gel with 0-100% ethyl acetate:hexanes to provide the desired compound (590 mg, 51%).

Example 65 Step d

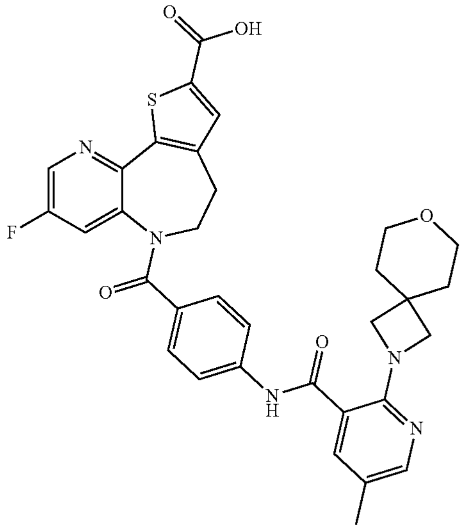 [SMILES: Cc1cnc(N2CC3(CCOCC3)C2)c(C(=O)Nc2ccc(C(=O)N3CCc4cc(C(=O)O)sc4-c4ncc(F)cc43)cc2)c1]

The compound from step c (590 mg, 0.919 mmol) was stirred in methanol (0.5 M). The mixture was diluted with water to a final concentration of 0.4 M. Powdered NaOH (735 mg, 18.39 mmol) was added. Reaction mixture stirred at 50° C. for 1 h. The majority of methanol was removed under a stream of nitrogen gas. The pH was adjusted to 3 by dropwise addition of 4 M aq. HCl. The product was extracted with ethyl acetate (3 times), concentrated, and taken on directly to the next step.

Examples 65-69 shown in table 5 were prepared using the procedure similar to those of example 1 step g or example 3 from the corresponding intermediates.

TABLE 5

| Example | Structure | ESI-MS m/z: [M + H]$^+$ |
|---|---|---|
| 65 | 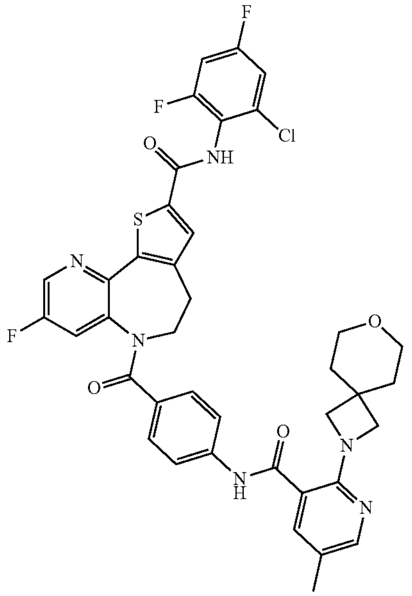 [SMILES: Cc1cnc(N2CC3(CCOCC3)C2)c(C(=O)Nc2ccc(C(=O)N3CCc4cc(C(=O)Nc5c(F)cc(F)cc5Cl)sc4-c4ncc(F)cc43)cc2)c1] | 774.0 |
| 66 | 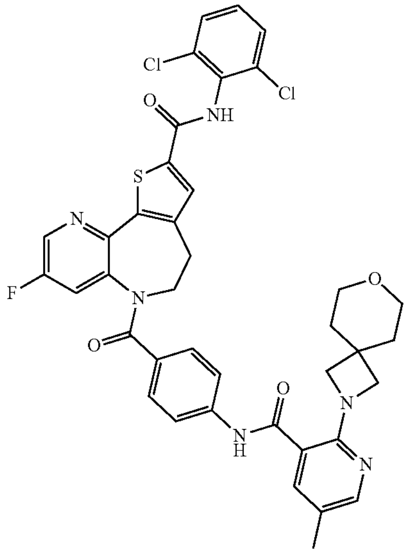 | 771.0 |

TABLE 5-continued
| Example | Structure | ESI-MS m/z: [M + H]+ |
| --- | --- | --- |
| 67 | 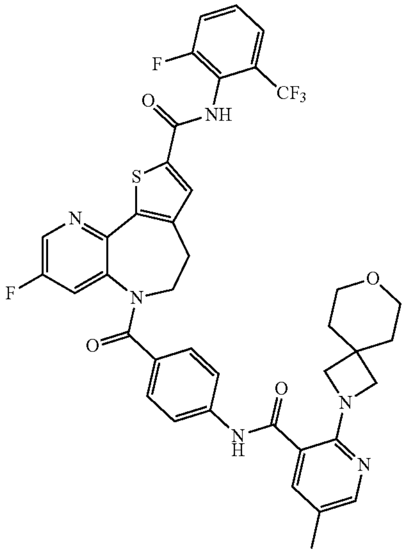 | 789.35 |
| 68 | 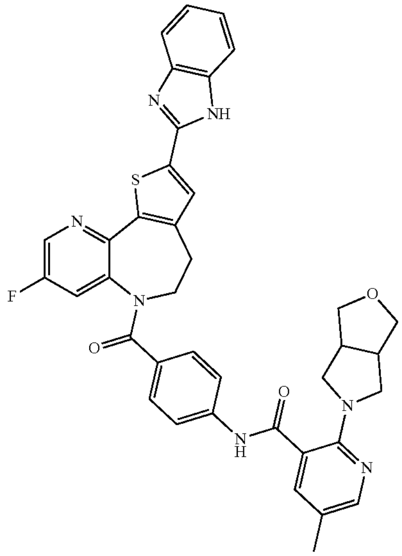 [SMILES: Cc1cnc(N2CC3COCC3C2)c(C(=O)Nc2ccc(C(=O)N3CCc4cc(-c5nc6ccccc6[nH]5)sc4-c4ncc(F)cc43)cc2)c1] | 686.20 |
| 69 | 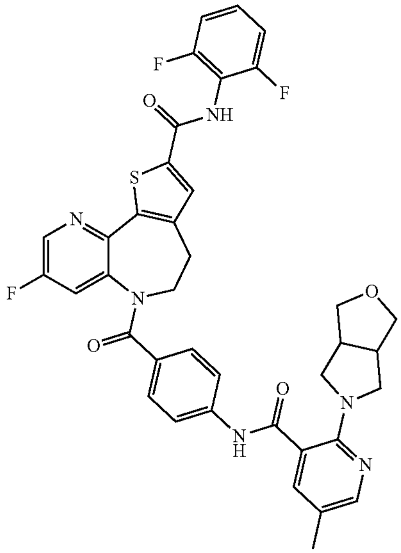 [SMILES: Cc1cnc(N2CC3COCC3C2)c(C(=O)Nc2ccc(C(=O)N3CCc4cc(C(=O)Nc5c(F)cccc5F)sc4-c4ncc(F)cc43)cc2)c1] | 725.20 |
Scheme 14
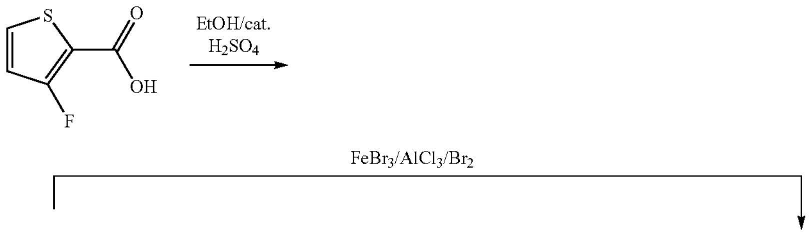

-continued
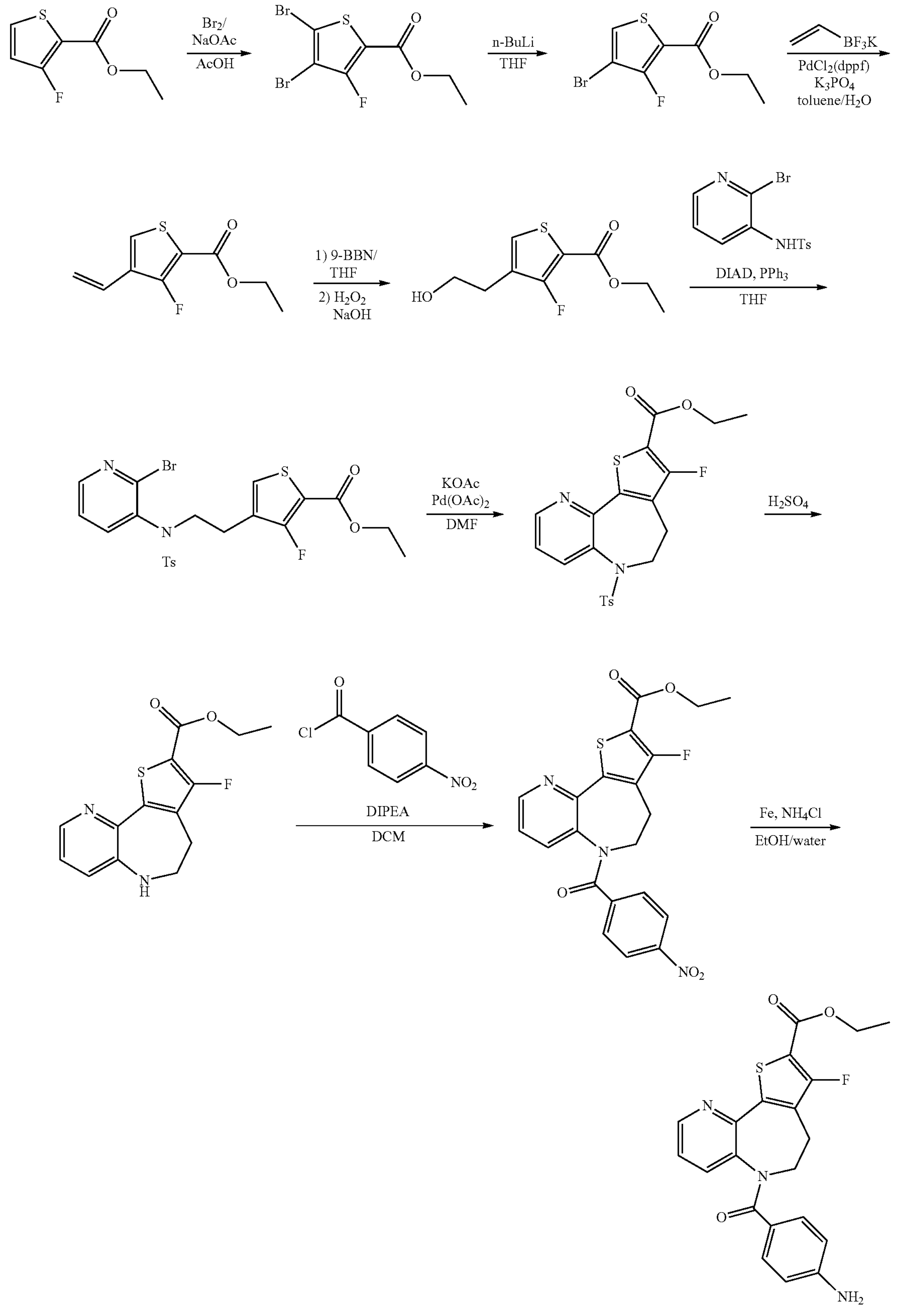

Scheme 15
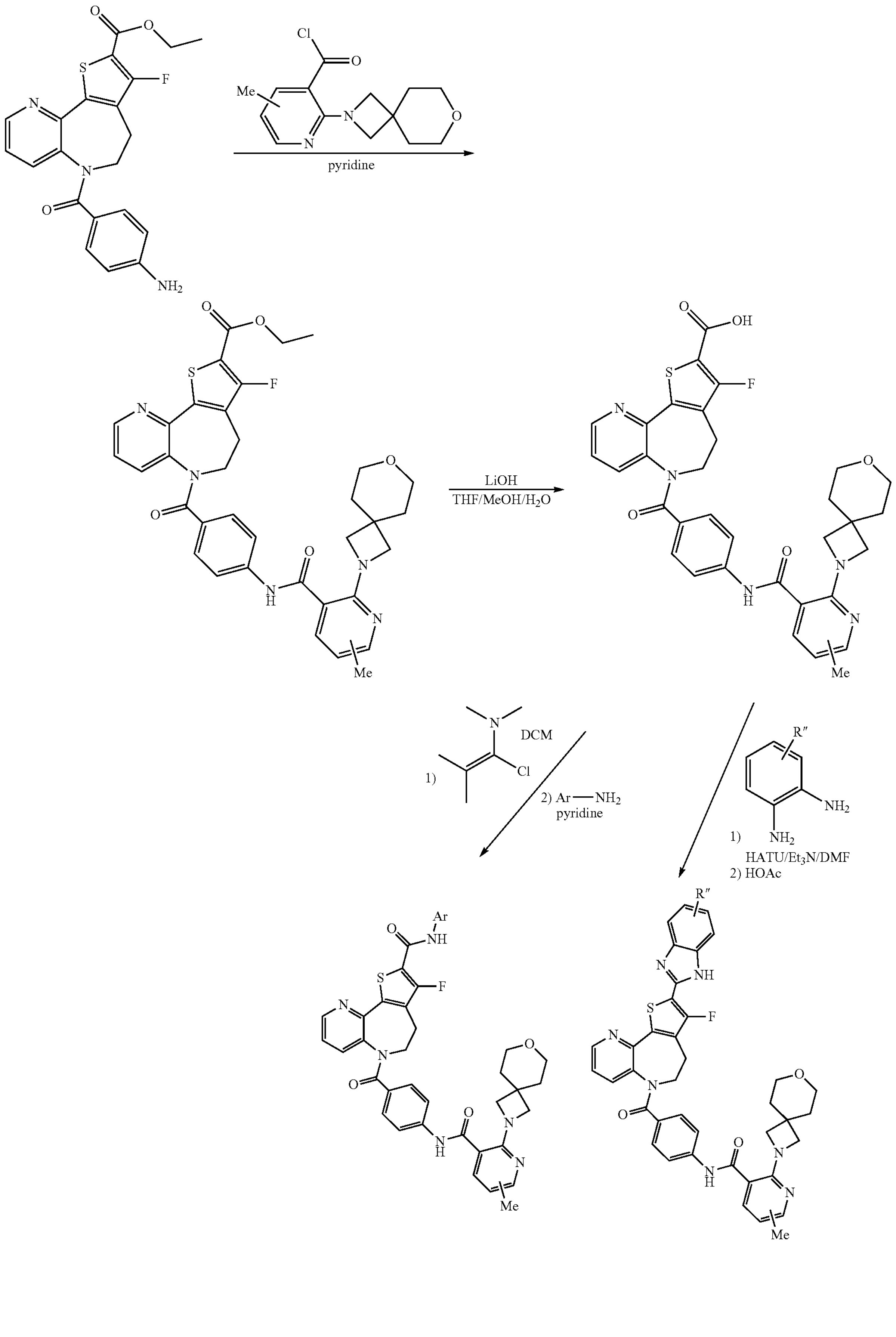

Example 70

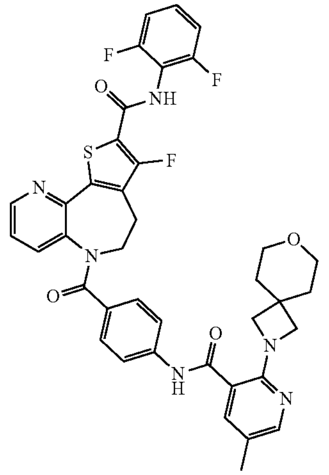 [SMILES: Cc1cnc(N2CC3(CCOCC3)C2)c(C(=O)Nc2ccc(C(=O)N3CCc4c(sc(C(=O)Nc5c(F)cccc5F)c4F)-c4ncccc43)cc2)c1]

Example 70 Step a

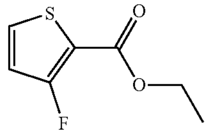

To a solution of 3-fluorothiophene-2-carboxylic acid (2.5 g, 17.11 mmol) in ethanol (24.91 ml) was added $H_2SO_4$ (0.249 ml), and the mixture was stirred at 100° C. for 12 hr. The reaction mixture was quenched with saturated sodium bicarbonate, adjusted the pH to 7 and extracted with EtOAc (3×30 mL). The combined organic phases were dried over $Na_2SO_4$, and concentrated to give ethyl 3-fluorothiophene-2-carboxylate (2.13 g).

Example 70 Step b

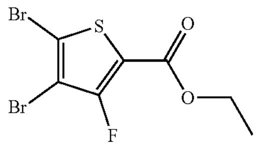

Ethyl 3-fluorothiophene-2-carboxylate (2.13 g, 12.23 mmol) in a suspension of sodium acetate (7.46 g, 91 mmol) and AcOH (20.73 ml) was treated with bromine (5.66 ml, 110 mmol). The reaction mixture was stirred at 75° C. under $N_2$ for 136 h. The reaction mixture was poured onto ice-cold saturated aqueous $NaHCO_3$ and aqueous $NaHSO_3$. The mixture was stirred with $Et_2O$ (100 mL) for 30 min. Extraction with $Et_2O$ (3×150 mL) gave an organic layer that was washed with $H_2O$ (150 mL) and saturated aqueous NaCl (150 mL), dried ($MgSO_4$), and concentrated to give ethyl 4,5-dibromo-3-fluorothiophene-2-carboxylate (2.61 g, 7.86 mmol, 64.3% yield).

Example 70 Step c

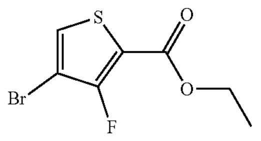

To an oven-dried vial, ethyl 4,5-dibromo-3-fluorothiophene-2-carboxylate (4.33 g, 13.04 mmol) was dissolved THF (130 ml) and cooled to −100° C. (dry ice in diethyl ether). Then, n-BuLi (5.22 ml, 13.04 mmol, 2.5M in hexanes) was dropwise added and stirred at −100° C. for 30 mins. The reaction was quenched by addition of water (11.75 ml, 652 mmol) and allowed to warm to room temperature. The reaction mixture was diluted with water and extracted with EtOAc (3×50 mL). The combined organic layers were dried over $Na_2SO_4$, filtered and concentrated to dryness. The crude product was added to a silica gel column and was eluted with ethyl acetate/hexane 0% to 40% to give ethyl 4-bromo-3-fluorothiophene-2-carboxylate (1.92 g) as an orange oil. Alternatively, this compound can be made from ethyl 3-fluorothiophene-2-carboxylate (example 70 step a) as following: $AlCl_3$(68.79 g, 517.2 mmol) was added in portions to the solution of ethyl 3-fluorothiophene-2-carboxylate (15 g, 86.2 mmol) and $FeBr_3$ (2.55 g, 8.62 mmol) in $CHCl_3$(200 ml) at 0° C. $Br_2$(18 g, 112 mmol) in $CHCl_3$(10 ml) was added dropwise at 0° C. The reaction mixture was stirred at room temperature under $N_2$ for 24 hrs. The reaction mixture was poured into ice-cold saturated aqueous $NaHSO_3$. The aquesous layer was extracted with DCM, organic layer was washed with $H_2O$, brine, dried over $Na_2SO_4$ and concentrated. The crude product was purified by C-18 FLASH with $MeCN/H_2O$=50% to 75% to give desired compound 5 (10.43 g) as orange oil and dibrominated product (example 70 step b, 9 g).

Example 70 Step d

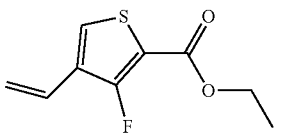

To a solution of ethyl 4-bromo-3-fluorothiophene-2-carboxylate (1.92 g, 7.59 mmol) in toluene (40.5 ml) and water (10.12 ml) was added trifluoro(vinyl)-14-borane, potassium salt (1.067 g, 7.97 mmol), $K_3PO_4$ (4.83 g, 22.76 mmol) and $PdCl_2$(dppf) (0.278 g, 0.379 mmol). The reaction was allowed to stir overnight at 90° C. under nitrogen. The reaction was quenched with water and extracted with EtOAc (3×). The combined organic phases were dried over $Na_2SO_4$, and concentrated in vacuo. The crude product was added to a silica gel column and was eluted with ethyl acetate/hexane 0% to 15% (eluted at 12%) to give ethyl 3-fluoro-4-vinylthiophene-2-carboxylate (1.16 g) as a yellowish oil.

Example 70 Step e

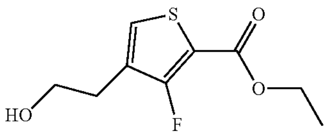

To a mixture of ethyl 3-fluoro-4-vinylthiophene-2-carboxylate (1.16 g, 5.79 mmol) in THF (66.6 ml) was slowly added 9-BBN (33.8 ml, 16.92 mmol) at 0° C., allowed to warm room temperature and stirred for 16 hrs. The reaction mixture was cooled to 0° C. and slow addition of hydrogen peroxide (13.35 ml, 218 mmol) followed by treatment with NaOH (54.5 ml, 218 mmol). Then, water (14 mL) was added and extract with ethyl acetate (3×150 mL). The combined organic layers were dried over $Na_2SO_4$, filtered and concentrated to dryness. The crude product was purified by silica gel column with ethyl acetate/hexane 0% to 50% to give ethyl 3-fluoro-4-(2-hydroxyethyl)thiophene-2-carboxylate (0.84 g) as a clear oil.

Example 70 Step f

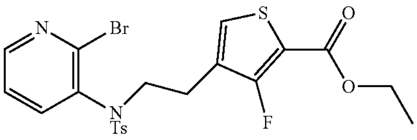 [SMILES: CCOC(=O)c1scc(CCN(c2cccnc2Br)S(=O)(=O)c2ccc(C)cc2)c1F]

A mixture of N-(2-bromopyridin-3-yl)-4-methylbenzenesulfonamide (3.19 g, 9.76 mmol), 2-(diphenylphosphanyl)pyridine (2.57 g, 9.76 mmol), and ethyl 3-fluoro-4-(2-hydroxyethyl)thiophene-2-carboxylate (2.13 g, 9.76 mmol) in dry THF (48.8 ml) was stirred at 0° C. To the reaction mixture, DIAD (1.898 ml, 9.76 mmol) was added slowly dropwise to the reaaction mixture and stirred at room temperature for one hour. The solvent was removed under reduced pressure, and the residue was purified on silica gel with 0-100% ethyl acetate: hexanes to provide ethyl 4-(2-((N-(2-bromopyridin-3-yl)-4-methylphenyl)sulfonamido)ethyl)-3-fluorothiophene-2-carboxylate (4.61 g).

Example 70 Step g

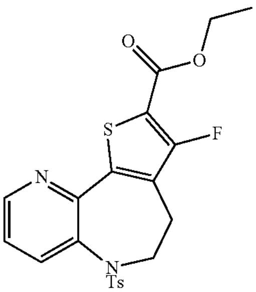 [SMILES: CCOC(=O)c1sc2c(c1F)CCN(S(=O)(=O)c1ccc(C)cc1)c1cccnc1-2]

To an oven-dried vial, add ethyl 4-(2-((N-(2-bromopyridin-3-yl)-4-methylphenyl) sulfonamido)-ethyl)-3-fluorothiophene-2-carboxylate (4.61 g, 8.74 mmol), $Pd(OAc)_2$ (0.196 g, 0.874 mmol) and potassium acetate (6.00 g, 61.2 mmol). The vial was sealed and evacuated and refilled with nitrogen (3 times). Via syringe, DIVIF (43.7 ml) was added and heated to 70° C. overnight. The reaction mixture was cooled and poured into water. The aqueous solution was extracted with EtOAc (3×). The organic layer was dried with sodium sulfate, filtered and concentrated. The crude product was added to a silica gel column and was eluted with ethyl acetate/hexane 0% to 100% to give ethyl 8-fluoro-5-tosyl-6,7-dihydro-5H-pyrido[3,2-b]thieno[2,3-d]azepine-9-carboxylate (1.37 g) as an oil.

Example 70 Step h

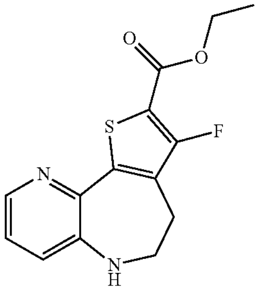 [SMILES: CCOC(=O)c1sc2c(c1F)CCNc1cccnc1-2]

In a vial, ethyl 8-fluoro-5-tosyl-6,7-dihydro-5H-pyrido[3,2-b]thieno[2,3-d]azepine-9-carboxylate (1.37 g, 3.07 mmol) was dissolved in $H_2SO_4$ (15.34 ml) and heated to 50° C. After one hour, the reaction mixture was cooled and diluted with 10 volumes of water. The pH was adjusted to 3 with solid NaOH. The product was extracted with ethyl acetate (3×). The combined organic layers were dried with $Na_2SO_4$, filtered and concentrated. The crude product was taken forward without further purification yielding ethyl 8-fluoro-6,7-dihydro-5H-pyrido[3,2-b]thieno[2,3-d]azepine-9-carboxylate (771 mg).

Example 70 Step i

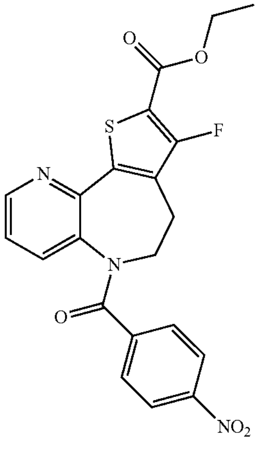 [SMILES: CCOC(=O)c1sc2c(c1F)CCN(C(=O)c1ccc([N+](=O)[O-])cc1)c1cccnc1-2]

In a vial, ethyl 8-fluoro-6,7-dihydro-5H-pyrido[3,2-b]thieno[2,3-d]azepine-9-carboxylate (.771 mg, 2.64 mmol) and 4-nitrobenzoyl chloride (0.587 g, 3.16 mmol) were dissolved in DCM (26.4 ml). Hunig's base (1.152 ml, 6.59 mmol) was slowly added and the resulting solution was allowed to stir overnight at room temperature. The reaction mixture was diluted with DCM (50 mL), washed with brine, dried with $Na_2SO_4$ and concentrated. The crude product was purified by silica column with 0-100% EtOAc/hexane to obtain ethyl 8-fluoro-5-(4-nitrobenzoyl)-6,7-dihydro-5H-pyrido[3,2-b]thieno[2,3-d]azepine-9-carboxylate (79 g). ESI-MS m/z: 441.8 [M+H]$^+$.

Example 70 Step j

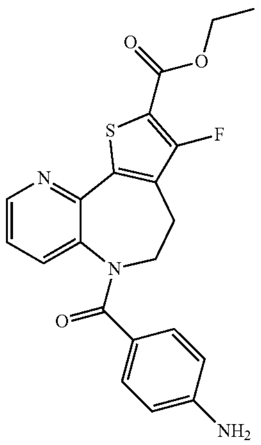

In a vial, ethyl 8-fluoro-5-(4-nitrobenzoyl)-6,7-dihydro-5H-pyrido[3,2-b]thieno[2,3-d]azepine-9-carboxylate (794 mg, 1.799 mmol), iron (502 mg, 8.99 mmol), and ammonium chloride (962 mg, 17.99 mmol) were suspended in EtOH (23.982 ml) and water (11.99 ml). The vial was sealed and heated to 80° C. for 2 hrs. The reaction mixture was cooled to room temperature and passed through a plug of celite eluting with EtOAc. The organic layer was concentrated and sat. aq. $NaHCO_3$ was added to adjust the pH to 8. At this point, DCM/MeOH (10:1) was added and the organic layer was separated and dried over $MgSO_4$. The crude product was taken forward without further purification yielding ethyl 5-(4-aminobenzoyl)-8-fluoro-6,7-dihydro-5H-pyrido[3,2-b]thieno[2,3-d]azepine-9-carboxylate (691 mg). ESI-MS m/z: 411.8 [M+H]$^+$.

Example 70 Step k

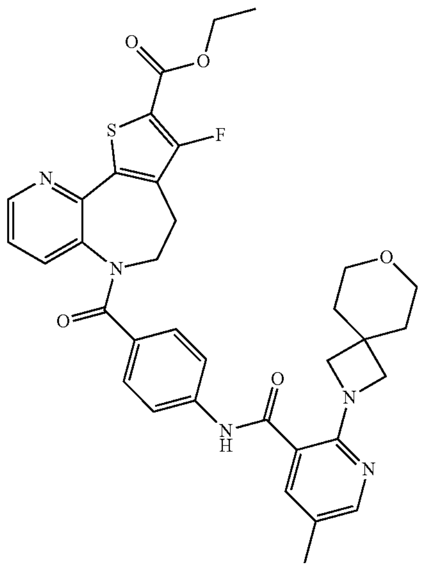 [SMILES: CCOC(=O)c1sc2c(c1F)CCN(C(=O)c1ccc(NC(=O)c3cc(C)cnc3N3CC4(CCOCC4)C3)cc1)c1cccnc1-2]

In a vial, 5-methyl-2-(7-oxa-2-azaspiro[3.5]nonan-2-yl) nicotinic acid (529 mg, 2.015 mmol) was dissolved in DCM (15.994 ml) and 1-chloro-N,N,2-trimethylprop-1-en-1-amine (0.444 ml, 3.36 mmol) was added dropwise. The reaction was allowed to stir for 1 h until complete disappearance of starting material by LCMS. The reaction was concentrated and ethyl 5-(4-aminobenzoyl)-8-fluoro-6,7-dihydro-5H-pyrido[3,2-b]thieno[2,3-d]azepine-9-carboxylate (691 mg, 1.679 mmol) added as a solution in pyridine (0.800 ml). The reaction mixture was allowed to stir at room temperature overnight. The reaction mixture was concentrated and loaded onto a column eluting with 0-100% Hex/EtOAc yielding ethyl 8-fluoro-5-(4-(5-methyl-2-(7-oxa-2-azaspiro[3.5]nonan-2-yl)nicotinamido)benzoyl)-6,7-dihydro-5H-pyrido[3,2-b]thieno[2,3-d]azepine-9-carboxylate (532 mg). ESI-MS m/z: 656.0 [M+H]$^+$.

Example 70 Step 1

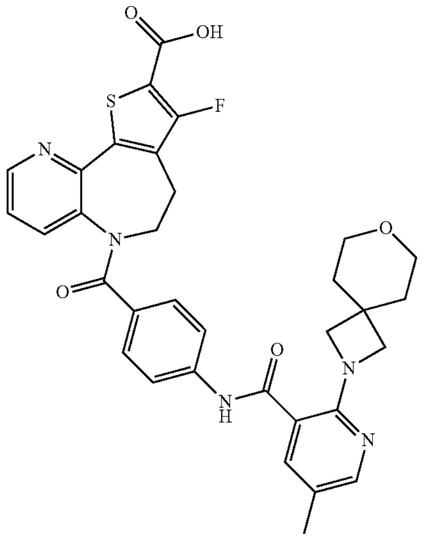 [SMILES: Cc1cnc(N2CC3(CCOCC3)C2)c(C(=O)Nc2ccc(C(=O)N3CCc4c(sc(C(=O)O)c4F)-c4ncccc43)cc2)c1]

In a vial, ethyl 8-fluoro-5-(4-(5-methyl-2-(7-oxa-2-azaspiro[3.5]nonan-2-yl)nicotinamido)-benzoyl)-6,7-dihydro-5H-pyrido[3,2-b]thieno[2,3-d]azepine-9-carboxylate (532 mg, 0.811 mmol) was dissolved in THF (6638 μl), MeOH (738 μl), and Water (738 μl). To the vial was added lithium hydroxide hydrate (340 mg, 8.11 mmol) and the reaction was allowed to stir at room temperature overnight. To the vial, water and 4M HCl were added to adjust to pH=2-3. The aqueous layer was washed with DCM and the organic layer dried over Mg $SO_4$, filtered and concentrated to give 8-fluoro-5-(4-(5-methyl-2-(7-oxa-2-azaspiro[3.5]nonan-2-yl)nicotinamido)benzoyl)-6,7-dihydro-5H-pyrido[3,2-b]thieno[2,3-d]azepine-9-carboxylic acid (468 mg) as a yellow solid. ESI-MS m/z: 628.0 [M+H]$^+$.

Example 70 Step m

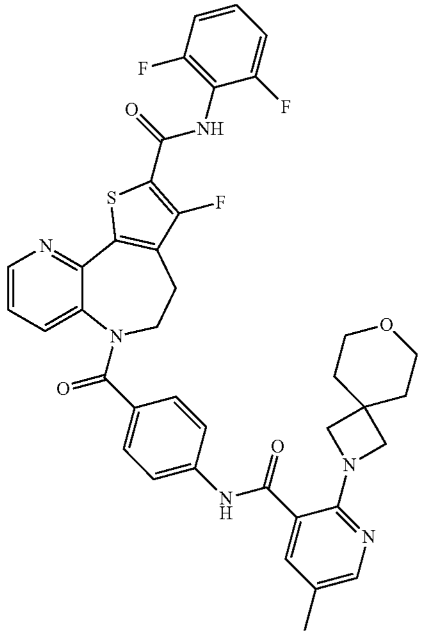 [SMILES: Cc1cnc(N2CC3(CCOCC3)C2)c(C(=O)Nc2ccc(C(=O)N3CCc4c(sc(C(=O)Nc5c(F)cccc5F)c4F)-c4ncccc43)cc2)c1]

To an oven-dried vial, 8-fluoro-5-(4-(5-methyl-2-(7-oxa-2-azaspiro[3.5]nonan-2-yl)nicotinamido)benzoyl)-6,7-dihydro-5H-pyrido[3,2-b]thieno[2,3-d]azepine-9-carboxylic acid (234 mg, 0.373 mmol) was dissolved in DCM (1864 μl). 1-chloro-N,N,-2-trimethylprop-1-en-1-amine (99 μl, 0.746 mmol) was added dropwise and allowed to stir at room temperature for 2 hours. The reaction mixture was concentrated and to the subsequent residue was added 2,6-difluoroaniline (161 μl, 1.491 mmol), DCM (1864 μl) and pyridine (121 μl, 1.491 mmol). The reaction mixture was stirred at room temperature overnight. The reaction mixture was concentrated and the crude product was added to a silica gel column and was eluted with methanol/dichloromethane 0% to 10% to give the product. Next, the material was purified using preparatory HPLC (MeCN/$H_2O$) yielding N-(2,6-difluorophenyl)-8-fluoro-5-(4-(5-methyl-2-(7-oxa-2-azaspiro[3.5]nonan-2-yl)nicotinamido)benzoyl)-6,7-dihydro-5H-pyrido[3,2-b]thieno[2,3-d]azepine-9-carboxamide (85 mg) as a white solid. ESI-MS m/z: 739.1 $[M+H]^+$.

Example 71

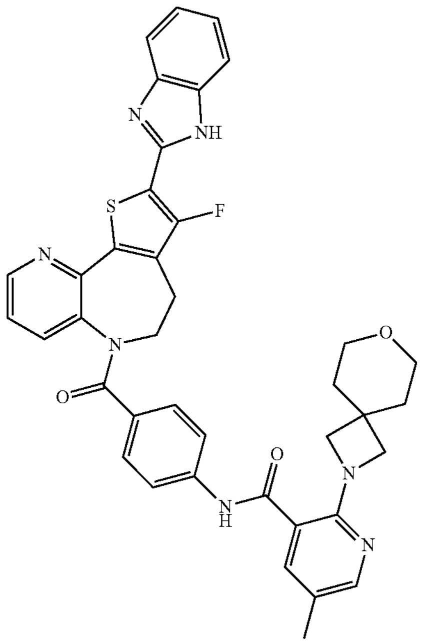 [SMILES: Cc1cnc(N2CC3(CCOCC3)C2)c(C(=O)Nc2ccc(C(=O)N3CCc4c(sc(-c5nc6ccccc6[nH]5)c4F)-c4ncccc43)cc2)c1]

Example 71 Step a

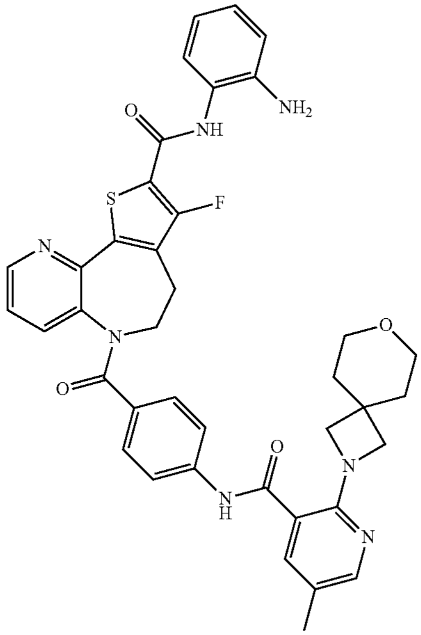 [SMILES: Cc1cnc(N2CC3(CCOCC3)C2)c(C(=O)Nc2ccc(C(=O)N3CCc4c(sc(C(=O)Nc5ccccc5N)c4F)-c4ncccc43)cc2)c1]

To a solution of 8-fluoro-5-(4-(5-methyl-2-(7-oxa-2-azaspiro[3.5]nonan-2-yl)nicotinamido)-benzoyl)-6,7-dihydro-5H-pyrido[3,2-b]thieno[2,3-d]azepine-9-carboxylic acid (234 mg, 0.373 mmol), EDC (86 mg, 0.447 mmol), and HOBt (68.5 mg, 0.447 mmol) in DMF (2868 μl) was added benzene-1,2-diamine (60.5 mg, 0.559 mmol). The reaction mixture was stirred at room temperature for 24 hours. The reaction mixture was poured into water and extracted with EtOAc (3×). The organic layers were combined, washed with saturated $NaHCO_3$ and brine, and dried over $Na_2SO_4$. The solution was filtrated, concentrated in vacuo, and taken forward without purification yielding N-(2-aminophenyl)-8-fluoro-5-(4-(5-methyl-2-(7-oxa-2-azaspiro[3.5]nonan-2-yl)nicotinamido)benzoyl)-6,7-dihydro-5H-pyrido[3,2-b]thieno[2,3-d]azepine-9-carboxamide (268 mg). ESI-MS m/z: 718.0 $[M+H]^+$.

Example 71 Step b

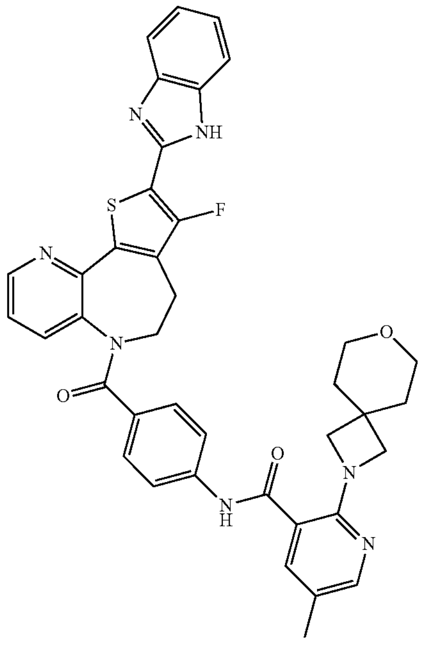 [SMILES: Cc1cnc(N2CC3(CCOCC3)C2)c(C(=O)Nc2ccc(C(=O)N3CCc4c(sc(-c5nc6ccccc6[nH]5)c4F)-c4ncccc43)cc2)c1]

In a vial, N-(2-aminophenyl)-8-fluoro-5-(4-(5-methyl-2-(7-oxa-2-azaspiro[3.5]nonan-2-yl)nicotinamido)benzoyl)-6,7-dihydro-5H-pyrido[3,2-b]thieno[2,3-d]azepine-9-carboxamide (268 mg, 0.373 mmol) was dissolved in acetic acid (9334 μl). The vial was sealed and heated to 100° C. for 2 hours. The vial was cooled to room temperature and concentrated. Saturated aqueous $NaHCO_3$ and dichloromethane (10 mL) were added. The aqueous layer was washed with dichloromethane (3×10 mL). The combined organic layers were dried over $MgSO_4$ and concentrated. The crude product was added to a silica gel column and was eluted with methanol/dichloromethane 0% to 20% to give product. Next, the material was purified by preparatory HPLC ($MeCN/H_2O$) to give the title compound (45 mg). ESI-MS m/z: 700.0 $[M+H]^+$.

Examples 72-80 shown in table 6 were prepared using the procedure similar to those of example 1 step g or example 3 from the corresponding intermediates.

TABLE 6

| Example | Structure | ESI-MS m/z: $[M + H]^+$ |
|---|---|---|
| 72 | 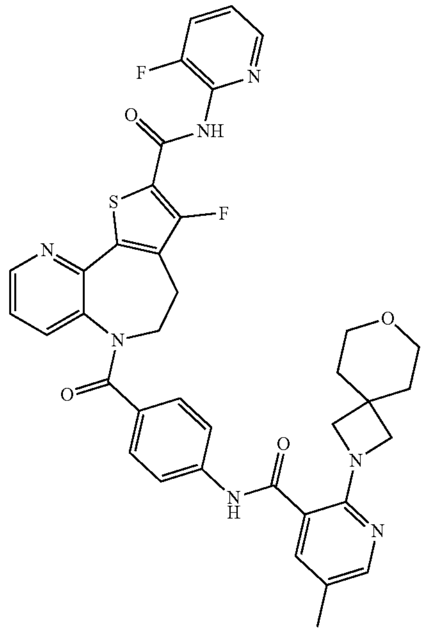 [SMILES: Cc1cnc(N2CC3(CCOCC3)C2)c(C(=O)Nc2ccc(C(=O)N3CCc4c(sc(C(=O)Nc5ncccc5F)c4F)-c4ncccc43)cc2)c1] | 722.4 |
| 73 | 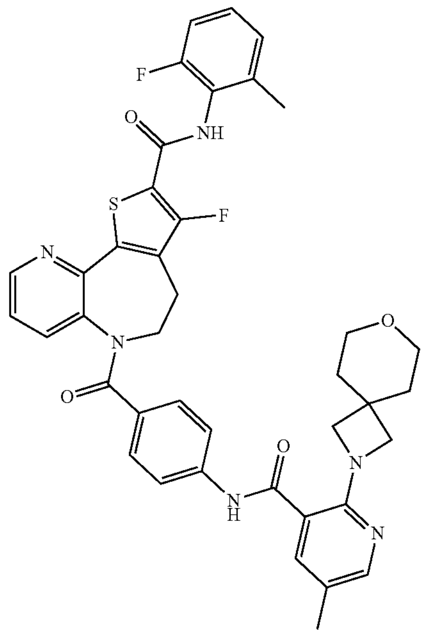 [SMILES: Cc1cnc(N2CC3(CCOCC3)C2)c(C(=O)Nc2ccc(C(=O)N3CCc4c(sc(C(=O)Nc5c(C)cccc5F)c4F)-c4ncccc43)cc2)c1] | 735.35 |

TABLE 6-continued
| Example | Structure | ESI-MS m/z: [M + H]+ |
|---|---|---|
| 74 | 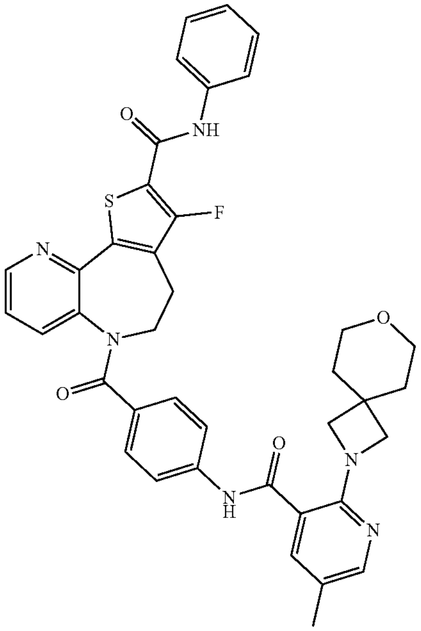 [SMILES: Cc1cnc(N2CC3(CCOCC3)C2)c(C(=O)Nc2ccc(C(=O)N3CCc4c(sc(C(=O)Nc5ccccc5)c4F)-c4ncccc43)cc2)c1] | 703.2 |
| 75 | 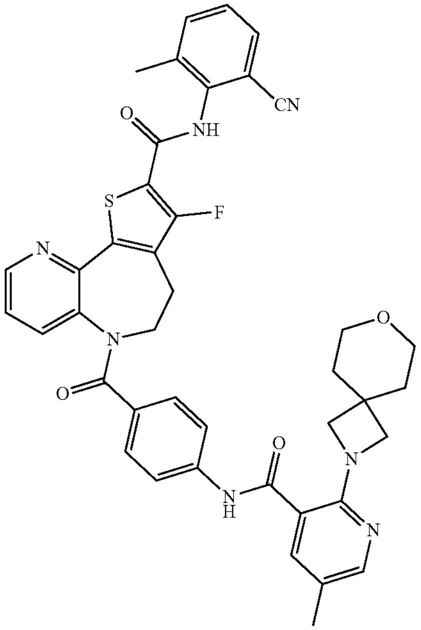 [SMILES: Cc1cnc(N2CC3(CCOCC3)C2)c(C(=O)Nc2ccc(C(=O)N3CCc4c(sc(C(=O)Nc5c(C)cccc5C#N)c4F)-c4ncccc43)cc2)c1] | 742.35 |
TABLE 6-continued
| Example | Structure | ESI-MS m/z: [M + H]+ |
|---|---|---|
| 76 | 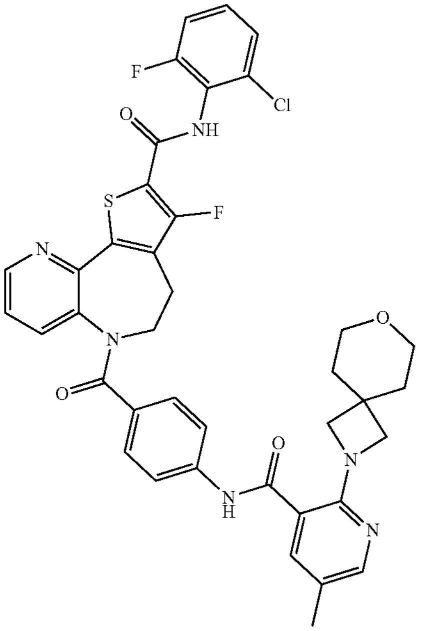 [SMILES: Cc1cnc(N2CC3(CCOCC3)C2)c(C(=O)Nc2ccc(C(=O)N3CCc4c(sc(C(=O)Nc5c(F)cccc5Cl)c4F)-c4ncccc43)cc2)c1] | 755.3 |
| 77 | 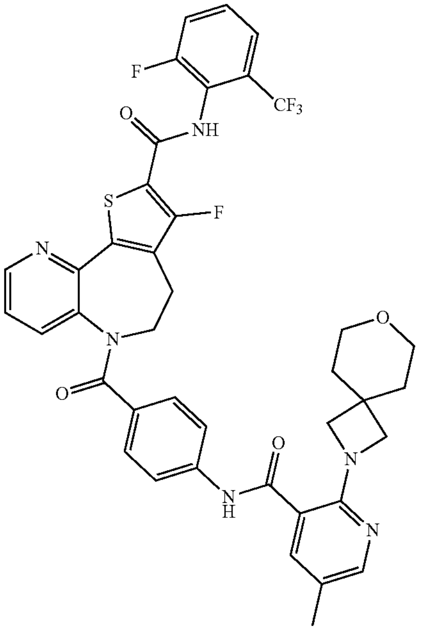 [SMILES: Cc1cnc(N2CC3(CCOCC3)C2)c(C(=O)Nc2ccc(C(=O)N3CCc4c(sc(C(=O)Nc5c(F)cccc5C(F)(F)F)c4F)-c4ncccc43)cc2)c1] | 789.35 |

TABLE 6-continued
| Example | Structure | ESI-MS m/z: [M + H]+ |
|---|---|---|
| 78 | 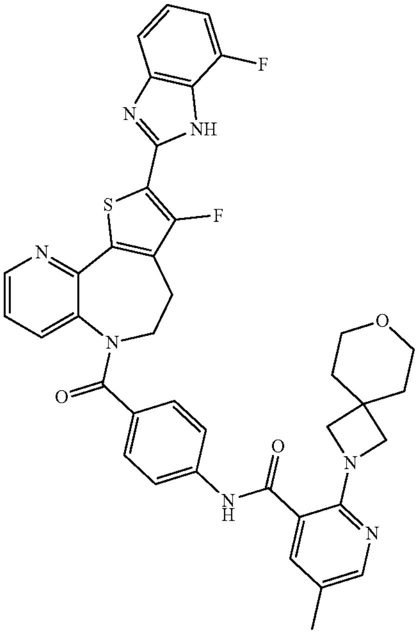 [SMILES: Cc1cnc(N2CC3(CCOCC3)C2)c(C(=O)Nc2ccc(C(=O)N3CCc4c(sc(-c5nc6cccc(F)c6[nH]5)c4F)-c4ncccc43)cc2)c1] | 718.2 |
| 79 | 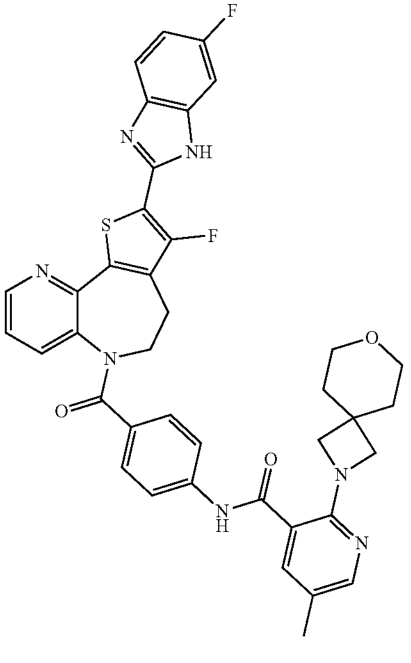 [SMILES: Cc1cnc(N2CC3(CCOCC3)C2)c(C(=O)Nc2ccc(C(=O)N3CCc4c(sc(-c5nc6ccc(F)cc6[nH]5)c4F)-c4ncccc43)cc2)c1] | 718.2 |
TABLE 6-continued
| Example | Structure | ESI-MS m/z: [M + H]+ |
|---|---|---|
| 80 | 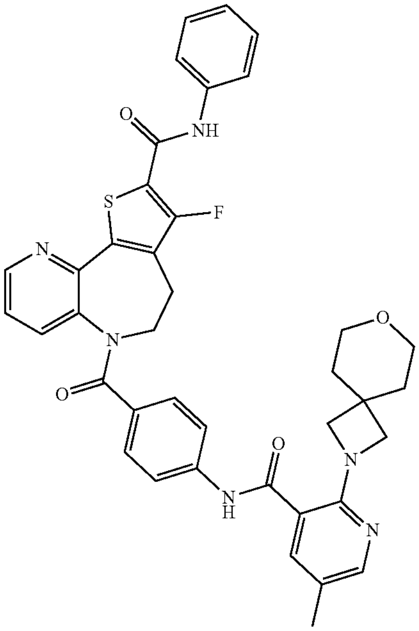 [SMILES: Cc1cnc(N2CC3(CCOCC3)C2)c(C(=O)Nc2ccc(C(=O)N3CCc4c(sc(C(=O)Nc5ccccc5)c4F)-c4ncccc43)cc2)c1] | 703.2 |
Example 81
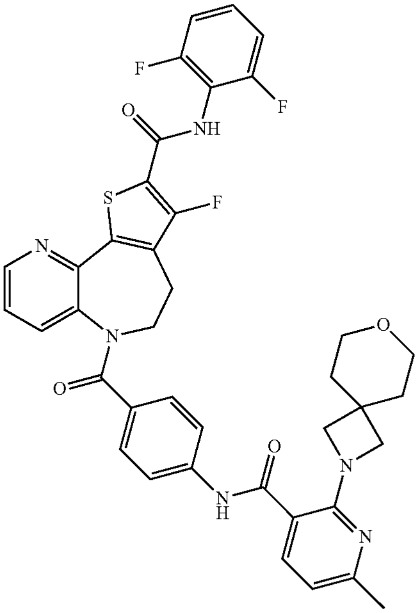 [SMILES: Cc1ccc(C(=O)Nc2ccc(C(=O)N3CCc4c(sc(C(=O)Nc5c(F)cccc5F)c4F)-c4ncccc43)cc2)c(N2CC3(CCOCC3)C2)n1]
Example 81 was prepared in a similar fashion to Example 70, step k through step m using 6-methyl-2-(7-oxa-2-azaspiro[3.5]nonan-2-yl) nicotinic acid. ESI-MS m/z: 739.0 $[M+H]^+$.

Example 82

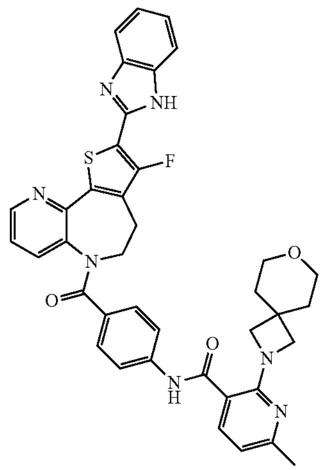 [SMILES: Cc1ccc(C(=O)Nc2ccc(C(=O)N3CCc4c(sc(-c5nc6ccccc6[nH]5)c4F)-c4ncccc43)cc2)c(N2CC3(CCOCC3)C2)n1]

Example 82 was prepared in a similar fashion to example 71, step a and b using 8-fluoro-5-(4-(6-methyl-2-(7-oxa-2-azaspiro[3.5]nonan-2-yl)nicotinamido)benzoyl)-6,7-dihydro-5H-pyrido[3,2-b]thieno[2,3-d]azepine-9-carboxylic acid. ESI-MS m/z: 700.0 $[M+H]^+$.

Examples 83-88 shown in table 7 were prepared using the procedure similar to those of example 1 step g or example 3 from the corresponding intermediates.

TABLE 7

| Example | Structure | ESI-MS m/z: $[M + H]^+$ |
|---|---|---|
| 83 | 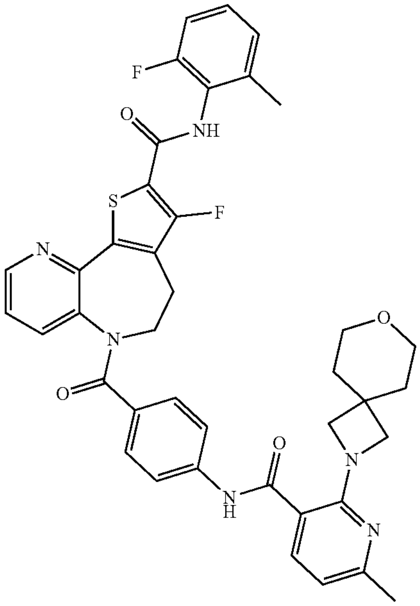 [SMILES: Cc1ccc(C(=O)Nc2ccc(C(=O)N3CCc4c(sc(C(=O)Nc5c(C)cccc5F)c4F)-c4ncccc43)cc2)c(N2CC3(CCOCC3)C2)n1] | 735.25 |

TABLE 7-continued

| Example | Structure | ESI-MS m/z: $[M + H]^+$ |
|---|---|---|
| 84 | 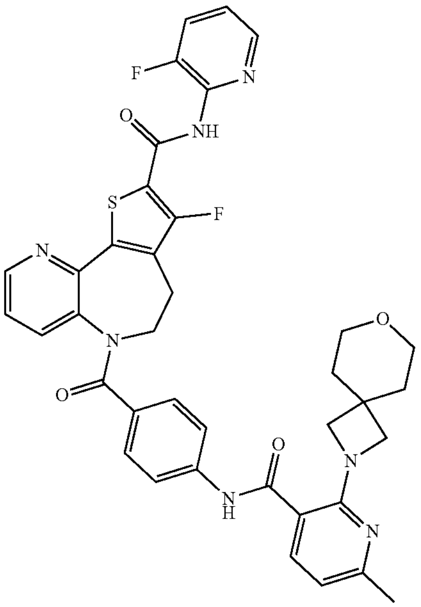 [SMILES: Cc1ccc(C(=O)Nc2ccc(C(=O)N3CCc4c(sc(C(=O)Nc5ncccc5F)c4F)-c4ncccc43)cc2)c(N2CC3(CCOCC3)C2)n1] | 722.2 |
| 85 | 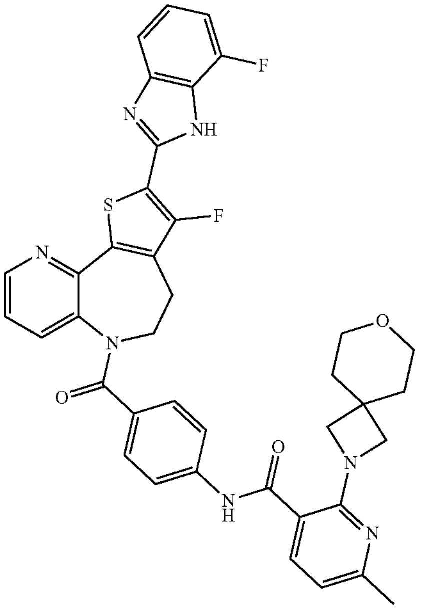 [SMILES: Cc1ccc(C(=O)Nc2ccc(C(=O)N3CCc4c(sc(-c5nc6cccc(F)c6[nH]5)c4F)-c4ncccc43)cc2)c(N2CC3(CCOCC3)C2)n1] | 718.3 |

TABLE 7-continued
| Example | Structure | ESI-MS m/z: [M + H]+ |
|---|---|---|
| 86 | 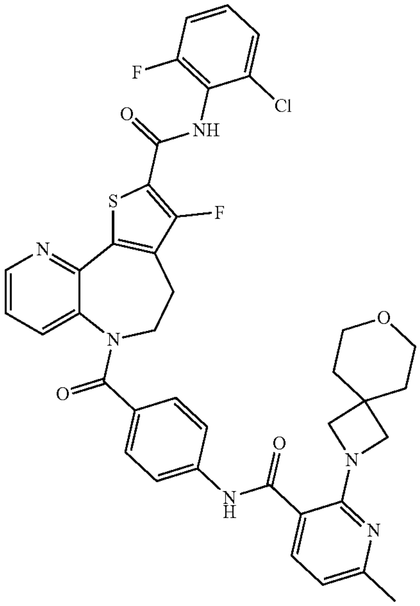 [SMILES: Cc1ccc(C(=O)Nc2ccc(C(=O)N3CCc4c(sc(C(=O)Nc5c(F)cccc5Cl)c4F)-c4ncccc43)cc2)c(N2CC3(CCOCC3)C2)n1] | 755.2 |
| 87 | 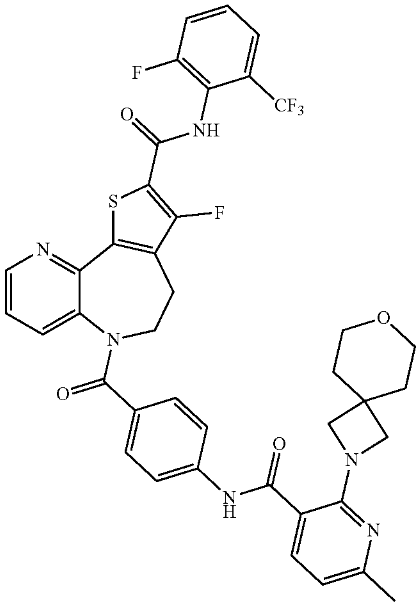 | 789.15 |
| 88 | 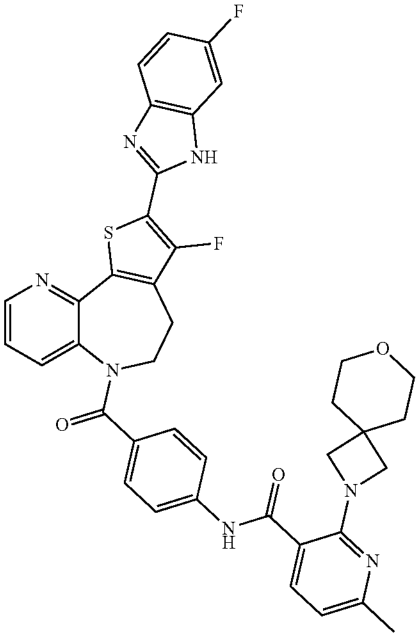 [SMILES: Cc1ccc(C(=O)Nc2ccc(C(=O)N3CCc4c(sc(-c5nc6ccc(F)cc6[nH]5)c4F)-c4ncccc43)cc2)c(N2CC3(CCOCC3)C2)n1] | 718.2 |

Scheme 15
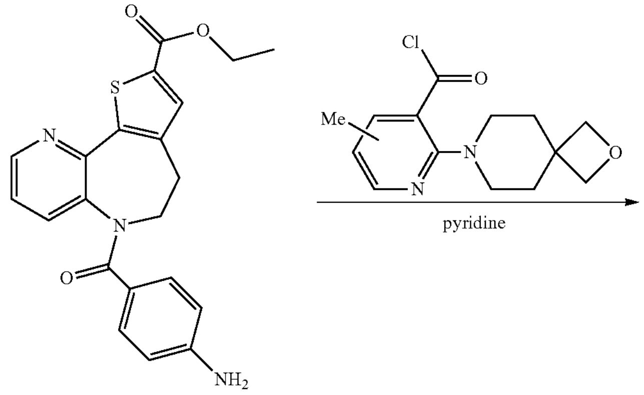
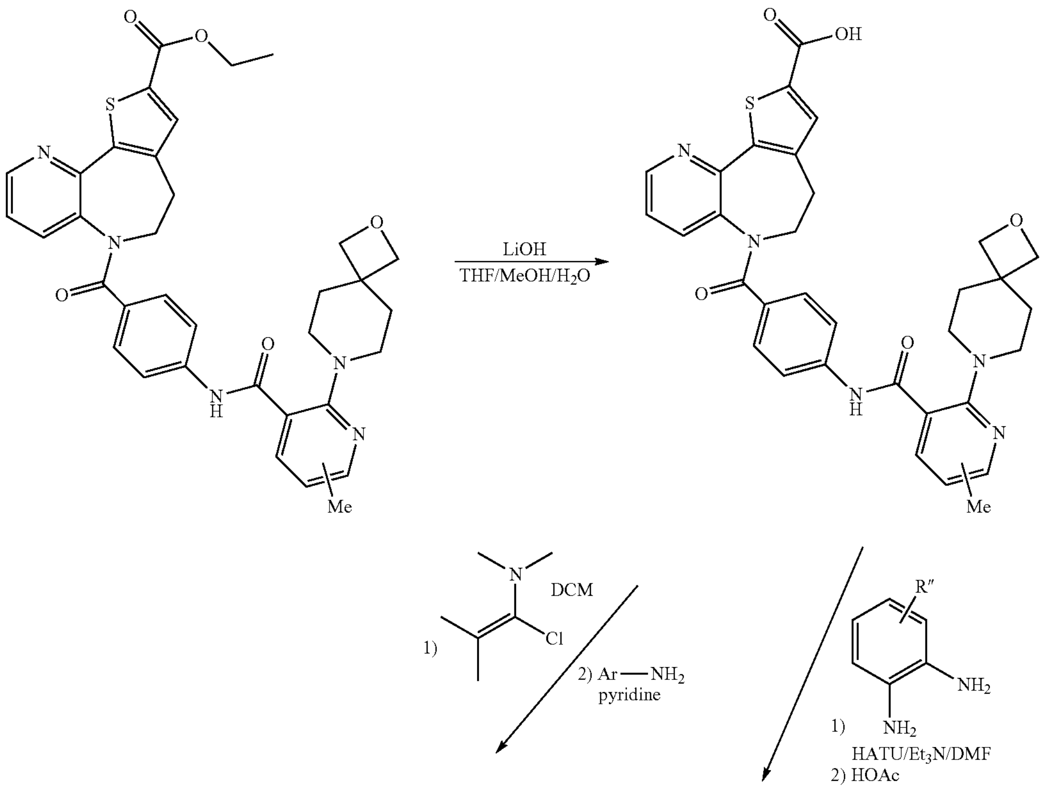

-continued

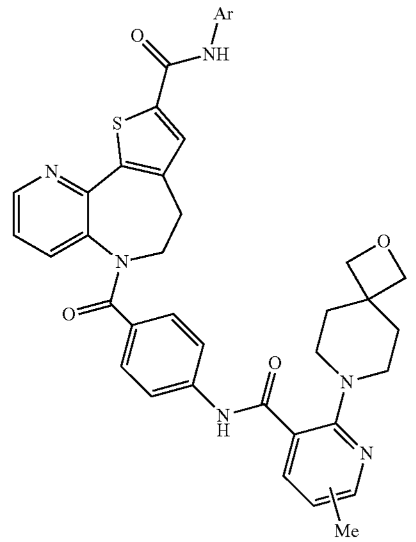

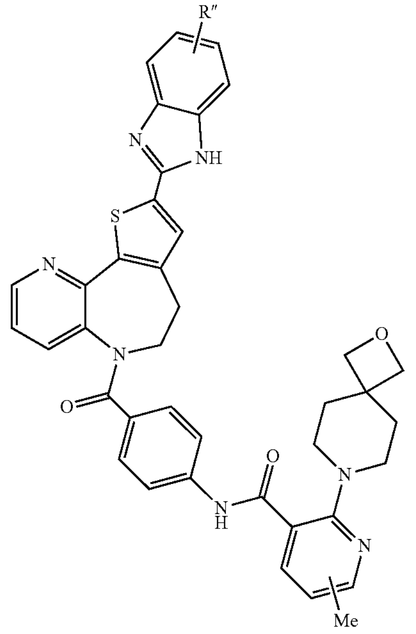

Example 89

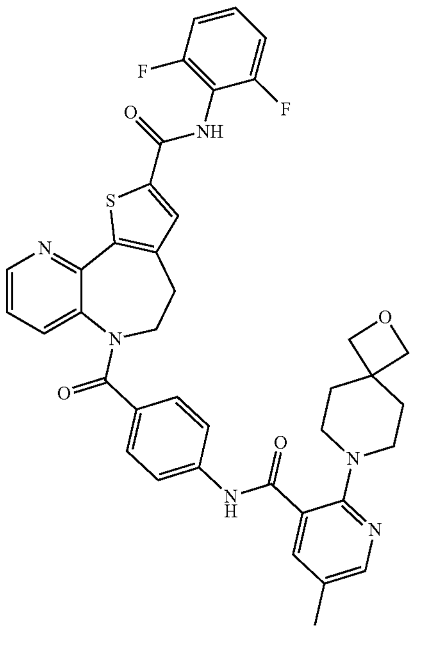 [SMILES: Cc1cnc(N2CCC3(CC2)COC3)c(C(=O)Nc2ccc(C(=O)N3CCc4cc(C(=O)Nc5c(F)cccc5F)sc4-c4ncccc43)cc2)c1]

Example 89 Step a

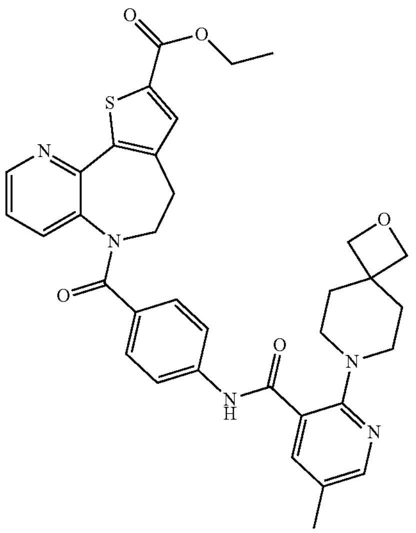 [SMILES: CCOC(=O)c1cc2c(s1)-c1ncccc1N(C(=O)c1ccc(NC(=O)c3cc(C)cnc3N3CCC4(CC3)COC4)cc1)CC2]

1-chloro-2-methylprop-1-en-1-yl)dimethylamine (2.23 g, 17 mmol) was added to the solution of 5-methyl-2-(2-oxa-7-azaspiro[3.5]nonan-7-yl)nicotinic acid (1.5 g, 5.7 mmol) in DCM (20 mL). The mixture was stirred for 1 hour before bening concentrated. The compound (from example 4 step b, 2.48 g, 6.3 mmol) and pyridine (2 mL) in DCM (5 mL) was dropwise added. The mixture was stirred for 1 hour. The solution was evaporated and purified by reverse phase C18 column chromatography (MeCN/$H_2O$) to give the title compound as a yellow solid (1.1 g). ESI-MS m/z: 638.25 $[M+H]^-$.

Example 89 Step b

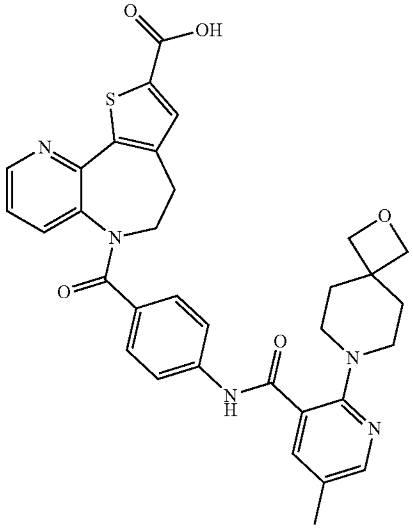 [SMILES: Cc1cnc(N2CCC3(CC2)COC3)c(C(=O)Nc2ccc(C(=O)N3CCc4cc(C(=O)O)sc4-c4ncccc43)cc2)c1]

A mixture of the compound from step a (1.05 g, 1.7 mmol) and LiOH (395 mg, 17 mmol) in MeOH (10 mL) and water (10 mL) was stirred for 1 hour at 50° C. The mixture was concentrated and adjusted to pH=6 with $H_2SO_4$(10%), evaporated, purified by reverse phase C18 column chromatography (MeCN/$H_2O$) to give the title compound as a yellow solid (500 mg). ESI-MS m/z: 610.30 $[M+H]^+$.

Example 89 Step c

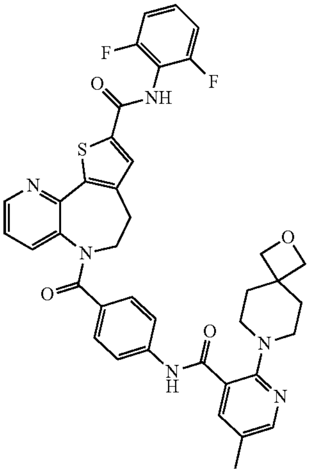 [SMILES: Cc1cnc(N2CCC3(CC2)COC3)c(C(=O)Nc2ccc(C(=O)N3CCc4cc(C(=O)Nc5c(F)cccc5F)sc4-c4ncccc43)cc2)c1]

1-chloro-2-methylprop-1-en-1-yl)dimethylamine (39 mg, 0.30 mmol) was added to the solution of the compound from step b (60 mg, 0.098 mmol) in DCM (3 mL). The mixture was stirred for 1 hour. 2,6-difluoroaniline (50 mg, 0.39 mmol) and pyridine (1 mL) in DCM (3 mL) was dropwise added. The mixture was stirred for 1 hour and evaporated and purified by reverse phase C18 column chromatography (MeCN/$H_2O$) and Prep-HPLC to give the titled compound as a light yellow solid (10.6 mg). ESI-MS m/z: 721.35 $[M+H]^+$. $^1$H NMR (400 MHz, DMSO-$d_6$) δ 1.78 (t, J=5.4 Hz, 4H), 2.23 (s, 3H), 3.06 (t, J=5.4 Hz, 4H), 3.28 (s, 3H), 4.29 (s, 4H), 5.03 (s, 1H), 7.03-7.15 (m, 3H), 7.24 (t, J=8.4 Hz, 3H), 7.44 (p, J=7.5 Hz, 1H), 7.59 (d, J=8.3 Hz, 2H), 7.71 (d, J=2.3 Hz, 1H), 7.96 (s, 1H), 8.16 (s, 1H), 8.42 (d, J=4.6 Hz, 1H), 10.27 (s, 1H), 10.76 (s, 1H).

Examples 90-98 shown in table 8 were prepared using the procedure similar to those of example 1 step g or example 3 from the corresponding intermediates.

TABLE 8

| Example | Structure | ESI-MS m/z: $[M + H]^+$ |
| --- | --- | --- |
| 90 | 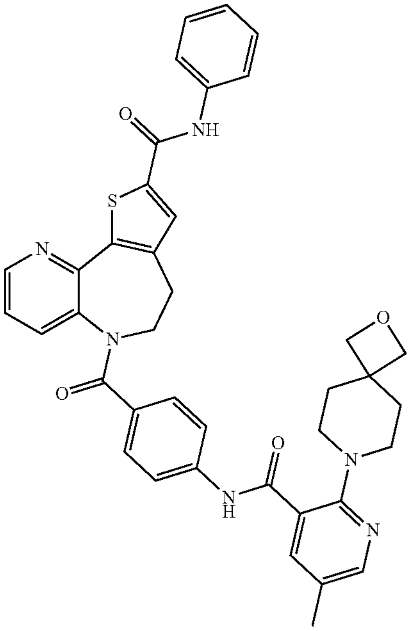 [SMILES: Cc1cnc(N2CCC3(CC2)COC3)c(C(=O)Nc2ccc(C(=O)N3CCc4cc(C(=O)Nc5ccccc5)sc4-c4ncccc43)cc2)c1] | 685.2 |
| 91 | 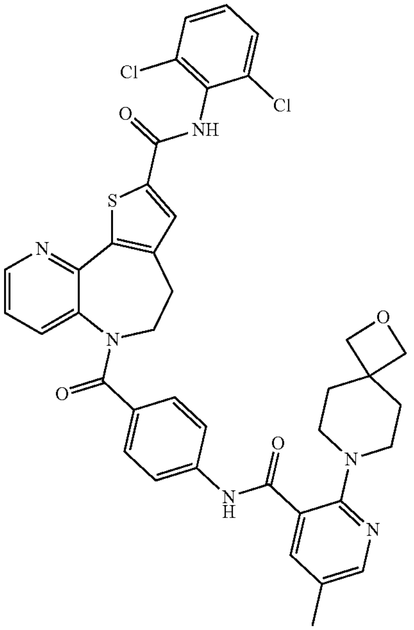 [SMILES: Cc1cnc(N2CCC3(CC2)COC3)c(C(=O)Nc2ccc(C(=O)N3CCc4cc(C(=O)Nc5c(Cl)cccc5Cl)sc4-c4ncccc43)cc2)c1] | 753.1 |

TABLE 8-continued
| Example | Structure | ESI-MS m/z: [M + H]+ |
|---|---|---|
| 92 | 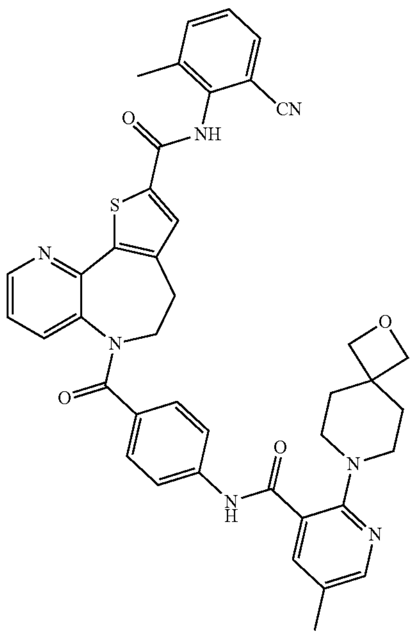 [SMILES: Cc1cnc(N2CCC3(CC2)COC3)c(C(=O)Nc2ccc(C(=O)N3CCc4cc(C(=O)Nc5c(C)cccc5C#N)sc4-c4ncccc43)cc2)c1] | 724.2 |
| 93 | 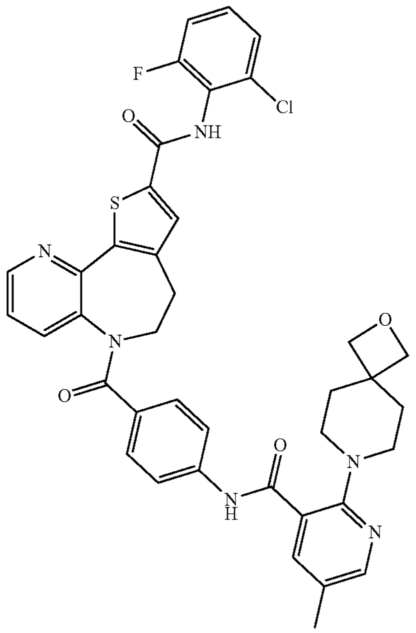 [SMILES: Cc1cnc(N2CCC3(CC2)COC3)c(C(=O)Nc2ccc(C(=O)N3CCc4cc(C(=O)Nc5c(F)cccc5Cl)sc4-c4ncccc43)cc2)c1] | 737.2 |
TABLE 8-continued
| Example | Structure | ESI-MS m/z: [M + H]+ |
|---|---|---|
| 94 | 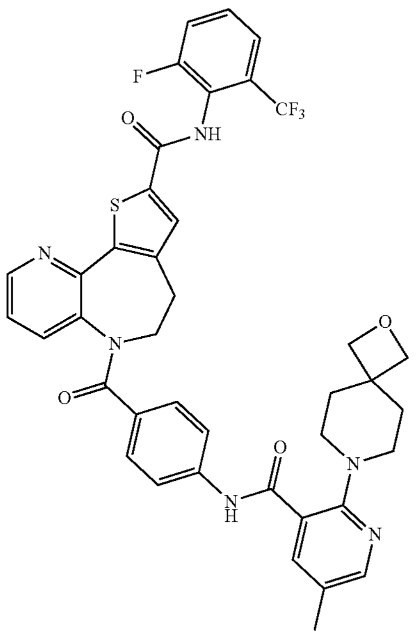 [SMILES: Cc1cnc(N2CCC3(CC2)COC3)c(C(=O)Nc2ccc(C(=O)N3CCc4cc(C(=O)Nc5c(F)cccc5C(F)(F)F)sc4-c4ncccc43)cc2)c1] | 771.15 |
| 95 | 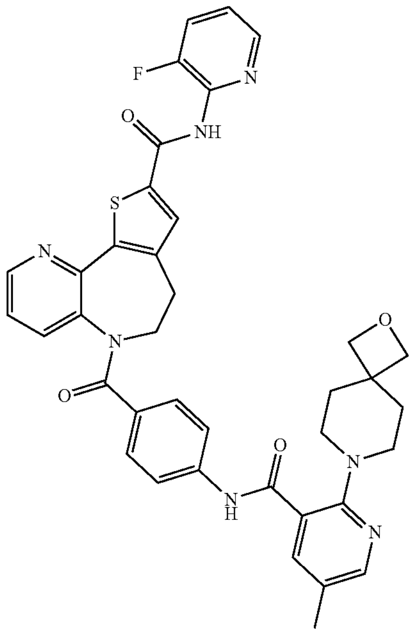 [SMILES: Cc1cnc(N2CCC3(CC2)COC3)c(C(=O)Nc2ccc(C(=O)N3CCc4cc(C(=O)Nc5ncccc5F)sc4-c4ncccc43)cc2)c1] | 704.2 |

TABLE 8-continued
| Example | Structure | ESI-MS m/z: [M + H]+ |
| --- | --- | --- |
| 96 | 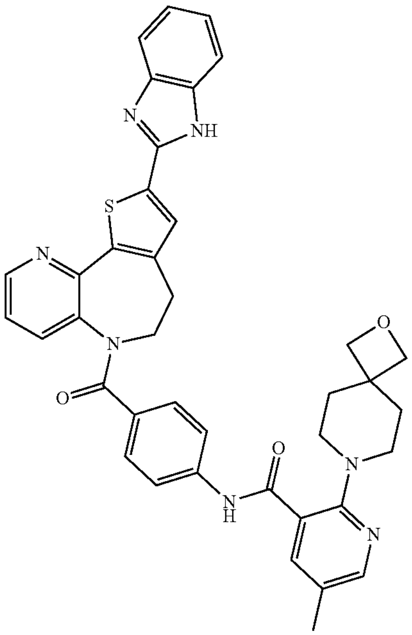 [SMILES: Cc1cnc(N2CCC3(CC2)COC3)c(C(=O)Nc2ccc(C(=O)N3CCc4cc(-c5nc6ccccc6[nH]5)sc4-c4ncccc43)cc2)c1] | 602.3 |
| 97 | 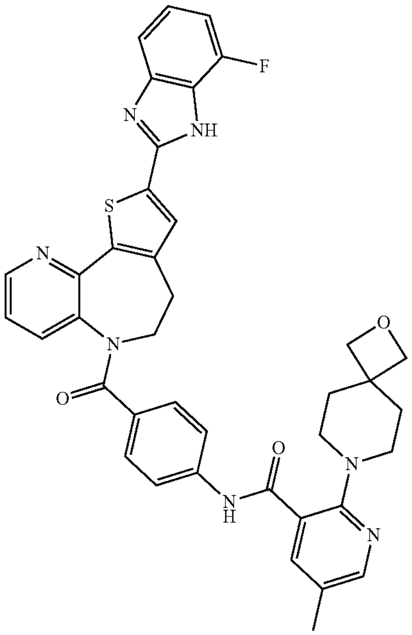 [SMILES: Cc1cnc(N2CCC3(CC2)COC3)c(C(=O)Nc2ccc(C(=O)N3CCc4cc(-c5nc6cccc(F)c6[nH]5)sc4-c4ncccc43)cc2)c1] | 700.2 |
TABLE 8-continued
| Example | Structure | ESI-MS m/z: [M + H]+ |
| --- | --- | --- |
| 98 | 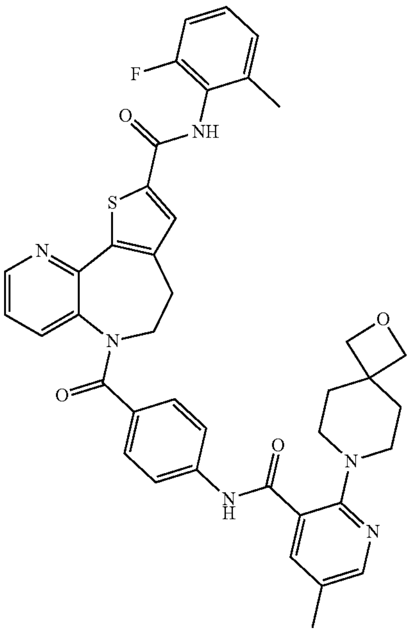 [SMILES: Cc1cnc(N2CCC3(CC2)COC3)c(C(=O)Nc2ccc(C(=O)N3CCc4cc(C(=O)Nc5c(C)cccc5F)sc4-c4ncccc43)cc2)c1] | 717.3 |

Scheme 16
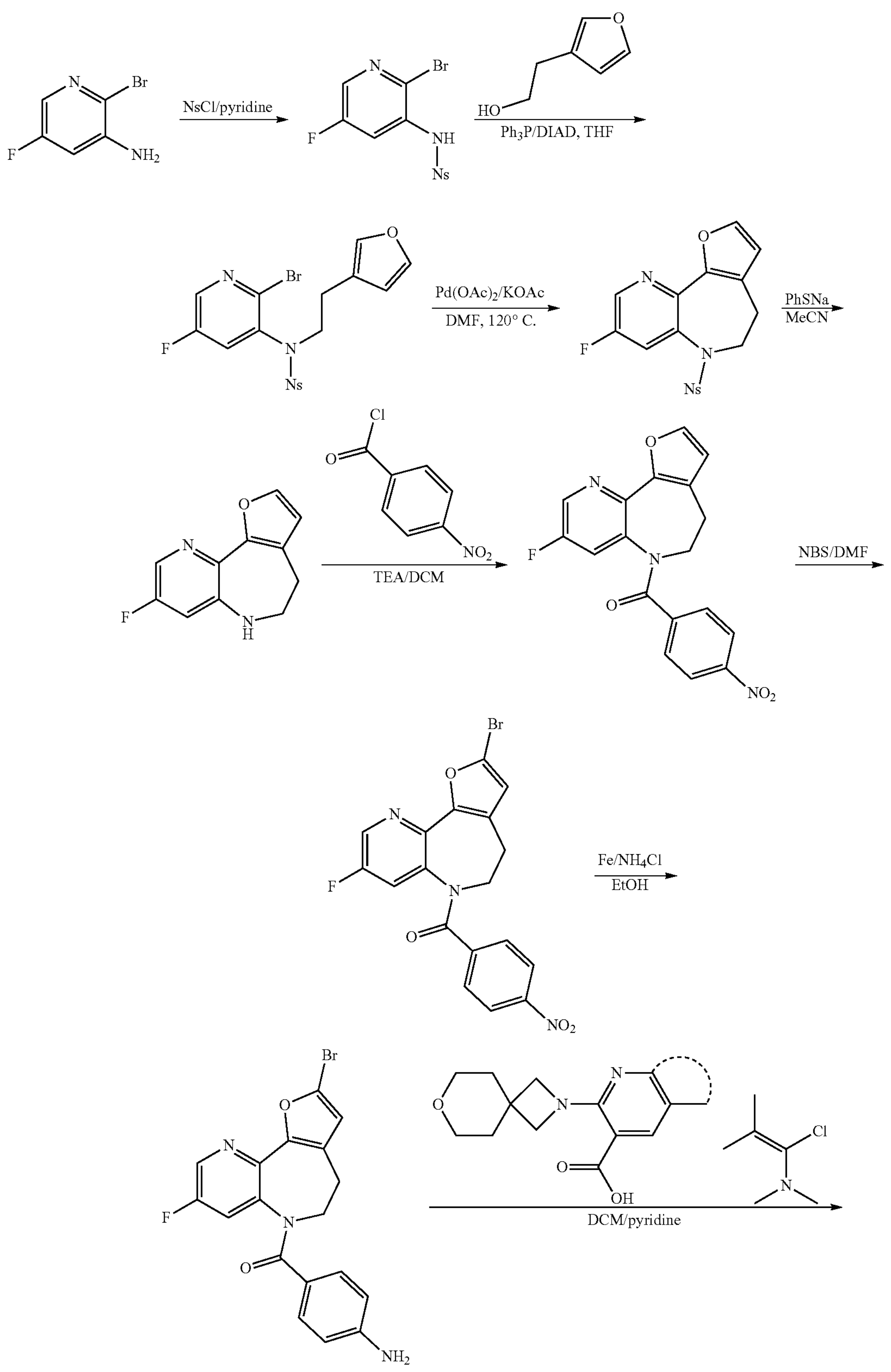

-continued
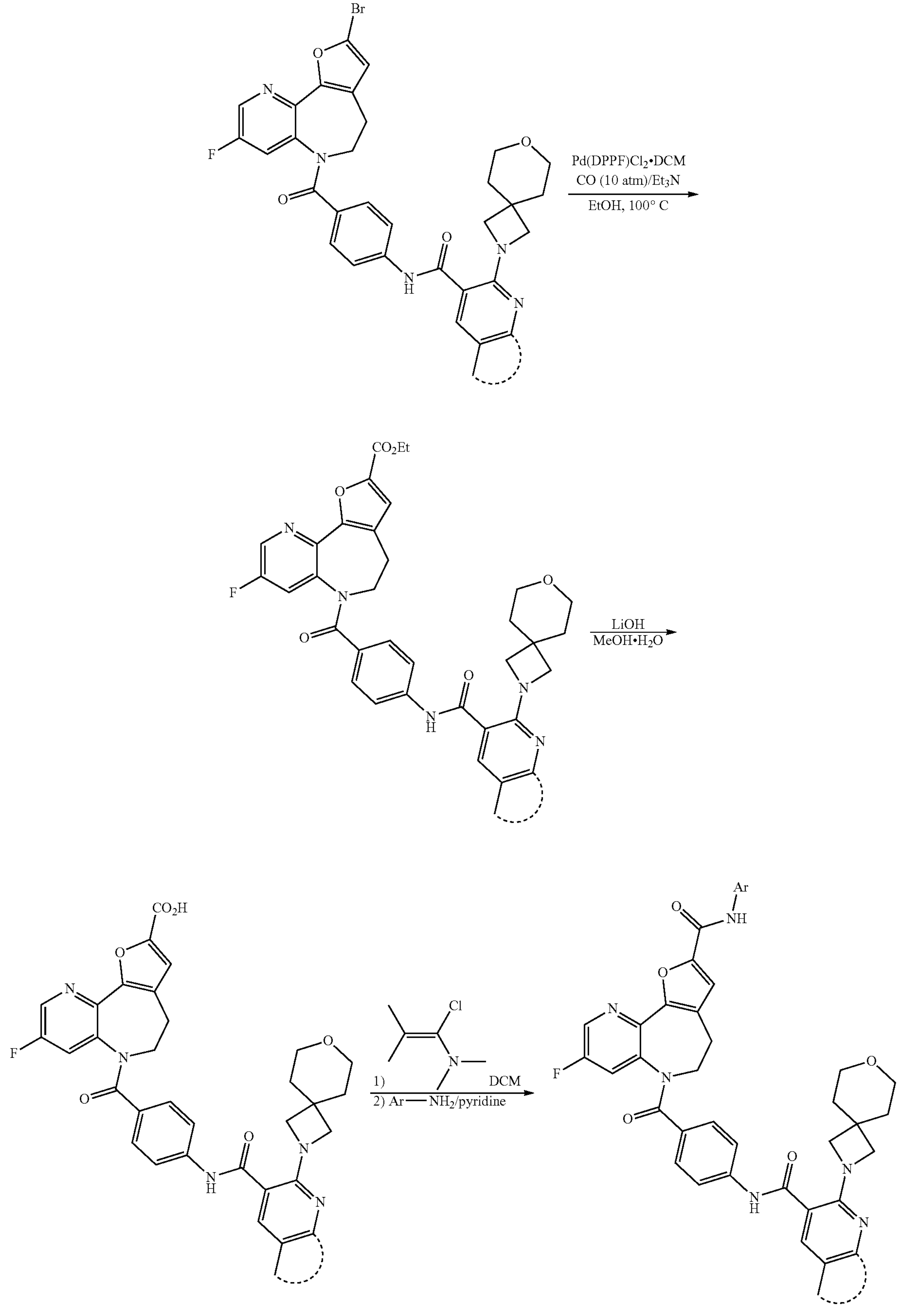

-continued

Ns =

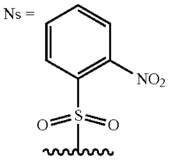

Example 99

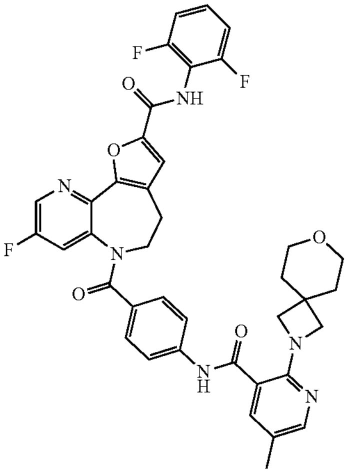 [SMILES: Cc1cnc(N2CC3(CCOCC3)C2)c(C(=O)Nc2ccc(C(=O)N3CCc4cc(C(=O)Nc5c(F)cccc5F)oc4-c4ncc(F)cc43)cc2)c1]

Example 99 Step a

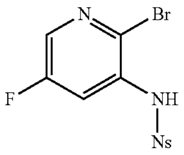

2-nitrobenzenesulfonyl chloride (29.0 g, 131.25 mol) was added to a mixture of 2-bromo-5-fluoropyridin-3-amine (19.1 g, 100 mmol, 1 equiv) in pyridine (100 mL) at 0° C. in portion. The mixture was allowed to warm to room temperature and stirred for 6.5 hrs, diluted with 700 mL EA and washed with $H_2O$ (4×150 mL). The organic layer was concentrated under vacuum. The residue was purified by C18 flash chromatography ($H_2O$/MeCN) to provide the title compound as a brown solid (16.8 g). ESI-MS m/z: 376.00 $[M+H]^+$.

Example 99 Step b

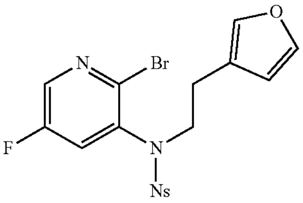

To a mixture of the compound from step a (5.56 g, 14.78 mmol) and 2-(furan-3-yl)ethan-1-ol (6.63 g, 59.13 mmol) in THF (70 mL) was dropwise added DIAD (6.0 g, 29.67 mmol) at 0° C. under nitrogen atmosphere. After being stirred for 30 min, the mixture was allowed to warm to room temperature and stirred for overnight. The reaction mixture was concentrated under vacuum. The residue was purified by silica gel chromatography (PE:EA=5:1) togive the the title compound as amorphous solid (4.9 g). ESI-MS m/z: 469.90 $[M+H]^+$. $^1H$ NMR (400 MHz, DMSO-$d_6$) δ 2.55-2.78 (m, 2H), 3.40-3.90 (m, 2H), 6.38 (dd, J=1.8, 0.9 Hz, 1H), 7.48-7.52 (m, 1H), 7.55 (t, J=1.7 Hz, 1H), 7.83-7.89 (m, 2H), 8.02-7.92 (m, 3H), 8.59 (d, J=2.8 Hz, 1H).

Example 99 Step c

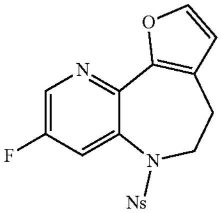

A mixture of the compound from step b (18.3 g, 38.91 mmol), $Pd(OAc)_2$ (874 mg, 3.89 mmol) and KOAc (22.91 g, 233.44 mmol) in DMF (150 mL) was stirred at 120° C. under nitrogen atmosphere for 1 h. The mixture was filtered through celite and washed with EA (500 mL). The filtrate was washed with $H_2O$ (4×100 mL) and brine. The organic layer was dried over $Na_2SO_4$, filtered and concentrated under vacuum. The residue was purified by silica gel chromatography (PE/EA=3/1 to PE/EA=1/1) to give the title compound as a brown solid (9.5 g). ESI-MS m/z: 390.00 $[M+H]^+$.

Example 99 Step d

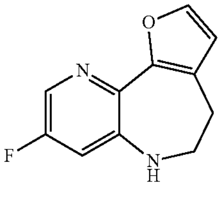

A mixture of the compound from step c (9.5 g, 24.40 mmol) and PhSNa (19.28 g, 146.06 mmol) in MeCN (150 mL) was stirred at room temperature for overnight. After being concentrated under vacuum, the residue was purified by silica gel chromatography (PE:EA=3:1 to 1:1) to provide the title compound as a brown solid (3.8 g). ESI-MS m/z: 205.10 $[M+H]^+$.

Example 99 Step e

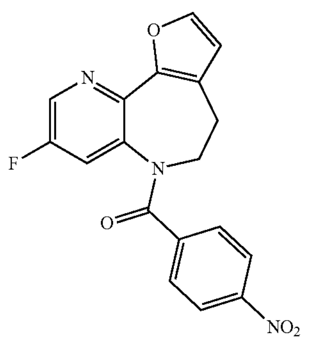 [SMILES: O=C(c1ccc([N+](=O)[O-])cc1)N1CCc2ccoc2-c2ncc(F)cc21]

The title compound was prepared using a procedure similar to that used to prepare the compound in example 54 step e. ESI-MS m/z: 354.05 [M+H]$^+$.

Example 99 Step f

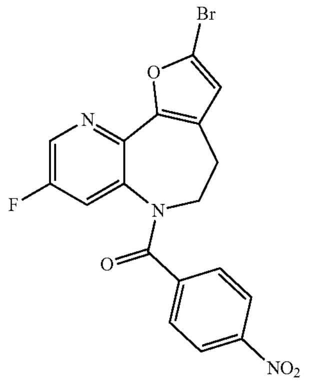

The title compound was prepared using a procedure similar to that used to prepare the compound in example 54 step f ESI-MS m/z: 432.00 [M+H]$^+$. $^1$H NMR (400 MHz, DMSO-$d_6$) δ 2.87-3.19 (m, 3H), 4.94 (s, 1H), 6.84 (s, 1H), 7.32 (d, J=8.1 Hz, 2H), 7.50 (d, J=9.4 Hz, 1H), 8.06-8.22 (m, 2H), 8.51 (s, 1H).

Example 99 Step g

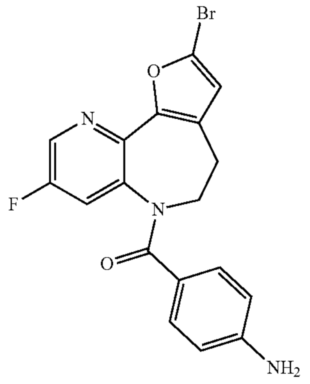 [SMILES: O=C(c1ccc([N+](=O)[O-])cc1)N1CCc2cc(Br)oc2-c2ncc(F)cc21]

The title compound was prepared using a procedure similar to that used to prepare the compound in example 54 step g. ESI-MS m/z: 402.00 [M+H]$^+$.

Example 99 Step h

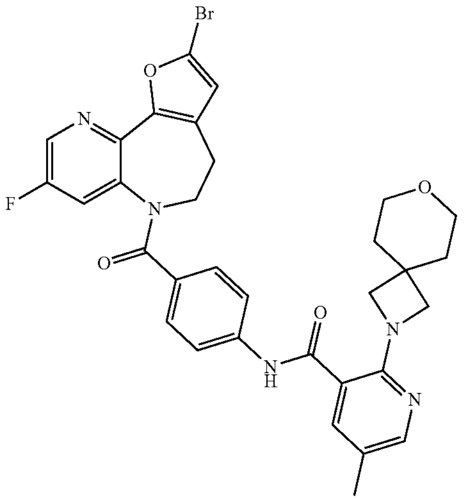 [SMILES: Cc1cnc(N2CC3(CCOCC3)C2)c(C(=O)Nc2ccc(C(=O)N3CCc4cc(Br)oc4-c4ncc(F)cc43)cc2)c1]

The title compound was prepared using a procedure similar to that used to prepare the compound in example 54 step h from the compound from step h and 5-methyl-2-(7-oxa-2-azaspiro[3.5]-nonan-2-yl)nicotinic acid. ESI-MS m/z: 646.05 [M+H]$^+$.

Example 99 Step i

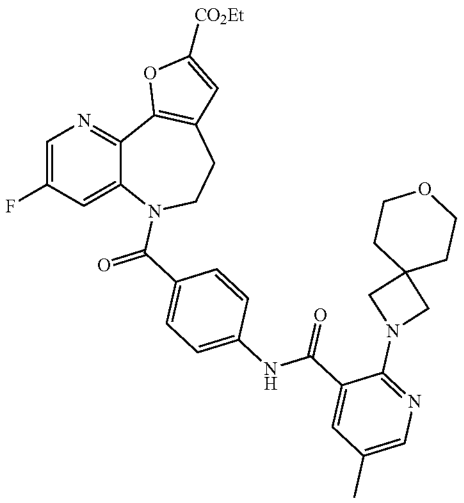

The title compound was prepared using a procedure similar to that used to prepare the compound in example 54 step i. ESI-MS m/z: 640.20 [M+H]$^+$.

Example 99 Step j

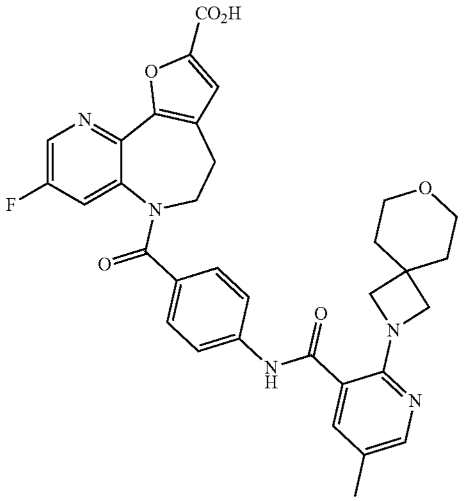 [SMILES: Cc1cnc(N2CC3(CCOCC3)C2)c(C(=O)Nc2ccc(C(=O)N3CCc4cc(C(=O)O)oc4-c4ncc(F)cc43)cc2)c1]

The title compound was prepared using a procedure similar to that used to prepare the compound in example 54 step j. ESI-MS m/z: 612.20 $[M+H]^+$.

Example 99 Step k

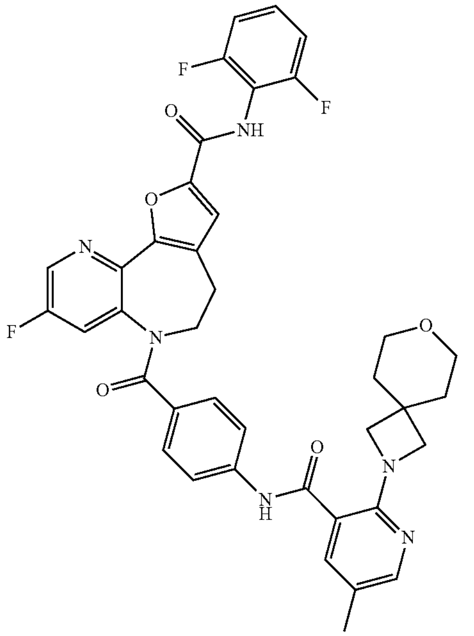 [SMILES: Cc1cnc(N2CC3(CCOCC3)C2)c(C(=O)Nc2ccc(C(=O)N3CCc4cc(C(=O)Nc5c(F)cccc5F)oc4-c4ncc(F)cc43)cc2)c1]

The title compound was prepared using a procedure similar to that used to prepare the compound in example 1 step g. ESI-MS m/z: 723.15 $[M+H]^+$. $^1H$ NMR (300 MHz, DMSO-$d_6$) δ 1.63 (m, 4H), 2.18 (s, 3H), 2.27 (s, 3H), 3.13 (d, J=24.2 Hz, 3H), 3.46 (t, J=5.1 Hz, 4H), 3.61 (s, 4H), 5.02 (s, 1H), 6.91 (d, J=8.0 Hz, 1H), 7.04 (d, J=8.3 Hz, 2H), 7.16 (m, 3H), 7.31 (m, 2H), 7.46-7.62 (m, 3H), 7.87 (m, 1H), 8.04 (m, 1H), 9.55 (s, 1H), 10.39 (s, 1H).

Examples 100-108 shown in table 9 were prepared using the procedure similar to those of example 1 step g or example 3 from the corresponding intermediates.

TABLE 9

| Example | Structure | ESI-MS m/z: $[M + H]^+$ |
|---|---|---|
| 100 | 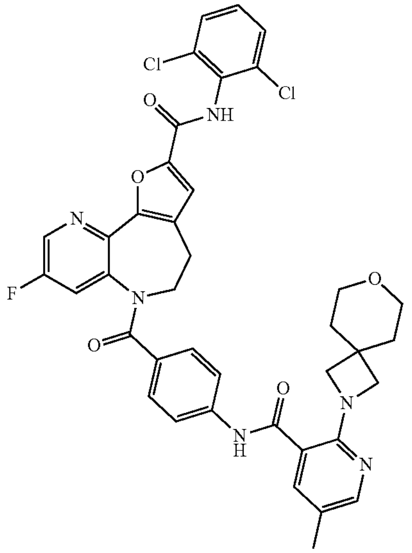 | 755.1 |
| 101 | 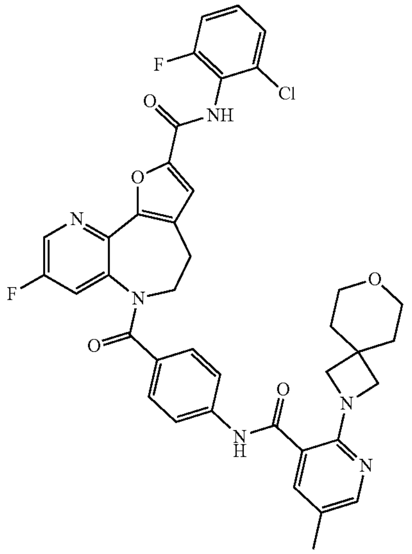 | 739.3 |

TABLE 9-continued
| Example | Structure | ESI-MS m/z: [M + H]+ |
|---|---|---|
| 102 | 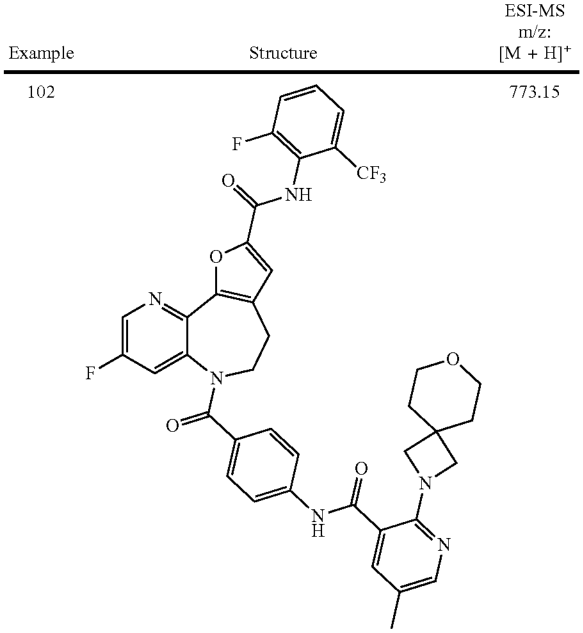 | 773.15 |
| 103 | 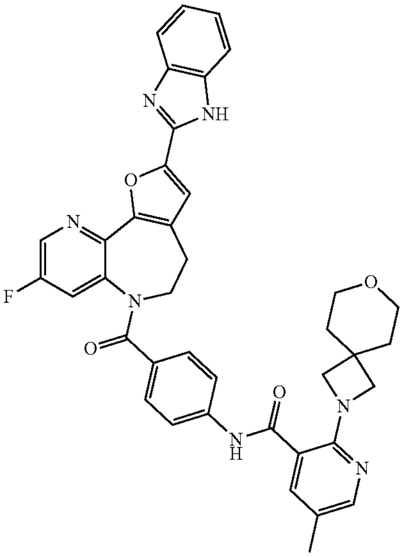 | 684.25 |
| 104 | 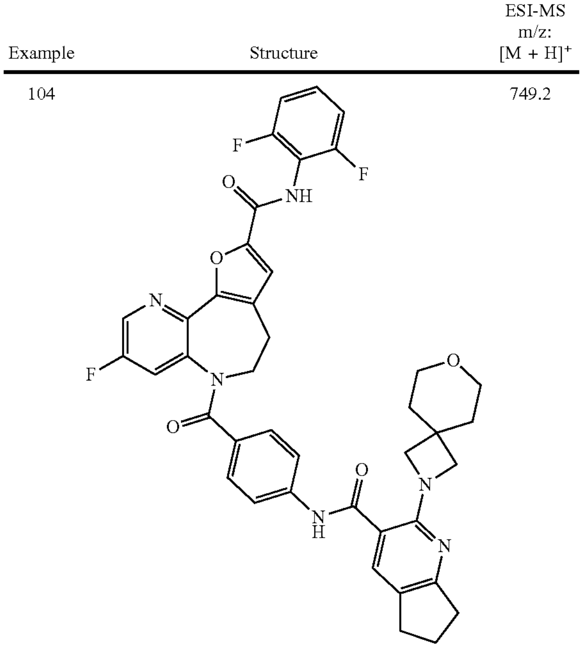 | 749.2 |
| 105 | 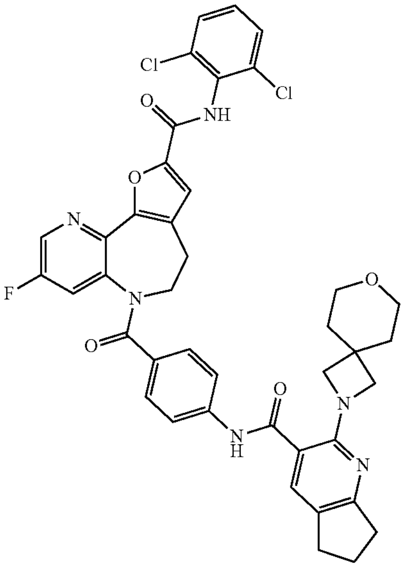 | 781.1 |

TABLE 9-continued

| Example | Structure | ESI-MS m/z: [M + H]+ |
|---|---|---|
| 106 | 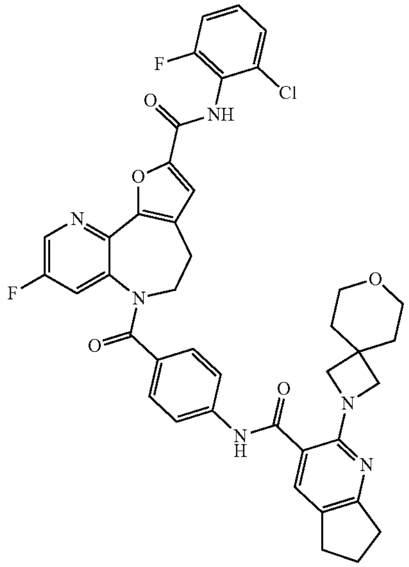 | 765.15 |
| 107 | 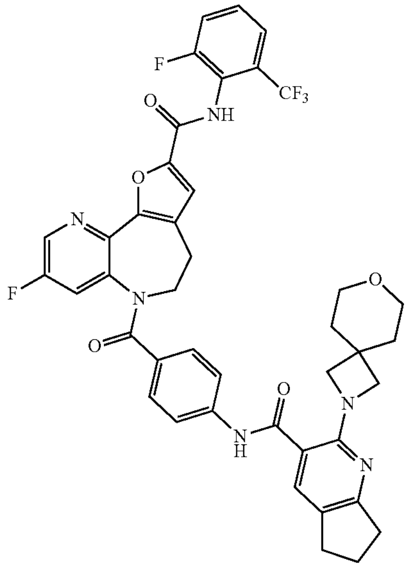 | 799.2 |

TABLE 9-continued

| Example | Structure | ESI-MS m/z: [M + H]+ |
|---|---|---|
| 108 | 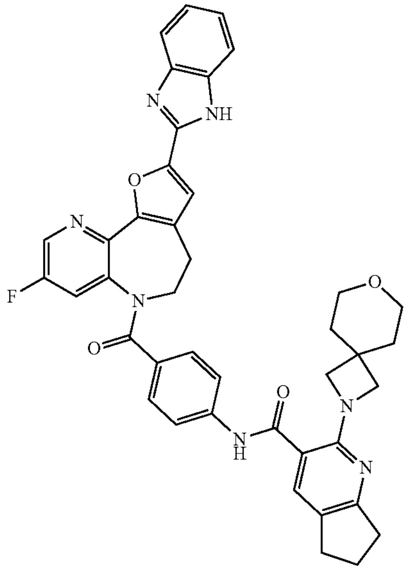 [SMILES: O=C(Nc1ccc(C(=O)N2CCc3cc(-c4nc5ccccc5[nH]4)oc3-c3ncc(F)cc32)cc1)c1cc2c(nc1N1CC3(CCOCC3)C1)CCC2] | 710.2 |

Example 109

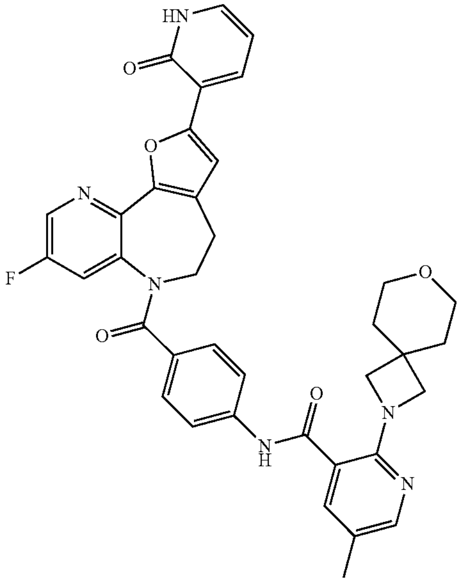 [SMILES: Cc1cnc(N2CC3(CCOCC3)C2)c(C(=O)Nc2ccc(C(=O)N3CCc4cc(-c5ccc[nH]c5=O)oc4-c4ncc(F)cc43)cc2)c1]

Example 109

A solution of the compound from example 99 step h (80 mg, 0.124 mmol), (2-oxo-1,2-dihydropyridin-3-yl)boronic acid (17.2 mg, 0.124 mmol), $Na_2CO_3$ (51.2 mg, 0.371 mmol), $Pd(PPh_3)_4$ (14.35 mg, 0.012 mmol), DCM (0.5 mL) and MeOH (1 mL) was heated at 115° C. for 40 min via microwave reactor. The mixture was diluted with water and then extracted with EtOAc. The organic phase was dried, filtered and concentrated. The residue was purified by silica gel column chromatography eluting with 0-5% MeOH/DCM to give the title compound as a yellow foam (40 mg). ESI-MS m/z: 661.27 $[M+H]^+$.

Example 110

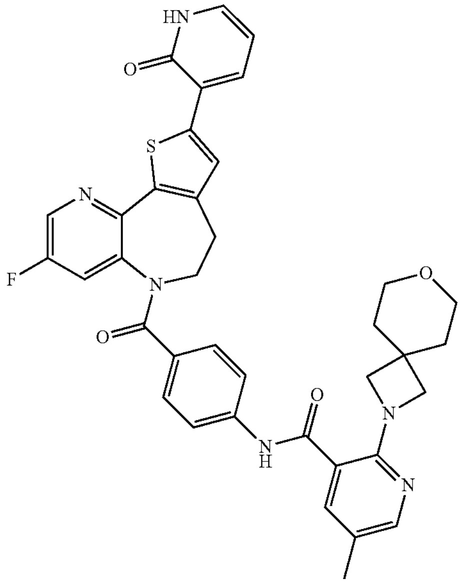

Example 110 Step a

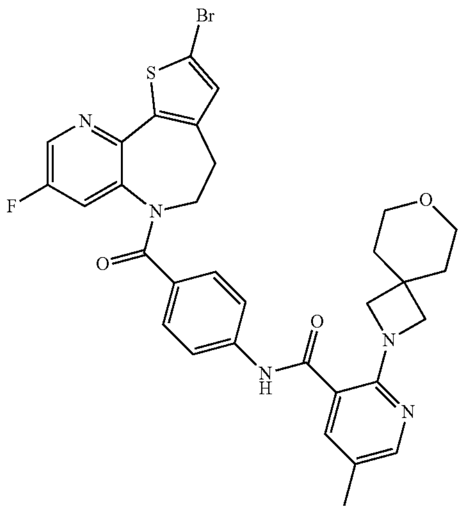 [SMILES: Cc1cnc(N2CC3(CCOCC3)C2)c(C(=O)Nc2ccc(C(=O)N3CCc4cc(Br)sc4-c4ncc(F)cc43)cc2)c1]

The title compound was prepared using a procedure similar to that used to prepare the compound in example 99 step h and the compound from example 54 step g and 5-methyl-2-(7-oxa-2-azaspiro[3.5]-nonan-2-yl)nicotinic acid.

Example 110 Step b

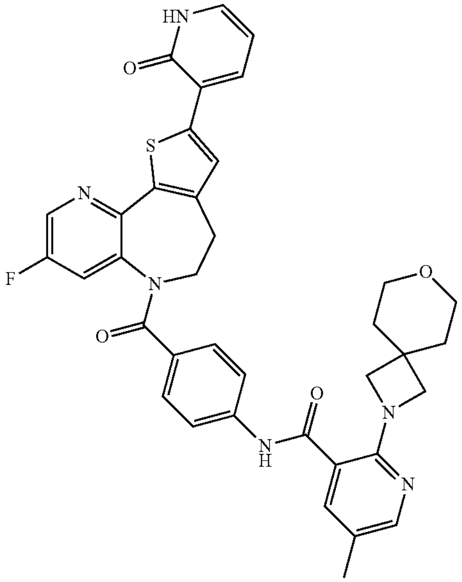 [SMILES: Cc1cnc(N2CC3(CCOCC3)C2)c(C(=O)Nc2ccc(C(=O)N3CCc4cc(-c5ccc[nH]c5=O)sc4-c4ncc(F)cc43)cc2)c1]

The title compound was prepared using a procedure similar to that used to prepare the compound in example 109 from the compound from step a and (2-oxo-1,2-dihydropyridin-3-yl)boronic acid. ESI-MS m/z: 677.25 $[M+H]^+$.

Scheme 17
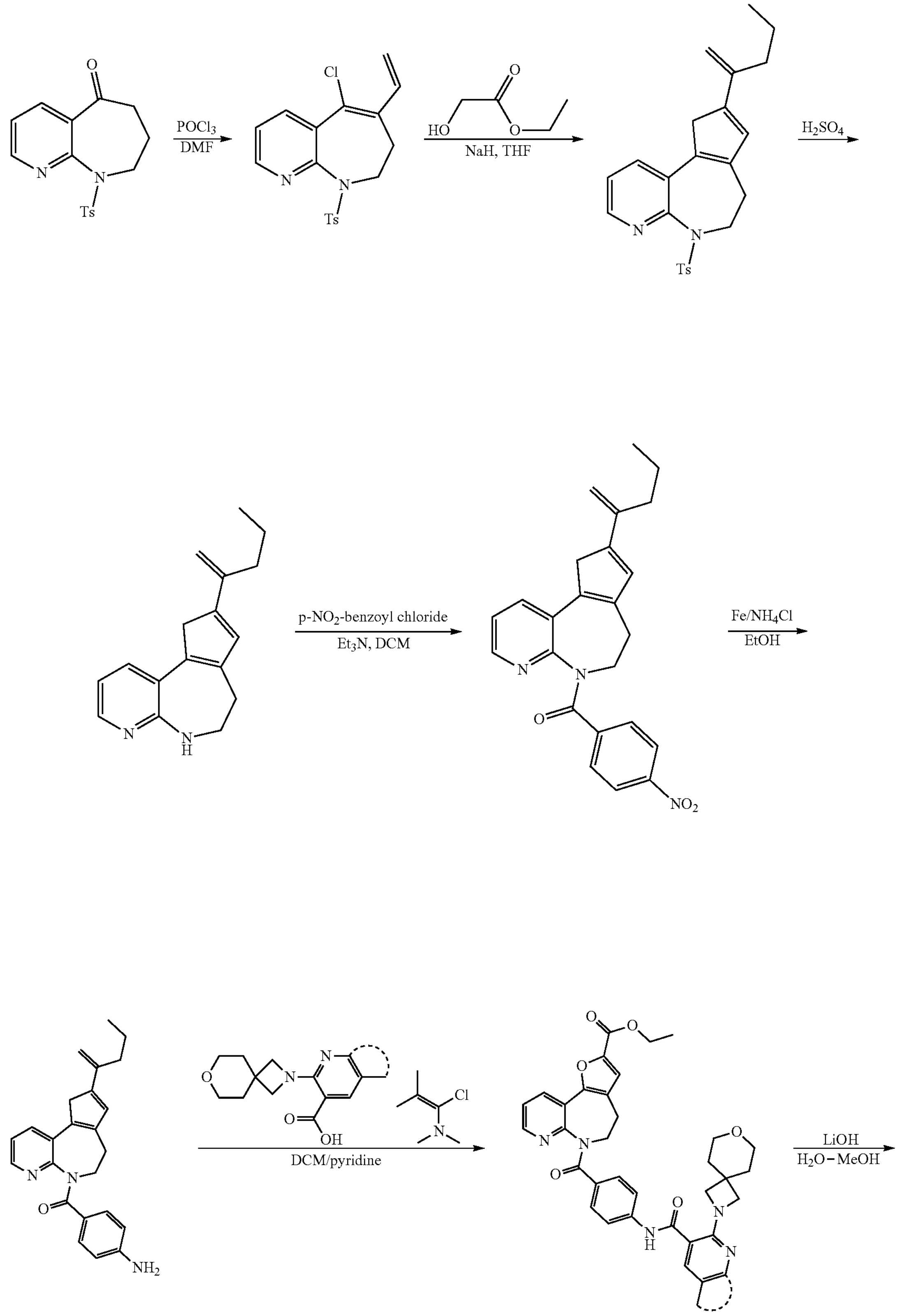

-continued

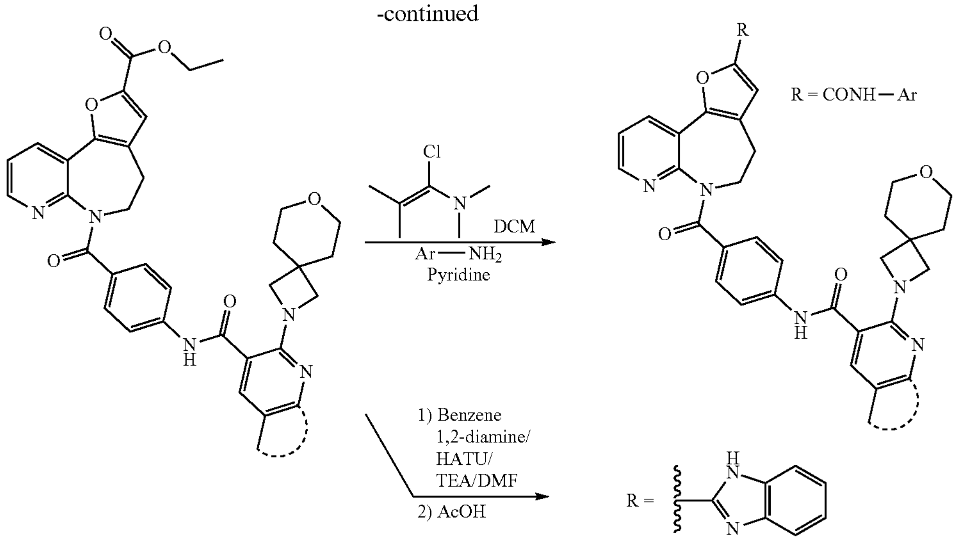

Example 111

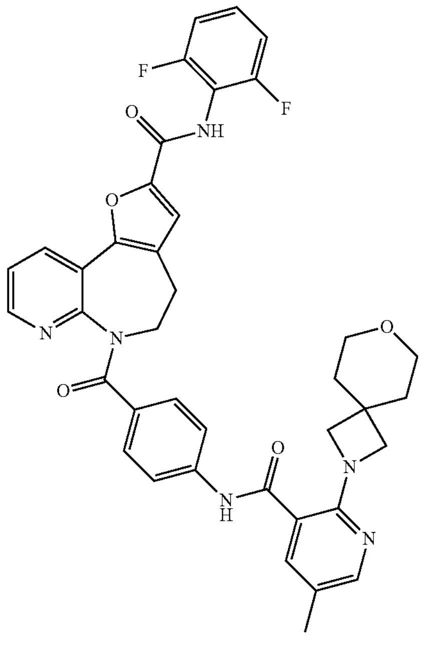 [SMILES: Cc1cnc(N2CC3(CCOCC3)C2)c(C(=O)Nc2ccc(C(=O)N3CCc4cc(C(=O)Nc5c(F)cccc5F)oc4-c4cccnc43)cc2)c1]

Example 111 Step a

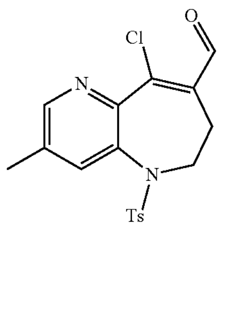 [SMILES: Cc1ccc(S(=O)(=O)N2CCC(C=O)=C(Cl)c3ncc(C)cc32)cc1]

$POCl_3$ (4.2 g, 27.50 mmol) was dropwise added to DMF (10 mL) at 0° C. under nitrogen atmosphere. Then, a mixture of the compound from example 13 step b (2.9 g, 9.17 mmol) in DMF (5 mL) was dropwise added to the above reaction mixture at 0° C. The reaction mixture was allowed to warm to room temperature, heated at 80° C. for 2 hrs under nitrogen atmosphere. After cooling, the reaction mixture was diluted with saturated KOAc solution, extracted with EA and and separated. The aqueous layer was extracted with EtOAc. The combined organic layer was washed with water (three times) and brine dried over sodium sulfate, filtered and concentrated to dryness. The crude product was purified by silica gel column chromatography to afford the title compound (1.6 g) as a brown solid. ESI-MS m/z: 363.25 $[M+H]^+$.

Example 111 Step b

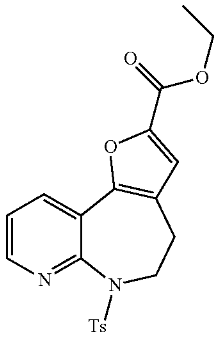 [SMILES: CCOC(=O)c1cc2c(o1)-c1cccnc1N(S(=O)(=O)c1ccc(C)cc1)CC2]

To a mixture of ethyl 2-hydroxyacetate (1004.2 mg, 9.65 mmol) in THF (10 mL) was portionwise added NaH (231.5 mg, 9.65 mmol) and was stirred for 30 min at 0° C. under nitrogen atmosphere. The solution of the compound from step a (700 mg, 1.93 mmol) in THF (5 mL) was dropwise added to the above reaction mixture at 0° C. Then, it was allowed to warm to room temperature and stirred for additional 1 hr under $N_2$ atmosphere. The reaction mixture was dropwise added into 2N HCl (100 mL) solution and extracted with EA (3×100 mL). The combined organic layer was washed with water and brine, dried over sodium sulfate, filtered and concentrated to dryness. The crude product was purified by reverse phase chromatography to afford the title compound (360 mg) as a brown solid. ESI-MS m/z: 413.15 $[M+H]^+$.

Example 111 Step c

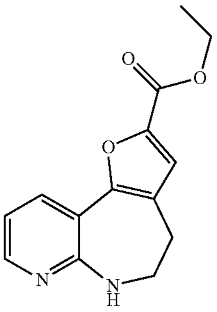 [SMILES: CCOC(=O)c1cc2c(o1)-c1cccnc1NCC2]

A mixture of the compound from step b (330 mg, 0.80 mmol) and concentrated $H_2SO_4$ (5 mL, 90%) was stirred for 30 min at 50° C. The mixture was cooled in an ice bath and basified to pH 8 with 4M NaOH. The solution was extracted with EA. The organic phase was dried over anhydrous $Na_2SO_4$ and concentrated under reduced pressure to afford the desired compound (170 mg) as a brown solid. ESI-MS m/z: 259.10 $[M+H]^+$.

Example 111 Step d

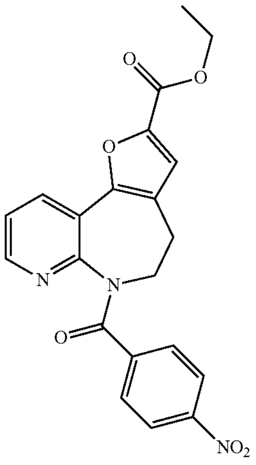 [SMILES: CCOC(=O)c1cc2c(o1)-c1cccnc1N(C(=O)c1ccc([N+](=O)[O-])cc1)CC2]

The title compound was prepared using a procedure similar to that used to prepare the compound in example 1 step c. ESI-MS m/z: 408.25 $[M+H]^+$.

Example 111 Step e

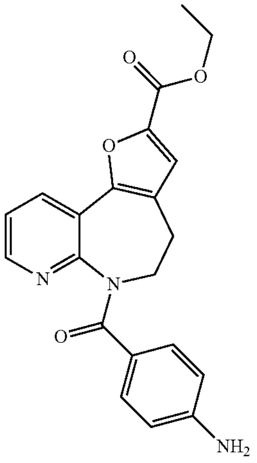 [SMILES: CCOC(=O)c1cc2c(o1)-c1cccnc1N(C(=O)c1ccc(N)cc1)CC2]

The title compound was prepared using a procedure similar to that used to prepare the compound in example 1 step d. ESI-MS m/z: 378.15 $[M+H]^+$.

Example 111 Step f

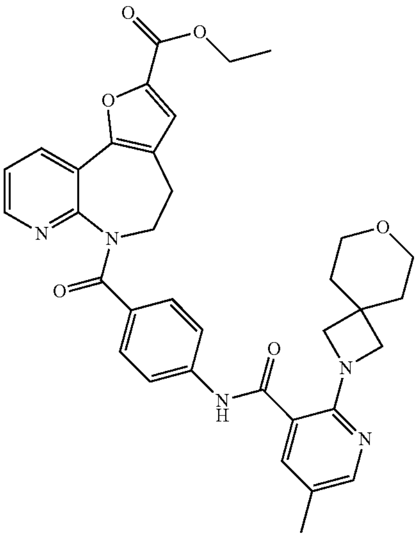 [SMILES: CCOC(=O)c1cc2c(o1)-c1cccnc1N(C(=O)c1ccc(NC(=O)c3cc(C)cnc3N3CC4(CCOCC4)C3)cc1)CC2]

The title compound was prepared using a procedure similar to that used to prepare the compound in example 70 step k. ESI-MS m/z: 622.25 $[M+H]^+$.

Example 111 Step g

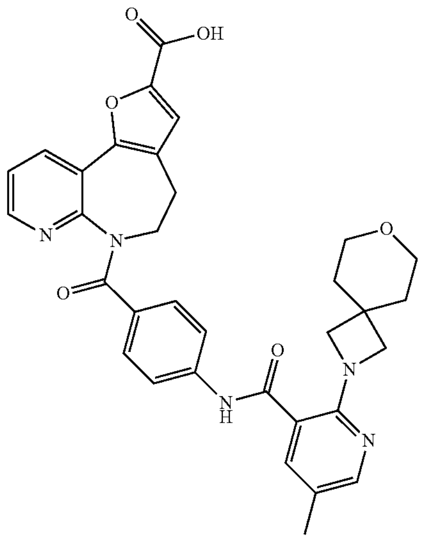 [SMILES: Cc1cnc(N2CC3(CCOCC3)C2)c(C(=O)Nc2ccc(C(=O)N3CCc4cc(C(=O)O)oc4-c4cccnc43)cc2)c1]

The title compound was prepared using a procedure similar to that used to prepare the compound in example 70 step 1. ESI-MS m/z: 594.20 [M+H]$^+$.

Examples 111-114 shown in the table 10 were prepared using a procedure similar to that used to prepare the compound in example 1 step g and example 3 from the corresponding intermediates.

TABLE 10

| Example | Structure | ESI-MS m/z: [M + H]$^+$ |
| --- | --- | --- |
| 111 | 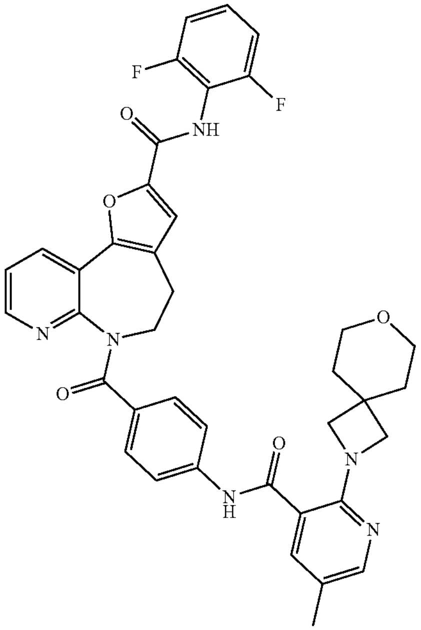 | 705.25 |

TABLE 10-continued

| Example | Structure | ESI-MS m/z: [M + H]$^+$ |
| --- | --- | --- |
| 112 | 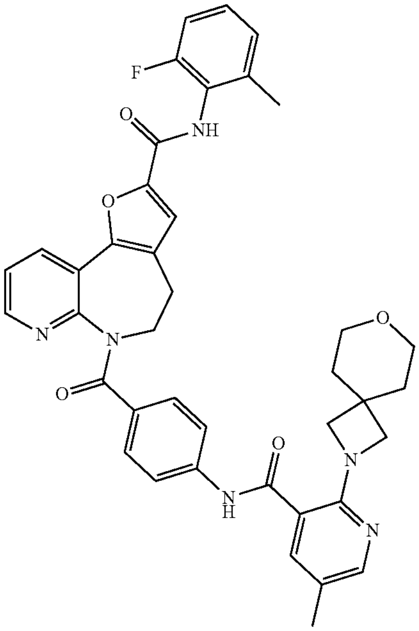 | 701.25 |
| 113 | 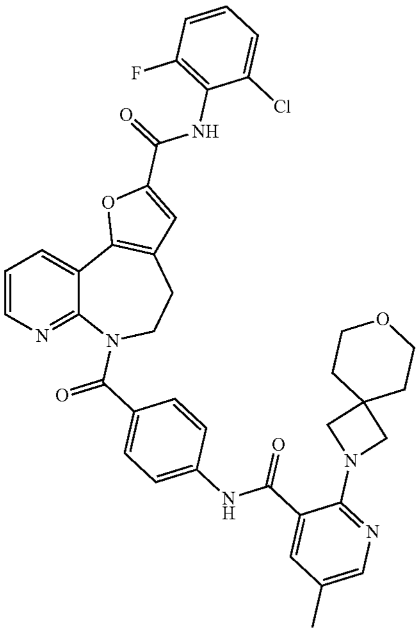 | 721.25 |

TABLE 10-continued
| Example | Structure | ESI-MS m/z: [M + H]+ |
|---|---|---|
| 114 | 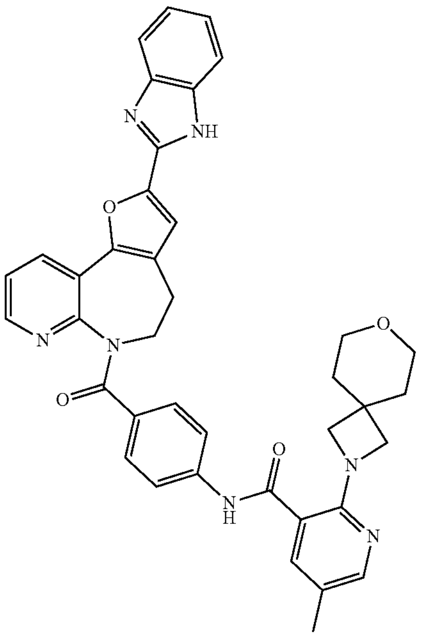 [SMILES: Cc1cnc(N2CC3(CCOCC3)C2)c(C(=O)Nc2ccc(C(=O)N3CCc4cc(-c5nc6ccccc6[nH]5)oc4-c4cccnc43)cc2)c1] | 666.35 |
Scheme 18
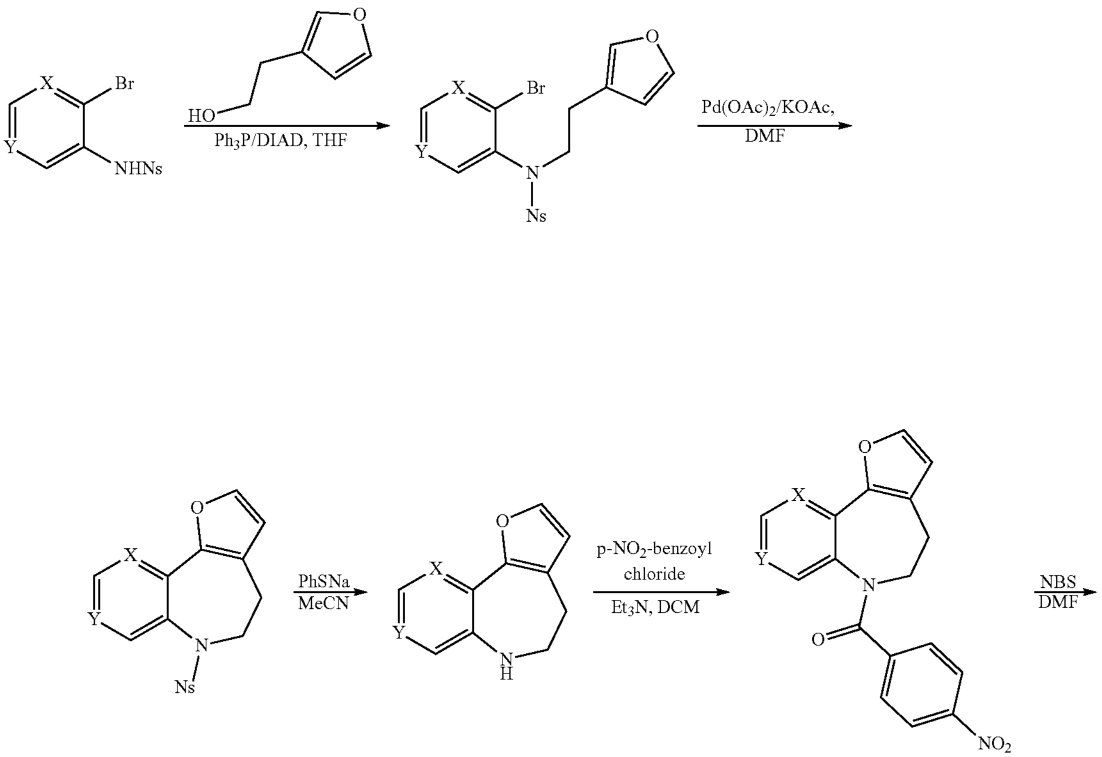

-continued
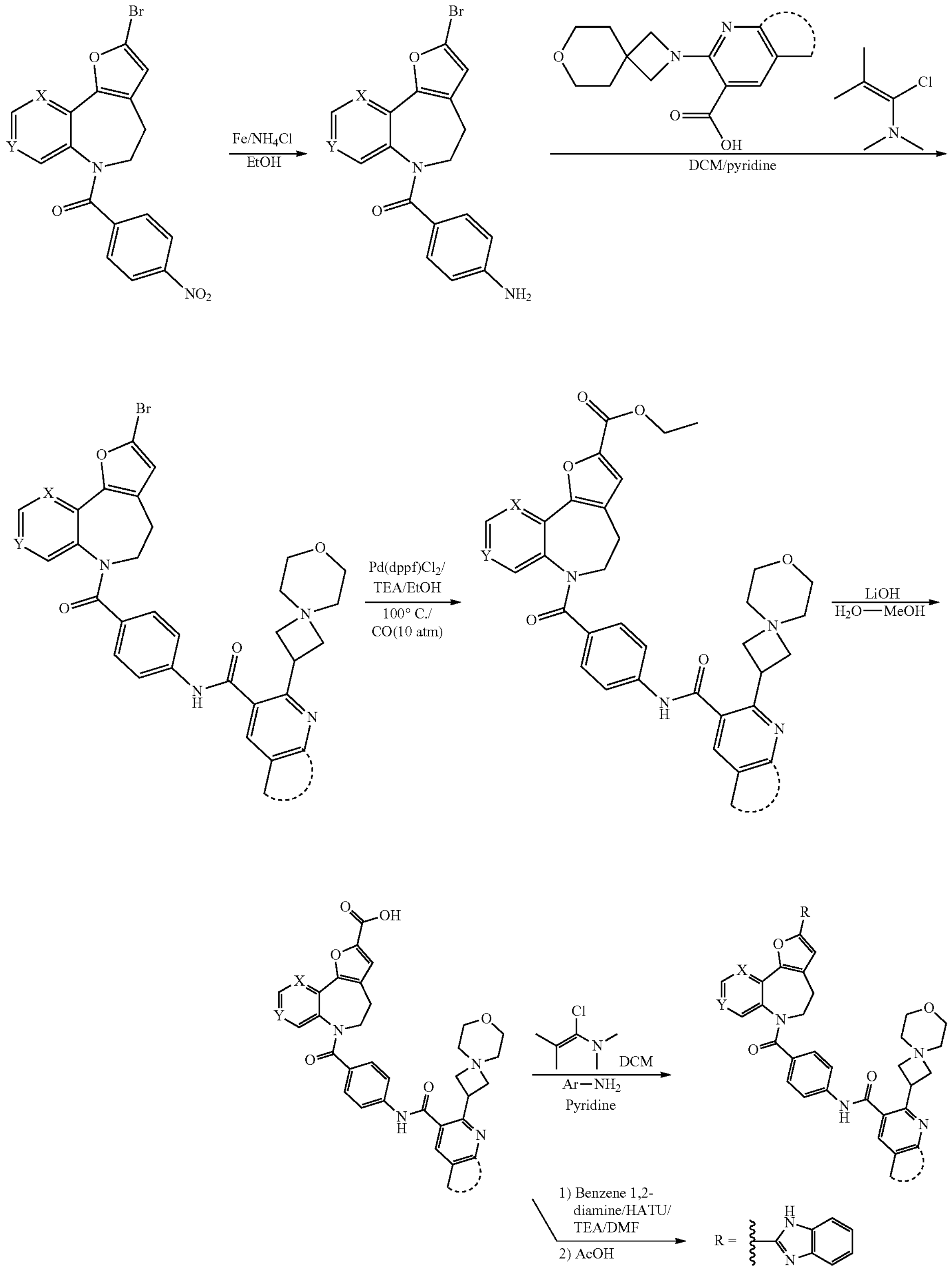
X = N; Y = CH
X = CH; Y = N
R = CONH—Ar

Examples 115-127 shown in table 11 were prepared using the procedure similar to those of example 1 step g or example 3 from the corresponding starting materials and intermediates.
TABLE 11
| Example | Structure | ESI-MS m/z: [M + H]+ |
|---|---|---|
| 115 | 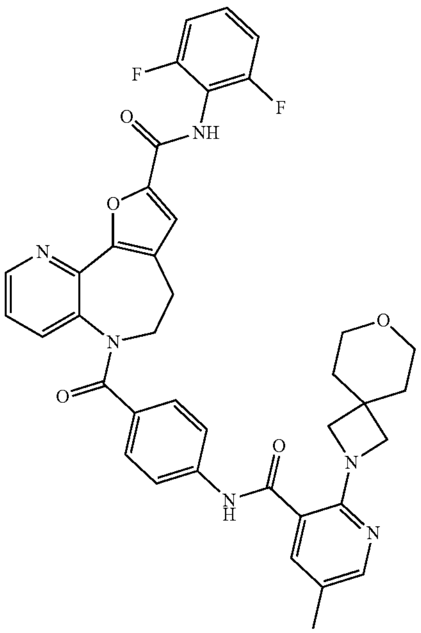 [SMILES: Cc1cnc(N2CC3(CCOCC3)C2)c(C(=O)Nc2ccc(C(=O)N3CCc4cc(C(=O)Nc5c(F)cccc5F)oc4-c4ncccc43)cc2)c1] | 705.15 |
| 116 | 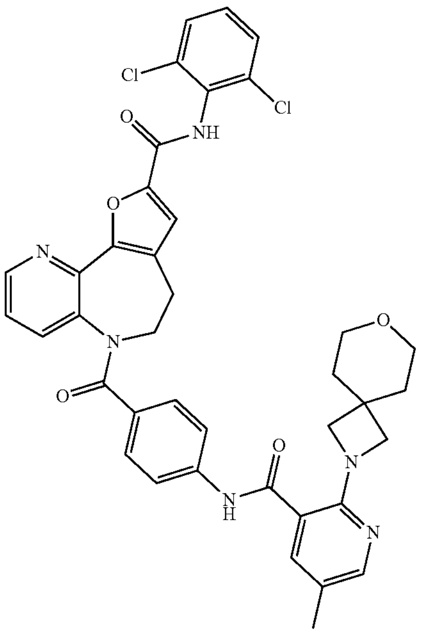 [SMILES: Cc1cnc(N2CC3(CCOCC3)C2)c(C(=O)Nc2ccc(C(=O)N3CCc4cc(C(=O)Nc5c(Cl)cccc5Cl)oc4-c4ncccc43)cc2)c1] | 735.15 |
TABLE 11-continued
| Example | Structure | ESI-MS m/z: [M + H]+ |
|---|---|---|
| 117 | 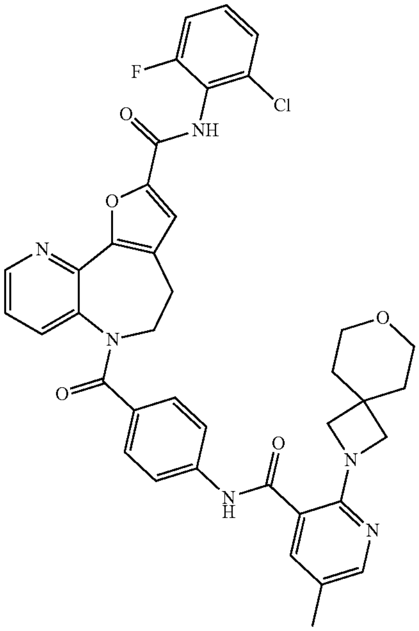 [SMILES: Cc1cnc(N2CC3(CCOCC3)C2)c(C(=O)Nc2ccc(C(=O)N3CCc4cc(C(=O)Nc5c(F)cccc5Cl)oc4-c4ncccc43)cc2)c1] | 721.15 |
| 118 | 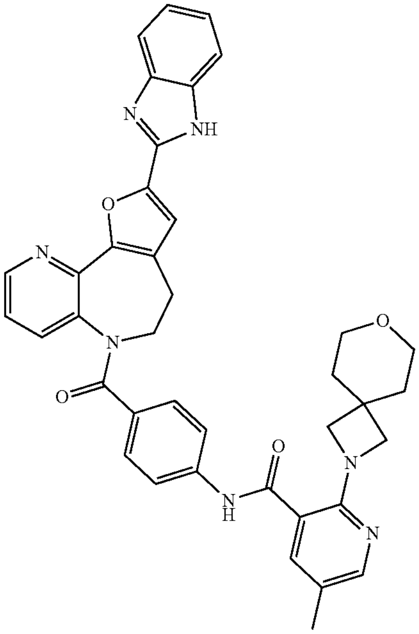 [SMILES: Cc1cnc(N2CC3(CCOCC3)C2)c(C(=O)Nc2ccc(C(=O)N3CCc4cc(-c5nc6ccccc6[nH]5)oc4-c4ncccc43)cc2)c1] | 666.3 |

TABLE 11-continued
| Example | Structure | ESI-MS m/z: [M + H]+ |
|---|---|---|
| 119 | 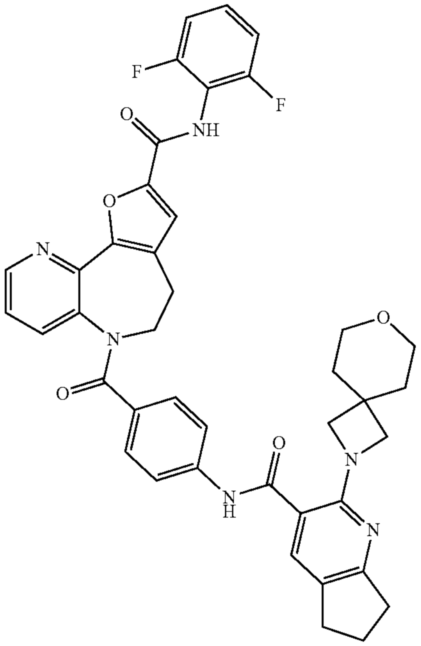 [SMILES: O=C(Nc1c(F)cccc1F)c1cc2c(o1)-c1ncccc1N(C(=O)c1ccc(NC(=O)c3cc4c(nc3N3CC5(CCOCC5)C3)CCC4)cc1)CC2] | 729.2 |
| 120 | 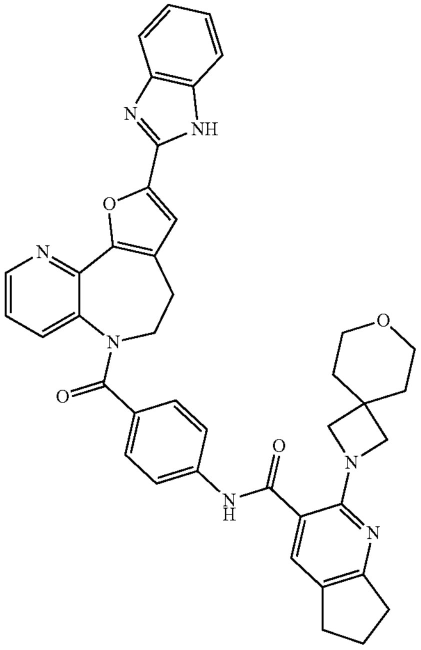 [SMILES: O=C(Nc1ccc(C(=O)N2CCc3cc(-c4nc5ccccc5[nH]4)oc3-c3ncccc32)cc1)c1cc2c(nc1N1CC3(CCOCC3)C1)CCC2] | 690.2 |
TABLE 11-continued
| Example | Structure | ESI-MS m/z: [M + H]+ |
|---|---|---|
| 121 | 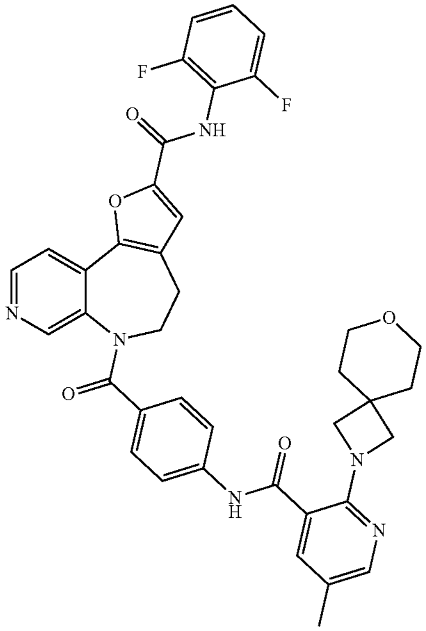 | 705.2 |
| 122 | 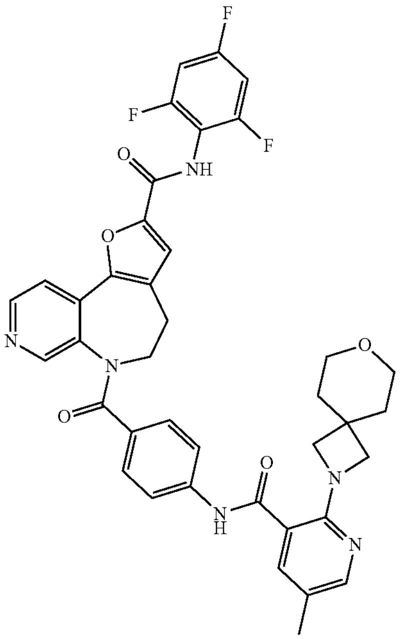 [SMILES: Cc1cnc(N2CC3(CCOCC3)C2)c(C(=O)Nc2ccc(C(=O)N3CCc4cc(C(=O)Nc5c(F)cc(F)cc5F)oc4-c4ccncc43)cc2)c1] | 723.2 |

TABLE 11-continued
| Example | Structure | ESI-MS m/z: $[M + H]^+$ |
|---|---|---|
| 123 | 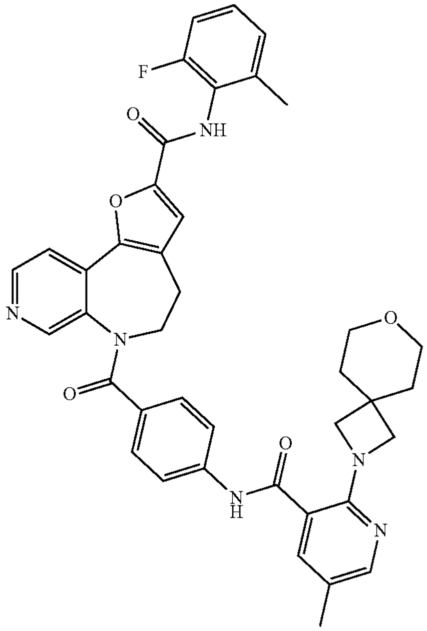 | 701.25 |
| 124 | 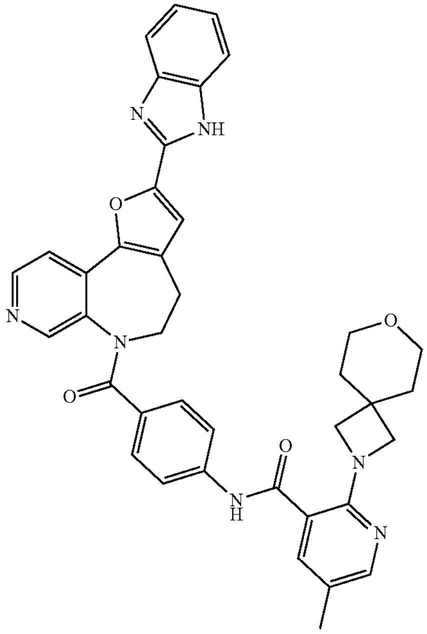 [SMILES: Cc1cnc(N2CC3(CCOCC3)C2)c(C(=O)Nc2ccc(C(=O)N3CCc4cc(-c5nc6ccccc6[nH]5)oc4-c4ccncc43)cc2)c1] | 666.25 |
| 125 | 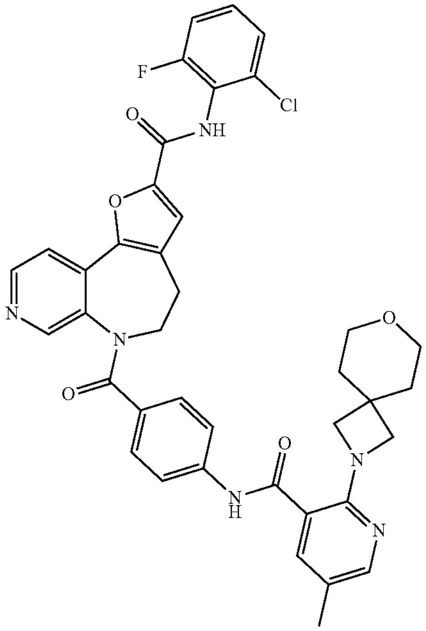 | 721.15 |
| 126 | 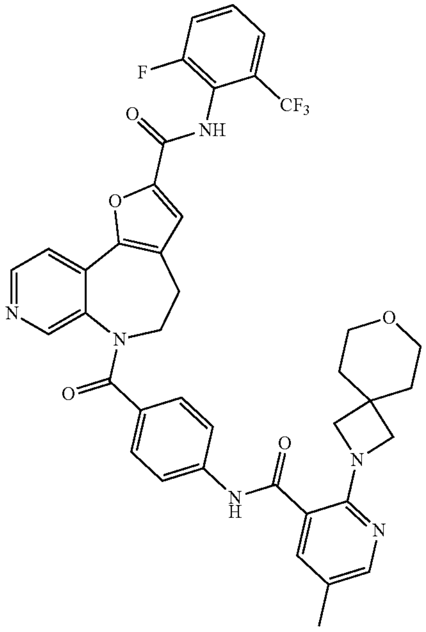 | 755.2 |

TABLE 11-continued
| Example | Structure | ESI-MS m/z: [M + H]+ |
|---|---|---|
| 127 | 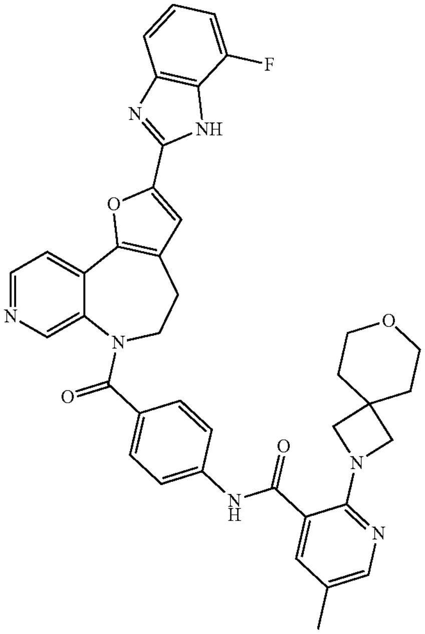 [SMILES: Cc1cnc(N2CC3(CCOCC3)C2)c(C(=O)Nc2ccc(C(=O)N3CCc4cc(-c5nc6cccc(F)c6[nH]5)oc4-c4ccncc43)cc2)c1] | 684.3 |
Scheme 19
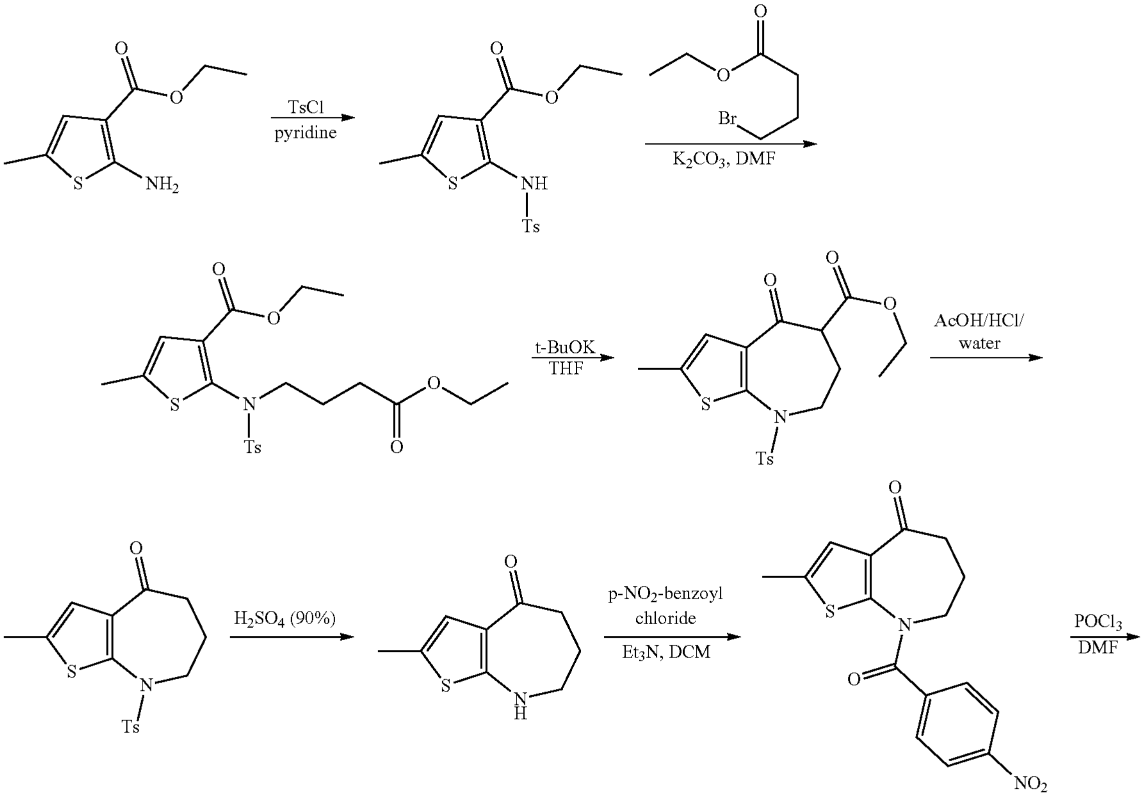

-continued
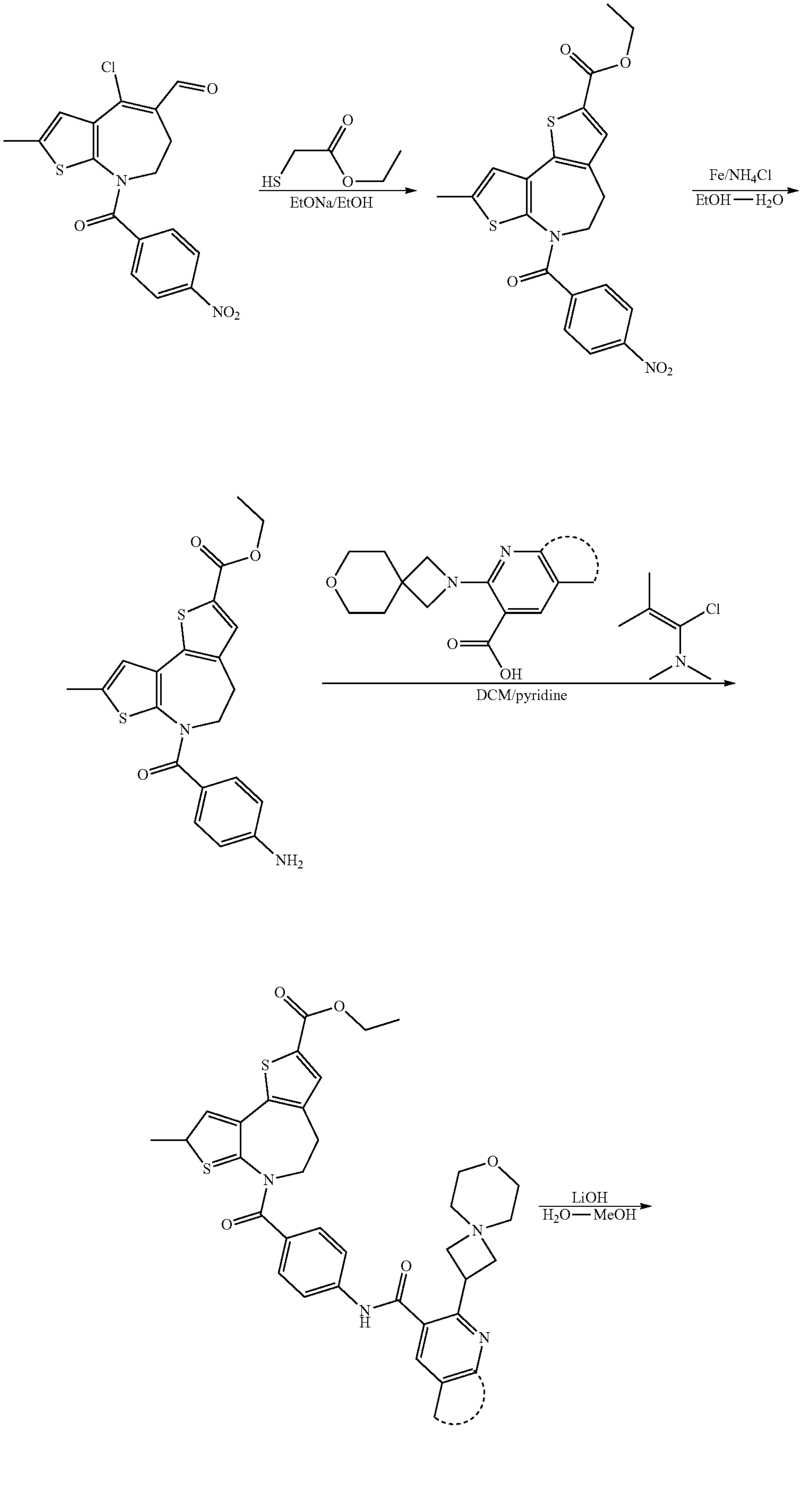

-continued

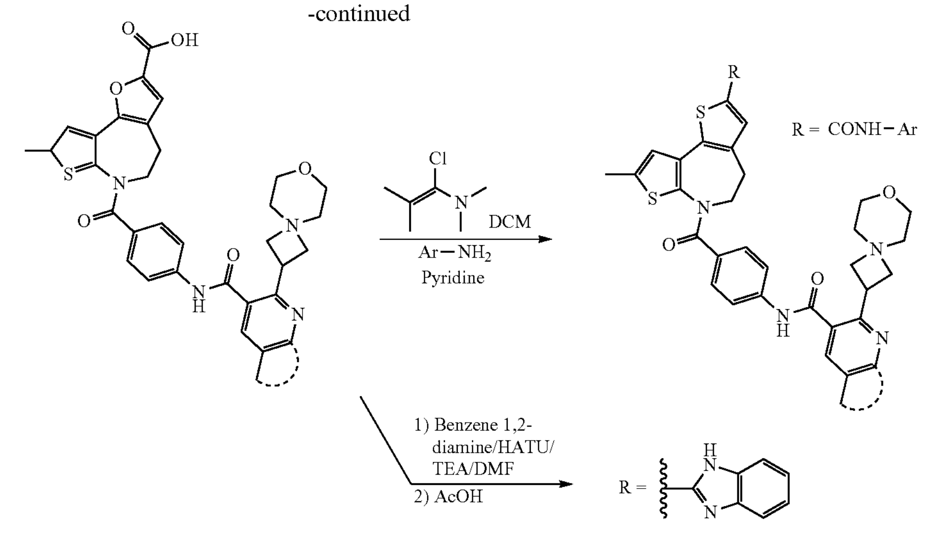

Example 128

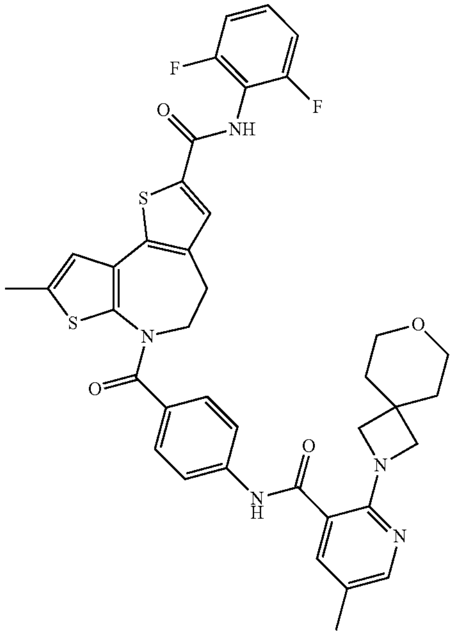 [SMILES: Cc1cnc(N2CC3(CCOCC3)C2)c(C(=O)Nc2ccc(C(=O)N3CCc4cc(C(=O)Nc5c(F)cccc5F)sc4-c4cc(C)sc43)cc2)c1]

Example 128 Step a

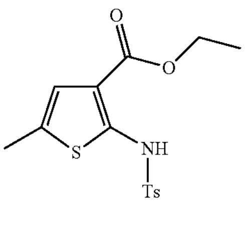 [SMILES: CCOC(=O)c1cc(C)sc1NS(=O)(=O)c1ccc(C)cc1]

To a mixture of ethyl 2-amino-5-methylthiophene-3-carboxylate (10 g, 53.98 mmol) in pyridine was added TsCl (1.13 g, 59.38 mmol) in portions at 0° C. The resulting mixture was stirred for 3 h at 60° C. under $N_2$ atmosphere. The mixture was allowed to cool down to room temperature, quenched by addition of water at room temperature. The precipitated solids were collected by filtration and washed with HCl (2M aq) and water (3×300 mL) and dried to provide the title compound (18 g) as a brown solid. ESI-MS m/z: 340.05 $[M+H]^+$.

Example 128 Step b

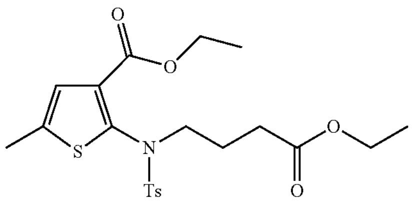 [SMILES: CCOC(=O)CCCN(c1sc(C)cc1C(=O)OCC)S(=O)(=O)c1ccc(C)cc1]

A mixture of the compound from step a (18 g, 53.03 mmol), ethyl 4-bromobutanoate (1.2 g, 63.64 mmol) and $K_2CO_3$(2.20 g, 159.1 mmol) in DMF (100 mL) was stirred at 120° C. under $N_2$ atmosphere for 2 hours. The resulting mixture was allowed to cool down to room temperature. The resulting mixture was diluted with water (300 mL). The aqueous layer was extracted with EtOAc (3×300 mL). The combined organic layer was washed with water and brine, dried over sodium sulfate, filtered and concentrated to dryness. The residue was purified by silica gel column chromatography with ethyl acetate/PE (0:1 to 8:92) to afford the title compound (25 g) as a yellow green oil. ESI-MS m/z: 454.10 $[M+H]^+$.

Example 128 Step c

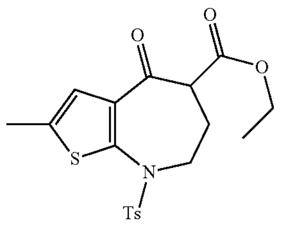 [SMILES: CCOC(=O)C1CCN(S(=O)(=O)c2ccc(C)cc2)c2sc(C)cc2C1=O]

To a mixture of the compound from step b (25 g, 55.12 mmol) in THF (300 mL) was added t-BuOK (9.3 g, 82.9 mmol) at room temperature. The resulting mixture was stirred for 3-4 h at 40° C. under $N_2$ atmosphere. The resulting mixture was diluted with water (200 mL). The aqueous layer was extracted with EtOAc (3×300 mL). The combined organic layer was washed with water (three times) and brine. dried over sodium sulfate, filtered and concentrated to dryness. The residue was purified by silica gel column chromatography, eluted with PE/EtOAc (90:10) to afford the title compound (20 g) as a brown solid. ESI-MS m/z: 408.10 $[M+H]^+$.

Example 128 Step d

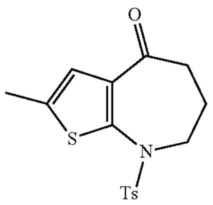 [SMILES: Cc1ccc(S(=O)(=O)N2CCCC(=O)c3cc(C)sc32)cc1]

Into a 500 mL round-bottom flask were added the compound from step c (20 g, 49.08 mmol) in AcOH:HCl:$H_2O$ (10:4:1) (250 mL) at room temperature. The resulting mixture was stirred overnight at 70° C. The mixture was allowed to cool down to room temperature. The reaction was quenched with 4N NaOH (aq.) at 0° C. The resulting mixture was extracted with EtOAc (3×300 mL). The combined organic layers were washed with brine (2×200 mL), dried over anhydrous $Na_2SO_4$. After filtration, the filtrate was concentrated under reduced pressure to give the crude compound (17 g, crude) as light brown solid. ESI-MS m/z: 336.00 $[M+H]^+$.

Example 128 Step e

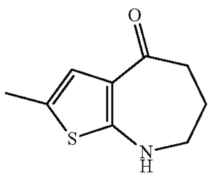

A mixture of the compound from step d (3 g, 8.94 mmol) in $H_2SO_4$ (90% in $H_2O$, 10 mL) was stirred at room temperature for 2 hours. The mixture was basified to pH~9 with 4 M NaOH (aq). The resulting mixture was extracted with EtOAc (3×200 mL). The combined organic layers were washed with brine (2×200 mL), dried over anhydrous $Na_2SO_4$. After filtration, the filtrate was concentrated under reduced pressure to give the crude compound (1.7 g) as a light brown oil.

ESI-MS m/z: 181.90 $[M+H]^+$.

Example 128 Step f

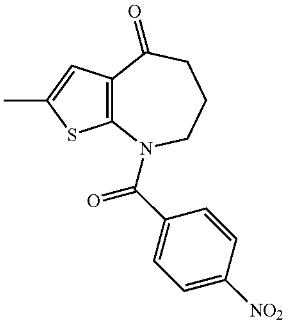 [SMILES: Cc1cc2c(s1)N(C(=O)c1ccc([N+](=O)[O-])cc1)CCCC2=O]

The title compound was prepared using a procedure similar to that used to prepare the compound in example 1 step c. ESI-MS m/z: 331.05 $[M+H]^+$.

Example 128 Step g

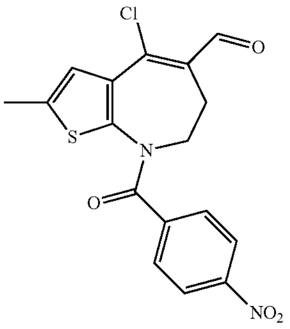 [SMILES: Cc1cc2c(s1)N(C(=O)c1ccc([N+](=O)[O-])cc1)CCC(C=O)=C2Cl]

The title compound was prepared using a procedure similar to that used to prepare the compound in intermediate 1 step f. MS m/z: 377.05 $[M+H]^+$.

Example 128 Step h

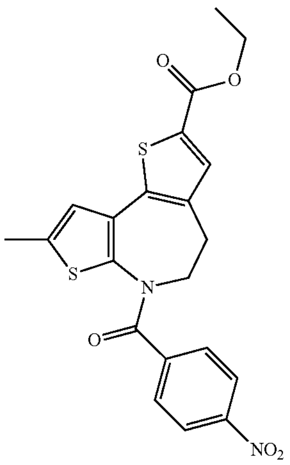 [SMILES: CCOC(=O)c1cc2c(s1)-c1cc(C)sc1N(C(=O)c1ccc([N+](=O)[O-])cc1)CC2]

The title compound was prepared using a procedure similar to that used to prepare the compound in intermediate 1 step g. ESI-MS m/z: 442.95 $[M+H]^+$.

Example 128 Step i

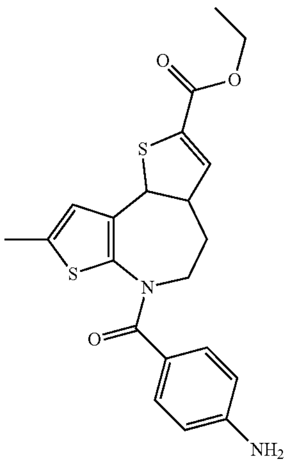 [SMILES: CCOC(=O)C1=CC2CCN(C(=O)c3ccc(N)cc3)c3sc(C)cc3C2S1]

The title compound was prepared using a procedure similar to that used to prepare the compound in example 1 step d. ESI-MS m/z: 413.05 $[M+H]^+$.

Example 128 Step j

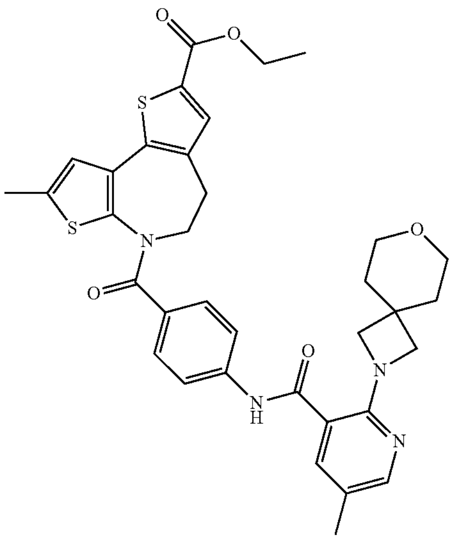 [SMILES: CCOC(=O)c1cc2c(s1)-c1cc(C)sc1N(C(=O)c1ccc(NC(=O)c3cc(C)cnc3N3CC4(CCOCC4)C3)cc1)CC2]

The title compound was prepared using a procedure similar to that used to prepare the compound in example 70 step k. ESI-MS m/z: 413.05 $[M+H]^+$.

Example 128 Step k

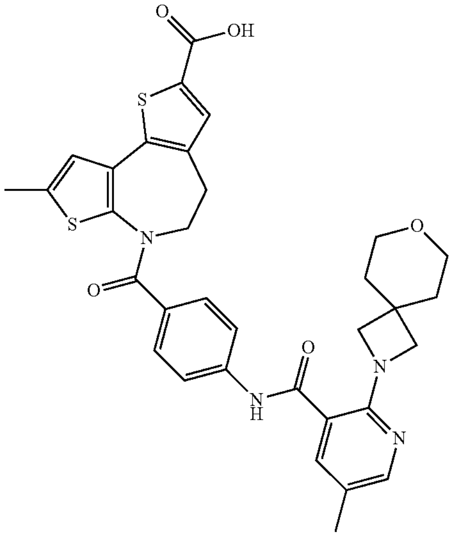 [SMILES: Cc1cnc(N2CC3(CCOCC3)C2)c(C(=O)Nc2ccc(C(=O)N3CCc4cc(C(=O)O)sc4-c4cc(C)sc43)cc2)c1]

The title compound was prepared using a procedure similar to that used to prepare the compound in example 70 step 1. ESI-MS m/z: 629.20 $[M+H]^+$.

Example 128 Step 1

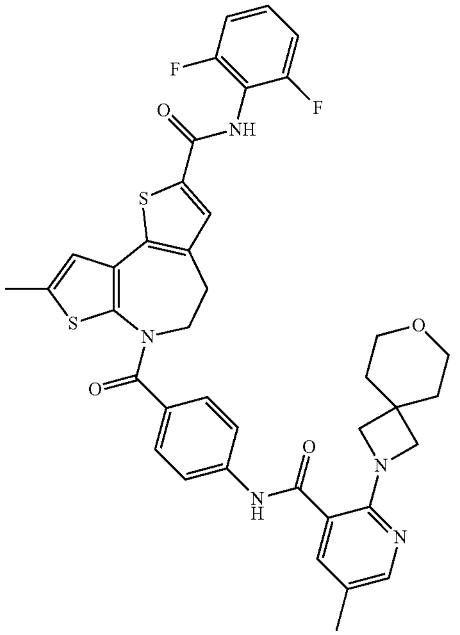 [SMILES: Cc1cnc(N2CC3(CCOCC3)C2)c(C(=O)Nc2ccc(C(=O)N3CCc4cc(C(=O)Nc5c(F)cccc5F)sc4-c4cc(C)sc43)cc2)c1]

The title compound was prepared using the procedure similar to those of example 1 step g the corresponding intermediates. ESI-MS m/z: 740.00 $[M+H]^+$. $^1H$ NMR (400 MHz, DMSO-$d_6$) δ 1.65 (t, J=5.2 Hz, 4H), 2.20 (s, 3H), 2.27-2.36 (m, 3H), 3.26 (t, J=5.3 Hz, 2H), 3.48 (t, J=5.1 Hz, 4H), 3.65 (s, 4H), 4.01 (s, 2H), 6.96 (d, J=1.3 Hz, 1H), 7.23 (t, J=8.1 Hz, 2H), 7.30-7.48 (m, 3H), 7.54 (d, J=2.2 Hz, 1H), 7.72 (d, J=8.3 Hz, 2H), 7.88 (s, 1H), 8.03-8.12 (m, 1H), 10.19 (s, 1H), 10.50 (s, 1H).

Examples 129-132 shown in table 12 were prepared using the procedure similar to those of example 1 step g or example 3 from the corresponding intermediates.

TABLE 12

| Example | Structure | ESI-MS m/z: $[M + H]^+$ |
|---|---|---|
| 129 | 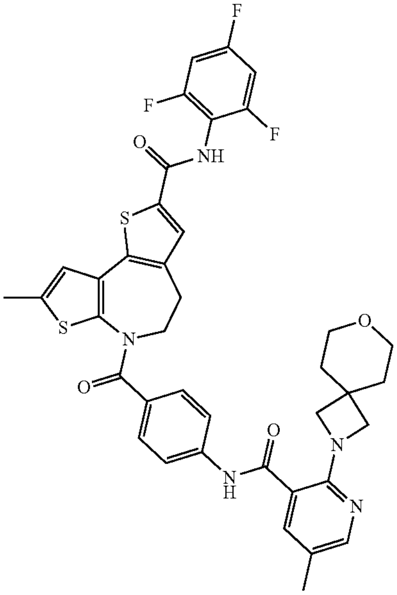 [SMILES: Cc1cnc(N2CC3(CCOCC3)C2)c(C(=O)Nc2ccc(C(=O)N3CCc4cc(C(=O)Nc5c(F)cc(F)cc5F)sc4-c4cc(C)sc43)cc2)c1] | 758.05 |

TABLE 12-continued

| Example | Structure | ESI-MS m/z: $[M + H]^+$ |
|---|---|---|
| 130 | 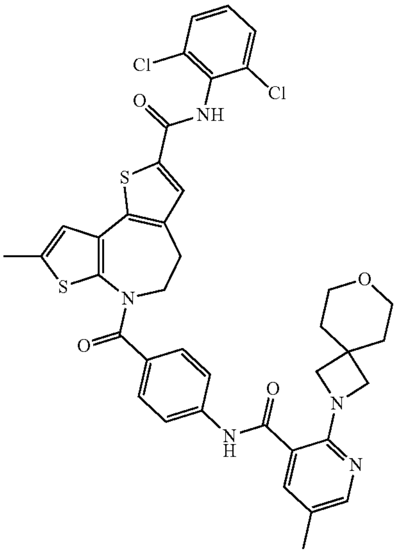 [SMILES: Cc1cnc(N2CC3(CCOCC3)C2)c(C(=O)Nc2ccc(C(=O)N3CCc4cc(C(=O)Nc5c(Cl)cccc5Cl)sc4-c4cc(C)sc43)cc2)c1] | 771.15 |
| 131 | 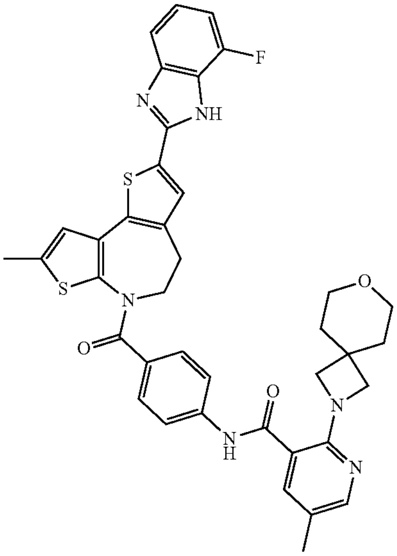 [SMILES: Cc1cnc(N2CC3(CCOCC3)C2)c(C(=O)Nc2ccc(C(=O)N3CCc4cc(-c5nc6cccc(F)c6[nH]5)sc4-c4cc(C)sc43)cc2)c1] | 719.05 |

TABLE 12-continued
| Example | Structure | ESI-MS m/z: [M + H]$^+$ |
|---|---|---|
| 132 | 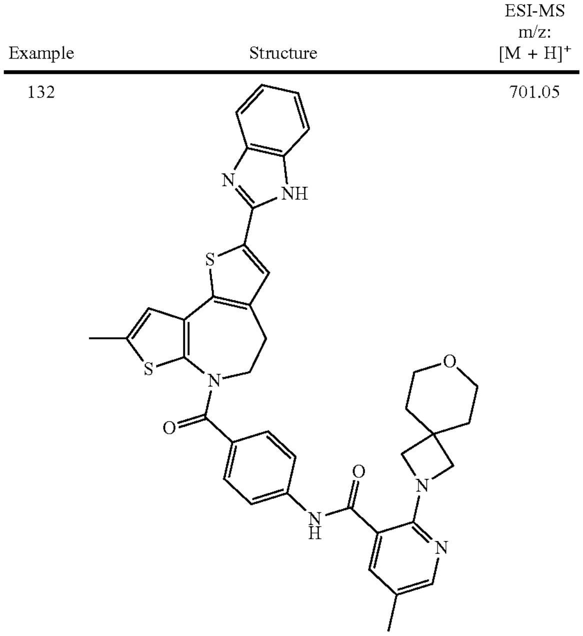 | 701.05 |
Scheme 20
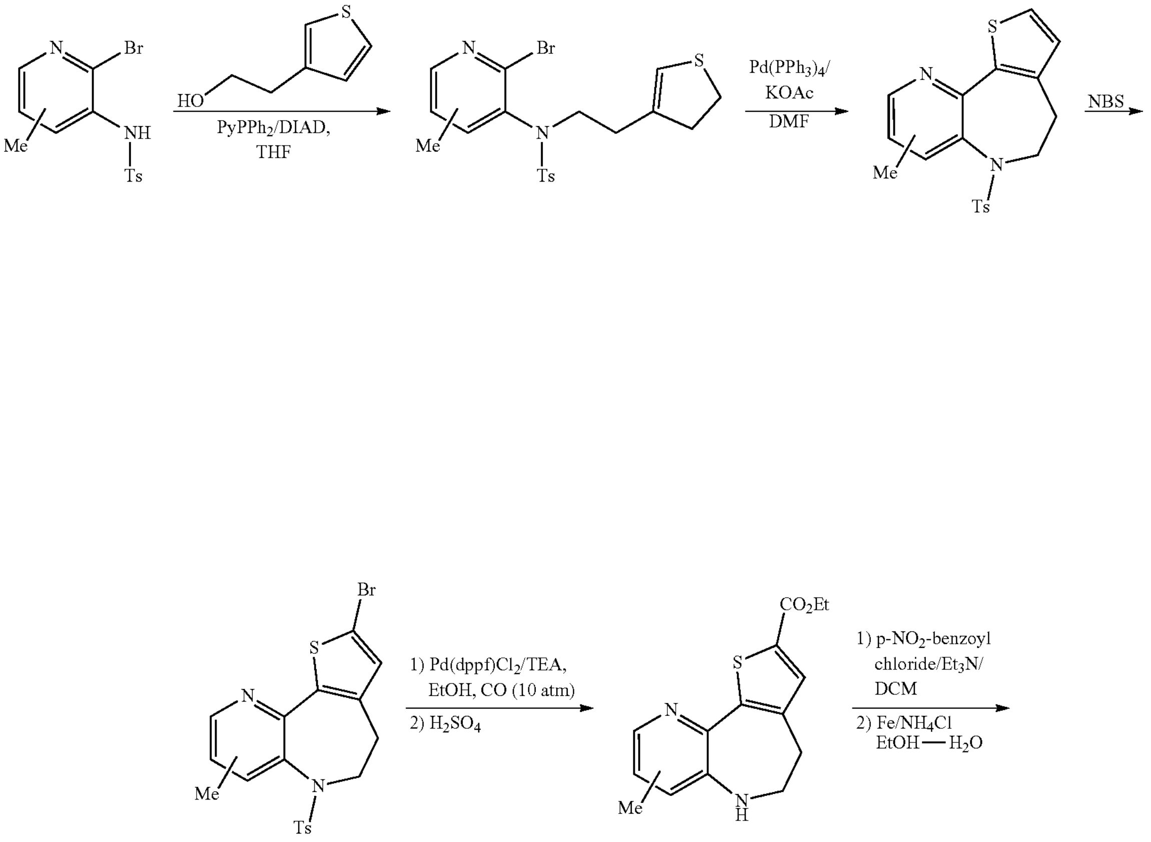

-continued
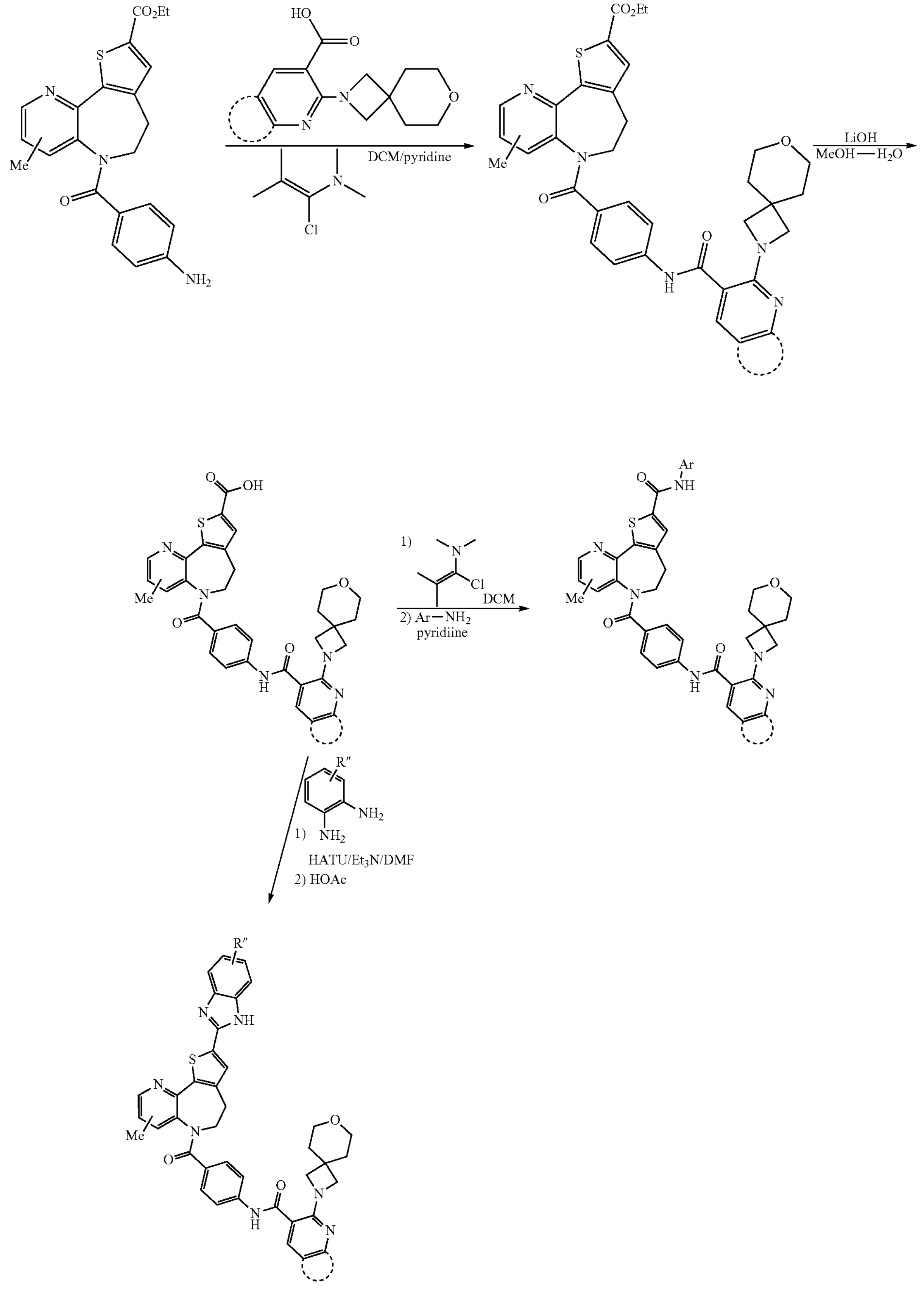

Example 133

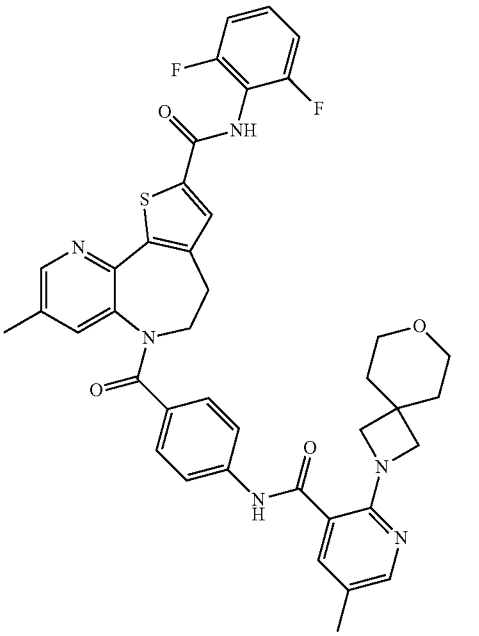 [SMILES: Cc1cnc(N2CC3(CCOCC3)C2)c(C(=O)Nc2ccc(C(=O)N3CCc4cc(C(=O)Nc5c(F)cccc5F)sc4-c4ncc(C)cc43)cc2)c1]

Example 133 Step a

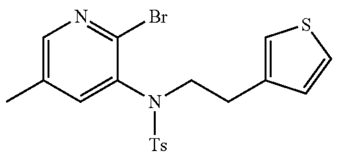 [SMILES: Cc1ccc(S(=O)(=O)N(CCc2ccsc2)c2cc(C)cnc2Br)cc1]

A mixture of N-(2-bromo-5-methylpyridin-3-yl)-4-methylbenzenesulfoamide (10 g, 29.307 mmol), 2-(thiophen-3-yl)ethan-1-ol (3.76 g, 0.029 mmol), 2-(diphenylphosphanyl) pyridine (9.2 6 g, 0.035 mmol), DIAD (8.77 g, 0.038 mmol) in THF (100 mL) was stirred at room temperature for 3 hrs. The residue was dissolved in EtOAc (700 mL) and washed with 4M-HCl (2×500 mL). The combined organic layers were concentrated to dryness. 4M-HCl in dioxane (500 mL) was added to the reside, stirred for 1.5 hrs and evaporated. Then, the residue was dissolved with EtOAc (150 ml) and treated with petroleum ether (1 L). The precipitated solids were collected by filtration and washed with petroleum ether (3×100 mL) and dried to give the title compound (12 g) as a light yellow solid. ESI-MS m/z: 451.05 $[M+H]^+$.

Example 133 Step b

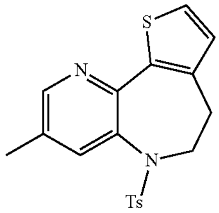 [SMILES: Cc1ccc(S(=O)(=O)N2CCc3ccsc3-c3ncc(C)cc32)cc1]

A mixture of the compound from step a (12 g, 26.584 mmol), $Pd(PPh_3)_4$ (3.07 g, 3 mmol) and KOAc (7.83 g, 0.080 mmol) in DMF (65 mL) was stirred at 100° C. for 3 hrs. The reaction mixture was then quenched by the addition of water (200 mL). The resulting solution was extracted with EtOAc (2×200 mL). The combined organic layer was washed with water (three times) and brine. dried over sodium sulfate, filtered and concentrated to dryness. The residue was purified by silica gel column chromatography to afford the title compound (3.9 g) as a yellow solid. ESI-MS m/z: 371.10 $[M+H]^+$.

Example 133 Step c

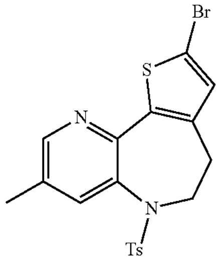 [SMILES: Cc1ccc(S(=O)(=O)N2CCc3cc(Br)sc3-c3ncc(C)cc32)cc1]

The title compound was prepared using the procedure similar to that of example 54 step f from the corresponding intermediate. ESI-MS m/z: 449.05 $[M+H]^+$.

Example 133 Step d

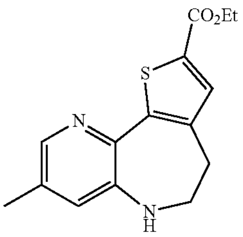 [SMILES: CCOC(=O)c1cc2c(s1)-c1ncc(C)cc1NCC2]

The title compound was prepared using the procedure similar to those of example 54 step d and i from the corresponding intermediate. ESI-MS m/z: 413.15 $[M+H]^+$.

Example 133 Step e

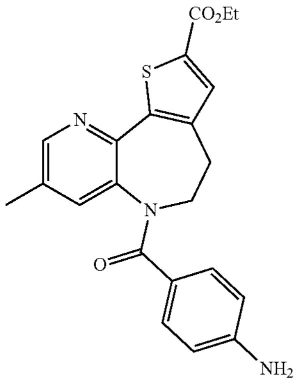 [SMILES: CCOC(=O)c1cc2c(s1)-c1ncc(C)cc1N(C(=O)c1ccc(N)cc1)CC2]

The title compound was prepared using the procedure similar to those of example 54 step e and f from the corresponding intermediate. ESI-MS m/z: 408.15 [M+H]$^+$.

Example 133 Step f

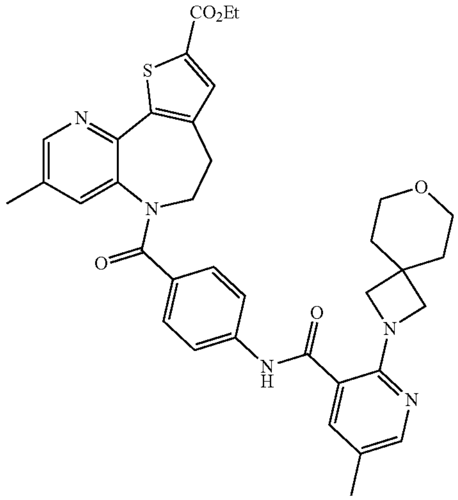

The title compound was prepared using the procedure similar to that of example 54 step h from the corresponding intermediates. ESI-MS m/z: 752.25 [M+H]$^+$.

Example 133 Step g

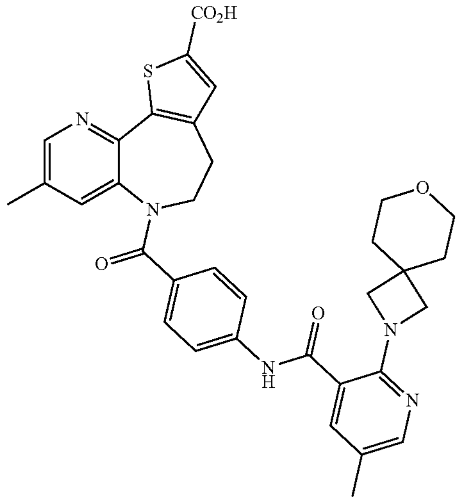 [SMILES: Cc1cnc(N2CC3(CCOCC3)C2)c(C(=O)Nc2ccc(C(=O)N3CCc4cc(C(=O)O)sc4-c4ncc(C)cc43)cc2)c1]

The title compound was prepared using the procedure similar to that of example 54 step j from the corresponding intermediate. ESI-MS m/z: 624.25 [M+H]$^+$.

Example 133 Step h

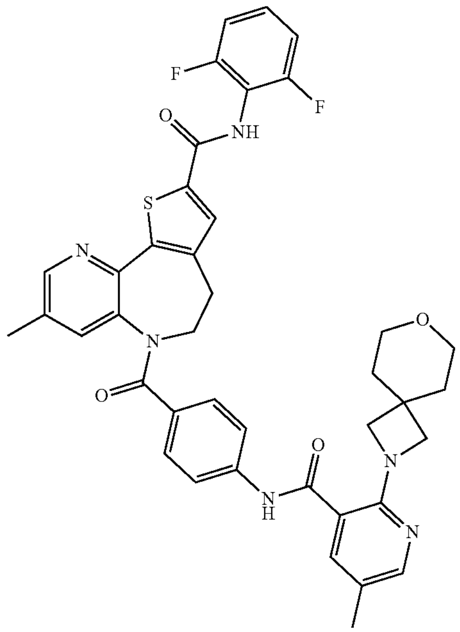

The title compound was prepared using the procedure similar to that of example 1 step g from the corresponding intermediate. ESI-MS m/z: 735.35 [M+H]$^+$. $^1$H NMR (400 MHz, DMSO-$d_6$) δ 1.63 (t, J=5.3 Hz, 4H), 2.08 (s, 3H), 2.18 (s, 3H), 3.25-3.30 (m, 3H), 3.47 (d, J=6.2 Hz, 4H), 3.62 (t, J=5.2 Hz, 4H), 4.78-5.20 (m, 1H), 7.08-7.13 (m, 3H), 7.24 (t, J=8.2 Hz, 2H), 7.42-7.50 (m, 1H), 7.50 (d, J=2.2 Hz, 1H), 7.59 (d, J=8.4 Hz, 2H), 7.93 (s, 1H), 8.05 (d, J=2.1 Hz, 1H), 8.28 (d, J=1.7 Hz, 1H), 10.24 (s, 1H), 10.43 (s, 1H).

Examples 134-150, 161-164 shown in table 13 were prepared using the procedure similar to those of example 1 step g or example 3 from the corresponding intermediates.
TABLE 13
| Example | Structure | ESI-MS m/z: [M + H]+ |
|---|---|---|
| 134 | 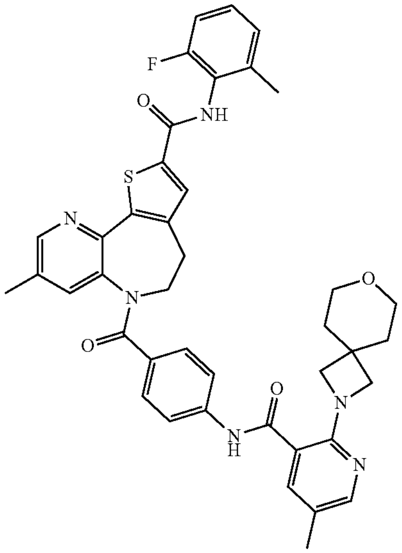 [SMILES: Cc1cnc(N2CC3(CCOCC3)C2)c(C(=O)Nc2ccc(C(=O)N3CCc4cc(C(=O)Nc5c(C)cccc5F)sc4-c4ncc(C)cc43)cc2)c1] | 730.27 |
| 135 | 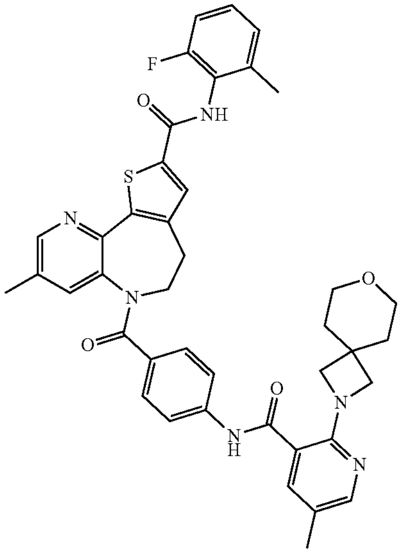 | 718.2 |
TABLE 13-continued
| Example | Structure | ESI-MS m/z: [M + H]+ |
|---|---|---|
| 136 | 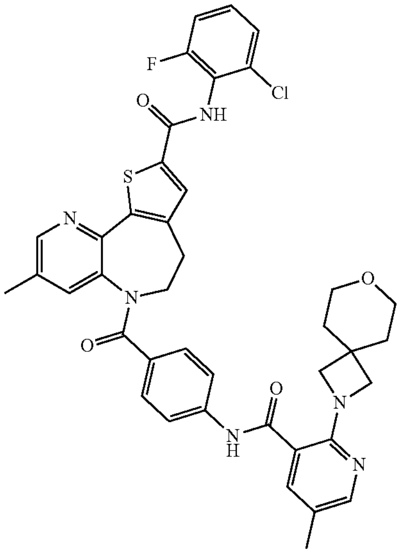 | 751.3 |
| 137 | 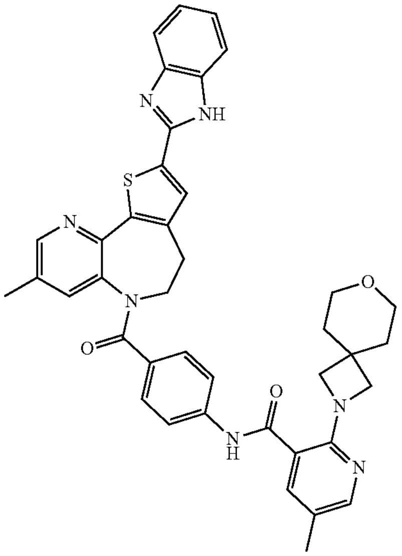 [SMILES: Cc1cnc(N2CC3(CCOCC3)C2)c(C(=O)Nc2ccc(C(=O)N3CCc4cc(-c5nc6ccccc6[nH]5)sc4-c4ncc(C)cc43)cc2)c1] | 696.35 |

TABLE 13-continued
| Example | Structure | ESI-MS m/z: [M + H]+ |
| --- | --- | --- |
| 138 | 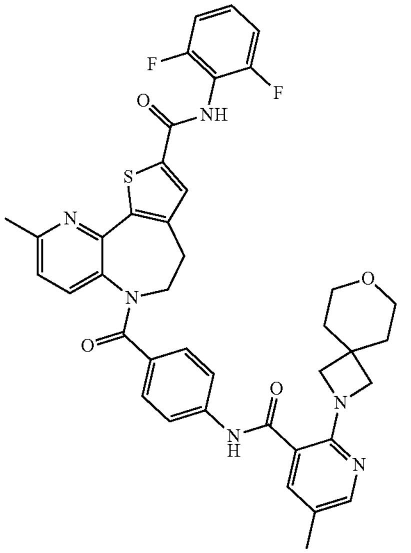 | 735.25 |
| 139 | 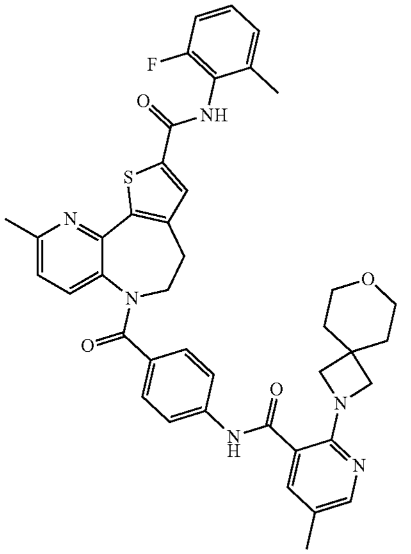 | 731.25 |
TABLE 13-continued
| Example | Structure | ESI-MS m/z: [M + H]+ |
| --- | --- | --- |
| 140 | 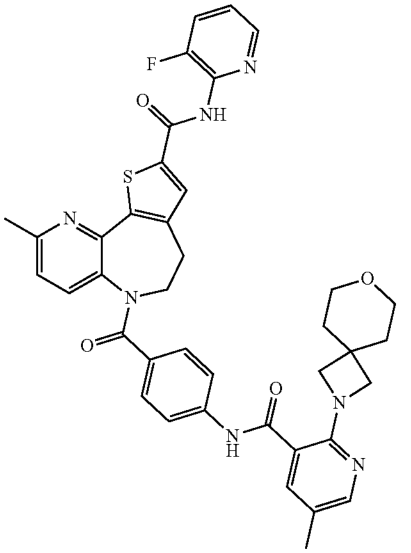 [SMILES: Cc1cnc(N2CC3(CCOCC3)C2)c(C(=O)Nc2ccc(C(=O)N3CCc4cc(C(=O)Nc5ncccc5F)sc4-c4nc(C)ccc43)cc2)c1] | 718.4 |
| 141 | 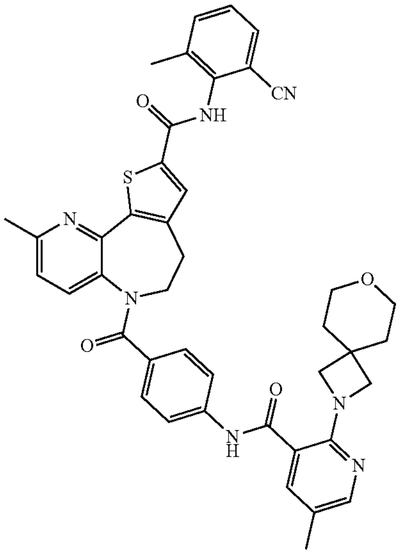 [SMILES: Cc1cnc(N2CC3(CCOCC3)C2)c(C(=O)Nc2ccc(C(=O)N3CCc4cc(C(=O)Nc5c(C)cccc5C#N)sc4-c4nc(C)ccc43)cc2)c1] | 738.25 |

TABLE 13-continued
| Example | Structure | ESI-MS m/z: [M + H]+ |
|---|---|---|
| 142 | 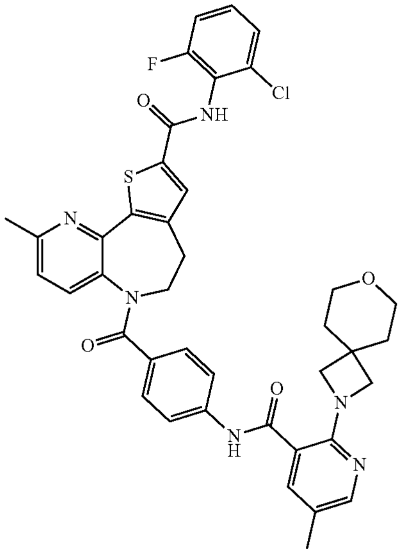 | 751.15 |
| 143 | 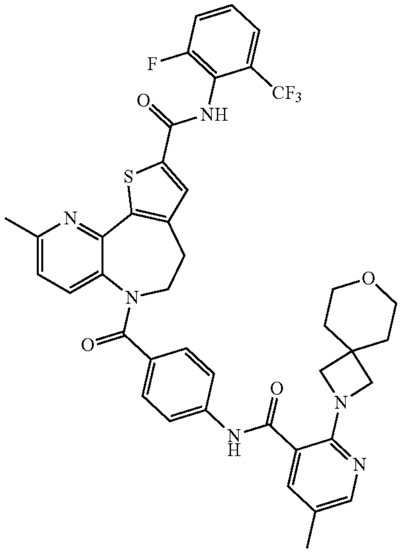 | 785.2 |
TABLE 13-continued
| Example | Structure | ESI-MS m/z: [M + H]+ |
|---|---|---|
| 144 | 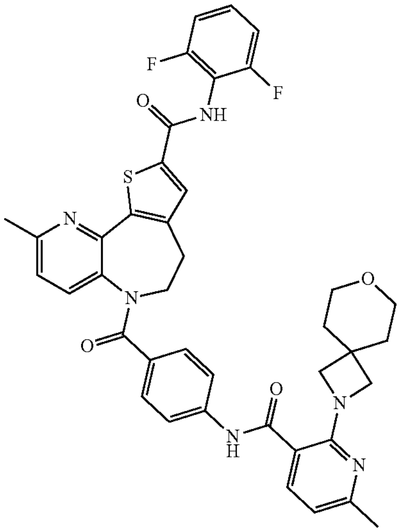 | 735.15 |
| 145 | 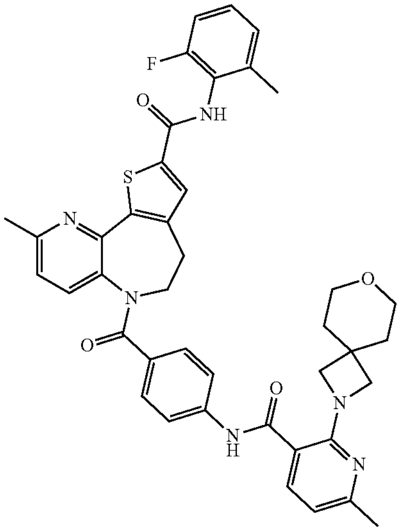 | 731.20 |

TABLE 13-continued
| Example | Structure | ESI-MS m/z: [M + H]+ |
|---|---|---|
| 146 | 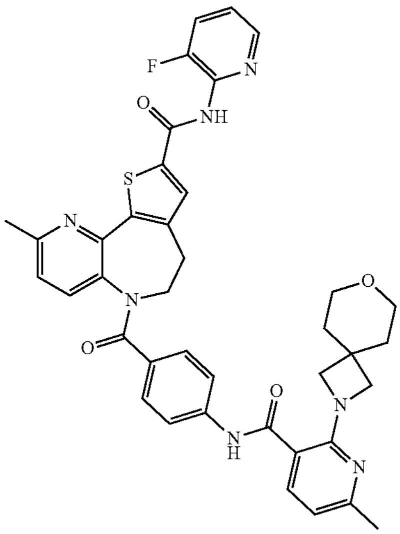 [SMILES: Cc1ccc2c(n1)-c1sc(C(=O)Nc3ncccc3F)cc1CCN2C(=O)c1ccc(NC(=O)c2ccc(C)nc2N2CC3(CCOCC3)C2)cc1] | 718.20 |
| 147 | 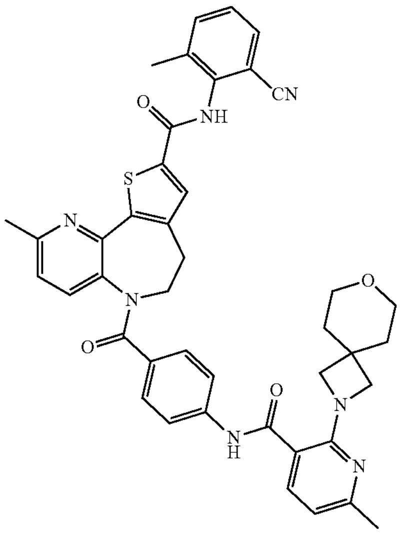 [SMILES: Cc1ccc2c(n1)-c1sc(C(=O)Nc3c(C)cccc3C#N)cc1CCN2C(=O)c1ccc(NC(=O)c2ccc(C)nc2N2CC3(CCOCC3)C2)cc1] | 738.25 |
TABLE 13-continued
| Example | Structure | ESI-MS m/z: [M + H]+ |
|---|---|---|
| 148 | 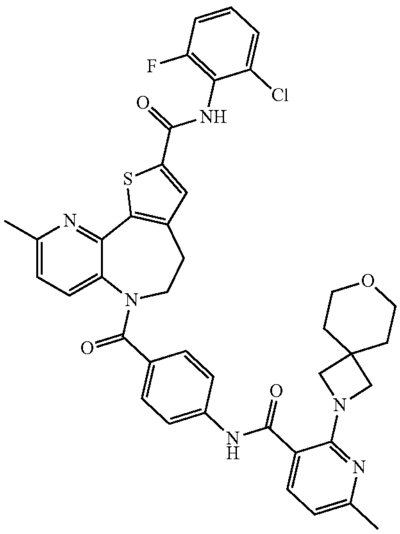 | 751.15 |
| 149 | 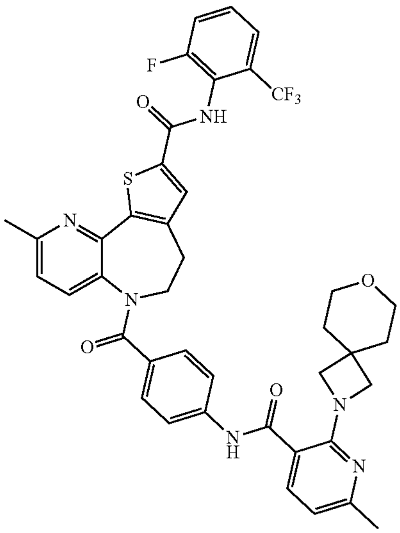 | 785.20 |

TABLE 13-continued
| Example | Structure | ESI-MS m/z: [M + H]+ |
|---|---|---|
| 150 | 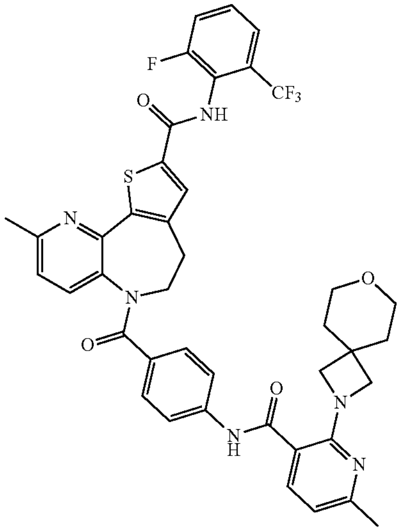 | 696.20 |
| 161 | 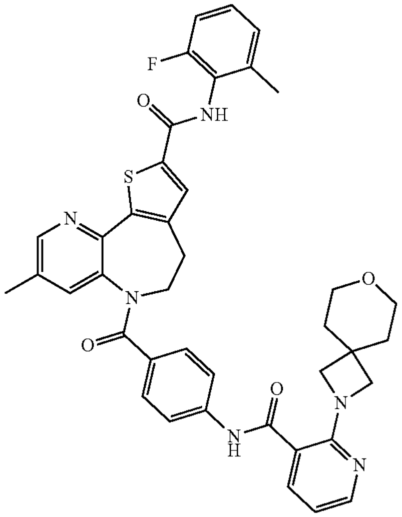 [SMILES: Cc1cnc2c(c1)N(C(=O)c1ccc(NC(=O)c3cccnc3N3CC4(CCOCC4)C3)cc1)CCc1cc(C(=O)Nc3c(C)cccc3F)sc1-2] | 717.25 |
| 162 | 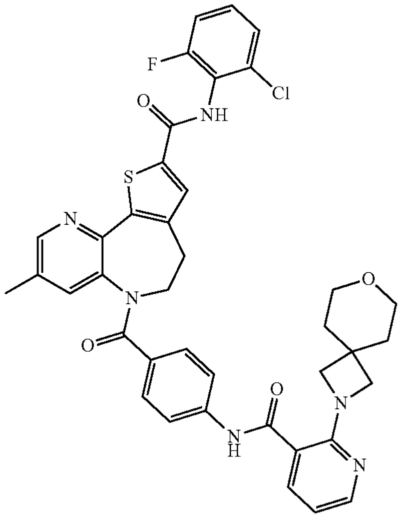 [SMILES: Cc1cnc2c(c1)N(C(=O)c1ccc(NC(=O)c3cccnc3N3CC4(CCOCC4)C3)cc1)CCc1cc(C(=O)Nc3c(F)cccc3Cl)sc1-2] | 737.20 |
TABLE 13-continued
| Example | Structure | ESI-MS m/z: [M + H]+ |
|---|---|---|
| 163 | 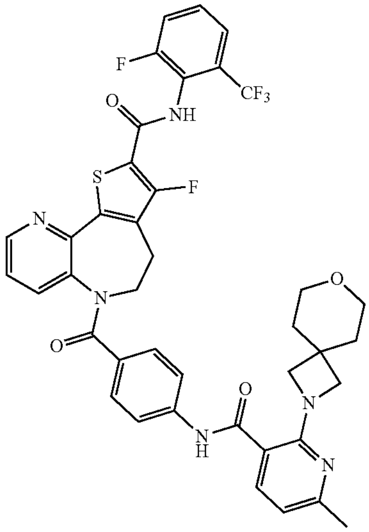 [SMILES: Cc1ccc(C(=O)Nc2ccc(C(=O)N3CCc4c(sc(C(=O)Nc5c(F)cccc5C(F)(F)F)c4F)-c4ncccc43)cc2)c(N2CC3(CCOCC3)C2)n1] | 789.18 |
| 164 | 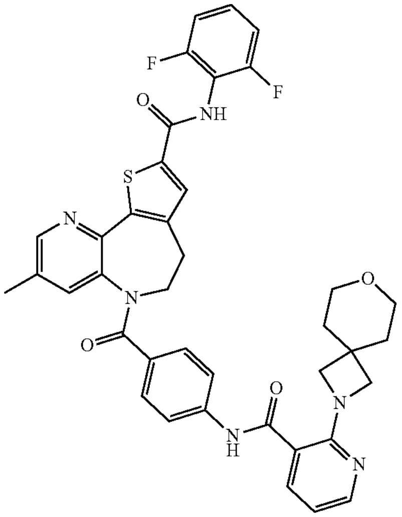 [SMILES: Cc1cnc2c(c1)N(C(=O)c1ccc(NC(=O)c3cccnc3N3CC4(CCOCC4)C3)cc1)CCc1cc(C(=O)Nc3c(F)cccc3F)sc1-2] | 721.25 |

Scheme 21
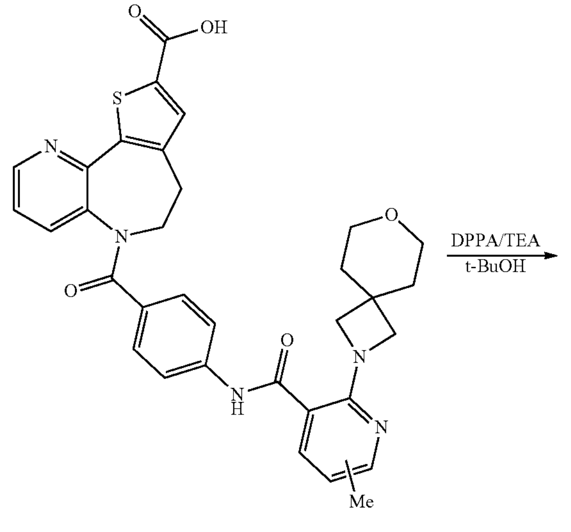
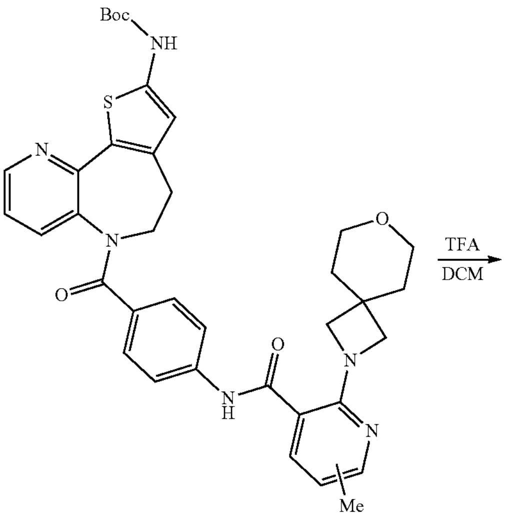
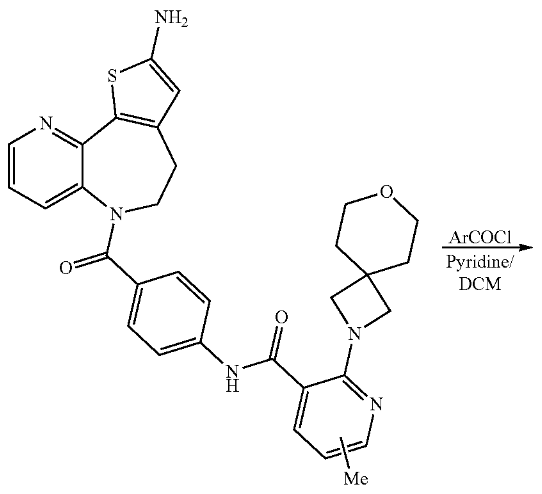
-continued
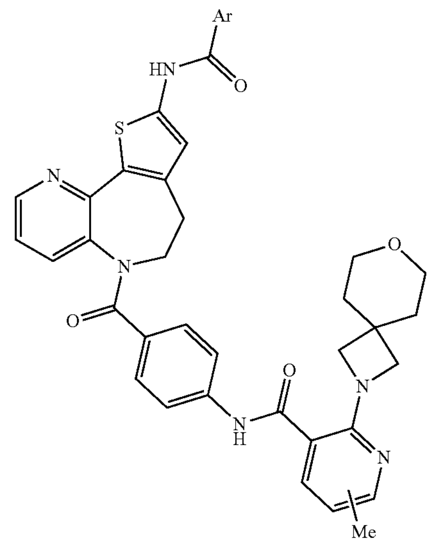
Example 151
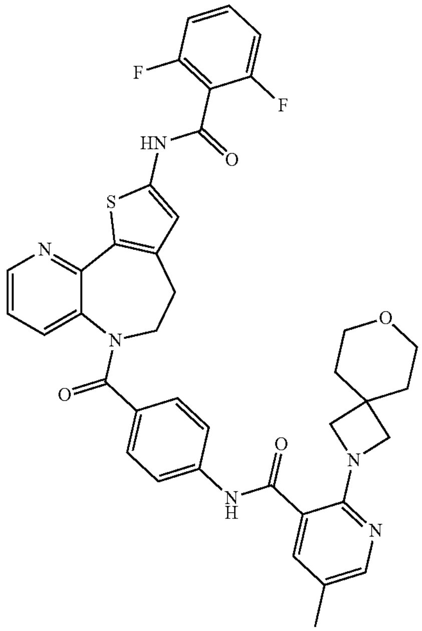

Example 151

Step a

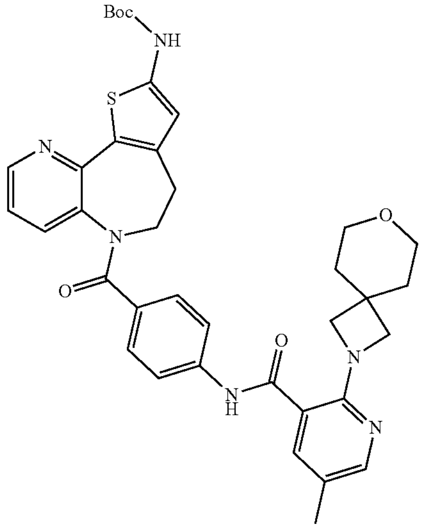 [SMILES: Cc1cnc(N2CC3(CCOCC3)C2)c(C(=O)Nc2ccc(C(=O)N3CCc4cc(NC(=O)OC(C)(C)C)sc4-c4ncccc43)cc2)c1]

To a mixture of the compound from example 7 step e (60 mg, 0.098 mmol) in 2-methylpropan-2-ol (10 mL) were added TEA (29.87 mg, 0.295 mmol) and DPPA (54.12 mg, 0.197 mmol) and stirred at 80° C. for 5 hrs. The reaction was then quenched by the addition of 200 mL of water. The resulting solution was extracted with ethyl acetate (2×200 mL) and the organic layers comb fined and concentrated. The crude product was purified by reverse phase flash to afford the title compound (25.6 mg) as a white solid. ESI-MS m/z: 681.40 $[M+H]^+$.

Example 151 Step b

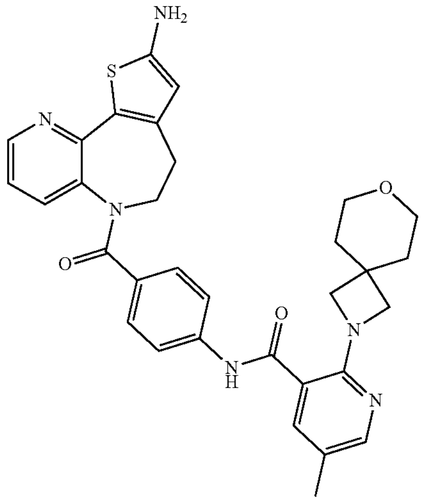 [SMILES: Cc1cnc(N2CC3(CCOCC3)C2)c(C(=O)Nc2ccc(C(=O)N3CCc4cc(N)sc4-c4ncccc43)cc2)c1]

To a mixture of the compound from step a (1.58 g, 2.321 mmol) in DCM (50 mL) was treated with TFA (50 mL) and was stirred at room temperature for 1 hr. The reaction was cooled to 0° C. and then quenched by the addition of 200 mL of water and adjusted to pH=8 by addition of sat. $NaHCO_3$ sol'n. The resulting solution was extracted with 2×200 mL of DCM. The combined organic layers were washed with water (three times) and brine, dried over sodium sulfate, filtered and concentrated to dryness. The residue was purified by reverse phase C-18 column chromatography to afford the title compound (410 mg) as a yellow solid.

ESI-MS m/z:581.20 $[M+H]^+$.

Example 151 Step c

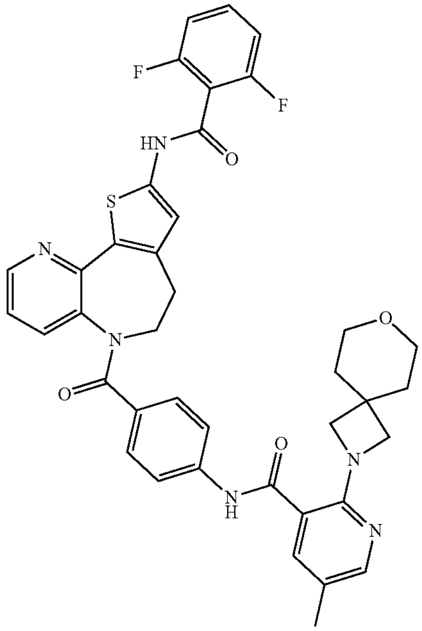

A solution of 2,6-difluorobenzoic acid (27 mg, 0.17 mmol) and (1-chloro-2-methylprop-1-en-1-yl)dimethylamine (51 mg, 0.38 mmol) in DCM (2 mL) was stirred for 30 mins at room temperature. The resulting mixture was concentrated under vacuum. Then, the compound from step b (50 mg, 0.09 mmol) and pyridine (0.1 mL) in DCM (3 mL) were added and stirred for 1 hour at room temperature. The reaction was concentrated and purified by reverse phase column chromatography to give the title compound (10.7 mg, 17%) as a white solid. ESI-MS m/z: 721.30 $[M+H]^+$. $^1H$ NMR (400 MHz, DMSO-$d_6$) δ 1.63 (t, J=5.3 Hz, 4H), 2.18 (s, 3H), 3.07-3.20 (m, 3H), 3.43-3.50 (m, 4H), 3.62 (s, 4H), 4.77-5.21 (m, 1H), 6.78 (s, 1H), 6.96-7.03 (m, 3H), 7.17 (s, 1H), 7.31 (t, J=8.3 Hz, 2H), 7.51 (s, 1H), 7.56 (d, J=8.3 Hz, 2H), 7.61-7.70 (m, 1H), 8.05 (s, 1H), 8.34 (d, J=4.6 Hz, 1H), 10.42 (s, 1H), 12.14 (s, 1H).

Examples 152-160 shown in table 14 were prepared using the procedure similar to that of example 151 step c from the corresponding intermediates.

TABLE 14
| Example | Structure | ESI-MS m/z: [M + H]+ |
|---|---|---|
| 152 | 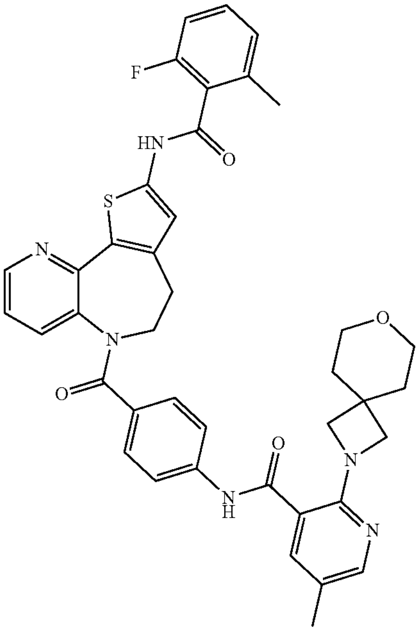 [SMILES: Cc1cnc(N2CC3(CCOCC3)C2)c(C(=O)Nc2ccc(C(=O)N3CCc4cc(NC(=O)c5c(C)cccc5F)sc4-c4ncccc43)cc2)c1] | 717.35 |
| 153 | 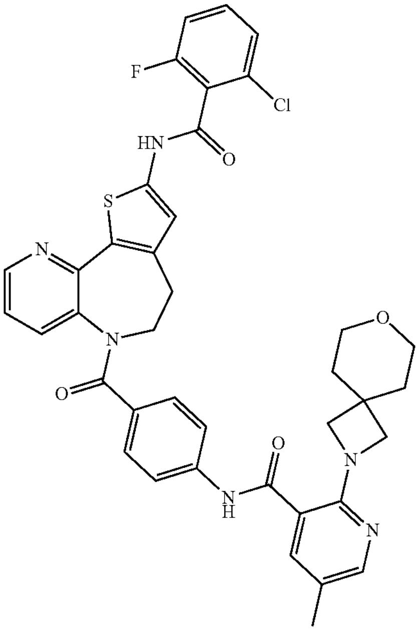 | 737.30 |
TABLE 14-continued
| Example | Structure | ESI-MS m/z: [M + H]+ |
|---|---|---|
| 154 | 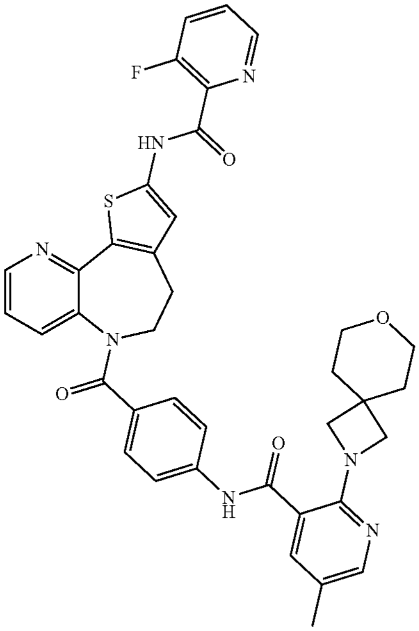 [SMILES: Cc1cnc(N2CC3(CCOCC3)C2)c(C(=O)Nc2ccc(C(=O)N3CCc4cc(NC(=O)c5ncccc5F)sc4-c4ncccc43)cc2)c1] | 704.35 |
| 155 | 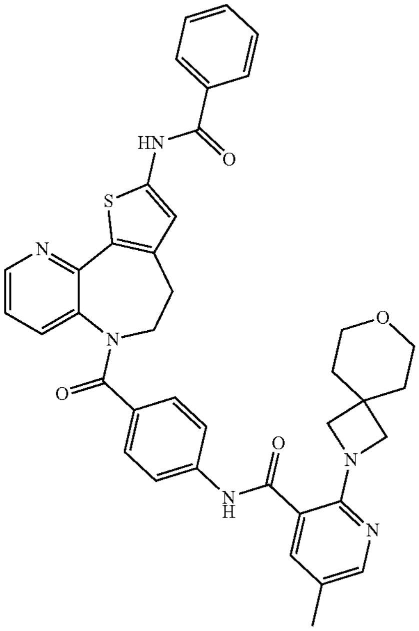 [SMILES: Cc1cnc(N2CC3(CCOCC3)C2)c(C(=O)Nc2ccc(C(=O)N3CCc4cc(NC(=O)c5ccccc5)sc4-c4ncccc43)cc2)c1] | 685.25 |

TABLE 14-continued
| Example | Structure | ESI-MS m/z: [M + H]+ |
| --- | --- | --- |
| 156 | 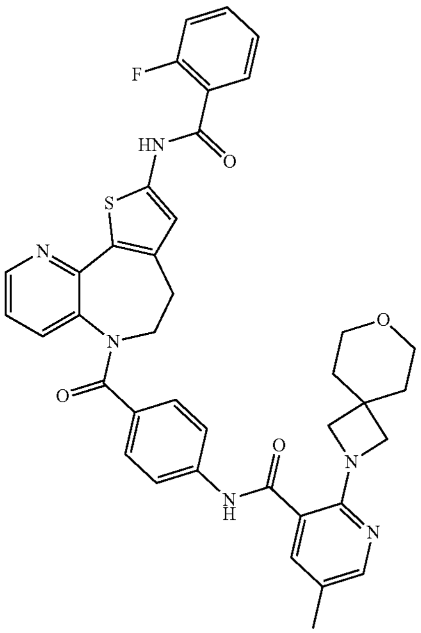 [SMILES: Cc1cnc(N2CC3(CCOCC3)C2)c(C(=O)Nc2ccc(C(=O)N3CCc4cc(NC(=O)c5ccccc5F)sc4-c4ncccc43)cc2)c1] | 703.35 |
| 157 | 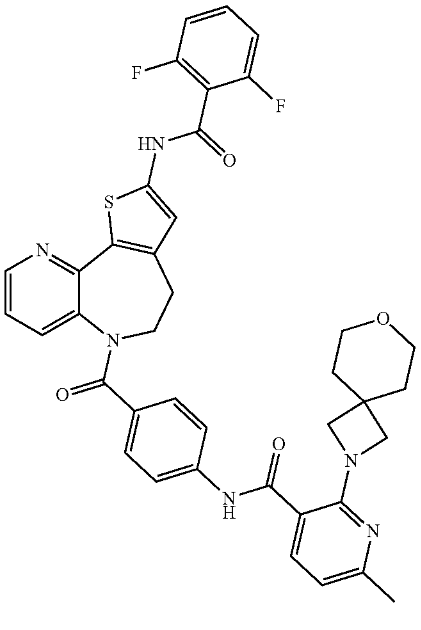 | 721.35 |
TABLE 14-continued
| Example | Structure | ESI-MS m/z: [M + H]+ |
| --- | --- | --- |
| 158 | 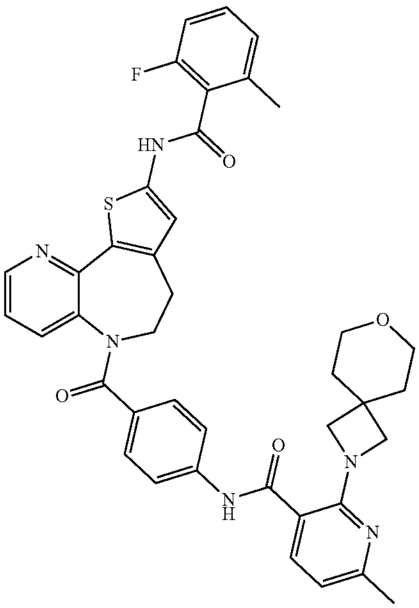 [SMILES: Cc1ccc(C(=O)Nc2ccc(C(=O)N3CCc4cc(NC(=O)c5c(C)cccc5F)sc4-c4ncccc43)cc2)c(N2CC3(CCOCC3)C2)n1] | 717.25 |
| 159 | 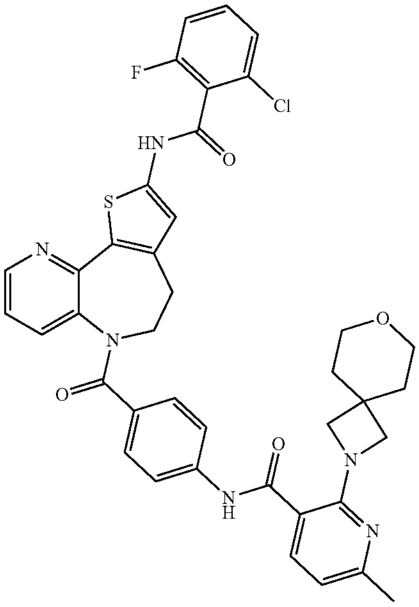 | 737.20 |

TABLE 14-continued
| Example | Structure | ESI-MS m/z: [M + H]+ |
|---|---|---|
| 160 | 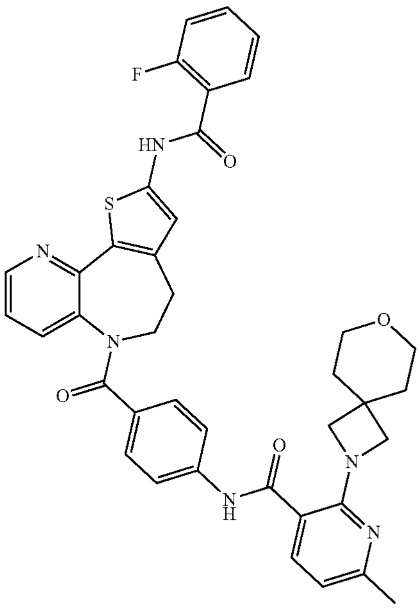 [SMILES: Cc1ccc(C(=O)Nc2ccc(C(=O)N3CCc4cc(NC(=O)c5ccccc5F)sc4-c4ncccc43)cc2)c(N2CC3(CCOCC3)C2)n1] | 703.40 |
The following examples are prepared by using procedures similar to those described above:
| Example | Structure |
|---|---|
| 165 | 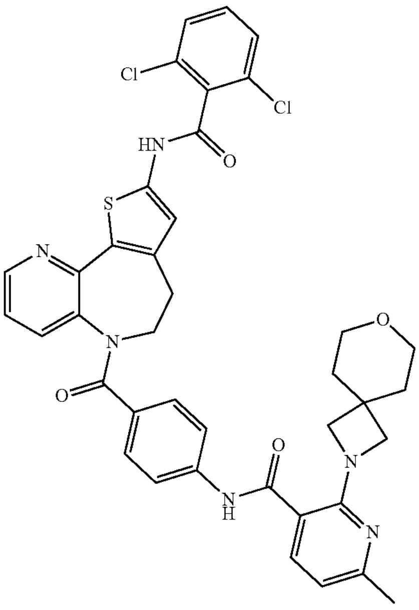 [SMILES: Cc1ccc(C(=O)Nc2ccc(C(=O)N3CCc4cc(NC(=O)c5c(Cl)cccc5Cl)sc4-c4ncccc43)cc2)c(N2CC3(CCOCC3)C2)n1] |
-continued
| Example | Structure |
|---|---|
| 166 | 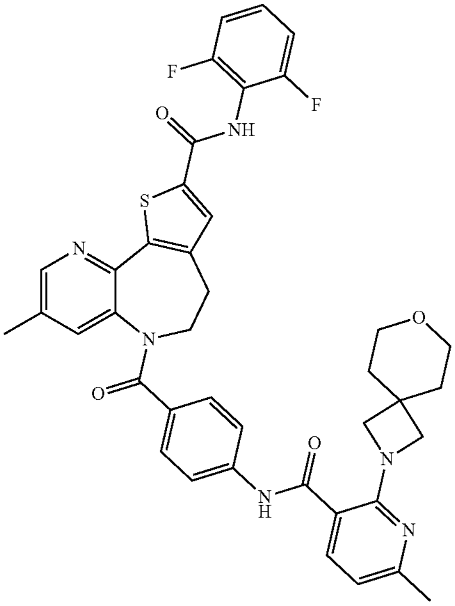 [SMILES: Cc1cnc2c(c1)N(C(=O)c1ccc(NC(=O)c3ccc(C)nc3N3CC4(CCOCC4)C3)cc1)CCc1cc(C(=O)Nc3c(F)cccc3F)sc1-2] |
| 167 | 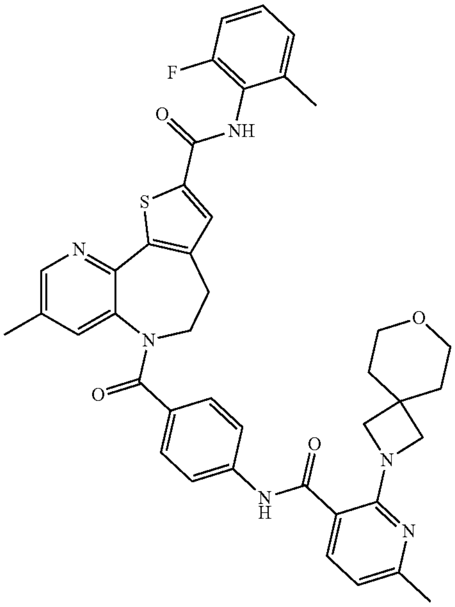 [SMILES: Cc1cnc2c(c1)N(C(=O)c1ccc(NC(=O)c3ccc(C)nc3N3CC4(CCOCC4)C3)cc1)CCc1cc(C(=O)Nc3c(C)cccc3F)sc1-2] |

-continued

| Example | Structure |
|---|---|
| 168 | 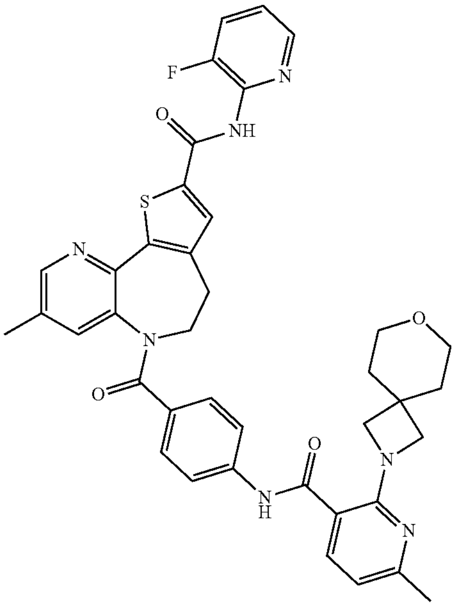 [SMILES: Cc1cnc2c(c1)N(C(=O)c1ccc(NC(=O)c3ccc(C)nc3N3CC4(CCOCC4)C3)cc1)CCc1cc(C(=O)Nc3ncccc3F)sc1-2] |
| 169 | 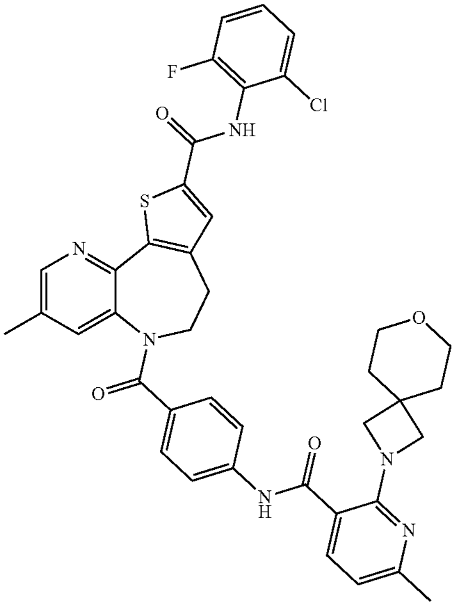 |

-continued

| Example | Structure |
|---|---|
| 170 | 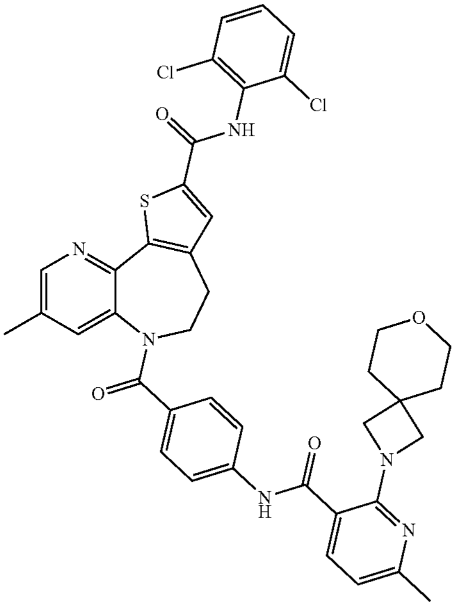 [SMILES: Cc1cnc2c(c1)N(C(=O)c1ccc(NC(=O)c3ccc(C)nc3N3CC4(CCOCC4)C3)cc1)CCc1cc(C(=O)Nc3c(Cl)cccc3Cl)sc1-2] |
| 171 | 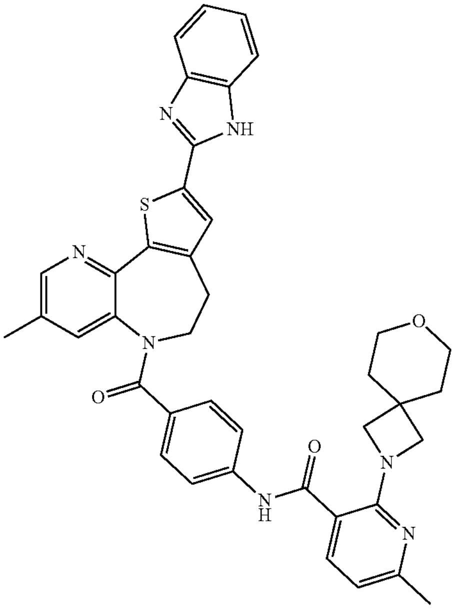 [SMILES: Cc1cnc2c(c1)N(C(=O)c1ccc(NC(=O)c3ccc(C)nc3N3CC4(CCOCC4)C3)cc1)CCc1cc(-c3nc4ccccc4[nH]3)sc1-2] |

ASSAYS

Introduction

RSV is a single stranded negative sense RNA virus that causes respiratory tract infections which can be dangerous to infants, the elderly, and immunosuppressed individuals. Currently there is no vaccine, and therapeutic options are both costly and of limited effectiveness. These approved treatments are Ribavirin, and Palivizumab/Synagis (a monoclonal antibody). RSV has two genotypes, A and B, which differ primarily in the structure of the virus' surface "G" attachment protein. Our current primary screen focusses on RSV-A and uses an in vitro cytoprotection assay where compounds are added in 2-fold dilutions to cells which are then subjected to fully replicative viral particles. Cell viability is measured several days later along with separate measurements of compound cytotoxicity. This report focuses on the results of our most recent screening of compounds.

Methods

HEp-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days.

The control compound currently used in the RSV assay is RSV-604, a ~2.4 μM $EC_{50}$ nucleocapsid inhibitor previously developed by Novartis. Following extensive parameter testing, the final assay is run as follows: HEp-2 cells are seeded into the inner 60 wells of a 96-well plate at 8,000 cells per well in a volume of 50 μL using Growth Media (DMEM without phenol red, 1% L-Glut, 1% Penn/Strep, 1% nonessential amino acids, 10% FBS). 2-Fold serial dilutions of control and test compounds are added to the wells in duplicate in a total volume of 25 μL. Viral stock is then added to the wells in a volume of 25 μL, bringing the total volume of each well to 100 μL. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 uL of growth media containing an equal quantity of sucrose as those wells receiving the viral stock in order to keep consistent in media and volume conditions. The outer wells of the plate are filled with 125 μL of growth media to act as a thermal and evaporative moat around the test wells. Following a 4-day incubation period, the plates are read using ATPlite (50 uL added per well), which quantifies the amount of ATP (a measure of cell health) present in each well. Assay plates are read using the Envision luminometer. In parallel, cytotoxicity is examined on an additional 96-well plate treated in an identical manner, but substituting the 25 μL of viral stock for 25 μL of growth media. These data are used to calculate the $EC_{50}$ of each compound. $EC_{50}$ ranges are as follows: A<0.01 μM; B 0.01-0.05 μM; C>0.05 μM.

TABLE 15

Summary of Activities

| Example | Human RSV-A ("Long" strain) $EC_{50}$ | Example | Human RSV-A ("Long" strain) $EC_{50}$ |
|---|---|---|---|
| 1 | C | 2 | B |
| 3 | C | 4 | A |
| 5 | A | 6 | C |
| 7 | A | 8 | A |
| 9 | A | 10 | A |
| 11 | A | 12 | A |
| 13 | A | 14 | B |
| 15 | A | 16 | A |
| 17 | B | 18 | B |

TABLE 15-continued

Summary of Activities

| Example | Human RSV-A ("Long" strain) $EC_{50}$ | Example | Human RSV-A ("Long" strain) $EC_{50}$ |
|---|---|---|---|
| 19 | A | 20 | A |
| 21 | A | 22 | A |
| 23 | A | 24 | A |
| 25 | A | 26 | A |
| 27 | A | 28 | A |
| 29 | A | 30 | B |
| 31 | A | 32 | A |
| 33 | A | 34 | A |
| 35 | A | 36 | B |
| 37 | A | 38 | B |
| 39 | A | 40 | A |
| 41 | A | 42 | A |
| 43 | B | 44 | A |
| 45 | A | 46 | A |
| 47 | B | 48 | B |
| 49 | B | 50 | C |
| 51 | B | 52 | B |
| 53 | C | 54 | B |
| 55 | A | 56 | A |
| 57 | B | 58 | A |
| 59 | A | 60 | B |
| 61 | A | 62 | A |
| 63 | A | 64 | A |
| 65 | A | 66 | A |
| 67 | C | 68 | B |
| 69 | B | 70 | A |
| 71 | A | 72 | A |
| 73 | A | 74 | A |
| 75 | A | 76 | A |
| 77 | B | 78 | A |
| 79 | A | 80 | A |
| 81 | A | 82 | A |
| 83 | A | 84 | A |
| 85 | A | 86 | A |
| 87 | A | 88 | A |
| 89 | A | 90 | B |
| 91 | A | 92 | B |
| 93 | A | 94 | B |
| 95 | B | 96 | B |
| 97 | B | 98 | A |
| 99 | A | 100 | B |
| 101 | A | 102 | B |
| 103 | B | 104 | A |
| 105 | A | 106 | A |
| 107 | A | 108 | B |
| 109 | B | 110 | B |
| 111 | B | 112 | C |
| 113 | C | 114 | C |
| 115 | B | 116 | B |
| 117 | B | 118 | B |
| 119 | A | 120 | B |
| 121 | B | 122 | C |
| 123 | C | 124 | C |
| 125 | B | 126 | C |
| 127 | C | 128 | B |
| 129 | C | 130 | C |
| 131 | B | 132 | B |
| 133 | A | 134 | A |
| 135 | A | 136 | A |
| 137 | A | 138 | B |
| 139 | B | 140 | B |
| 141 | C | 142 | B |
| 143 | C | 144 | B |
| 145 | C | 146 | B |
| 147 | C | 148 | C |
| 149 | C | 150 | B |
| 151 | A | 152 | A |
| 153 | A | 154 | A |
| 155 | A | 156 | A |
| 157 | A | 158 | B |
| 159 | B | 160 | A |
| 161 | A | 162 | A |
| 163 | A | 164 | A |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I):

(I)

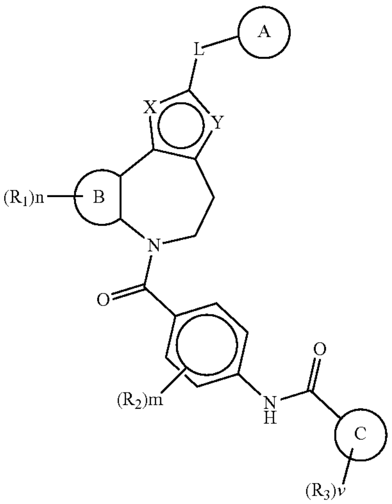

or a pharmaceutically acceptable salt thereof, wherein:

Ⓐ is selected from the group consisting of:

1) optionally substituted aryl;

2) optionally substituted heteroaryl;

3) optionally substituted —$C_3$-$C_{12}$ cycloalkenyl;

4) optionally substituted 3- to 12-membered heterocycloalkyl;

5) optionally substituted arylalkyl;

6) optionally substituted heteroarylalkyl;

7) optionally substituted-$C_3$-$C_{12}$ cycloalkyl-$C_1$-$C_6$ alkyl;

8) optionally substituted-$C_3$-$C_{12}$ cycloalkenyl-$C_1$-$C_6$ alkyl; and 9) optionally substituted 3- to 12-membered heterocycloalkyl-$C_1$-$C_6$ alkyl;

Ⓑ is selected from the groups below;

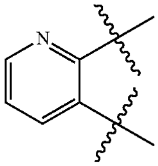 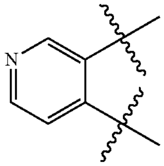 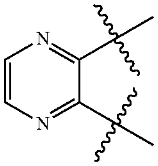

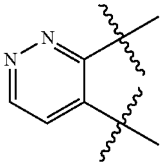 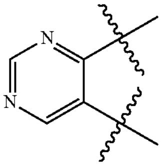 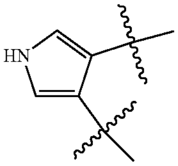

-continued

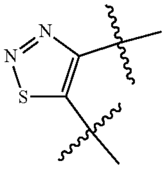 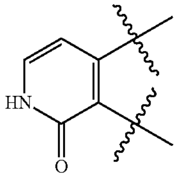 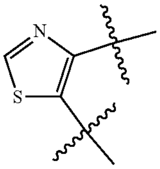

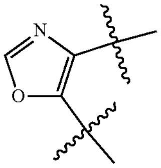 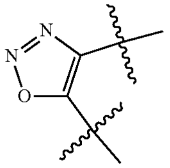 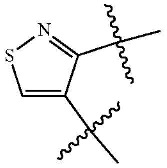

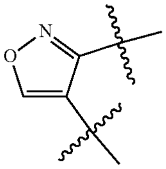 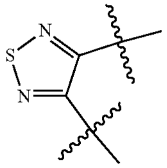 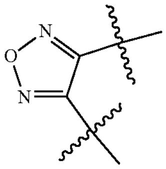

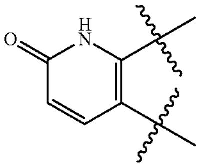 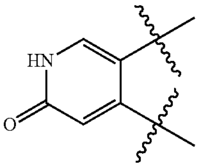

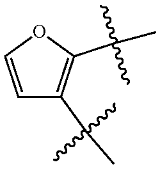 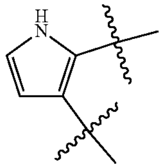

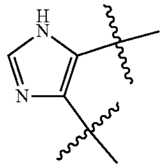 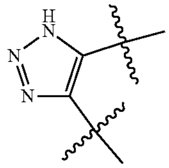,

Ⓒ is aryl or heteroaryl;

L is absent, —CONH—, or —NHCO—;

One of X and Y is selected from O, S, and $NR_4$, and the other is N or $CR_5$;

Each $R_1$ and $R_2$ is independently selected from the group consisting of: halogen, cyano, nitro, hydroxyl, protected hydroxyl, amino, protected amino, optionally substituted —$C_1$-$C_8$ alkyl, and optionally substituted —$C_1$-$C_8$ alkoxy;

Each $R_3$ is independently selected from the group consisting of:

1) halogen;

2) optionally substituted —$C_1$-$C_8$ alkoxy;

3) optionally substituted —$C_1$-$C_8$ alkyl;

4) optionally substituted —$C_2$-$C_8$ alkenyl;

5) optionally substituted —$C_2$-$C_8$ alkynyl;

6) optionally substituted —$C_3$-$C_{12}$ cycloalkyl;

7) optionally substituted —$C_3$-$C_{12}$ cycloalkenyl;

8) optionally substituted 3- to 12-membered heterocycloalkyl;

9) optionally substituted aryl;

10) optionally substituted heteroaryl;

11) optionally substituted arylalkyl;

12) optionally substituted aryloxy;

13) —$C(O)R_{12}$;

14) —C(O)NR$_{13}$R$_{14}$;
15) —C(O)NR$_{11}$S(O)$_2$R$_{12}$;
16) —S(O)$_2$NR$_{13}$R$_{14}$;
17) —NR$_{13}$R$_{14}$;
18) —NR$_{11}$S(O)$_2$R$_{12}$;
19) —NR$_{11}$C(O)R$_{12}$;
20) —NR$_{11}$C(O)NR$_{13}$R$_{14}$; and
21) —NR$_{11}$C(O)NHS(O)$_2$R$_{12}$, n is 0, 1, 2, 3 or 4;
m is 0, 1, 2, 3 or 4;
v is 0, 1, 2, or 3;
R$_4$ is hydrogen or optionally substituted —C$_1$-C$_8$ alkyl;
R$_5$ is hydrogen, halogen, optionally substituted —C$_1$-C$_8$ alkyl, or optionally substituted —C$_1$-C$_8$ alkoxy;
R$_{12}$ at each occurrence is independently selected from the group consisting of:

1) Hydrogen;
2) Halogen;
3) Hydroxyl;
4) optionally substituted —C$_1$-C$_8$ alkoxy;
5) optionally substituted —C$_1$-C$_8$ alkyl;
6) optionally substituted —C$_2$-C$_8$ alkenyl;
7) optionally substituted —C$_2$-C$_8$ alkynyl;
8) optionally substituted —C$_3$-C$_8$ cycloalkyl;
9) optionally substituted —C$_3$-C$_8$ cycloalkenyl;
10) optionally substituted 3- to 8-membered heterocycloalkyl;
11) optionally substituted aryl;
12) optionally substituted arylalkyl;
13) optionally substituted heteroaryl; and
14) optionally substituted heteroarylalkyl;

R$_{11}$, R$_{13}$ and R$_{14}$ are each independently selected from hydrogen, optionally substituted —C$_1$-C$_8$-alkyl, optionally substituted —C$_2$-C$_8$-alkenyl, optionally substituted —C$_2$-C$_8$-alkynyl;
optionally substituted —C$_3$-C$_8$-cycloalkyl, optionally substituted 3- to 8-membered heterocyclic, optionally substituted aryl, optionally substituted arylalkyl, optionally substituted heteroaryl, and optionally substituted heteroarylalkyl; alternatively R$_{13}$ and R$_{14}$ are taken together with the nitrogen atom they attached to form a heterocyclic ring.

2. The compound of claim 1, wherein L is —CONH— or —NHCO—.

3. The compound of claim 1, wherein (A) is derived from one of the groups below by removal of a ring hydrogen atom:

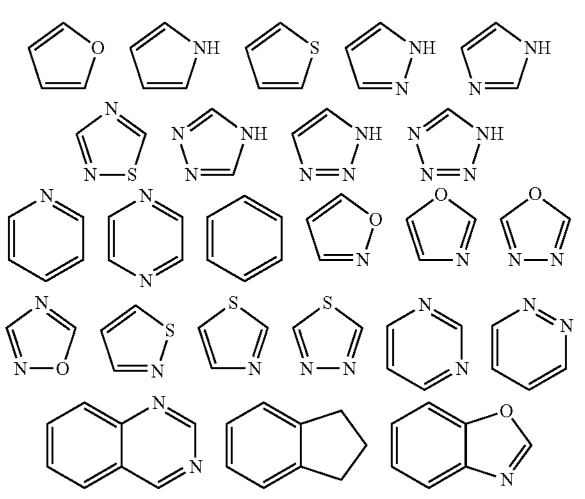

-continued

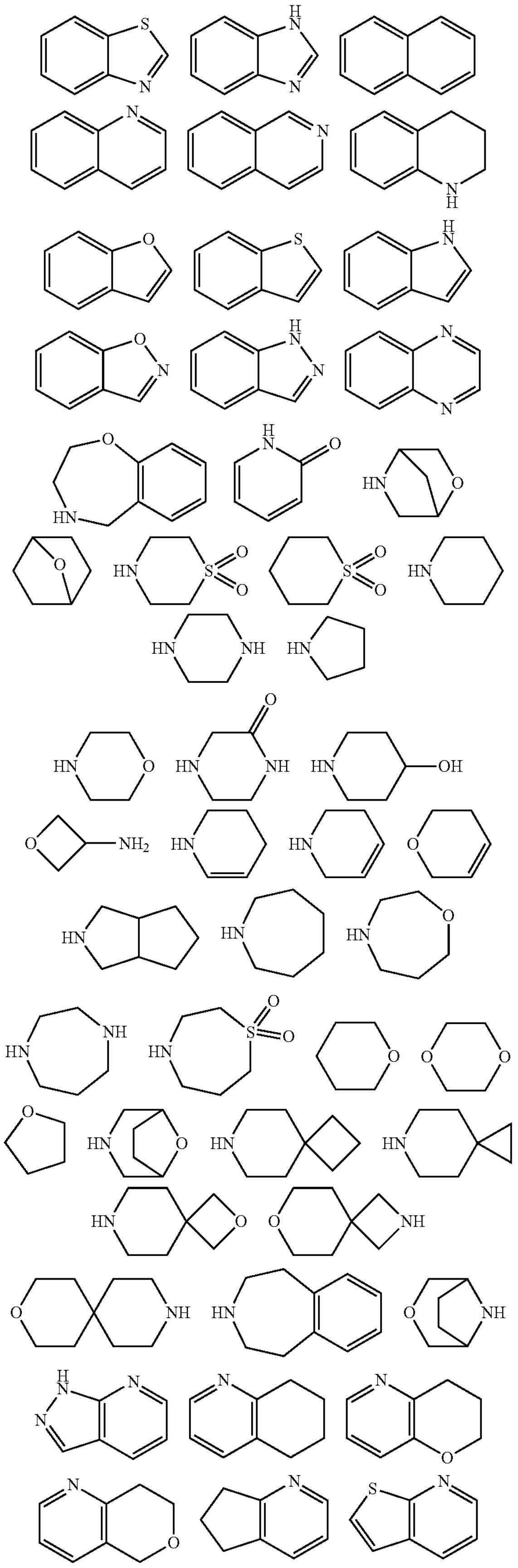

-continued

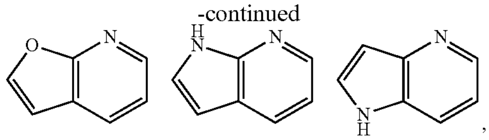

, wherein each group is optionally substituted.

4. The compound of claim 1, wherein Ⓐ is one of the groups below

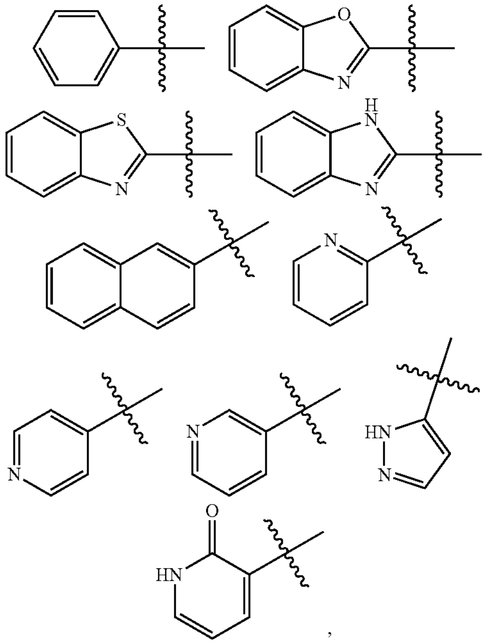

, wherein each group is optionally substituted.

5. The compound of claim 1, wherein Ⓒ is derived from one of the groups below by removal of one hydrogen atom:

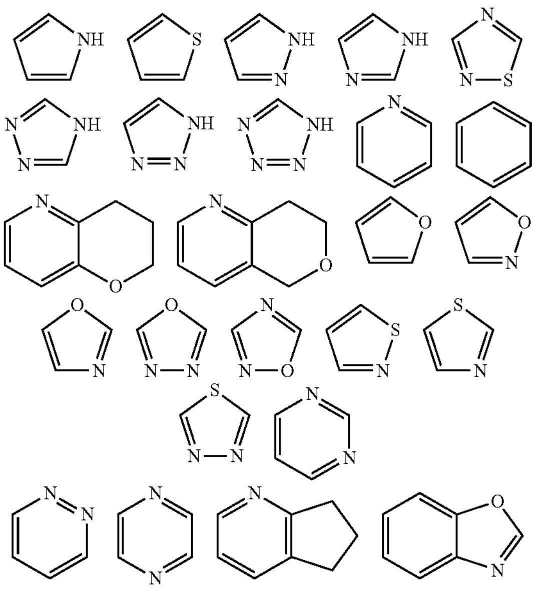

-continued

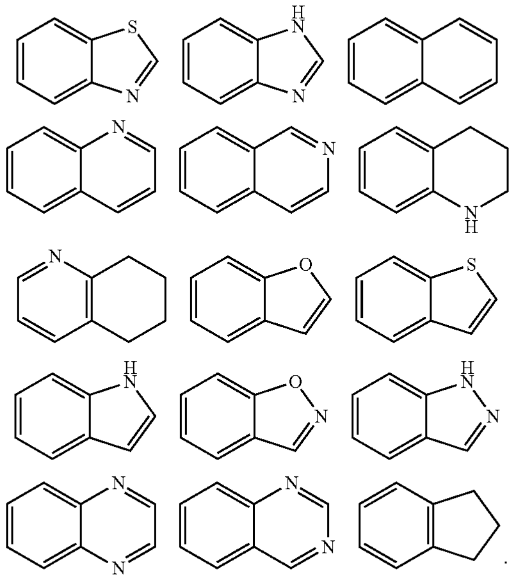

.

6. The compound of claim 1, wherein $R_3$ is selected from one of the following groups, wherein each of the groups is optionally substituted:

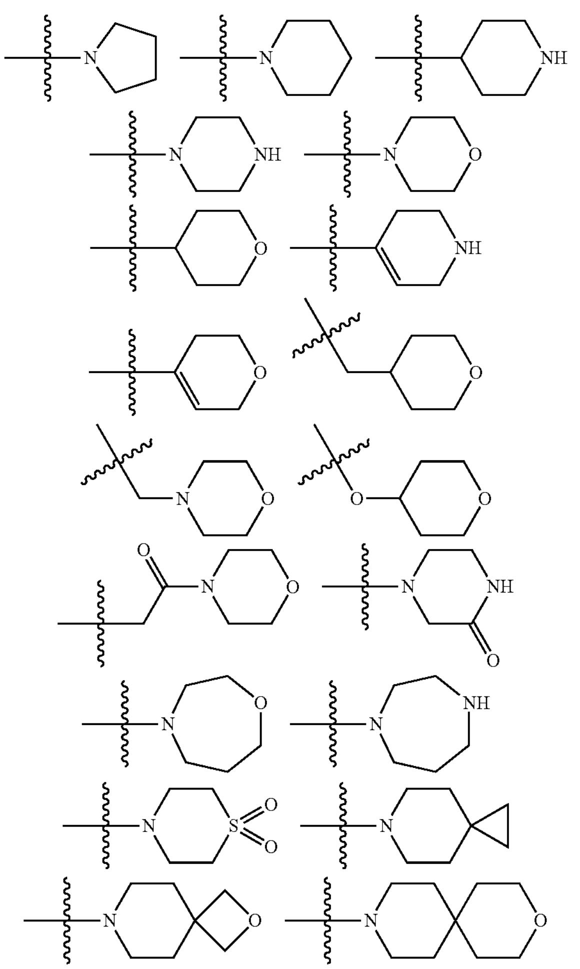

-continued
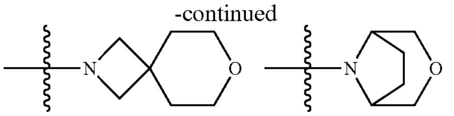
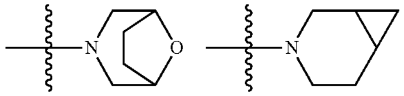
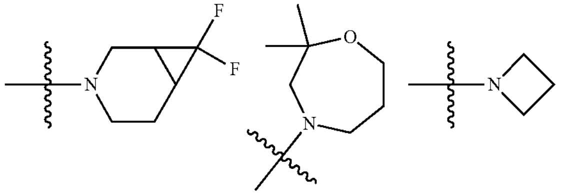
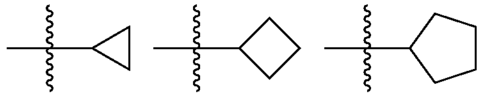
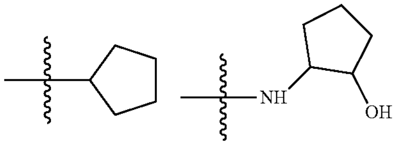
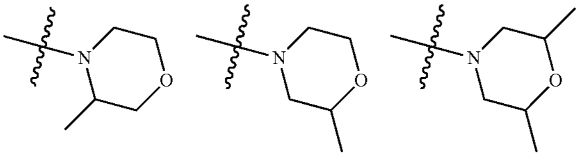
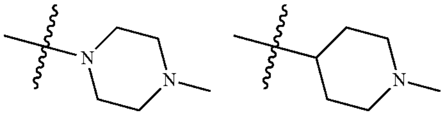
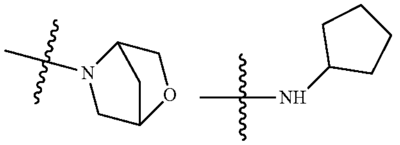
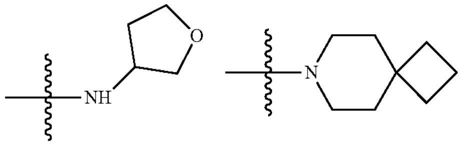
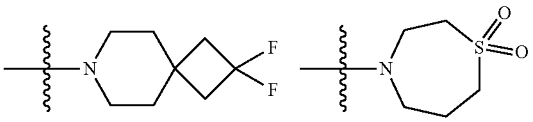
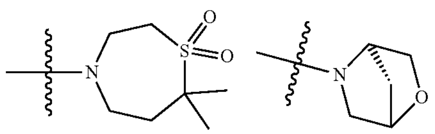
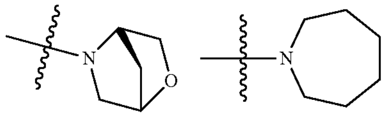
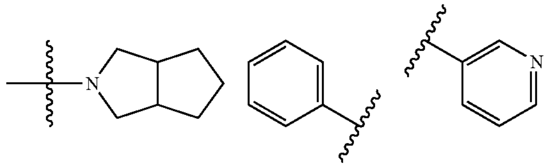
-continued
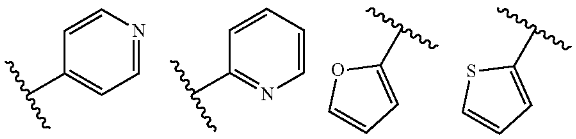
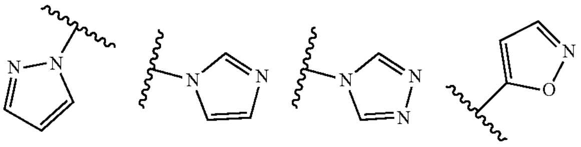
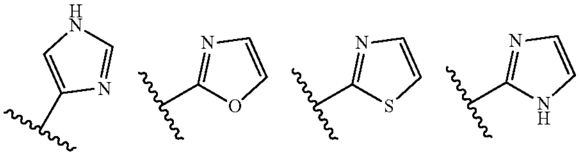
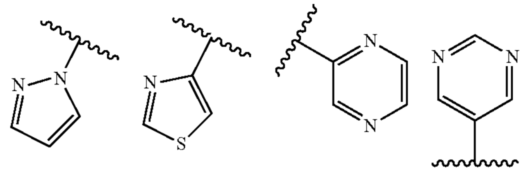
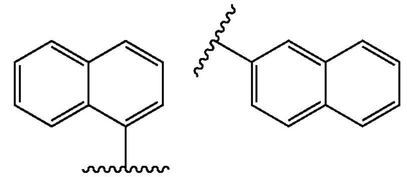
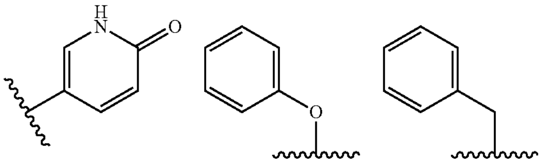
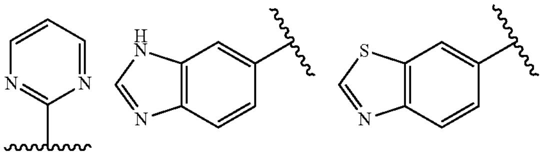
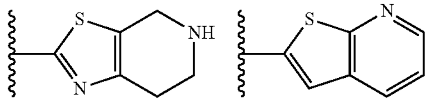
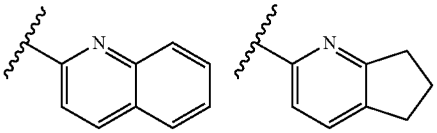
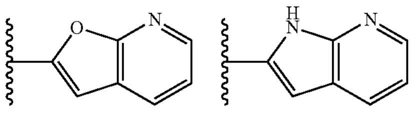
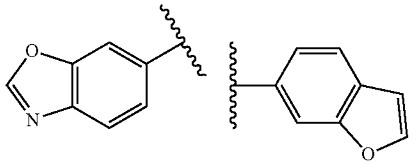

-continued
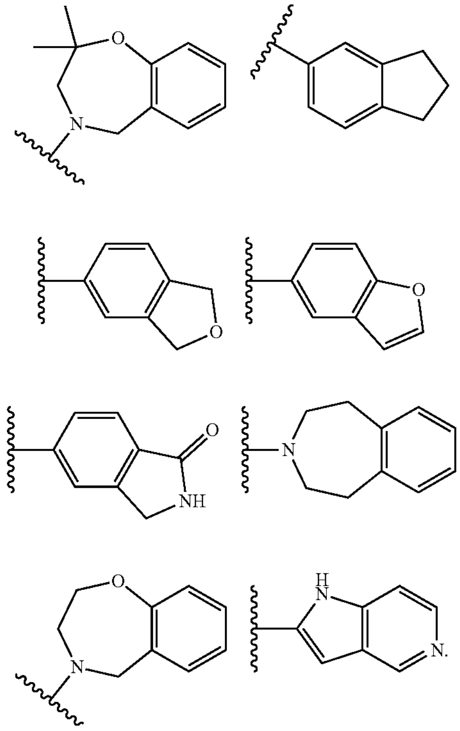
7. The compound of claim 1, wherein
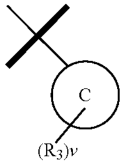
is represented by
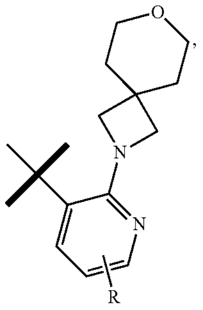
where R is hydrogen or methyl.
8. The compound of claim 1, represented by one of Formulas (IIa-1)~(IIa-4), or (IIb-1)~(IIb-4), or (IIc-1)~(IIc-4), or a pharmaceutically acceptable salt thereof:
(IIa-1)
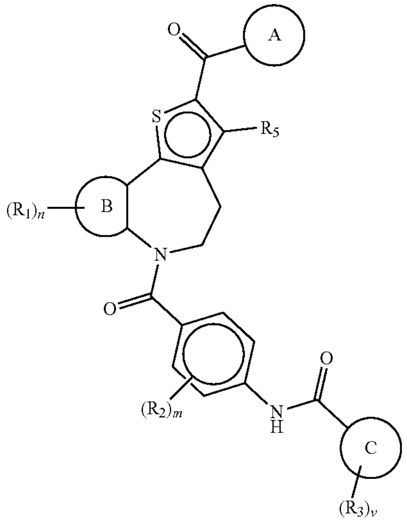
(IIa-2)
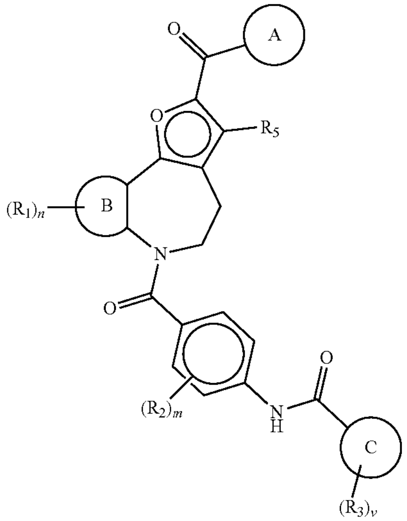
(IIa-3)
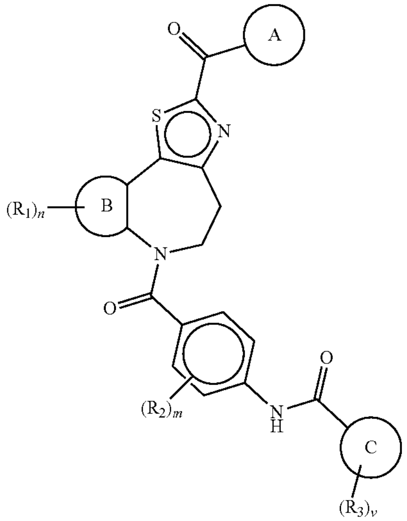

-continued
(IIa-4)
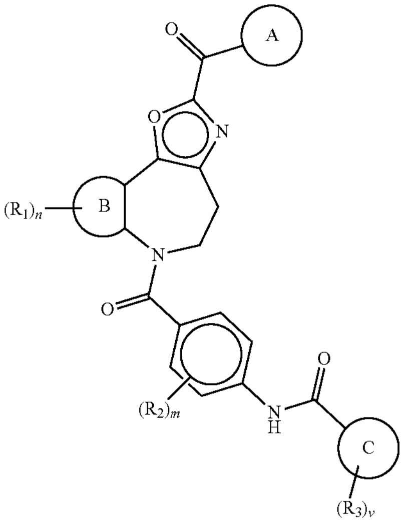
(IIb-1)
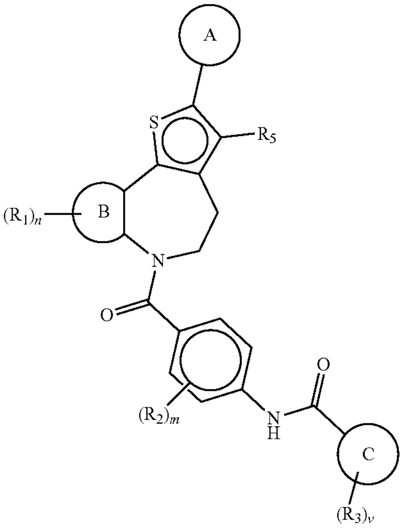
(IIb-2)
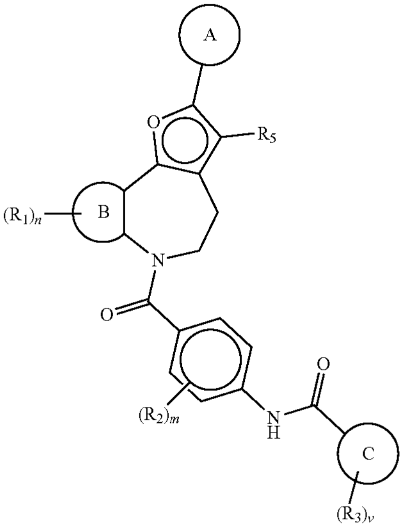
-continued
(IIb-3)
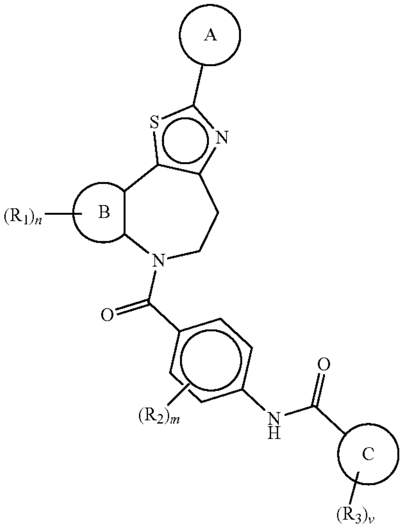
(IIb-4)
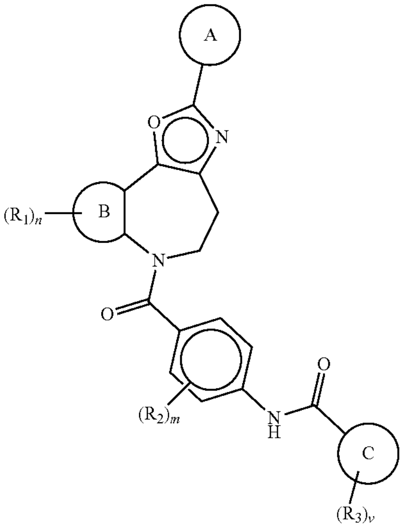
(IIc-1)
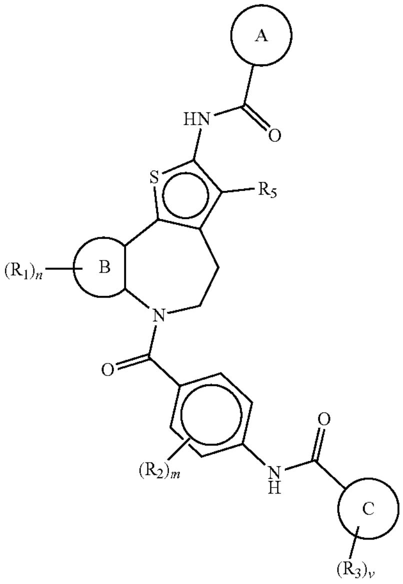

-continued
(IIc-2)
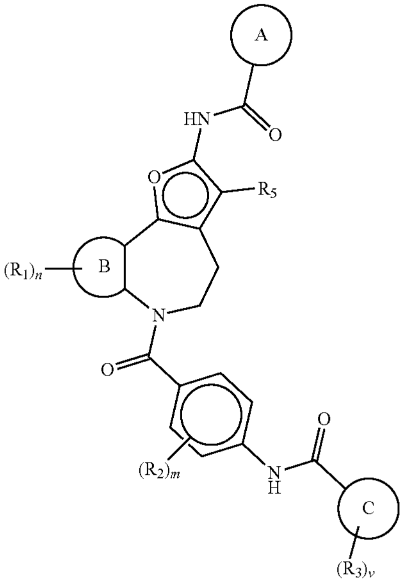
(IIc-3)
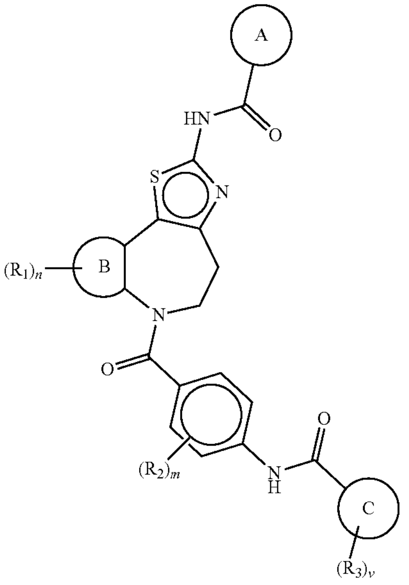
-continued
(IIc-4)
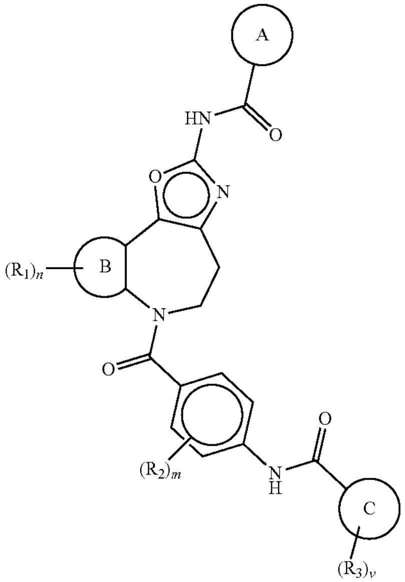
,
wherein Ⓐ, Ⓑ, Ⓒ, $R_1$, $R_2$, $R_3$, $R_5$, n, m, and v are as defined in claim 1.
9. The compound of claim 1, represented by one of Formulas (IIIa)~(IIId), or a pharmaceutically acceptable salt thereof:
(IIIa)
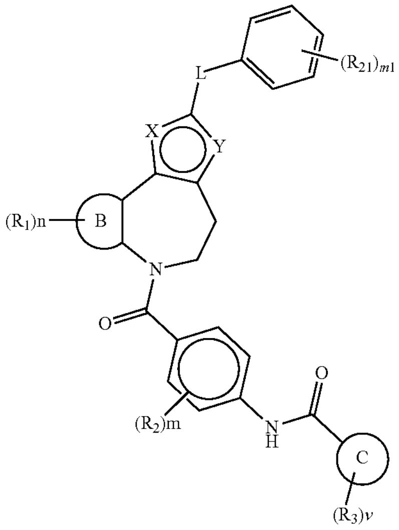

-continued (IIIb)

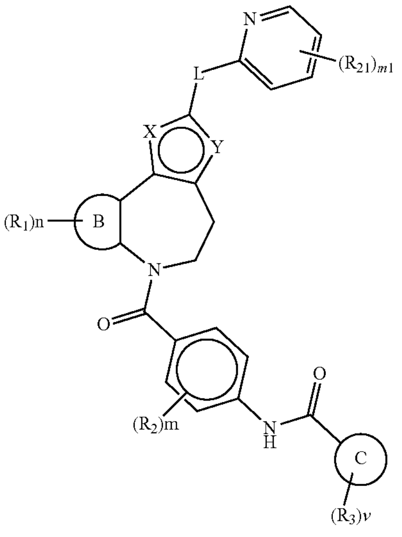

(IIIc)

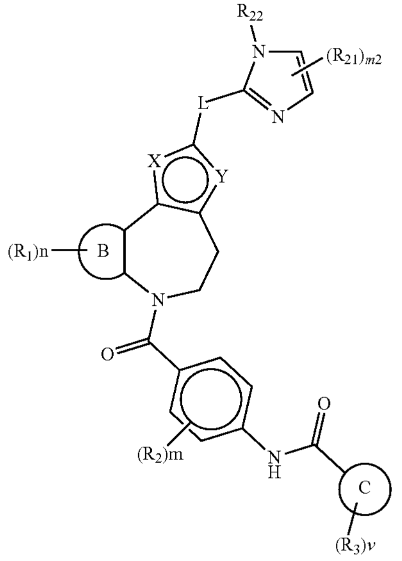

-continued (IIId)

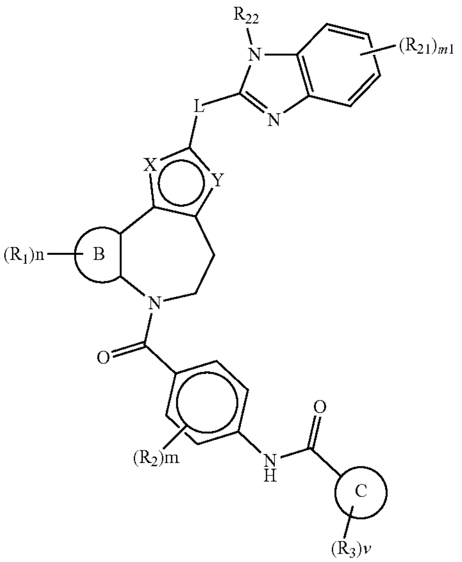

wherein Ⓑ, Ⓒ, L, $R_1$, $R_2$, $R_3$, n, m, and v are as defined in claim 1; m1 is 0, 1, 2, 3 or 4; m2 is 0, 1 or 2; each $R_{22}$ is independently selected from hydrogen and —$CH_3$; and each $R_{21}$ is independently selected from halogen, —$NH_2$, optionally substituted —$C_1$-$C_3$ alkyl, and optionally substituted —$C_1$-$C_3$ alkoxy.

10. The compound of claim 1, represented by one of Formulas (IIIa-1)~(IIId-1), or (IIIa-2)~(IIId-2), or (IIIa-3)~(IIId-3), or (IIIa-4)~(IIId-4), or a pharmaceutically acceptable salt thereof:

(IIIa-1)

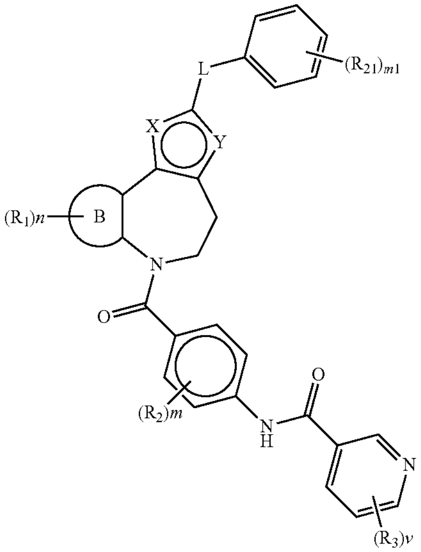

-continued
(IIIb-1)
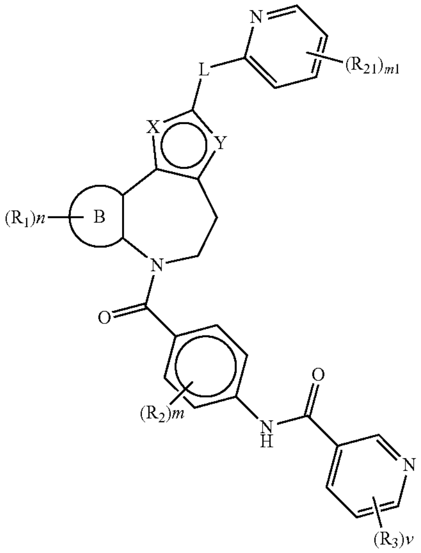
(IIId-1)
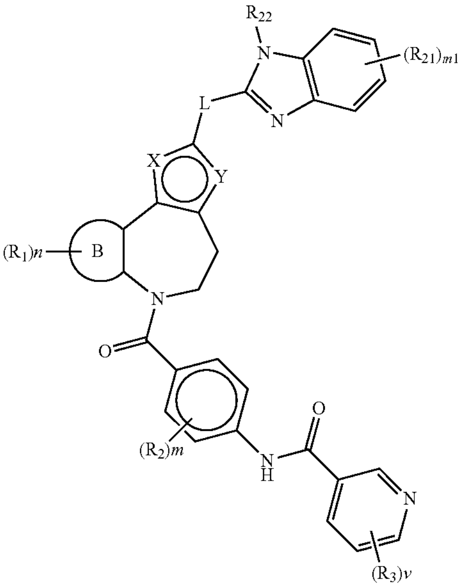
(IIIc-1)
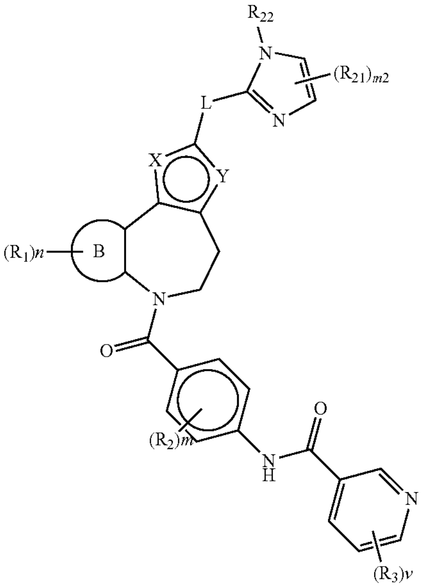
(IIIa-2)
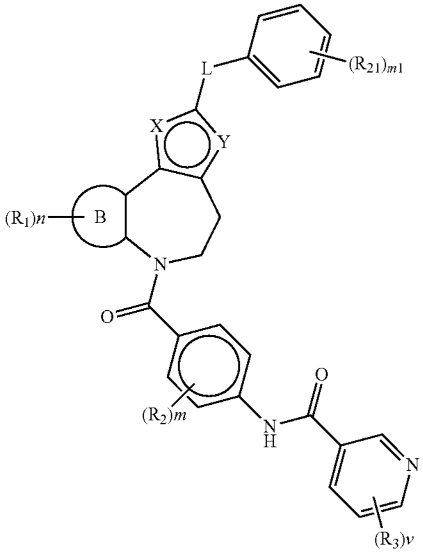

-continued
(IIIb-2)
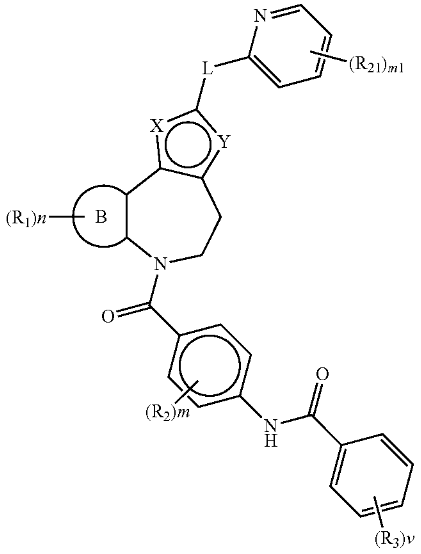
(IIIc-2)
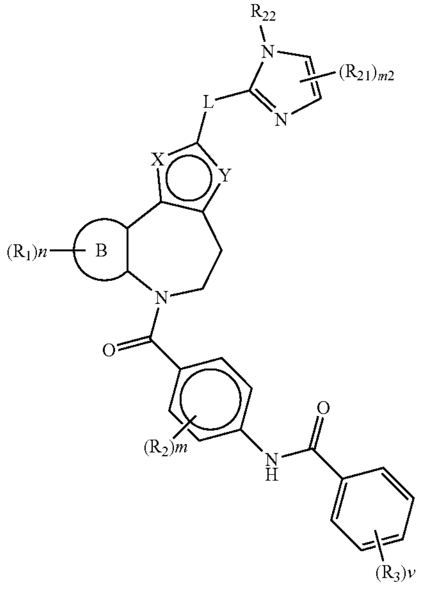
-continued
(IIId-2)
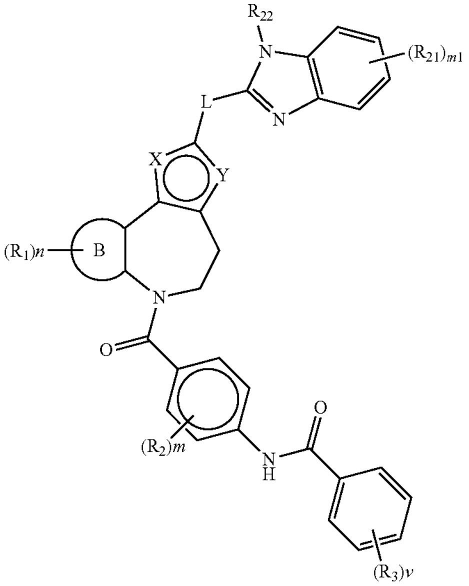
(IIIa-3)
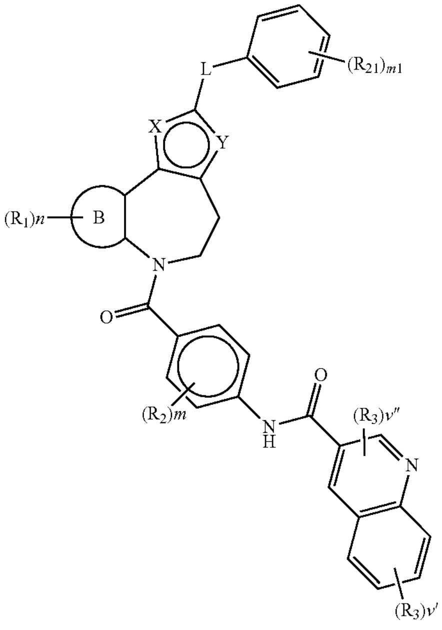

-continued
(IIIb-3)
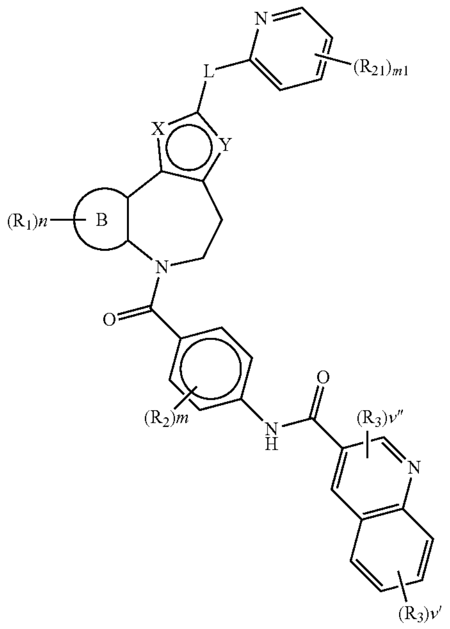
(IIId-3)
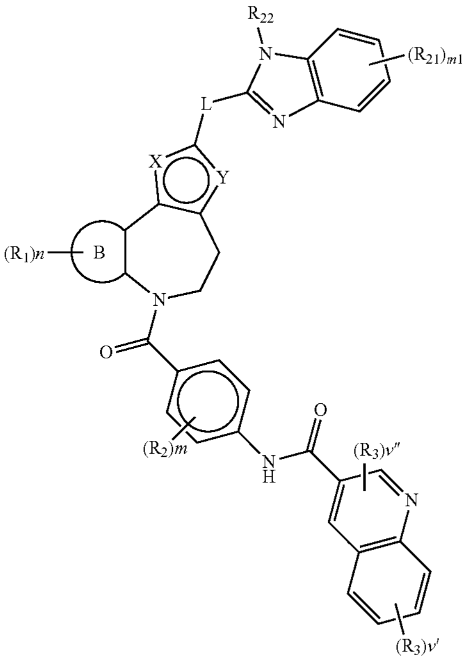
(IIIc-3)
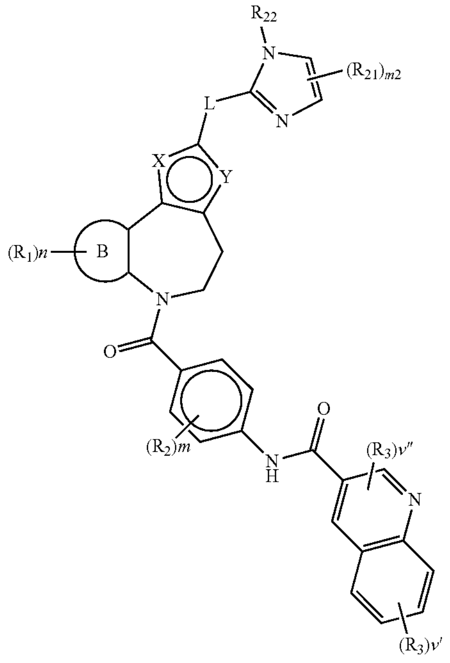
(IIIa-4)
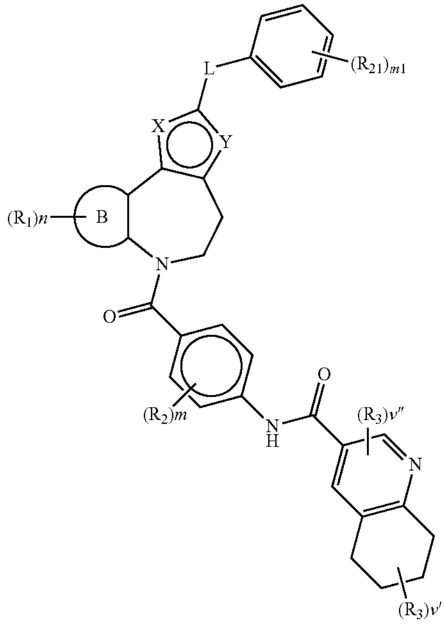

-continued (IIIb-4)

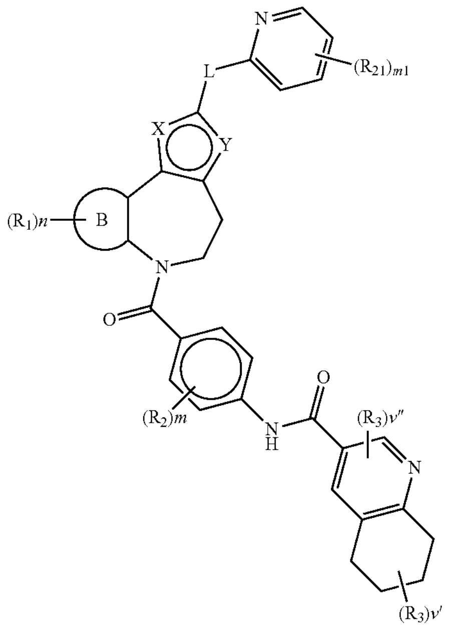

(IIIc-4)

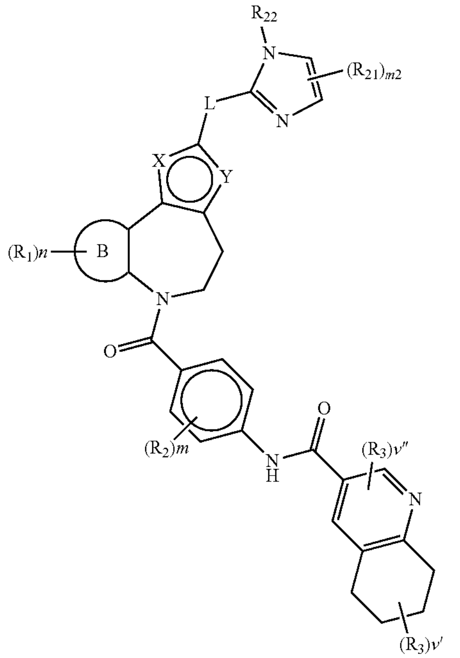

-continued (IIId-4)

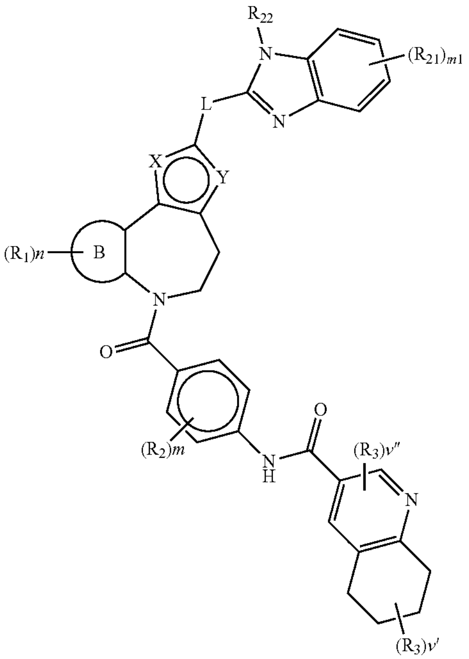

wherein Ⓑ, X, Y, L, $R_1$, $R_2$, $R_3$, n and m are as defined in claim 1, m1 is 0, 1, 2, 3 or 4; m2 is 0, 1 or 2; v' is 0, 1, 2, or 3; v" is 0, 1, or 2; each $R_{22}$ is independently selected from hydrogen and —$CH_3$; and each $R_{21}$ is independently selected from halogen, —$NH_2$, optionally substituted —$C_1$-$C_3$ alkyl, and optionally substituted —$C_1$-$C_3$ alkoxy.

11. The compound of claim 1, represented by one of Formulas (IVa-1)~(IVd-1), or (IVa-2)~(IVd-2), or (IVa-3)~(IVd-3), or (IVa-4)~(IVd-4), or a pharmaceutically acceptable salt thereof:

(IVa-1)

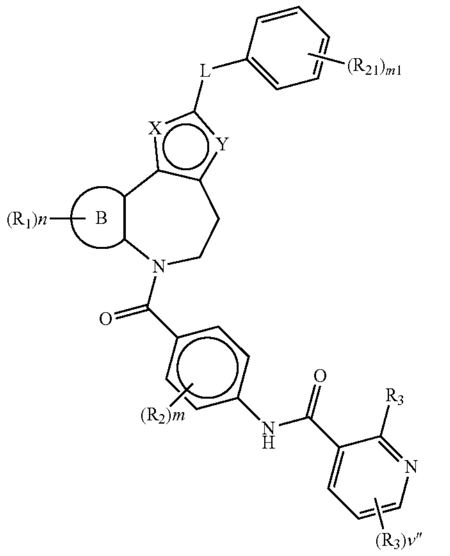

-continued
(IVb-1)
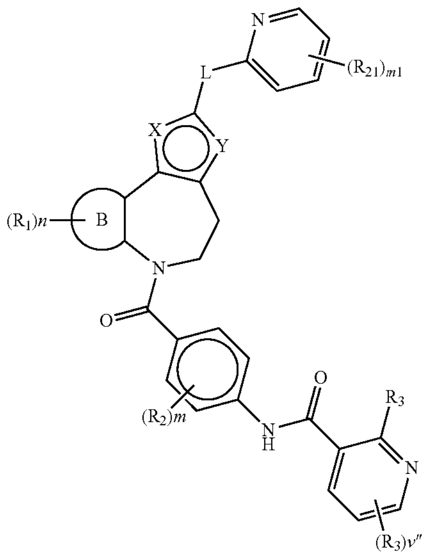
(IVc-1)
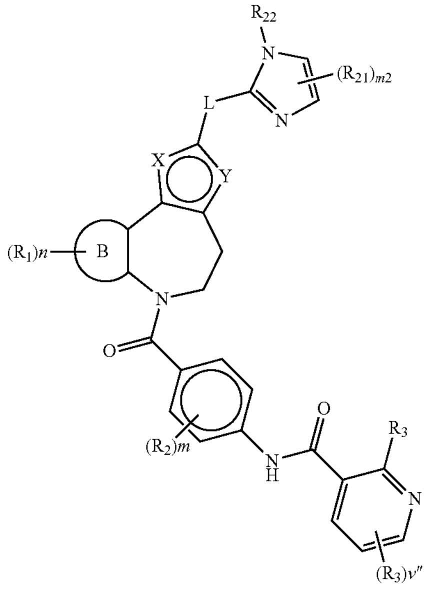
-continued
(IVd-1)
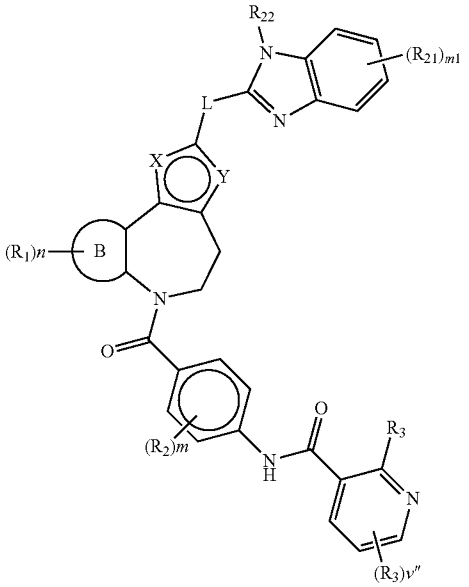
(IVa-2)
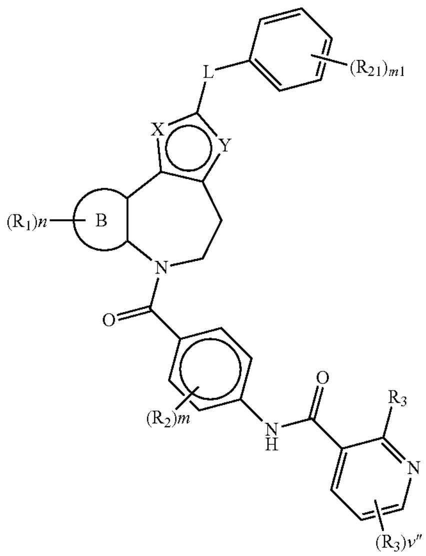

-continued
(IVb-2)
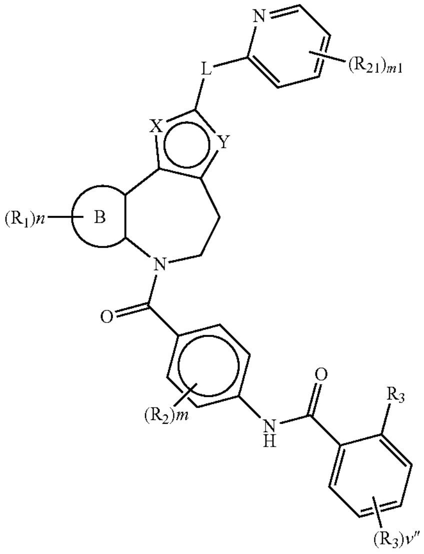
(IVc-2)
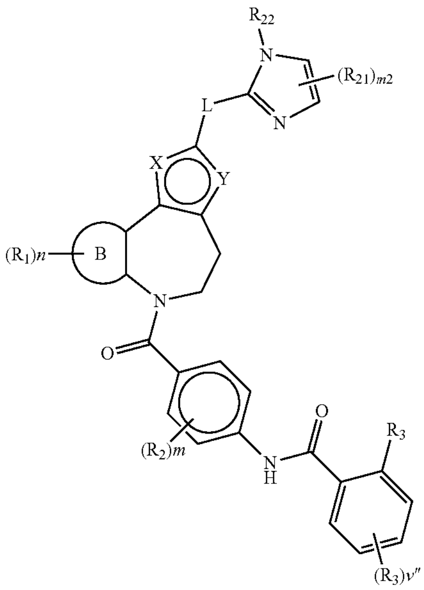
-continued
(IVd-2)
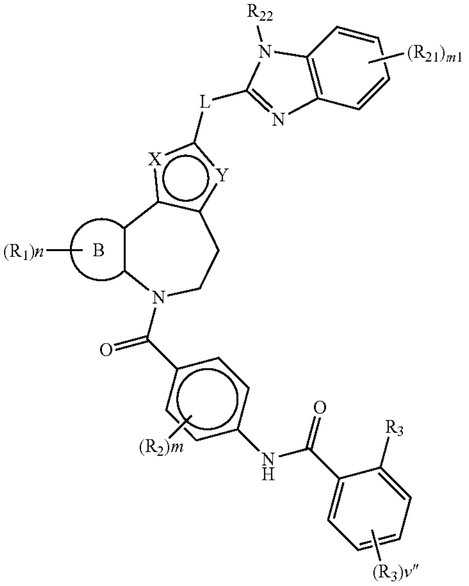
(IVa-3)
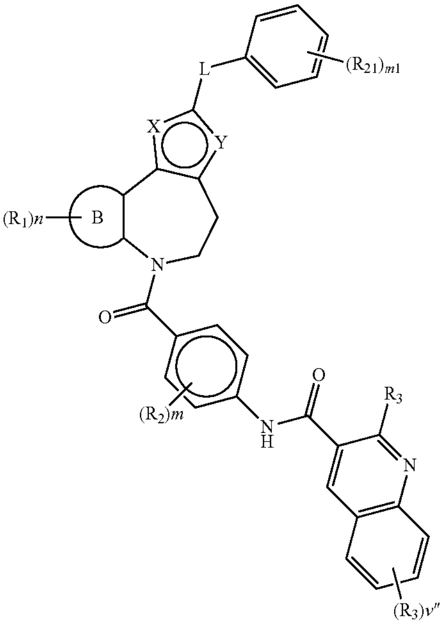

-continued
(IVb-3)
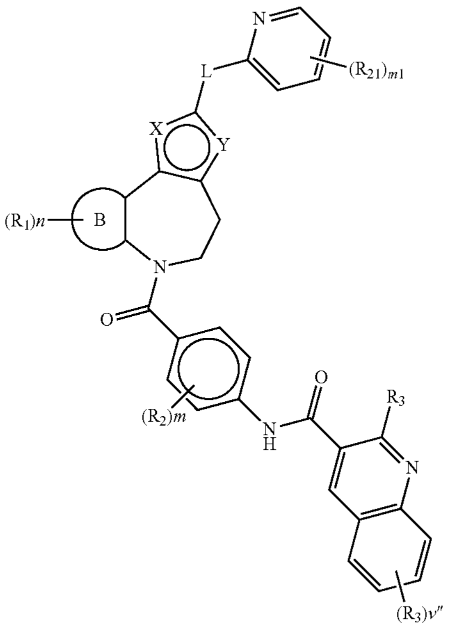
(IVd-3)
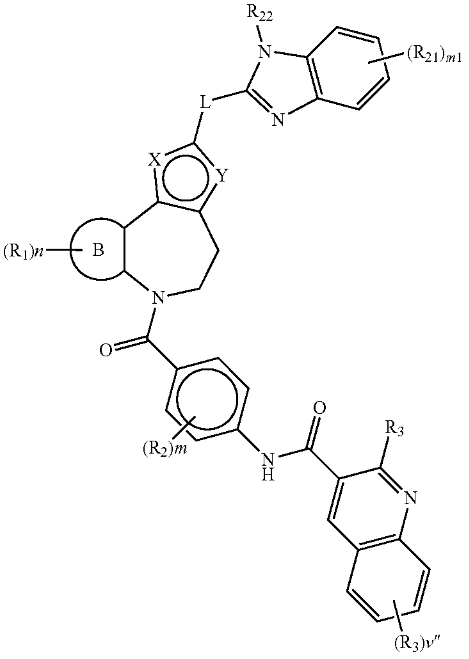
(IVc-3)
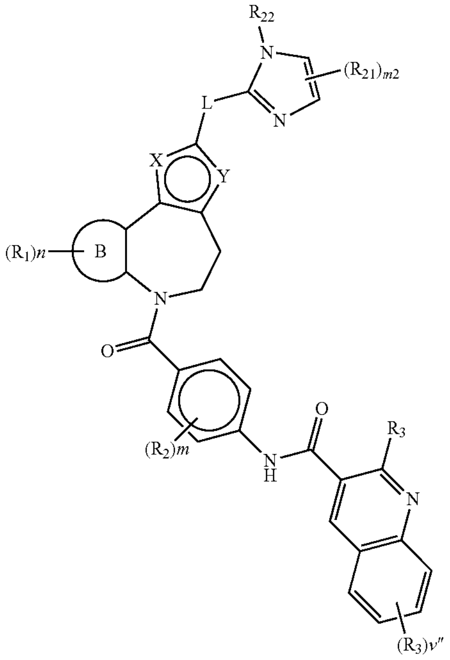
(IVa-4)
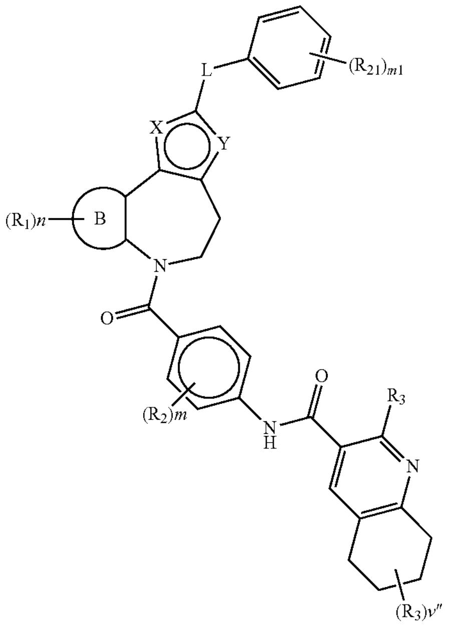

-continued (IVb-4)

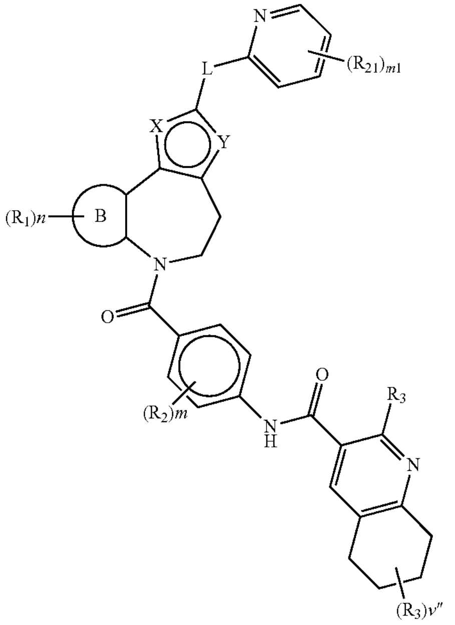

(IVc-4)

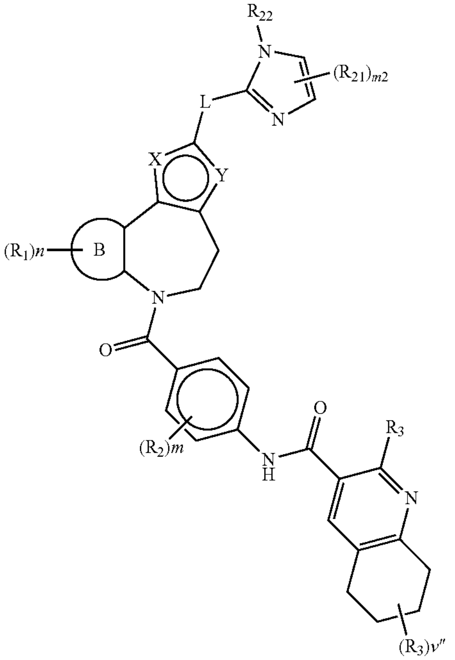

-continued (IVd-4)

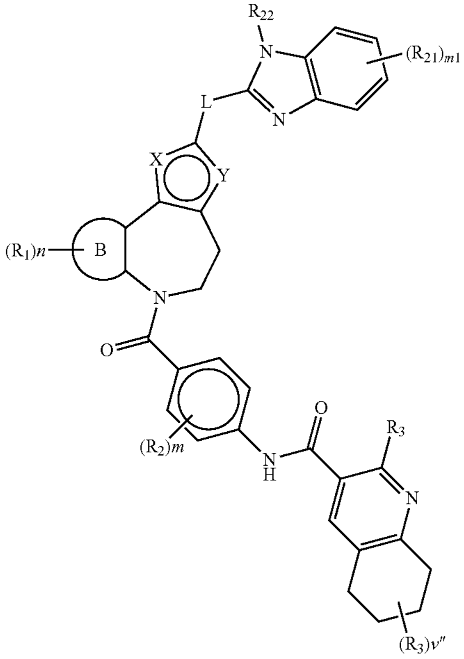

wherein Ⓑ, X, Y, L, $R_1$, $R_2$, $R_3$, n and m are as defined in claim 1, m1 is 0, 1, 2, 3 or 4; m2 is 0, 1 or 2; v' is 0, 1, 2, or 3; v" is 0, 1, or 2; each $R_{22}$ is independently selected from hydrogen and —$CH_3$; and each $R_{21}$ is independently selected from halogen, —$NH_2$, optionally substituted —$C_1$-$C_3$ alkyl, and optionally substituted —$C_1$-$C_3$ alkoxy.

12. The compound of claim 1, represented by one of Formulas (V-1) to (V-4), or a pharmaceutically acceptable salt thereof:

(V-1)

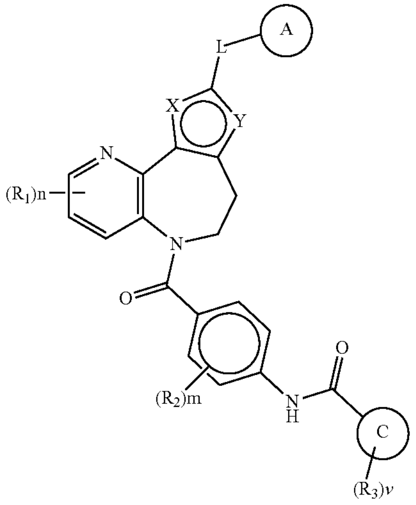

-continued
(V-2)
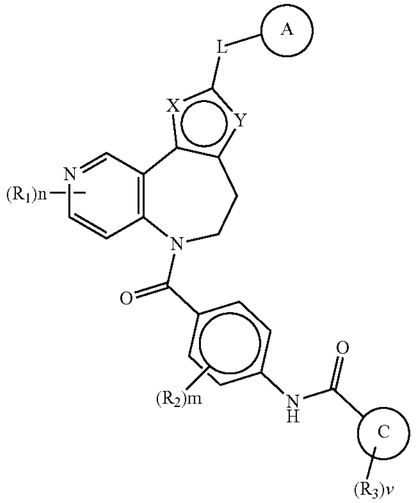
(V-3)
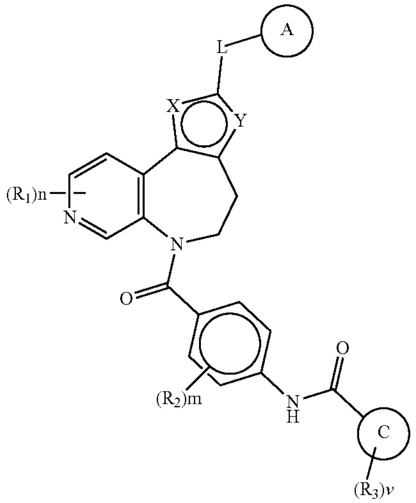
(V-4)
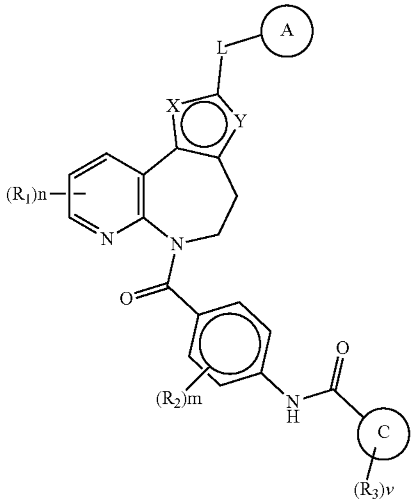
wherein Ⓐ, Ⓒ, X, Y, L, $R_1$, $R_2$, $R_3$, n, m, and v are as defined in claim 1.
13. The compound of claim 1, represented by one of Formulas (VI-1) to (VI-4), or a pharmaceutically acceptable salt thereof:
(VI-1)
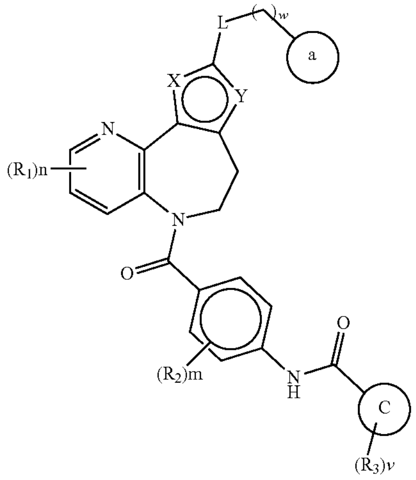
(VI-2)
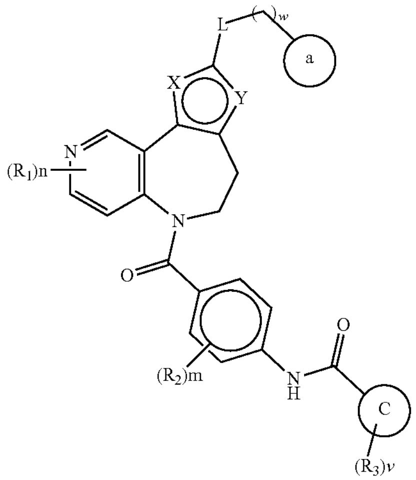
(VI-3)
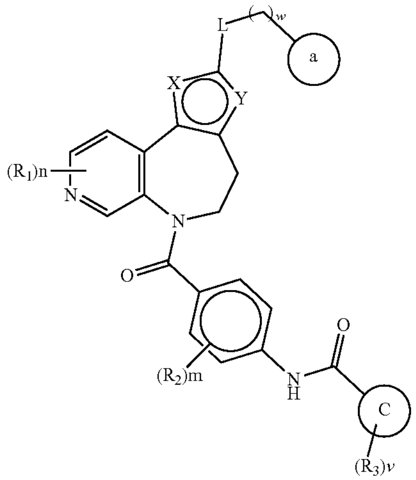

(VI-4)
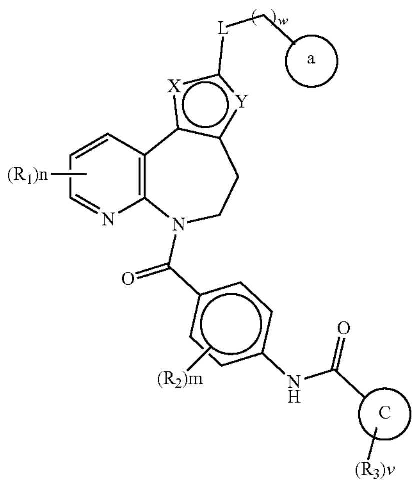
wherein Ⓒ, X, Y, L, $R_1$, $R_2$, $R_3$, n, m, and v are as defined in claim 1; w is 1, 2 or 3; and ⓐ is derived from one of the following groups by removal of a ring hydrogen atom:
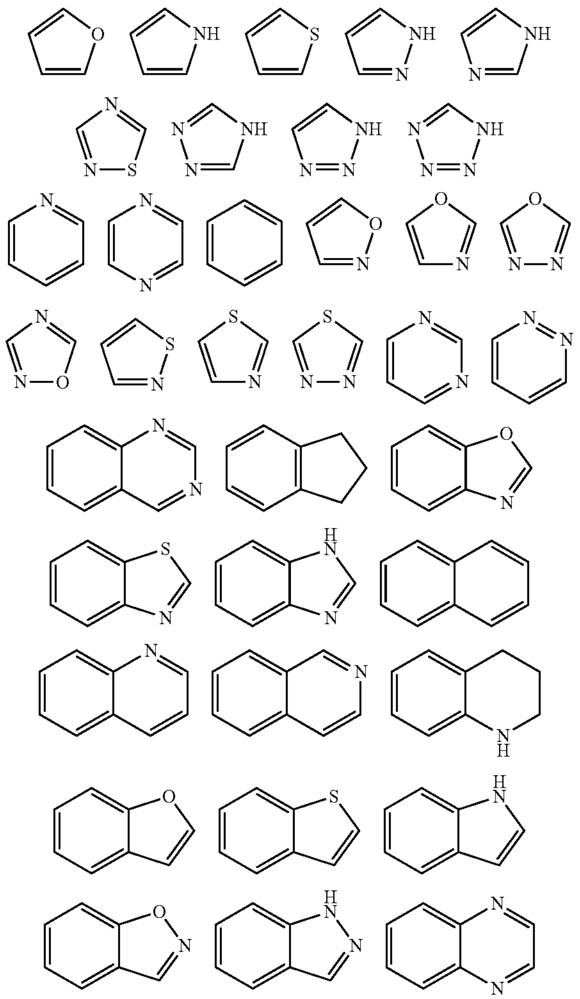
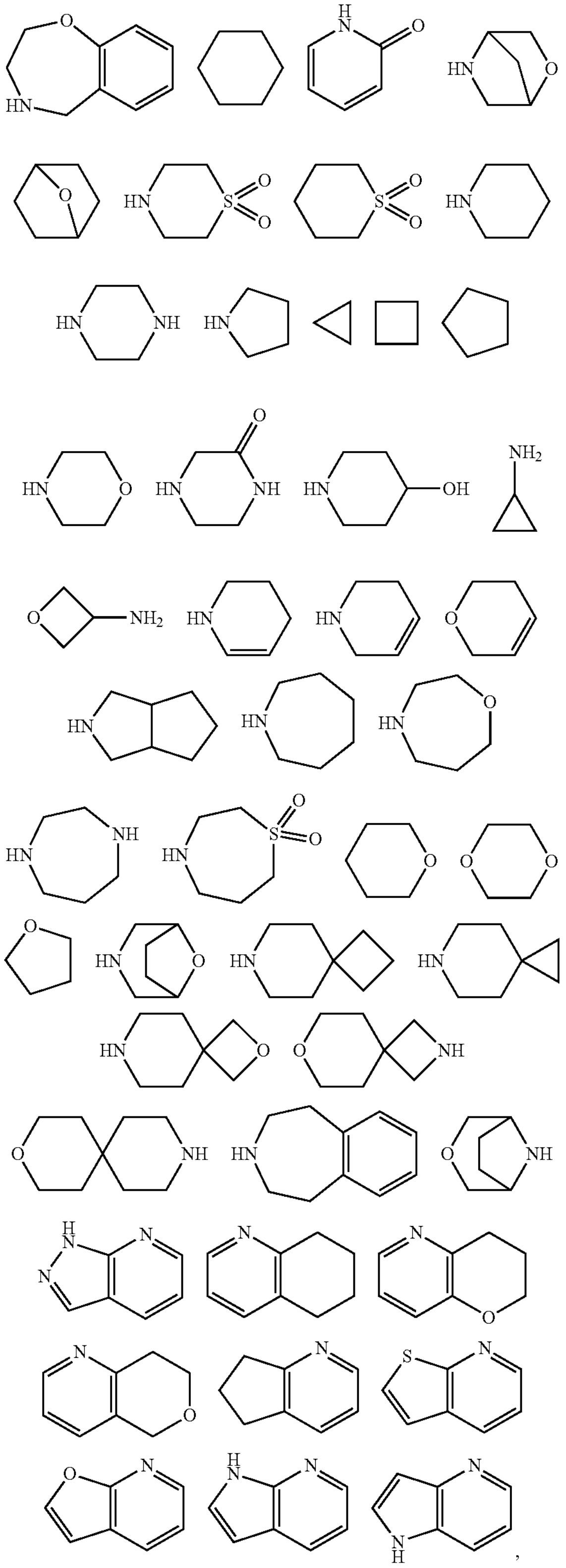
,
wherein each group is optionally substituted.
14. The compound of claim 1, represented by one of Formulas (VII-1)~(VII-4), or a pharmaceutically acceptable salt thereof:

(VII-1)
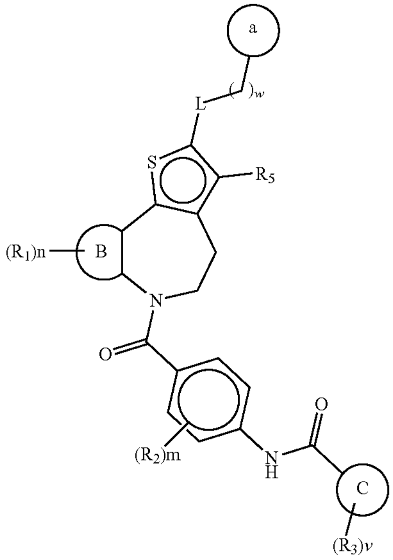
(VII-2)
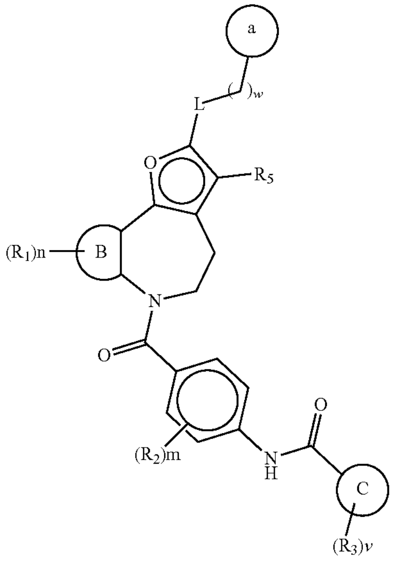
-continued
(VII-3)
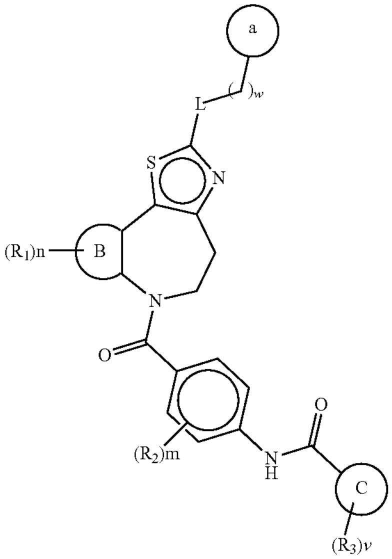
(VII-4)
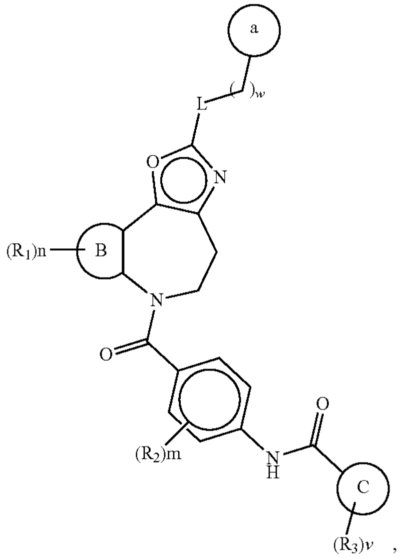
,
wherein Ⓑ, Ⓒ, L, $R_1$, $R_2$, $R_3$, $R_5$, n, m, and v are as defined in claim 1; w is 1, 2 or 3; and ⓐ is derived from one of the following groups by removal of a ring hydrogen atom:
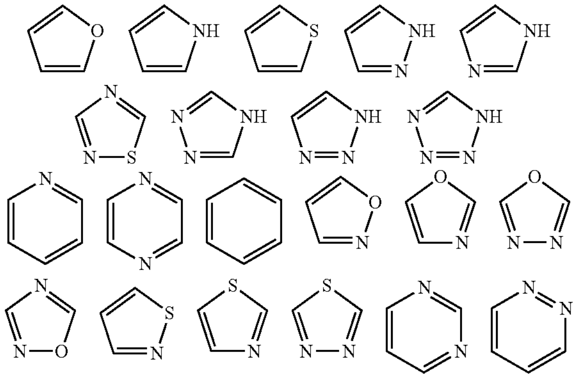

-continued
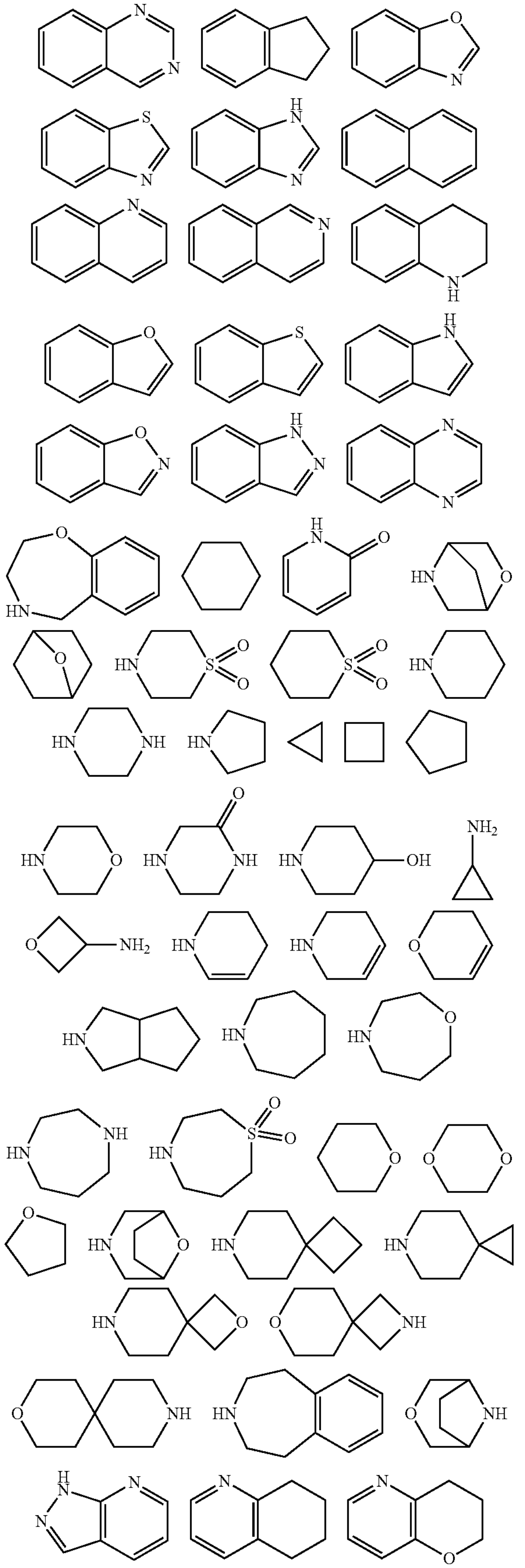
-continued
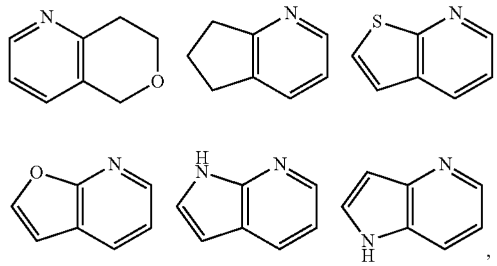
,
wherein each group is optionally substituted.
15. The compound of claim 1, represented by one of Formulas (VIII-1)~(VIII-4), or a pharmaceutically acceptable salt thereof:
(VIII-1)
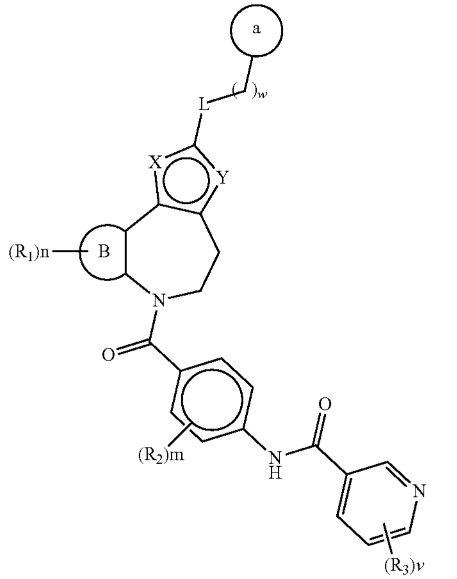
(VIII-2)
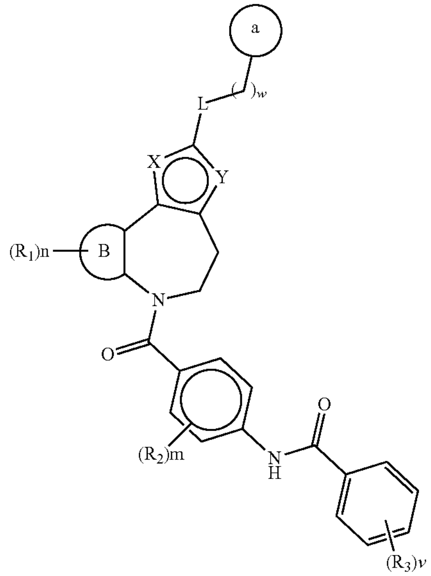

-continued
(VIII-3)
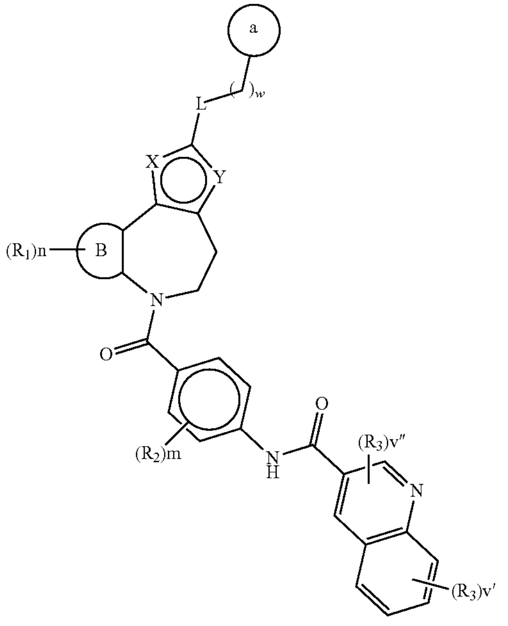
(VIII-4)
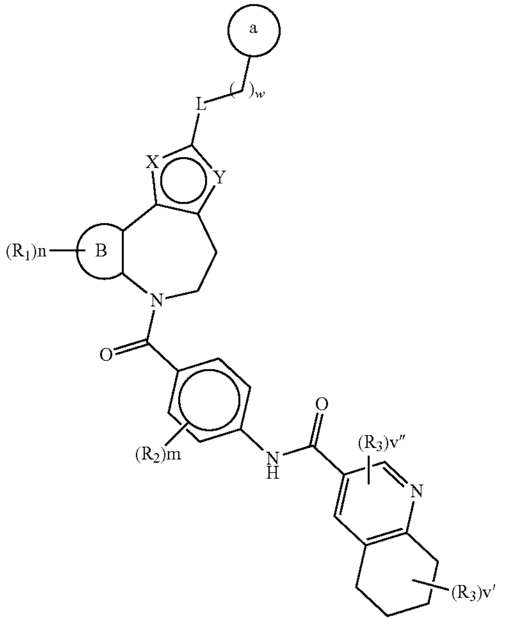
wherein Ⓑ, L, X, Y, $R_1$, $R_2$, $R_3$, n, m, and v are as defined in claim 1; v' is 0, 1, 2, or 3; v" is 0, 1, or 2; w is 1, 2 or 3; and ⓐ is derived from one of the following groups by removal of a ring hydrogen atom:
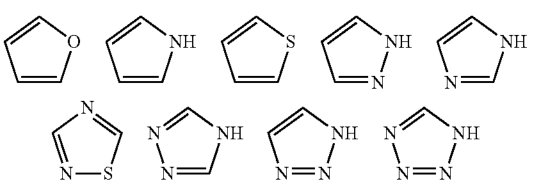
-continued
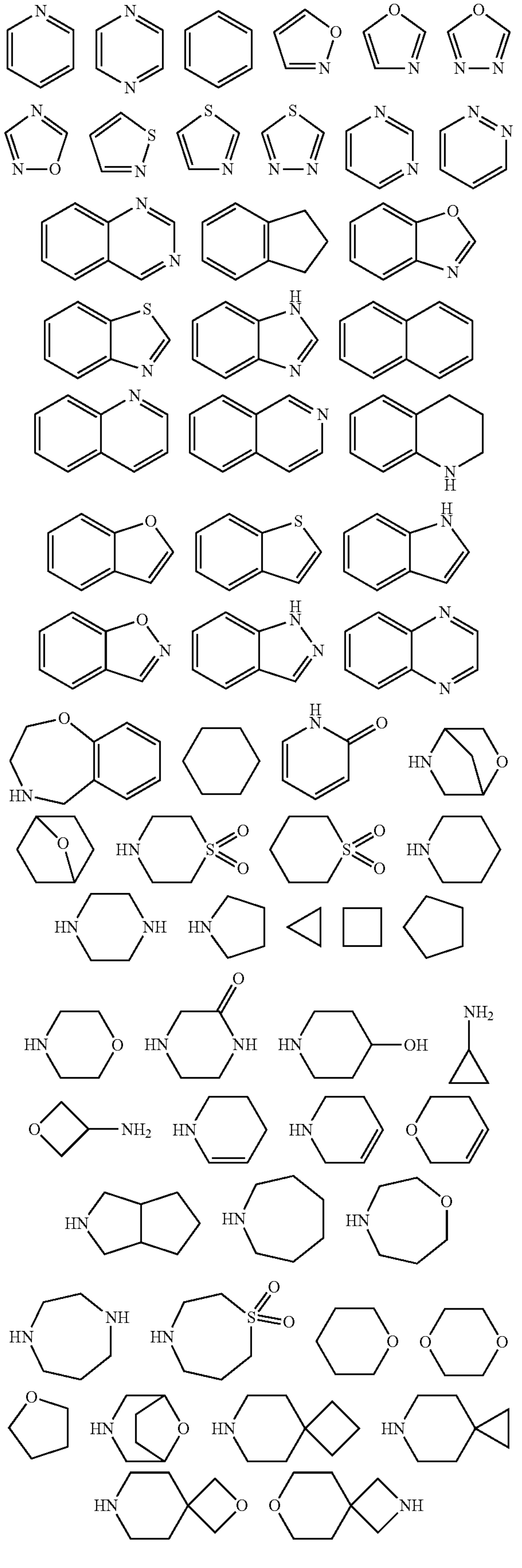

-continued
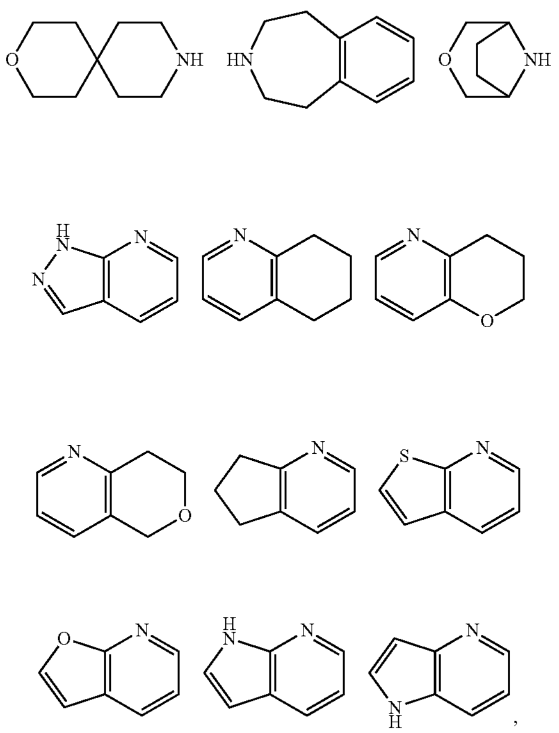
,
wherein each group is optionally substituted.
16. A compound selected from the compounds set forth below or a pharmaceutically acceptable salt thereof:
| Compound | Structure |
|---|---|
| 1 | 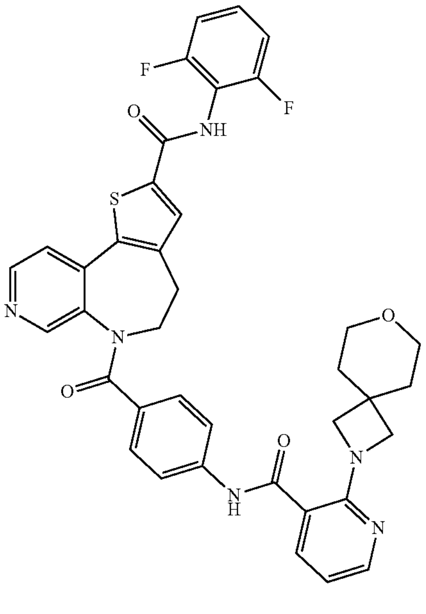 [SMILES: O=C(Nc1c(F)cccc1F)c1cc2c(s1)-c1ccncc1N(C(=O)c1ccc(NC(=O)c3cccnc3N3CC4(CCOCC4)C3)cc1)CC2] |
-continued
| Compound | Structure |
|---|---|
| 2 | 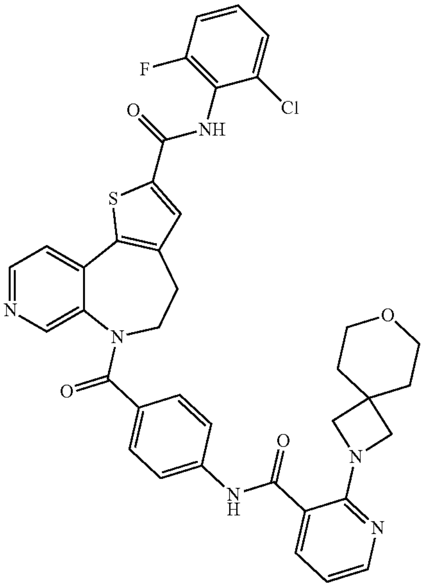 [SMILES: O=C(Nc1c(F)cccc1Cl)c1cc2c(s1)-c1ccncc1N(C(=O)c1ccc(NC(=O)c3cccnc3N3CC4(CCOCC4)C3)cc1)CC2] |
| 3 | 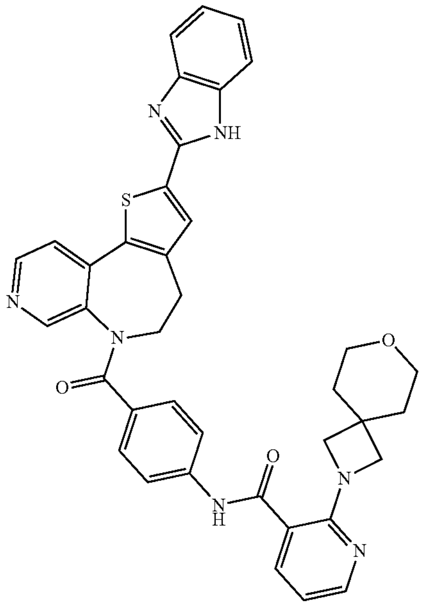 [SMILES: O=C(Nc1ccc(C(=O)N2CCc3cc(-c4nc5ccccc5[nH]4)sc3-c3ccncc32)cc1)c1cccnc1N1CC2(CCOCC2)C1] |

-continued
| Compound | Structure |
|---|---|
| 4 | 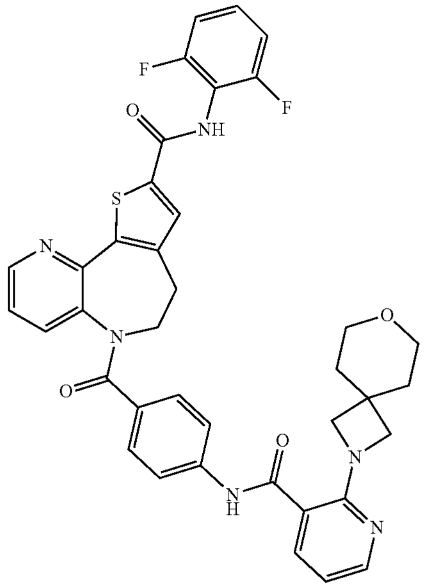 [SMILES: O=C(Nc1c(F)cccc1F)c1cc2c(s1)-c1ncccc1N(C(=O)c1ccc(NC(=O)c3cccnc3N3CC4(CCOCC4)C3)cc1)CC2] |
| 5 | 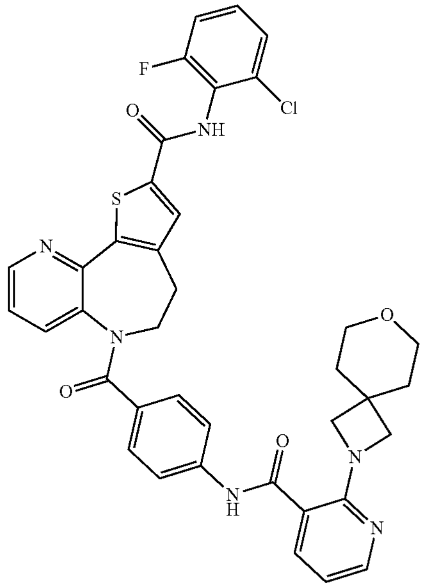 [SMILES: O=C(Nc1c(F)cccc1Cl)c1cc2c(s1)-c1ncccc1N(C(=O)c1ccc(NC(=O)c3cccnc3N3CC4(CCOCC4)C3)cc1)CC2] |
-continued
| Compound | Structure |
|---|---|
| 6 | 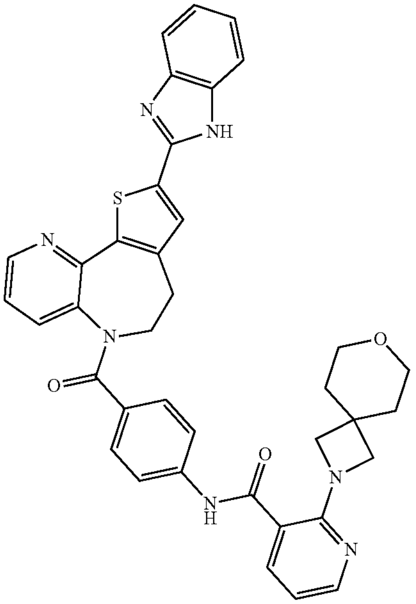 [SMILES: O=C(Nc1ccc(C(=O)N2CCc3cc(-c4nc5ccccc5[nH]4)sc3-c3ncccc32)cc1)c1cccnc1N1CC2(CCOCC2)C1] |
| 7 | 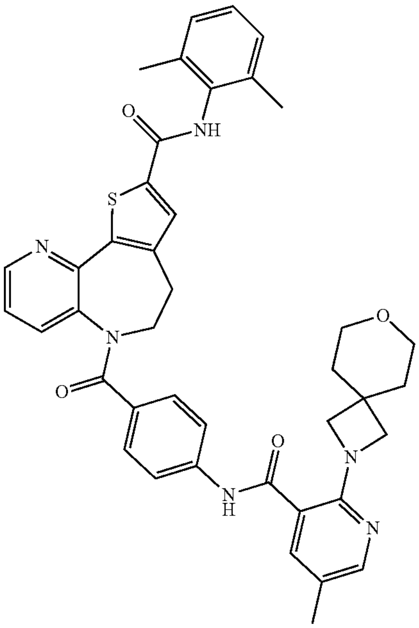 [SMILES: Cc1cnc(N2CC3(CCOCC3)C2)c(C(=O)Nc2ccc(C(=O)N3CCc4cc(C(=O)Nc5c(C)cccc5C)sc4-c4ncccc43)cc2)c1] |

-continued
| Compound | Structure |
|---|---|
| 8 | 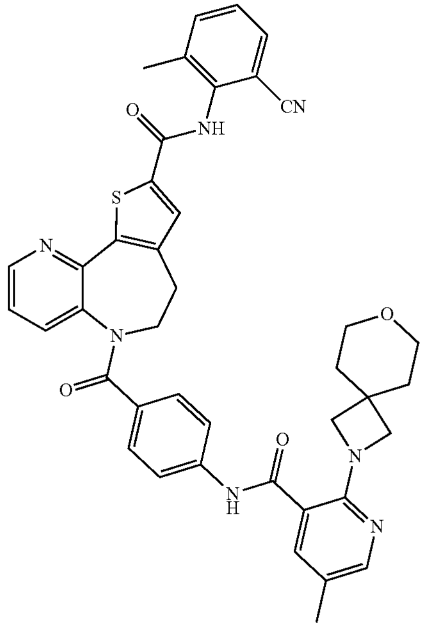 [SMILES: Cc1cnc(N2CC3(CCOCC3)C2)c(C(=O)Nc2ccc(C(=O)N3CCc4cc(C(=O)Nc5c(C)cccc5C#N)sc4-c4ncccc43)cc2)c1] |
| 9 | 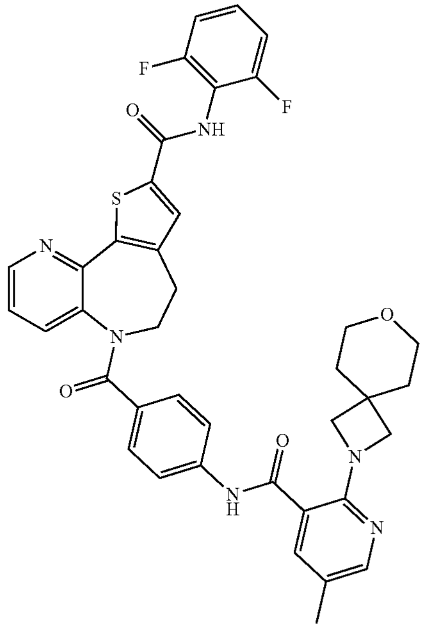 [SMILES: Cc1cnc(N2CC3(CCOCC3)C2)c(C(=O)Nc2ccc(C(=O)N3CCc4cc(C(=O)Nc5c(F)cccc5F)sc4-c4ncccc43)cc2)c1] |
-continued
| Compound | Structure |
|---|---|
| 10 | 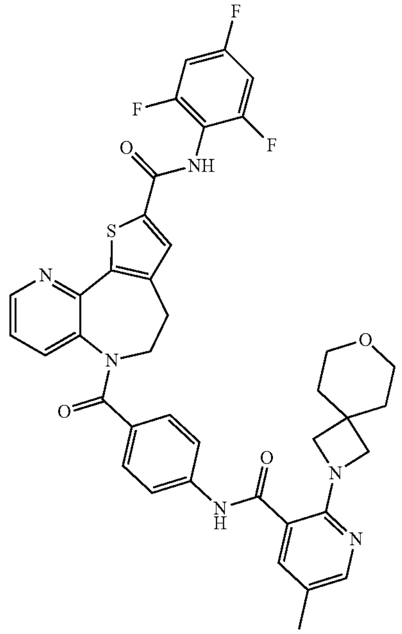 [SMILES: Cc1cnc(N2CC3(CCOCC3)C2)c(C(=O)Nc2ccc(C(=O)N3CCc4cc(C(=O)Nc5c(F)cc(F)cc5F)sc4-c4ncccc43)cc2)c1] |
| 11 | 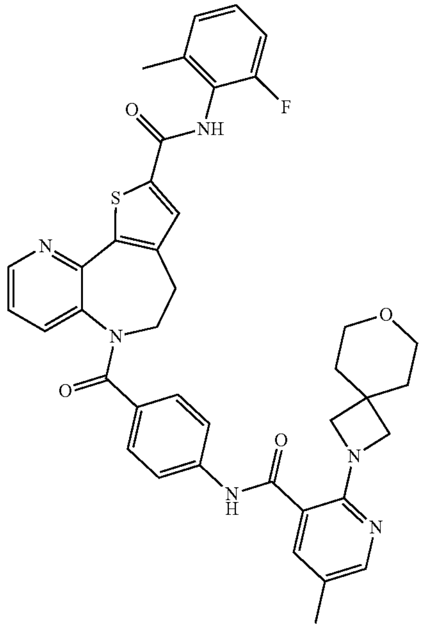 |

-continued
| Compound | Structure |
|---|---|
| 12 | 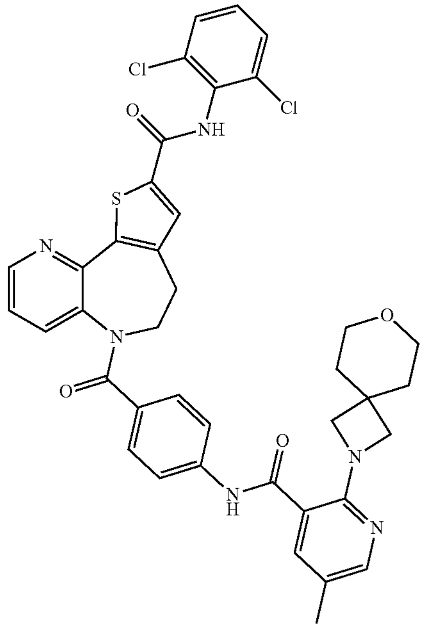 [SMILES: Cc1cnc(N2CC3(CCOCC3)C2)c(C(=O)Nc2ccc(C(=O)N3CCc4cc(C(=O)Nc5c(Cl)cccc5Cl)sc4-c4ncccc43)cc2)c1] |
| 13 | 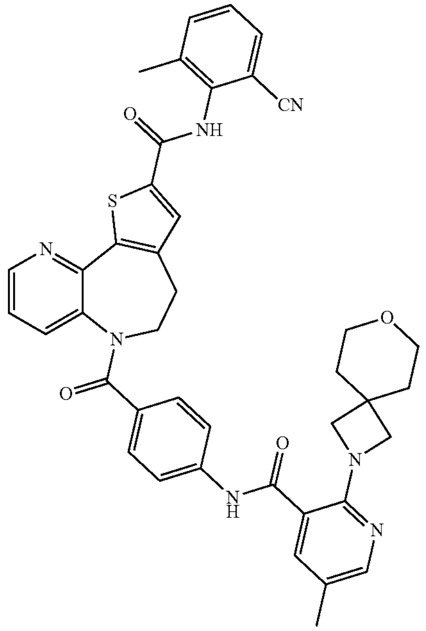 [SMILES: Cc1cnc(N2CC3(CCOCC3)C2)c(C(=O)Nc2ccc(C(=O)N3CCc4cc(C(=O)Nc5c(C)cccc5C#N)sc4-c4ncccc43)cc2)c1] |
-continued
| Compound | Structure |
|---|---|
| 14 | 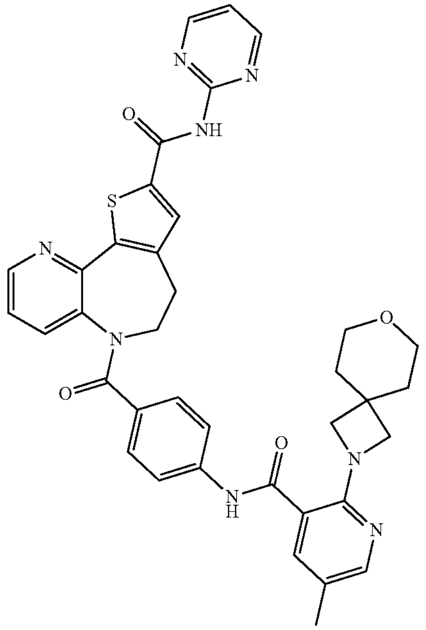 [SMILES: Cc1cnc(N2CC3(CCOCC3)C2)c(C(=O)Nc2ccc(C(=O)N3CCc4cc(C(=O)Nc5ncccn5)sc4-c4ncccc43)cc2)c1] |
| 15 | 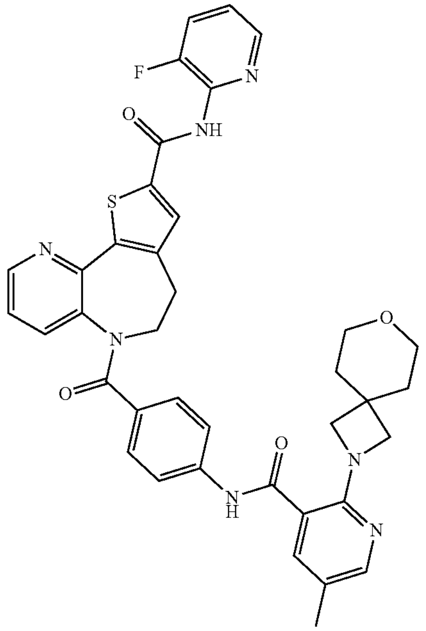 [SMILES: Cc1cnc(N2CC3(CCOCC3)C2)c(C(=O)Nc2ccc(C(=O)N3CCc4cc(C(=O)Nc5ncccc5F)sc4-c4ncccc43)cc2)c1] |

-continued
| Compound | Structure |
|---|---|
| 16 | 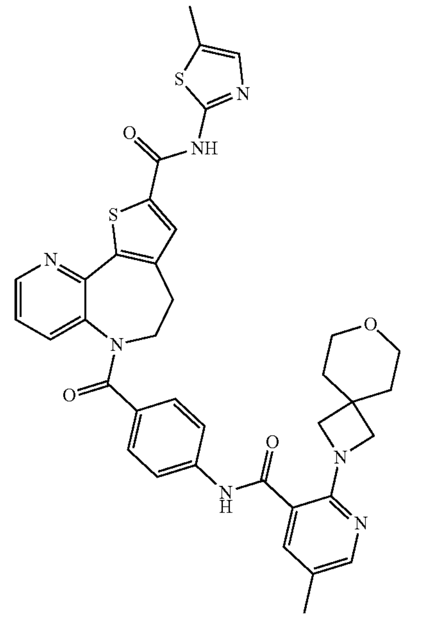 [SMILES: Cc1cnc(N2CC3(CCOCC3)C2)c(C(=O)Nc2ccc(C(=O)N3CCc4cc(C(=O)Nc5ncc(C)s5)sc4-c4ncccc43)cc2)c1] |
| 17 | 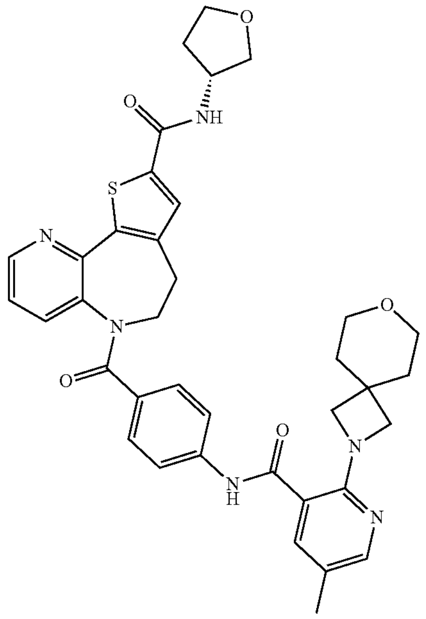 [SMILES: Cc1cnc(N2CC3(CCOCC3)C2)c(C(=O)Nc2ccc(C(=O)N3CCc4cc(C(=O)N[C@@H]5CCOC5)sc4-c4ncccc43)cc2)c1] |
-continued
| Compound | Structure |
|---|---|
| 18 | 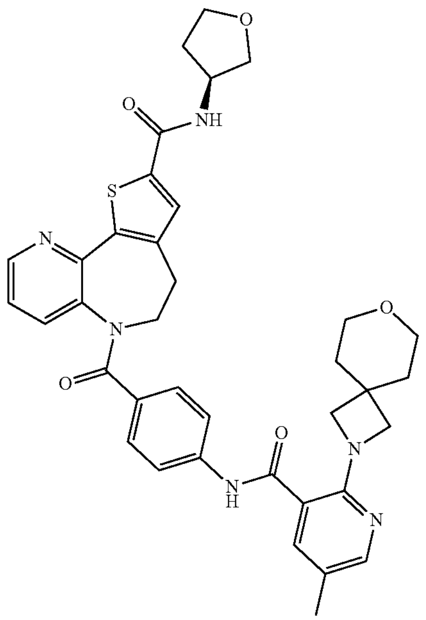 [SMILES: Cc1cnc(N2CC3(CCOCC3)C2)c(C(=O)Nc2ccc(C(=O)N3CCc4cc(C(=O)N[C@H]5CCOC5)sc4-c4ncccc43)cc2)c1] |
| 19 | 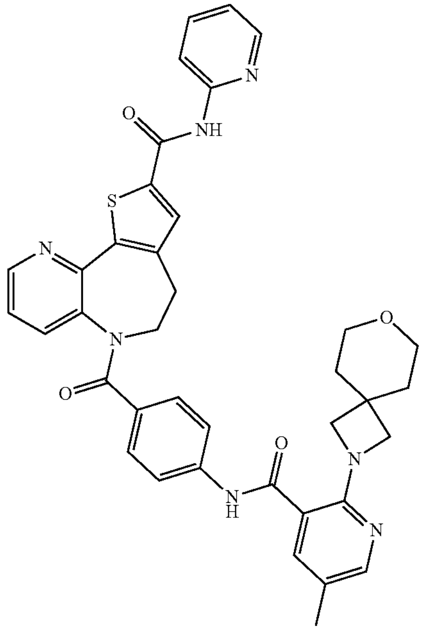 [SMILES: Cc1cnc(N2CC3(CCOCC3)C2)c(C(=O)Nc2ccc(C(=O)N3CCc4cc(C(=O)Nc5ccccn5)sc4-c4ncccc43)cc2)c1] |

-continued
| Compound | Structure |
|---|---|
| 20 | 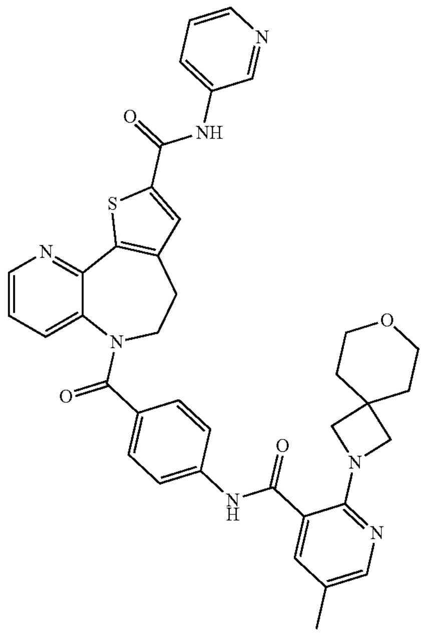 [SMILES: Cc1cnc(N2CC3(CCOCC3)C2)c(C(=O)Nc2ccc(C(=O)N3CCc4cc(C(=O)Nc5cccnc5)sc4-c4ncccc43)cc2)c1] |
| 21 | 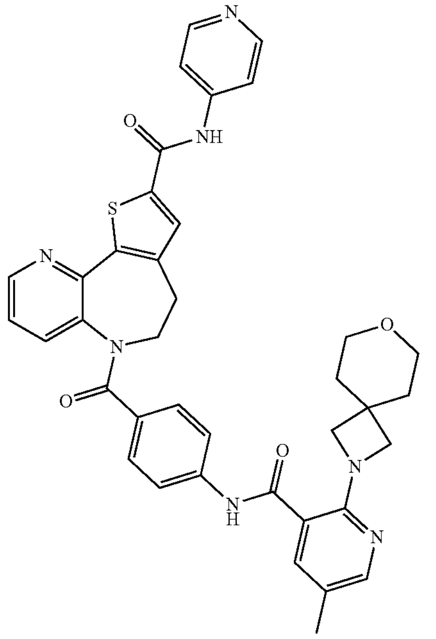 [SMILES: Cc1cnc(N2CC3(CCOCC3)C2)c(C(=O)Nc2ccc(C(=O)N3CCc4cc(C(=O)Nc5ccncc5)sc4-c4ncccc43)cc2)c1] |
-continued
| Compound | Structure |
|---|---|
| 22 | 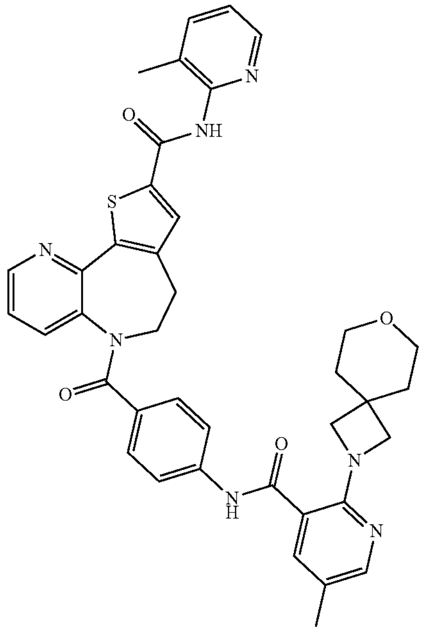 [SMILES: Cc1cnc(N2CC3(CCOCC3)C2)c(C(=O)Nc2ccc(C(=O)N3CCc4cc(C(=O)Nc5ncccc5C)sc4-c4ncccc43)cc2)c1] |
| 23 | 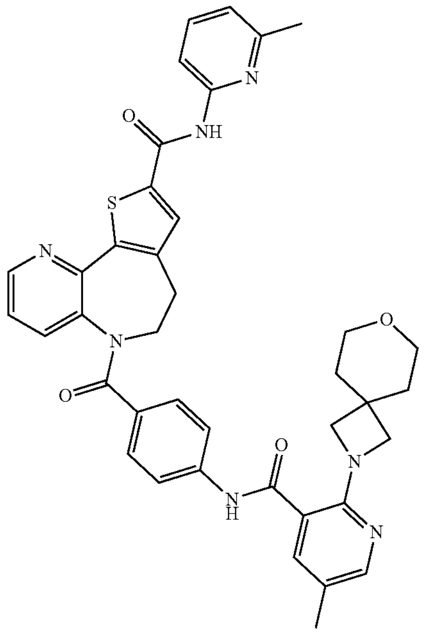 [SMILES: Cc1cnc(N2CC3(CCOCC3)C2)c(C(=O)Nc2ccc(C(=O)N3CCc4cc(C(=O)Nc5cccc(C)n5)sc4-c4ncccc43)cc2)c1] |

-continued
| Compound | Structure |
|---|---|
| 24 | 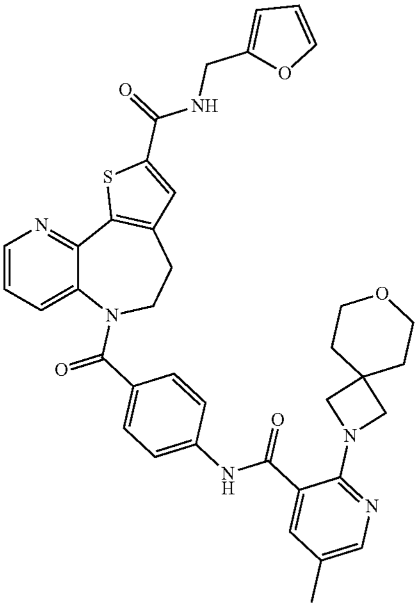 [SMILES: Cc1cnc(N2CC3(CCOCC3)C2)c(C(=O)Nc2ccc(C(=O)N3CCc4cc(C(=O)NCc5ccco5)sc4-c4ncccc43)cc2)c1] |
| 25 | 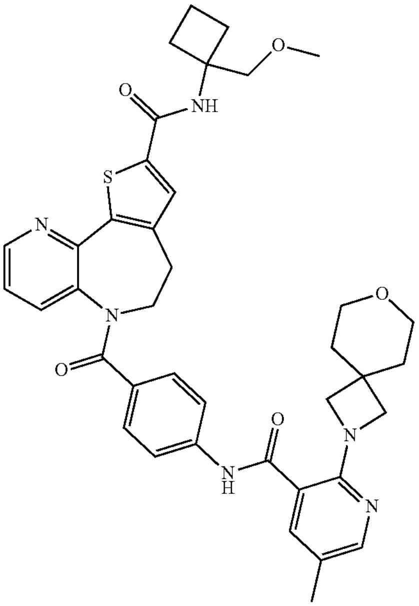 [SMILES: COCC1(NC(=O)c2cc3c(s2)-c2ncccc2N(C(=O)c2ccc(NC(=O)c4cc(C)cnc4N4CC5(CCOCC5)C4)cc2)CC3)CCC1] |
-continued
| Compound | Structure |
|---|---|
| 26 | 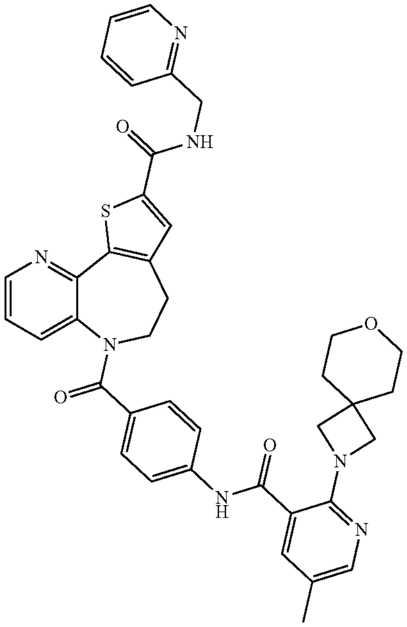 [SMILES: Cc1cnc(N2CC3(CCOCC3)C2)c(C(=O)Nc2ccc(C(=O)N3CCc4cc(C(=O)NCc5ccccn5)sc4-c4ncccc43)cc2)c1] |
| 27 | 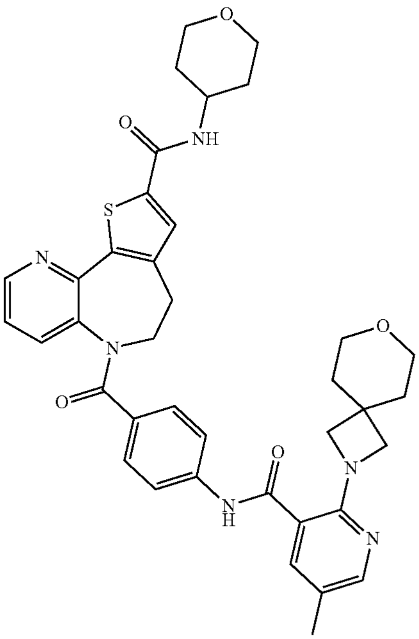 [SMILES: Cc1cnc(N2CC3(CCOCC3)C2)c(C(=O)Nc2ccc(C(=O)N3CCc4cc(C(=O)NC5CCOCC5)sc4-c4ncccc43)cc2)c1] |

-continued
| Compound | Structure |
|---|---|
| 28 | 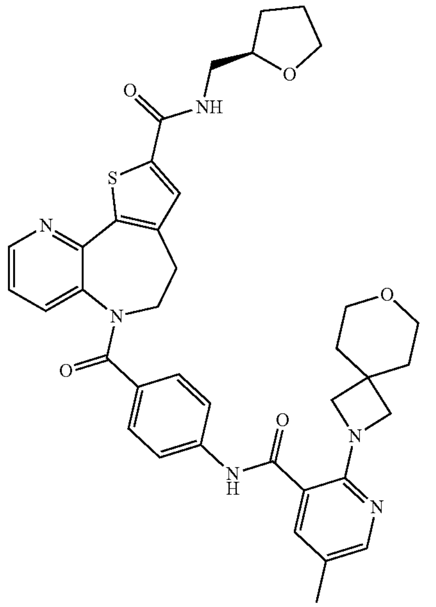 [SMILES: Cc1cnc(N2CC3(CCOCC3)C2)c(C(=O)Nc2ccc(C(=O)N3CCc4cc(C(=O)NC[C@H]5CCCO5)sc4-c4ncccc43)cc2)c1] |
| 29 | 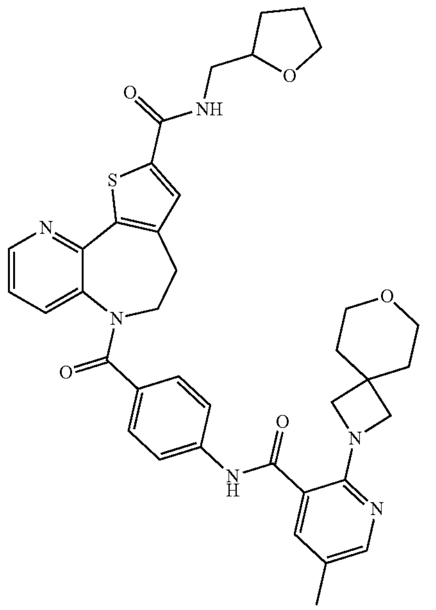 [SMILES: Cc1cnc(N2CC3(CCOCC3)C2)c(C(=O)Nc2ccc(C(=O)N3CCc4cc(C(=O)NCC5CCCO5)sc4-c4ncccc43)cc2)c1] |
-continued
| Compound | Structure |
|---|---|
| 30 | 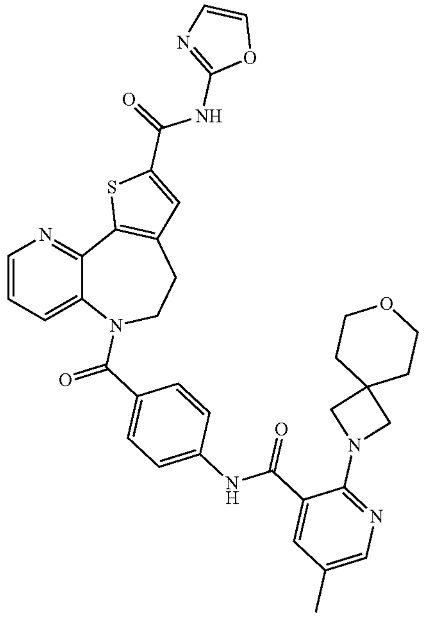 [SMILES: Cc1cnc(N2CC3(CCOCC3)C2)c(C(=O)Nc2ccc(C(=O)N3CCc4cc(C(=O)Nc5ncco5)sc4-c4ncccc43)cc2)c1] |
| 31 | 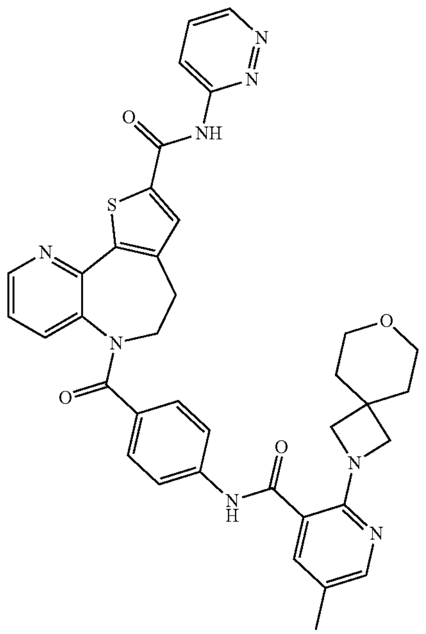 [SMILES: Cc1cnc(N2CC3(CCOCC3)C2)c(C(=O)Nc2ccc(C(=O)N3CCc4cc(C(=O)Nc5cccnn5)sc4-c4ncccc43)cc2)c1] |

-continued
| Compound | Structure |
|---|---|
| 32 | 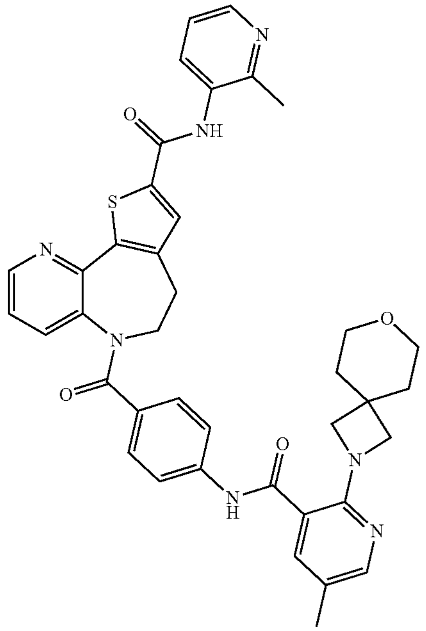 [SMILES: Cc1cnc(N2CC3(CCOCC3)C2)c(C(=O)Nc2ccc(C(=O)N3CCc4cc(C(=O)Nc5cccnc5C)sc4-c4ncccc43)cc2)c1] |
| 33 | 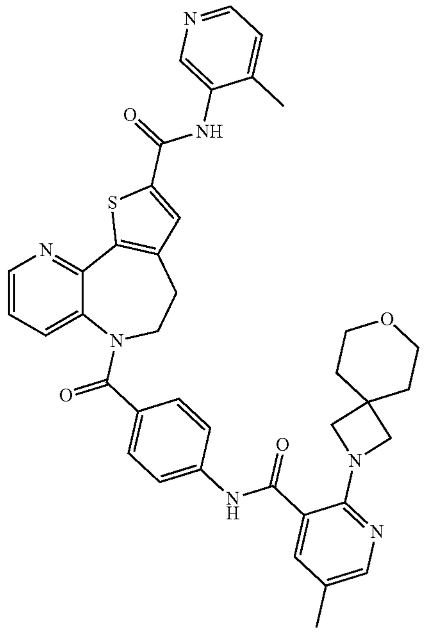 [SMILES: Cc1cnc(N2CC3(CCOCC3)C2)c(C(=O)Nc2ccc(C(=O)N3CCc4cc(C(=O)Nc5cnccc5C)sc4-c4ncccc43)cc2)c1] |
-continued
| Compound | Structure |
|---|---|
| 34 | 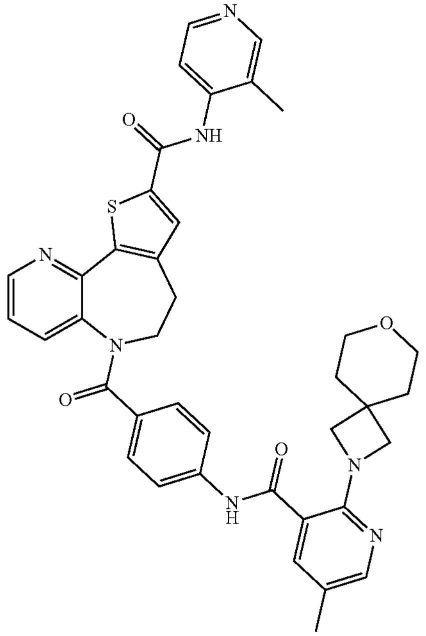 [SMILES: Cc1cnc(N2CC3(CCOCC3)C2)c(C(=O)Nc2ccc(C(=O)N3CCc4cc(C(=O)Nc5ccncc5C)sc4-c4ncccc43)cc2)c1] |
| 35 | 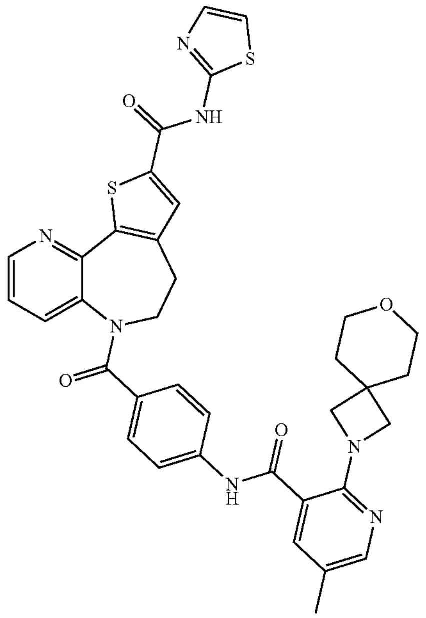 [SMILES: Cc1cnc(N2CC3(CCOCC3)C2)c(C(=O)Nc2ccc(C(=O)N3CCc4cc(C(=O)Nc5nccs5)sc4-c4ncccc43)cc2)c1] |

-continued
| Compound | Structure |
|---|---|
| 36 | 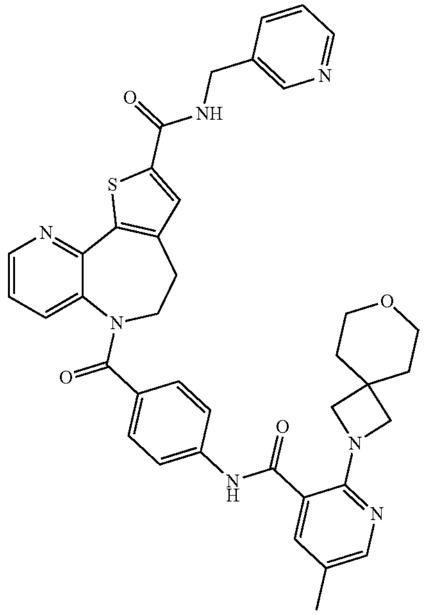 [SMILES: Cc1cnc(N2CC3(CCOCC3)C2)c(C(=O)Nc2ccc(C(=O)N3CCc4cc(C(=O)NCc5cccnc5)sc4-c4ncccc43)cc2)c1] |
| 37 | 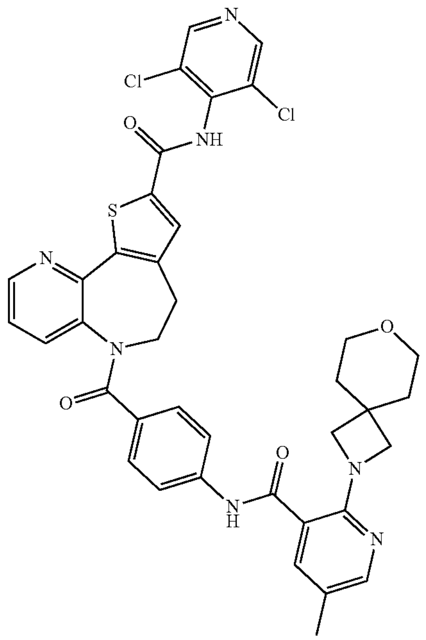 [SMILES: Cc1cnc(N2CC3(CCOCC3)C2)c(C(=O)Nc2ccc(C(=O)N3CCc4cc(C(=O)Nc5c(Cl)cncc5Cl)sc4-c4ncccc43)cc2)c1] |
-continued
| Compound | Structure |
|---|---|
| 38 | 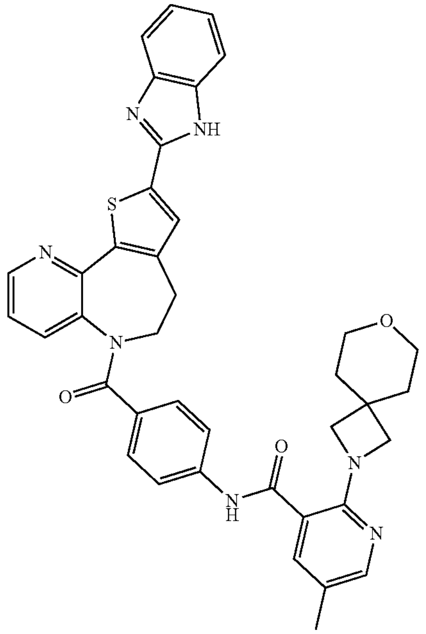 [SMILES: Cc1cnc(N2CC3(CCOCC3)C2)c(C(=O)Nc2ccc(C(=O)N3CCc4cc(-c5nc6ccccc6[nH]5)sc4-c4ncccc43)cc2)c1] |
| 39 | 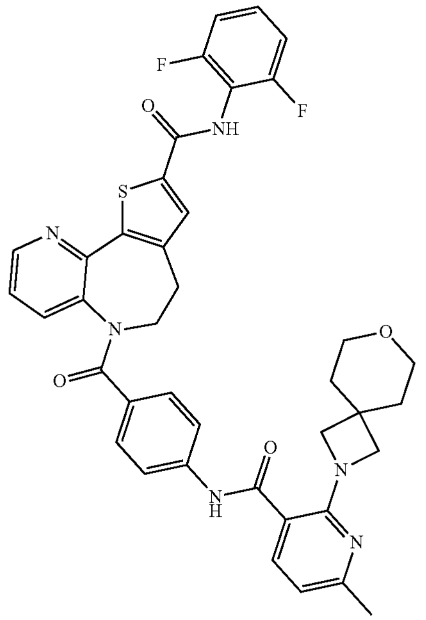 [SMILES: Cc1ccc(C(=O)Nc2ccc(C(=O)N3CCc4cc(C(=O)Nc5c(F)cccc5F)sc4-c4ncccc43)cc2)c(N2CC3(CCOCC3)C2)n1] |

-continued
| Compound | Structure |
|---|---|
| 40 | 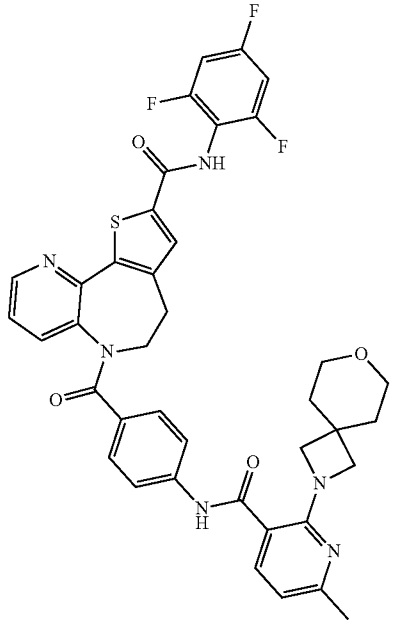 [SMILES: Cc1ccc(C(=O)Nc2ccc(C(=O)N3CCc4cc(C(=O)Nc5c(F)cc(F)cc5F)sc4-c4ncccc43)cc2)c(N2CC3(CCOCC3)C2)n1] |
| 41 | 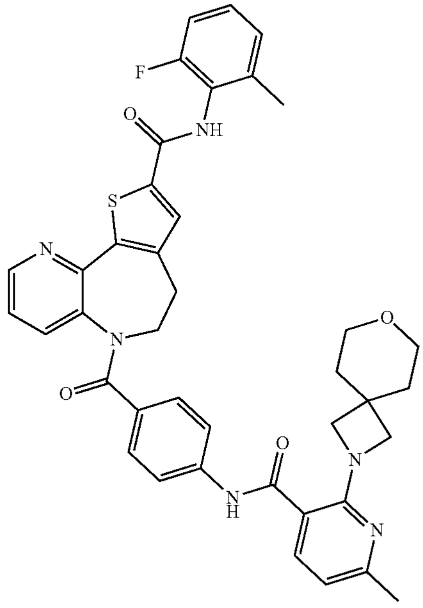 [SMILES: Cc1ccc(C(=O)Nc2ccc(C(=O)N3CCc4cc(C(=O)Nc5c(C)cccc5F)sc4-c4ncccc43)cc2)c(N2CC3(CCOCC3)C2)n1] |
-continued
| Compound | Structure |
|---|---|
| 42 | 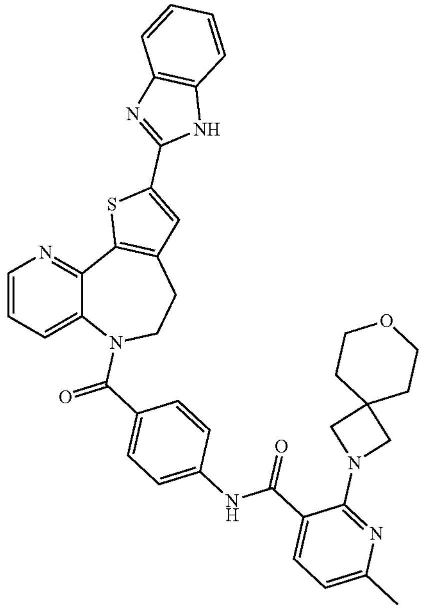 [SMILES: Cc1ccc(C(=O)Nc2ccc(C(=O)N3CCc4cc(-c5nc6ccccc6[nH]5)sc4-c4ncccc43)cc2)c(N2CC3(CCOCC3)C2)n1] |
| 43 | 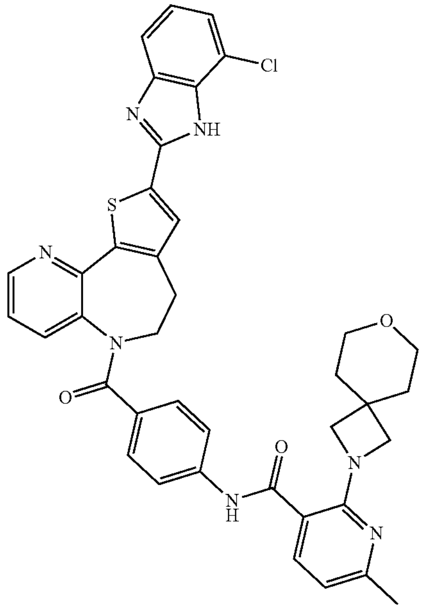 [SMILES: Cc1ccc(C(=O)Nc2ccc(C(=O)N3CCc4cc(-c5nc6cccc(Cl)c6[nH]5)sc4-c4ncccc43)cc2)c(N2CC3(CCOCC3)C2)n1] |

-continued
| Compound | Structure |
|---|---|
| 44 | 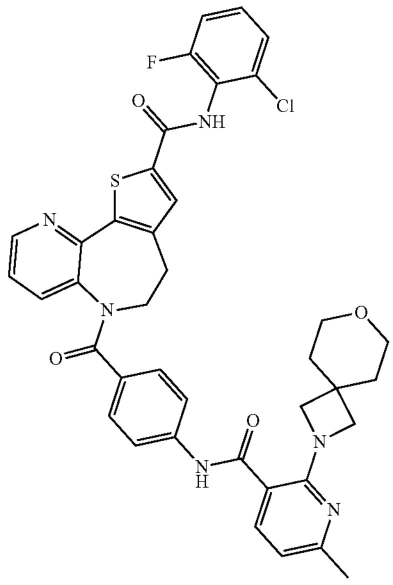 [SMILES: Cc1ccc(C(=O)Nc2ccc(C(=O)N3CCc4cc(C(=O)Nc5c(F)cccc5Cl)sc4-c4ncccc43)cc2)c(N2CC3(CCOCC3)C2)n1] |
| 45 | 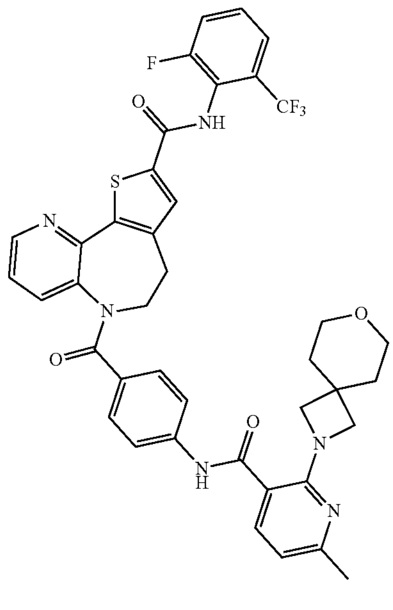 [SMILES: Cc1ccc(C(=O)Nc2ccc(C(=O)N3CCc4cc(C(=O)Nc5c(F)cccc5C(F)(F)F)sc4-c4ncccc43)cc2)c(N2CC3(CCOCC3)C2)n1] |
-continued
| Compound | Structure |
|---|---|
| 46 | 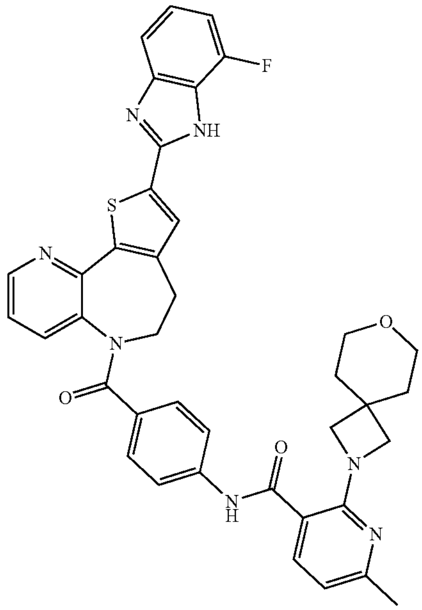 [SMILES: Cc1ccc(C(=O)Nc2ccc(C(=O)N3CCc4cc(-c5nc6cccc(F)c6[nH]5)sc4-c4ncccc43)cc2)c(N2CC3(CCOCC3)C2)n1] |
| 47 | 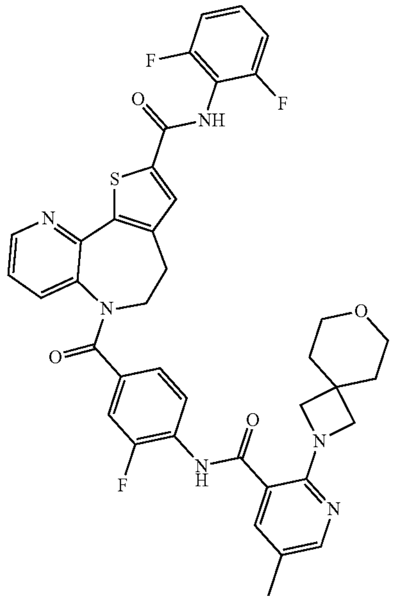 [SMILES: Cc1cnc(N2CC3(CCOCC3)C2)c(C(=O)Nc2ccc(C(=O)N3CCc4cc(C(=O)Nc5c(F)cccc5F)sc4-c4ncccc43)cc2F)c1] |

-continued
| Compound | Structure |
|---|---|
| 48 | 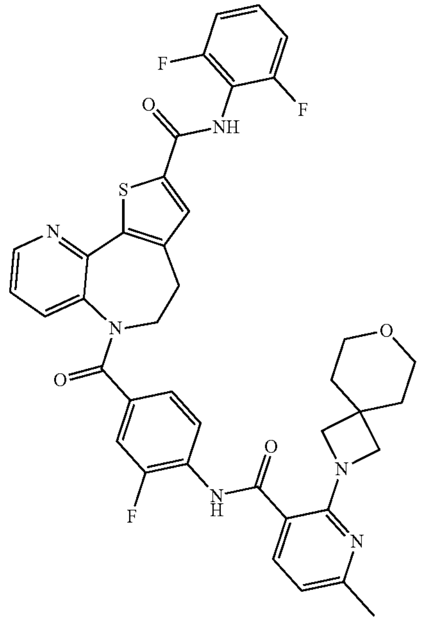 [SMILES: Cc1ccc(C(=O)Nc2ccc(C(=O)N3CCc4cc(C(=O)Nc5c(F)cccc5F)sc4-c4ncccc43)cc2F)c(N2CC3(CCOCC3)C2)n1] |
| 49 | 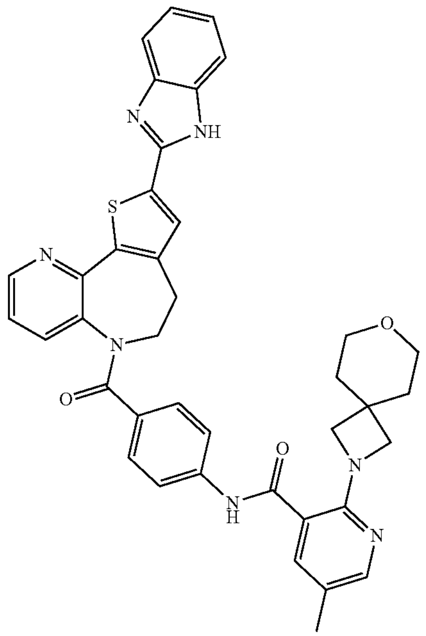 |
-continued
| Compound | Structure |
|---|---|
| 50 | 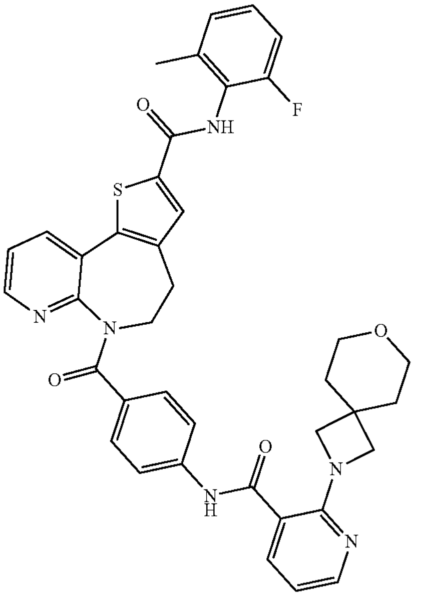 [SMILES: Cc1cccc(F)c1NC(=O)c1cc2c(s1)-c1cccnc1N(C(=O)c1ccc(NC(=O)c3cccnc3N3CC4(CCOCC4)C3)cc1)CC2] |
| 51 | 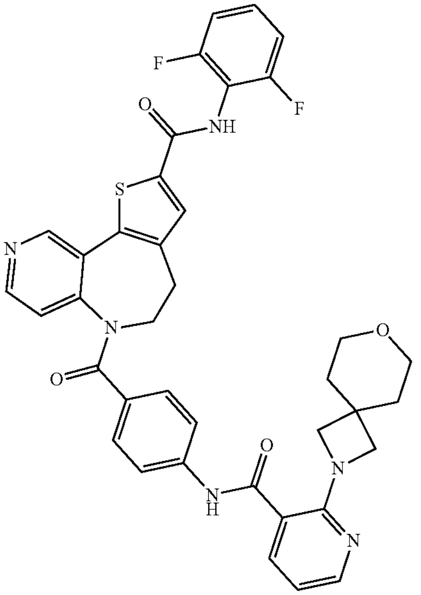 [SMILES: O=C(Nc1c(F)cccc1F)c1cc2c(s1)-c1cnccc1N(C(=O)c1ccc(NC(=O)c3cccnc3N3CC4(CCOCC4)C3)cc1)CC2] |

-continued
| Compound | Structure |
|---|---|
| 52 | 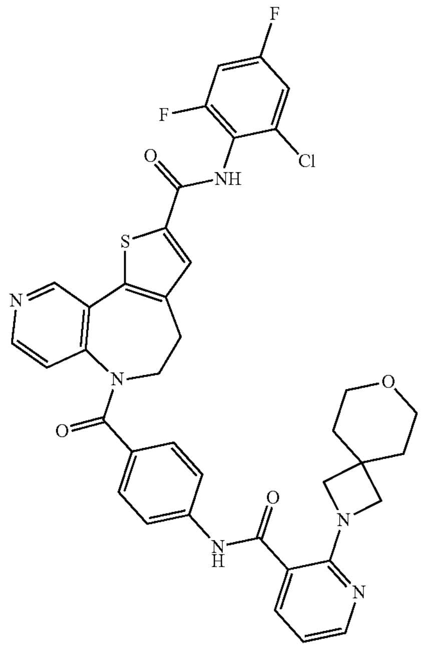 [SMILES: O=C(Nc1c(F)cc(F)cc1Cl)c1cc2c(s1)-c1cnccc1N(C(=O)c1ccc(NC(=O)c3cccnc3N3CC4(CCOCC4)C3)cc1)CC2] |
| 53 | 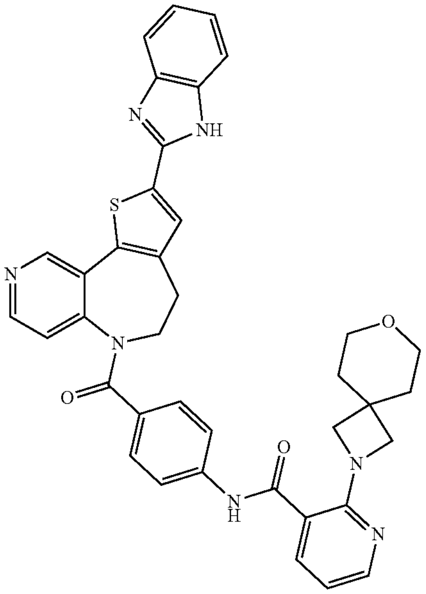 [SMILES: O=C(Nc1ccc(C(=O)N2CCc3cc(-c4nc5ccccc5[nH]4)sc3-c3cnccc32)cc1)c1cccnc1N1CC2(CCOCC2)C1] |
-continued
| Compound | Structure |
|---|---|
| 54 | 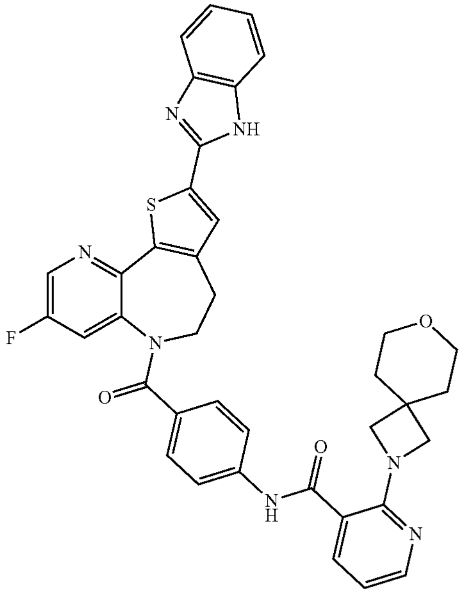 [SMILES: O=C(Nc1ccc(C(=O)N2CCc3cc(-c4nc5ccccc5[nH]4)sc3-c3ncc(F)cc32)cc1)c1cccnc1N1CC2(CCOCC2)C1] |
| 55 | 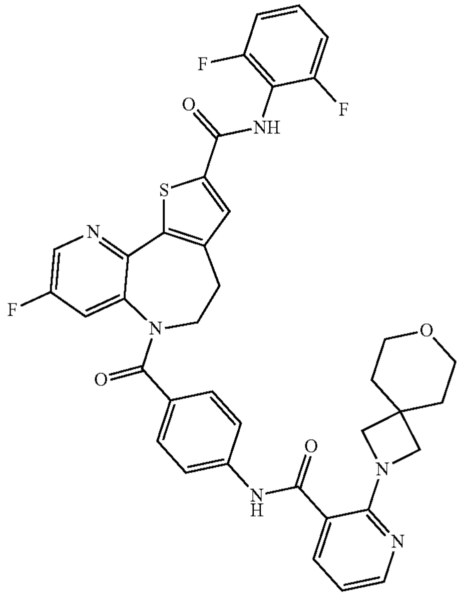 [SMILES: O=C(Nc1c(F)cccc1F)c1cc2c(s1)-c1ncc(F)cc1N(C(=O)c1ccc(NC(=O)c3cccnc3N3CC4(CCOCC4)C3)cc1)CC2] |

-continued
| Compound | Structure |
|---|---|
| 56 | 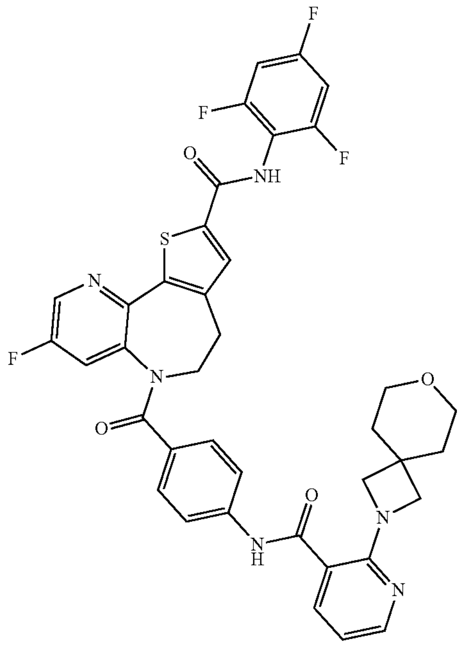 [SMILES: O=C(Nc1c(F)cc(F)cc1F)c1cc2c(s1)-c1ncc(F)cc1N(C(=O)c1ccc(NC(=O)c3cccnc3N3CC4(CCOCC4)C3)cc1)CC2] |
| 57 | 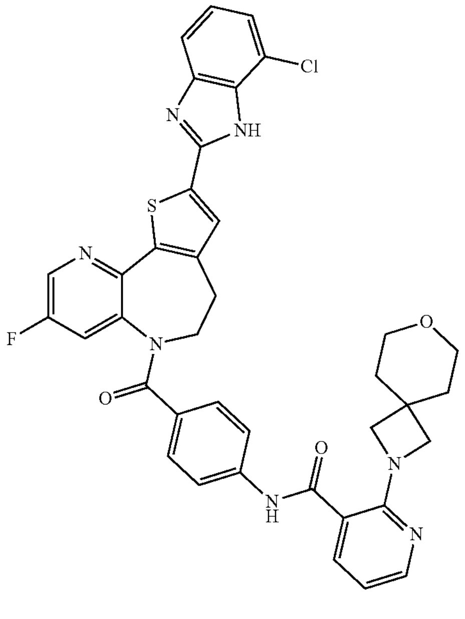 [SMILES: O=C(Nc1ccc(C(=O)N2CCc3cc(-c4nc5cccc(Cl)c5[nH]4)sc3-c3ncc(F)cc32)cc1)c1cccnc1N1CC2(CCOCC2)C1] |
-continued
| Compound | Structure |
|---|---|
| 58 | 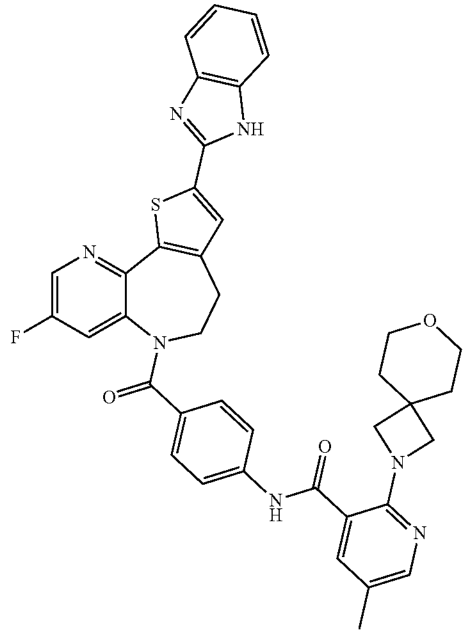 [SMILES: Cc1cnc(N2CC3(CCOCC3)C2)c(C(=O)Nc2ccc(C(=O)N3CCc4cc(-c5nc6ccccc6[nH]5)sc4-c4ncc(F)cc43)cc2)c1] |
| 59 | 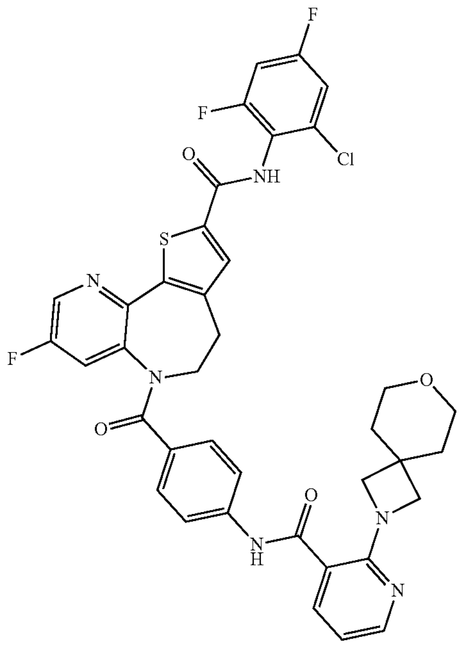 |

-continued
| Compound | Structure |
|---|---|
| 60 | 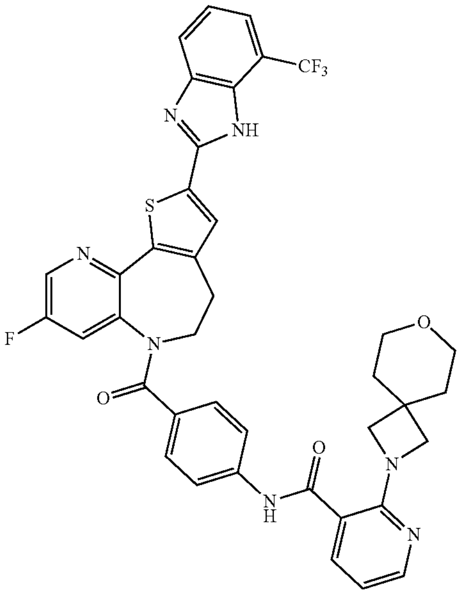 [SMILES: O=C(Nc1ccc(C(=O)N2CCc3cc(-c4nc5cccc(C(F)(F)F)c5[nH]4)sc3-c3ncc(F)cc32)cc1)c1cccnc1N1CC2(CCOCC2)C1] |
| 61 | 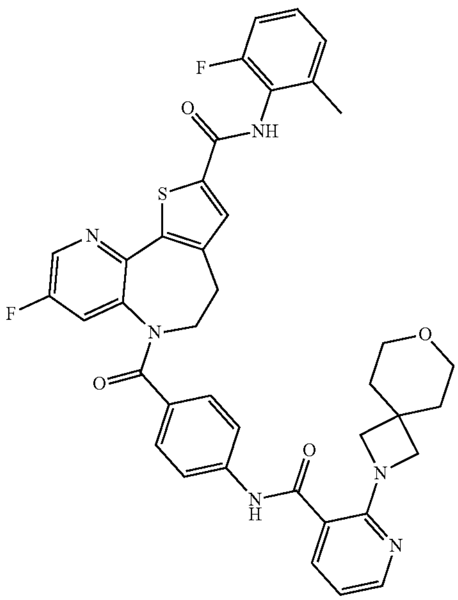 [SMILES: Cc1cccc(F)c1NC(=O)c1cc2c(s1)-c1ncc(F)cc1N(C(=O)c1ccc(NC(=O)c3cccnc3N3CC4(CCOCC4)C3)cc1)CC2] |
-continued
| Compound | Structure |
|---|---|
| 62 | 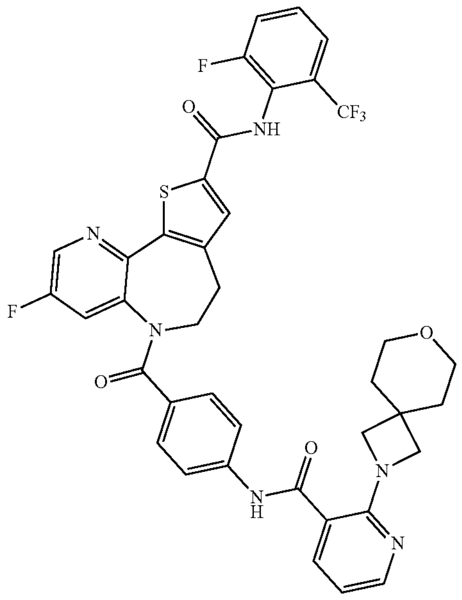 [SMILES: O=C(Nc1c(F)cccc1C(F)(F)F)c1cc2c(s1)-c1ncc(F)cc1N(C(=O)c1ccc(NC(=O)c3cccnc3N3CC4(CCOCC4)C3)cc1)CC2] |
| 63 | 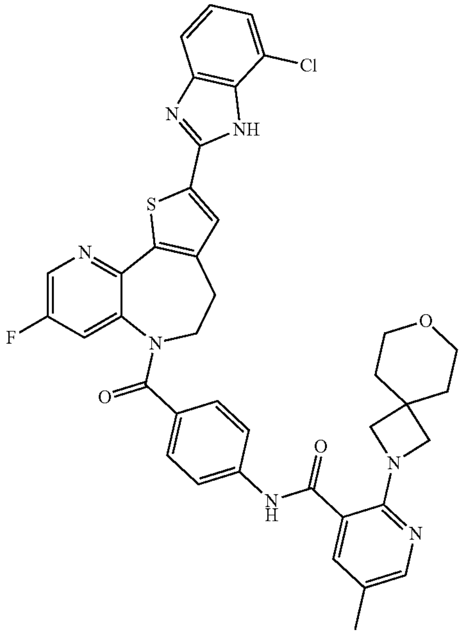 [SMILES: Cc1cnc(N2CC3(CCOCC3)C2)c(C(=O)Nc2ccc(C(=O)N3CCc4cc(-c5nc6cccc(Cl)c6[nH]5)sc4-c4ncc(F)cc43)cc2)c1] |

-continued
| Compound | Structure |
|---|---|
| 64 | 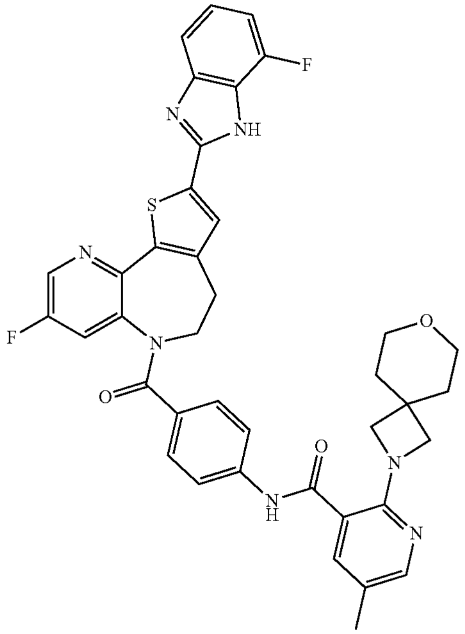 [SMILES: Cc1cnc(N2CC3(CCOCC3)C2)c(C(=O)Nc2ccc(C(=O)N3CCc4cc(-c5nc6cccc(F)c6[nH]5)sc4-c4ncc(F)cc43)cc2)c1] |
| 65 | 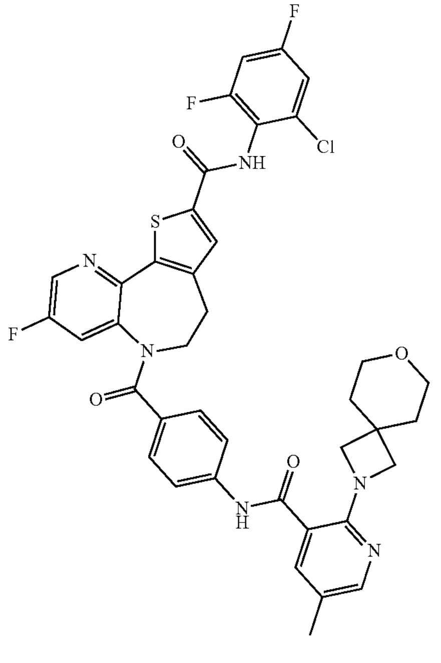 [SMILES: Cc1cnc(N2CC3(CCOCC3)C2)c(C(=O)Nc2ccc(C(=O)N3CCc4cc(C(=O)Nc5c(F)cc(F)cc5Cl)sc4-c4ncc(F)cc43)cc2)c1] |
-continued
| Compound | Structure |
|---|---|
| 66 | 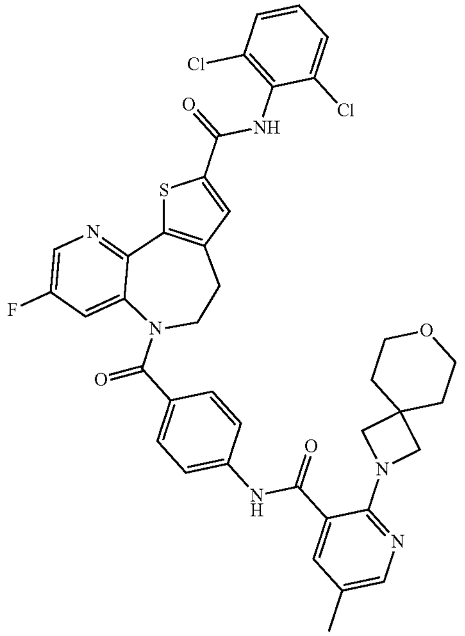 [SMILES: Cc1cnc(N2CC3(CCOCC3)C2)c(C(=O)Nc2ccc(C(=O)N3CCc4cc(C(=O)Nc5c(Cl)cccc5Cl)sc4-c4ncc(F)cc43)cc2)c1] |
| 67 | 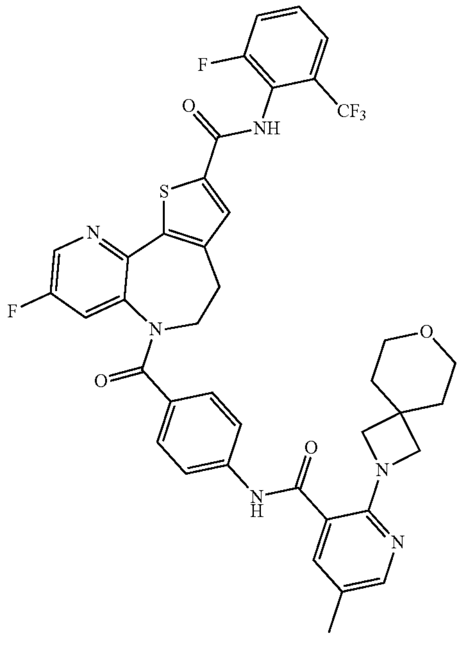 [SMILES: Cc1cnc(N2CC3(CCOCC3)C2)c(C(=O)Nc2ccc(C(=O)N3CCc4cc(C(=O)Nc5c(F)cccc5C(F)(F)F)sc4-c4ncc(F)cc43)cc2)c1] |

-continued
| Compound | Structure |
|---|---|
| 68 | 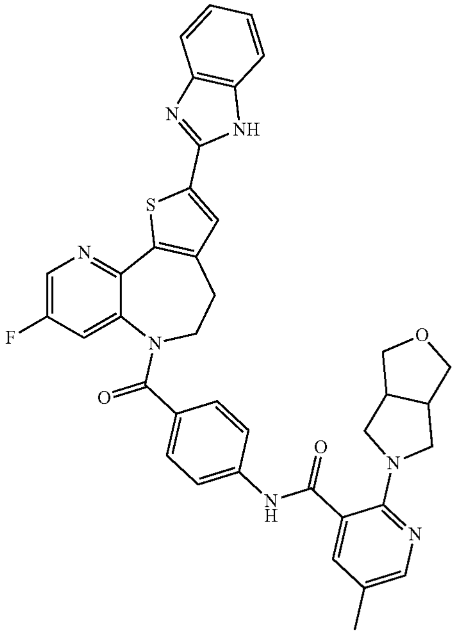 [SMILES: Cc1cnc(N2CC3COCC3C2)c(C(=O)Nc2ccc(C(=O)N3CCc4cc(-c5nc6ccccc6[nH]5)sc4-c4ncc(F)cc43)cc2)c1] |
| 69 | 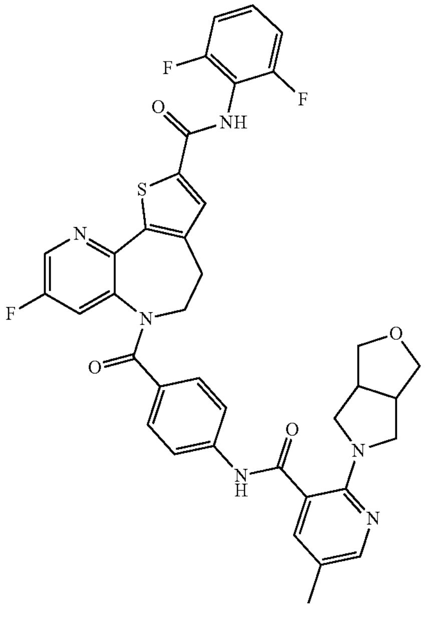 [SMILES: Cc1cnc(N2CC3COCC3C2)c(C(=O)Nc2ccc(C(=O)N3CCc4cc(C(=O)Nc5c(F)cccc5F)sc4-c4ncc(F)cc43)cc2)c1] |
-continued
| Compound | Structure |
|---|---|
| 70 | 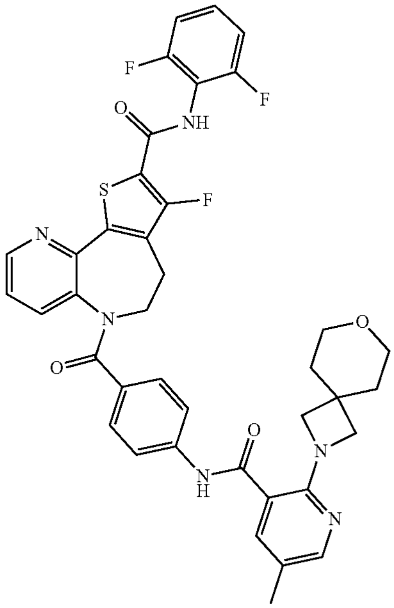 |
| 71 | 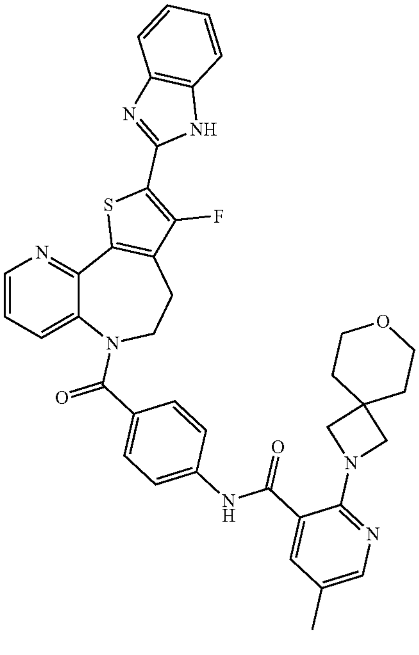 [SMILES: Cc1cnc(N2CC3(CCOCC3)C2)c(C(=O)Nc2ccc(C(=O)N3CCc4c(sc(-c5nc6ccccc6[nH]5)c4F)-c4ncccc43)cc2)c1] |

-continued
| Compound | Structure |
|---|---|
| 72 | 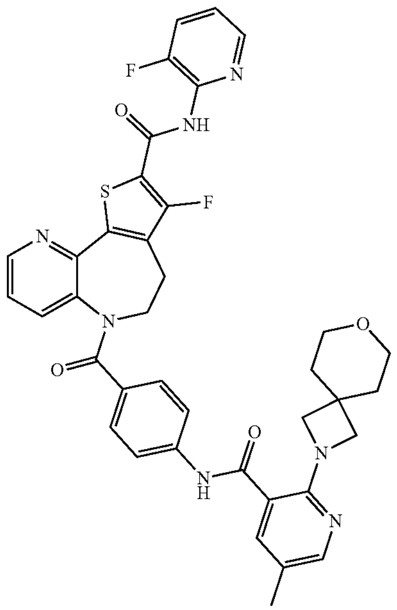 [SMILES: Cc1cnc(N2CC3(CCOCC3)C2)c(C(=O)Nc2ccc(C(=O)N3CCc4c(sc(C(=O)Nc5ncccc5F)c4F)-c4ncccc43)cc2)c1] |
| 73 | 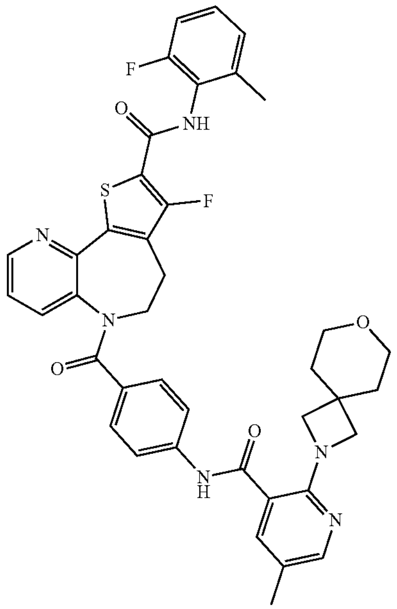 [SMILES: Cc1cnc(N2CC3(CCOCC3)C2)c(C(=O)Nc2ccc(C(=O)N3CCc4c(sc(C(=O)Nc5c(C)cccc5F)c4F)-c4ncccc43)cc2)c1] |
-continued
| Compound | Structure |
|---|---|
| 74 | 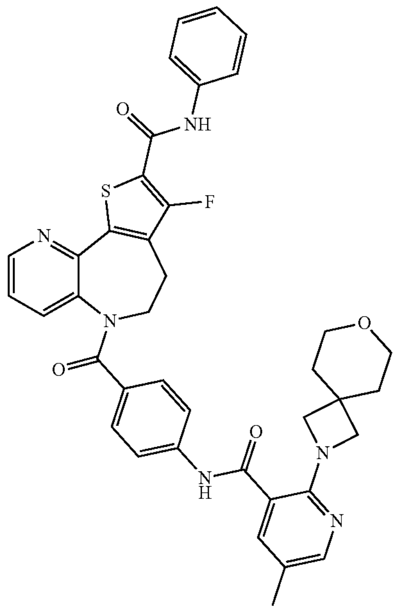 [SMILES: Cc1cnc(N2CC3(CCOCC3)C2)c(C(=O)Nc2ccc(C(=O)N3CCc4c(sc(C(=O)Nc5ccccc5)c4F)-c4ncccc43)cc2)c1] |
| 75 | 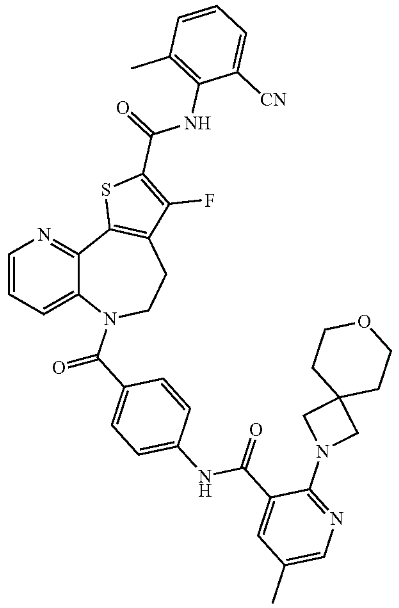 [SMILES: Cc1cnc(N2CC3(CCOCC3)C2)c(C(=O)Nc2ccc(C(=O)N3CCc4c(sc(C(=O)Nc5c(C)cccc5C#N)c4F)-c4ncccc43)cc2)c1] |

-continued
| Compound | Structure |
|---|---|
| 76 | 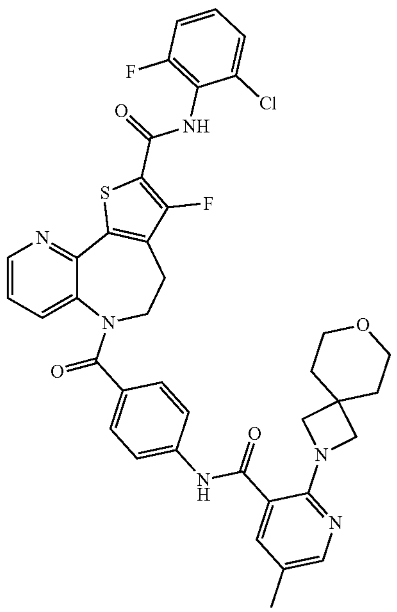 [SMILES: Cc1cnc(N2CC3(CCOCC3)C2)c(C(=O)Nc2ccc(C(=O)N3CCc4c(sc(C(=O)Nc5c(F)cccc5Cl)c4F)-c4ncccc43)cc2)c1] |
| 77 | 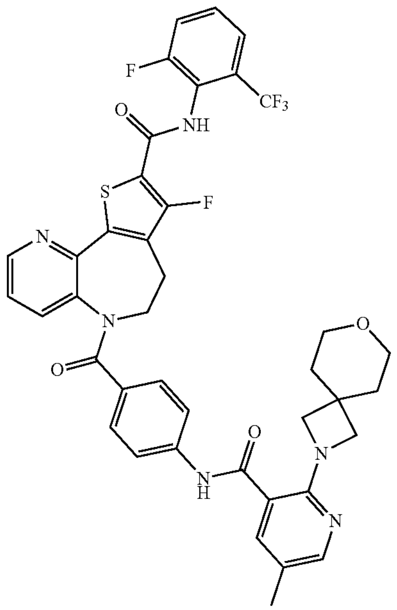 [SMILES: Cc1cnc(N2CC3(CCOCC3)C2)c(C(=O)Nc2ccc(C(=O)N3CCc4c(sc(C(=O)Nc5c(F)cccc5C(F)(F)F)c4F)-c4ncccc43)cc2)c1] |
-continued
| Compound | Structure |
|---|---|
| 78 | 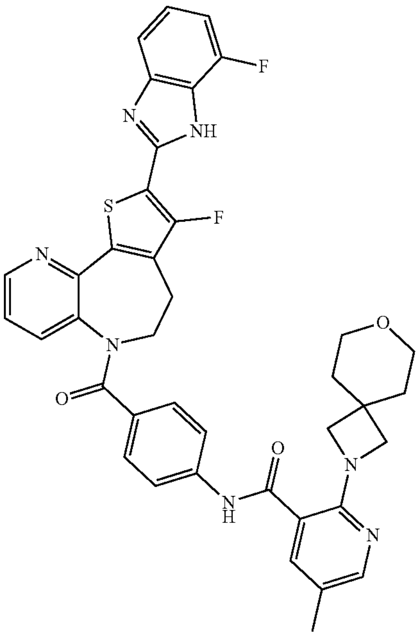 [SMILES: Cc1cnc(N2CC3(CCOCC3)C2)c(C(=O)Nc2ccc(C(=O)N3CCc4c(sc(-c5nc6cccc(F)c6[nH]5)c4F)-c4ncccc43)cc2)c1] |
| 79 | 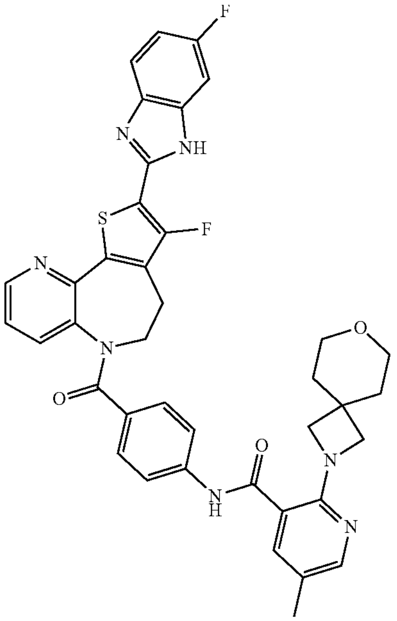 [SMILES: Cc1cnc(N2CC3(CCOCC3)C2)c(C(=O)Nc2ccc(C(=O)N3CCc4c(sc(-c5nc6ccc(F)cc6[nH]5)c4F)-c4ncccc43)cc2)c1] |

| Compound | Structure |
|---|---|
| 80 | 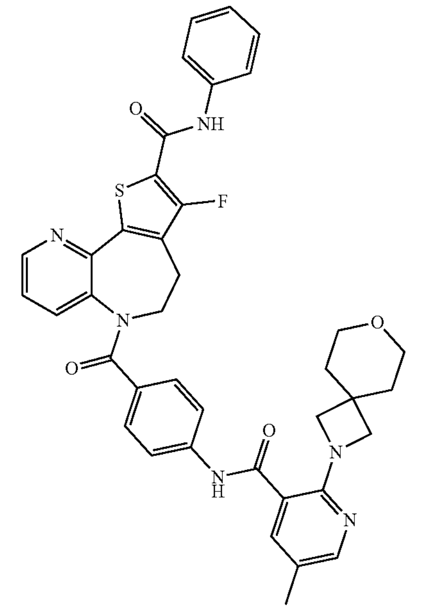 [SMILES: Cc1cnc(N2CC3(CCOCC3)C2)c(C(=O)Nc2ccc(C(=O)N3CCc4c(sc(C(=O)Nc5ccccc5)c4F)-c4ncccc43)cc2)c1] |
| 81 | 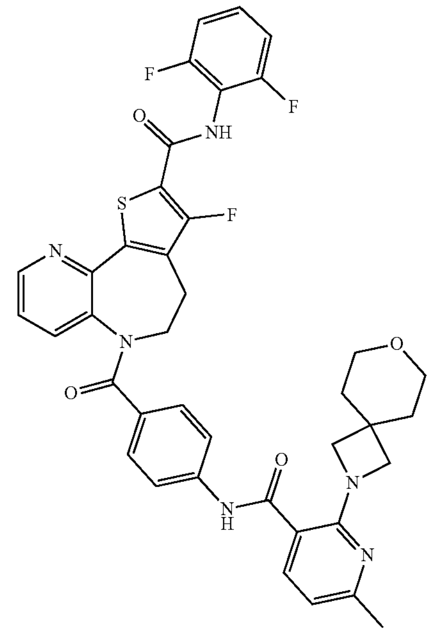 [SMILES: Cc1ccc(C(=O)Nc2ccc(C(=O)N3CCc4c(sc(C(=O)Nc5c(F)cccc5F)c4F)-c4ncccc43)cc2)c(N2CC3(CCOCC3)C2)n1] |
| 82 | 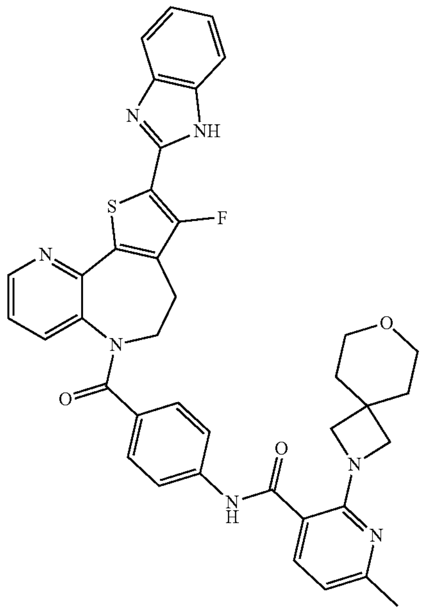 [SMILES: Cc1ccc(C(=O)Nc2ccc(C(=O)N3CCc4c(sc(-c5nc6ccccc6[nH]5)c4F)-c4ncccc43)cc2)c(N2CC3(CCOCC3)C2)n1] |
| 83 | 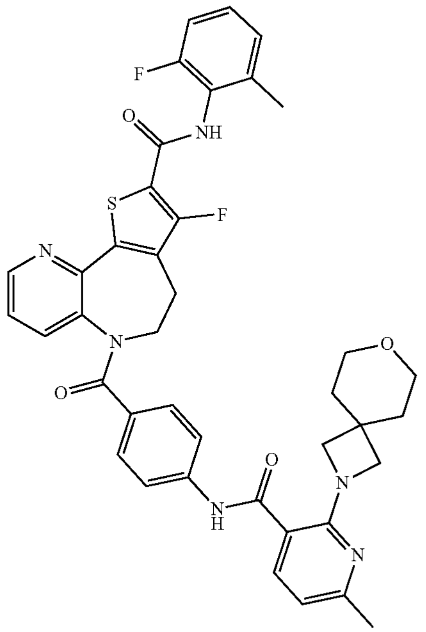 [SMILES: Cc1ccc(C(=O)Nc2ccc(C(=O)N3CCc4c(sc(C(=O)Nc5c(C)cccc5F)c4F)-c4ncccc43)cc2)c(N2CC3(CCOCC3)C2)n1] |

-continued
| Compound | Structure |
|---|---|
| 84 | 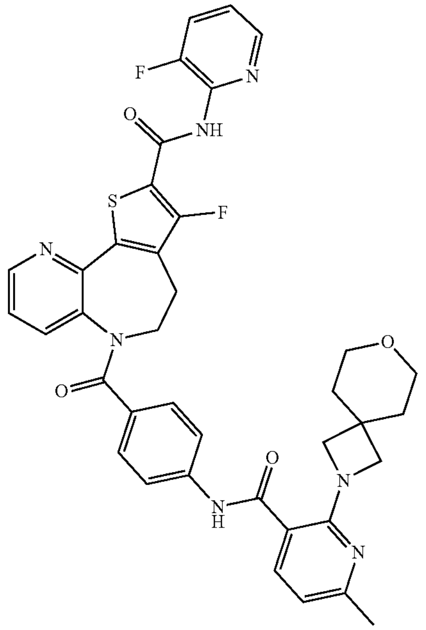 [SMILES: Cc1ccc(C(=O)Nc2ccc(C(=O)N3CCc4c(sc(C(=O)Nc5ncccc5F)c4F)-c4ncccc43)cc2)c(N2CC3(CCOCC3)C2)n1] |
| 85 | 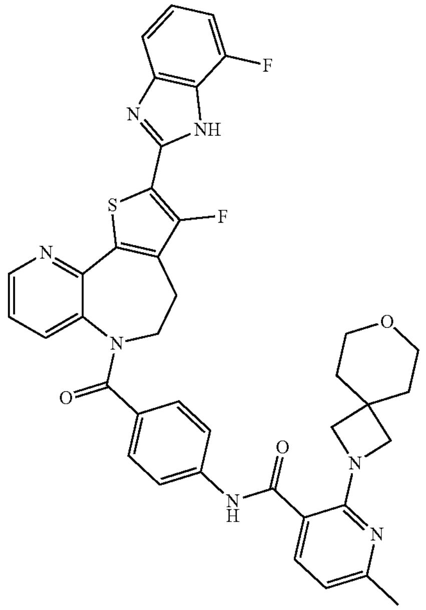 [SMILES: Cc1ccc(C(=O)Nc2ccc(C(=O)N3CCc4c(sc(-c5nc6cccc(F)c6[nH]5)c4F)-c4ncccc43)cc2)c(N2CC3(CCOCC3)C2)n1] |
-continued
| Compound | Structure |
|---|---|
| 86 | 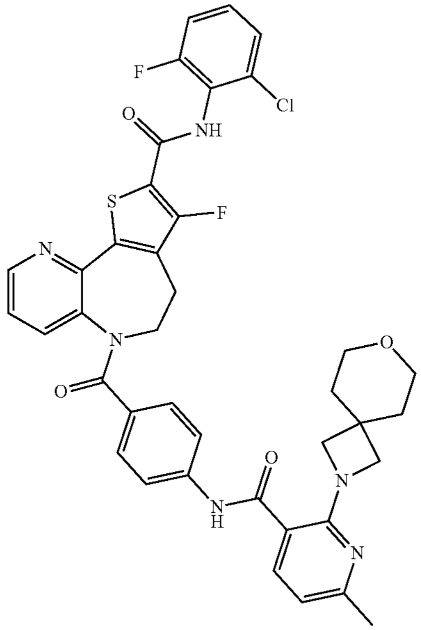 [SMILES: Cc1ccc(C(=O)Nc2ccc(C(=O)N3CCc4c(sc(C(=O)Nc5c(F)cccc5Cl)c4F)-c4ncccc43)cc2)c(N2CC3(CCOCC3)C2)n1] |
| 87 | 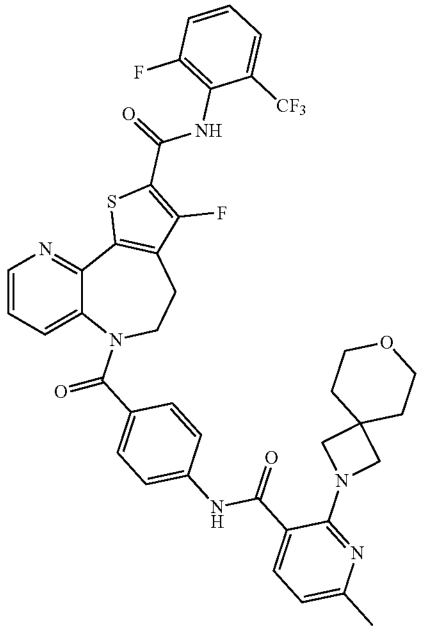 |

-continued
| Compound | Structure |
|---|---|
| 88 | 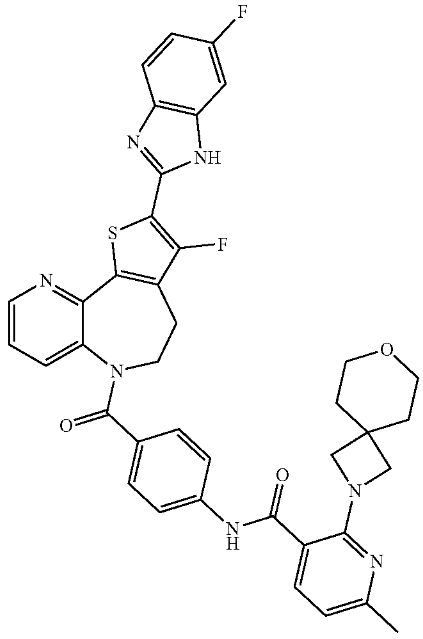 [SMILES: Cc1ccc(C(=O)Nc2ccc(C(=O)N3CCc4c(sc(-c5nc6ccc(F)cc6[nH]5)c4F)-c4ncccc43)cc2)c(N2CC3(CCOCC3)C2)n1] |
| 89 | 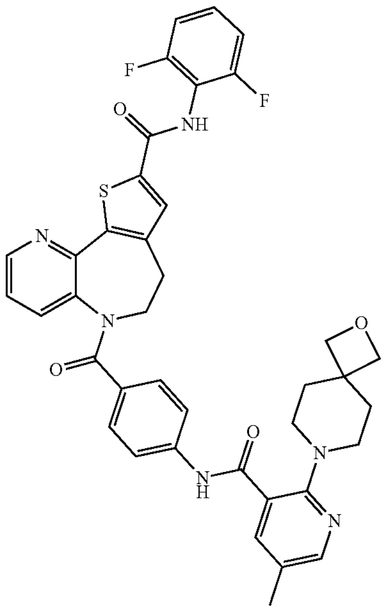 [SMILES: Cc1cnc(N2CCC3(CC2)COC3)c(C(=O)Nc2ccc(C(=O)N3CCc4cc(C(=O)Nc5c(F)cccc5F)sc4-c4ncccc43)cc2)c1] |
-continued
| Compound | Structure |
|---|---|
| 90 | 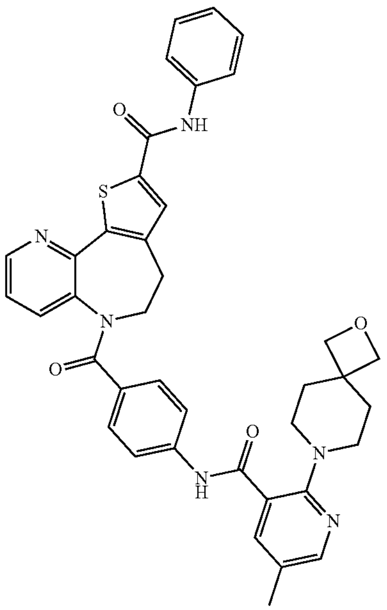 [SMILES: Cc1cnc(N2CCC3(CC2)COC3)c(C(=O)Nc2ccc(C(=O)N3CCc4cc(C(=O)Nc5ccccc5)sc4-c4ncccc43)cc2)c1] |
| 91 | 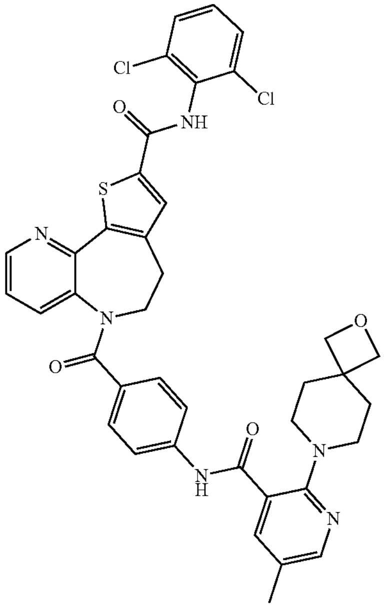 [SMILES: Cc1cnc(N2CCC3(CC2)COC3)c(C(=O)Nc2ccc(C(=O)N3CCc4cc(C(=O)Nc5c(Cl)cccc5Cl)sc4-c4ncccc43)cc2)c1] |

-continued
| Compound | Structure |
| --- | --- |
| 92 | 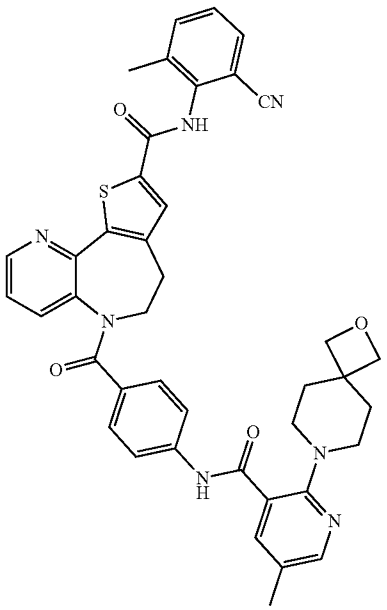 [SMILES: Cc1cnc(N2CCC3(CC2)COC3)c(C(=O)Nc2ccc(C(=O)N3CCc4cc(C(=O)Nc5c(C)cccc5C#N)sc4-c4ncccc43)cc2)c1] |
| 93 | 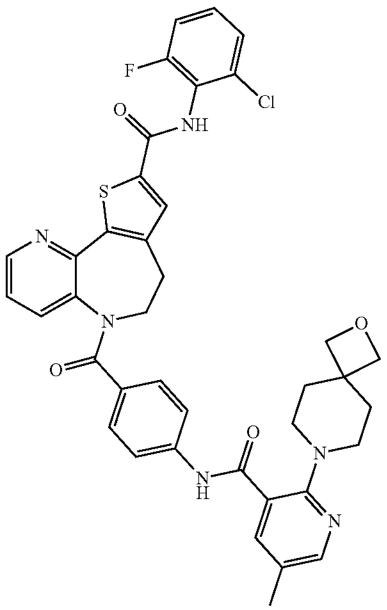 [SMILES: Cc1cnc(N2CCC3(CC2)COC3)c(C(=O)Nc2ccc(C(=O)N3CCc4cc(C(=O)Nc5c(F)cccc5Cl)sc4-c4ncccc43)cc2)c1] |
-continued
| Compound | Structure |
| --- | --- |
| 94 | 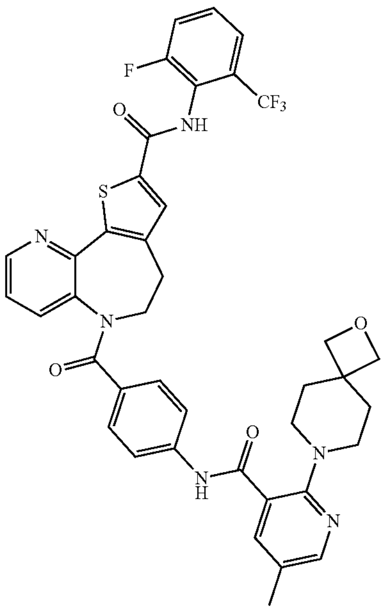 [SMILES: Cc1cnc(N2CCC3(CC2)COC3)c(C(=O)Nc2ccc(C(=O)N3CCc4cc(C(=O)Nc5c(F)cccc5C(F)(F)F)sc4-c4ncccc43)cc2)c1] |
| 95 | 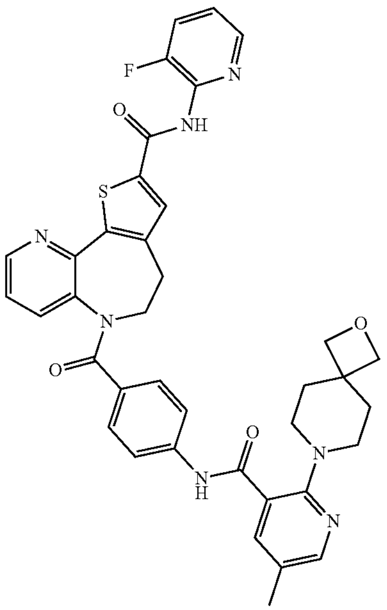 [SMILES: Cc1cnc(N2CCC3(CC2)COC3)c(C(=O)Nc2ccc(C(=O)N3CCc4cc(C(=O)Nc5ncccc5F)sc4-c4ncccc43)cc2)c1] |

-continued
| Compound | Structure |
|---|---|
| 96 | 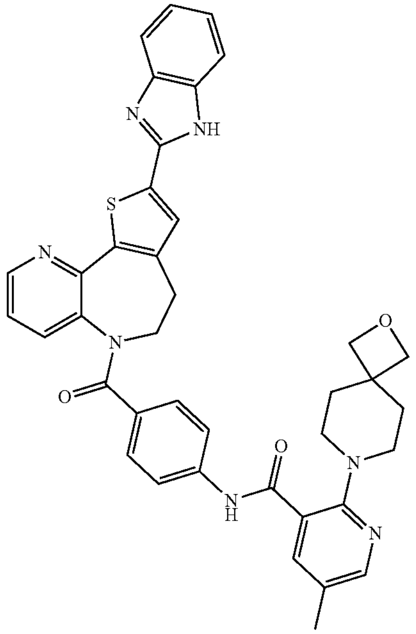 [SMILES: Cc1cnc(N2CCC3(CC2)COC3)c(C(=O)Nc2ccc(C(=O)N3CCc4cc(-c5nc6ccccc6[nH]5)sc4-c4ncccc43)cc2)c1] |
| 97 | 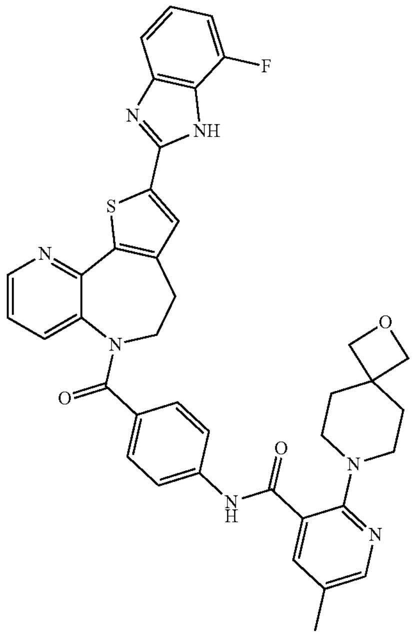 [SMILES: Cc1cnc(N2CCC3(CC2)COC3)c(C(=O)Nc2ccc(C(=O)N3CCc4cc(-c5nc6cccc(F)c6[nH]5)sc4-c4ncccc43)cc2)c1] |
-continued
| Compound | Structure |
|---|---|
| 98 | 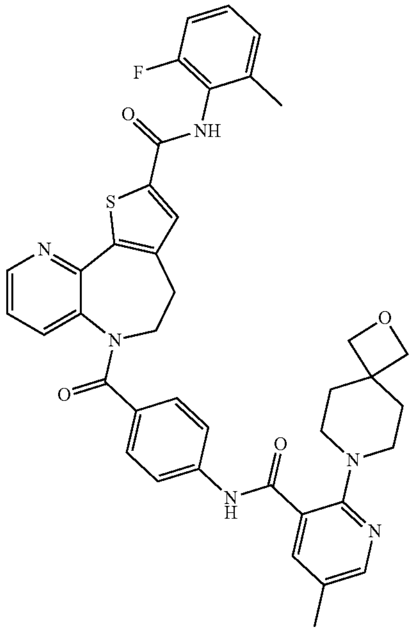 [SMILES: Cc1cnc(N2CCC3(CC2)COC3)c(C(=O)Nc2ccc(C(=O)N3CCc4cc(C(=O)Nc5c(C)cccc5F)sc4-c4ncccc43)cc2)c1] |
| 99 | 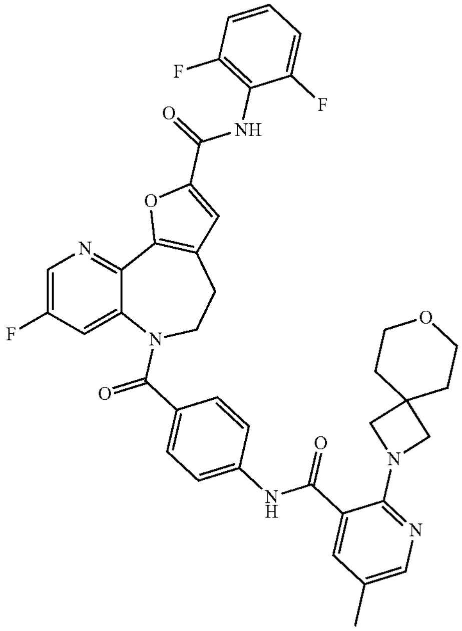 [SMILES: Cc1cnc(N2CC3(CCOCC3)C2)c(C(=O)Nc2ccc(C(=O)N3CCc4cc(C(=O)Nc5c(F)cccc5F)oc4-c4ncc(F)cc43)cc2)c1] |

-continued
| Compound | Structure |
|---|---|
| 100 | 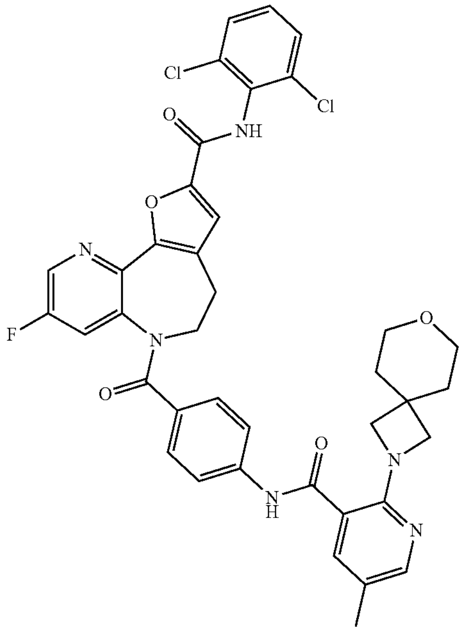 [SMILES: Cc1cnc(N2CC3(CCOCC3)C2)c(C(=O)Nc2ccc(C(=O)N3CCc4cc(C(=O)Nc5c(Cl)cccc5Cl)oc4-c4ncc(F)cc43)cc2)c1] |
| 101 | 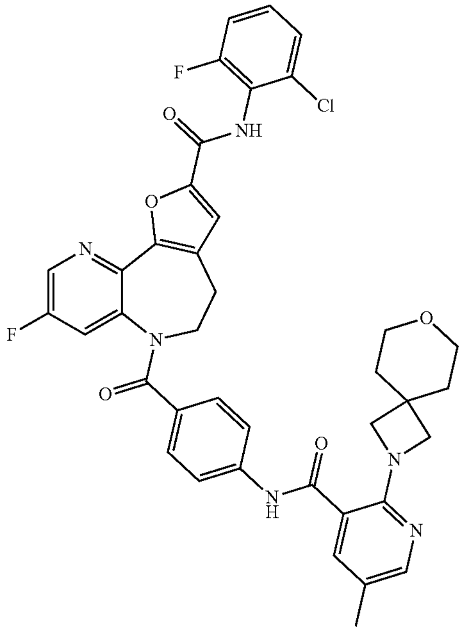 [SMILES: Cc1cnc(N2CC3(CCOCC3)C2)c(C(=O)Nc2ccc(C(=O)N3CCc4cc(C(=O)Nc5c(F)cccc5Cl)oc4-c4ncc(F)cc43)cc2)c1] |
-continued
| Compound | Structure |
|---|---|
| 102 | 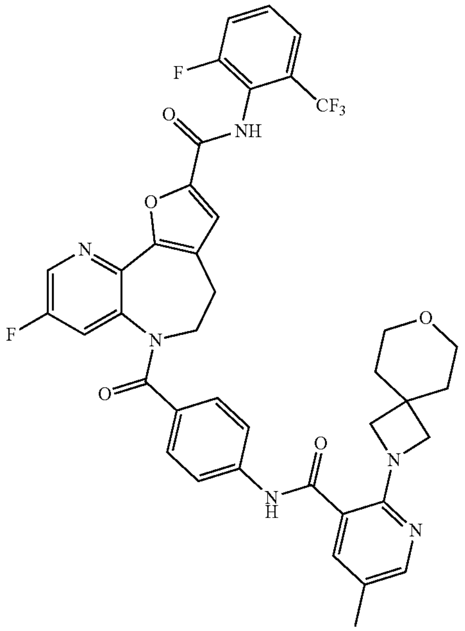 [SMILES: Cc1cnc(N2CC3(CCOCC3)C2)c(C(=O)Nc2ccc(C(=O)N3CCc4cc(C(=O)Nc5c(F)cccc5C(F)(F)F)oc4-c4ncc(F)cc43)cc2)c1] |
| 103 | 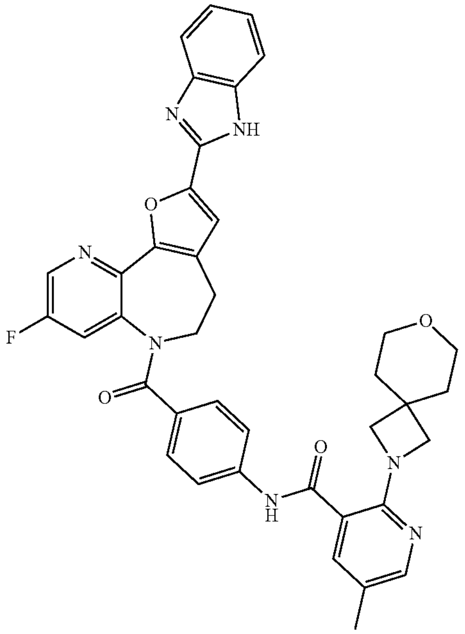 |

-continued
| Compound | Structure |
|---|---|
| 104 | 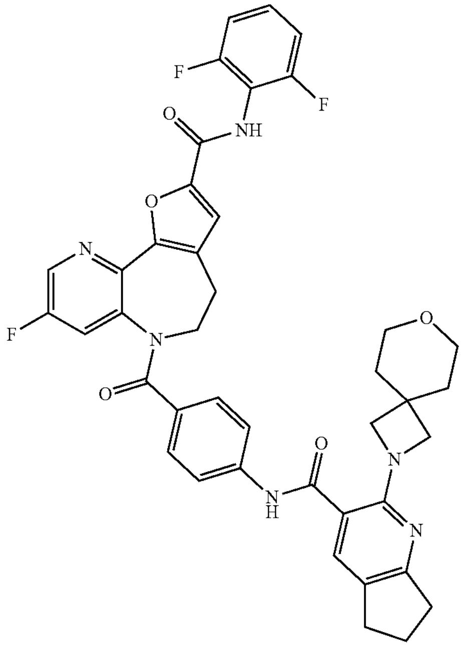 [SMILES: O=C(Nc1c(F)cccc1F)c1cc2c(o1)-c1ncc(F)cc1N(C(=O)c1ccc(NC(=O)c3cc4c(nc3N3CC5(CCOCC5)C3)CCC4)cc1)CC2] |
| 105 | 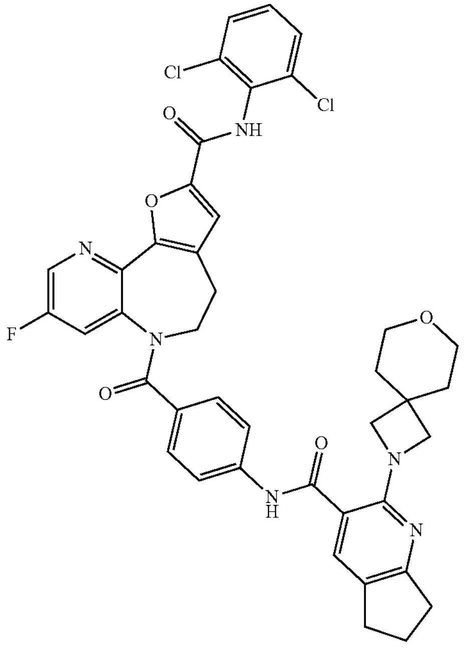 [SMILES: O=C(Nc1c(Cl)cccc1Cl)c1cc2c(o1)-c1ncc(F)cc1N(C(=O)c1ccc(NC(=O)c3cc4c(nc3N3CC5(CCOCC5)C3)CCC4)cc1)CC2] |
-continued
| Compound | Structure |
|---|---|
| 106 | 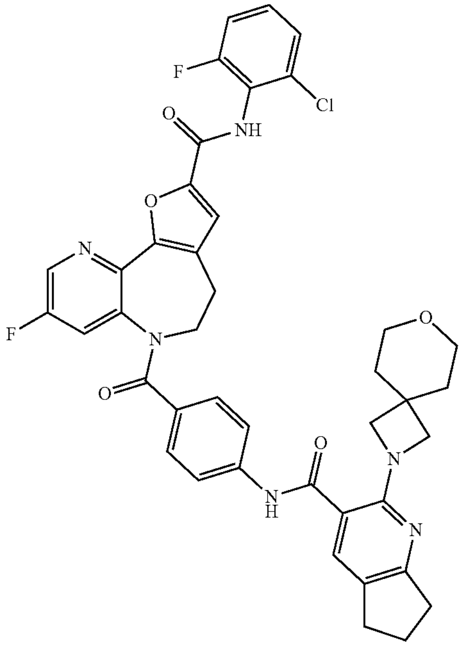 |
| 107 | 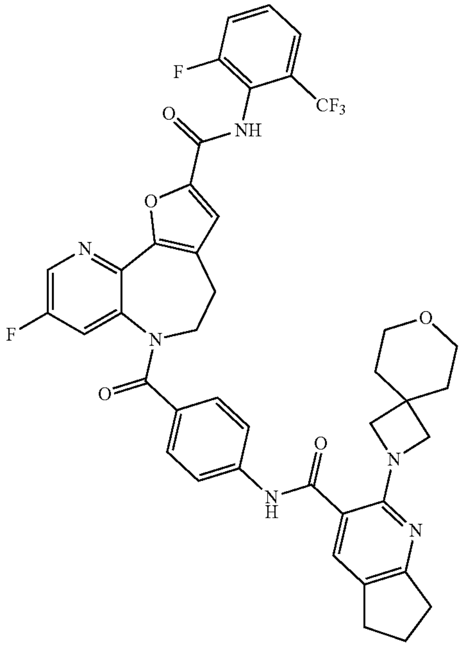 [SMILES: O=C(Nc1c(F)cccc1C(F)(F)F)c1cc2c(o1)-c1ncc(F)cc1N(C(=O)c1ccc(NC(=O)c3cc4c(nc3N3CC5(CCOCC5)C3)CCC4)cc1)CC2] |

| Compound | Structure |
| --- | --- |
| 108 | 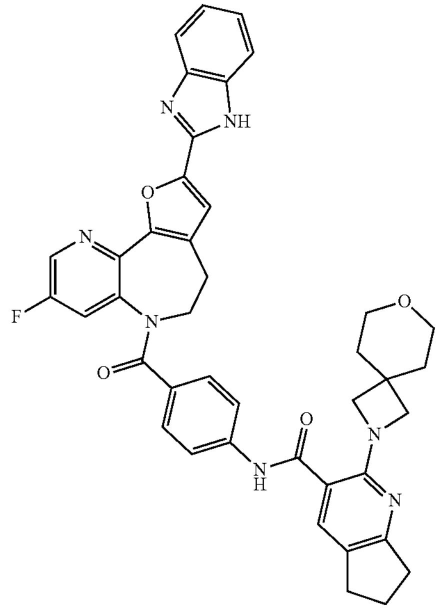 [SMILES: O=C(Nc1ccc(C(=O)N2CCc3cc(-c4nc5ccccc5[nH]4)oc3-c3ncc(F)cc32)cc1)c1cc2c(nc1N1CC3(CCOCC3)C1)CCC2] |
| 109 | 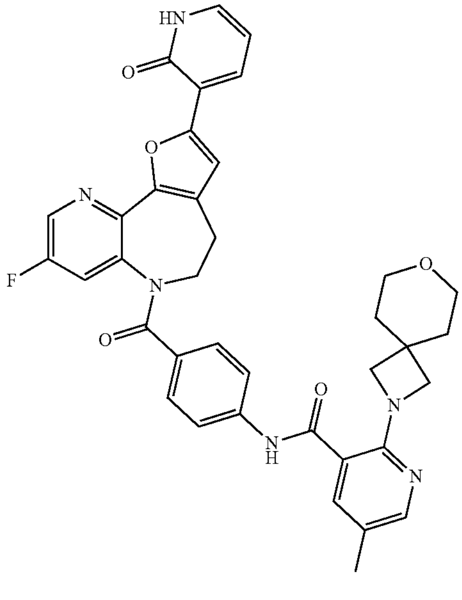 [SMILES: Cc1cnc(N2CC3(CCOCC3)C2)c(C(=O)Nc2ccc(C(=O)N3CCc4cc(-c5ccc[nH]c5=O)oc4-c4ncc(F)cc43)cc2)c1] |
| Compound | Structure |
| --- | --- |
| 110 | 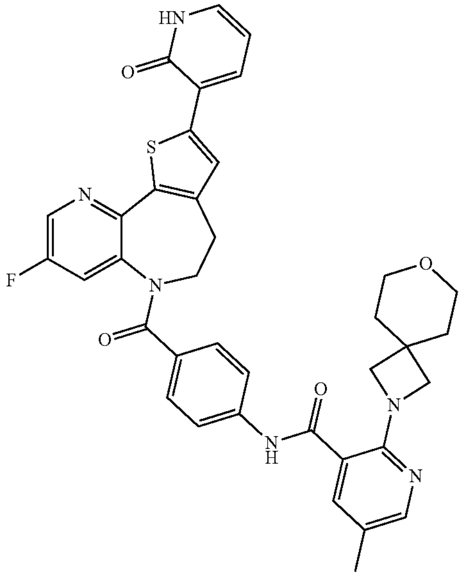 [SMILES: Cc1cnc(N2CC3(CCOCC3)C2)c(C(=O)Nc2ccc(C(=O)N3CCc4cc(-c5ccc[nH]c5=O)sc4-c4ncc(F)cc43)cc2)c1] |
| 111 | 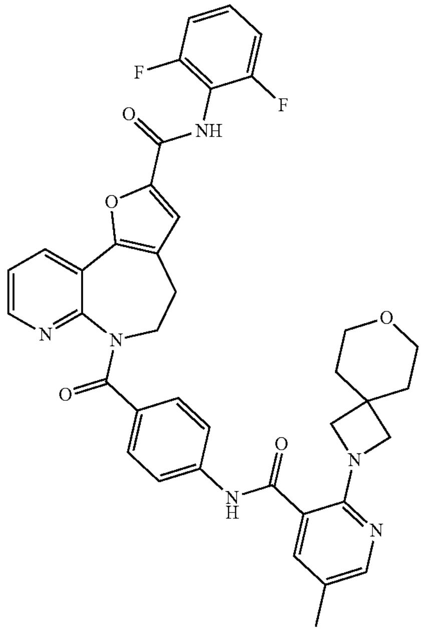 [SMILES: Cc1cnc(N2CC3(CCOCC3)C2)c(C(=O)Nc2ccc(C(=O)N3CCc4cc(C(=O)Nc5c(F)cccc5F)oc4-c4cccnc43)cc2)c1] |

| Compound | Structure |
|---|---|
| 112 | 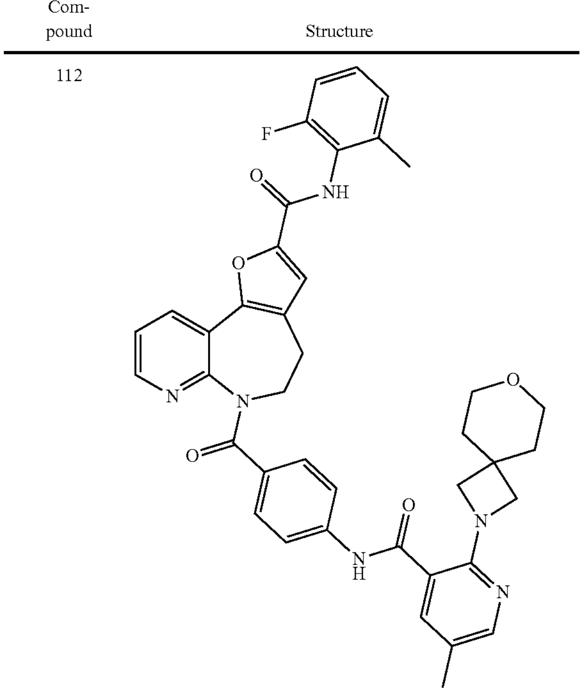 |
| 113 | 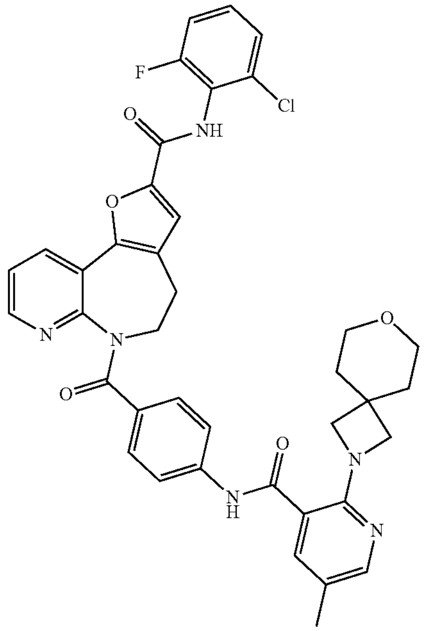 [SMILES: Cc1cnc(N2CC3(CCOCC3)C2)c(C(=O)Nc2ccc(C(=O)N3CCc4cc(C(=O)Nc5c(C)cccc5F)oc4-c4cccnc43)cc2)c1] |
| Compound | Structure |
|---|---|
| 114 | 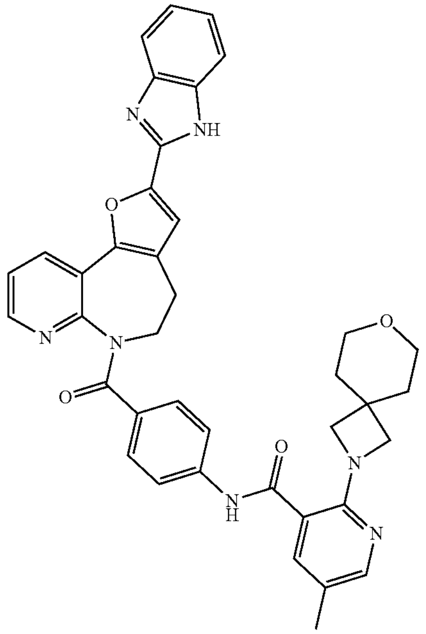 [SMILES: Cc1cnc(N2CC3(CCOCC3)C2)c(C(=O)Nc2ccc(C(=O)N3CCc4cc(-c5nc6ccccc6[nH]5)oc4-c4cccnc43)cc2)c1] |
| 115 | 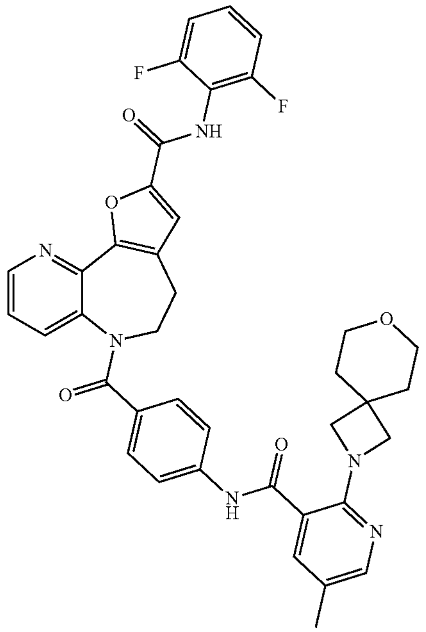 [SMILES: Cc1cnc(N2CC3(CCOCC3)C2)c(C(=O)Nc2ccc(C(=O)N3CCc4cc(C(=O)Nc5c(F)cccc5F)oc4-c4ncccc43)cc2)c1] |

-continued
| Compound | Structure |
|---|---|
| 116 | 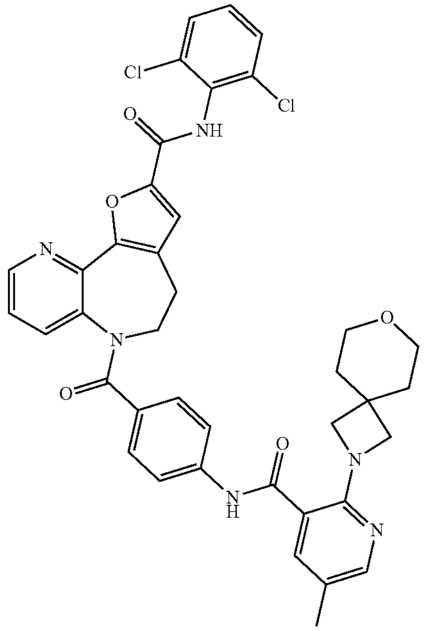 [SMILES: Cc1cnc(N2CC3(CCOCC3)C2)c(C(=O)Nc2ccc(C(=O)N3CCc4cc(C(=O)Nc5c(Cl)cccc5Cl)oc4-c4ncccc43)cc2)c1] |
| 117 | 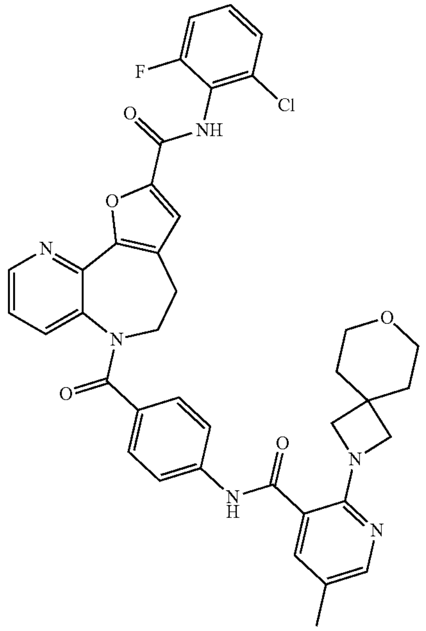 [SMILES: Cc1cnc(N2CC3(CCOCC3)C2)c(C(=O)Nc2ccc(C(=O)N3CCc4cc(C(=O)Nc5c(F)cccc5Cl)oc4-c4ncccc43)cc2)c1] |
-continued
| Compound | Structure |
|---|---|
| 118 | 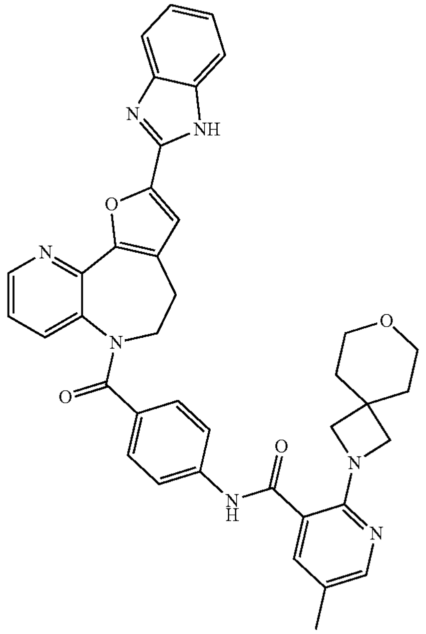 [SMILES: Cc1cnc(N2CC3(CCOCC3)C2)c(C(=O)Nc2ccc(C(=O)N3CCc4cc(-c5nc6ccccc6[nH]5)oc4-c4ncccc43)cc2)c1] |
| 119 | 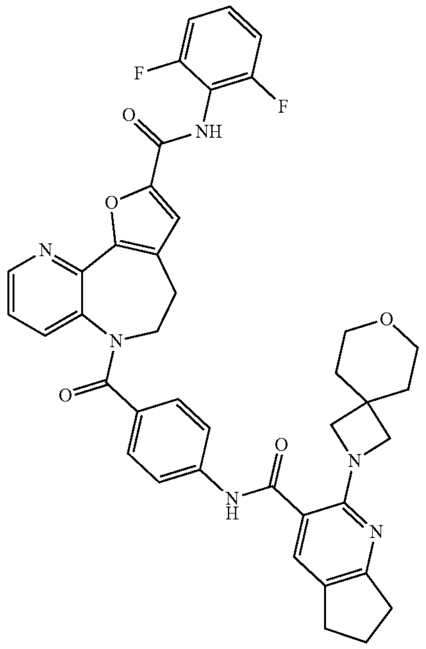 [SMILES: O=C(Nc1c(F)cccc1F)c1cc2c(o1)-c1ncccc1N(C(=O)c1ccc(NC(=O)c3cc4c(nc3N3CC5(CCOCC5)C3)CCC4)cc1)CC2] |

-continued
| Compound | Structure |
|---|---|
| 120 | 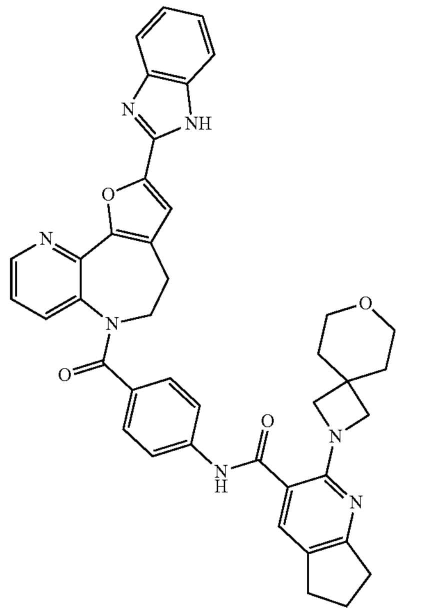 [SMILES: O=C(Nc1ccc(C(=O)N2CCc3cc(-c4nc5ccccc5[nH]4)oc3-c3ncccc32)cc1)c1cc2c(nc1N1CC3(CCOCC3)C1)CCC2] |
| 121 | 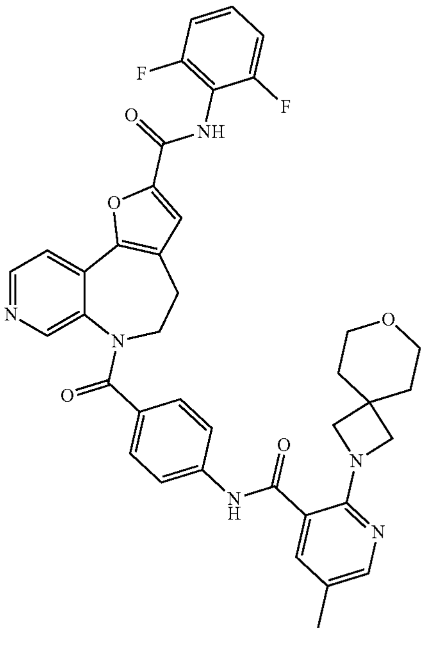 [SMILES: Cc1cnc(N2CC3(CCOCC3)C2)c(C(=O)Nc2ccc(C(=O)N3CCc4cc(C(=O)Nc5c(F)cccc5F)oc4-c4ccncc43)cc2)c1] |
-continued
| Compound | Structure |
|---|---|
| 122 | 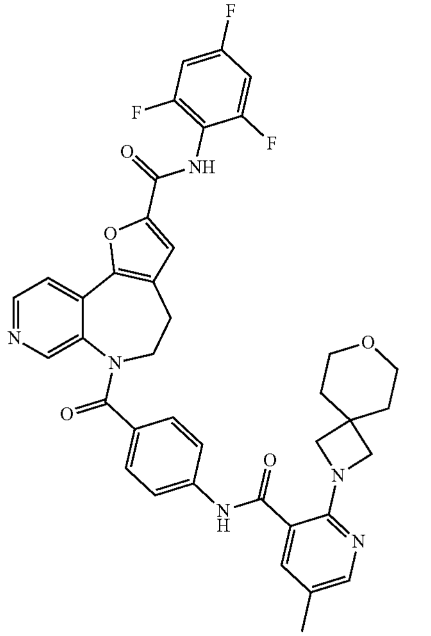 [SMILES: Cc1cnc(N2CC3(CCOCC3)C2)c(C(=O)Nc2ccc(C(=O)N3CCc4cc(C(=O)Nc5c(F)cc(F)cc5F)oc4-c4ccncc43)cc2)c1] |
| 123 | 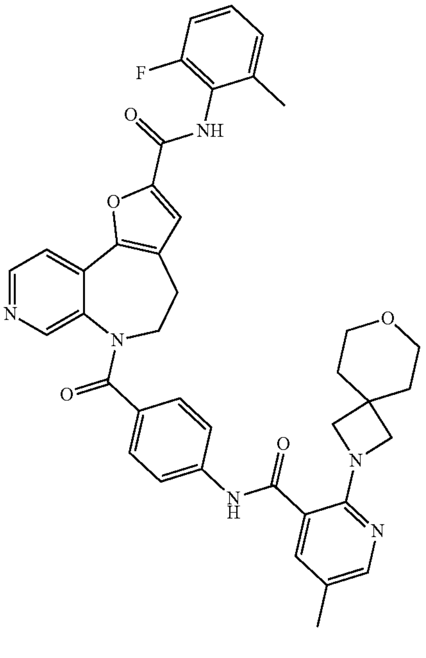 [SMILES: Cc1cnc(N2CC3(CCOCC3)C2)c(C(=O)Nc2ccc(C(=O)N3CCc4cc(C(=O)Nc5c(C)cccc5F)oc4-c4ccncc43)cc2)c1] |

-continued
| Compound | Structure |
| --- | --- |
| 124 | 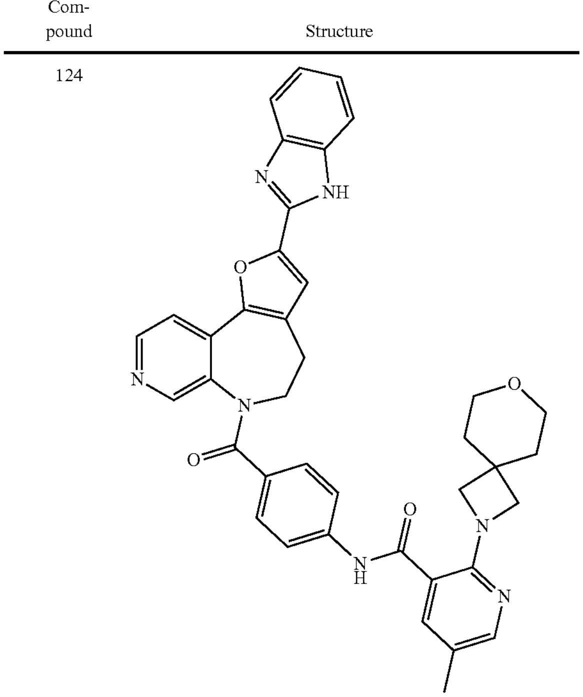 |
| 125 | 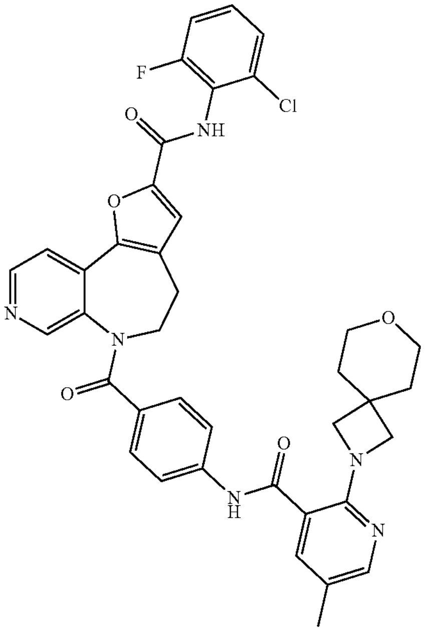 [SMILES: Cc1cnc(N2CC3(CCOCC3)C2)c(C(=O)Nc2ccc(C(=O)N3CCc4cc(C(=O)Nc5c(F)cccc5Cl)oc4-c4ccncc43)cc2)c1] |
-continued
| Compound | Structure |
| --- | --- |
| 126 | 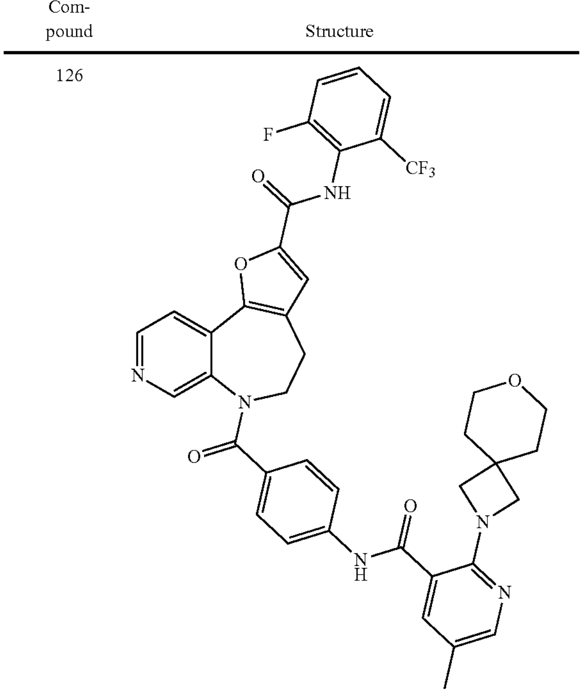 |
| 127 | 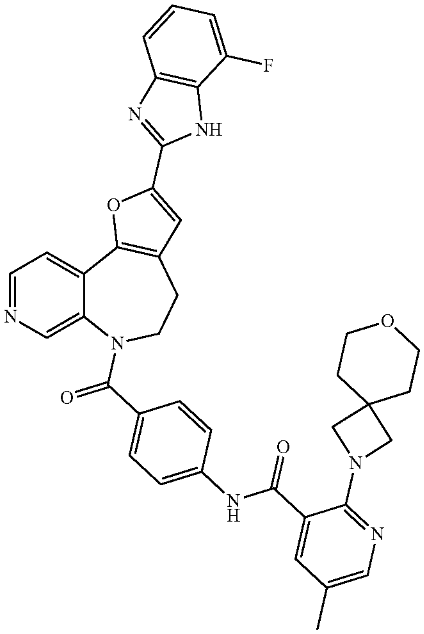 [SMILES: Cc1cnc(N2CC3(CCOCC3)C2)c(C(=O)Nc2ccc(C(=O)N3CCc4cc(-c5nc6cccc(F)c6[nH]5)oc4-c4ccncc43)cc2)c1] |

-continued
| Compound | Structure |
|---|---|
| 131 | 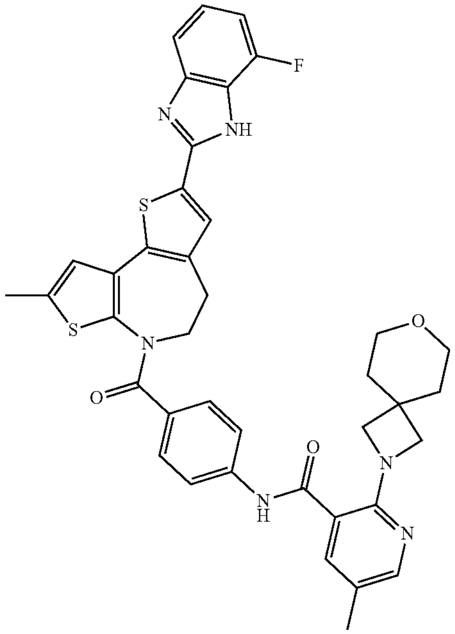 [SMILES: Cc1cnc(N2CC3(CCOCC3)C2)c(C(=O)Nc2ccc(C(=O)N3CCc4cc(-c5nc6cccc(F)c6[nH]5)sc4-c4cc(C)sc43)cc2)c1] |
| 132 | 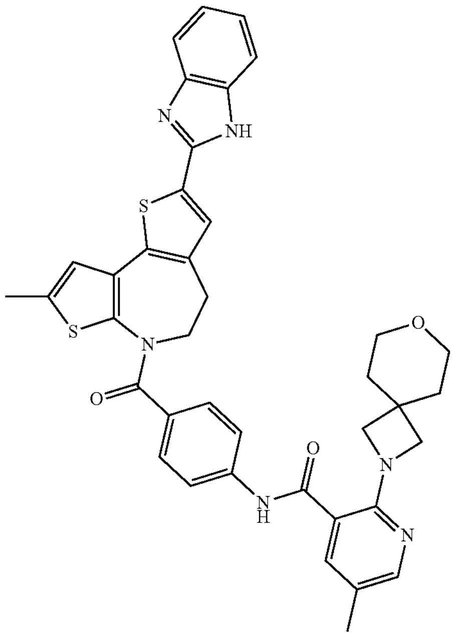 [SMILES: Cc1cnc(N2CC3(CCOCC3)C2)c(C(=O)Nc2ccc(C(=O)N3CCc4cc(-c5nc6ccccc6[nH]5)sc4-c4cc(C)sc43)cc2)c1] |
-continued
| Compound | Structure |
|---|---|
| 133 | 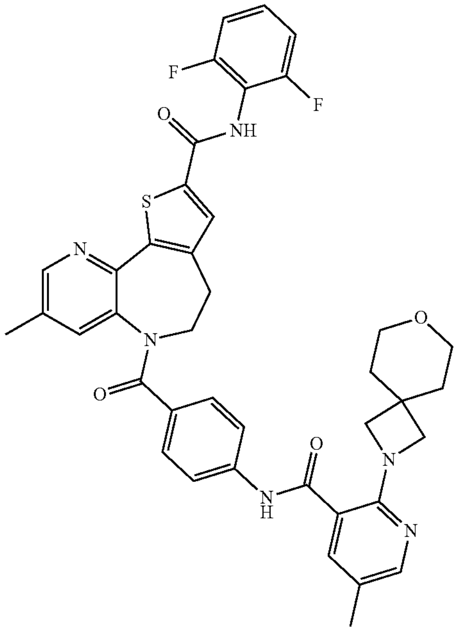 [SMILES: Cc1cnc(N2CC3(CCOCC3)C2)c(C(=O)Nc2ccc(C(=O)N3CCc4cc(C(=O)Nc5c(F)cccc5F)sc4-c4ncc(C)cc43)cc2)c1] |
| 134 | 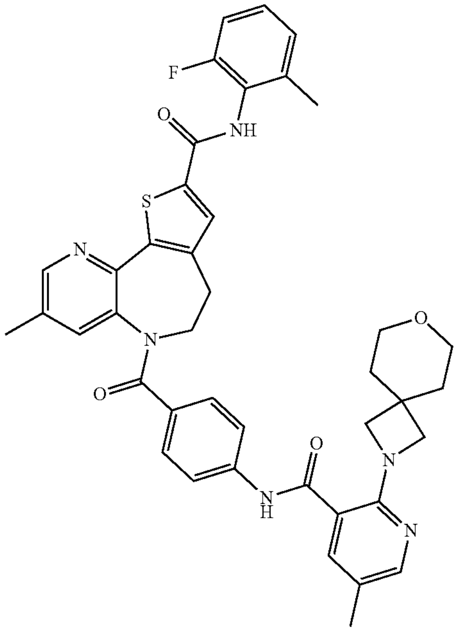 [SMILES: Cc1cnc(N2CC3(CCOCC3)C2)c(C(=O)Nc2ccc(C(=O)N3CCc4cc(C(=O)Nc5c(C)cccc5F)sc4-c4ncc(C)cc43)cc2)c1] |

-continued
| Compound | Structure |
|---|---|
| 135 | 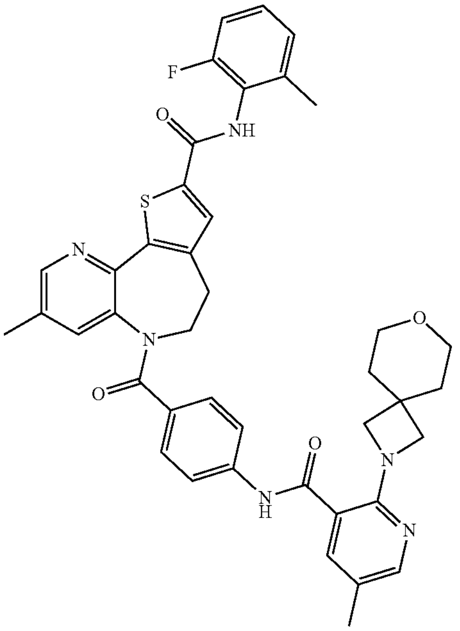 [SMILES: Cc1cnc(N2CC3(CCOCC3)C2)c(C(=O)Nc2ccc(C(=O)N3CCc4cc(C(=O)Nc5c(C)cccc5F)sc4-c4ncc(C)cc43)cc2)c1] |
| 136 | 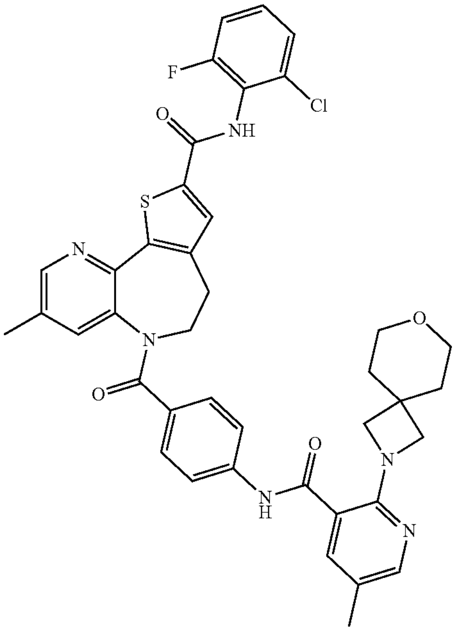 |
-continued
| Compound | Structure |
|---|---|
| 137 | 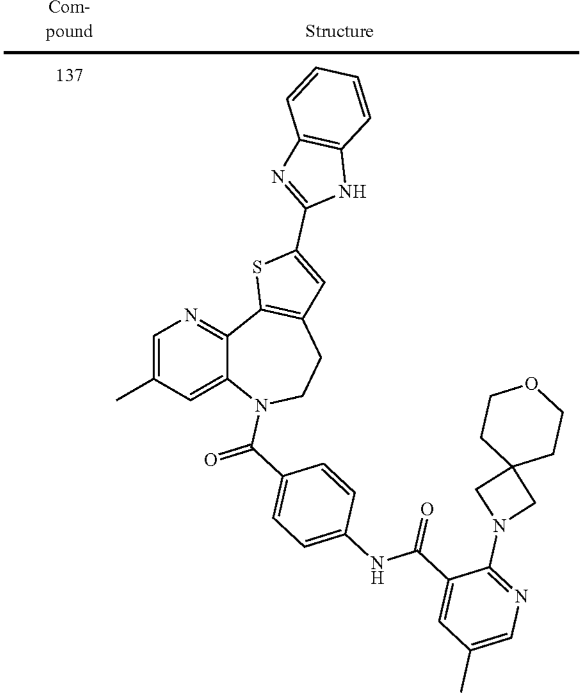 |
| 138 | 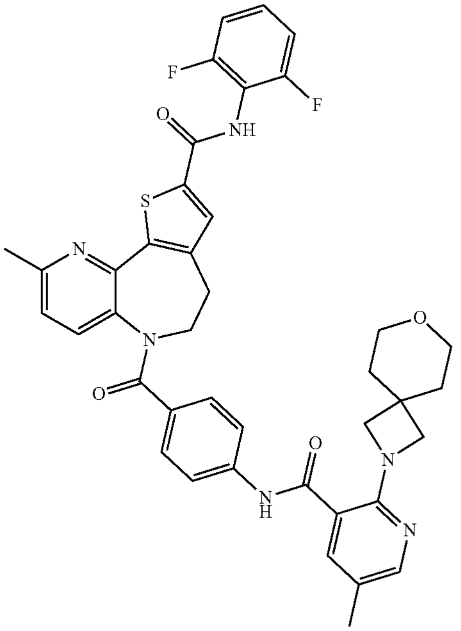 [SMILES: Cc1cnc(N2CC3(CCOCC3)C2)c(C(=O)Nc2ccc(C(=O)N3CCc4cc(C(=O)Nc5c(F)cccc5F)sc4-c4nc(C)ccc43)cc2)c1] |

-continued
| Compound | Structure |
|---|---|
| 139 | 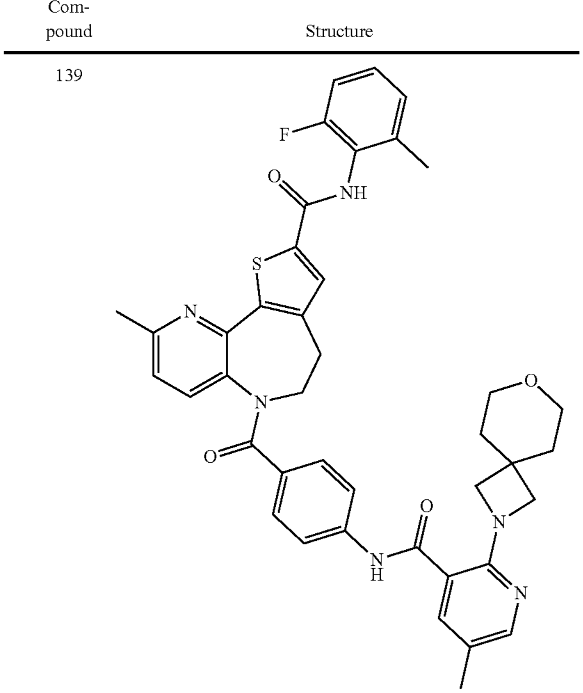 |
| 140 | 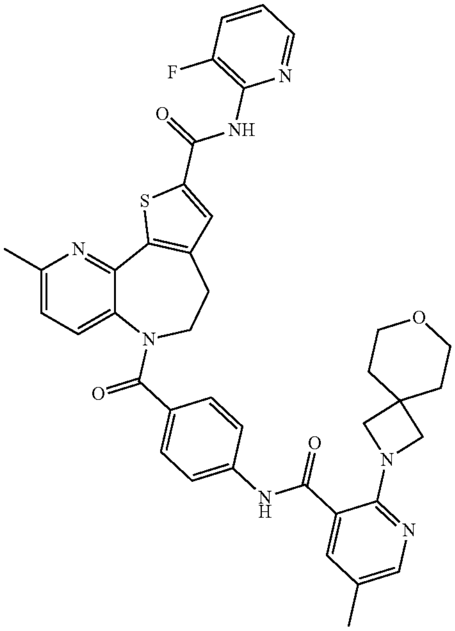 [SMILES: Cc1cnc(N2CC3(CCOCC3)C2)c(C(=O)Nc2ccc(C(=O)N3CCc4cc(C(=O)Nc5ncccc5F)sc4-c4nc(C)ccc43)cc2)c1] |
-continued
| Compound | Structure |
|---|---|
| 141 | 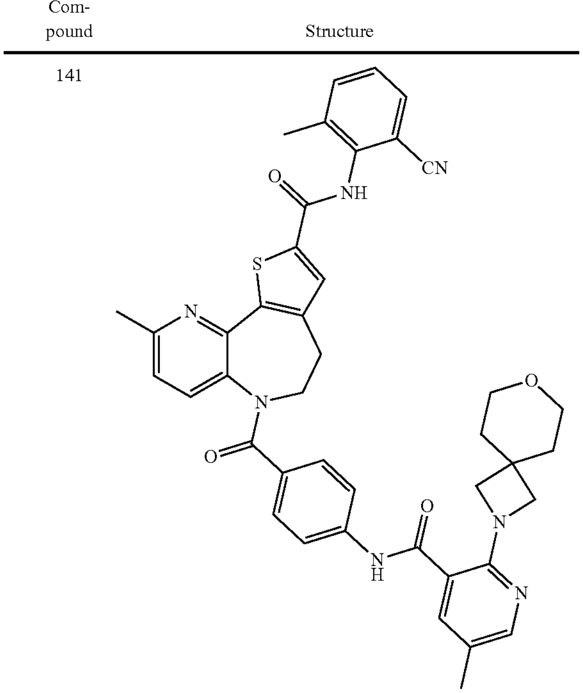 |
| 142 | 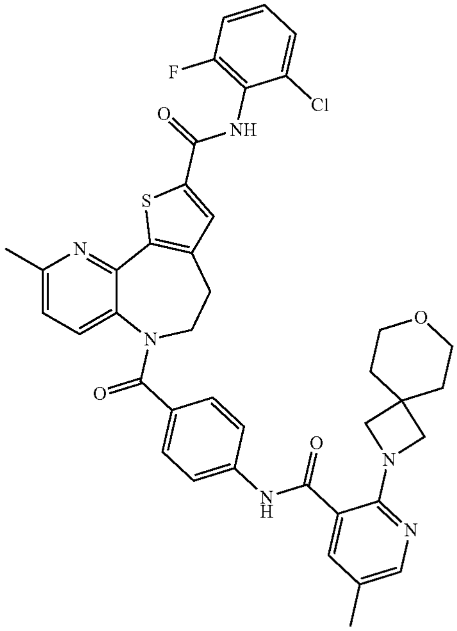 [SMILES: Cc1cnc(N2CC3(CCOCC3)C2)c(C(=O)Nc2ccc(C(=O)N3CCc4cc(C(=O)Nc5c(F)cccc5Cl)sc4-c4nc(C)ccc43)cc2)c1] |

-continued
| Compound | Structure |
| --- | --- |
| 143 | 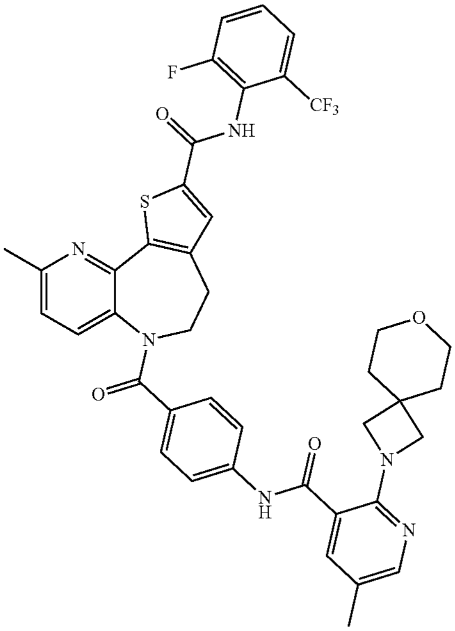 [SMILES: Cc1cnc(N2CC3(CCOCC3)C2)c(C(=O)Nc2ccc(C(=O)N3CCc4cc(C(=O)Nc5c(F)cccc5C(F)(F)F)sc4-c4nc(C)ccc43)cc2)c1] |
| 144 | 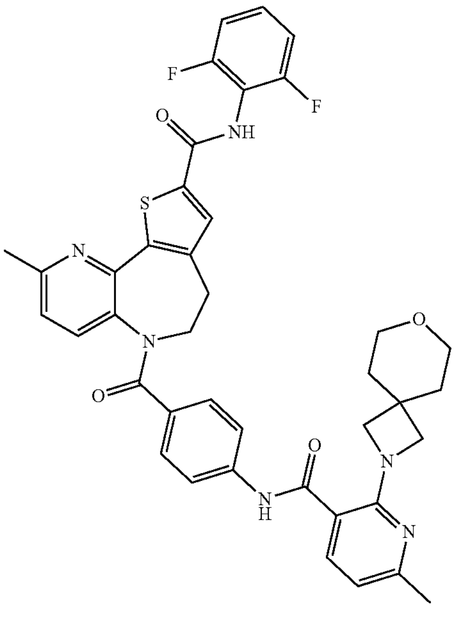 [SMILES: Cc1ccc2c(n1)-c1sc(C(=O)Nc3c(F)cccc3F)cc1CCN2C(=O)c1ccc(NC(=O)c2ccc(C)nc2N2CC3(CCOCC3)C2)cc1] |
-continued
| Compound | Structure |
| --- | --- |
| 145 | 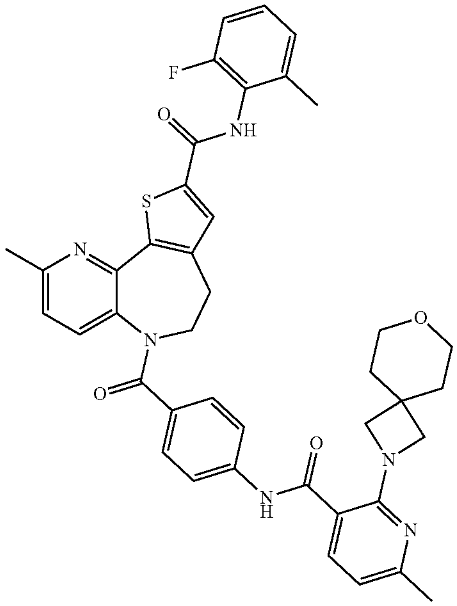 [SMILES: Cc1ccc2c(n1)-c1sc(C(=O)Nc3c(C)cccc3F)cc1CCN2C(=O)c1ccc(NC(=O)c2ccc(C)nc2N2CC3(CCOCC3)C2)cc1] |
| 146 | 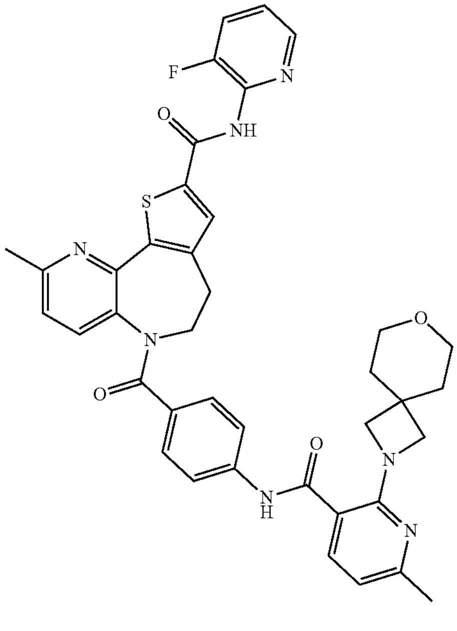 [SMILES: Cc1ccc2c(n1)-c1sc(C(=O)Nc3ncccc3F)cc1CCN2C(=O)c1ccc(NC(=O)c2ccc(C)nc2N2CC3(CCOCC3)C2)cc1] |

-continued
| Compound | Structure |
|---|---|
| 147 | 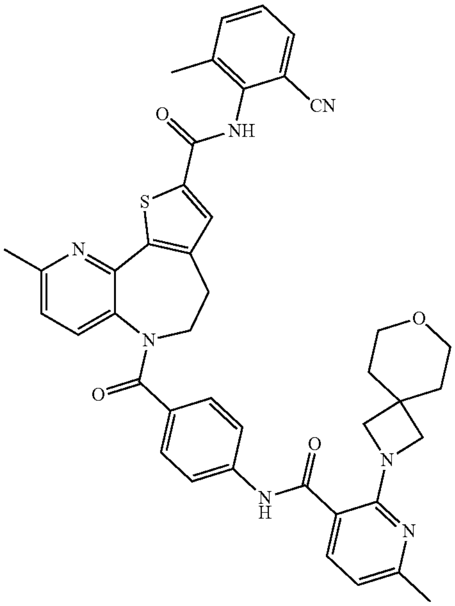 [SMILES: Cc1ccc2c(n1)-c1sc(C(=O)Nc3c(C)cccc3C#N)cc1CCN2C(=O)c1ccc(NC(=O)c2ccc(C)nc2N2CC3(CCOCC3)C2)cc1] |
| 148 | 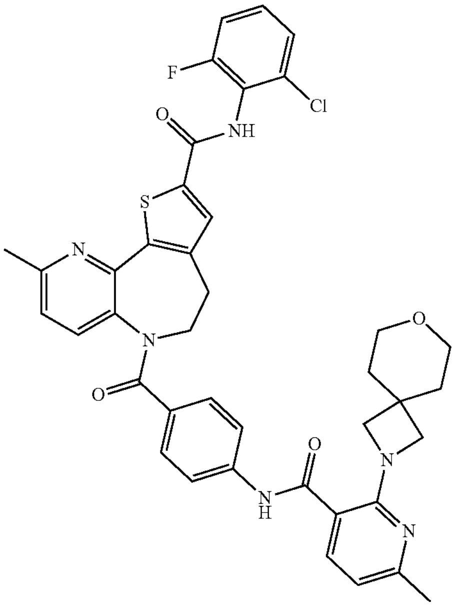 [SMILES: Cc1ccc2c(n1)-c1sc(C(=O)Nc3c(F)cccc3Cl)cc1CCN2C(=O)c1ccc(NC(=O)c2ccc(C)nc2N2CC3(CCOCC3)C2)cc1] |
-continued
| Compound | Structure |
|---|---|
| 149 | 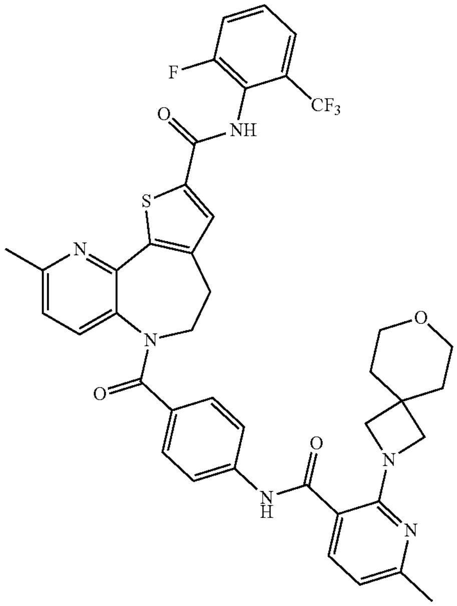 [SMILES: Cc1ccc2c(n1)-c1sc(C(=O)Nc3c(F)cccc3C(F)(F)F)cc1CCN2C(=O)c1ccc(NC(=O)c2ccc(C)nc2N2CC3(CCOCC3)C2)cc1] |
| 150 | 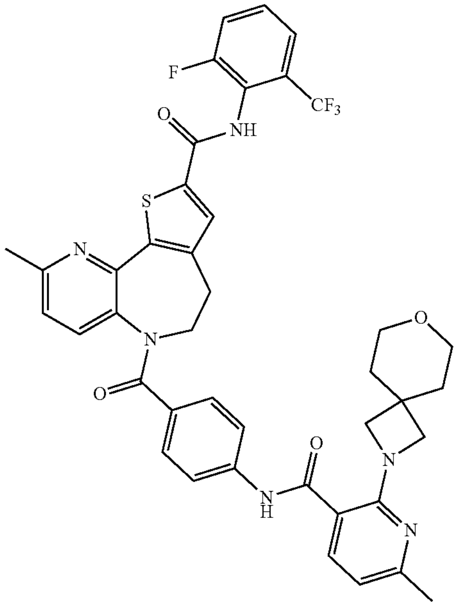 [SMILES: Cc1ccc2c(n1)-c1sc(C(=O)Nc3c(F)cccc3C(F)(F)F)cc1CCN2C(=O)c1ccc(NC(=O)c2ccc(C)nc2N2CC3(CCOCC3)C2)cc1] |

-continued
| Compound | Structure |
|---|---|
| 151 | 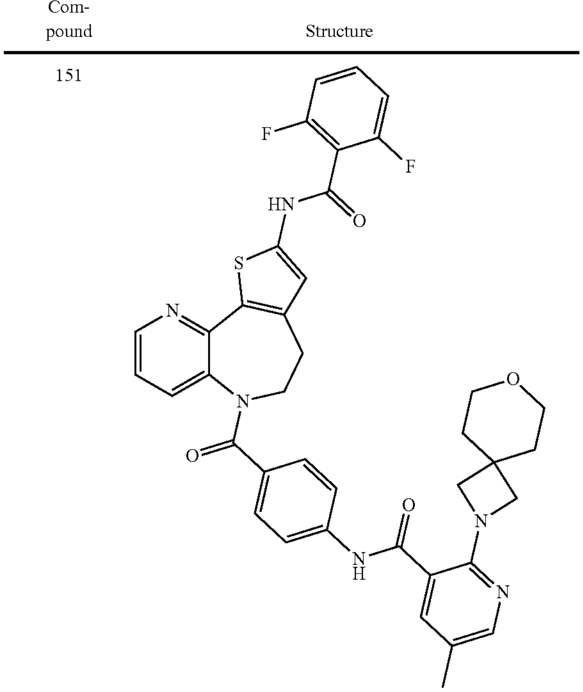 |
| 152 | 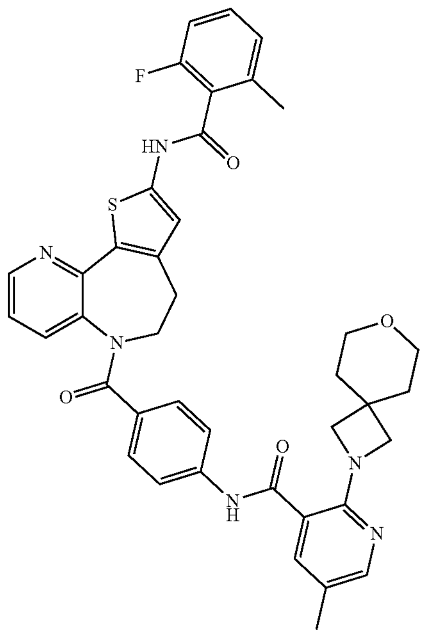 [SMILES: Cc1cnc(N2CC3(CCOCC3)C2)c(C(=O)Nc2ccc(C(=O)N3CCc4cc(NC(=O)c5c(C)cccc5F)sc4-c4ncccc43)cc2)c1] |
-continued
| Compound | Structure |
|---|---|
| 153 | 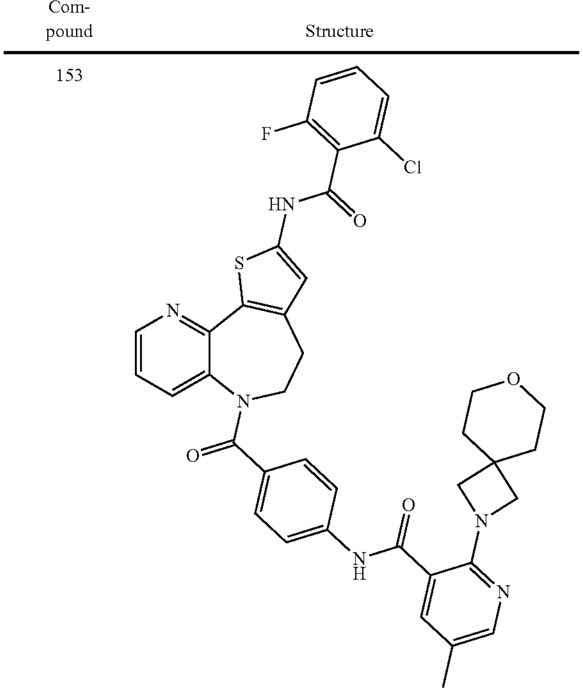 |
| 154 | 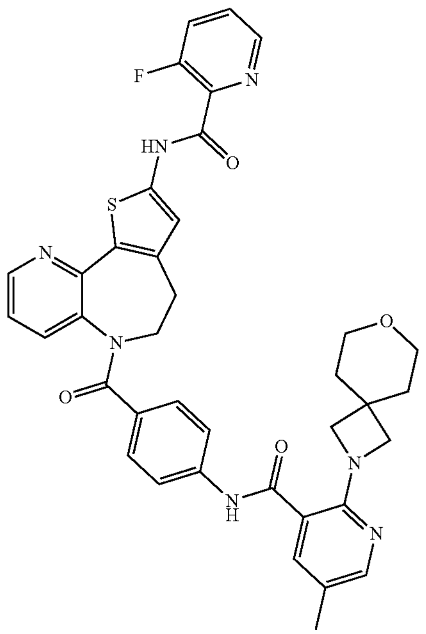 [SMILES: Cc1cnc(N2CC3(CCOCC3)C2)c(C(=O)Nc2ccc(C(=O)N3CCc4cc(NC(=O)c5ncccc5F)sc4-c4ncccc43)cc2)c1] |

-continued
| Compound | Structure |
|---|---|
| 155 | 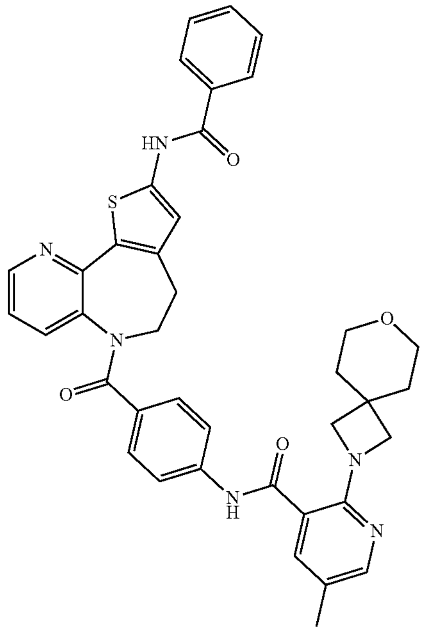 [SMILES: Cc1cnc(N2CC3(CCOCC3)C2)c(C(=O)Nc2ccc(C(=O)N3CCc4cc(NC(=O)c5ccccc5)sc4-c4ncccc43)cc2)c1] |
| 156 | 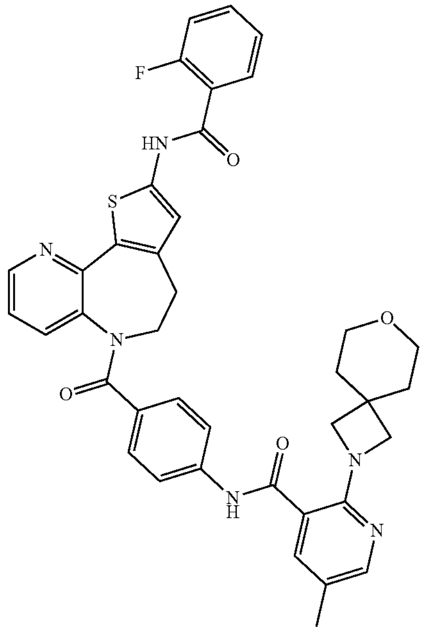 [SMILES: Cc1cnc(N2CC3(CCOCC3)C2)c(C(=O)Nc2ccc(C(=O)N3CCc4cc(NC(=O)c5ccccc5F)sc4-c4ncccc43)cc2)c1] |
-continued
| Compound | Structure |
|---|---|
| 157 | 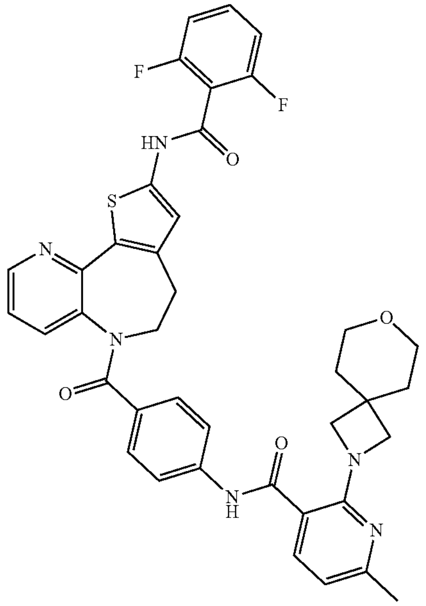 [SMILES: Cc1ccc(C(=O)Nc2ccc(C(=O)N3CCc4cc(NC(=O)c5c(F)cccc5F)sc4-c4ncccc43)cc2)c(N2CC3(CCOCC3)C2)n1] |
| 158 | 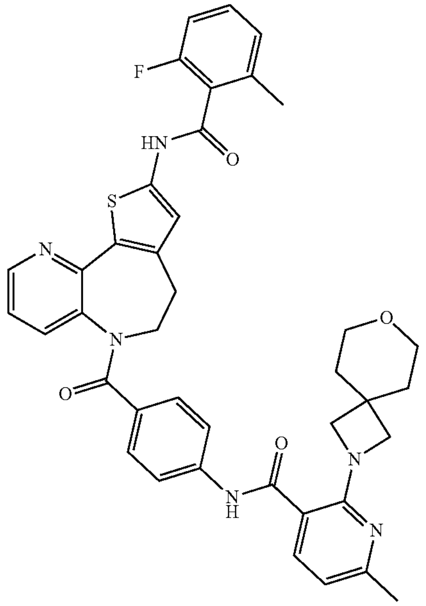 [SMILES: Cc1ccc(C(=O)Nc2ccc(C(=O)N3CCc4cc(NC(=O)c5c(C)cccc5F)sc4-c4ncccc43)cc2)c(N2CC3(CCOCC3)C2)n1] |

-continued
| Compound | Structure |
|---|---|
| 159 | 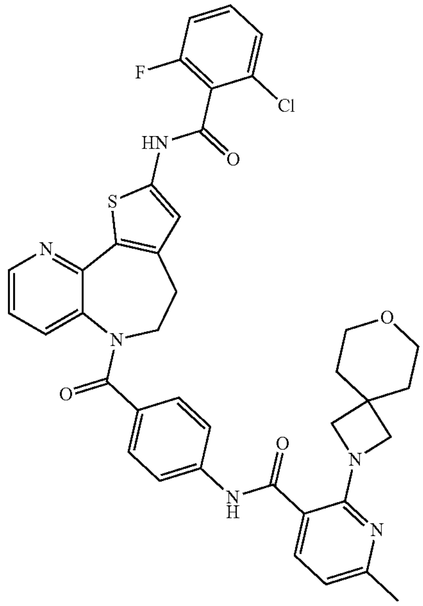 [SMILES: Cc1ccc(C(=O)Nc2ccc(C(=O)N3CCc4cc(NC(=O)c5c(F)cccc5Cl)sc4-c4ncccc43)cc2)c(N2CC3(CCOCC3)C2)n1] |
| 160 | 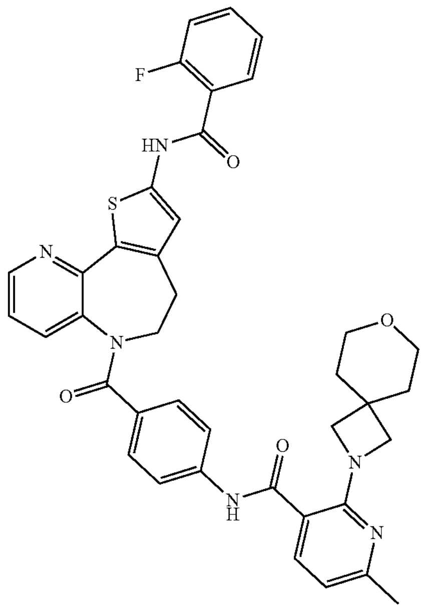 [SMILES: Cc1ccc(C(=O)Nc2ccc(C(=O)N3CCc4cc(NC(=O)c5ccccc5F)sc4-c4ncccc43)cc2)c(N2CC3(CCOCC3)C2)n1] |
-continued
| Compound | Structure |
|---|---|
| 161 | 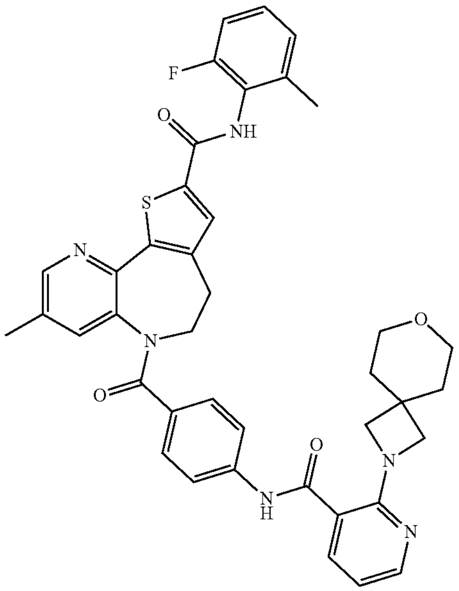 [SMILES: Cc1cnc2c(c1)N(C(=O)c1ccc(NC(=O)c3cccnc3N3CC4(CCOCC4)C3)cc1)CCc1cc(C(=O)Nc3c(C)cccc3F)sc1-2] |
| 162 | 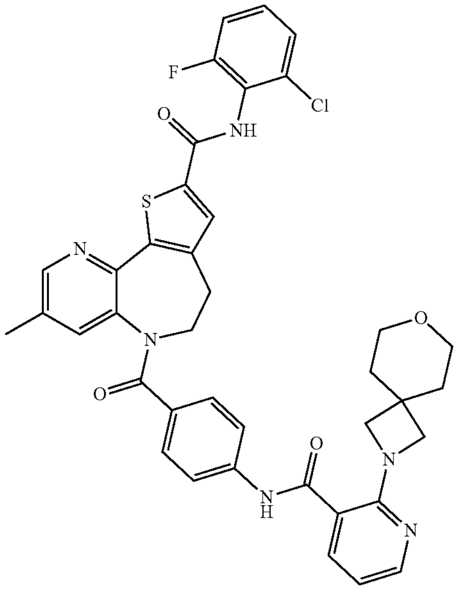 [SMILES: Cc1cnc2c(c1)N(C(=O)c1ccc(NC(=O)c3cccnc3N3CC4(CCOCC4)C3)cc1)CCc1cc(C(=O)Nc3c(F)cccc3Cl)sc1-2] |

| Compound | Structure |
|---|---|
| 163 | 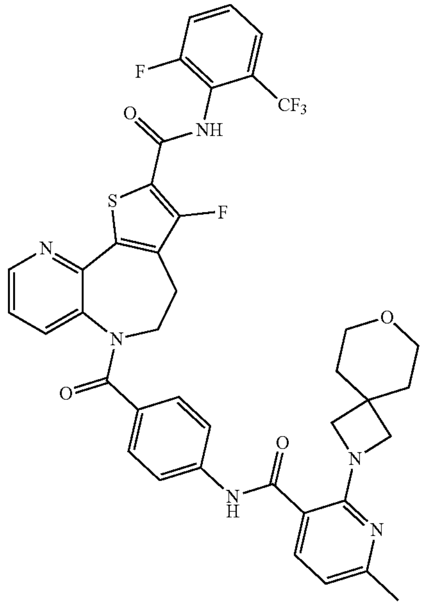 [SMILES: Cc1ccc(C(=O)Nc2ccc(C(=O)N3CCc4c(sc(C(=O)Nc5c(F)cccc5C(F)(F)F)c4F)-c4ncccc43)cc2)c(N2CC3(CCOCC3)C2)n1] |
| 164 | 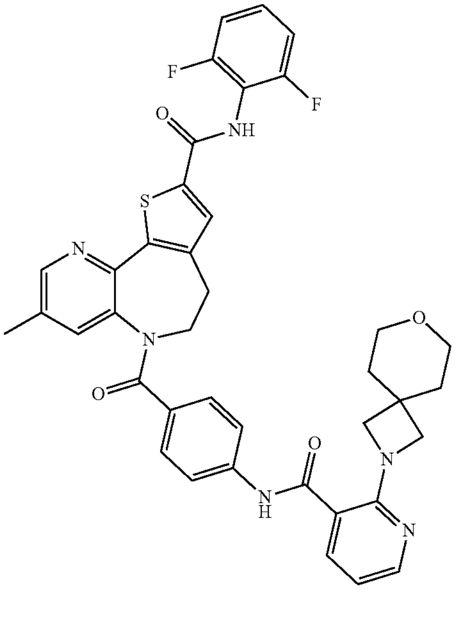 [SMILES: Cc1cnc2c(c1)N(C(=O)c1ccc(NC(=O)c3cccnc3N3CC4(CCOCC4)C3)cc1)CCc1cc(C(=O)Nc3c(F)cccc3F)sc1-2] |
| Compound | Structure |
|---|---|
| 165 | 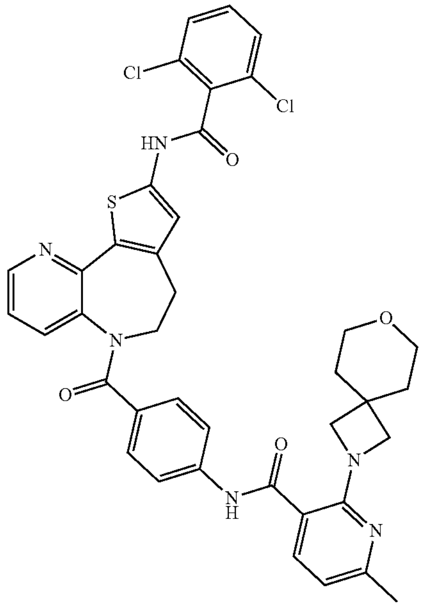 [SMILES: Cc1ccc(C(=O)Nc2ccc(C(=O)N3CCc4cc(NC(=O)c5c(Cl)cccc5Cl)sc4-c4ncccc43)cc2)c(N2CC3(CCOCC3)C2)n1] |
| 166 | 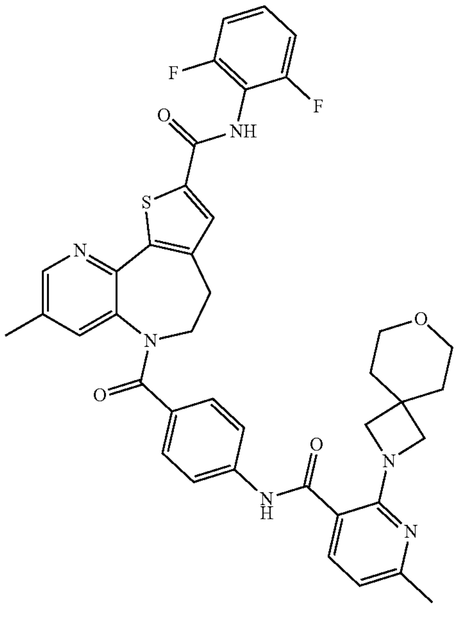 [SMILES: Cc1cnc2c(c1)N(C(=O)c1ccc(NC(=O)c3ccc(C)nc3N3CC4(CCOCC4)C3)cc1)CCc1cc(C(=O)Nc3c(F)cccc3F)sc1-2] |

-continued
| Compound | Structure |
|---|---|
| 167 | 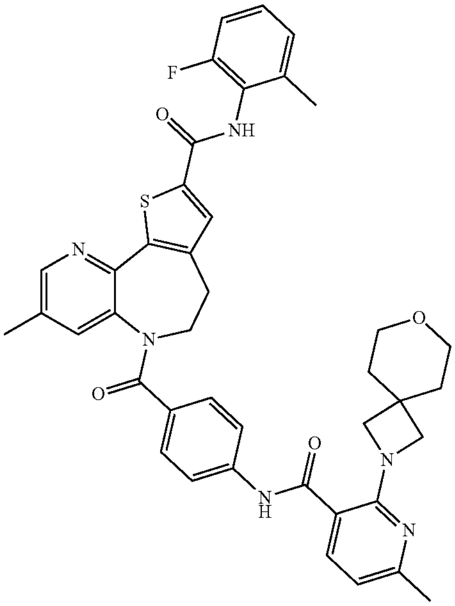 [SMILES: Cc1cnc2c(c1)N(C(=O)c1ccc(NC(=O)c3ccc(C)nc3N3CC4(CCOCC4)C3)cc1)CCc1cc(C(=O)Nc3c(C)cccc3F)sc1-2] |
| 168 | 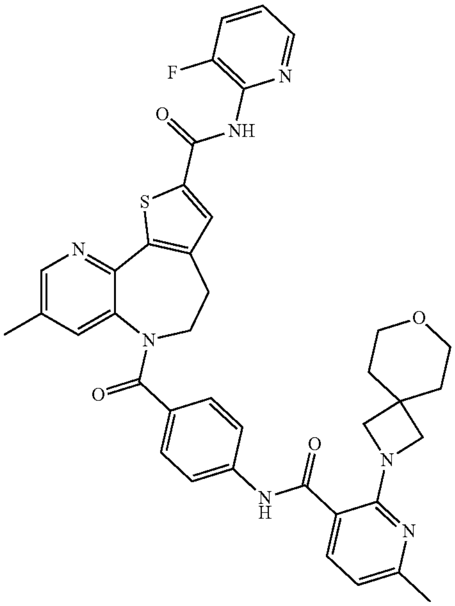 [SMILES: Cc1cnc2c(c1)N(C(=O)c1ccc(NC(=O)c3ccc(C)nc3N3CC4(CCOCC4)C3)cc1)CCc1cc(C(=O)Nc3ncccc3F)sc1-2] |
-continued
| Compound | Structure |
|---|---|
| 169 | 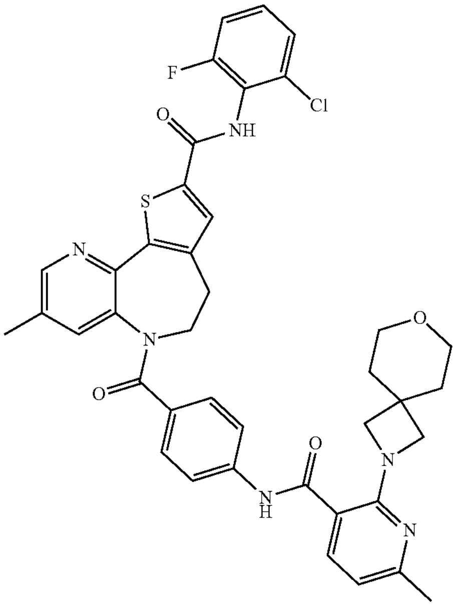 [SMILES: Cc1cnc2c(c1)N(C(=O)c1ccc(NC(=O)c3ccc(C)nc3N3CC4(CCOCC4)C3)cc1)CCc1cc(C(=O)Nc3c(F)cccc3Cl)sc1-2] |
| 170 | 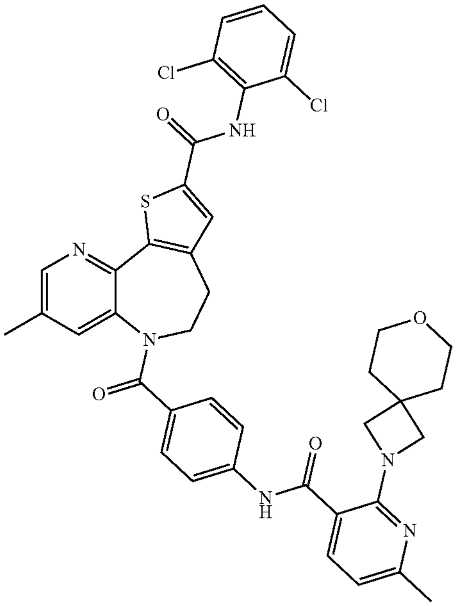 [SMILES: Cc1cnc2c(c1)N(C(=O)c1ccc(NC(=O)c3ccc(C)nc3N3CC4(CCOCC4)C3)cc1)CCc1cc(C(=O)Nc3c(Cl)cccc3Cl)sc1-2] |

-continued

| Compound | Structure |
|---|---|
| 171 | 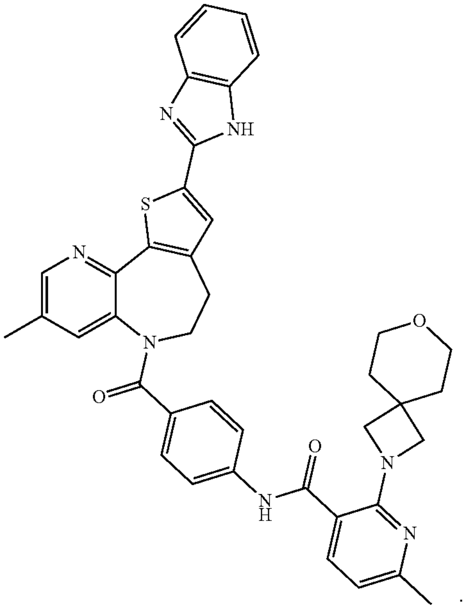 [SMILES: Cc1cnc2c(c1)N(C(=O)c1ccc(NC(=O)c3ccc(C)nc3N3CC4(CCOCC4)C3)cc1)CCc1cc(-c3nc4ccccc4[nH]3)sc1-2] |

17. A pharmaceutical composition comprising a compound according to claim 1 and a pharmaceutically acceptable carrier, diluent or excipient.

18. A method of treating an RSV infection in a subject in need thereof, comprising administering to the subject a therapeutically effective amount of a compound or a combination of compounds of claim 1.

19. The method of claim 18 further comprising the step of administering to the subject an additional anti-RSV agent.

20. The method of claim 18, further comprising administering to the subject a steroid anti-inflammatory compound.

21. A method of treating RSV and influenza in a subject in need thereof, comprising administering to the subject a therapeutically effective amount of a compound of claim 1 and a therapeutically effective amount of an anti-influenza agent.

22. The method of claim 19, wherein the compound and the additional anti-RSV agent are co-formulated.

23. The method of claim 19, wherein the compound and the additional anti-RSV agent are co-administered.

* * * * *

UNITED STATES PATENT AND TRADEMARK OFFICE
CERTIFICATE OF CORRECTION

PATENT NO. : 10,851,115 B2
APPLICATION NO. : 16/023363
DATED : December 1, 2020
INVENTOR(S) : In Jong Kim et al.

It is certified that error appears in the above-identified patent and that said Letters Patent is hereby corrected as shown below:

In the Claims

<u>At Column 286</u>

In Claim 10, structure (IIIa-2), delete "

(IIIa-2)

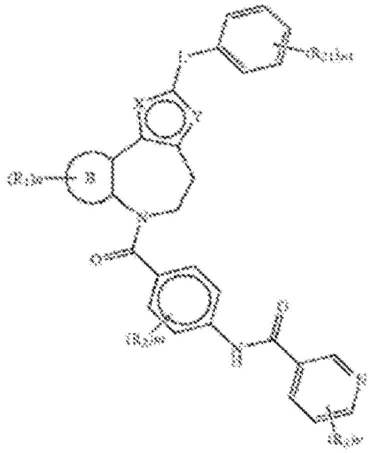

" and insert

-- 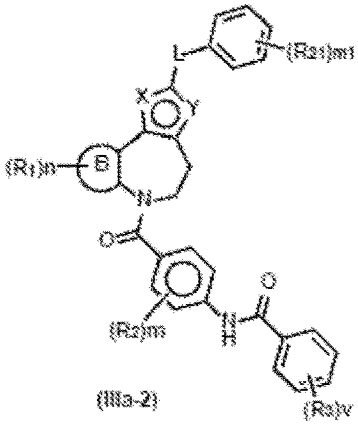

(IIIa-2)

--.

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*

At Column 294
(IVa-2)
In Claim 11, structure (IVa-2), delete “ 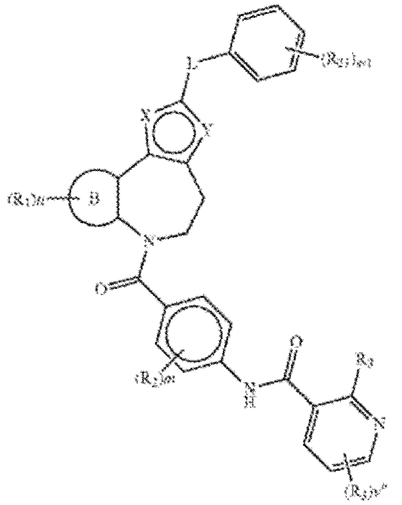 ” and insert
-- 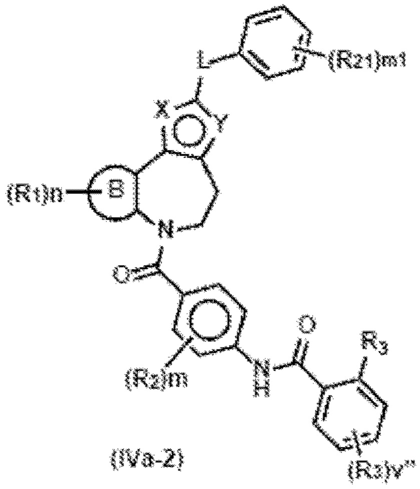
(IVa-2)
--.